(12) United States Patent
Yoshikawa et al.

(10) Patent No.: US 12,171,777 B2
(45) Date of Patent: Dec. 24, 2024

(54) METHODS OF MAKING A CYCLIC DINUCLEOTIDE

(71) Applicant: TAKEDA PHARMACEUTICAL COMPANY LIMITED, Osaka (JP)

(72) Inventors: Masato Yoshikawa, Fujisawa Kanagawa (JP); Morihisa Saitoh, Fujisawa Kanagawa (JP); Taisuke Kato, Fujisawa Kanagawa (JP); Yayoi Nakayama, Fujisawa Kanagawa (JP); Tomohiro Seki, Fujisawa Kanagawa (JP); Yasuo Nakagawa, Fujisawa Kanagawa (JP); Yusuke Tominari, Fujisawa Kanagawa (JP); Masaki Seto, Fujisawa Kanagawa (JP); Yusuke Sasaki, Fujisawa Kanagawa (JP); Masanori Okaniwa, Fujisawa Kanagawa (JP); Tsuneo Oda, Fujisawa Kanagawa (JP); Akito Shibuya, Fujisawa Kanagawa (JP); Kosuke Hidaka, Fujisawa Kanagawa (JP); Zenyu Shiokawa, Fujisawa Kanagawa (JP); Shumpei Murata, Fujisawa Kanagawa (JP); Atsutoshi Okabe, Fujisawa Kanagawa (JP); Yoshihisa Nakada, Fujisawa Kanagawa (JP); Michiyo Mochizuki, Fujisawa Kanagawa (JP); Brian Scott Freeze, Boston, MA (US); Taisuke Tawaraishi, Fujisawa Kanagawa (JP); Yasufumi Wada, Fujisawa Kanagawa (JP); Paul D. Greenspan, Acton, MA (US)

(73) Assignee: Takeda Pharmaceutical Company Limited, Osaka (JP)

(*) Notice: Subject to any disclaimer, the term of this patent is extended or adjusted under 35 U.S.C. 154(b) by 0 days.

(21) Appl. No.: 18/310,467

(22) Filed: May 1, 2023

(65) Prior Publication Data
US 2024/0066047 A1    Feb. 29, 2024

Related U.S. Application Data

(60) Continuation of application No. 17/065,242, filed on Oct. 7, 2020, now Pat. No. 11,666,594, which is a (Continued)

(30) Foreign Application Priority Data

Dec. 1, 2016  (JP) ................ 2016-234553
May 30, 2017 (JP) ................ 2017-107216

(51) Int. Cl.
  *A61K 31/7084* (2006.01)
  *A61K 31/7076* (2006.01)
  (Continued)

(52) U.S. Cl.
  CPC ...... *A61K 31/7084* (2013.01); *A61K 31/7076* (2013.01); *A61K 47/6807* (2017.08);
  (Continued)

(58) Field of Classification Search
  CPC .......... A61K 31/7084; A61K 47/6807; A61K 31/7076; A61P 35/00; C07H 21/00; C07H 21/02
  (Continued)

(56) References Cited

U.S. PATENT DOCUMENTS

| 5,547,941 A | 8/1996 | Battistini et al. |
| 7,569,555 B2 | 8/2009 | Karaolis |

(Continued)

FOREIGN PATENT DOCUMENTS

| CN | 106667914 A | 5/2017 |
| EP | 1740192 B1 | 6/2012 |

(Continued)

OTHER PUBLICATIONS

Seela et al. 7-Functionalized 7-deazapurine ß-D and ß-L-ribonucleosides related to tubercidin and 7-deazainosine: glycosylation of pyrrolo[2,3-d]pyrimidines with 1-O-acetyl-2,3,5-tri-O-benzoyl-ß-D or B-L-ribofuranose. Tetrahedron 63 (2007) 9850-9861. (Year: 2007).*

(Continued)

*Primary Examiner* — Yih-Horng Shiao
(74) *Attorney, Agent, or Firm* — Sterne, Kessler, Goldstein & Fox P.L.L.C.

(57) ABSTRACT

The present disclosure provides a compound having a STING agonistic activity, which may be expected to be useful as an agent for the prophylaxis or treatment of STING-related diseases.

The present disclosure relates to a compound represented by the formula (I):

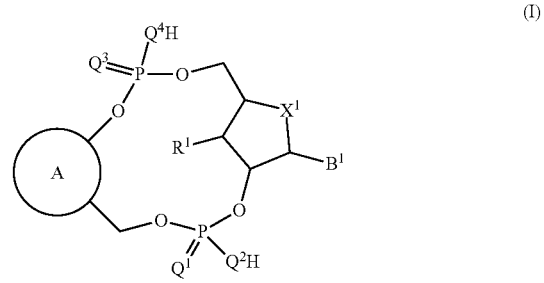

wherein each symbol is as defined in the description, or a salt thereof.

20 Claims, 11 Drawing Sheets

Specification includes a Sequence Listing.

Related U.S. Application Data division of application No. 16/185,258, filed on Nov. 9, 2018, now Pat. No. 10,980,825, which is a continuation of application No. PCT/IB2017/057588, filed on Dec. 1, 2017.

(60) Provisional application No. 62/589,300, filed on Nov. 21, 2017.

(51) Int. Cl.
    *A61K 47/68*     (2017.01)
    *A61P 35/00*     (2006.01)
    *C07H 21/00*     (2006.01)
    *C07H 21/02*     (2006.01)

(52) U.S. Cl.
CPC .............. *A61P 35/00* (2018.01); *C07H 21/00* (2013.01); *C07H 21/02* (2013.01)

(58) Field of Classification Search
USPC .................................................. 514/47
See application file for complete search history.

(56) References Cited

U.S. PATENT DOCUMENTS

| | | |
|---|---|---|
| 7,592,326 B2 | 9/2009 | Karaolis |
| 7,709,458 B2 | 5/2010 | Karaolis |
| 8,367,716 B2 | 2/2013 | Karaolis |
| 8,450,293 B2 | 5/2013 | Jones et al. |
| 9,090,646 B2 | 7/2015 | Jones et al. |
| 9,549,944 B2 | 1/2017 | Dubensky et al. |
| 9,597,391 B2 | 3/2017 | Ebenson et al. |
| 9,695,212 B2 | 7/2017 | Dubensky et al. |
| 9,718,848 B2 | 8/2017 | Adams et al. |
| 9,724,408 B2 | 8/2017 | Dubensky et al. |
| 9,770,467 B2 | 9/2017 | Dubensky et al. |
| 9,840,533 B2 | 12/2017 | Patel et al. |
| 10,980,825 B2 | 4/2021 | Yoshikawa et al. |
| 11,001,605 B2 | 5/2021 | Genieser et al. |
| 11,666,594 B2 | 6/2023 | Yoshikawa et al. |
| 2006/0167241 A1 | 7/2006 | Hayakawa et al. |
| 2007/0149462 A1 | 6/2007 | Iyer et al. |
| 2011/0110936 A1 | 5/2011 | Nam et al. |
| 2014/0341976 A1 | 11/2014 | Dubensky et al. |
| 2015/0056224 A1 | 2/2015 | Dubensky et al. |
| 2017/0044206 A1 | 2/2017 | Altman et al. |
| 2017/0146519 A1 | 5/2017 | Defilippis et al. |
| 2018/0093964 A1 | 4/2018 | Altman et al. |
| 2022/0168330 A1 | 6/2022 | Xu et al. |

FOREIGN PATENT DOCUMENTS

| | | |
|---|---|---|
| EP | 1729781 B1 | 10/2012 |
| WO | WO-2005089777 A1 | 9/2005 |
| WO | WO-2006045041 A2 | 4/2006 |
| WO | WO-2007054279 A2 | 5/2007 |
| WO | WO-2009133560 A1 | 11/2009 |
| WO | WO-2011003025 A1 | 1/2011 |
| WO | WO-2013185052 A1 | 12/2013 |
| WO | WO-2014093936 A1 | 6/2014 |
| WO | WO-2014099824 A1 | 6/2014 |
| WO | WO-2014109256 A1 | 7/2014 |
| WO | WO-2014179335 A1 | 11/2014 |
| WO | WO-2014179760 A1 | 11/2014 |
| WO | WO-2014189805 A1 | 11/2014 |
| WO | WO-2014189806 A1 | 11/2014 |
| WO | WO-2015017652 A1 | 2/2015 |
| WO | WO-2015074145 A1 | 5/2015 |
| WO | WO-2015077354 A1 | 5/2015 |
| WO | WO 2015/185565 * | 12/2015 |
| WO | WO-2015185565 A1 | 12/2015 |
| WO | WO 2016/096174 * | 6/2016 |
| WO | WO-2016096174 A1 | 6/2016 |
| WO | WO-2016096577 A1 | 6/2016 |
| WO | WO-2017123657 A1 | 7/2016 |
| WO | WO-2016120305 A1 | 8/2016 |
| WO | WO-2016145102 A1 | 9/2016 |
| WO | WO-2017011444 A1 | 1/2017 |
| WO | WO-2017011622 A1 | 1/2017 |
| WO | WO-2017019896 A1 | 2/2017 |
| WO | WO-2017027645 A1 | 2/2017 |
| WO | WO-2017027646 A1 | 2/2017 |
| WO | WO-2017075477 A1 | 5/2017 |
| WO | WO-2017093933 A1 | 6/2017 |
| WO | WO-2017100305 A2 | 6/2017 |
| WO | WO-2017106740 A1 | 6/2017 |
| WO | WO-2017123669 A1 | 7/2017 |
| WO | WO-2017161349 A1 | 9/2017 |
| WO | WO-2017165506 A1 | 9/2017 |
| WO | WO-2018172206 A1 | 9/2017 |
| WO | WO-2017175147 A1 | 10/2017 |
| WO | WO-2017175156 A1 | 10/2017 |
| WO | WO-2017186711 A1 | 11/2017 |
| WO | WO-2018009466 A1 | 1/2018 |
| WO | WO-2018009648 A1 | 1/2018 |
| WO | WO-2018009652 A1 | 1/2018 |
| WO | WO-2018013887 A1 | 1/2018 |
| WO | WO-2018013908 A1 | 1/2018 |
| WO | WO-2018198076 A1 | 1/2018 |
| WO | WO-2018198084 A1 | 1/2018 |
| WO | WO-2018045204 A1 | 3/2018 |
| WO | WO-2018060323 A1 | 4/2018 |
| WO | WO-2018065360 A1 | 4/2018 |
| WO | WO-2018098203 A1 | 5/2018 |
| WO | WO-2018118664 A1 | 6/2018 |
| WO | WO-2018118665 A1 | 6/2018 |
| WO | WO-2018119117 A1 | 6/2018 |
| WO | WO-2018138684 A1 | 8/2018 |
| WO | WO-2018138685 A2 | 8/2018 |
| WO | WO-2018140831 A1 | 8/2018 |
| WO | WO-2018152450 A1 | 8/2018 |
| WO | WO-2018152453 A1 | 8/2018 |
| WO | WO-2018156625 A1 | 8/2018 |
| WO | WO-2018200812 A1 | 11/2018 |
| WO | WO-2019043634 A2 | 3/2019 |
| WO | WO-2019046496 A1 | 3/2019 |
| WO | WO-2019046500 A1 | 3/2019 |
| WO | WO-2019055750 A1 | 3/2019 |

OTHER PUBLICATIONS

Clivio, P., et al., "(3'-5')-Cyclic dinucleotides: synthetic strategies and biological potential," Chemical Reviews 113(10):7354-7401, American Chemical Society, United States (Oct. 2013).

Corrales, L., et al., "Direct Activation of STING in the Tumor Microenvironment Leads to Potent and Systemic Tumor Regression and Immunity," Cell Reports 11(7):1018-1030, Cell Press, United States (May 2015).

Danilchanka, O., and Mekalanos, J. J., "Cyclic dinucleotides and the innate immune response," Cell 154(5):962-970, Elsevier, Netherlands (Aug. 2013).

Ertem, G., and Ferris, J.P., "Synthesis of RNA oligomers on heterogeneous templates," Nature 379(6562):238-40, Nature Publishing Group, United Kingdom (Jan. 1996).

Fu, J., et al., "STING agonist formulated cancer vaccines can cure established tumors resistant to PD-1 blockade," Science Translational Medicine 283(7):1-11, American Association for the Advancement of Science, United States (Apr. 2015).

Gaffney, B. L., et al., "One-flask Syntheses of c-di-GMP and the [Rp, Rp] and [Rp, Sp] Thiophosphate Analogs," Organic Letters 12(14):3269-3271, American Chemical Society, United States (Jul. 2010).

Ishikawa, H., and Barber, G. N., "STING is an endoplasmic reticulum adaptor that facilitates innate immune signalling," Nature 455(7213):674-78, Macmillan Publishers, United Kingdom (Oct. 2008).

International Search Report and Written Opinion for International Application No. PCT/US2018/029570, European Patent Office, Netherlands, mailed on Aug. 17, 2018, 12 pages.

(56) References Cited

OTHER PUBLICATIONS

Karaolis, D. K. R., et al., "3',5'-Cyclic diguanylic acid (c-di-GMP) inhibits basal and growth factor-stimulated human colon cancer cell proliferation," Biochemical and Biophysical Research Communications 329(1):40-45, Elsevier, Netherlands (Apr. 2005).
Lioux, T. et al., "Design, Synthesis, and Biological Evaluation of Novel Cyclic Adenosine-Inosine Monophosphate (cAIMP) Analogs That Activate Stimulator of Interferon Genes (STING)," Journal of Medicinal Chemistry 59(22):10253-10267, American Chemical Society, United States (Nov. 2016).
Sawai, H., et al., "Synthesis of 2' -5' linked Oligouridylates in aqueous medium using the $Pd^{2+}$ Ion," Chem Phann Bull 29(8):2237-2245, Pharmaceutical Society of Japan, Japan (Sep. 1981).
Sawai, H., et al., "Preparation and properties of Oligocytidylates with 2' -5' Internucleotide linkage," Bull Chem Soc Jpn 58:361-66, The Chemical Society of Japan, Japan (Jan. 1985).
Schwede, F., et al., "The Chemistry of the Noncanonical Cyclic Dinucleotide 2'3'-cGAMP and its analogs," in the Handbook of Experimental Pharmacology 238:359-384, Seifert, R., Ed., Springer International Publishing, Switzerland (2015, published online Jul. 2016).
Shanahan, C. A., et al., "Differential Analogue Binding by two classes of c-di-GMP riboswitches," J Am Chem Soc 133(39):15578-92, American Chemical Society, United States (Oct. 2011).
Shi, H., et al., "Molecular basis for the specific recognition of the metazoan cyclic GMP-AMP by the innate immune adaptor protein STING," Proc Natl Acad Sci USA 112(29)8947-52, United States National Academy of Sciences, United States (Jul. 2015).
Steinberger, O., et al., "Elevated expression of the CD4 receptor and cell cycle arrest are induced in Jurkat cells by treatment with the novel cyclic dinucleotide 3',5'-cyclic diguanylic acid," FEBS Letters 44(1):125-29, Elsevier, Netherlands (Feb. 1999).
Zhao, J., et al., "Thiophosphate analogs of c-di-GMP: Impact on polymorphism," Nucleosides Nucleotides Nucleic Acids 28(5):352-378, Taylor and Francis, United Kingdom (May 2010).
Yan, H., et al., "Synthesis and immunostimulatory properties of the phosphorothioate analogues of cdiGMP," Bioorganic & Medicinal Chem Lett 18(20):5631-34, Elsevier, Netherlands (published on line Aug. 2008, published in print Oct. 2008).
International Search Report and Written Opinion for International Application No. PCT/IB2017/057588, European Patent Office, Netherlands, mailed on Jun. 6, 2018, 21 pages.
Baird, J. R., et al., "Radiotherapy Combined with Novel STING-Targeting Oligonucleotides Results in Regression of Established Tumors," Cancer Res 76(1):50-61, American Association for Cancer Research, United States (2016).
Cheng, N., et al., "A nanoparticle-incorporated STING activator enhances antitumor immunity in PD-L1-insensitive models of triple-negative breast cancer," JCI insight 3(22):e120638, 20 pages, American Society for Clinical Investigation, United States (Nov. 2018).
Dialer, C. R., et al., "A Click-Chemistry Linked 2'3'-cGAMP Analogue," Chemistry 25(8):2089-2095, Wiley-VCH, Germany (Feb. 2019).

Hanson, M. C., et al., "Nanoparticulate STING agonists are potent lymph node-targeted vaccine adjuvants," J Clin Invest 125(6):2532-46, American Society for Clinical Investigation, United States (Jun. 2015).
Koshy, S. T., et al., "Liposomal Delivery Enhances Immune Activation by STING Agonists for Cancer Immunotherapy," Adv Biosyst 1(1-2):1600013, 24 pages, Wiley-Liss, United States (Feb. 2017).
Leach, D. G., et al., "STINGel: Controlled release of a cyclic dinucleotide for enhanced cancer immunotherapy," Biomaterials 163:67-75, Elsevier, Netherlands (May 2018).
Miyabe, H., et al., "A new adjuvant delivery system 'cyclic di-GMP/YSK05 liposome' for cancer immunotherapy," Journal of Controlled Release 184:20-27, Elsevier, Netherlands (Jun. 2014).
Nakamura, T., et al., "Liposomes loaded with a STING pathway ligand, cyclic di-GMP, enhance cancer immunotherapy against metastatic melanoma," Journal of Controlled Release 216:149-157, Elsevier, Netherlands (Oct. 2015).
Ramanjulu, J. M., et al., "Design of amidobenzimidazole STING receptor agonists with systemic activity," Nature 564(7736):439-443, Springer Nature Limited, Germany (Dec. 2018).
Sato, Y., et al., "A pH-sensitive cationic lipid facilitates the delivery of liposomal siRNA and gene silencing activity in vitro and in vivo," Journal of Controlled Release 163(3):267-276, Elsevier, Netherlands (Nov. 2012).
Seela, F., et al., "7-Functionalized 7-deazapurine β-d and β-1-ribonucleosides related to tubercidin and 7-deazainosine: glycosylation of pyrrolo[2,3-d]pyrimidines with 1-O-acetyl-2,3,5-tri-O-benzoyl-β-d or β-1-ribofuranose," Tetrahedron 63(39):9850-9861, Elsevier, Netherlands (Sep. 2007).
Sercombe, L., et al., "Advances and Challenges of Liposome Assisted Drug Delivery," Frontiers in Pharmacology 6:286, Frontiers Media, Switzerland (Dec. 2015).
Third Party Observation in International Application No. PCT/IB2017/057588, filed Dec. 1, 2017, Takeda Pharmaceutical Company Limited, Date of Submission: Mar. 29, 2019, 2 pages.
Wilson, D. R., et al., "Biodegradable STING agonist nanoparticles for enhanced cancer immunotherapy," Nanomedicine 14(2):237-46, Elsevier, Netherlands (Feb. 2018).
Yang, J., et al., "Preclinical characterization of GSK532, a novel STING agonist with potent anti-tumor activity," Cancer Research 78(13): Abstract 5554, Proceedings of AACR Annual Meeting, Apr. 14-18, American Association for Cancer Research, United States (Jul. 2018).
Seela, F., et al., "7-Halogenated 7-deazapurine 2'-C-methylribonucleosides," Collect Czech Chem Commun 76(12):1413-1431, Institute of Organic Chemistry and Biochemistry, Czechia (Nov. 2011).
Miles, D. L., et al., "Interferon induction: a conformational hypothesis," Proc Natl Acad Sci USA 76(3):1018-1021, National Academy of Sciences, United States (Mar. 1979).
GenCore—Sequence search result, 20220705_ 112334_us-17-065-242-1, pp. 1-22 (Jul. 2022).
GenCore—Sequence search result, 20220705_ 112334_us-17-065-242-2, pp. 1-18 (Jul. 2022).

\* cited by examiner

METHODS OF MAKING A CYCLIC DINUCLEOTIDE

REFERENCE TO SEQUENCE LISTING SUBMITTED ELECTRONICALLY

The content of the electronically submitted sequence listing (Name: 3817_040005_SeqListing_ST26.xml; Size: 15,846 bytes; Date of Creation: Sep. 27, 2023) submitted in this application is incorporated herein by reference in its entirety.

TECHNICAL FIELD

The present disclosure provides a cyclic dinucleotide having a STING (stimulator of interferon genes) agonistic activity, which may be useful as an agent for the prophylaxis or treatment of cancer and other diseases.

BACKGROUND OF THE INVENTION

STING is a receptor recognizing nucleic acid different from TLR (toll-like receptor). Examples of the natural ligand to be recognized include bacteria/protozoa-derived cyclic dinucleotides (CDNs), 2',3'-cGAMP synthesized by the upstream cGAS (cyclic GMP-AMP synthase), and the like (*Trends in Immunology* 35:88-93 (2014)). It is reported that 2',3'-cGAMP, which is one of natural ligands, is decomposed by ENPP1 (ecto-nucleotide-pyrophosphatase/phosphodiesterase), which is one of pyrophosphatases/phosphodiesterases, and that the other CDNs are decomposed by phosphodiesterase (*Nat Chem Biol* 10:1043-1048 (2014); *Cell Res* 25:539-550 (2015); *Biochemistry* 55:837-849 (2016)). STING is activated by these natural ligands, and induces the phosphorylation of TBK1 (TANK binding kinase 1) in the downstream, and activates IRF3 (Interferon regulatory factor 3) signal and NFkB signal in the further downstream, and thereby type-I interferon (IFN) response is induced (*Trends in Immunology* 35:88-93 (2014)). The importance of STING signal on cancer are indicated by a test using a knockout mouse. It is reported that in tumor-allografted mice using knockout mice for STING and its downstream signal, IRF3, the cancer cells grow by suppression of cancer immune system, compared with in wild-type mouse (*Immunity* 41: 830-842 (2014)). In addition, it is also reported that the cancer cell growth in a tumor-allografted mouse is suppressed by radiation therapy, but in knockout mice for STING and IFNAR1 (interferon (alpha and beta) receptor 1, receptor of type-I IFN produced by the downstream signal), the effect by the radiation therapy is reduced (*Immunity* 41:843-852 (2014)). For those reasons, it is considered that STING plays an important role on suppression of cancer cell growth, and the activation of the immune signal, which is induced by the activation of STING, leads to anticancer activity. Therefore, STING agonist may be used as an anticancer agent targeting cancer immunity. In addition, the activation of STING is considered to plays an important role on immune effect of vaccine, since the activation activates natural immunity (*Ther Adv Vaccines* 1:131-143 (2013)). Therefore, STING agonist may be used as an adjuvant for various vaccines.

The following cyclicdinucleotides are known.

Patent Document 1 (WO 2014/093936) discloses a compound represented by the following formula:

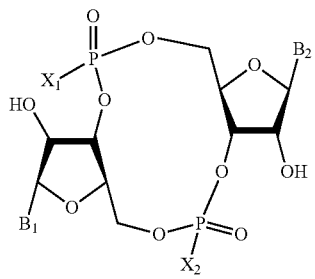

wherein each symbol is as defined in Patent Document 1, which according to Patent Document 1 is a STING-dependent TBK1 activator, and is useful for the treatment of cancer (particularly solid cancer) and the like, and also useful as an adjuvant.

Patent Document 2 (WO 2014/189805) discloses a compound represented by the following formula:

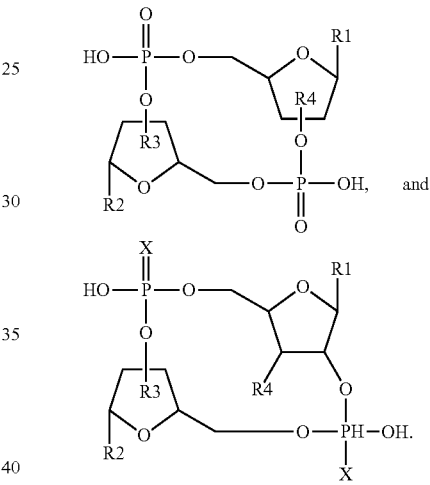

wherein each symbol is as defined in Patent Document 2, which according to Patent Document 2 is an immune stimulator via STING, and is useful for the treatment of cancer and the like.

Patent Document 3 (WO 2015/077354) and Non-Patent Document 8 (Cell reports 11, 1018-1030 (2015)) disclose a compound represented by the following formula:

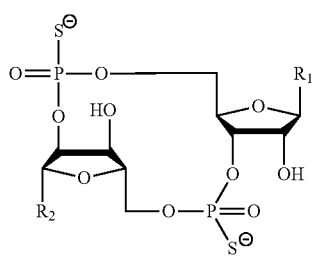

wherein each symbol is as defined in Patent Document 3, which according to Patent Document 3 is a STING agonist, and is useful for the treatment of cancer and the like.

Patent Document 4 (WO 2013/185052) and Non-Patent Document 9 (*Sci. Transl. Med.* 283, 283ra52 (2015)) disclose c-di-AMP, c-di-GMP, c-di-IMP, c-AMP-GMP, c-AMP-IMP and c-GMP-IMP, which according to Patent Document 4 are STING-dependent TBK1 activators.

Patent Document 5 (WO 2014/189806) discloses a compound represented by the following formula:

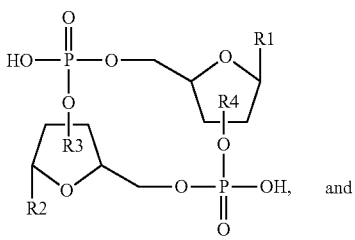

and

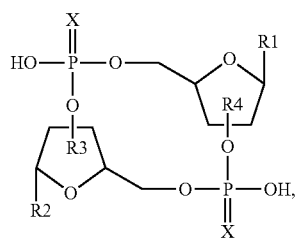

wherein each symbol is as defined in Patent Document 5, which according to Patent Document 5 inhibits STING-dependent signal transduction, and is useful for the treatment of autoimmune disease and the like.

Patent Document 6 (WO 2015/185565) discloses a compound represented by the following formula:

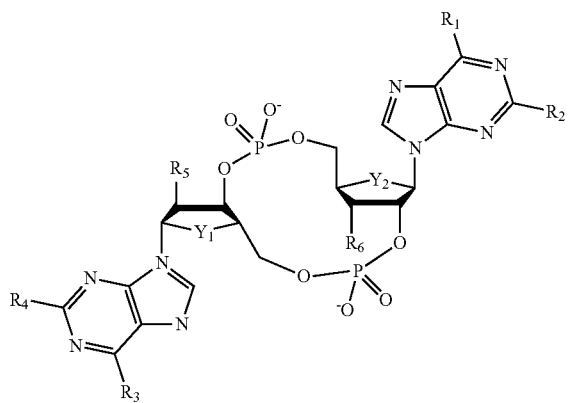

wherein each symbol is as defined in Patent Document 6, which according to Patent Document 6 is a STING modulator, and is useful for the treatment of inflammation, allergic autoimmune disease, cancer and the like, and also useful as a vaccine adjuvant.

Patent Document 7 (WO 2014/179760) discloses a compound represented by the following formula:

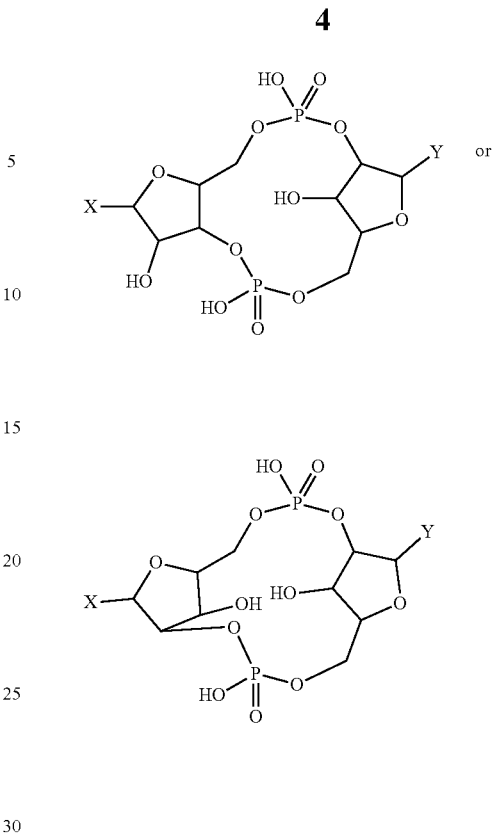

wherein each symbol is as defined in Patent Document 7, which according to Patent Document 7 can increase Type I interferon production, and is useful for the treatment of cancer, autoimmune disease, allergic reaction and the like, and also useful as an adjuvant.

Patent Document 8 (WO 2014/179335) and Non-Patent Document 10 (Mol. Cell 154, 748-762 (2013)) disclose a compound represented by the following formula:

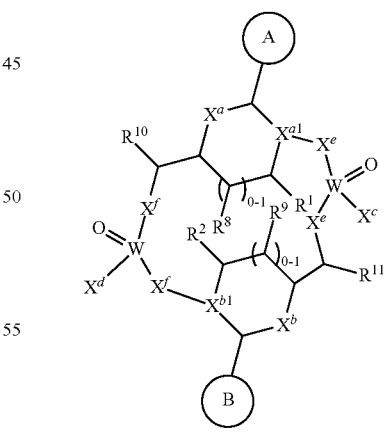

wherein each symbol is as defined in Patent Document 8, which according to Patent Document 8 can increases Type I interferon production, and is useful for the treatment of diseases characterized by inflammation, autoimmune disease, Sjögren's syndrome and the like.

Patent Document 9 (WO 2015/017652) discloses a compound represented by the following formula.

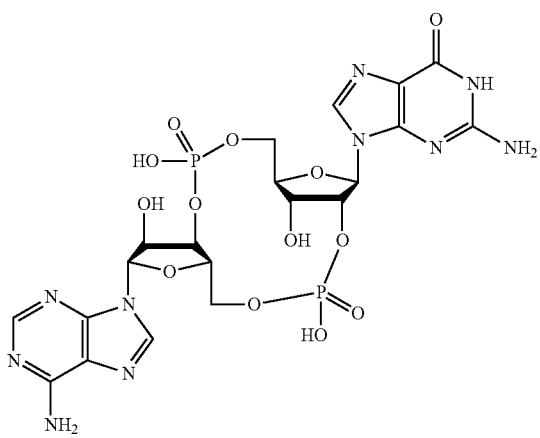

which according to Patent Document 9 is a STING modulator, and is useful for the treatment of cancer, autoimmune disease and the like, and also useful as a vaccine.

Patent Document 10 (WO 2016/096577) discloses a compound represented by the following formula.

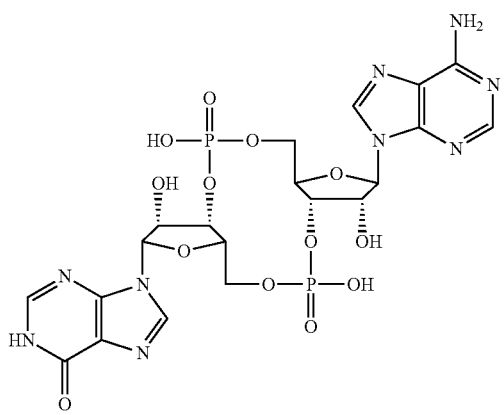 [SMILES: Nc1ncnc2c1ncn2C1OC2COP(=O)(O)O[C@@H]3C(COP(=O)(O)O[C@H]2[C@H]1O)OC(n1cnc2c(=O)[nH]cnc21)[C@@H]3O]

which according to Patent Document 10 is a STING agonist, and is useful for the treatment of cancer (particularly solid pancreatic cancer) and the like.

Patent Document 11 (WO 2011/003025) discloses a compound represented by the following formula.

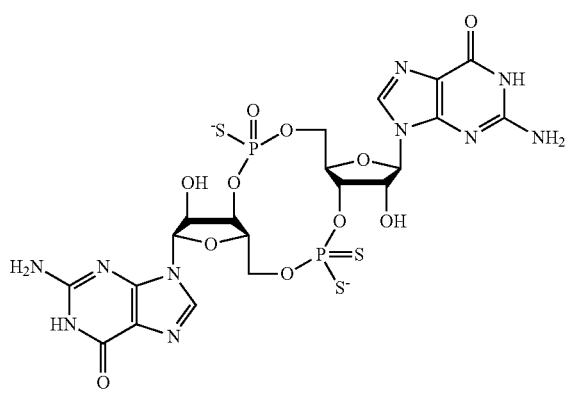

Which according to Patent Document 11 is a STING agonist.

Patent Document 12 (WO 2016/096174) discloses a compound represented by the following formula.

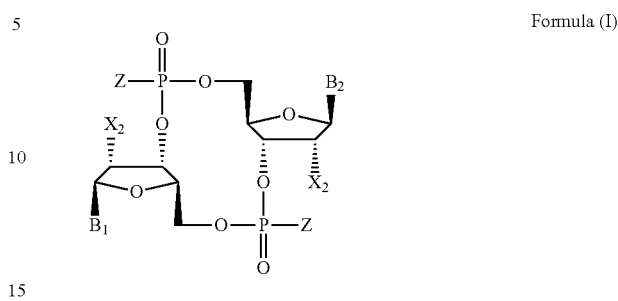

Formula (I)

which according to Patent Document 12 is a STING agonist.

Patent Document 13 (WO 2016/120305) discloses a compound represented by the following formula.

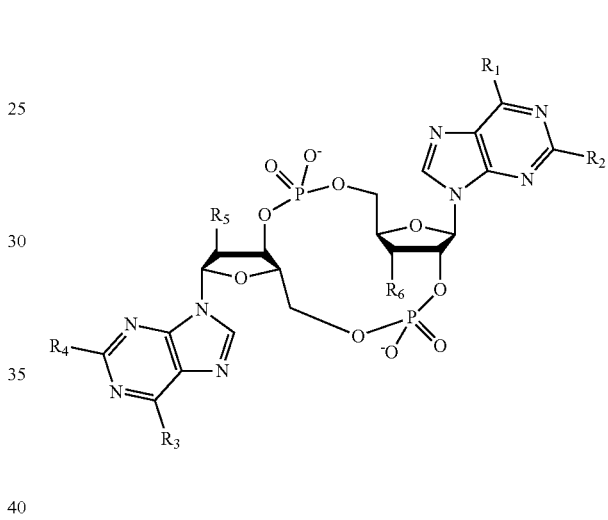

which according to Patent Document 13 is a STING agonist.

Patent Document 14 (WO 2016/145102) discloses a compound represented by the following formula:

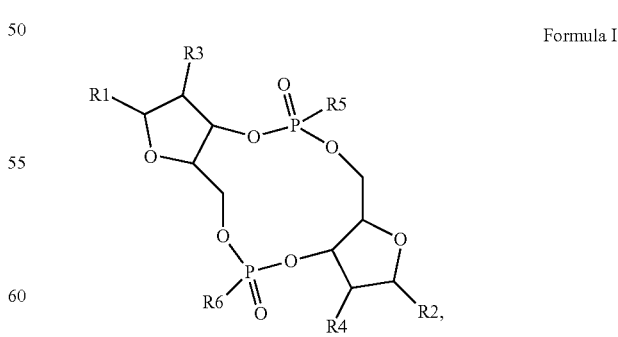

Formula I wherein each symbol is as defined in Patent Document 14, which according to Patent Document 14 is a STING agonist.

Patent Document 15 (WO 2017/027646) discloses a compound represented by the following formula:

(I″)

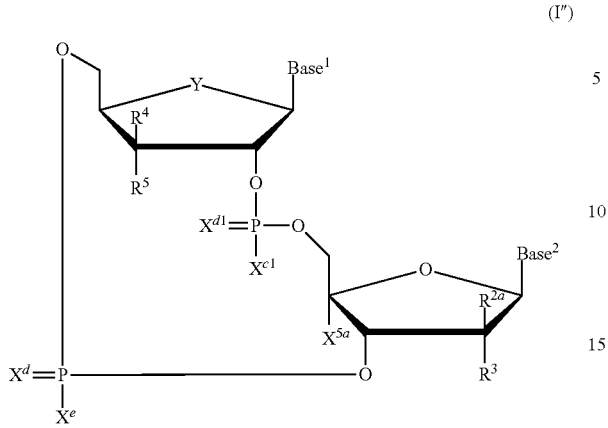

wherein each symbol is as defined in Patent Document 15, which according to Patent Document 15 is a STING agonist.

Patent Document 16 WO 2017/075477) discloses a compound represented by the following formula:

Formula I

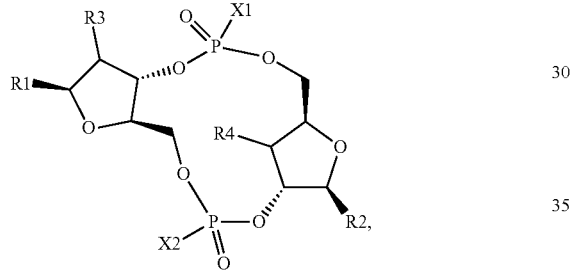

wherein each symbol is as defined in Patent Document 16, which according to Patent Document 16 is a STING agonist.

Patent Document 17 (WO 2017/027645) discloses a compound represented by the following formula:

(II)

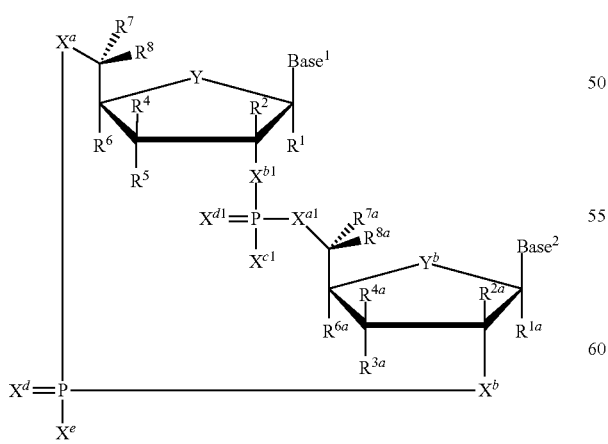

wherein each symbol is as defined in Patent Document 17, which according to Patent Document 17 is a STING agonist.

BRIEF SUMMARY OF THE INVENTION

In one aspect, the disclosure provides a compound represented by the formula (I):

(I)

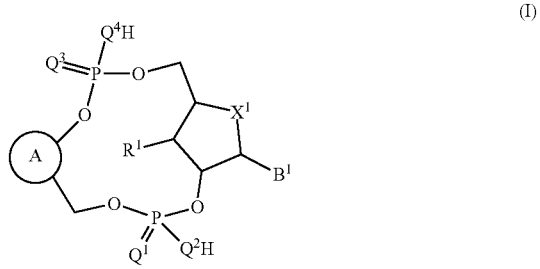

wherein:

the partial structure represented by formula (A-1):

(A-1)

is a partial structure represented by formula (IIA):

(IIA)

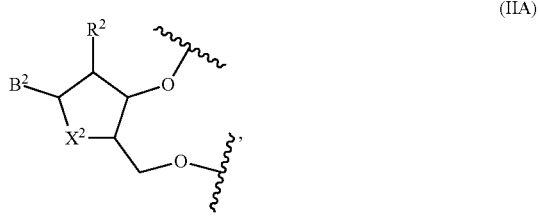

or a partial structure represented by formula (IIB):

(IIB)

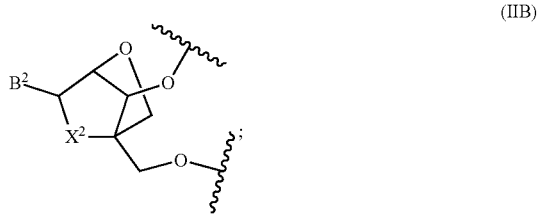

$R^1$ and $R^2$ are each independently a hydroxy group or a halogen atom;

$B^1$ is a group represented by

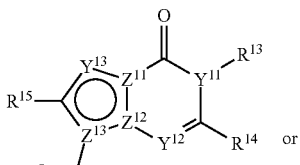

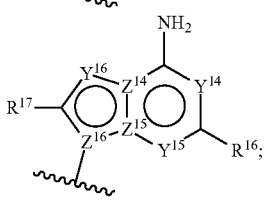

$R^{13}$, $R^{14}$, $R^{15}$, $R^{16}$ and $R^{17}$ are each independently a hydrogen atom or a substituent;

$Y^{11}$, $Y^{12}$, $Y^{13}$, $Y^{14}$, $Y^{15}$ and $Y^{16}$ are each independently N or $CR^{1a}$;

$Z^{11}$, $Z^{12}$, $Z^{13}$, $Z^{14}$, $Z^{15}$ and $Z^{16}$ are each independently N or C;

$R^{1a}$ is a hydrogen atom or a substituent;

$B^2$ is a group represented by

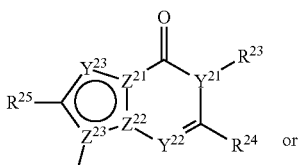

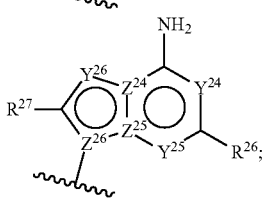

$R^{23}$, $R^{24}$, $R^{25}$, $R^{26}$ and $R^{27}$ are each independently a hydrogen atom or a substituent, $Y^{21}$, $Y^{22}$, $Y^{23}$, $Y^{24}$, $Y^{25}$ and $Y^{26}$ are each independently N or $CR^{2a}$;

$Z^{21}$, $Z^{22}$, $Z^{23}$, $Z^{24}$, $Z^{25}$ and $Z^{26}$ are each independently N or C;

$R^{2a}$ is a hydrogen atom or a substituent;

provided that i) at least one of $Y^{11}$, $Y^{12}$, $Y^{13}$, $Y^{14}$, $Y^{15}$ and $Y^{16}$ is $CR^{1a}$, ii) at least one of $Y^{21}$, $Y^{22}$, $Y^{23}$, $Y^{24}$, $Y^{25}$ and $Y^{26}$ is $CR^{2a}$, or iii) at least one of $Z^{13}$, $Z^{16}$, $Z^{23}$ and $Z^{26}$ is C; $X^1$ and $X^2$ are each independently an oxygen atom or a sulfur atom; and $Q^1$, $Q^2$, $Q^3$ and $Q^4$ are each independently an oxygen atom or a sulfur atom, or a salt thereof (hereinafter sometimes to be referred to as compound (I)).

In another aspect, the disclosure provides a compound represented by the formula (I), wherein at least one of $B^1$ and $B^2$ is

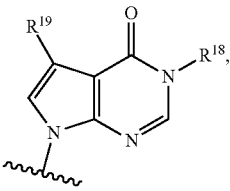

$R^{18}$ is hydrogen or C1-6 alkyl; and
$R^{19}$ is a halogen atom, or a salt thereof.
In another aspect, $X^1$ and $X^2$ are O.
In another aspect, the disclosure provides a compound represented by the formula (I), wherein
$B^1$ is

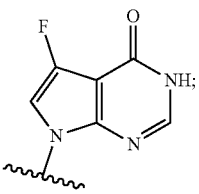 [SMILES: *n1cc(F)c2c(=O)[nH]cnc21]

and
$B^2$ is

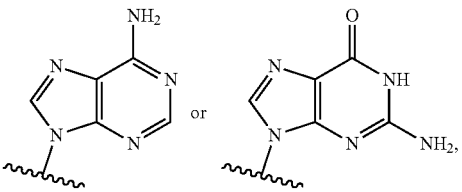 [SMILES: *n1cnc2c(N)ncnc21 ; *n1cnc2c(=O)[nH]c(N)nc21]

or a salt thereof. In another aspect, $X^1$ and $X^2$ are O.

In another aspect, the disclosure provides 7-((5R,7R,8R,12aR,14R,15R,15aR,16R)-14-(6-amino-9H-purin-9-yl)-15-fluoro-2,10,16-trihydroxy-2,10-dioxidooctahydro-12H-5,8-methanofuro[3,2-1][1,3,6,9,11,2,10]pentaoxadiphosphacyclotetradecin-7-yl)-5-fluoro-3,7-dihydro-4H-pyrrolo[2,3-d]pyrimidin-4-one, or a salt thereof.

In another aspect, the disclosure provides 7-((2R,5R,7R,8R,12aR,14R,15R,15aR,16R)-14-(6-amino-9H-purin-9-yl)-15-fluoro-10,16-dihydroxy-2,10-dioxido-2-sulfanyloctahydro-12H-5,8-methanofuro[3,2-1][1,3,6,9,11,2,10]pentaoxadiphosphacyclotetradecin-7-yl)-5-fluoro-3,7-dihydro-4H-pyrrolo[2,3-d]pyrimidin-4-one, or a salt thereof.

In another aspect, the disclosure provides 2-amino-9-((5R,7R,8R,12aR,14S,15S,15aS,16R)-14-(4-aminopyrazolo[1,5-a][1,3,5]triazin-8-yl)-2,10,15,16-tetrahydroxy-2,10-dioxidooctahydro-12H-5,8-methanofuro[3,2-1][1,3,6,9,11,2,10]pentaoxadiphosphacyclotetradecin-7-yl)-1,9-dihydro-6H-purin-6-one, or a salt thereof.

In another aspect, the disclosure provides 7-((2R,5R,7R,8R,10R,12aR,14R,15R,15aR,16R)-14-(6-amino-9H-purin-9-yl)-15-fluoro-16-hydroxy-2,10-dioxido-2,10-disulfanyloctahydro-12H-5,8-methanofuro[3,2-1][1,3,6,9,11,2,10]pentaoxadiphosphacyclotetradecin-7-yl)-5-fluoro-3,7-dihydro-4H-pyrrolo[2,3-d]pyrimidin-4-one, or a salt thereof.

In another aspect, the disclosure provides a compound having Formula (XIV):

(CD-L)<sub>n</sub>-A  (XIV)

or a pharmaceutically acceptable salt thereof, wherein:
CD is a group represented by any one of Formula (XX)-(XXIX), see below;
L is a linker;
A is an antibody, antibody fragment, or antigen-binding fragment;
n is 1-10.

In another aspect, the disclosure provides a compound having Formula (XIV), or a pharmaceutically acceptable salt thereof, wherein A is an antibody.

In another aspect, the disclosure provides a compound having Formula (XIV), or a pharmaceutically acceptable salt thereof, wherein A is an antigen-binding fragment.

In another aspect, the disclosure provides medicament comprising the compound or salt of formula (I). In another embodiment, the medicament is a STING agonist. In another embodiment, the medicament is an agent for the prophylaxis or treatment of cancer.

In another aspect, the disclosure provides a method of activating a STING in a mammal, which comprises administering an effective amount of a compound having formula (I), or a salt thereof, to the mammal.

In another aspect, the disclosure provides a method for the prophylaxis or treatment of cancer in a mammal, which comprises administering an effective amount of the compound having formula (I), or a salt thereof, to the mammal.

In another aspect, the disclosure provides a compound having formula (I), or a salt thereof, for use in prevention or treatment of cancer.

In another aspect, the disclosure provides the use of the compound having formula (I), or a salt thereof, for the production of an agent for the prophylaxis or treatment of cancer.

DETAILED DESCRIPTION OF THE INVENTION

Figure 1:
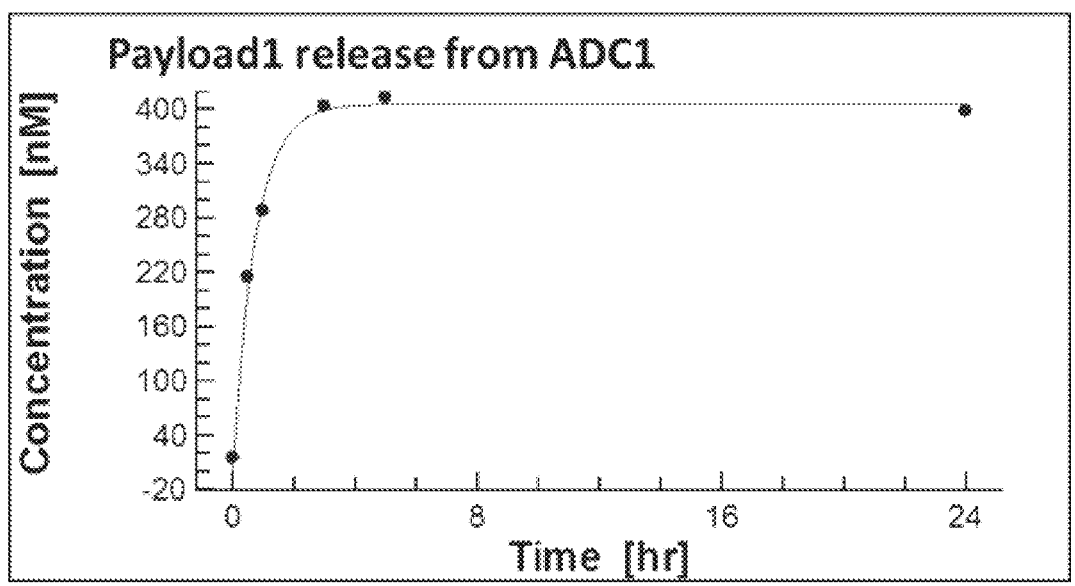
FIG. 1 is a line graph showing Payload 1 release from ADC1.

The present disclosure is explained in detail below.

The definition of each substituent used in the present specification is described in detail in the following. Unless otherwise specified, each substituent has the following definition.

In the present specification, examples of the "halogen atom" include fluorine, chlorine, bromine and iodine.

In the present specification, examples of the "$C_{1-6}$ alkyl group" include methyl, ethyl, propyl, isopropyl, butyl, isobutyl, sec-butyl, tert-butyl, pentyl, isopentyl, neopentyl, 1-ethylpropyl, hexyl, isohexyl, 1,1-dimethylbutyl, 2,2-dimethylbutyl, 3,3-dimethylbutyl and 2-ethylbutyl.

In the present specification, examples of the "optionally halogenated $C_{1-6}$ alkyl group" include a $C_{1-6}$ alkyl group optionally having 1 to 7, preferably 1 to 5, halogen atoms. Specific examples thereof include methyl, chloromethyl, difluoromethyl, trichloromethyl, trifluoromethyl, ethyl, 2-bromoethyl, 2,2,2-trifluoroethyl, tetrafluoroethyl, pentafluoroethyl, propyl, 2,2-difluoropropyl, 3,3,3-trifluoropropyl, isopropyl, butyl, 4,4,4-trifluorobutyl, isobutyl, sec-butyl, tert-butyl, pentyl, isopentyl, neopentyl, 5,5,5-trifluoropentyl, hexyl and 6,6,6-trifluorohexyl.

In the present specification, examples of the "$C_{2-6}$ alkenyl group" include ethenyl, 1-propenyl, 2-propenyl, 2-methyl-1-propenyl, 1-butenyl, 2-butenyl, 3-butenyl, 3-methyl-2-butenyl, 1-pentenyl, 2-pentenyl, 3-pentenyl, 4-pentenyl, 4-methyl-3-pentenyl, 1-hexenyl, 3-hexenyl and 5-hexenyl.

In the present specification, examples of the "$C_{2-6}$ alkenyl group" include ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl and 4-methyl-2-pentynyl.

In the present specification, examples of the "$C_{3-10}$ cycloalkyl group" include cyclopropyl, cyclobutyl, cyclopentyl, cyclohexyl, cycloheptyl, cyclobutyl, bicyclo[2.2.1]heptyl, bicyclo[2.2.2]octyl, bicyclo[3.2.1]octyl and adamantyl.

In the present specification, examples of the "optionally halogenated $C_{3-10}$ cycloalkyl group" include a $C_{3-10}$ cycloalkyl group optionally having 1 to 7, preferably 1 to 5, halogen atoms. Specific examples thereof include cyclopropyl, 2,2-difluorocyclopropyl, 2,3-difluorocyclopropyl, cyclobutyl, difluorocyclobutyl, cyclopentyl, cyclohexyl, cycloheptyl and cyclooctyl.

In the present specification, examples of the "$C_{3-10}$ cycloalkenyl group" include cyclopropenyl, cyclobutenyl, cyclopentenyl, cyclohexenyl, cycloheptenyl and cyclooctenyl.

In the present specification, examples of the "$C_{6-14}$ aryl group" include phenyl, 1-naphthyl, 2-naphthyl, 1-anthryl, 2-anthryl and 9-anthryl.

In the present specification, examples of the "$C_{7-16}$ aralkyl group" include benzyl, phenethyl, naphthylmethyl and phenylpropyl.

In the present specification, examples of the "$C_{1-6}$ alkoxy group" include methoxy, ethoxy, propoxy, isopropoxy, butoxy, isobutoxy, sec-butoxy, tert-butoxy, pentyloxy and hexyloxy.

In the present specification, examples of the "optionally halogenated $C_{1-6}$ alkoxy group" include a $C_{1-6}$ alkoxy group optionally having 1 to 7, preferably 1 to 5, halogen atoms. Specific examples thereof include methoxy, difluoromethoxy, trifluoromethoxy, ethoxy, 2,2,2-trifluoroethoxy, propoxy, isopropoxy, butoxy, 4,4,4-trifluorobutoxy, isobutoxy, sec-butoxy, pentyloxy and hexyloxy.

In the present specification, examples of the "$C_{3-10}$ cycloalkyloxy group" include cyclopropyloxy, cyclobutyloxy, cyclopentyloxy, cyclohexyloxy, cycloheptyloxy and cyclooctyloxy.

In the present specification, examples of the "$C_{1-6}$ alkylthio group" include methylthio, ethylthio, propylthio, isopropylthio, butylthio, sec-butylthio, tert-butylthio, pentylthio and hexylthio.

In the present specification, examples of the "optionally halogenated $C_{1-6}$ alkylthio group" include a $C_{1-6}$ alkylthio group optionally having 1 to 7, preferably 1 to 5, halogen atoms. Specific examples thereof include methylthio, difluoromethylthio, tilfluoromethylthio, ethylthio, propylthio, isopropylthio, butylthio, 4,4,4-trifluorobutylthio, pentylthio and hexylthio.

In the present specification, examples of the "$C_{1-6}$ alkyl-carbonyl group" include acetyl, propanoyl, butanoyl, 2-methylpropanoyl, pentanoyl, 3-methylbutanoyl, 2-methylbutanoyl, 2,2-dimethylpropanoyl, hexanoyl and heptanoyl.

In the present specification, examples of the "optionally halogenated $C_{1-6}$ alkyl-carbonyl group" include a $C_{1-6}$ alkyl-carbonyl group optionally having 1 to 7, preferably 1 to 5, halogen atoms. Specific examples thereof include acetyl, chloroacetyl, trifluoroacetyl, trichloroacetyl, propanoyl, butanoyl, pentanoyl and hexanoyl.

In the present specification, examples of the "$C_{1-6}$ alkoxy-carbonyl group" include methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, pentyloxycarbonyl and hexyloxycarbonyl.

In the present specification, examples of the "$C_{6-14}$ aryl-carbonyl group" include benzoyl, 1-naphthoyl and 2-naphthoyl.

In the present specification, examples of the "$C_{7-16}$ aralkyl-carbonyl group" include phenylacetyl and phenylpropionyl.

In the present specification, examples of the "5- to 14-membered aromatic heterocyclylcarbonyl group" include nicotinoyl, isonicotinoyl, thenoyl and furoyl.

In the present specification, examples of the "3- to 14-membered non-aromatic heterocyclylcarbonyl group" include morpholinylcarbonyl, piperidinylcarbonyl and pyrrolidinylcarbonyl.

In the present specification, examples of the "mono- or di-$C_{1-6}$ alkyl-carbamoyl group" include methylcarbamoyl, ethylcarbamoyl, dimethylcarbamoyl, diethylcarbamoyl and N-ethyl-N-methylcarbamoyl.

In the present specification, examples of the "mono- or di-$C_{7-16}$ aralkyl-carbamoyl group" include benzylcarbamoyl and phenethylcarbamoyl.

In the present specification, examples of the "$C_{1-6}$ alkylsulfonyl group" include methylsulfonyl, ethylsulfonyl, propylsulfonyl, isopropylsulfonyl, butylsulfonyl, sec-butylsulfonyl and tert-butylsulfonyl.

In the present specification, examples of the "optionally halogenated $C_{1-6}$ alkylsulfonyl group" include a $C_{1-6}$ alkylsulfonyl group optionally having 1 to 7, preferably 1 to 5, halogen atoms. Specific examples thereof include methylsulfonyl, difluoromethylsulfonyl, trifluoromethylsulfonyl, ethylsulfonyl, propylsulfonyl, isopropylsulfonyl, butylsulfonyl, 4,4,4-trifluorobutylsulfonyl, pentylsulfonyl and hexylsulfonyl.

In the present specification, examples of the "$C_{6-14}$ arylsulfonyl group" include phenylsulfonyl, 1-naphthylsulfonyl and 2-naphthylsulfonyl.

In the present specification, examples of the "substituent" include a halogen atom, a cyano group, a nitro group, an optionally substituted hydrocarbon group, an optionally substituted heterocyclic group, an acyl group, an optionally substituted amino group, an optionally substituted carbamoyl group, an optionally substituted thiocarbamoyl group, an optionally substituted sulfamoyl group, an optionally substituted hydroxy group, an optionally substituted sulfanyl (SH) group and an optionally substituted silyl group.

In the present specification, examples of the "hydrocarbon group" (including "hydrocarbon group" of "optionally substituted hydrocarbon group") include a $C_{1-6}$ alkyl group, a $C_{2-6}$ alkenyl group, a $C_{2-6}$ alkynyl group, a $C_{3-10}$ cycloalkyl group, a $C_{3-10}$ cycloalkenyl group, a $C_{6-14}$ aryl group and a $C_{7-16}$ aralkyl group.

In the present specification, examples of the "optionally substituted hydrocarbon group" include a hydrocarbon group optionally having substituent(s) selected from the following Substituent group A.

"Substituent Group A:"
(1) a halogen atom,
(2) a nitro group,
(3) a cyano group,
(4) an oxo group,
(5) a hydroxy group,
(6) an optionally halogenated $C_{1-6}$ alkoxy group,
(7) a $C_{6-14}$ aryloxy group (e.g., phenoxy, naphthoxy),
(8) a $C_{7-16}$ aralkyloxy group (e.g., benzyloxy),
(9) a 5- to 14-membered aromatic heterocyclyloxy group (e.g., pyridyloxy),
(10) a 3- to 14-membered non-aromatic heterocyclyloxy group (e.g., morpholinyloxy, piperidinyloxy),
(11) a $C_{1-6}$ alkyl-carbonyloxy group (e.g., acetoxy, propanoyloxy),
(12) a $C_{6-14}$ aryl-carbonyloxy group (e.g., benzoyloxy, 1-naphthoyloxy, 2-naphthoyloxy),
(13) a $C_{1-6}$ alkoxy-carbonyloxy group (e.g., methoxycarbonyloxy, ethoxycarbonyloxy, propoxycarbonyloxy, butoxycarbonyloxy),
(14) a mono- or di-$C_{1-6}$ alkyl-carbamoyloxy group (e.g., methylcarbamoyloxy, ethylcarbamoyloxy, dimethylcarbamoyloxy, diethylcarbamoyloxy),
(15) a $C_{6-14}$ aryl-carbamoyloxy group (e.g., phenylcarbamoyloxy, naphthyl carbamoyloxy),
(16) a 5- to 14-membered aromatic heterocyclylcarbonyloxy group (e.g., nicotinoyloxy),
(17) a 3- to 14-membered non-aromatic heterocyclylcarbonyloxy group (e.g., morpholinylcarbonyloxy, piperidinylcarbonyloxy),
(18) an optionally halogenated $C_{1-6}$ alkylsulfonyloxy group (e.g., methylsulfonyloxy, trifluoromethylsulfonyloxy),
(19) a $C_{6-14}$ arylsulfonyloxy group optionally substituted by a $C_{1-6}$ alkyl group (e.g., phenylsulfonyloxy, toluenesulfonyloxy),
(20) an optionally halogenated $C_{1-6}$ alkylthio group,

(21) a 5- to 14-membered aromatic heterocyclic group,
(22) a 3- to 14-membered non-aromatic heterocyclic group,
(23) a formyl group,
(24) a carboxy group,
(25) an optionally halogenated $C_{1-6}$ alkyl-carbonyl group,
(26) a $C_{6-14}$ aryl-carbonyl group,
(27) a 5- to 14-membered aromatic heterocyclylcarbonyl group,
(28) a 3- to 14-membered non-aromatic heterocyclylcarbonyl group,
(29) a $C_{1-6}$ alkoxy-carbonyl group,
(30) a $C_{6-14}$ aryloxy-carbonyl group (e.g., phenyloxycarbonyl, 1-naphthyloxycarbonyl, 2-naphthyloxycarbonyl),
(31) a $C_{7-16}$ aralkyloxy-carbonyl group (e.g., benzyloxycarbonyl, phenethyloxycarbonyl),
(32) a carbamoyl group,
(33) a thiocarbamoyl group,
(34) a mono- or di-$C_{1-6}$ alkyl-carbamoyl group,
(35) a $C_{6-14}$ aryl-carbamoyl group (e.g., phenylcarbamoyl),
(36) a 5- to 14-membered aromatic heterocyclylcarbamoyl group (e.g., pyridylcarbamoyl, thienylcarbamoyl),
(37) a 3- to 14-membered non-aromatic heterocyclylcarbamoyl group (e.g., morpholinylcarbamoyl, piperidinylcarbamoyl),
(38) an optionally halogenated $C_{1-6}$ alkylsulfonyl group,
(39) a $C_{6-14}$ arylsulfonyl group,
(40) a 5- to 14-membered aromatic heterocyclylsulfonyl group (e.g., pyridylsulfonyl, thienylsulfonyl),
(41) an optionally halogenated $C_{1-6}$ alkylsulfinyl group,
(42) a $C_{6-14}$ arylsulfinyl group (e.g., phenylsulfinyl, 1-naphthylsulfinyl, 2-naphthylsulfinyl),
(43) a 5- to 14-membered aromatic heterocyclylsulfinyl group (e.g., pyridylsulfinyl, thienylsulfinyl),
(44) an amino group,
(45) a mono- or di-$C_{1-6}$ alkylamino group (e.g., methylamino, ethylamino, propylamino, isopropylamino, butylamino, dimethylamino, diethylamino, dipropylamino, dibutylamino, N-ethyl-N-methylamino),
(46) a mono- or di-$C_{6-14}$ arylamino group (e.g., phenylamino),
(47) a 5- to 14-membered aromatic heterocyclylamino group (e.g., pyridylamino),
(48) a $C_{7-16}$ aralkylamino group (e.g., benzylamino),
(49) a formylamino group,
(50) a $C_{1-6}$ alkyl-carbonylamino group (e.g., acetylamino, propanoylamino, butanoylamino),
(51) a ($C_{1-6}$ alkyl)($C_{1-6}$ alkyl-carbonyl) amino group (e.g., N-acetyl-N-methylamino),
(52) a $C_{6-14}$ aryl-carbonylamino group (e.g., phenylcarbonylamino, naphthylcarbonylamino),
(53) a $C_{1-6}$ alkoxy-carbonylamino group (e.g., methoxycarbonylamino, ethoxycarbonylamino, propoxycarbonylamino, butoxycarbonylamino, tert-butoxycarbonylamino),
(54) a $C_{7-16}$ aralkyloxy-carbonylamino group (e.g., benzyloxycarbonylamino),
(55) a $C_{1-6}$ alkylsulfonylamino group (e.g., methylsulfonylamino, ethylsulfonylamino),
(56) a $C_{6-14}$ arylsulfonylamino group optionally substituted by a $C_{1-6}$ alkyl group (e.g., phenylsulfonylamino, toluenesulfonylamino),
(57) an optionally halogenated $C_{1-6}$ alkyl group,
(58) a $C_{2-6}$ alkenyl group,
(59) a $C_{2-6}$ alkynyl group,
(60) a $C_{3-10}$ cycloalkyl group,
(61) a $C_{3-10}$ cycloalkenyl group, and
(62) a $C_{6-14}$ aryl group.

The number of the above-mentioned substituents in the "optionally substituted hydrocarbon group" is, for example, 1 to 5, preferably 1 to 3. When the number of the substituents is two or more, the respective substituents may be the same or different.

In the present specification, examples of the "heterocyclic group" (including "heterocyclic group" of "optionally substituted heterocyclic group") include (i) an aromatic heterocyclic group, (ii) a non-aromatic heterocyclic group and (iii) a 7- to 10-membered bridged heterocyclic group, each containing, as a ring-constituting atom besides carbon atom, 1 to 4 heteroatoms selected from a nitrogen atom, a sulfur atom and an oxygen atom.

In the present specification, examples of the "aromatic heterocyclic group" (including "5- to 14-membered aromatic heterocyclic group") include a 5- to 14-membered (preferably 5- to 10-membered) aromatic heterocyclic group containing, as a ring-constituting atom besides carbon atom, 1 to 4 heteroatoms selected from a nitrogen atom, a sulfur atom and an oxygen atom.

Preferable examples of the "aromatic heterocyclic group" include 5- or 6-membered monocyclic aromatic heterocyclic groups such as thienyl, furyl, pyrrolyl, imidazolyl, pyrazolyl, thiazolyl, isothiazolyl, oxazolyl, isoxazolyl, pyridyl, pyrazinyl, pyrimidinyl, pyridazinyl, 1,2,4-oxadiazolyl, 1,3,4-oxadiazolyl, 1,2,4-thiadiazolyl, 1,3,4-thiadiazolyl, triazolyl, tetrazolyl, triazinyl and the like; and 8- to 14-membered fused polycyclic (preferably bi or tricyclic) aromatic heterocyclic groups such as benzothiophenyl, benzofuranyl, benzimidazolyl, benzoxazolyl, benzisoxazolyl, benzothiazolyl, benzisothiazolyl, benzotriazolyl, imidazopyridinyl, thienopyridinyl, furopyridinyl, pyrrolopyridinyl, pyrazolopyridinyl, oxazolopyridinyl, thiazolopyridinyl, imidazopyrazinyl, imidazopyrimidinyl, thienopyrimidinyl, furopyrimidinyl, pyrrolopyrimidinyl, pyrazolopyrimidinyl, oxazolopyrimidinyl, thiazolopyrimidinyl, pyrazolotriazinyl, naphtho[2,3-b]thienyl, phenoxathiinyl, indolyl, isoindolyl, 1H-indazolyl, purinyl, isoquinolyl, quinolyl, phthalazinyl, naphthyridinyl, quinoxalinyl, quinazolinyl, cinnolinyl, carbazolyl, β-carbolinyl, phenanthridinyl, acridinyl, phenazinyl, phenothiazinyl, phenoxazinyl and the like.

In the present specification, examples of the "non-aromatic heterocyclic group" (including "3- to 14-membered non-aromatic heterocyclic group") include a 3- to 14-membered (preferably 4- to 10-membered) non-aromatic heterocyclic group containing, as a ring-constituting atom besides carbon atom, 1 to 4 heteroatoms selected from a nitrogen atom, a sulfur atom and an oxygen atom.

Preferable examples of the "non-aromatic heterocyclic group" include 3- to 8-membered monocyclic non-aromatic heterocyclic groups such as aziridinyl, oxiranyl, thieranyl, azetidinyl, oxetanyl, thietanyl, tetrahydrothienyl, tetrahydrofuranyl, pyrrolinyl, pyrrolidinyl, imidazolinyl, imidazolidinyl, oxazolinyl, oxazolidinyl, pyrazolinyl, pyrazolidinyl, thiazolinyl, thiazolidinyl, tetrahydroisothiazolyl, tetrahydrooxazolyl, tetrahydroisooxazolyl, piperidinyl, piperazinyl, tetrahydropyridinyl, dihydropyridinyl, dihydrothiopyranyl, tetrahydropyrimidinyl, tetrahydropyridazinyl, dihydropyranyl, tetrahydropyranyl, tetrahydrothiopyranyl, morpholinyl, thiomorpholinyl, azepanyl, diazepanyl, azepinyl, oxepanyl, azocanyl, diazocanyl and the like; and 9- to 14-membered fused polycyclic (preferably bi or tricyclic) non-aromatic heterocyclic groups such as dihydrobenzofuranyl, dihydrobenzimidazolyl, dihydrobenzoxazolyl, dihydrobenzothiazolyl, dihydrobenzisothiazolyl, dihydronaphtho[2,3-b]thienyl, tetrahydroisoquinolyl, tetrahydroquinolyl, 4H-quinolizinyl, indolinyl, isoindolinyl, tetrahydrothieno[2,3-c]pyridinyl, tetrahydrobenzazepinyl, tetrahydroquinoxalinyl, tetrahydrophenanthridinyl, hexahydrophenothiazinyl, hexahydrophenoxazinyl, tetrahydrophthalazinyl, tetrahydronaphthyridinyl, tetrahydroquinazolinyl, tetrahydrocinnolinyl, tetrahydrocarbazolyl, tetrahydro-β-carbolinyl, tetrahydroacrydinyl, tetrahydrophenazinyl, tetrahydrothioxanthenyl, octahydroisoquinolyl and the like.

In the present specification, preferable examples of the "7- to 10-membered bridged heterocyclic group" include quinuclidinyl and 7-azabicyclo[2.2.1]heptanyl.

In the present specification, examples of the "nitrogen-containing heterocyclic group" include a "heterocyclic group" containing at least one nitrogen atom as a ring-constituting atom.

In the present specification, examples of the "optionally substituted heterocyclic group" include a heterocyclic group optionally having substituent(s) selected from the above-mentioned "Substituent group A.

The number of the substituents in the "optionally substituted heterocyclic group" is, for example, 1 to 3. When the number of the substituents is two or more, the respective substituents may be the same or different.

In the present specification, examples of the "acyl group" include a formyl group, a carboxy group, a carbamoyl group, a thiocarbamoyl group, a sulfino group, a sulfo group, a sulfamoyl group and a phosphono group, each optionally having "1 or 2 substituents selected from a $C_{1-6}$ alkyl group, a $C_{2-6}$ alkenyl group, a $C_{3-10}$ cycloalkyl group, a $C_{3-10}$ cycloalkenyl group, a $C_{6-14}$ aryl group, a $C_{7-16}$ aralkyl group, a 5- to 14-membered aromatic heterocyclic group and a 3- to 14-membered non-aromatic heterocyclic group, each of which optionally has 1 to 3 substituents selected from a halogen atom, an optionally halogenated $C_{1-6}$ alkoxy group, a hydroxy group, a nitro group, a cyano group, an amino group and a carbamoyl group".

Examples of the "acyl group" also include a hydrocarbon-sulfonyl group, a heterocyclylsulfonyl group, a hydrocarbon-sulfinyl group and a heterocyclylsulfinyl group.

Here, the hydrocarbon-sulfonyl group means a hydrocarbon group-bonded sulfonyl group, the heterocyclylsulfonyl group means a heterocyclic group-bonded sulfonyl group, the hydrocarbon-sulfinyl group means a hydrocarbon group-bonded sulfinyl group and the heterocyclylsulfinyl group means a heterocyclic group-bonded sulfinyl group.

Preferable examples of the "acyl group" include a formyl group, a carboxy group, a $C_{1-6}$ alkyl-carbonyl group, a $C_{2-6}$ alkenyl-carbonyl group (e.g., crotonoyl), a $C_{3-10}$ cycloalkyl-carbonyl group (e.g., cyclobutanecarbonyl, cyclopentanecarbonyl, cyclohexanecarbonyl, cycloheptanecarbonyl), a $C_{3-10}$ cycloalkenyl-carbonyl group (e.g., 2-cyclohexenecarbonyl), a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a $C_{6-14}$ aryloxy-carbonyl group (e.g., phenyloxycarbonyl, naphthyloxycarbonyl), a $C_{7-16}$ aralkyloxy-carbonyl group (e.g., benzyloxycarbonyl, phenethyloxycarbonyl), a carbamoyl group, a mono- or di-$C_{1-6}$ alkyl-carbamoyl group, a mono- or di-$C_{2-6}$ alkenyl-carbamoyl group (e.g., diallylcarbamoyl), a mono- or di-$C_{3-10}$ cycloalkyl-carbamoyl group (e.g., cyclopropylcarbamoyl), a mono- or di-$C_{6-14}$ aryl-carbamoyl group (e.g., phenylcarbamoyl), a mono- or di-$C_{7-16}$ aralkyl-carbamoyl group, a 5- to 14-membered aromatic heterocyclylcarbamoyl group (e.g., pyridylcarbamoyl), a thiocarbamoyl group, a mono- or di-$C_{1-6}$ alkyl-thiocarbamoyl group (e.g., methylthiocarbamoyl, N-ethyl-N-methylthiocarbamoyl), a mono- or di-$C_{2-6}$ alkenyl-thiocarbamoyl group (e.g., diallylthiocarbamoyl), a mono- or di-$C_{3-10}$ cycloalkyl-thiocarbamoyl group (e.g., cyclopropylthiocarbamoyl, cyclohexylthiocarbamoyl), a mono- or di-$C_{6-14}$ aryl-thiocarbamoyl group (e.g., phenylthiocarbamoyl), a mono- or di-$C_{7-16}$ aralkyl-thiocarbamoyl group (e.g., benzylthiocarbamoyl, phenethylthiocarbamoyl), a 5- to 14-membered aromatic heterocyclylthiocarbamoyl group (e.g., pyridylthiocarbamoyl), a sulfino group, a $C_{1-6}$ alkylsulfinyl group (e.g., methylsulfinyl, ethylsulfinyl), a sulfo group, a $C_{1-6}$ alkylsulfonyl group, a $C_{6-14}$ arylsulfonyl group, a phosphono group and a mono- or di-$C_{1-6}$ alkylphosphono group (e.g., dimethylphosphono, diethylphosphono, diisopropylphosphono, dibutylphosphono).

In the present specification, examples of the "optionally substituted amino group" include an amino group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a 07.16 aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group, a mono- or di-$C_{7-16}$ aralkyl-carbamoyl group, a $C_{1-6}$ alkylsulfonyl group and a $C_{6-14}$ arylsulfonyl group, each of which optionally has 1 to 3 substituents selected from "Substituent group A".

Preferable examples of the optionally substituted amino group include an amino group, a mono- or di-(optionally halogenated $C_{1-6}$ alkyl) amino group (e.g., methylamino, trifluoromethylamino, dimethylamino, ethylamino, diethylamino, propylamino, dibutylamino), a mono- or di-$C_{2-6}$ alkenylamino group (e.g., diallylamino), a mono- or di-$C_{3-10}$ cycloalkylamino group (e.g., cyclopropylamino, cyclohexylamino), a mono- or di-$C_{6-14}$ arylamino group (e.g., phenylamino), a mono- or di-$C_{7-16}$ aralkylamino group (e.g., benzylamino, dibenzylamino), a mono- or di-(optionally halogenated $C_{1-6}$ alkyl)-carbonylamino group (e.g., acetylamino, propionylamino), a mono- or di-$C_{6-14}$ aryl-carbonylamino group (e.g., benzoylamino), a mono- or di-$C_{7-16}$ aralkyl-carbonylamino group (e.g., benzylcarbonylamino), a mono- or di-5- to 14-membered aromatic heterocyclylcarbonylamino group (e.g., nicotinoylamino, isonicotinoylamino), a mono- or di-3- to 14-membered non-aromatic heterocyclylcarbonylamino group (e.g., piperidinylcarbonylamino), a mono- or di-$C_{1-6}$ alkoxy-carbonylamino group (e.g., tert-butoxycarbonylamino), a 5- to 14-membered aromatic heterocyclylamino group (e.g., pyridylamino), a carbamoylamino group, a (mono- or di-$C_{1-6}$ alkyl-carbamoyl) amino group (e.g., methylcarbamoylamino), a (mono- or di-$C_{7-16}$ aralkyl-carbamoyl) amino group (e.g., benzylcarbamoylamino), a $C_{1-6}$ alkylsulfonylamino group (e.g., methylsulfonylamino, ethylsulfonylamino), a $C_{6-14}$ arylsulfonylamino group (e.g., phenylsulfonylamino), a ($C_{1-6}$ alkyl) ($C_{1-6}$ alkyl-carbonyl) amino group (e.g., N-acetyl-N-methylamino) and a ($C_{1-6}$ alkyl)($C_{6-14}$ aryl-carbonyl) amino group (e.g., N-benzoyl-N-methylamino).

In the present specification, examples of the "optionally substituted carbamoyl group" include a carbamoyl group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group and a mono- or di-$C_{7-16}$ aralkyl-carbamoyl group, each of which optionally has 1 to 3 substituents selected from "Substituent group A".

Preferable examples of the optionally substituted carbamoyl group include a carbamoyl group, a mono- or di-$C_{1-6}$ alkyl-carbamoyl group, a mono- or di-$C_{2-6}$ alkenyl-carbamoyl group (e.g., diallylcarbamoyl), a mono- or di-$C_{3-10}$ cycloalkyl-carbamoyl group (e.g., cyclopropylcarbamoyl, cyclohexylcarbamoyl), a mono- or di-$C_{6-14}$ aryl-carbamoyl group (e.g., phenylcarbamoyl), a mono- or di-$C_{7-16}$ aralkyl-carbamoyl group, a mono- or di-$C_{1-6}$ alkyl-carbonyl-carbamoyl group (e.g., acetylcarbamoyl, propionylcarbamoyl), a mono- or di-$C_{6-14}$ aryl-carbonyl-carbamoyl group (e.g., benzoylcarbamoyl) and a 5- to 14-membered aromatic heterocyclylcarbamoyl group (e.g., pyridylcarbamoyl).

In the present specification, examples of the "optionally substituted thiocarbamoyl group" include a thiocarbamoyl group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group and a mono- or di-$C_{7-16}$ aralkyl-carbamoyl group, each of which optionally has 1 to 3 substituents selected from "Substituent group A".

Preferable examples of the optionally substituted thiocarbamoyl group include a thiocarbamoyl group, a mono- or di-$C_{1-6}$ alkyl-thiocarbamoyl group (e.g., methylthiocarbamoyl, ethylthiocarbamoyl, dimethylthiocarbamoyl, diethylthiocarbamoyl, N-ethyl-N-methylthiocarbamoyl), a mono- or di-$C_{2-6}$ alkenyl-thiocarbamoyl group (e.g., diallylthiocarbamoyl), a mono- or di-$C_{3-10}$ cycloalkyl-thiocarbamoyl group (e.g., cyclopropylthiocarbamoyl, cyclohexylthiocarbamoyl), a mono- or di-$C_{6-14}$ aryl-thiocarbamoyl group (e.g., phenylthiocarbamoyl), a mono- or di-$C_{7-16}$ aralkyl-thiocarbamoyl group (e.g., benzylthiocarbamoyl, phenethylthiocarbamoyl), a mono- or di-$C_1$ alkyl-carbonyl-thiocarbamoyl group (e.g., acetylthiocarbamoyl, propionylthiocarbamoyl), a mono- or di-$C_{6-14}$ aryl-carbonyl-thiocarbamoyl group (e.g., benzoylthiocarbamoyl) and a 5- to 14-membered aromatic heterocyclylthiocarbamoyl group (e.g., pyridylthiocarbamoyl).

In the present specification, examples of the "optionally substituted sulfamoyl group" include a sulfamoyl group optionally having "1 or 2 substituents selected from a $C_{1-6}$ alkyl group, a $C_{2-6}$ alkenyl group, a 03.10 cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group and a mono- or di-$C_{7-16}$ aralkyl-carbamoyl group, each of which optionally has 1 to 3 substituents selected from "Substituent group A".

Preferable examples of the optionally substituted sulfamoyl group include a sulfamoyl group, a mono- or di-$C_{1-6}$ alkyl-sulfamoyl group (e.g., methylsulfamoyl, ethylsulfamoyl, dimethylsulfamoyl, dethylsulfamoyl, N-ethyl-N-methylsulfamoyl), a mono- or di-$C_{2-6}$ alkenyl-sulfamoyl group (e.g., diallylsulfamoyl), a mono- or di-$C_{3-10}$ cycloalkyl-sulfamoyl group (e.g., cyclopropylsulfamoyl, cyclohexylsulfamoyl), a mono- or di-$C_{6-14}$ aryl-sulfamoyl group (e.g., phenylsulfamoyl), a mono- or di-$C_{7-16}$ aralkyl-sulfamoyl group (e.g., benzylsulfamoyl, phenethylsulfamoyl), a mono- or di-$C_{1-6}$ alkyl-carbonyl-sulfamoyl group (e.g., acetylsulfamoyl, propionylsulfamoyl), a mono- or di-$C_{6-14}$ aryl-carbonyl-sulfamoyl group (e.g., benzoylsulfamoyl) and a 5- to 14-membered aromatic heterocyclylsulfamoyl group (e.g., pyridylsulfamoyl).

In the present specification, examples of the "optionally substituted hydroxy group" include a hydroxy group optionally having "a substituent selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group, a mono- or di-$C_{7-16}$ aralkyl-carbamoyl group, a $C_{1-6}$ alkylsulfonyl group and a 06.14 arylsulfonyl group, each of which optionally has 1 to 3 substituents selected from "Substituent group A".

Preferable examples of the optionally substituted hydroxy group include a hydroxy group, a $C_{1-6}$ alkoxy group, a $C_{2-6}$ alkenyloxy group (e.g., allyloxy, 2-butenyloxy, 2-pentenyloxy, 3-hexenyloxy), a $C_{3-10}$ cycloalkyloxy group (e.g., cyclohexyloxy), a $C_{6-14}$ aryloxy group (e.g., phenoxy, naphthyloxy), a $C_{7-16}$ aralkyloxy group (e.g., benzyloxy, phenethyloxy), a $C_{1-6}$ alkyl-carbonyloxy group (e.g., acetyloxy, propionyloxy, butyryloxy, isobutyryloxy, pivaloyloxy), a $C_{6-14}$ aryl-carbonyloxy group (e.g., benzoyloxy), a $C_{7-16}$ aralkyl-carbonyloxy group (e.g., benzylcarbonyloxy), a 5- to 14-membered aromatic heterocyclylcarbonyloxy group (e.g., nicotinoyloxy), a 3- to 14-membered non-aromatic heterocyclylcarbonyloxy group (e.g., piperidinylcarbonyloxy), a $C_{1-6}$ alkoxy-carbonyloxy group (e.g., tert-butoxycarbonyloxy), a 5- to 14-membered aromatic heterocyclyloxy group (e.g., pyridyloxy), a carbamoyloxy group, a $C_{1-6}$ alkyl-carbamoyloxy group (e.g., methylcarbamoyloxy), a $C_{7-16}$ aralkyl-carbamoyloxy group (e.g., benzylcarbamoyloxy), a $C_{1-6}$ alkylsulfonyloxy group (e.g., methylsulfonyloxy, ethylsulfonyloxy) and a $C_{6-14}$ arylsulfonyloxy group (e.g., phenylsulfonyloxy).

In the present specification, examples of the "optionally substituted sulfanyl group" include a sulfanyl group optionally having "a substituent selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group and a 5- to 14-membered aromatic heterocyclic group, each of which optionally has 1 to 3 substituents selected from "Substituent group A" and a halogenated sulfanyl group.

Preferable examples of the optionally substituted sulfanyl group include a sulfanyl (—SH) group, a $C_{1-6}$ alkylthio group, a $C_{2-6}$ alkenylthio group (e.g., allylthio, 2-butenylthio, 2-pentenylthio, 3-hexenylthio), a $C_{3-10}$ cycloalkylthio group (e.g., cyclohexylthio), a $C_{6-14}$ arylthio group (e.g., phenylthio, naphthylthio), a $C_{7-16}$ aralkylthio group (e.g., benzylthio, phenethylthio), a $C_{1-6}$ alkyl-carbonylthio group (e.g., acetylthio, propionylthio, butyrylthio, isobutyrylthio, pivaloylthio), a $C_{6-14}$ aryl-carbonylthio group (e.g., benzoylthio), a 5- to 14-membered aromatic heterocyclylthio group (e.g., pyridylthio) and a halogenated thio group (e.g., pentafluorothio).

In the present specification, examples of the "optionally substituted silyl group" include a silyl group optionally having "1 to 3 substituents selected from a $C_{1-6}$ alkyl group, a $C_{2-6}$ alkenyl group, a $C_{3-10}$ cycloalkyl group, a $C_{6-14}$ aryl group and a $C_{7-16}$ aralkyl group, each of which optionally has 1 to 3 substituents selected from "Substituent group A". Examples of the optionally substituted silyl group include a tri-$C_{1-6}$ alkylsilyl group (e.g., trimethylsilyl, tert-butyl(dimethyl)silyl).

The term "antibody-drug conjugate" or "ADC" as used herein refers to a compound that is linked to an antibody and is defined by the formula $(CD-L)_n-A$, wherein CD is a group represented by any one of Formula (XX)-(XXIX), see below, L is a linker, A is a protein, e.g., an antibody, and n is 1-10. In one embodiment, the linker is represented by $-X^3-T-Z-Q-$, wherein $X^3$ is a divalent radical that connects CD to the rest of linker, or is absent, T is a peptide, or is absent, Z is a spacer, and Q is heterobifunctional group or a heterotifunctional group. By way of illustration, the following generic formula shows an ADC of the disclosure having a para-aminobenzyl-based connector, an alanine-alanine-based dipeptide, a propanone-based spacer, and a succinimide thioether-based heterobifunctional group.

Some cleavable linkers are cleaved by peptidases ("peptidase cleavable linkers"). Only certain peptides are readily cleaved inside or outside cells, see e.g. Trout et al., 79 Proc. Natl. Acad. Sci. USA, 626-629 (1982) and Umemoto et al. 43 Int. J. Cancer, 677-684 (1989). Furthermore, peptides are composed of α-amino acid units and peptidic bonds, which chemically are amide bonds between the carboxylate of one amino acid and the amino group of a second amino acid. Other amide bonds, such as the bond between a carboxylate and the α-amino acid group of lysine, are understood not to be peptidic bonds and are considered non-cleavable.

Some linkers are cleaved by esterases ("esterase cleavable linkers"). Only certain esters can be cleaved by esterases present inside or outside of cells. Esters are formed by the condensation of a carboxylic acid and an alcohol. Simple esters are esters produced with simple alcohols, such as aliphatic alcohols, and small cyclic and small aromatic alcohols.

In some embodiments, the cleavable linker component comprises a peptide comprising one to ten amino acid residues. In these embodiments, the peptide allows for cleavage of the linker by a protease, thereby facilitating release of the cyclic dinucleotide upon exposure to intracellular proteases, such as lysosomal enzymes (Doronina et al. (2003) Nat. Biotechnol. 21:778-784). Exemplary peptides include, but are not limited to, dipeptides, tripeptides, tetrapeptides, and pentapeptides. Exemplary dipeptides

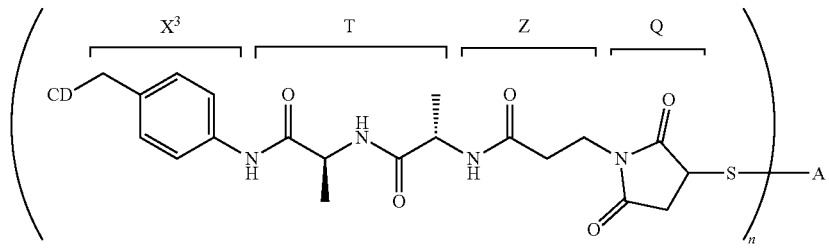

In the present disclosure, the term "linker" refers to any chemical moiety capable of linking a protein, e.g., antibody, antibody fragment (e.g., antigen binding fragments) or functional equivalent to a cyclic dinucleotide. Linkers may be susceptible to cleavage (a "cleavable linker") thereby facilitating release of the cyclic dinucleotide. For example, such cleavable linkers may be susceptible to acid-induced cleavage, photo-induced cleavage, peptidase-induced cleavage, esterase-induced cleavage, and disulfide bond cleavage, at conditions under which the cyclic dinucleotide and/or the antibody remains active. Alternatively, linkers may be substantially resistant to cleavage (a "noncleavable linker").

In the present disclosure, non-cleavable linkers are any chemical moiety capable of linking a cyclic dinucleotide to an antibody in a stable, covalent manner and does not fall off under the categories listed above for cleavable linkers. Thus, non-cleavable linkers are substantially resistant to acid-induced cleavage, photo-induced cleavage, peptidase-induced cleavage, esterase-induced cleavage and disulfide bond cleavage. Furthermore, non-cleavable refers to the ability of the chemical bond in the linker or adjoining to the linker to withstand cleavage induced by an acid, photolabile-cleaving agent, a peptidase, an esterase, or a chemical or physiological compound that cleaves a disulfide bond, at conditions under which a cyclic dinucleotide and/or the antibody does not lose its activity.

include, but are not limited to, alanine-alanine (ala-ala), valine-citrulline (vc or val-cit), alanine-phenylalanine (af or ala-phe); phenylalanine-lysine (fk or phe-lys); phenylalanine-homolysine (phe-homolys); and N-methyl-valine-citrulline (Me-val-cit). Exemplary tripeptides include, but are not limited to, glycine-valine-citrulline (gly-val-cit) and glycine-glycine-glycine (gly-gly-gly).

A peptide may comprise naturally-occurring and/or non-natural amino acid residues. The term "naturally-occurring amino acid" refer to Ala, Asp, Cys, Glu, Phe, Gly, His, He, Lys, Leu, Met, Asn, Pro, Gin, Arg, Ser, Thr, Val, Trp, and Tyr. "Non-natural amino acids" (i.e., amino acids do not occur naturally) include, by way of non-limiting example, homoserine, homoarginine, citrulline, phenylglycine, taurine, iodotyrosine, seleno-cysteine, norleucine ("Nle"), norvaline ("Nva"), beta-alanine, L- or D-naphthalanine, ornithine ("Orn"), and the like. Peptides can be designed and optimized for enzymatic cleavage by a particular enzyme, for example, a tumor-associated protease, cathepsin B, C and D, or a plasmin protease.

Amino acids also include the D-forms of natural and non-natural amino acids.

"D-" designates an amino acid having the "D" (dextrorotary) configuration, as opposed to the configuration in the naturally occurring ("L-") amino acids. Natural and non-natural amino acids can be purchased commercially (Sigma Chemical Co., Advanced Chemtech) or synthesized using methods known in the art.

In the present disclosure, the term "heterobifunctional group" or the term "heterotrifunctional group" refers to a chemical moiety that connects a linker and another therapeutically active molecule, e.g., protein, e.g., an antibody. See, e.g., WO 2017/191579. Heterobi- and tri-functional groups are characterized as having different reactive groups at either end of the chemical moiety. Non-limiting exemplary heterobifunctional groups include:

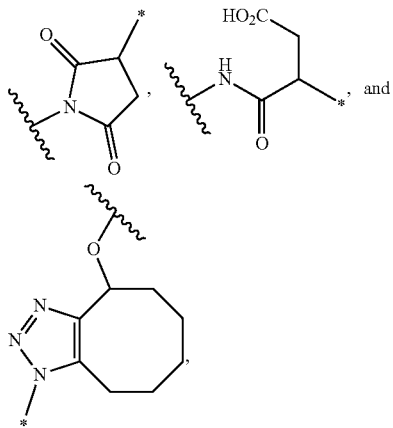

wherein the "*" indicates the attachment point to any available carbon atom, nitrogen atom, oxygen atom, or sulfur atom attached to the antibody. In embodiment, the heterobifunctional group is

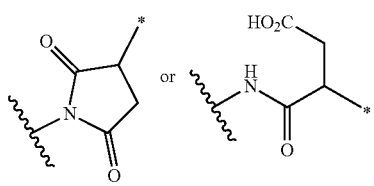

and is attached to a sulfur atom attached to the antibody.

A non-limiting exemplary heterotrifunctional group is:

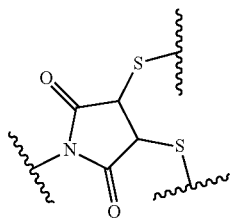 [SMILES: *SC1C(=O)N(*)C(=O)C1S*]

In the present disclosure, the term "spacer" refers to chemical moiety that connects a heterobi- and tri-functional group to the rest of the linker, e.g., a peptide, or, if a heterobi- or tri-functional group is absent, connects the rest of the linker or the cyclic dinucleotide to any available carbon atom, nitrogen atom, oxygen atom, or sulfur atom attached to the antibody. Non-limiting exemplary spacers include —NH—, —S—, —O—, —NHC(=O)CH$_2$CH$_2$—, —S(=O)$_2$—CH$_2$CH$_2$—, —C(=O)NHNH, —C(=O)O—, —C(=O)NH—, —CH$_2$—, —CH$_2$CH$_2$—, —CH$_2$CH$_2$CH$_2$—, —CH$_2$=CH$_2$—, —C≡C—, —CH=N—O—, polyethylene glycol (PEG),

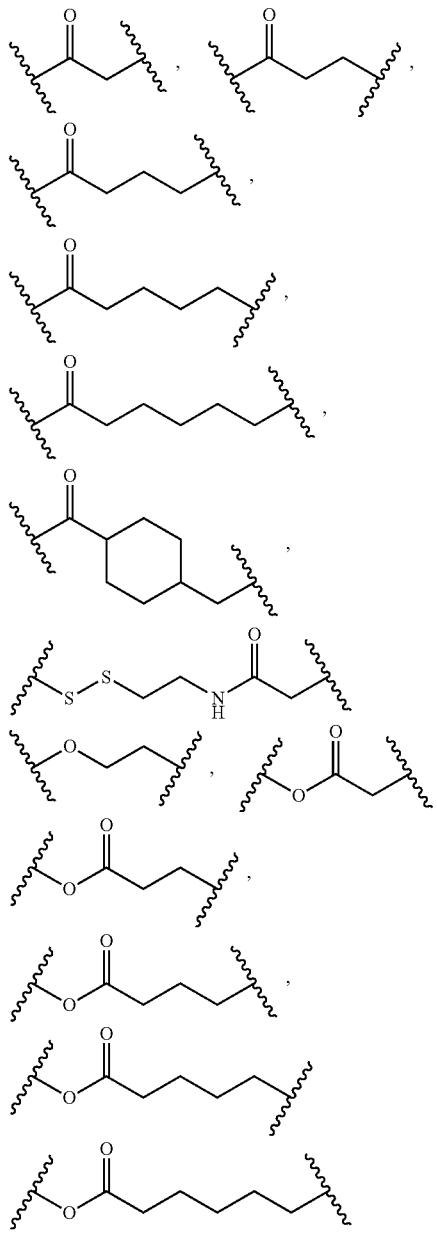

The term "drug antibody ratio" or "DAR" refers to the number of CDs linked to A (i.e., a protein, e.g., an antibody or antigen-binding fragment thereof). Thus, in the ADC having the generic formula (CD-L)$_n$-A, the DAR is defined by the variable "n."

When referring to a compound having formula (CD-L)$_n$-A representing an individual ADC, the DAR refers to the number of CDs linked to the individual A, e.g., n is an integer of 1 to 10.

When referring to a compound having formula (CD-L)$_n$-A representing a plurality of ADCs, the DAR refers to the average number of cyclic dinucleotides linked to the As, e.g., n is an integer or fraction of 1 to 10). Thus, by way of an example, a compound having formula (CD-L)$_n$-A comprising a first ADC with 3 cyclic dinucleotides per A and a second ADC with 4 cyclic dinucleotides per A would have a DAR, i.e., an "n," of 3.5

The terms "polypeptide," "peptide," and "protein" are used interchangeably herein to refer to polymers of amino acids of any length. The polymer can be linear or branched, it can comprise modified amino acids, and it can be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art. It is understood that, because the polypeptides of this disclosure are based upon antibodies, in certain embodiments, the polypeptides can occur as single chains or associated chains.

A "monoclonal" antibody or antigen-binding fragment thereof refers to a homogeneous antibody or antigen-binding fragment population involved in the highly specific recognition and binding of a single antigenic determinant, or epitope. This is in contrast to polyclonal antibodies that typically include different antibodies directed against different antigenic determinants. The term "monoclonal" antibody or antigen-binding fragment thereof encompasses both intact and full-length monoclonal antibodies as well as antibody fragments (such as Fab, Fab', F(ab')2, Fv), single chain (scFv) mutants, fusion proteins comprising an antibody portion, and any other modified immunoglobulin molecule comprising an antigen recognition site. Furthermore, "monoclonal" antibody or antigen-binding fragment thereof refers to such antibodies and antigen-binding fragments thereof made in any number of manners including but not limited to by hybridoma, phage selection, recombinant expression, and transgenic animals.

The term "humanized" antibody or antigen-binding fragment thereof refers to forms of non-human (e.g. murine) antibodies or antigen-binding fragments that are specific immunoglobulin chains, chimeric immunoglobulins, or fragments thereof that contain minimal non-human (e.g., murine) sequences. Typically, humanized antibodies or antigen-binding fragments thereof are human immunoglobulins in which residues from the complementary determining region (CDR) are replaced by residues from the CDR of a non human species (e.g. mouse, rat, rabbit, hamster) that have the desired specificity, affinity, and capability ("CDR grafted") (Jones et al., Nature 321:522-525 (1986); Riechmann et al., Nature 332:323-327 (1988); Verhoeyen et al., Science 239:1534-1536 (1988)). In some instances, the Fv framework region (FR) residues of a human immunoglobulin are replaced with the corresponding residues in an antibody or fragment from a non-human species that has the desired specificity, affinity, and capability. The humanized antibody or antigen-binding fragment thereof can be further modified by the substitution of additional residues either in the Fv framework region and/or within the replaced non-human residues to refine and optimize antibody or antigen-binding fragment thereof specificity, affinity, and/or capability. In general, the humanized antibody or antigen-binding fragment thereof will comprise substantially all of at least one, and typically two or three, variable domains containing all or substantially all of the CDR regions that correspond to the non-human immunoglobulin whereas all or substantially all of the FR regions are those of a human immunoglobulin consensus sequence. The humanized antibody or antigen-binding fragment thereof can also comprise at least a portion of an immunoglobulin constant region or domain (Fc), typically that of a human immunoglobulin. Examples of methods used to generate humanized antibodies are described in U.S. Pat. No. 5,225,539; Roguska et al., Proc. Natl. Acad. Sci., USA, 91(3):969-973 (1994), and Roguska et al., Protein Eng. 9(10):895-904 (1996). In some embodiments, a "humanized antibody" is a resurfaced antibody.

A "variable region" of an antibody refers to the variable region of the antibody light chain or the variable region of the antibody heavy chain, either alone or in combination. The variable regions of the heavy and light chain each consist of four framework regions (FR) connected by three complementarity determining regions (CDRs) also known as hypervariable regions. The CDRs in each chain are held together in close proximity by the FRs and, with the CDRs from the other chain, contribute to the formation of the antigen-binding site of antibodies. There are at least two techniques for determining CDRs: (1) an approach based on cross-species sequence variability (i.e., Kabat et al. Sequences of Proteins of Immunological Interest, (5th ed., 1991, National Institutes of Health, Bethesda Md.)); and (2) an approach based on crystallographic studies of antigen-antibody complexes (Al-Iazikani et al (1997) J. Molec. Biol. 273:927-948)). In addition, combinations of these two approaches are sometimes used in the art to determine CDRs.

The Kabat numbering system is generally used when referring to a residue in the variable domain (approximately residues 1-107 of the light chain and residues 1-113 of the heavy chain) (e.g., Kabat et al., Sequences of Immunological Interest. 5th Ed. Public Health Service, National Institutes of Health, Bethesda, Md. (1991)). Unless explicitly indicated otherwise, the numbering system used herein is the Kabat numbering system.

The amino acid position numbering as in Kabat, refers to the numbering system used for heavy chain variable domains or light chain variable domains of the compilation of antibodies in Kabat et al., Sequences of Proteins of Immunological Interest, 5th Ed. Public Health Service, National Institutes of Health, Bethesda, Md. (1991). Using this numbering system, the actual linear amino acid sequence can contain fewer or additional amino acids corresponding to a shortening of, or insertion into, a FR or CDR of the variable domain. For example, a heavy chain variable domain can include a single amino acid insert (residue 52a according to Kabat) after residue 52 of H2 and inserted residues (e.g. residues 82a, 82b, and 82c, etc. according to Kabat) after heavy chain FR residue 82. The Kabat numbering of residues can be determined for a given antibody by alignment at regions of homology of the sequence of the antibody with a "standard" Kabat numbered sequence. Chothia refers instead to the location of the structural loops (Chothia and Lesk J. Mol. Biol. 196:901-917 (1987)).

The end of the Chothia CDR-H1 loop when numbered using the Kabat numbering convention varies between H32 and H34 depending on the length of the loop (this is because the Kabat numbering scheme places the insertions at H35A and H35B; if neither 35A nor 35B is present, the loop ends at 32; if only 35A is present, the loop ends at 33; if both 35A and 35B are present, the loop ends at 34). The AbM hypervariable regions represent a compromise between the Kabat CDRs and Chothia structural loops, and are used by Oxford Molecular's AbM antibody modeling software.

| Loop | Kabat | AbM | Chothia |
| --- | --- | --- | --- |
| L1 | L24-L34 | L24-L34 | L24-L34 |
| L2 | L50-L56 | L50-L56 | L50-56 |

| Loop | Kabat | AbM | Chothia |
| --- | --- | --- | --- |
| L3 | L89-L97 | L89-L97 | L89-L97 |
| H1 | H31-H35B | H26-H35B | H26-H32_34 |
| | | | (Kabat Numbering) |
| H1 | H31-35 | H26-H35 | H26-32 |
| | | | (Chothia Numbering) |
| H2 | H50-H65 | H50-H58 | H52-H56 |
| H3 | H95-H102 | H95-H102 | H95-H102 |

In certain aspects, the CDRs of an antibody or antigen-binding fragment thereof can be determined according to the Chothia numbering scheme, which refers to the location of immunoglobulin structural loops (see, e.g., Chothia C & Lesk A M, (1987), J Mol Biol 196: 901-917; Al-Lazikani B et al., (1997) J Mol Biol 273: 927-948; Chothia C et al., (1992) J Mol Biol 227: 799-817; Tramontano A et at, (1990) J Mol Biol 215(1): 175-82; and U.S. Pat. No. 7,709,226). Typically, when using the Kabat numbering convention, the Chothia CDR-H1 loop is present at heavy chain amino acids 26 to 32, 33, or 34, the Chothia CDR-H2 loop is present at heavy chain amino acids 52 to 56, and the Chothia CDR-H3 loop is present at heavy chain amino acids 95 to 102, while the Chothia CDR-L1 loop is present at light chain amino acids 24 to 34, the Chothia CDR-L2 loop is present at light chain amino acids 50 to 56, and the Chothia CDR-L3 loop is present at light chain amino acids 89 to 97. The end of the Chothia CDR-H1 loop when numbered using the Kabat numbering convention varies between H32 and H34 depending on the length of the loop (this is because the Kabat numbering scheme places the insertions at H35A and H35B; if neither 35A nor 35B is present, the loop ends at 32; if only 35A is present, the loop ends at 33; if both 35A and 35B are present, the loop ends at 34).

In certain aspects, the CDRs of an antibody or antigen-binding fragment thereof can be determined according to the IMGT numbering system as described in Lefranc M-P, (1999) The Immunologist 7: 132-136 and Lefranc M-P et al., (1999) Nucleic Acids Res 27: 209-212. According to the IMGT numbering scheme, VH-CDR1 is at positions 26 to 35, VH-CDR2 is at positions 51 to 57, VH-CDR3 is at positions 93 to 102, VL-CDR1 is at positions 27 to 32, VL-CDR2 is at positions 50 to 52, and VL-CDR3 is at positions 89 to 97.

In certain aspects, the CDRs of an antibody or antigen-binding fragment thereof can be determined according to MacCallum R M el al., (1996) J Mol Biol 262: 732-745. See also, e.g., Martin A. "Protein Sequence and Structure Analysis of Antibody Variable Domains," in *Antibody Engineering*, Kontermann and Dubel, eds., Chapter 31, pp. 422-439, Springer-Verlag, Berlin (2001).

In certain aspects, the CDRs of an antibody or antigen-binding fragment thereof can be determined according to the AbM numbering scheme, which refers AbM hypervariable regions which represent a compromise between the Kabat CDRs and Chothia structural loops, and are used by Oxford Molecular's AbM antibody modeling software (Oxford Molecular Group, Inc.).

The term "human" antibody means an antibody produced by a human or an antibody having an amino acid sequence corresponding to an antibody produced by a human made using any technique known in the art. This definition of a human antibody includes intact or full-length antibodies, fragments thereof, and/or antibodies comprising at least one human heavy and/or light chain polypeptide such as, for example, an antibody comprising murine light chain and human heavy chain polypeptides.

The term "chimeric" antibodies refers to antibodies wherein the amino acid sequence of the immunoglobulin molecule is derived from two or more species. Typically, the variable region of both light and heavy chains corresponds to the variable region of antibodies derived from one species of mammals (e.g. mouse, rat, rabbit, etc.) with the desired specificity, affinity, and capability while the constant regions are homologous to the sequences in antibodies derived from another (usually human) to avoid eliciting an immune response in that species.

The term "epitope" or "antigenic determinant" are used interchangeably herein and refer to that portion of an antigen capable of being recognized and specifically bound by a particular antibody. When the antigen is a polypeptide, epitopes can be formed both from contiguous amino acids and noncontiguous amino acids juxtaposed by tertiary folding of a protein. Epitopes formed from contiguous amino acids are typically retained upon protein denaturing, whereas epitopes formed by tertiary folding are typically lost upon protein denaturing. An epitope typically includes at least 3, and more usually, at least 5 or 8-10 amino acids in a unique spatial conformation.

"Binding affinity" generally refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (Kd). Affinity can be measured by common methods known in the art, including those described herein. Low-affinity antibodies generally bind antigen slowly and tend to dissociate readily, whereas high-affinity antibodies generally bind antigen faster and tend to remain bound longer. A variety of methods of measuring binding affinity are known in the art, any of which can be used for purposes of the present disclosure. Specific illustrative embodiments are described in the following.

"Or better" when used herein to refer to binding affinity refers to a stronger binding between a molecule and its binding partner. "Or better" when used herein refers to a stronger binding, represented by a smaller numerical Kd value. For example, an antibody which has an affinity for an antigen of "0.6 nM or better", the antibody's affinity for the antigen is <0.6 nM, i.e. 0.59 nM, 0.58 nM, 0.57 nM etc. or any value less than 0.6 nM.

By "specifically binds," it is generally meant that an antibody binds to an epitope via its antigen binding domain, and that the binding entails some complementarity between the antigen binding domain and the epitope. According to this definition, an antibody is said to "specifically bind" to an epitope when it binds to that epitope, via its antigen binding domain more readily than it would bind to a random, unrelated epitope. The term "specificity" is used herein to qualify the relative affinity by which a certain antibody binds to a certain epitope. For example, antibody "A" may be deemed to have a higher specificity for a given epitope than antibody "B," or antibody "A" may be said to bind to epitope "C" with a higher specificity than it has for related epitope "D."

By "preferentially binds," it is meant that the antibody specifically binds to an epitope more readily than it would bind to a related, similar, homologous, or analogous epitope.

Thus, an antibody which "preferentially binds" to a given epitope would more likely bind to that epitope than to a related epitope, even though such an antibody may cross-react with the related epitope.

An antibody is said to "competitively inhibit" binding of a reference antibody to a given epitope if the antibody preferentially binds to that epitope or an overlapping epitope to the extent that it blocks, to some degree, binding of the reference antibody to the epitope. Competitive inhibition may be determined by any method known in the art, for example, competition ELISA assays. An antibody may be said to competitively inhibit binding of the reference antibody to a given epitope by at least 90%, at least 80%, at least 70%, at least 60%, or at least 50%.

The phrase "substantially similar," or "substantially the same", as used herein, denotes a sufficiently high degree of similarity between two numeric values (generally one associated with an antibody of the disclosure and the other associated with a reference/comparator antibody) such that one of skill in the art would consider the difference between the two values to be of little or no biological and/or statistical significance within the context of the biological characteristic measured by said values (e.g., Kd values). The difference between said two values can be less than about 50%, less than about 40%, less than about 30%, less than about 20%, or less than about 10% as a function of the value for the reference/comparator antibody.

A polypeptide, antibody, polynucleotide, vector, cell, or composition which is "isolated" is a polypeptide, antibody, polynucleotide, vector, cell, or composition which is in a form not found in nature. Isolated polypeptides, antibodies, polynucleotides, vectors, cell or compositions include those which have been purified to a degree that they are no longer in a form in which they are found in nature. In some embodiments, an antibody, polynucleotide, vector, cell, or composition which is isolated is substantially pure.

As used herein, "substantially pure" refers to material which is at least 50% pure (i.e., free from contaminants), at least 90% pure, at least 95% pure, at least 98% pure, or at least 99% pure.

The term "antibody" refers an immunoglobulin molecule that recognizes and specifically binds to a target, such as a protein, polypeptide, peptide, carbohydrate, polynucleotide, lipid, or combinations of the foregoing through at least one antigen recognition site within the variable region of the immunoglobulin molecule. As used herein, the term "antibody" encompasses intact polyclonal antibodies, intact monoclonal antibodies, chimeric antibodies, humanized antibodies, human antibodies, fusion proteins comprising an antibody, and any other modified immunoglobulin molecule so long as the antibodies exhibit the desired biological activity. An antibody can be of any the five major classes of immunoglobulins: IgA, IgD, IgE, IgG, and IgM, or subclasses (isotypes) thereof (e.g. IgG1, IgG2, IgG3, IgG4, IgA1 and IgA2), based on the identity of their heavy-chain constant domains referred to as alpha, delta, epsilon, gamma, and mu, respectively. The different classes of immunoglobulins have different and well known subunit structures and three-dimensional configurations. Antibodies can be naked or conjugated to other molecules such as toxins, radioisotopes, etc. As used herein, the term "antibody" encompasses bispecific and multispecific antibodies.

The term "antibody fragment" refers to a portion of an intact antibody. An "antigen-binding fragment" refers to a portion of an intact antibody that binds to an antigen. An antigen-binding fragment can contain the antigenic determining variable regions of an intact antibody. Examples of antibody fragments include, but are not limited to Fab, Fab', F(ab')2, and Fv fragments, linear antibodies, and single chain antibodies. An "antigen-binding fragment" can be a bispecific or multispecific antigen-binding fragment.

The term "drug delivery agent" as used herein refers to a chemical moiety that alters the distribution, targeting, or lifetime of the molecule into which it is incorporated. In some embodiments a drug delivery agent provides an enhanced affinity for a selected target, e.g., molecule, cell or cell type, compartment, receptor e.g., a cellular or organ compartment, tissue, organ or region of the body, as compared to a species absent such a drug delivery agent. Drug delivery agents providing enhanced affinity for a selected target are termed targeting drug delivery agents. See, e.g., WO 2013/075035 A1. All patents, patent applications, and publications cited herein are fully incorporated by reference in their entirety.

The term "drug delivery conjugate" as used herein refers to a compound comprising any one of Formula (XX)-(XXIX), a drug delivery agent and, optionally, a covalent linker.

Some drug delivery agents have endosomolytic properties. Endosomolytic drug delivery agents promote the lysis of the endosome and/or transport of any one of Formula (XX)-(XXIX), from the endosome to the cytoplasm of the cell. The endosomolytic drug delivery agent may be a polyanionic peptide or peptidomimetic which shows pH-dependent membrane activity and fusogenicity. In one embodiment, the endosomolytic drug delivery agent assumes its active conformation at endosomal pH. The "active" conformation is that conformation in which the endosomolytic drug delivery agent promotes lysis of the endosome and/or transport of Formula (XX)-(XXIX) from the endosome to the cytoplasm of the cell. Exemplary endosomolytic drug delivery agents include the GALA peptide (Subbarao et al., Biochemistry, 1987, 26: 2964-2972), the EALA peptide (Vogel et al., J. Am. Chem. Soc, 1996, 118: 1581-1586), and their derivatives (Turk et al., Biochem. Biophys. Acta, 2002, 1559: 56-68). In one embodiment, the endosomolytic component may contain a chemical group. e.g., an amino acid, which will undergo a change in charge or protonation in response to a change in pH. The endosomolytic component may be linear or branched.

Drug delivery agents can improve transport, hybridization, and specificity properties of the resultant drug delivery conjugate.

Drug delivery agents can include therapeutic modifiers, e.g., for enhancing uptake; diagnostic compounds or reporter groups e.g., for monitoring distribution; and cross-linking agents. General examples include lipids, steroids, vitamins, carbohydrates, proteins, peptides, polyamines, synthetic polymers or oligomers (such as PEG's), peptidomimetics, or any combinations thereof.

Drug delivery agents can include a naturally occurring substance, such as a protein, e.g., human serum albumin (HSA), low-density lipoprotein (LDL), high-density lipoprotein (HDL), or globulin; a carbohydrate, e.g., a dextran, pullulan, chitin, chitosan, inulin, cyclodextrin or hyaluronic acid; or a lipid. The drug delivery agent may also be a recombinant or synthetic molecule, such as a synthetic polymer or oligomer, e.g., a synthetic polyamino acid, an oligonucleotide, e.g., an aptamer. Examples of polyamino acids include a polylysine (PLL), poly L-aspartic acid, poly L-glutamic acid. Other examples of synthetic polymers or oligomers include styrene-maleic acid anhydride copolymer, poly(L-lactide-co-glycolied) copolymer, divinyl ether-maleic anhydride copolymer, N-(2-hydroxypropyl)methacrylamide copolymer (HMPA), polyethylene glycol (PEG), polyvinyl alcohol (PVA), polyurethane, poly(2-ethylacrylic acid), N-isopropylacrylamide polymers, or polyphosphazine. Example of polyamines include: polyethylenimine, polylysine (PLL), spermine, spermidine, polyamine, pseudopeptide-polyamine, peptidomimetic polyamine, dendrimer polyamine, arginine, amidine, protamine, cationic lipid, cationic porphyrin, quaternary salt of a polyamine, or an alpha helical peptide.

Drug delivery agents can also include targeting groups, e.g., a cell or tissue targeting agent, e.g., a lectin, glycoprotein, lipid or protein, e.g., an antibody, that binds to a specified cell type. A targeting group can be a thyrotropin, melanotropin, lectin, glycoprotein, surfactant protein A, Mucin carbohydrate, multivalent lactose, multivalent galactose, N-acetyl-galactosamine, N-acetyl-gulucosamine multivalent mannose, multivalent fucose, glycosylated polyaminoacids, multivalent galactose, transferrin, bisphosphonate, polyglutamate, polyaspartate, a lipid, cholesterol, a steroid, bile acid, folate, vitamin B 12, biotin, an RGD peptide, an RGD peptide mimetic or an aptamer.

Other examples of drug delivery agents include dyes, intercalating agents (e.g., acridines), cross-linkers (e.g., psoralene, mitomycin C), porphyrins (TPPC4, texaphyrin, Sapphyrin), polycyclic aromatic hydrocarbons (e.g., phenazine, dihydrophenazine), artificial endonucleases or a chelator (e.g., EDTA), lipophilic molecules, e.g., cholesterol, cholic acid, adamantane acetic acid, 1-pyrene butyric acid, dihydrotestosterone, 1,3-Bis-0(hexadecyl)glycerol, geranyloxyhexyl group, hexadecylglycerol, borneol, menthol, 1,3-propanediol, heptadecyl group, palmitic acid, myristic acid, 03-(oleoyl)lithocholic acid, 03-(oleoyl)cholenic acid, dimethoxytrityl, or phenoxazine) and peptide conjugates (e.g., antennapedia peptide, Tat peptide), alkylating agents, phosphate, amino, mercapto, PEG (e.g., PEG-40K), MPEG, [MPEG]2, polyamino, alkyl, substituted alkyl, radiolabeled markers, enzymes, haptens (e.g., biotin), transport/absorption facilitators (e.g., aspirin, vitamin E, folic acid), synthetic ribonucleases (e.g., imidazole, bisimidazole, histamine, imidazole clusters, acridine-imidazole conjugates, Eu3+ complexes of tetraazamacrocycles), dinitrophenyl, HRP, or AP.

Drug delivery agents may also include hormones and hormone receptors. They can also include non-peptidic species, such as lipids, lectins, carbohydrates, vitamins, cofactors, multivalent lactose, multivalent galactose, N-acetyl-galactosamine, N-acetyl-gulucosamine multivalent mannose, multivalent fucose, or aptamers. The drug delivery agent can be, for example, a lipopolysaccharide, an activator of p38 MAP kinase, or an activator of NF-KB.

The drug delivery agent can be a substance, which can increase the uptake of any one of Formula (XX)-(XXIX) into the cell, for example, by disrupting the cell's cytoskeleton, e.g., by disrupting the cell's microtubules, microfilaments, and/or intermediate filaments.

The drug delivery agent can increase the uptake of any one of Formula (XX)-(XXIX) into the cell by, for example, activating an inflammatory response. Exemplary drug delivery agents that would have such an effect include tumor necrosis factor alpha (TNFalpha), interleukin-1 beta, or gamma interferon.

In one embodiment, the drug delivery agent is a lipid or lipid-based molecule. Such a lipid or lipid-based molecule can bind a serum protein, e.g., human serum albumin (HSA). An HSA binding drug delivery agent allows for distribution of the drug delivery conjugate to a target tissue, e.g., a non-kidney target tissue of the body. Other molecules that can bind HSA can also be used as drug delivery agents. For example, naproxen or aspirin can be used. A lipid or lipid-based drug delivery agent can (a) increase resistance to degradation of the drug delivery conjugate, (b) increase targeting or transport into a target cell or cell membrane, and/or (c) can be used to adjust binding to a serum protein, e.g., HSA. A lipid or lipid-based drug delivery agent can also enable the formation of nanoparticles, such as micelles, which can impact the biodistribution of any one of Formula (XX)-(XXIX).

A lipid based drug delivery agent can be used to modulate, e.g., control the binding of the drug delivery conjugate to a target tissue. For example, a lipid or lipid-based drug delivery agent that binds to HSA more strongly will be less likely to be targeted to the kidney and therefore less likely to be cleared from the body. A lipid or lipid-based drug delivery agent that binds to HSA less strongly can be used to target the conjugate to the kidney.

In one embodiment, the lipid based drug delivery agent binds HSA with a sufficient affinity such that the drug delivery conjugate is distributed to a non-kidney tissue. In one embodiment, the affinity is not so strong that the HSA-drug delivery agent binding cannot be reversed.

In another embodiment, the lipid based drug delivery agent binds HSA weakly or not at all, such that the drug delivery conjugate is distributed to the kidney. Other moieties that target to kidney cells can also be used in place of or in addition to the lipid based drug delivery agent.

In another embodiment, the drug delivery agent is a moiety, e.g., a vitamin, which is taken up by a target cell, e.g., a proliferating cell. These are particularly useful for treating disorders characterized by unwanted cell proliferation, e.g., of the malignant or non malignant type, e.g., cancer cells. Exemplary vitamins include vitamin A, E, and K. Other exemplary vitamins include B vitamins, e.g., folic acid, B 12, riboflavin, biotin, pyridoxal or other vitamins or nutrients taken up by cancer cells. Also included are HAS, low density lipoprotein (LDL) and high-density lipoprotein (HDL).

In another embodiment, the drug delivery agent is a cell-permeation agent, e.g., a helical cell-permeation agent. In one embodiment, the agent is amphipathic. Exemplary amphipathic agents include a peptide such as tat or antennopedia, and a lipid-PEG conjugate. If the agent is a peptide, it can be modified, including a peptidylmimetic, invertomers, non-peptide or pseudo-peptide linkages, and use of D-amino acids. In one embodiment, the helical agent is an alpha-helical agent having a lipophilic and a lipophobic phase.

The drug delivery agent can be a peptide or peptidomimetic. A peptidomimetic (also referred to herein as an oligopeptidomimetic) is a molecule capable of folding into a defined three-dimensional structure similar to a natural peptide. The peptide or peptidomimetic moiety can be about 5-50 amino acids long, e.g., about 5, 10, 15, 20, 25, 30, 35, 40, 45, or 50 amino acids long. A peptide or peptidomimetic can be, for example, a cell permeation peptide, cationic peptide, amphipathic peptide, or hydrophobic peptide (e.g., consisting primarily of Tyr, Trp or Phe). The peptide moiety can be a dendrimer peptide, constrained peptide or cross-linked peptide. In another embodiment, the peptide moiety can include a hydrophobic membrane translocation sequence (MTS). An exemplary hydrophobic MTS-containing peptide is RFGF. An RFGF analogue containing a hydrophobic MTS can also be a targeting moiety. The peptide moiety can be a "delivery" peptide, which can carry large polar molecules including peptides, oligonucleotides, and protein across cell membranes. For example, certain sequences from the HIV Tat protein and the *Drosophila* Antennapedia have been found to be capable of functioning as delivery peptides. A peptide or peptidomimetic can be encoded by a random sequence of DNA, such as a peptide identified from a phage-display library, or one-bead-one-compound (OBOC) combinatorial library (Lam et ah, Nature, 354:82-84, 1991). In one embodiment, the peptide or peptidomimetic is a cell targeting peptide such as an arginine-glycine-aspartic acid (RGD)-peptide, or RGD mimic. A peptide moiety can range in length from about 5 amino acids to about 40 amino acids. The peptide moieties can have a structural modification, such as to increase stability or direct conformational properties. Any of the structural modifications described below can be utilized. An RGD peptide moiety can be used to target a tumor cell, such as an endothelial tumor cell or a breast cancer tumor cell (Zitzmann et ah, Cancer Res., 62:5139-43, 2002). An RGD peptide can facilitate targeting of any one of Formula (XX)-(XXIX) to tumors of a variety of other tissues, including the lung, kidney, spleen, or liver (Aoki et ah, Cancer Gene Therapy 8:783-787, 2001).

In some embodiments, the RGD peptide will facilitate targeting of a drug delivery conjugate to the kidney. The RGD peptide can be linear or cyclic, and can be modified, e.g., glycosylated or methylated to facilitate targeting to specific tissues. For example, a glycosylated RGD peptide can deliver a drug delivery conjugate to a tumor cell expressing civB3 (Haubner et ah, Jour. Nucl. Med., 42:326-336, 2001). Peptides that target markers enriched in proliferating cells can be used. For example, RGD containing peptides and peptidomimetic s can target cancer cells, in particular cells that exhibit an integrin. Thus, one could use RGD peptides, cyclic peptides containing RGD, RGD peptides that include D-amino acids, as well as synthetic RGD mimics. In addition to RGD, one can use other moieties that target the integrin drug delivery agent. Generally, such drug delivery agents can be used to control proliferating cells and angiogeneis. Preferred conjugates of this type of drug delivery agent target PECAM-1, VEGF, or other cancer gene, e.g., a cancer gene described herein.

A "cell permeation peptide" is capable of permeating a cell, e.g., a mammalian cell, such as a human cell. A cell permeation peptide can include a RALA peptide. (Molecular Therapy: Nucleic Acids, 2017, 6, 249-258; J Control Release. 2014, 189:141-9; and Nanomedicine (Lond). 2015, 10(19): 2989-3001). A cell permeation peptide can also include a nuclear localization signal (NLS). For example, a cell permeation peptide can be a bipartite amphipathic peptide, such as MPG, which is derived from the fusion peptide domain of HIV-1 gp41 and the NLS of SV40 large T antigen (Simeoni et al, Nucl. Acids Res. 31:2717-2724, 2003). A cell permeation peptide may form a nano particle.

In one embodiment, a targeting peptide can be an amphipathic a-helical peptide. Exemplary amphipathic a-helical peptides include, but are not limited to, cecropins, lycotoxins, paradaxins, buforin, CPF, bombinin-like peptide (BLP), cathelicidins, ceratotoxins, *S. clava* peptides, hagfish intestinal antimicrobial peptides (HFIAPs), magainines, brevinins-2, dermaseptins, melittins, pleurocidin, H2A peptides, *Xenopus* peptides, esculentinis-1, and caerins. A number of factors will preferably be considered to maintain the integrity of helix stability. For example, a maximum number of helix stabilization residues will be utilized (e.g., leu, ala, or lys), and a minimum number helix destabilization residues will be utilized (e.g., proline, or cyclic monomeric units. The capping residue will be considered (for example Gly is an exemplary N-capping residue and/or C-terminal amidation can be used to provide an extra H-bond to stabilize the helix. Formation of salt bridges between residues with opposite charges, separated by i+3, or i+4 positions can provide stability. For example, cationic residues such as lysine, arginine, homo-arginine, omithine or histidine can form salt bridges with the anionic residues glutamate or aspartate.

Peptide and peptidomimetic drug delivery agents include those having naturally occurring or modified peptides, e.g., D or L peptides; a, 13, or 7 peptides; N-methyl peptides; azapeptides; peptides having one or more amide, i.e., peptide, linkages replaced with one or more urea, thiourea, carbamate, or sulfonyl urea linkages; or cyclic peptides.

The targeting drug delivery agent can be any drug delivery agent that is capable of targeting a specific receptor. Examples are: folate, GalNAc, galactose, mannose, mannose-6P, clusters of sugars such as GalNAc cluster, mannose cluster, galactose cluster, or an apatamer. A cluster is a combination of two or more sugar units. The targeting drug delivery agents also include integrin receptor drug delivery agents, Chemokine receptor drug delivery agents, transferrin, biotin, serotonin receptor drug delivery agents, PSMA, endothelin, GCPII, somatostatin, LDL and HDL drug delivery agents. The drug delivery agents can also be based on nucleic acid, e.g., an aptamer. The aptamer can be unmodified or have any combination of modifications disclosed herein.

Endosomal release agents include imidazoles, poly or oligoimidazoles, PEIs, peptides, fusogenic peptides, polycaboxylates, polyacations, masked oligo or poly cations or anions, acetals, polyacetals, ketals/polyketyals, orthoesters, polymers with masked or unmasked cationic or anionic charges, dendrimers with masked or unmasked cationic or anionic charges.

Drug delivery agent can be a PK modulator (pharmacokinetic modulator). PK modulators include lipophiles, bile acids, steroids, phospholipid analogues, peptides, protein binding agents, PEG, vitamins etc. Exemplary PK modulators include, but are not limited to, cholesterol, fatty acids, cholic acid, lithocholic acid, dialkylglycerides, diacylglyceride, phospholipids, sphingolipids, naproxen, ibuprofen, vitamin E, biotin etc.

Oligonucleotides that comprise a number of phosphorothioate linkages are also known to bind to serum protein, thus short oligonucleotides, e.g., oligonucleotides of about 5 bases, 10 bases, 15 bases or 20 bases, comprising multiple phosphorothioate linkages in the backbone are also amenable to the present invention as drug delivery agents (e.g., as PK modulating drug delivery agents).

In addition, aptamers that bind serum components (e.g., serum proteins) are also amenable to the present disclosure as PK modulating drug delivery agents.

When the drug delivery agent comprises a combination of two or more moieties, e.g., a lipid and a carbohydrate, e.g., a lipid and a peptide, the two or more moieties can all have the same properties, all have different properties, or some moieties have the same properties while others have different properties. For example, a drug delivery agent can have targeting properties, endosomolytic activity, and/or PK modulating properties. For example, one moiety of a drug delivery agent can be hydrophilic, and another can be hydrophobic. In some embodiments, the moieties have different properties.

Drug delivery agents and linkers are described in U.S. Pat. Nos. 7,745,608; 7,626,014; 8,034,921; US 2005/0164235;

and WO 2013/075035. All patents, patent applications, and publications cited herein are fully incorporated by reference in their entirety.

The definition of each symbol in the formula (I) is explained in detail in the following embodiments.

In one embodiment, the partial structure:

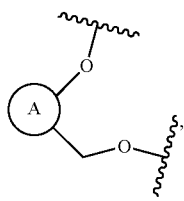

is a partial structure represented by formula (IIA):

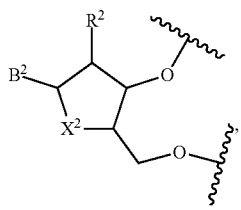

a partial structure represented by formula (IIB):

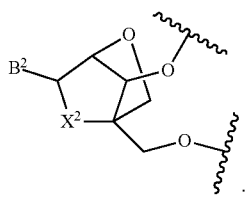

In another embodiment, the partial structure:

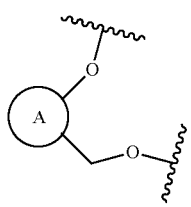

is a partial structure represented by the formula (IIA):

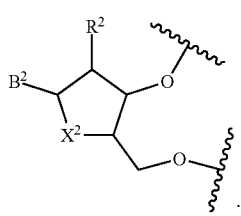

In another embodiment, the partial structure represented by the formula (IIA):

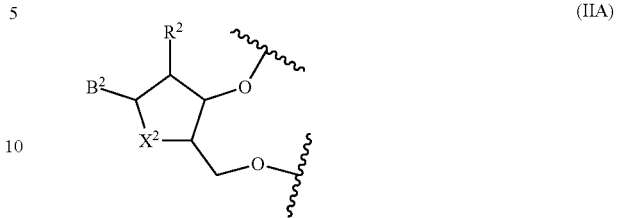

is a partial structure represented by the formula (IIAa):

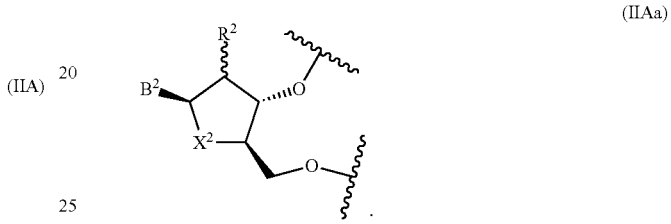

In another embodiment, the partial structure represented by the formula (IIA):

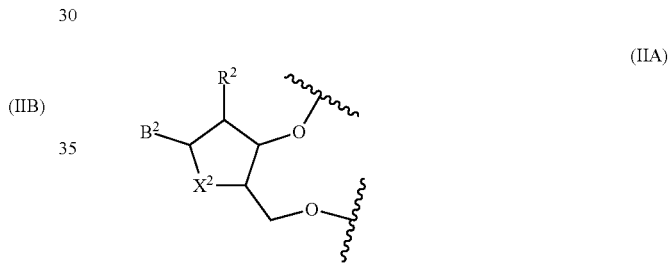

is a partial structure represented by the formula (IIAb):

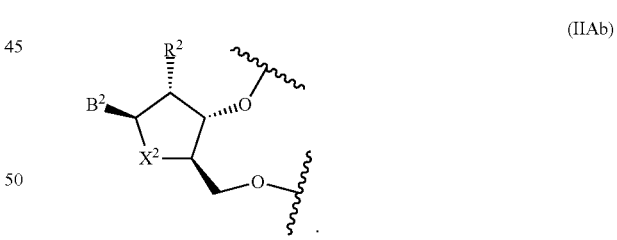

In another embodiment, the partial structure represented by the formula (IIB):

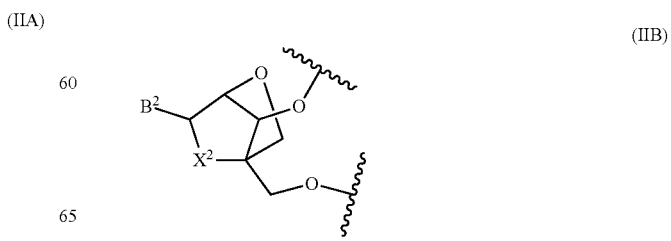

is a partial structure represented by the formula (IIBa):

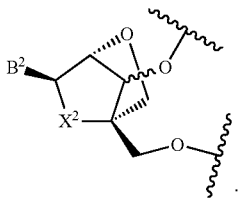
(IIBa)

In another embodiment, the partial structure represented by the formula (IIB):

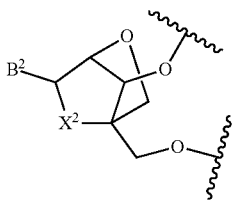
(IIB)

is a partial structure represented by the formula (IIBb):

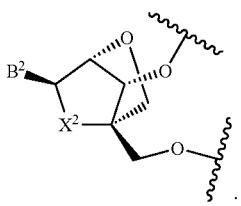
(IIBb)

In another embodiment, the partial structure:

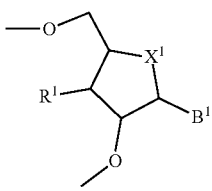

is

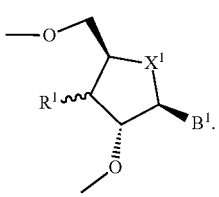

In another embodiment, the partial structure:

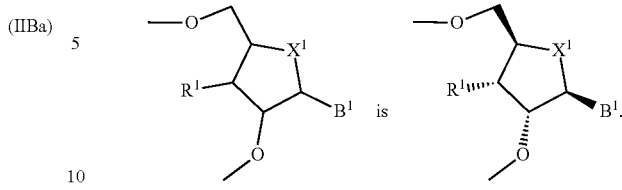

In another embodiment, $R^1$ and $R^2$ are each independently a hydroxy group or a halogen atom.
In another embodiment, $R^1$ and $R^2$ are each independently a hydroxy group or a fluorine atom.
In another embodiment, $R^1$ is a hydroxy group.
In another embodiment, $R^2$ is a hydroxy group or a fluorine atom.
In another embodiment, $B^1$ is a group represented by

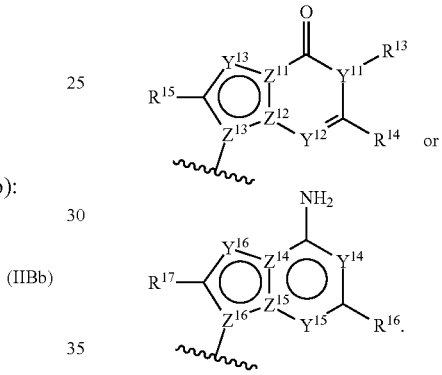

In another embodiment, $R^{13}$, $R^{14}$, $R^{15}$, $R^{16}$ and $R^{17}$ are each independently a hydrogen atom or a substituent.
In another embodiment, $Y^{11}$, $Y^{12}$, $Y^{13}$, $Y^{14}$, $Y^{15}$ and $Y^{16}$ are each independently N or $CR^{1a}$.
In another embodiment, $Z^{11}$, $Z^{12}$, $Z^{13}$, $Z^{14}$, $Z^{15}$ and $Z^{16}$ are each independently N or C.
In another embodiment, $R^{1a}$ is a hydrogen atom or a substituent.
In another embodiment, $R^{13}$ is a hydrogen atom.
In another embodiment, $R^{14}$ is a hydrogen atom or an optionally substituted amino group,
In another embodiment, $R^{14}$ is a hydrogen atom or an amino group.
In another embodiment, $R^{14}$ is a hydrogen atom.
In another embodiment, $R^{15}$ is preferably a hydrogen atom.
In another embodiment, $R^{13}$ and $R^{15}$ are both hydrogen atoms, and $R^{14}$ is a hydrogen atom or an optionally substituted amino group (particularly a hydrogen atom or an amino group).
In another embodiment, $R^{13}$, $R^{14}$ and $R^{15}$ are all hydrogen atoms.
In another embodiment, $R^{16}$ is a hydrogen atom.
In another embodiment, $R^{17}$ is a hydrogen atom.
In another embodiment, $Y^{11}$ is N.
In another embodiment, $Y^{12}$ is N or CH.
In another embodiment, $Y^{12}$ is N.
In another embodiment, $Y^{13}$ is N or $CR^{1a}$ wherein $R^{1a}$ is a halogen atom (e.g., a fluorine atom).
In another embodiment, $Y^{13}$ is N or CF.
In another embodiment, $Y^{13}$ is CF.

In another embodiment, $Y^{11}$ is N, $Y^{12}$ is N or CH, and $Y^{13}$ is N or $CR^{1a}$ wherein $R^{1a}$ is a halogen atom (e.g., a fluorine atom).

In another embodiment, $Y^{11}$ is N, $Y^{12}$ is N or CH, and $Y^{13}$ is N or CF.

In another embodiment, $Y^{11}$ is N, $Y^{12}$ is N, and $Y^{13}$ is CF, $Y^{11}$ is N, $Y^{12}$ is N, and $Y^{13}$ is N, or $Y^{11}$ is N, $Y^{12}$ is CH, and $Y^{13}$ is N.

In another embodiment, $Y^{11}$ is N, $Y^{12}$ is N, and $Y^{13}$ is CF.

In another embodiment, $Y^{14}$ is N.

In another embodiment, $Y^{15}$ is N.

In another embodiment, $Y^{16}$ is N or $CR^{1a}$ wherein $R^{1a}$ is a halogen atom (e.g., a fluorine atom).

In another embodiment, $Y^{16}$ is N or CF.

In another embodiment, $Y^{16}$ is N.

In another embodiment, $Y^{14}$ is N, $Y^{15}$ is N, and $Y^{16}$ is N or $CR^{1a}$ wherein $R^{1a}$ is a halogen atom (e.g., a fluorine atom).

In another embodiment, $Y^{14}$ is N, $Y^{15}$ is N, and $Y^{16}$ is N or CF.

In another embodiment, $Y^{14}$ is N, $Y^{15}$ is N, and $Y^{16}$ is N, or $Y^{14}$ is N, $Y^{15}$ is N, and $Y^{16}$ is CF.

In another embodiment, $Y^{14}$ is N, $Y^{15}$ is N, and $Y^{16}$ is N.

In another embodiment, $Z^{11}$ is C.

In another embodiment, $Z^{12}$ is C.

In another embodiment, $Z^{13}$ is N.

In another embodiment, $Z^{11}$ is C, $Z^{12}$ is C, and $Z^{13}$ is N.

In another embodiment, $Z^{14}$ is preferably C.

In another embodiment, $Z^{15}$ is preferably C.

In another embodiment, $Z^{16}$ is preferably N.

In another embodiment, $Z^{14}$ is C, $Z^{15}$ is C, and $Z^{16}$ is N.

In another embodiment, $B^2$ is a group represented by

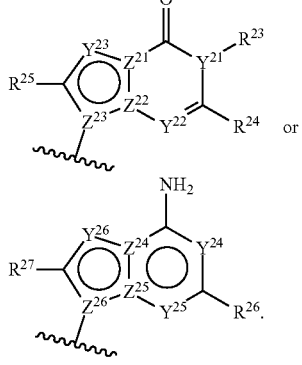

In another embodiment, $R^{23}$, $R^{24}$, $R^{25}$, $R^{26}$ and $R^{27}$ are each independently a hydrogen atom or a substituent.

In another embodiment, $Y^{21}$, $Y^{22}$, $Y^{23}$, $Y^{24}$, $Y^{25}$ and $Y^{26}$ are each independently N or $CR^{2a}$.

In another embodiment, $Z^{21}$, $Z^{22}$, $Z^{23}$, $Z^{24}$, $Z^{25}$ and $Z^{26}$ are each independently N or C.

In another embodiment, $R^{2a}$ is a hydrogen atom or a substituent.

In another embodiment, $R^{23}$ is a hydrogen atom.

In another embodiment, $R^{24}$ is a hydrogen atom or an optionally substituted amino group.

In another embodiment, $R^{24}$ is a hydrogen atom or an amino group.

In another embodiment, $R^{24}$ is a hydrogen atom.

In another embodiment, $R^{25}$ is a hydrogen atom.

In another embodiment, $R^{26}$ is a hydrogen atom.

In another embodiment, $R^{27}$ is a hydrogen atom.

In another embodiment, $Y^{21}$ is N.

In another embodiment, $Y^{22}$ is N.

In another embodiment, $Y^{23}$ is N or $CR^{2a}$ wherein $R^{2a}$ is a halogen atom (e.g., a fluorine atom).

In another embodiment, $Y^{23}$ is N or CF.

In another embodiment, $Y^{23}$ is CF.

In another embodiment, $Y^{21}$ is N, $Y^{22}$ is N, and $Y^{23}$ is N or $CR^{2a}$ wherein $R^{2a}$ is a halogen atom (e.g., a fluorine atom).

In another embodiment, $Y^{21}$ is N, $Y^{22}$ is N, and $Y^{23}$ is N or CF.

In another embodiment, $Y^{21}$ is N, $Y^{22}$ is N, and $Y^{23}$ is CF, or $Y^{21}$ is N, $Y^{22}$ is N, and $Y^{23}$ is N.

In another embodiment, $Y^{21}$ is N, $Y^{22}$ is N, and $Y^{23}$ is CF.

In another embodiment, $Y^{24}$ is N.

In another embodiment, $Y^{25}$ is N or CH.

In another embodiment, $Y^{25}$ is N.

In another embodiment, $Y^{26}$ is N or $CR^{2a}$ wherein $R^{2a}$ is a halogen atom (e.g., a fluorine atom).

In another embodiment, $Y^{26}$ is N or CF.

In another embodiment, $Y^{26}$ is N.

In another embodiment, $Y^{24}$ is N, $Y^{25}$ is N or CH, and $Y^{26}$ is N or $CR^{2a}$ wherein $R^{2a}$ is a halogen atom (e.g., a fluorine atom).

In another embodiment, $Y^{24}$ is N, $Y^{25}$ is N or CH, and $Y^{26}$ is N or CF.

In another embodiment, $Y^{24}$ is N, $Y^{25}$ is N, and $Y^{26}$ is N; $Y^{24}$ is N, $Y^{25}$ is N, and $Y^{26}$ is CF; or $Y^{24}$ is N, $Y^{25}$ is CH, and $Y^{26}$ is N.

In another embodiment, $Y^{24}$ is N, $Y^{25}$ is N, and $Y^{26}$ is N.

In another embodiment, $Z^{21}$ is N or C

In another embodiment, $Z^{21}$ is C.

In another embodiment, $Z^{22}$ is C.

In another embodiment, $Z^{23}$ is N or C.

In another embodiment, $Z^{23}$ is N.

In another embodiment, $Z^{21}$ is N or C, $Z^{22}$ is C, and $Z^{23}$ is N or C.

In another embodiment, $Z^{21}$ is C, $Z^{22}$ is C, and $Z^{23}$ is N, or $Z^{21}$ is N, $Z^{22}$ is C, and $Z^{23}$ is C.

In another embodiment, $Z^{21}$ is C, $Z^{22}$ is C, and $Z^{23}$ is N.

In another embodiment, $Z^{24}$ is N or C.

In another embodiment, $Z^{24}$ is C.

In another embodiment, $Z^{25}$ is C.

In another embodiment, $Z^{26}$ is N or C.

In another embodiment, $Z^{26}$ is N.

In another embodiment, $Z^{24}$ is N or C, $Z^{25}$ is C, and $Z^{26}$ is N or C.

In another embodiment, $Z^{24}$ is C, $Z^{25}$ is C, and $Z^{26}$ is N, or $Z^{24}$ is N, $Z^{25}$ is C, and $Z^{26}$ is C.

In another embodiment, $Z^{24}$ is C, $Z^{25}$ is C, and $Z^{26}$ is N.

In another embodiment, $B^1$ and $B^2$ are each independently

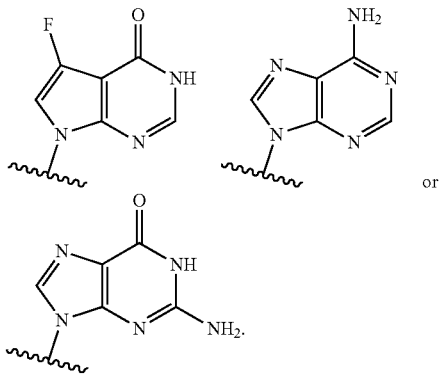

In another embodiment, at least one of $B^1$ and $B^2$ is

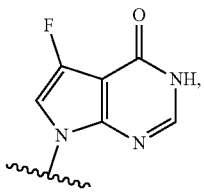 [SMILES: *n1cc(F)c2c(=O)[nH]cnc21]

and in this case, the other is

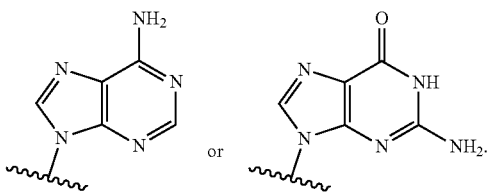 [SMILES: *n1cnc2c(N)ncnc21 ; *n1cnc2c(=O)[nH]c(N)nc21]

In another embodiment, $B^1$ is

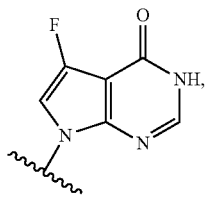 [SMILES: *n1cc(F)c2c(=O)[nH]cnc21]

$B^2$ is

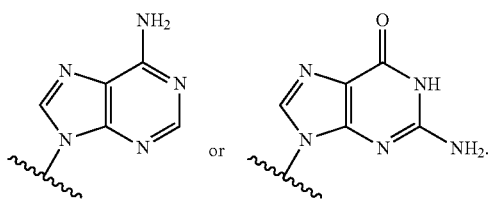 [SMILES: *n1cnc2c(N)ncnc21 ; *n1cnc2c(=O)[nH]c(N)nc21]

In another embodiment,
i) at least one of $Y^{11}$, $Y^{12}$, $Y^{13}$, $Y^{14}$, $Y^{15}$ and $Y^{16}$ is $CR^{18}$,
ii) at least one of $Y^{21}$, $Y^{22}$, $Y^{23}$, $Y^{24}$, $Y^{25}$ and $Y^{26}$ is $CR^{23}$, or
iii) at least one of $Z^{13}$, $Z^{16}$, $Z^{23}$ and $Z^{26}$ is C.

In another embodiment, $X^1$ and $X^2$ are each independently an oxygen atom or a sulfur atom.

In another embodiment, $X^1$ and $X^2$ are both oxygen atoms.

In another embodiment, $Q^1$, $Q^2$, $Q^3$ and $Q^4$ are each independently an oxygen atom or a sulfur atom.

In another embodiment, $Q^1$ is an oxygen atom.

In another embodiment, $Q^3$ is an oxygen atom.

In another embodiment, $Q^1$ and $Q^3$ are both oxygen atoms, and $Q^2$ and $Q^4$ are each independently an oxygen atom or a sulfur atom.

In another embodiment, $Q^1$ is an oxygen atom, $Q^2$ is an oxygen atom or a sulfur atom, $Q^3$ is an oxygen atom, and $Q^4$ is an oxygen atom or a sulfur atom.

In another embodiment, $Q^1$ is an oxygen atom, $Q^2$ is a sulfur atom, $Q^3$ is an oxygen atom, and $Q^4$ is a sulfur atom.

In another embodiment, Compound (I) is a compound represented by the formula (Ia):

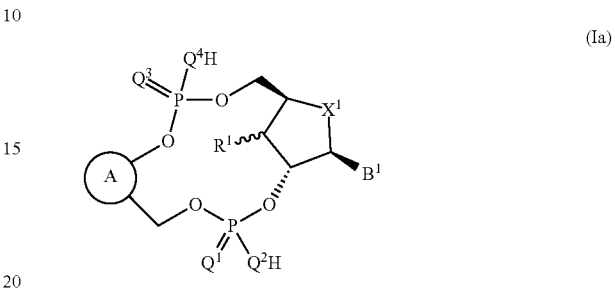

(Ia)

wherein the partial structure:

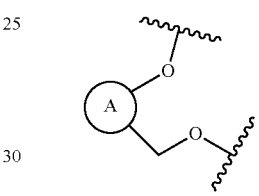

is a partial structure represented by the formula (IIAa):

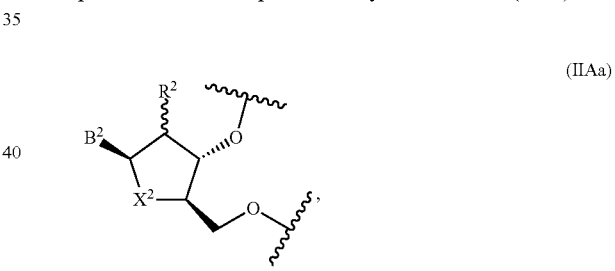

(IIAa)

or a partial structure represented by the formula (IIBa):

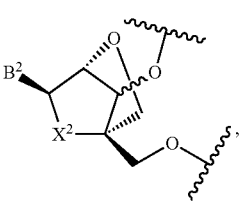

(IIBa)

or a salt thereof (hereinafter sometimes to be referred to as compound (Ia)).

In another embodiment, Compound (I) is a compound represented by the formula (Ib):

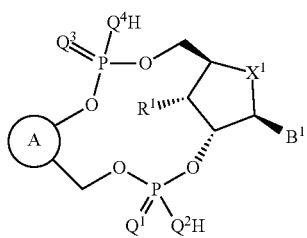
(Ib)

wherein the partial structure:

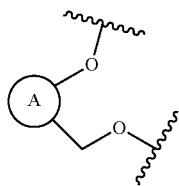

is a partial structure represented by the formula (IIAb):

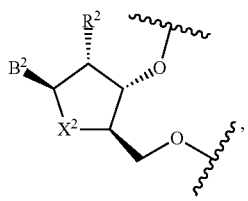
(IIAb)

or a partial structure represented by the formula (IIBb):

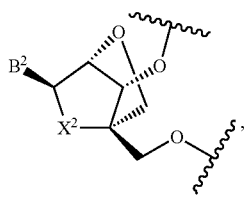
(IIBb)

or a salt thereof (hereinafter sometimes to be referred to as compound (Ib)).

Examples of compound (I) include the following compounds.

Compound A1

Compound A1 is a compound having formula (I), wherein the partial structure:

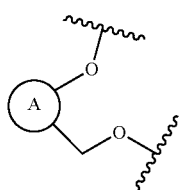

is a partial structure represented by the formula (IIA):

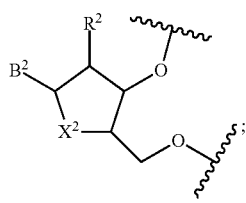
(IIA)

$R^1$ is a hydroxy group;
$R^2$ is a hydroxy group or a halogen atom (e.g., a fluorine atom);
$B^1$ is a group represented by

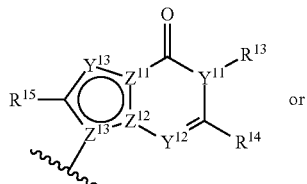

or

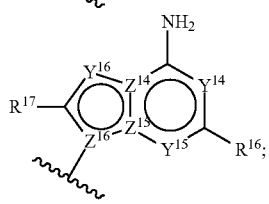

$R^{13}$ is a hydrogen atom;
$R^{14}$ is a hydrogen atom or an optionally substituted amino group;
$R^{15}$ is a hydrogen atom;
$R^{16}$ is a hydrogen atom;
$R^{17}$ is a hydrogen atom;
$Y^{11}$ is N;
$Y^{12}$ is N or CH;
$Y^{13}$ is N or $CR^{1a}$ wherein $R^{1a}$ is a halogen atom (e.g., a fluorine atom);
$Y^{14}$ is N;
$Y^{15}$ is N;
$Y^{16}$ is N or $CR^{1a}$ wherein $R^{1a}$ is a halogen atom (e.g., a fluorine atom);
$Z^{11}$ is C;
$Z^{12}$ is C;
$Z^{13}$ is N;
$Z^{14}$ is C;
$Z^{15}$ is C;
$Z^{16}$ is N;
$B^2$ is a group represented by

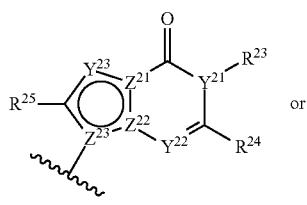

or

-continued

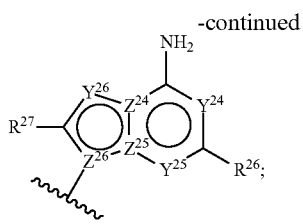

R²³ is a hydrogen atom;
R²⁴ is a hydrogen atom;
R²⁵ is a hydrogen atom;
R²⁶ is a hydrogen atom;
R²⁷ is a hydrogen atom;
Y²¹ is N;
Y²² is N;
Y²³ is N or CR²ᵃ wherein R²ᵃ is a halogen atom (e.g., a fluorine atom);
Y²⁴ is N;
Y²⁵ is N or CH;
Y²⁶ is N or CR²ᵃ wherein R²ᵃ is a halogen atom (e.g., a fluorine atom);
Z²¹ is N or C;
Z²² is C;
Z²³ is N or C;
Z²⁴ is N or C;
Z²⁵ is C;
Z²⁶ is N or C;
provided that
i) at least one of Y¹¹, Y¹², Y¹³, Y¹⁴, Y¹⁵ and Y¹⁶ is CR¹ᵃ,
ii) at least one of Y²¹, Y²², Y²³, Y²⁴, Y²⁵ and Y²⁶ is CR²ᵃ, or
iii) at least one of Z¹³, Z¹⁶, Z²³ and Z²⁶ is C;
X¹ and X² are each independently an oxygen atom or a sulfur atom; and
Q¹, Q², Q³ and Q⁴ are each independently an oxygen atom or a sulfur atom.

Compound B1

Compound B1 is a compound having formula (I), wherein the partial structure:

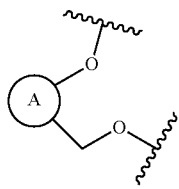

is a partial structure represented by the formula (IIA):

(IIA)

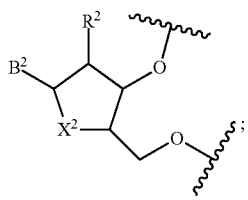

R¹ is a hydroxy group;
R² is a hydroxy group or a fluorine atom;

B¹ is a group represented by

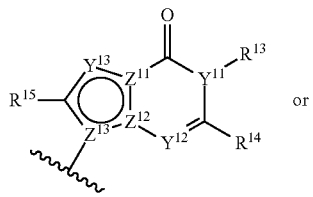

or

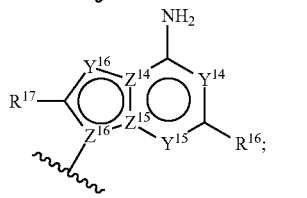

R¹³ is a hydrogen atom;
R¹⁴ is a hydrogen atom or an amino group;
R¹⁵ is a hydrogen atom;
R¹⁶ is a hydrogen atom;
R¹⁷ is a hydrogen atom;
Y¹¹ is N;
Y¹² is N or CH;
Y¹³ is N or CF;
(e.g., Y¹¹ is N, Y¹² is N, and Y¹³ is CF; Y¹¹ is N, Y¹² is N, and Y¹³ is N; or Y¹¹ is N, Y¹² is CH, and Y¹³ is N);
Y¹⁴ is N;
Y¹⁵ is N;
Y¹⁶ is N or CF;
(e.g., Y¹⁴ is N, Y¹⁵ is N, and Y¹⁶ is N; or Y¹⁴ is N, Y¹⁵ is N, and Y¹⁶ is CF);
Z¹¹ is C;
Z¹² is C;
Z¹³ is N;
Z¹⁴ is C;
Z¹⁵ is C;
Z¹⁶ is N;

B² is a group represented by

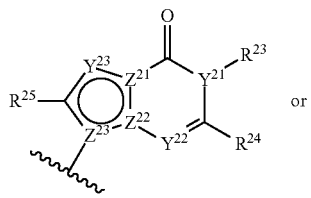

or

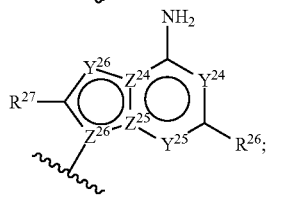

R²³ is a hydrogen atom;
R²⁴ is a hydrogen atom;
R²⁵ is a hydrogen atom;
R²⁶ is a hydrogen atom;
R²⁷ is a hydrogen atom;
Y²¹ is N;
Y²² is N;
Y²³ is N or CF;
(e.g., Y²¹ is N, Y²² is N, and Y²³ is CF; or Y²¹ is N, Y²² is N, and Y²³ is N);

$Y^{24}$ is N;
$Y^{25}$ is N or CH;
$Y^{26}$ is N or CF;
(e.g., $Y^{24}$ is N, $Y^{25}$ is N, and $Y^{26}$ is N; $Y^{24}$ is N, $Y^{25}$ is N, and $Y^{26}$ is CF; or $Y^{24}$ is N, $Y^{25}$ is CH, and $Y^{26}$ is N);
$Z^{21}$ is N or C;
$Z^{22}$ is C;
$Z^{23}$ is N or C;
(e.g., $Z^{21}$ is C, $Z^{22}$ is C, and $Z^{23}$ is N; or $Z^{21}$ is N, $Z^{22}$ is C, and $Z^{23}$ is C);
$Z^{24}$ is N or C;
$Z^{25}$ is C;
$Z^{26}$ is N or C;
(e.g., $Z^{24}$ is C, $Z^{25}$ is C, and $Z^{26}$ is N; or $Z^{24}$ is N, $Z^{25}$ is C, and $Z^{26}$ is C) provided that
i) at least one of $Y^{11}$, $Y^{12}$, $Y^{13}$, $Y^{14}$, $Y^{15}$ and $Y^{16}$ is $CR^{18}$,
ii) at least one of $Y^{21}$, $Y^{22}$, $Y^{23}$, $Y^{24}$, $Y^{25}$ and $Y^{26}$ is $CR^{23}$, or
iii) at least one of $Z^{13}$, $Z^{16}$, $Z^{23}$ and $Z^{26}$ is C;
$X^1$ and $X^2$ are both oxygen atoms;
$Q^1$ is an oxygen atom;
$Q^2$ is an oxygen atom or a sulfur atom;
$Q^3$ is an oxygen atom; and
$Q^4$ is an oxygen atom or a sulfur atom.

Compound A1-a

Compound A1-a is a compound having formula (Ia) wherein the partial structure:

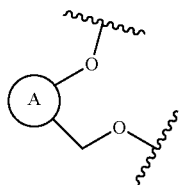

is a partial structure represented by the formula (IIAa):

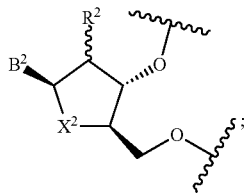

(IIAa)

$R^1$ is a hydroxy group;
$R^2$ is a hydroxy group or a halogen atom (preferably a fluorine atom);
$B^1$ is a group represented by

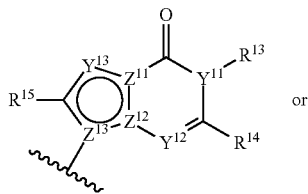

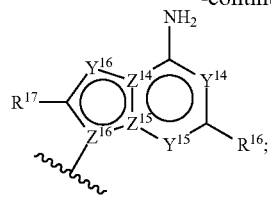

$R^{13}$ is a hydrogen atom;
$R^{14}$ is a hydrogen atom or an optionally substituted amino group;
$R^{15}$ is a hydrogen atom;
$R^{16}$ is a hydrogen atom;
$R^{17}$ is a hydrogen atom;
$Y^{11}$ is N;
$Y^{12}$ is N or CH;
$Y^{13}$ is N or $CR^{1a}$ wherein $R^{1a}$ is a halogen atom (e.g., a fluorine atom);
$Y^{14}$ is N;
$Y^{15}$ is N;
$Y^{16}$ is N or $CR^{1a}$ wherein $R^{1a}$ is a halogen atom (e.g., a fluorine atom);
$Z^{11}$ is C;
$Z^{12}$ is C;
$Z^{13}$ is N;
$Z^{14}$ is C;
$Z^{15}$ is C;
$Z^{16}$ is N;
$B^2$ is a group represented by

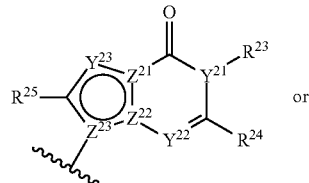

or

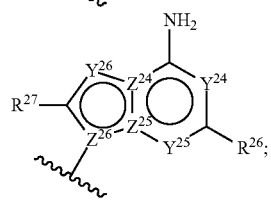

$R^{23}$ is a hydrogen atom;
$R^{24}$ is a hydrogen atom;
$R^{25}$ is a hydrogen atom;
$R^{26}$ is a hydrogen atom;
$R^{27}$ is a hydrogen atom;
$Y^{21}$ is N;
$Y^{22}$ is N;
$Y^{23}$ is N or $CR^{2a}$ wherein $R^{2a}$ is a halogen atom (e.g., a fluorine atom);
$Y^{24}$ is N;
$Y^{25}$ is N or CH;
$Y^{26}$ is N or $CR^{2a}$ wherein $R^{2a}$ is a halogen atom (e.g., a fluorine atom);
$Z^{21}$ is N or C;
$Z^{22}$ is C;
$Z^{23}$ is N or C;
$Z^{24}$ is N or C;

$Z^{25}$ is C;
$Z^{26}$ is N or C;
provided that
i) at least one of $Y^{11}$, $Y^{12}$, $Y^{13}$, $Y^{14}$, $Y^{15}$ and $Y^{16}$ is $CR^{1a}$,
ii) at least one of $Y^{21}$, $Y^{22}$, $Y^{23}$, $Y^{24}$, $Y^{25}$ and $Y^{26}$ is $CR^{2a}$, or
iii) at least one of $Z^{13}$, $Z^{16}$, $Z^{23}$ and $Z^{26}$ is C;
$X^1$ and $X^2$ are each independently an oxygen atom or a sulfur atom; and
$Q^1$, $Q^2$, $Q^3$ and $Q^4$ are each independently an oxygen atom or a sulfur atom.

Compound B1-a

Compound B1-a is a compound having formula (Ia) wherein the partial structure:

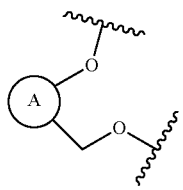

is a partial structure represented by the formula (IIAa):

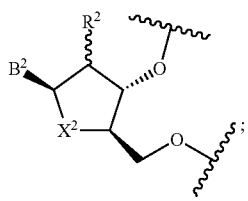

(IIAa)

$R^1$ is a hydroxy group;
R is a hydroxy group or a fluorine atom;
$B^1$ is a group represented by

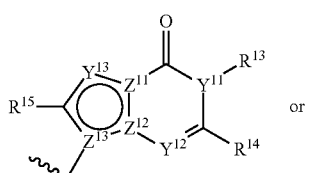

or

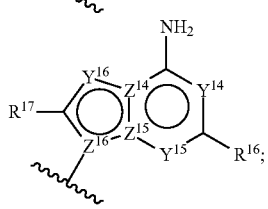

$R^{13}$ is a hydrogen atom;
$R^{14}$ is a hydrogen atom or an amino group;
$R^{15}$ is a hydrogen atom;
$R^{16}$ is a hydrogen atom;
$R^{17}$ is a hydrogen atom;
$Y^{11}$ is N;
$Y^{12}$ is N or CH;
$Y^{13}$ is N or CF;
(e.g., $Y^{11}$ is N, $Y^{12}$ is N, and $Y^{13}$ is CF; $Y^{11}$ is N, $Y^{12}$ is N, and $Y^{13}$ is N; or $Y^{11}$ is N, $Y^{12}$ is CH, and $Y^{13}$ is N);

$Y^{14}$ is N;
$Y^{15}$ is N;
$Y^{16}$ is N or CF;
(e.g., $Y^{14}$ is N, $Y^{15}$ is N, and $Y^{16}$ is N; or $Y^{14}$ is N, $Y^{15}$ is N, and $Y^{16}$ is CF);
$Z^{11}$ is C;
$Z^{12}$ is C;
$Z^{13}$ is N;
$Z^{14}$ is C;
$Z^{15}$ is C;
$Z^{16}$ is N;
$B^2$ is a group represented by

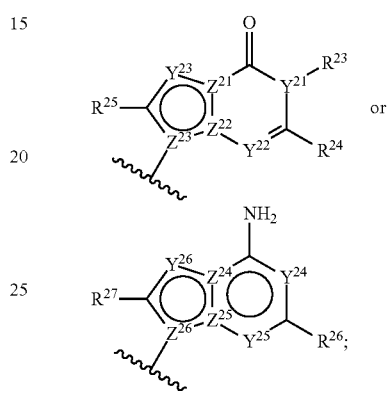

$R^{23}$ is a hydrogen atom;
$R^{24}$ is a hydrogen atom;
$R^{25}$ is a hydrogen atom;
$R^{26}$ is a hydrogen atom;
$R^{27}$ is a hydrogen atom;
$Y^{21}$ is N;
$Y^{22}$ is N;
$Y^{23}$ is N or CF;
(e.g., $Y^{21}$ is N, $Y^{22}$ is N, and $Y^{23}$ is CF; or $Y^{21}$ is N, $Y^{22}$ is N, and $Y^{23}$ is N)
$Y^{24}$ is N;
$Y^{25}$ is N or CH;
$Y^{26}$ is N or CF;
(e.g., $Y^{24}$ is N, $Y^{25}$ is N, and $Y^{26}$ is N; $Y^{24}$ is N, $Y^{25}$ is N, and $Y^{26}$ is CF; or $Y^{24}$ is N, $Y^{25}$ is CH, and $Y^{26}$ is N);
$Z^{21}$ is N or C;
$Z^{22}$ is C;
$Z^{23}$ is N or C;
(e.g., $Z^{21}$ is C, $Z^{22}$ is C, and $Z^{23}$ is N; or $Z^{21}$ is N, $Z^{22}$ is C, and $Z^{23}$ is C);
$Z^{24}$ is N or C;
$Z^{25}$ is C;
$Z^{26}$ is N or C;
(e.g., $Z^{24}$ is C, $Z^{25}$ is C, and $Z^{26}$ is N, or $Z^{24}$ is N, $Z^{25}$ is C, and $Z^{26}$ is C); provided that
i) at least one of $Y^{11}$, $Y^{12}$, $Y^{13}$, $Y^{14}$, $Y^{15}$ and $Y^{16}$ is $CR^{1a}$,
ii) at least one of $Y^{21}$, $Y^{22}$, $Y^{23}$, $Y^{24}$, $Y^{25}$ and $Y^{26}$ is $CR^{2a}$, or
iii) at least one of $Z^{13}$, $Z^{16}$, $Z^{23}$ and $Z^{26}$ is C;
$X^1$ and $X^2$ are both oxygen atoms;
$Q^1$ is an oxygen atom;
$Q^2$ is an oxygen atom or a sulfur atom;
$Q^3$ is an oxygen atom; and
$Q^4$ is an oxygen atom or a sulfur atom.

Compound A1-b

Compound A1-b is a compound having formula (Ib) wherein the partial structure:

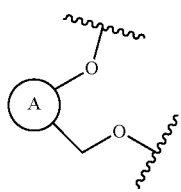

is a partial structure represented by the formula (IIAb):

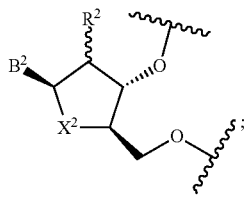

(IIAb)

$R^1$ is a hydroxy group;
$R^2$ is a hydroxy group or a halogen atom (e.g., a fluorine atom);
$B^1$ is a group represented by

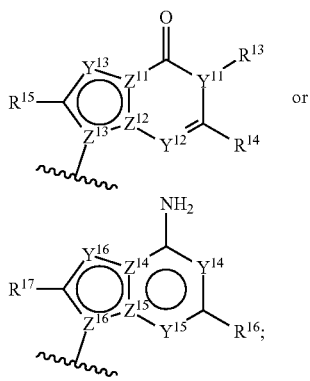

or $R^{13}$ is a hydrogen atom;
$R^{14}$ is a hydrogen atom or an optionally substituted amino group;
$R^{15}$ is a hydrogen atom;
$R^{16}$ is a hydrogen atom;
$R^{17}$ is a hydrogen atom;
$Y^{11}$ is N;
$Y^{12}$ is N or CH;
$Y^{13}$ is N or $CR^{1a}$ wherein $R^{1a}$ is a halogen atom (e.g., a fluorine atom);
$Y^{14}$ is N;
$Y^{15}$ is N;
$Y^{16}$ is N or $CR^{1a}$ wherein $R^{1a}$ is a halogen atom (e.g., a fluorine atom);
$Z^{11}$ is C;
$Z^{12}$ is C;
$Z^{13}$ is N;
$Z^{14}$ is C;
$Z^{15}$ is C;
$Z^{16}$ is N;

$B^2$ is a group represented by

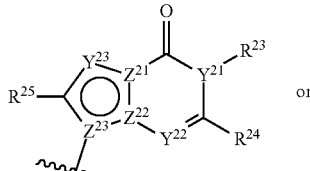

or

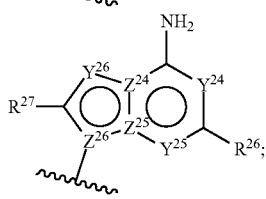

$R^{23}$ is a hydrogen atom;
$R^{24}$ is a hydrogen atom;
$R^{25}$ is a hydrogen atom;
$R^{26}$ is a hydrogen atom;
$R^{27}$ is a hydrogen atom;
$Y^{21}$ is N;
$Y^{22}$ is N;
$Y^{23}$ is N or $CR^{2a}$ wherein $R^{2a}$ is a halogen atom (e.g., a fluorine atom);
$Y^{24}$ is N;
$Y^{25}$ is N or CH;
$Y^{26}$ is N or $CR^{2a}$ wherein $R^{2a}$ is a halogen atom (e.g., a fluorine atom);
$Z^{21}$ is N or C;
$Z^{22}$ is C;
$Z^{23}$ is N or C;
$Z^{24}$ is N or C;
$Z^{25}$ is C;
$Z^{26}$ is N or C;
provided that
  i) at least one of $Y^{11}$, $Y^{12}$, $Y^{13}$, $Y^{14}$, $Y^{15}$ and $Y^{16}$ is $CR^{1a}$,
  ii) at least one of $Y^{21}$, $Y^{22}$, $Y^{23}$, $Y^{24}$, $Y^{25}$ and $Y^{26}$ is $CR^{2a}$, or
  iii) at least one of $Z^{13}$, $Z^{16}$, $Z^{23}$ and $Z^{26}$ is C;
$X^1$ and $X^2$ are each independently an oxygen atom or a sulfur atom; and
$Q^1$, $Q^2$, $Q^3$ and $Q^4$ are each independently an oxygen atom or a sulfur atom.

Compound B1-b

Compound B1-b is a compound having formula (Ib) wherein the partial structure:

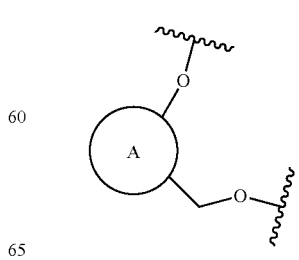

is a partial structure represented by the formula (IIAb):

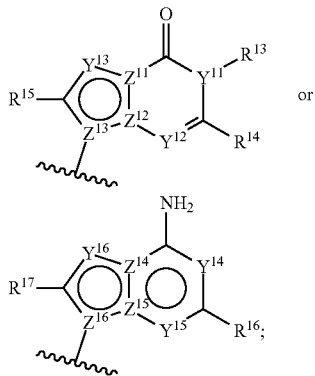
(IIAb)

$R^1$ is a hydroxy group;
R is a hydroxy group or a fluorine atom;
$B^1$ is a group represented by

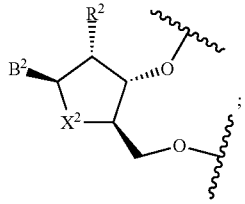

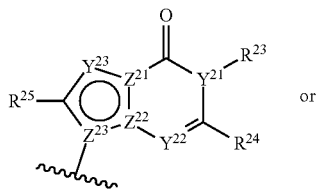

$R^{13}$ is a hydrogen atom;
$R^{14}$ is a hydrogen atom or an amino group;
$R^{15}$ is a hydrogen atom;
$R^{16}$ is a hydrogen atom;
$R^{17}$ is a hydrogen atom;
$Y^{11}$ is N;
$Y^{12}$ is N or CH;
$Y^{13}$ is N or CF;
(e.g., $Y^{11}$ is N, $Y^{12}$ is N, and $Y^{13}$ is CF; $Y^{11}$ is N, $Y^{12}$ is N, and $Y^{13}$ is N; or $Y^{11}$ is N, $Y^{12}$ is CH, and $Y^{13}$ is N);
$Y^{14}$ is N;
$Y^{15}$ is N;
$Y^{16}$ is N or CF;
(e.g., $Y^{14}$ is N, $Y^{15}$ is N, and $Y^{16}$ is N; or $Y^{14}$ is N, $Y^{15}$ is N, and $Y^{16}$ is CF);
$Z^{11}$ is C;
$Z^{12}$ is C;
$Z^{13}$ is N;
$Z^{14}$ is C;
$Z^{15}$ is C;
$Z^{16}$ is N;
$B^2$ is a group represented by

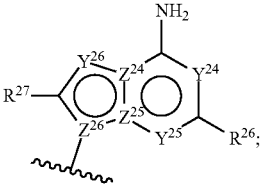

$R^{23}$ is a hydrogen atom;
$R^{24}$ is a hydrogen atom;
$R^{25}$ is a hydrogen atom;
$R^{26}$ is a hydrogen atom;
$R^{27}$ is a hydrogen atom;
$Y^{21}$ is N;
$Y^{22}$ is N;
$Y^{23}$ is N or CF;
(e.g., $Y^{21}$ is N, $Y^{22}$ is N, and $Y^{23}$ is CF; or $Y^{21}$ is N, $Y^{22}$ is N, and $Y^{23}$ is N);
$Y^{24}$ is N;
$Y^{25}$ is N or CH;
$Y^{26}$ is N or CF;
(e.g., $Y^{24}$ is N, $Y^{25}$ is N, and $Y^{26}$ is N; $Y^{24}$ is N, $Y^{25}$ is N, and $Y^{26}$ is CF; or $Y^{24}$ is N, $Y^{25}$ is CH, and $Y^{26}$ is N);
$Z^{21}$ is N or C;
$Z^{22}$ is C;
$Z^{23}$ is N or C;
(e.g., $Z^{21}$ is C, $Z^{22}$ is C, and $Z^{23}$ is N; or $Z^{21}$ is N, $Z^{22}$ is C, and $Z^{23}$ is C);
$Z^{24}$ is N or C;
$Z^{25}$ is C;
$Z^{26}$ is N or C;
(e.g., $Z^{24}$ is C, $Z^{25}$ is C, and $Z^{26}$ is N; or $Z^{24}$ is N, $Z^{25}$ is C, and $Z^{26}$ is C); provided that
i) at least one of $Y^{11}$, $Y^{12}$, $Y^{13}$, $Y^{14}$, $Y^{15}$ and $Y^{16}$ is $CR^{18}$,
ii) at least one of $Y^{21}$, $Y^{22}$, $Y^{23}$, $Y^{24}$, $Y^{25}$ and $Y^{26}$ is $CR^{2a}$, or
iii) at least one of $Z^{13}$, $Z^{16}$, $Z^{23}$ and $Z^{26}$ is C;
$X^1$ and $X^2$ are both oxygen atoms;
$Q^1$ is an oxygen atom;
$Q^2$ is an oxygen atom or a sulfur atom;
$Q^3$ is an oxygen atom; and
$Q^4$ is an oxygen atom or a sulfur atom.

Compound A2

Compound A2 is a compound having formula (I) wherein the partial structure:

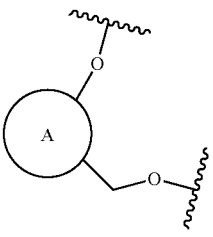

is a partial structure represented by the formula (IIA)

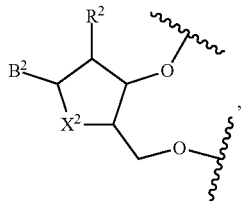
(IIA)

or
a partial structure represented by the formula (IIB):

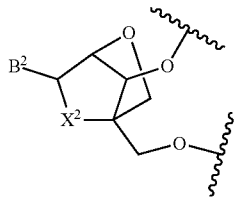
(IIB)

$R^1$ is a hydroxy group;
$R^2$ is a hydroxy group or a halogen atom (e.g., a fluorine atom);
$B^1$ is a group represented by

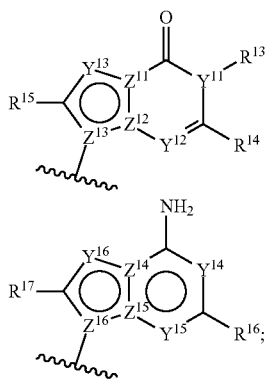

$R^{13}$ is a hydrogen atom;
$R^{14}$ is a hydrogen atom or an optionally substituted amino group;
$R^{15}$ is a hydrogen atom;
$R^{16}$ is a hydrogen atom;
$R^{17}$ is a hydrogen atom;
$Y^{11}$ is N;
$Y^{12}$ is N or CH;
$Y^{13}$ is N or $CR^{1a}$ wherein $R^{1a}$ is a halogen atom (e.g., a fluorine atom);
$Y^{14}$ is N;
$Y^{15}$ is N;
$Y^{16}$ is N or $CR^{1a}$ wherein $R^{1a}$ is a halogen atom (e.g., a fluorine atom);
$Z^{11}$ is C;
$Z^{12}$ is C;
$Z^{13}$ is N;
$Z^{14}$ is C;
$Z^{15}$ is C;
$Z^{16}$ is N;
$B^2$ is a group represented by

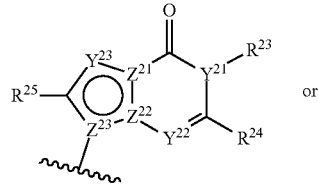 or

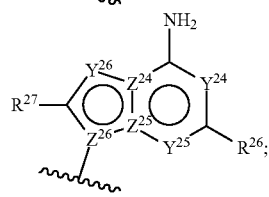

$R^{23}$ is a hydrogen atom;
$R^{24}$ is a hydrogen atom or an optionally substituted amino group;
$R^{25}$ is a hydrogen atom;
$R^{26}$ is a hydrogen atom;
$R^{27}$ is a hydrogen atom;
$Y^{21}$ is N;
$Y^{22}$ is N;
$Y^{23}$ is N or $CR^{2a}$ wherein $R^{2a}$ is a halogen atom (e.g., a fluorine atom);
$Y^{24}$ is N;
$Y^{25}$ is N or CH;
$Y^{26}$ is N or $CR^{2a}$ wherein $R^{2a}$ is a halogen atom (e.g., a fluorine atom);
$Z^{21}$ is N or C;
$Z^{22}$ is C;
$Z^{23}$ is N or C;
$Z^{24}$ is N or C;
$Z^{25}$ is C;
$Z^{26}$ is N or C;
provided that
i) at least one of $Y^{11}$, $Y^{12}$, $Y^{13}$, $Y^{14}$, $Y^{15}$ and $Y^{16}$ is $CR^{1a}$,
ii) at least one of $Y^{21}$, $Y^{22}$, $Y^{23}$, $Y^{24}$, $Y^{25}$ and $Y^{26}$ is $CR^{2a}$, or
iii) at least one of $Z^{13}$, $Z^{16}$, $Z^{23}$ and $Z^{26}$ is C;
$X^1$ and $X^2$ are each independently an oxygen atom or a sulfur atom; and
$Q^1$, $Q^2$, $Q^3$, and $Q^4$ are each independently an oxygen atom or a sulfur atom.

Compound B2

Compound B2 is a compound having formula (I) wherein the partial structure:

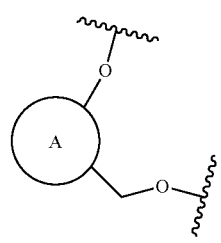

is a partial structure represented by the formula (IIA):

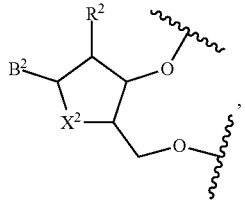
(IIA)

or
a partial structure represented by the formula (IIB):

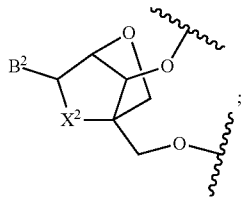
(IIB)

$R^1$ is a hydroxy group;
$R^2$ is a hydroxy group or a fluorine atom;
$B^1$ is a group represented by

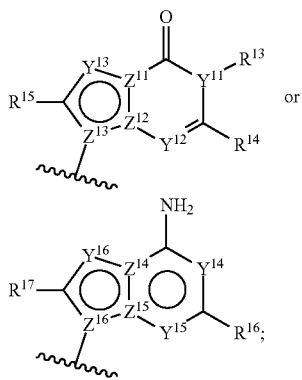

$R^{13}$ is a hydrogen atom;
$R^{14}$ is a hydrogen atom or an amino group;
$R^{15}$ is a hydrogen atom;
$R^{16}$ is a hydrogen atom;
$R^{17}$ is a hydrogen atom;
$Y^{11}$ is N;
$Y^{12}$ is N or CH;
$Y^{13}$ is N or CF;
(e.g., $Y^{11}$ is N, $Y^{12}$ is N, and $Y^{13}$ is CF; $Y^{11}$ is N, $Y^{12}$ is N, and $Y^{13}$ is N; or $Y^{11}$ is N, $Y^{12}$ is CH, and $Y^{13}$ is N);
$Y^{14}$ is N;
$Y^{15}$ is N;
$Y^{16}$ is N or CF;
(e.g., $Y^{14}$ is N, $Y^1$ is N, and $Y^{16}$ is N; or $Y^{14}$ is N, $Y^{15}$ is N, and $Y^{16}$ is CF);
$Z^{11}$ is C;
$Z^{12}$ is C;
$Z^{13}$ is N;
$Z^{14}$ is C;
$Z^{15}$ is C;
$Z^{16}$ is N;
$B^2$ is a group represented by

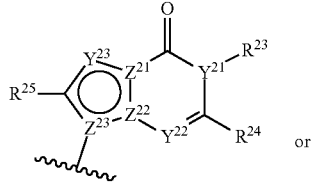
or

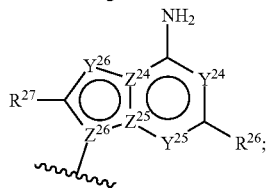

$R^{23}$ is a hydrogen atom;
$R^{24}$ is a hydrogen atom or an amino group;
$R^{25}$ is a hydrogen atom;
$R^{26}$ is a hydrogen atom;
$R^{27}$ is a hydrogen atom;
$Y^{21}$ is N;
$Y^{22}$ is N;
$Y^{23}$ is N or CF;
(e.g., $Y^{21}$ is N, $Y^{22}$ is N, and $Y^{23}$ is CF; or $Y^{21}$ is N, $Y^{22}$ is N, and $Y^{23}$ is N);
$Y^{24}$ is N;
$Y^{25}$ is N or CH;
$Y^{26}$ is N or CF;
(e.g., $Y^{24}$ is N, $Y^{25}$ is N, and $Y^{26}$ is N; $Y^{24}$ is N, $Y^{25}$ is N, and $Y^{26}$ is CF, or $Y^{24}$ is N, $Y^{25}$ is CH, and $Y^{26}$ is N);
$Z^{21}$ is N or C;
$Z^{22}$ is C;
$Z^{23}$ is N or C;
(e.g., $Z^{21}$ is C, $Z^{22}$ is C, and $Z^{23}$ is N; or $Z^{21}$ is N, $Z^{22}$ is C, and $Z^{23}$ is C);
$Z^{24}$ is N or C;
$Z^{25}$ is C;
$Z^{26}$ is N or C;
(e.g., $Z^{24}$ is C, $Z^{25}$ is C, and $Z^{26}$ is N; or $Z^{24}$ is N, $Z^{25}$ is C, and $Z^{26}$ is C) provided that
i) at least one of $Y^{11}$, $Y^{12}$, $Y^{13}$, $Y^{14}$, $Y^{15}$ and $Y^{16}$ is $CR^{1a}$,
ii) at least one of $Y^{21}$, $Y^{22}$, $Y^{23}$, $Y^{24}$, $Y^{25}$ and $Y^{26}$ is $CR^{2a}$, or
iii) at least one of $Z^{13}$, $Z^{16}$, $Z^{23}$ and $Z^{26}$ is C;
$X^1$ and $X^2$ are both oxygen atoms;
$Q^1$ is an oxygen atom;
$Q^2$ is an oxygen atom or a sulfur atom;
$Q^3$ is an oxygen atom; and
$Q^4$ is an oxygen atom or a sulfur atom.

Compound A2-a
Compound A2-a is a compound having formula (Ia) wherein the partial structure:

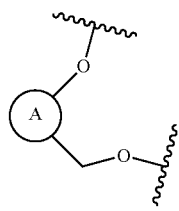

is a partial structure represented by the formula (IIAa):

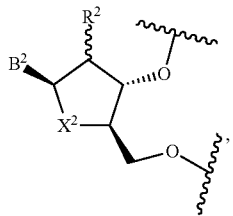
(IIAa)

or
a partial structure represented by the formula (IIBa):

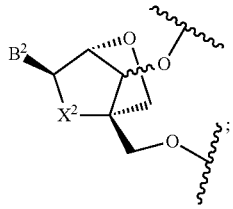
(IIBa)

$R^1$ is a hydroxy group;
$R^2$ is a hydroxy group or a halogen atom (e.g., a fluorine atom);
$B^1$ is a group represented by

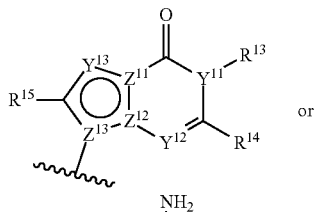
or
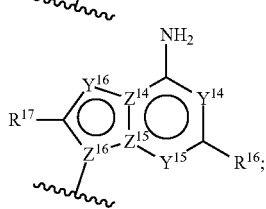

$R^{13}$ is a hydrogen atom;
$R^{14}$ is a hydrogen atom or an optionally substituted amino group;
$R^{15}$ is a hydrogen atom;
$R^{16}$ is a hydrogen atom;
$R^{17}$ is a hydrogen atom;
$Y^{11}$ is N;
$Y^{12}$ is N or CH;
$Y^{13}$ is N or $CR^{1a}$ wherein $R^{1a}$ is a halogen atom (e.g., a fluorine atom);
$Y^{14}$ is N;
$Y^{15}$ is N;
$Y^{16}$ is N or $CR^{1a}$ wherein $R^{1a}$ is a halogen atom (e.g., a fluorine atom);
$Z^{11}$ is C;
$Z^{12}$ is C;
$Z^{13}$ is N;
$Z^{14}$ is C;
$Z^{15}$ is C;
$Z^{16}$ is N;
$B^2$ is a group represented by

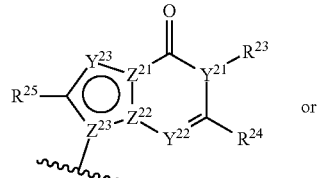
or
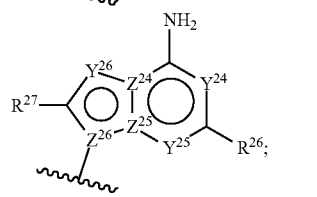

$R^{23}$ is a hydrogen atom;
$R^{24}$ is a hydrogen atom or an optionally substituted amino group;
$R^{25}$ is a hydrogen atom;
$R^{26}$ is a hydrogen atom;
$R^{27}$ is a hydrogen atom;
$Y^{21}$ is N;
$Y^{22}$ is N;
$Y^{23}$ is N or $CR^{2a}$ wherein $R^{2a}$ is a halogen atom (e.g., a fluorine atom);
$Y^{24}$ is N;
$Y^{25}$ is N or CH;
$Y^{26}$ is N or $CR^{2a}$ wherein $R^{2a}$ is a halogen atom (e.g., a fluorine atom);
$Z^{21}$ is N or C;
$Z^{22}$ is C;
$Z^{23}$ is N or C;
$Z^{24}$ is N or C;
$Z^{25}$ is C;
$Z^{26}$ is N or C;
provided that
i) at least one of $Y^{11}$, $Y^{12}$, $Y^{13}$, $Y^{14}$, $Y^{15}$ and $Y^{16}$ is $CR^{1a}$,
ii) at least one of $Y^{21}$, $Y^{22}$, $Y^{23}$, $Y^{24}$, $Y^{25}$ and $Y^{26}$ is $CR^{2a}$, or
iii) at least one of $Z^{13}$, $Z^{16}$, $Z^{23}$ and $Z^{26}$ is C;
$X^1$ and $X^2$ are each independently an oxygen atom or a sulfur atom; and
$Q^1$, $Q^2$, $Q^3$ and $Q^4$ are each independently an oxygen atom or a sulfur atom.

Compound B2-a
Compound B2-a is a compound having formula (I) wherein the partial structure:

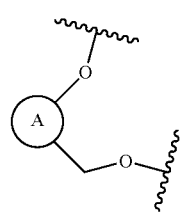

is a partial structure represented by the formula (IIAa):

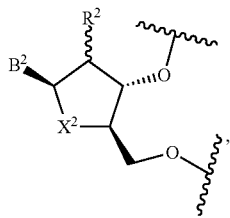

(IIAa)

or a partial structure represented by the formula (IIBa):

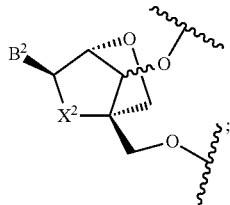

(IIBa)

$R^1$ is a hydroxy group;
$R^2$ is a hydroxy group or a fluorine atom;
$B^1$ is a group represented by

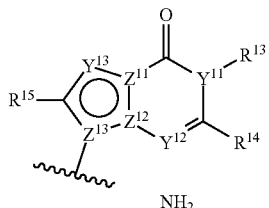

or

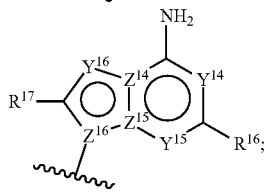

$R^{13}$ is a hydrogen atom;
$R^{14}$ is a hydrogen atom or an amino group;
$R^{15}$ is a hydrogen atom;
$R^{16}$ is a hydrogen atom;
$R^{17}$ is a hydrogen atom;
$Y^{11}$ is N;
$Y^{12}$ is N or CH;
$Y^{13}$ is N or CF;
(e.g., $Y^{11}$ is N, $Y^{12}$ is N, and $Y^{13}$ is CF; $Y^{11}$ is N, $Y^{12}$ is N, and $Y^{13}$ is N; or $Y^{11}$ is N, $Y^{12}$ is CH, and $Y^{13}$ is N);
$Y^{14}$ is N;
$Y^{15}$ is N;
$Y^{16}$ is N or CF;
(e.g., $Y^{14}$ is N, $Y^{15}$ is N, and $Y^{16}$ is N; or $Y^{14}$ is N, $Y^{15}$ is N, and $Y^{16}$ is CF);
$Z^{11}$ is C;
$Z^{12}$ is C;
$Z^{13}$ is N;
$Z^{14}$ is C;
$Z^{15}$ is C;
$Z^{16}$ is N;
$B^2$ is a group represented by

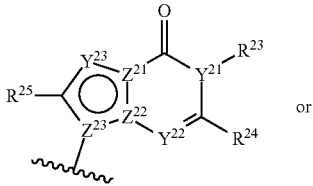

or

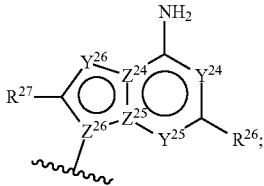

$R^{23}$ is a hydrogen atom;
$R^{24}$ is a hydrogen atom or an amino group;
$R^{25}$ is a hydrogen atom;
$R^{26}$ is a hydrogen atom;
$R^{27}$ is a hydrogen atom;
$Y^{21}$ is N;
$Y^{22}$ is N;
$Y^{23}$ is N or CF;
(e.g., $Y^{21}$ is N, $Y^{22}$ is N, and $Y^{23}$ is CF; or $Y^{21}$ is N, $Y^{22}$ is N, and $Y^{23}$ is N);
$Y^{24}$ is N;
$Y^{25}$ is N or CH;
$Y^{26}$ is N or CF;
(e.g., $Y^{24}$ is N, $Y^{25}$ is N, and $Y^{26}$ is N; $Y^{24}$ is N, $Y^{25}$ is N, and $Y^{26}$ is CF; or $Y^{24}$ is N, $Y^{25}$ is CH, and $Y^{26}$ is N);
$Z^{21}$ is N or C;
$Z^{22}$ is C;
$Z^{23}$ is N or C;
(e.g., $Z^{21}$ is C, $Z^{22}$ is C, and $Z^{23}$ is N; or $Z^{21}$ is N, $Z^{22}$ is C, and $Z^{23}$ is C);
$Z^{24}$ is N or C;
$Z^{25}$ is C;
$Z^{26}$ is N or C;
(e.g., $Z^{24}$ is C, $Z^{25}$ is C, and $Z^{26}$ is N; or $Z^{24}$ is N, $Z^{25}$ is C, and $Z^{26}$ is C); provided that
i) at least one of $Y^{11}$, $Y^{12}$, $Y^{13}$, $Y^{14}$, $Y^{15}$ and $Y^{16}$ is $CR^{1a}$,
ii) at least one of $Y^{21}$, $Y^{22}$, $Y^{23}$, $Y^{24}$, $Y^{25}$ and $Y^{26}$ is $CR^{2a}$, or
iii) at least one of $Z^{13}$, $Z^{16}$, $Z^{23}$ and $Z^{26}$ is C;
$X^1$ and $X^2$ are both oxygen atoms;
$Q^1$ is an oxygen atom;
$Q^2$ is an oxygen atom or a sulfur atom;
$Q^3$ is an oxygen atom; and
$Q^4$ is an oxygen atom or a sulfur atom.

Compound A2-b

Compound A2-b is a compound having formula (Ib) wherein the partial structure:

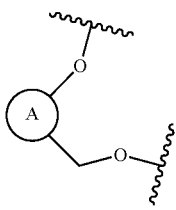

is a partial structure represented by the formula (IIAb):

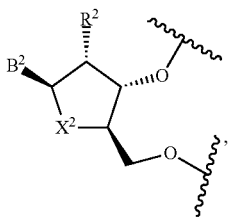
(IIAb)

or
a partial structure represented by the formula (IIBb):

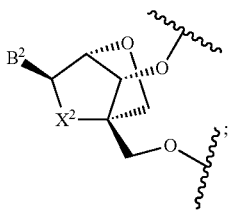
(IIBb)

$R^1$ is a hydroxy group;
$R^2$ is a hydroxy group or a halogen atom (e.g., a fluorine atom);
$B^1$ is a group represented by

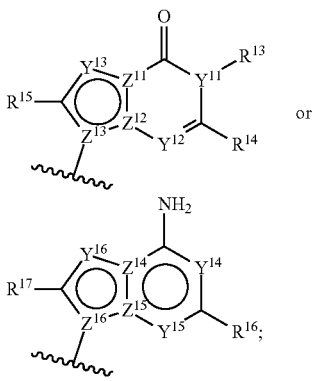

$R^{13}$ is a hydrogen atom;
$R^{14}$ is a hydrogen atom or an optionally substituted amino group;
$R^{15}$ is a hydrogen atom;
$R^{16}$ is a hydrogen atom;
$R^{17}$ is a hydrogen atom;
$Y^{11}$ is N;
$Y^{12}$ is N or CH;
$Y^{13}$ is N or $CR^{1a}$ wherein $R^{1a}$ is a halogen atom (e.g., a fluorine atom);
$Y^{14}$ is N;
$Y^{15}$ is N;
$Y^{16}$ is N or $CR^{1a}$ wherein $R^{1a}$ is a halogen atom (e.g., a fluorine atom);
$Z^{11}$ is C;
$Z^{12}$ is C;
$Z^{13}$ is N;
$Z^{14}$ is C;
$Z^{15}$ is C;
$Z^{16}$ is N;
$B^2$ is a group represented by

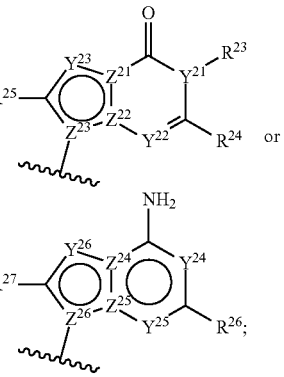

$R^{23}$ is a hydrogen atom;
$R^{24}$ is a hydrogen atom or an optionally substituted amino group;
$R^{25}$ is a hydrogen atom;
$R^{26}$ is a hydrogen atom;
$R^{27}$ is a hydrogen atom;
$Y^{21}$ is N;
$Y^{22}$ is N;
$Y^{23}$ is N or $CR^{2a}$ wherein $R^{2a}$ is a halogen atom (e.g., a fluorine atom);
$Y^{24}$ is N;
$Y^{25}$ is N or CH;
$Y^{26}$ is N or $CR^{2a}$ wherein $R^{2a}$ is a halogen atom (e.g., a fluorine atom);
$Z^{21}$ is N or C;
$Z^{22}$ is C;
$Z^{23}$ is N or C;
$Z^{24}$ is N or C;
$Z^{25}$ is C;
$Z^{26}$ is N or C;
provided that
i) at least one of $Y^{11}$, $Y^{12}$, $Y^{13}$, $Y^{14}$, $Y^{15}$ and $Y^{16}$ is $CR^{1a}$,
ii) at least one of $Y^{21}$, $Y^{22}$, $Y^{23}$, $Y^{24}$, $Y^{25}$ and $Y^{26}$ is $CR^{2a}$, or
iii) at least one of $Z^{13}$, $Z^{16}$, $Z^{23}$ and $Z^{26}$ is C;
$X^1$ and $X^2$ are each independently an oxygen atom or a sulfur atom; and
$Q^1$, $Q^2$, $Q^3$ and $Q^4$ are each independently an oxygen atom or a sulfur atom.

Compound B2-b

Compound B2-b is a compound having formula (Ib) wherein the partial structure:

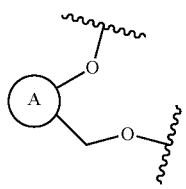

is a partial structure represented by the formula (IIAb):

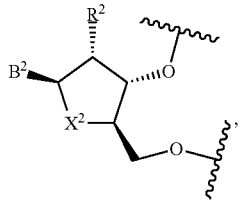
(IIAb)

or
a partial structure represented by the formula (IIBb):

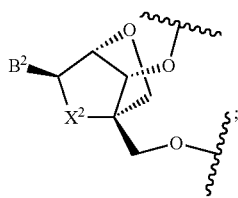
(IIBb)

$R^1$ is a hydroxy group;
$R^2$ is a hydroxy group or a fluorine atom;
$B^1$ is a group represented by

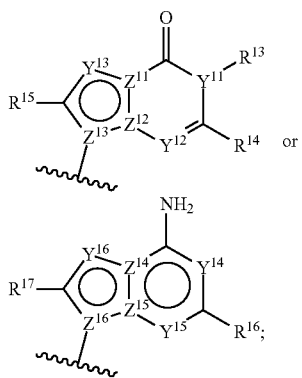

$R^{13}$ is a hydrogen atom;
$R^{14}$ is a hydrogen atom or an amino group;
$R^{15}$ is a hydrogen atom;
$R^{16}$ is a hydrogen atom;
$R^{17}$ is a hydrogen atom;
$Y^{11}$ is N;
$Y^{12}$ is N or CH;
$Y^{13}$ is N or CF;
(e.g., $Y^{11}$ is N, $Y^{12}$ is N, and $Y^{13}$ is CF; $Y^{11}$ is N, $Y^{12}$ is N, and $Y^{13}$ is N; or $Y^{11}$ is N, $Y^{12}$ is CH, and $Y^{13}$ is N);
$Y^{14}$ is N;
$Y^{15}$ is N;
$Y^{16}$ is N or CF;
(e.g., $Y^{14}$ is N, $Y^{15}$ is N, and $Y^{16}$ is N; or $Y^{14}$ is N, $Y^{15}$ is N, and $Y^{16}$ is CF);
$Z^{11}$ is C;
$Z^{12}$ is C;
$Z^{13}$ is N;
$Z^{14}$ is C;
$Z^{15}$ is C;
$Z^{16}$ is N;
$B^2$ is a group represented by

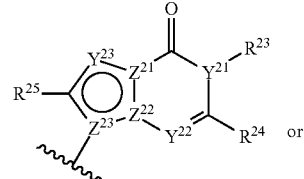 or

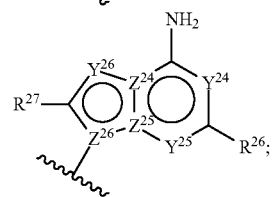

$R^{23}$ is a hydrogen atom;
$R^{24}$ is a hydrogen atom or an amino group;
$R^{25}$ is a hydrogen atom;
$R^{26}$ is a hydrogen atom;
$R^{27}$ is a hydrogen atom;
$Y^{21}$ is N;
$Y^{22}$ is N;
$Y^{23}$ is N or CF;
(e.g., $Y^{21}$ is N, $Y^{22}$ is N, and $Y^{23}$ is CF; or $Y^{21}$ is N, $Y^{22}$ is N, and $Y^{23}$ is N);
$Y^{24}$ is N;
$Y^{25}$ is N or CH;
$Y^{26}$ is N or CF;
(e.g., $Y^{24}$ is N, $Y^{25}$ is N, and $Y^{26}$ is N; $Y^{24}$ is N, $Y^{25}$ is N, and $Y^{26}$ is CF, or $Y^{24}$ is N, $Y^{25}$ is CH, and $Y^{26}$ is N);
$Z^{21}$ is N or C;
$Z^{22}$ is C;
$Z^{23}$ is N or C;
(e.g., $Z^{21}$ is C, $Z^{22}$ is C, and $Z^{23}$ is N; or $Z^{21}$ is N, $Z^{22}$ is C, and $Z^{23}$ is C)
$Z^{24}$ is N or C;
$Z^{25}$ is C;
$Z^{26}$ is N or C;
(e.g., $Z^{24}$ is C, $Z^{25}$ is C, and $Z^{26}$ is N; or $Z^{24}$ is N, $Z^{25}$ is C, and $Z^{26}$ is C)
provided that
i) at least one of $Y^{11}$, $Y^{12}$, $Y^{13}$, $Y^{14}$, $Y^{15}$ and $Y^{16}$ is $CR^{1a}$,
ii) at least one of $Y^{21}$, $Y^{22}$, $Y^{23}$, $Y^{24}$, $Y^{25}$ and $Y^{26}$ is $CR^{2a}$, or
iii) at least one of $Z^{13}$, $Z^{16}$, $Z^{23}$ and $Z^{26}$ is C;
$X^1$ and $X^2$ are both oxygen atoms;
$Q^1$ is an oxygen atom;
$Q^2$ is an oxygen atom or a sulfur atom;
$Q^3$ is an oxygen atom; and
$Q^4$ is an oxygen atom or a sulfur atom.
Compound C2
Compound C2 is a compound having formula (I) wherein the partial structure:

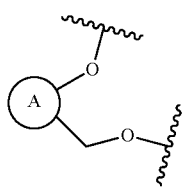

is a partial structure represented by the formula (IIA)

(IIA)
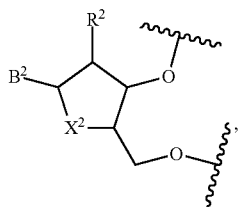

or
a partial structure represented by the formula (IIB):

(IIB)
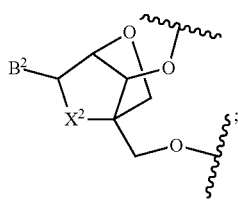

$R^1$ is a hydroxy group;
$R^2$ is a hydroxy group or a fluorine atom;
$B^1$ and $B^2$ are each independently

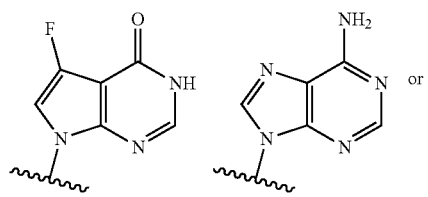

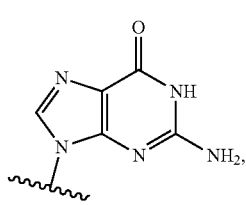

and
at least one of $B^1$ and $B^2$ is

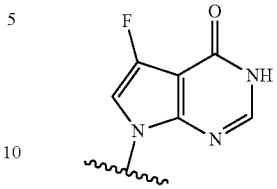

and, e.g., the other is

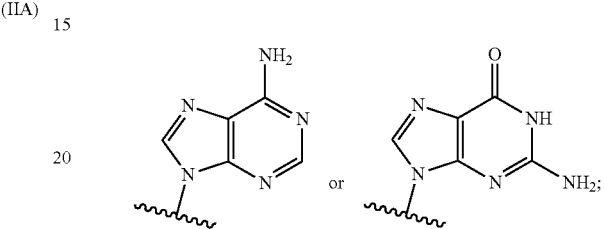

$X^1$ and $X^2$ are both oxygen atoms;
$Q^1$ is an oxygen atom;
$Q^2$ is an oxygen atom or a sulfur atom;
$Q^3$ is an oxygen atom; and
$Q^4$ is an oxygen atom or a sulfur atom.

Compound C2-a
Compound C2-a is a compound having formula (Ia) wherein the partial structure:

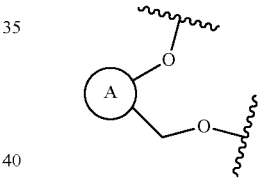

is a partial structure represented by the formula (IIAa):

(IIAa)
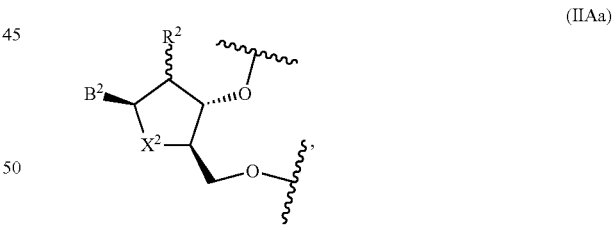

or
a partial structure represented by the formula (IIBa):

(IIBa)
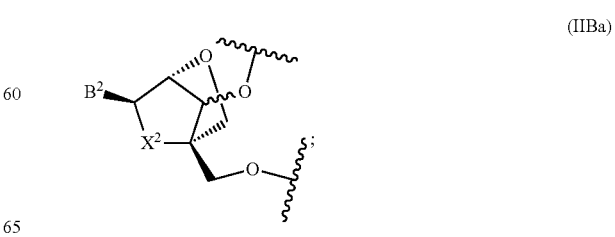

$R^1$ is a hydroxy group;

R² is a hydroxy group or a fluorine atom;
B¹ and B² are each independently

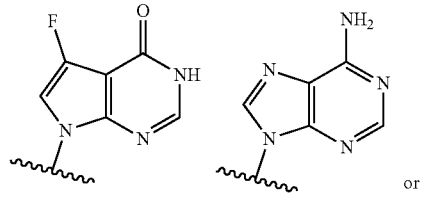

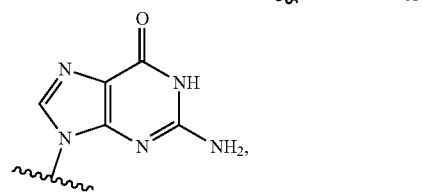

or and
at least one of B¹ and B² is

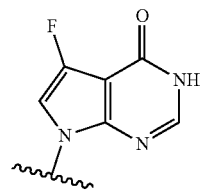

and, e.g., the other is

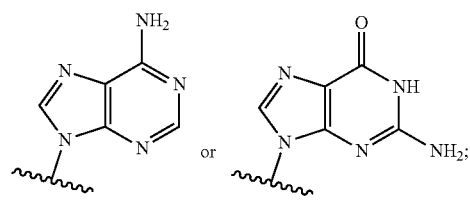

X¹ and X² are both oxygen atoms;
Q¹ is an oxygen atom;
Q² is an oxygen atom or a sulfur atom;
Q³ is an oxygen atom; and
Q⁴ is an oxygen atom or a sulfur atom.

Compound C2-b

Compound C2-b is a compound having formula (Ib) wherein the partial structure:

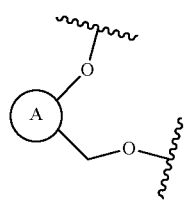

is a partial structure represented by the formula (IIAb):

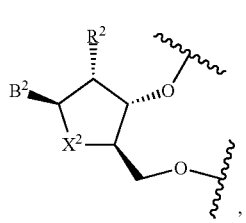

(IIAb)

or a partial structure represented by the formula (IIBb):

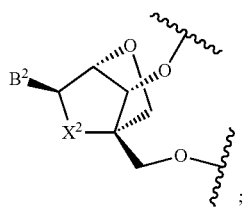

(IIBb)

R¹ is a hydroxy group;
R² is a hydroxy group or a fluorine atom;
B¹ and B² are each independently

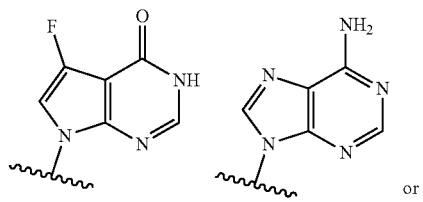

or

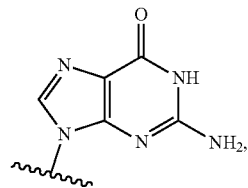

and
at least one of B¹ and B² is

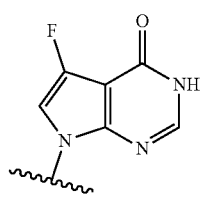 [SMILES: *n1cc(F)c2c(=O)[nH]cnc21]

and, e.g., the other is

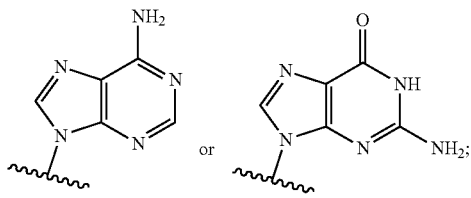 [SMILES: *n1cnc2c(N)ncnc21 ; *n1cnc2c(=O)[nH]c(N)nc21]

or

X¹ and X² are both oxygen atoms;
Q¹ is an oxygen atom;
Q² is an oxygen atom or a sulfur atom;
Q³ is an oxygen atom; and
Q⁴ is an oxygen atom or a sulfur atom.

Compound D2

Compound D2 is a compound having formula (I) wherein the partial structure:

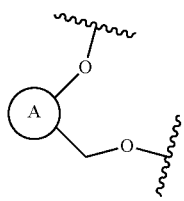

is a partial structure represented by the formula (IIA)

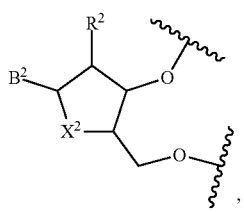
(IIA)

, or
a partial structure represented by the formula (IIB):

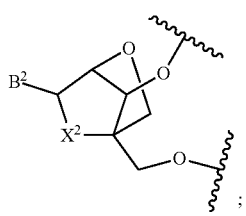
(IIB)

;

R¹ is a hydroxy group;
R² is a hydroxy group or a fluorine atom;

B¹ is a group represented by

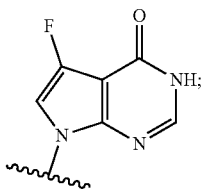 [SMILES: *n1cc(F)c2c(=O)[nH]cnc21]

B² is a group represented by

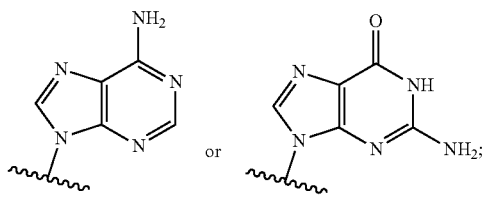 [SMILES: *n1cnc2c(N)ncnc21 ; *n1cnc2c(=O)[nH]c(N)nc21]

or

X¹ and X² are both oxygen atoms;
Q¹ is an oxygen atom;
Q² is an oxygen atom or a sulfur atom;
Q³ is an oxygen atom; and
Q⁴ is an oxygen atom or a sulfur atom.

Compound D2-a

Compound D2-a is a compound having formula (Ia) wherein the partial structure:

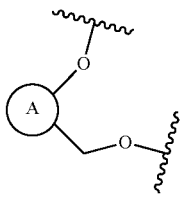

is a partial structure represented by the formula (IIAa):

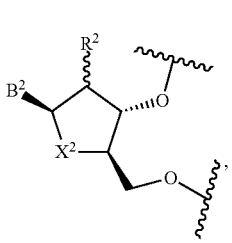
(IIAa)

, or
a partial structure represented by the formula (IIBa):

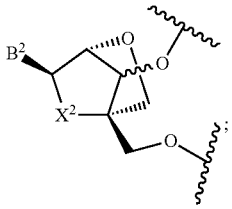
(IIBa)

;

$R^1$ is a hydroxy group;
$R^2$ is a hydroxy group or a fluorine atom;
$B^r$ is a group represented by

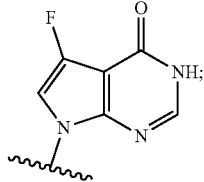 [SMILES: *n1cc(F)c2c(=O)[nH]cnc21]

$B^2$ is a group represented by

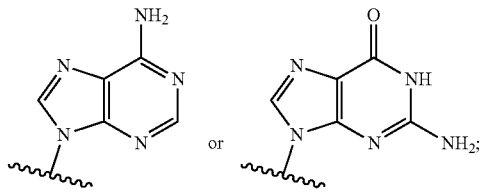 [SMILES: *n1cnc2c(N)ncnc21 ; *n1cnc2c(=O)[nH]c(N)nc21]

$X^1$ and $X^2$ are both oxygen atoms;
$Q^1$ is an oxygen atom;
$Q^2$ is an oxygen atom or a sulfur atom;
$Q^3$ is an oxygen atom; and
$Q^4$ is an oxygen atom or a sulfur atom.

Compound D2-b

Compound D2-b is a compound having formula (Ib) wherein the partial structure:

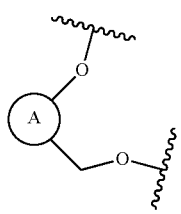

is a partial structure represented by the formula (IIAb):

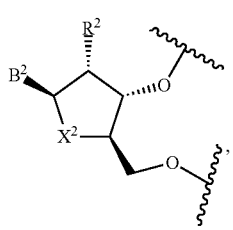

(IIAb)

or
a partial structure represented by the formula (IIBb):

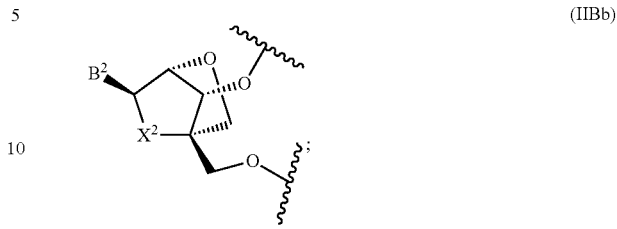

(IIBb)

$R^1$ is a hydroxy group;
$R^2$ is a hydroxy group or a fluorine atom;
$B^1$ is a group represented by

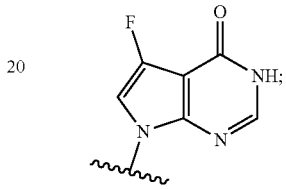

$B^2$ is a group represented by

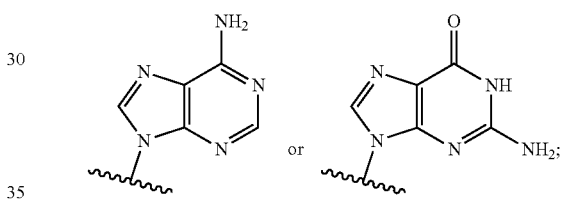

$X^1$ and $X^2$ are both oxygen atoms;
$Q^1$ is an oxygen atom;
$Q^2$ is an oxygen atom or a sulfur atom;
$Q^3$ is an oxygen atom; and
$Q^4$ is an oxygen atom or a sulfur atom.

Specific examples of compound (I) include the compounds of Examples 1 to 20 and 3a.

When compound (I) is in a form of a salt, the salt is preferably a pharmacologically acceptable salt. Examples include salts with inorganic base, salts with organic base, salts with inorganic acid, salts with organic acid, and salts with basic or acidic amino acid.

Preferable examples of the salt with inorganic base include alkali metal salts such as sodium salt, potassium salt and the like; alkaline-earth metal salts such as calcium salt, magnesium salt and the like; aluminium salt and ammonium salt.

Preferable examples of the salt with organic base include salts with trimethylamine, triethylamine, pyridine, picoline, ethanolamine, diethanolamine, triethanolamine, tromethamine [tris(hydroxymethyl)methylamine], tert-butylamine, cyclohexylamine, benzylamine, dicyclohexylamine and N,N-dibenzyl ethylene diamine.

Preferable examples of the salt with inorganic acid include salts with hydrochloric acid, hydrobromic acid, nitric acid, sulfuric acid and phosphoric acid.

Preferable examples of the salt with organic acid include salts with formic acid, acetic acid, trifluoroacetic acid, phthalic acid, fumaric acid, oxalic acid, tartaric acid, maleic acid, citric acid, succinic acid, malic acid, methanesulfonic acid, benzenesulfonic acid and p-toluenesulfonic acid.

Preferable examples of the salt with basic amino acid include salts with arginine, lysine and ornithine.

Preferable examples of the salt with acidic amino acid include salts with aspartic acid and glutamic acid.

When compound (1) is in a form of a salt, the salt is preferably a salt with triethylamine or sodium, more preferably a salt with triethylamine.

The production method of the compound of the present invention is explained in the followings.

The raw material compound and reagent used and the compound obtained in each step in the following production method may be each in a form of a salt, and examples of such salt include those similar to the salts of the compound of the present disclosure.

When the compound obtained in each step is a free form, it can be converted to the objective salt according to a method known per se. When the compound obtained in each step is a salt, it can be converted to the objective free form or the other salt according to a method known per se.

The compound obtained in each step can be used directly as the reaction mixture or as a crude product for the next reaction. Alternatively, the compound obtained in each step can be isolated and purified from a reaction mixture according to a method known per se, for example, a separation means such as concentration, crystallization, recrystallization, distillation, solvent extraction, fractional distillation, column chromatography and the like.

When the raw material compound and reagent used in each step are commercially available, the commercially available product can also be used directly.

In the reaction in each step, while the reaction time varies depending on the kind of the reagent and solvent to be used, it is generally 1 min-48 hr, preferably 10 min-8 hr, unless otherwise specified.

In the reaction in each step, while the reaction temperature varies depending on the kind of the reagent and solvent to be used, it is generally −78° C.-300° C., preferably −78° C.-150° C., unless otherwise specified.

In the reaction in each step, while the pressure varies depending on the kind of the reagent and solvent to be used, it is generally 1 atm-20 atm, preferably 1 atm-3 atm, unless otherwise specified.

Microwave synthesizer such as Initiator manufactured by Biotage and the like may be used for the reaction in each step. While the reaction temperature varies depending on the kind of the reagent and solvent to be used, it is generally room temperature-300° C., preferably 50° C.-250° C., unless otherwise specified. While the reaction time varies depending on the kind of the reagent and solvent to be used, it is generally 1 min-48 hr, preferably 1 min-8 hr, unless otherwise specified.

In the reaction in each step, the reagent is used in an amount of 0.5 equivalents-20 equivalents, preferably 0.8 equivalents-5 equivalents, relative to the substrate, unless otherwise specified. When the reagent is used as a catalyst, the reagent is used in an amount of 0.001 equivalent-1 equivalent, preferably 0.01 equivalent-0.2 equivalent, relative to the substrate. When the reagent is used as a reaction solvent, the reagent is used in a solvent amount.

Unless otherwise specified, the reaction in each step is carried out without solvent, or by dissolving or suspending the raw material compound in a suitable solvent. Examples of the solvent include those described in Examples and the following solvents.

alcohols: methanol, ethanol, tert-butyl alcohol, 2-methoxyethanol and the like;

ethers: diethyl ether, diphenyl ether, tetrahydrofuran, 1,2-dimethoxyethane and the like;

aromatic hydrocarbons: chlorobenzene, toluene, xylene and the like;

saturated hydrocarbons: cyclohexane, hexane and the like;

amides: N,N-dimethylformamide, N-methylpyrrolidone and the like;

halogenated hydrocarbons: dichloromethane, carbon tetrachloride and the like;

nitriles: acetonitrile and the like;

sulfoxides: dimethyl sulfoxide and the like;

aromatic organic bases: pyridine and the like;

anhydrides: acetic anhydride and the like;

organic acids: formic acid, acetic acid, trifluoroacetic acid and the like;

inorganic acids: hydrochloric acid, sulfuric acid and the like;

esters: ethyl acetate and the like;

ketones: acetone, methyl ethyl ketone and the like;

water.

The above-mentioned solvent can be used in a mixture of two or more kinds thereof in an appropriate ratio.

When a base is used for the reaction in each step, examples thereof include those described in Examples and the following bases.

inorganic bases: sodium hydroxide, magnesium hydroxide, sodium carbonate, calcium carbonate, sodium hydrogencarbonate and the like;

organic bases: triethylamine, diethylamine, pyridine, 4-dimethylaminopyridine, N,N-dimethylaniline, 1,4-diazabicyclo[2.2.2]octane, 1,8-diazabicyclo[5.4.0]-7-undecene, imidazole, piperidine and the like;

metal alkoxides: sodium ethoxide, potassium tert-butoxide and the like;

alkali metal hydrides: sodium hydride and the like;

metal amides: sodium amide, lithium diisopropylamide, lithium hexamethyldisilazide and the like;

organic lithiums: n-butyllithium and the like.

When an acid or an acid catalyst is used for the reaction in each step, examples thereof include those described in Examples and the following acids and acid catalysts.

inorganic acids: hydrochloric acid, sulfuric acid, nitric acid, hydrobromic acid, phosphoric acid and the like;

organic acids: acetic acid, trifluoroacetic acid, citric acid, p-toluenesulfonic acid, 10-camphorsulfonic acid and the like;

Lewis acid: boron trifluoride diethyl ether complex, zinc iodide, anhydrous aluminium chloride, anhydrous zinc chloride, anhydrous iron chloride and the like.

Unless otherwise specified, the reaction in each step is carried out according to a method known per se, for example, the method described in Jikken Kagaku Kouza, 5th Edition, vol. 13-19 (the Chemical Society of Japan ed.); Shin Jikken Kagaku Kouza, vol. 14-15 (the Chemical Society of Japan ed.); Fine Organic Chemistry, Revised 2nd Edition (L. F. Tietze, Th. Eicher, Nankodo); Organic Name Reactions, the Reaction Mechanism and Essence, Revised Edition (Hideo Togo, Kodansha); ORGANIC SYNTHESES Collective Volume I-VII (John Wiley & Sons Inc); Modern Organic Synthesis in the Laboratory A Collection of Standard Experimental Procedures (Jie Jack Li, OXFORD UNIVERSITY); Comprehensive Heterocyclic Chemistry III, Vol. 1-Vol. 14 (Elsevier Japan); Strategic Applications of Named Reactions in Organic Synthesis (translated by Kiyoshi Tomioka, Kagakudojin); Comprehensive Organic Transformations (VCH Publishers Inc.), 1989, or the like, or the method described in Examples.

In each step, the protection or deprotection reaction of an functional group is carried out according to a method known per se, for example, the method described in "Protective Groups in Organic Synthesis, 4th Ed", Wiley-Interscience, Inc., 2007 (Theodora W. Greene, Peter G. M. Wuts); "Protecting Groups 3rd Ed." Thieme, 2004 (P. J. Kocienski), or the like, or the method described in Examples.

Examples of the protecting group for a hydroxy group (e.g., a hydroxy group of an alcohol and the like, a phenolic hydroxy group) include ether-type protecting groups such as methoxymethyl ether, benzyl ether, tert-butyldimethylsilyl ether, tetrahydropyranyl ether and the like; carboxylate ester-type protecting groups such as acetate ester and the like; sulfonate ester-type protecting groups such as methanesulfonate ester and the like; and carbonate ester-type protecting groups such as tert-butylcarbonate and the like.

Examples of the protecting group for a carbonyl group of an aldehyde include acetal-type protecting groups such as dimethylacetal and the like; and cyclic acetal-type protecting groups such as 1,3-dioxane and the like.

Examples of the protecting group for a carbonyl group of a ketone include ketal-type protecting groups such as dimethylketal and the like; cyclic ketal-type protecting groups such as 1,3-dioxane and the like; oxime-type protecting groups such as O-methyloxime and the like; and hydrazone-type protecting groups such as N,N-dimethylhydrazone and the like.

Examples of the protecting group for a carboxyl group include ester-type protecting groups such as methyl ester and the like; and amide-type protecting groups such as N,N-dimethylamide and the like.

Examples of the protecting group for a thiol include ether-type protecting groups such as benzyl thioether and the like; and ester-type protecting groups such as thioacetate ester, thiocarbonate, thiocarbamate and the like.

Examples of the protecting group for an amino group and an aromatic heterocycle such as imidazole, pyrrole, indole and the like include carbamate-type protecting groups such as benzyl carbamate and the like; amide-type protecting groups such as acetamide, benzamide, isobutylamide and the like; alkyl amine-type protecting groups such as N-triphenylmethylamine and the like; and sulfonamide-type protecting groups such as methanesulfonamide and the like.

The protecting groups can be removed according to a method known per se (e.g., a method using acid, base, ultraviolet rays, hydrazine, phenylhydrazine, sodium N-methyl dithiocarbamate, tetrabutylammonium fluoride, palladium acetate or trialkylsilyl halide (e.g., trimethylsilyl iodide, trimethylsilyl bromide), a reduction method).

When reduction reaction is carried out in each step, examples of the reducing agent to be used include metal hydrides such as lithium aluminium hydride, sodium triacetoxyborohydride, sodium cyanoborohydride, diisobutylaluminium hydride (DIBAL-H), sodium borohydride, tetramethylammonium triacetoxyborohydride and the like; boranes such as borane tetrahydrofuran complex and the like; Raney nickel; Raney cobalt; hydrogen; formic acid; triethylsilane and the like. When carbon-carbon double bond or triple bond is reduced, a method using a catalyst such as palladium-carbon, Lindlar's catalyst and the like may be employed.

When oxidation reaction is carried out in each step, examples of the oxidizing agent to be used include peroxides such as m-chloroperbenzoic acid (mCPBA), hydrogen peroxide, tert-butyl hydroperoxide and the like; perchlorates such as tetrabutylammonium perchlorate and the like; chlorates such as sodium chlorate and the like; chlorites such as sodium chlorite and the like; periodic acids such as sodium periodate and the like; hypervalent iodine reagents such as iodosylbenzene and the like; reagents containing manganese such as manganese dioxide, potassium permanganate and the like; leads such as lead tetraacetate and the like; reagents containing chromium such as pyridinium chlorochromate (PCC), pyridinium dichromate (PDC), Jones reagent and the like; halogen compounds such as N-bromosuccinimide (NBS) and the like; oxygen; ozone; sulfur trioxido-pyridine complex; osmium tetroxide; selenium dioxide; 2,3-dichloro-5,6-dicyano-1,4-benzoquinone (DDQ) and the like.

When radical cyclization reaction is carried out in each step, examples of the radical initiator to be used include azo compounds such as azobisisobutyronitrile (AIBN) and the like; water-soluble radical initiators such as 4-4'-azobis-4-cyanopentanoic acid (ACPA) and the like; triethylboron in the presence of air or oxygen; benzoyl peroxide and the like. Examples of the radical reagent to be used include tributylstannane, tristrimethylsilylsilane, 1,1,2,2-tetraphenyldisilane, di phenylsilane, samarium iodide and the like.

When Wittig reaction is carried out in each step, examples of the Wittig reagent to be used include alkylidene phosphoranes and the like. The alkylidene phosphoranes can be prepared according to a method known per se, for example, by reacting a phosphonium salt with a strong base.

When Horner-Emmons reaction is carried out in each step, examples of the reagent to be used include phosphonoacetates such as methyl dimethylphosphonoacetate, ethyl diethylphosphonoacetate and the like; and bases such as alkali metal hydrides, organic lithiums and the like.

When Friedel-Crafts reaction is carried out in each step, examples of the reagent to be used include a combination of a Lewis acid and an acid chloride or a combination of a Lewis acid and an alkylating agent (e.g., an alkyl halide, an alcohol, an olefin). Alternatively, an organic acid or an inorganic acid can also be used instead of a Lewis acid, and an anhydride such as acetic anhydride and the like can also be used instead of an acid chloride.

When aromatic nucleophilic substitution reaction is carried out in each step, a nucleophile (e.g., an amine, imidazole) and a base (e.g., an organic base) are used as a reagent.

When nucleophilic addition reaction by a carbo anion, nucleophilic 1,4-addition reaction (Michael addition reaction) by a carbo anion or nucleophilic substitution reaction by a carbo anion is carried out in each step, examples of the base to be used for generation of the carbo anion include organic lithiums, metal alkoxides, inorganic bases, organic bases and the like.

When Grignard reagent is carried out in each step, examples of the Grignard reagent to be used include arylmagnesium halides such as phenylmagnesium bromide and the like; alkylmagnesium halides such as methylmagnesium bromide and the like, and the like. The Grignard reagent can be prepared according to a method known per se, for example, by reacting an alkyl halide or an aryl halide with metal magnesium in an ether or tetrahydrofuran as a solvent.

When Knoevenagel condensation reaction is carried out in each step, a compound having an activated methylene group with two electron withdrawing groups (e.g., malonic acid, diethyl malonate, malononitrile etc.) and a base (e.g., an organic base, a metal alkoxide, an inorganic base) are used as a reagent.

When Vilsmeier-Haack reaction is carried out in each step, phosphoryl chloride and an amide derivative (e.g., N,N-dimethylformamide etc.) are used as a reagent.

When azidation reaction of an alcohol, an alkyl halide or a sulfonate is carried out in each step, examples of the azidating agent to be used include diphenylphosphorylazide (DPPA), trimethylsilylazide, sodium azide and the like. For example, for the azidation reaction of an alcohol, a method using diphenylphosphorylazide and 1,8-diazabicyclo[5.4.0]undec-7-ene (DBU), a method using trimethylsilylazide and a Lewis acid, and the like are employed.

When reductive amination reaction is carried out in each step, examples of the reducing agent to be used include sodium triacetoxyborohydride, sodium cyanoborohydride, hydrogen and formic acid. When the substrate is an amine compound, examples of the carbonyl compound to be used include paraformaldehyde, aldehydes such as acetaldehyde and the like, and ketones such as cyclohexanone and the like. When the substrate is a carbonyl compound, examples of the amine to be used include ammonia, primary amines such as methylamine and the like; secondary amines such as dimethylamine and the like, and the like.

When Mitsunobu reaction is carried out in each step, an azodicarboxylate (e.g., diethyl azodicarboxylate (DEAD), diisopropyl azodicarboxylate (DIAD) etc.) and triphenylphosphine are used as a reagent.

When esterification reaction, amidation reaction or ureation reaction is carried out in each step, examples of the reagent to be used include acyl halides such as acid chlorides, acid bromides and the like; activated carboxylic acids such as anhydrides, activated esters, sulfates and the like. Examples of the activating agent of the carboxylic acid include carbodiimide condensing agents such as 1-ethyl-3-(3-dimethylaminopropyl)carbodiimide hydrochloride (WSCD) and the like; triazine condensing agents such as 4-(4,6-dimethoxy-1,3,5-triazin-2-yl)-4-methylmorpholinium chloride n-hydrate (DMT-MM) and the like; carbonate condensing agents such as 1,1-carbonyldiimidazole (CDI) and the like; diphenylphosphoryl azide (DPPA); benzotriazol-1-yloxy-trisdimethylaminophosphonium salt (BOP reagent); 2-chloro-1-methyl-pyridinium iodide (Mukaiyama reagent); thionyl chloride; lower alkyl haloformates such as ethyl chloroformate and the like; O-(7-azabenzotriazol-1-yl)-N,N,N',N'-tetramethyluronium hexafluorophosphorate (HATU); sulfuric acid; combinations thereof and the like. When carbodiimide condensing agent is used, an additive such as 1-hydroxybenzotriazole (HOBt), N-hydroxysuccinimide (HOSu), dimethylaminopyridine (DMAP) and the like may be added to the reaction system.

When coupling reaction is carried out in each step, examples of the metal catalyst to be used include palladium compounds such as palladium(II) acetate, tetrakis(triphenylphosphine)palladium(0), dichlorobis(triphenylphosphine)palladium(II), dichlorobis(triethylphosphine)palladium(II), tris(dibenzylideneacetone)dipalladium(0), 1,1'-bis(diphenylphosphino)ferrocene palladium(II) chloride and the like; nickel compounds such as tetrakis(triphenylphosphine)nickel(0) and the like; rhodium compounds such as tris(triphenylphosphine)rhodium(III) chloride and the like; cobalt compounds; copper compounds such as copper oxide, copper(I) iodide and the like; platinum compounds and the like. In addition, a base can be added to the reaction system, and examples thereof include inorganic bases and the like.

When thiocarbonylation reaction is carried out in each step, phosphorus pentasulfide is typically used as the thiocarbonylating agent. Alternatively, a reagent having a 1,3,2,4-dithiadiphosphetane-2,4-disulfide structure (e.g., 2,4-bis(4-methoxyphenyl)-1,3,2,4-dithiadiphosphetane-2,4-di sulfide (Lawesson reagent) etc.) can also be used instead of phosphorus pentasulfide.

When Wohl-Ziegler reaction is carried out in each step, examples of the halogenating agent to be used include N-iodosuccinimide, N-bromosuccinimide (NBS), N-chlorosuccinimide (NCS), bromine, sulfuryl chloride and the like. In addition, the reaction can be accelerated by subjecting a radical initiator such as heat, light, benzoyl peroxide, azobisisobutyronitrile and the like to the reaction system reaction.

When halogenation reaction of a hydroxy group is carried out in each step, examples of the halogenating agent to be used include hydrohalic acids and acid halides of inorganic acids, specifically, hydrochloric acid, thionyl chloride, phosphorus oxychloride and the like for chlorination, 48% hydrobromic acid and the like for bromination. In addition, a method of producing an alkyl halide by reacting an alcohol with triphenylphosphine and carbon tetrachloride or carbon tetrabromide or the like can be employed. Alternatively, a method of producing an alkyl halide via two step comprising converting an alcohol to the corresponding sulfonate, and then reacting the sulfonate with lithium bromide, lithium chloride or sodium iodide can also be employed.

When Arbuzov reaction is carried out in each step, examples of the reagent to be used include alkyl halides such as ethyl bromoacetate and the like; phosphites such as triethyl phosphite, tri(isopropyl) phosphite and the like, and the like.

When sulfonate esterification reaction is carried out in each step, examples of the sulfonating agent to be used include methanesulfonyl chloride, p-toluenesulfonyl chloride, methanesulfonic anhydride, p-toluenesulfonic anhydride and the like.

When hydrolysis reaction is carried out in each step, an acid or a base is used as a reagent. Examples of the acid include pyridine 2,2,2-trifluoroacetate. For acid hydrolysis reaction of t-butyl ester, formic acid, triethylsilane and the like may be added to reductively-trap t-butyl cation which is by-produced.

When dehydration reaction is carried out in each step, examples of the dehydrating agent to be used include sulfuric acid, diphosphorus pentaoxide, phosphorus oxychloride, N,N'-dicyclohexylcarbodiimide, alumina, polyphosphoric acid and the like.

Examples of the protecting group for a hydroxy group to be used in each step include ether-type protecting groups such as bis(4-methoxyphenyl)(phenyl)methyl ether and the like, in addition to those exemplified above.

Examples of the protecting group for an amino group to be used in each step include imidamide-type protecting groups such as N,N-dimethylformimidamide and the like, in addition to those exemplified above.

The deprotection reaction in each step can also be carried out using acetic acid, 1,1,1,3,3,3-hexafluoropropan-2-ol, triethylamine trihydrofluoride, methylamine, 2-methylpropan-2-amine or hydrogen fluoride-pyridine, trifluoroacetic acid, instead of those exemplified above.

When rearrangement reaction is carried out in each step, examples of the reagent to be used include bases such as triethylamine and the like.

When phosphoramidite reaction is carried out in each step, a phosphoramiditing agent (e.g., phosphordiamidites such as 3-((bis(diisopropylamino)phosphino)oxy)propanenitrile and the like; chlorophosphoramidites such as 2-cyanoethyl diisopropylchlorophosphoramidite and the like) and a base (e.g., organic bases) are used as a reagent.

When thiophosphoramidite reaction is carried out in each step, a thiophosphoramiditing agent (e.g., 2-cyanoethyl dipropan-2-ylphosphoramidochloridothioite) and a base (e.g., organic bases) are used as a reagent.

When H-phosphonation reaction is carried out in each step, examples of the H-phosphonating agent to be used include diphenyl phosphite and the like.

When H-thiophosphonation reaction is carried out in each step, examples of the H-thiophosphonating agent to be used include a combination of an activator such as diphenyl phosphite and the like and a sulfur atom source such as lithium sulfide and the like, and the like.

When condensation reaction is carried out in each step, examples of the activator to be used include pyridine 2,2, 2-trifluoroacetate, 1H-tetrazole, 5-(ethylsulfanyl)-1H-tetrazole (hereinafter sometimes to be referred to as 5-(ethylsulfanyl)-2H-tetrazole) and the like.

When oxidation reaction is carried out in each step, examples of the oxidizing agent to be used include halogens such as iodine and the like generally used for synthesis of nucleic acid, and the like, in addition to those exemplified above.

When sulfurization reaction is carried out in each step, examples of the sulfurizing agent to be used include 3H-benzo[c][1,2]dithiol-3-one, 3H-benzo[c][1,2]dithiol-3-one 1,1-dioxide, ((dimethylamino-methylidene)amino)-3H-1,2,4-dithiazoline-3-thione and the like. In addition, for example, sulfur-2,6-lutidine suspension, sulfur-carbon disulfide solution, tetramethylthiuram disulfide (TETD) (H. Vu et al., Tetrahedron Lett., 32, 3005-3008 (1991)), Beauge's reagent (R. P. Lyer et al., J. Am. Chem. Soc., 112, 1253-1254 (1990)) and Lawesson's reagent can also be used for sulfurization reaction. Moreover, as a method of formation of phosphorodithioate structure, the document by Marshall et al (Science 259: 1564-1570, 1993) and the document by Caruthers and Nielsen et al (WO 1989/011486) can be used as a reference.

When cyclization reaction is carried out in each step, examples of the activator to be used include 2-chloro-5,5-dimethyl-1,3,2-dioxaphosphinane 2-oxide, pivaloyl chloride, 2-(benzoyltriazol-1-yloxy)-1,3-dimethyl-2-pyrrolidin-1-yl-1,3,2-diazaphospholidinium hexafluorate (BOMP), N,N-bis(2-oxazolidinyl)phosphonic chloride (BopCl), pyrophosphoric acid and the like. When an activator is not used, the reaction may be carried out under heating. In addition, a base may be added to the reaction system. Examples of the base include organic bases and the like.

When bond-forming reaction between nucleobase and ribose is carried out in each step, examples of the activator to be used include trimethylsilyl N-(trimethylsilyl)acetimidate, trimethylsilyl trifluoromethanesulfonate and the like.

When the partial structure:

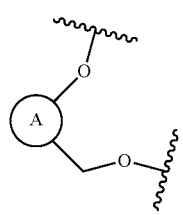

is a partial structure represented by the formula (IIA):

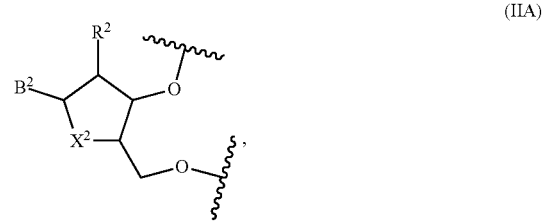

(IIA)

compound (IA) can be produced from compound (1a) or (1b) and compound (2a) or (2b) according to the below method.

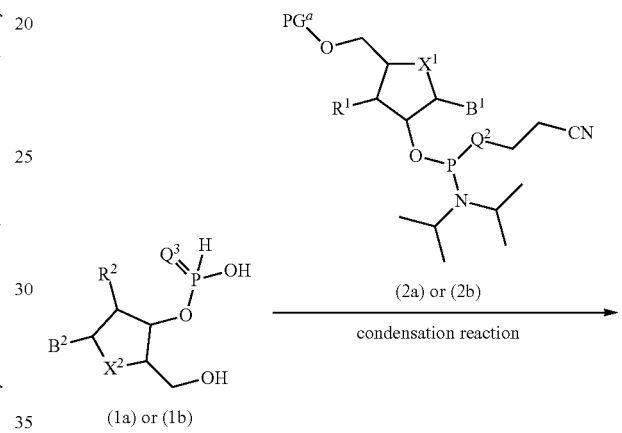

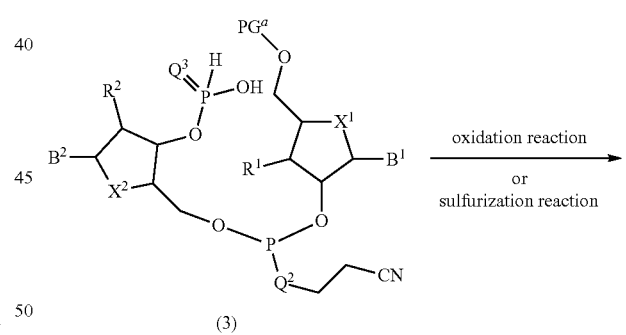

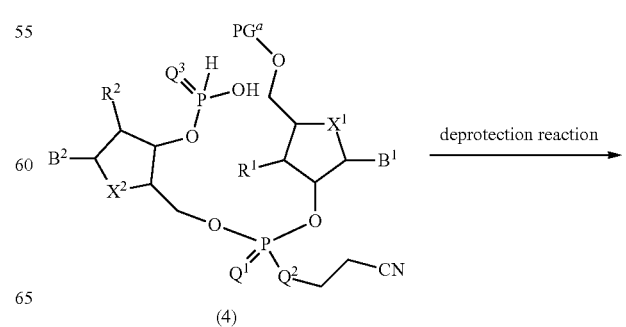

-continued

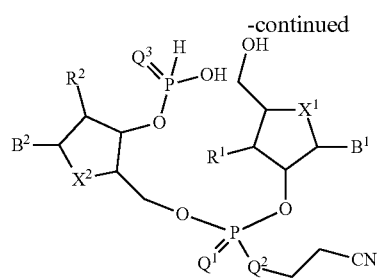
(5)

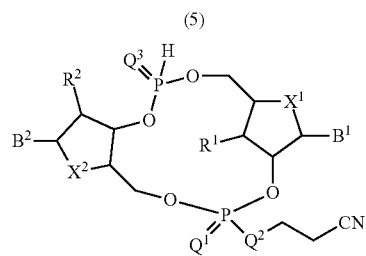
(6)

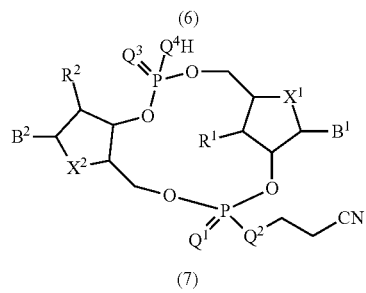
(7)

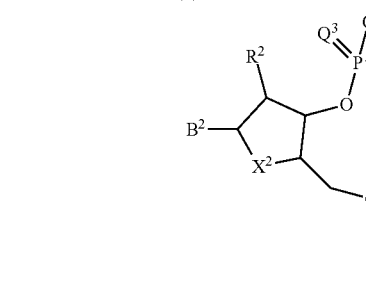
(IA)

wherein PG$^a$ is a hydroxy-protecting group, and the other symbols are as defined above.

Alternatively, when the partial structure:

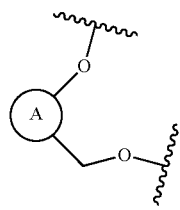

is the partial structure represented by the formula (IIA), compound (IA) can also be produced from compound (8a) or (8b) and compound (9a) or (9b) according to the below method.

cyclization reaction → oxidation reaction or sulfurization reaction → deprotection reaction →

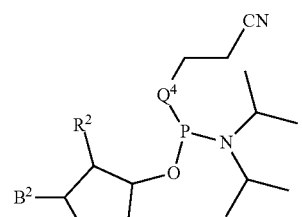

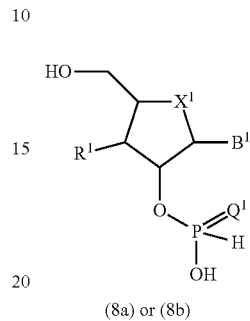
(8a) or (8b)

(9a) or (9b)
condensation reaction →

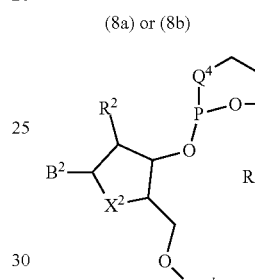
(10)

oxidation reaction or sulfurization reaction →

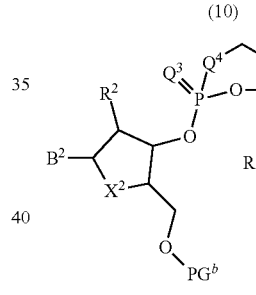
(11)

deprotection reaction →

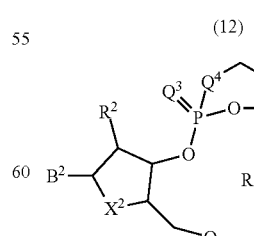
(12)

cyclization reaction →

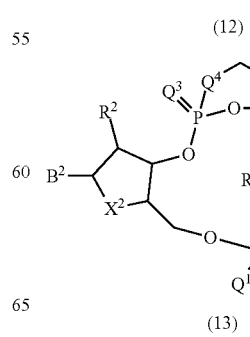
(13)

oxidation reaction or sulfurization reaction →

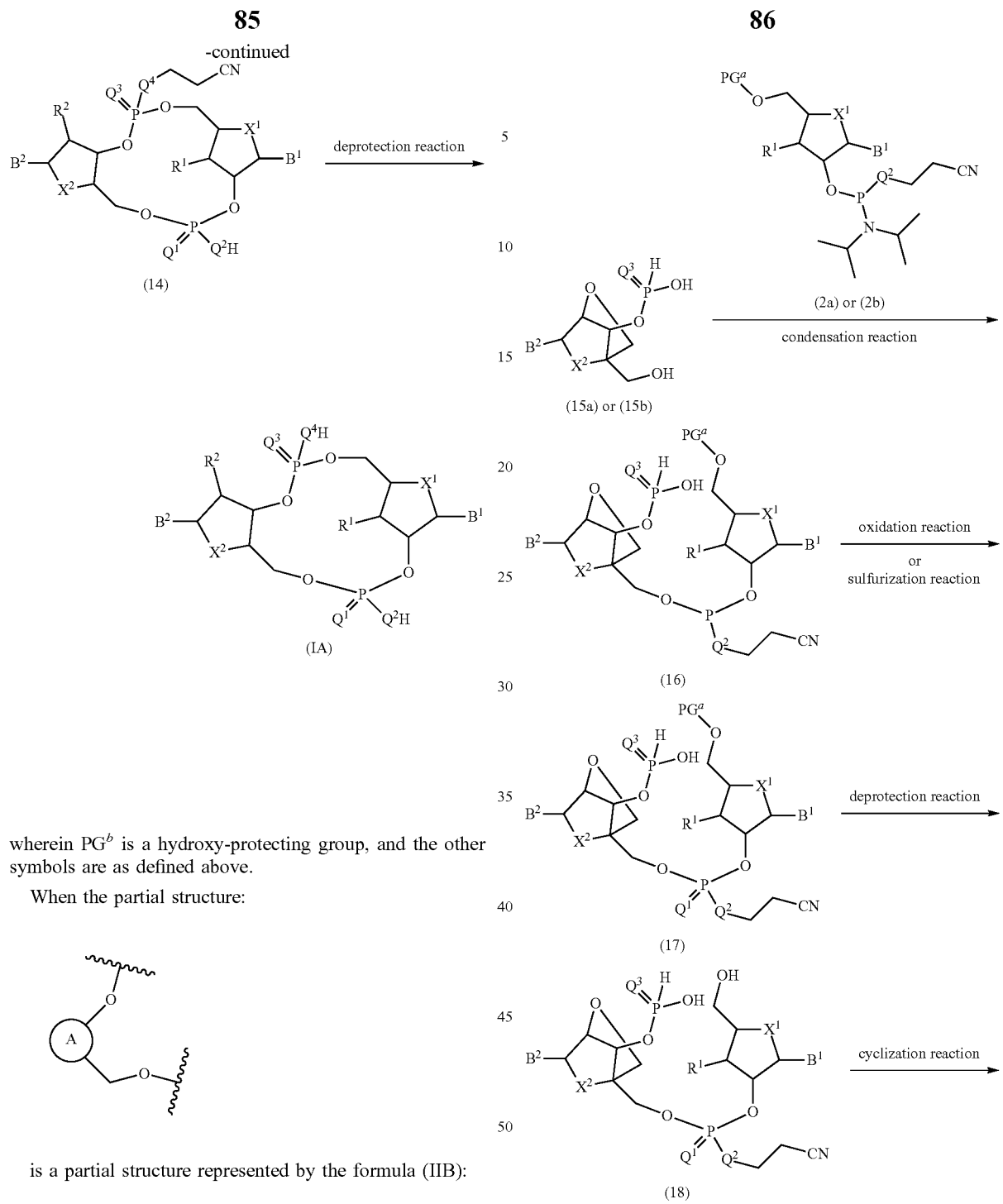
wherein PG$^b$ is a hydroxy-protecting group, and the other symbols are as defined above.
When the partial structure:
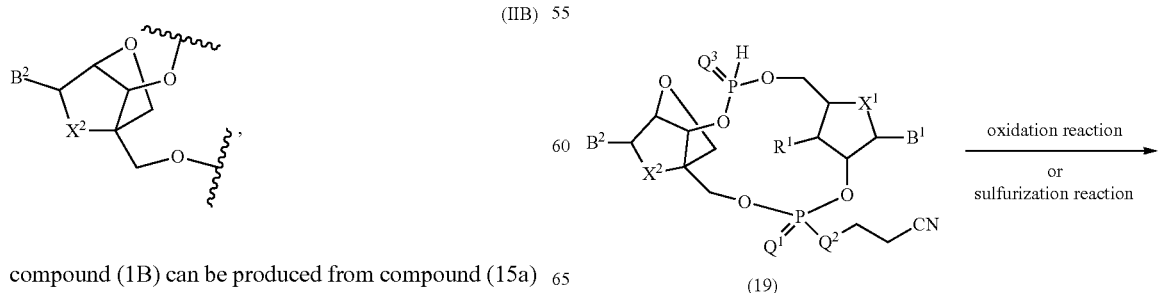
is a partial structure represented by the formula (IIB):
compound (1B) can be produced from compound (15a) or (15b) and compound (2a) or (2b) according to the below method.

87
-continued
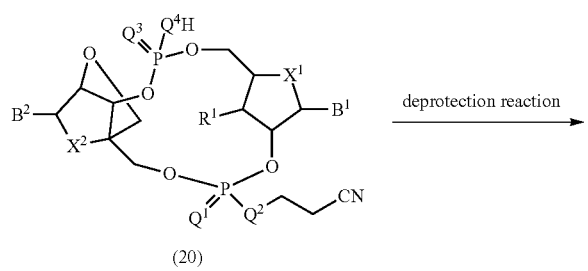
(20)
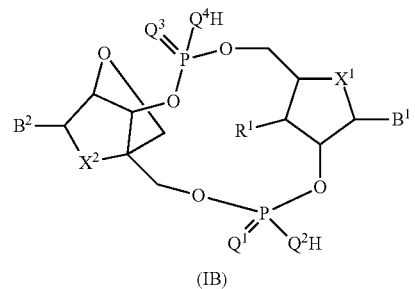
(IB)
wherein each symbol is as defined above.
Alternatively, when the partial structure:
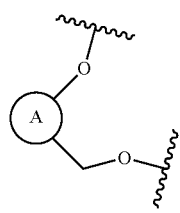
is the partial structure represented by the formula (IIB), compound (1B) can also be produced from compound (8a) or (8b) and compound (21a) or (21b) according to the below method.
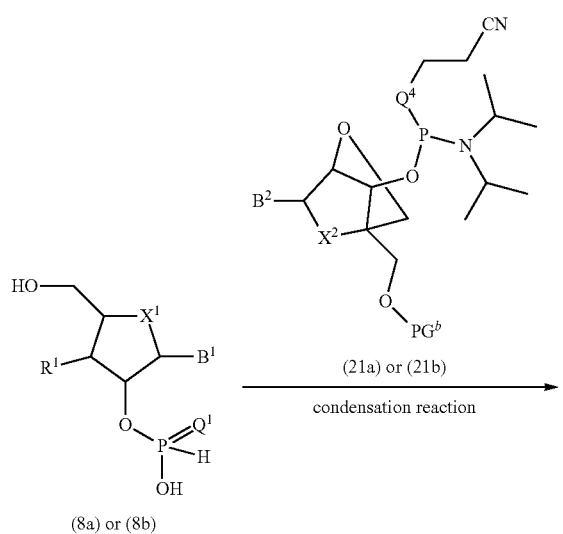
88
-continued
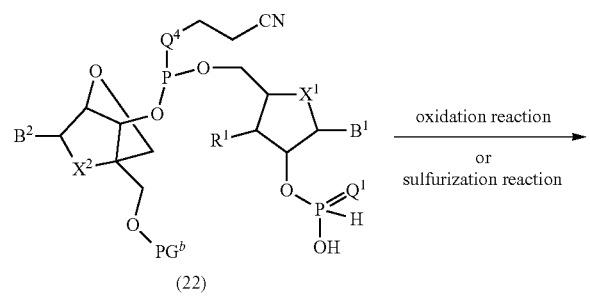
(22)
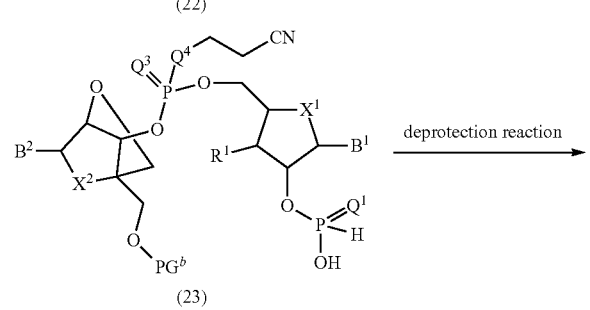
(23)
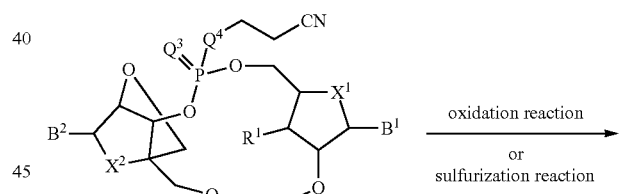
(24)
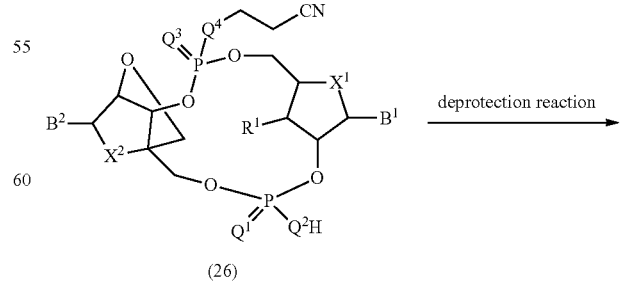
(25)
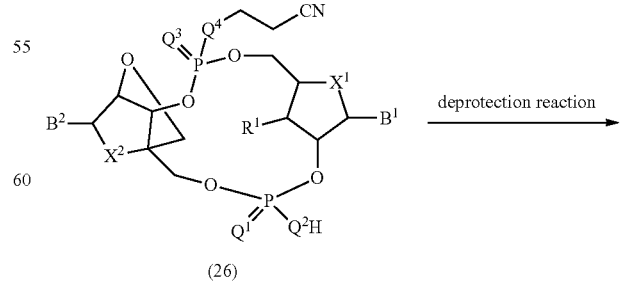
(26)

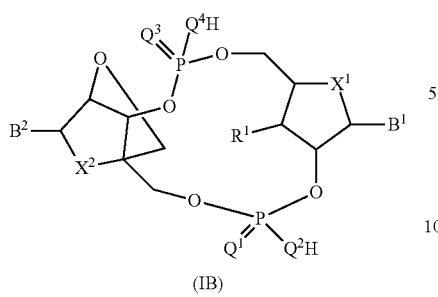

(IB)

wherein PG$^c$ is a hydroxy-protecting group, and the other symbols are as defined above.

Preferable examples of the hydroxy-protecting group for PG$^a$, PG$^b$ or PG$^c$ include ether-type protecting groups such as bis(4-methoxyphenyl)(phenyl)methyl ether, 3-hydroxy-1,1,3,3-tetraisopropyldisiloxanyl ether and the like.

When R$^1$ and R$^2$ are each a hydroxy group, the hydroxy group may be protected. Preferable examples of the hydroxy-protecting group include ether-type protecting groups such as tert-butyldimethylsilyl ether, 3-hydroxy-1,1,3,3-tetraisopropyldisiloxanyl ether and the like.

When R$^1$ is a hydroxyl group, the hydroxyl group and the hydroxyl group represented by PG$^a$ may be protected by a 1,1,3,3-tetraisopropyldisiloxanyl group:

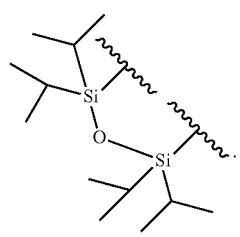 [SMILES: *[Si](O[Si](*)(C(C)C)C(C)C)(C(C)C)C(C)C]

In this case, a compound wherein the R$^1$ hydroxyl group is protected by a 3-hydroxy-1,1,3,3-tetraisopropyldisiloxanyl group:

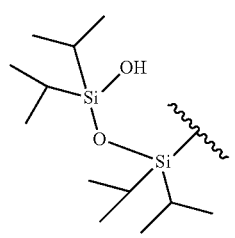 [SMILES: *[Si](O[Si](O)(C(C)C)C(C)C)(C(C)C)C(C)C]

is produced in the deprotection reaction for removal of PG$^a$.

When B$^1$ has a functional group, the functional group may be protected. For example, when B$^1$ is a group represented by

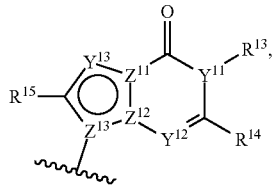

and

R$^{14}$ is —NH$_2$ group, the —NH$_2$ group may be protected. In addition, for example, when B$^1$ is a group represented by

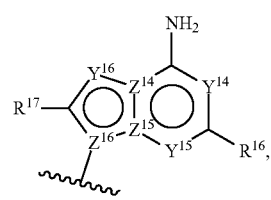

the —NH$_2$ group may be protected.

When B$^2$ has a functional group, the functional group may be protected. For example, when B$^2$ is a group represented by

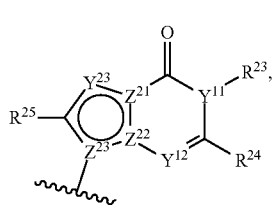

and

R$^{24}$ is —NH$_2$ group, the —NH$_2$ group may be protected. In addition, for example, when B$^2$ is a group represented by

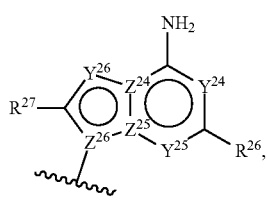

the —NH$_2$ group may be protected.

Preferable examples of the protecting group for the —NH$_2$ group include amide-type protecting groups such as benzamide, isobutylamide and the like, and imidamide-type protecting groups such as N,N-dimethylformimidamide and the like.

The above-mentioned compounds (1a), (1b), (9a) and (9b) can be produced from compound (27) according to the below method.

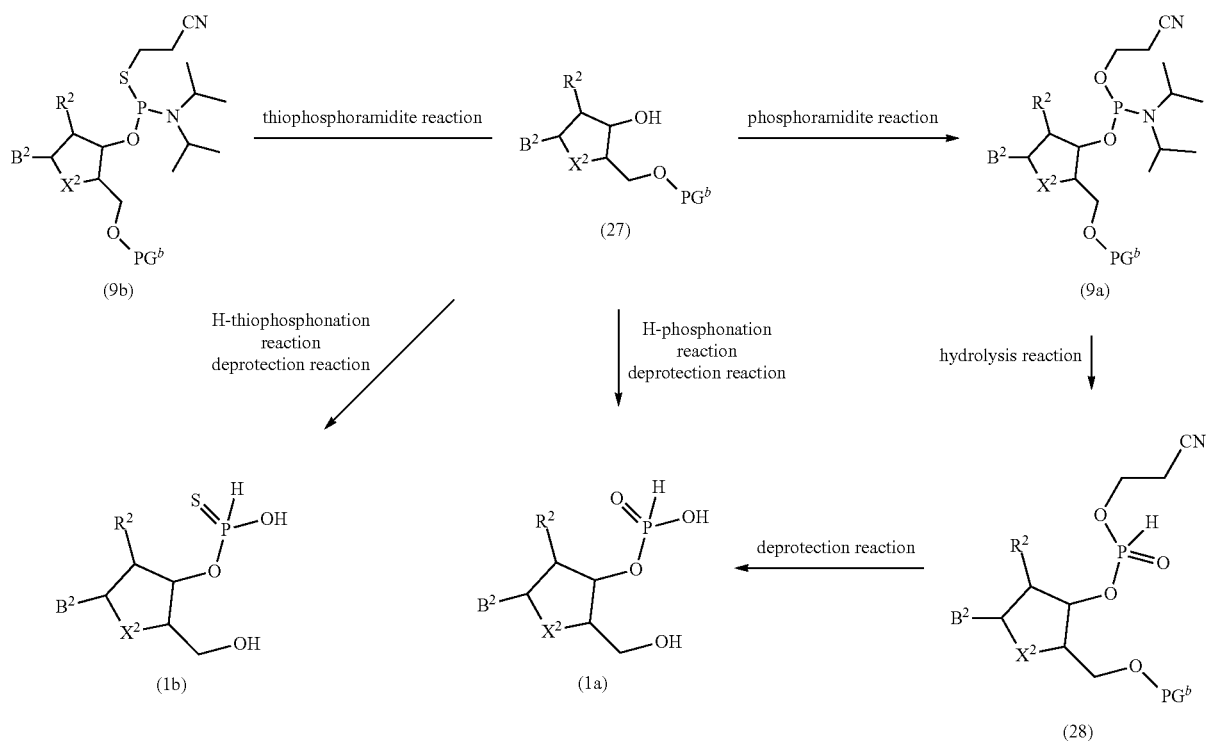
wherein each symbol is as defined above.
The above-mentioned compounds (2a), (2b), (8a) and (8b) can be produced from compound (29) according to the below method.
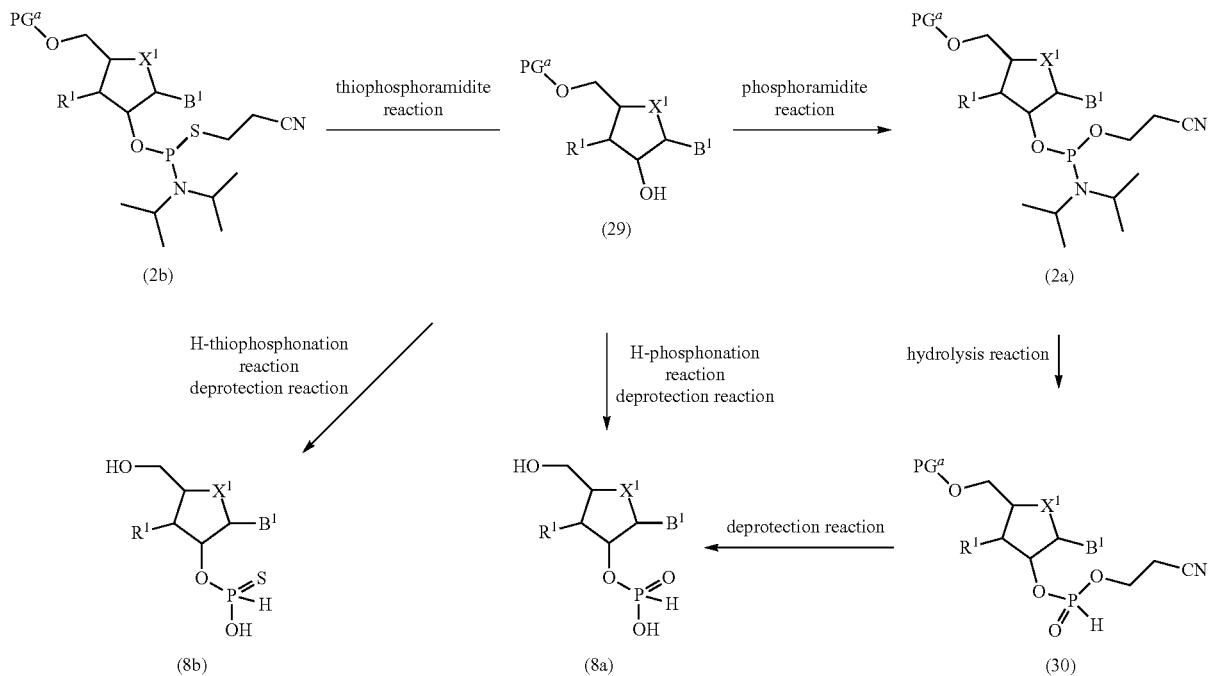
wherein each symbol is as defined above.

The above-mentioned compounds (15a), (15b), (21a) and (21b) can be produced from compound (31) according to the below method.

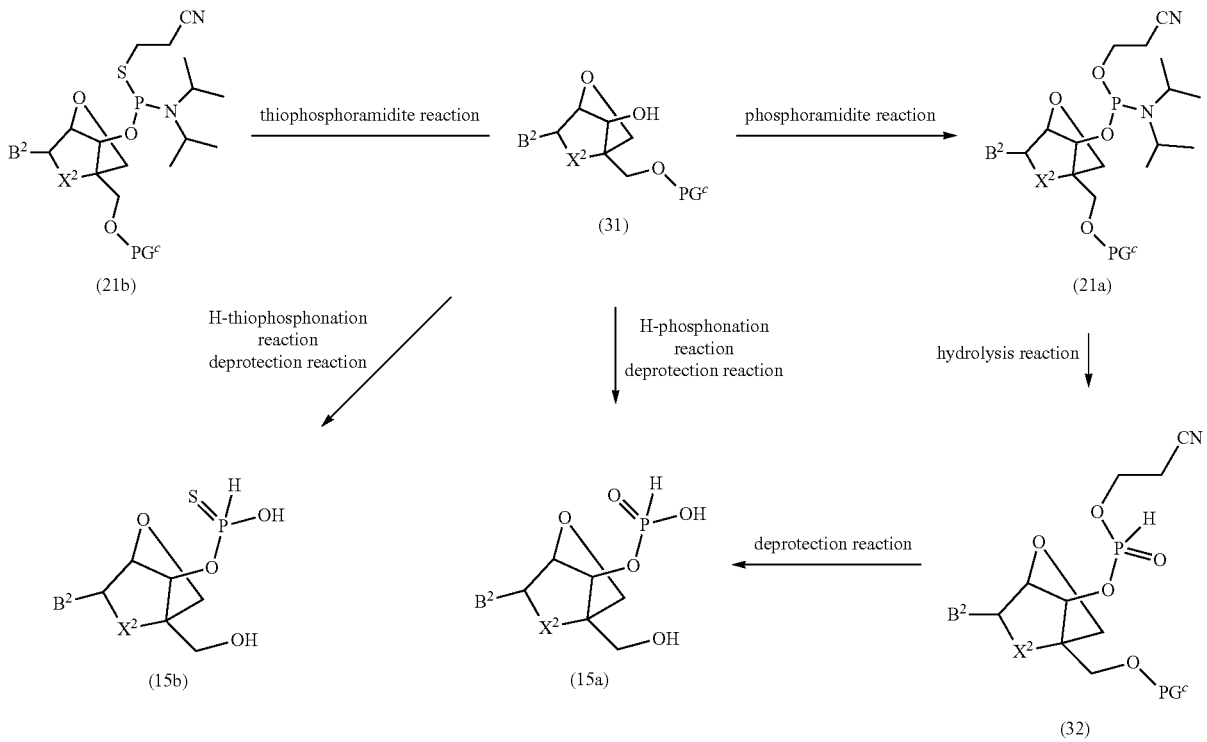

wherein each symbol is as defined above.

The substituent of the thus-obtained compound (I) can be subjected to modification (i.e., substituent introduction, functional group transformation) according to a means known per se to give the other compound or a salt thereof encompassed in Compound (I). Known general methods can be employed for the substituent introduction and functional group transformation, and examples thereof include conversion of a halogen atom (e.g., fluorine, chlorine, bromine, iodine) or an optionally halogenated $C_{1-6}$ alkylsulfonyl-oxy group [e.g., methanesulfonyloxy, ethanesulfonyloxy, trichloromethanesulfonyloxy, trifluoromethanesulfonyloxy (triflate)] to a methyl group, a cyclopropyl group, a vinyl group, a cyano group, a formyl group, a carbonyl group, a carboxyl group, a hydroxy group, an amino group, a boryl group and the like; conversion of a formyl group to an ethynyl group by Seyferth-Gilbert homologation reaction; conversion of an ester to a carboxy group by hydrolysis; conversion of a carboxy group to a carbamoyl group by amidation; conversion of a carboxy group to a hydroxymethyl group by reduction; conversion of a carbonyl group to an alcohol by reduction or alkylation; reductive amination of a carbonyl group; oximation of a carbonyl group; acylation of an amino group; ureation of an amino group; sulfonylation of an amino group; alkylation of an amino group; replacement or amination of an activated halogen by an amine; alkylation of a hydroxy group; and replacement or amination of a hydroxy group.

In case of the substituent introduction and functional group transformation, when the compound has a reactive moiety in which undesirable reaction may occur, a protecting group may be introduced into the reactive moiety in advance according to a method known per se as necessary. By removing the protecting group according to a method known per se after the objective reaction, the compound encompassed in the present disclosure can be produced.

For Example, when the raw material compound or intermediate has an amino group, a carboxyl group or a hydroxy group, these groups may be protected by a protecting group generally used in peptide chemistry and the like. By removing the protecting group as necessary after the reaction, the objective compound can be obtained.

When compound (I) contains an isomer such as an optical isomer, a stereoisomer, a regioisomer, a rotamer and the like, any isomer and a mixture thereof are also encompassed in compound (I) wherein. For example, when compound (I) contains an optical isomer, an optical isomer resolved from racemate compound is also encompassed in compound (I) wherein. These isomers can be obtained as a single product according to a synthetic method known per se and a separation method known per se (e.g., concentration, solvent extraction, column chromatography and recrystallization).

Compound (I) may be a crystal, and a single crystal form and a mixture of crystal forms are both encompassed in compound (I) wherein. The crystal can be produced by crystallizing according to a crystallization method known per se.

Compound (I) may be a pharmaceutically acceptable cocrystal or a salt thereof. The cocrystal or a salt thereof means a crystalline substance constituted with two or more special solids at room temperature, each having different physical properties (e.g., structure, melting point, melting heat, hygroscopicity and stability). The cocrystal or a salt thereof can be produced according to a cocrystallization method known per se.

Compound (I) may be a hydrate, a non-hydrate, a solvate or a non-solvate, and they are all encompassed in compound (I).

Compound (I) also encompasses a compound labeled or substituted with an isotope (e.g., $^2$H, $^3$H, $^{11}$C, $^{14}$C, $^{18}$F, $^{35}$S, $^{125}$I) and the like. The compound labeled or substituted with an isotope may be used, for example, as a tracer (PET tracer) used in positron emission tomography (PET), and is useful in the field of medical diagnosis and the like.

Compound (I) may be a prodrug.

The prodrug of compound (I) means a compound which is converted to compound (I) with a reaction due to an enzyme, gastric acid and the like under the physiological condition in the living body, that is, a compound which is converted to compound (I) by enzymatic oxidation, reduction, hydrolysis and the like; a compound which is converted to compound (I) by hydrolysis and the like due to gastric acid, and the like.

Examples of the prodrug for compound (I) include (1) a compound obtained by subjecting the amino in compound (I) to acylation, alkylation or phosphorylation (e.g., a compound obtained by subjecting the amino in compound (1) to eicosanoylation, alanylation, pentylaminocarbonylation, (5-methyl-2-oxo-1,3-dioxolen-4-yl)methoxycarbonylation, tetrahydrofuranylation, pyrrolidylmethylation, pivaloyloxymethylation, tert-butylation, ethoxycarbonylation, tert-butoxycarbonylation, acetylation or cyclopropylcarbonylation);

(2) a compound obtained by subjecting the hydroxy in compound (I) to acylation, alkylation, phosphorylation or boration (e.g., a compound obtained by subjecting the hydroxy in compound (I) to acetylation, palmitoylation, propanoylation, pivaloylation, succinylation, fumarylation, alanylation or dimethylaminomethylcarbonylation);

(3) a compound obtained by subjecting the carboxy in compound (I) to esterification or amidation (e.g., a compound obtained by subjecting the carboxy in compound (1) to ethyl esterification, phenyl esterification, carboxymethyl esterification, dimethylaminomethyl esterification, pivaloyloxymethyl esterification, ethoxycarbonyloxyethyl esterification, phthalidyl esterification, (S-methyl-2-oxo-1,3-dioxolen-4-yl) methyl esterification, cyclohexyloxycarbonylethyl esterification or methylamidation). These compounds can be produced from compound (I) according to a method known per se.

The prodrug of compound (I) may also be one which is converted to compound (I) under physiological conditions as described in "IYAKUHIN no KAIHATSU (Development of Pharmaceuticals)", Vol. 7, Design of Molecules, p. 163-198, Published by HIROKAWA SHOTEN (1990).

In the present specification, the prodrug may be in a form of a salt, and examples of such salt include those similar to the salts of the compound represented by the formula (I).

Compound (I) may also be used as a payload in an antibody (or peptidic antigen recognition sequence)-drug conjugate (the payload is the moiety corresponding to the above-mentioned drug). When compound (I) is used as a payload, compound (I) may be bonded to an antibody (or a peptidic antigen recognition sequence) via a linker.

Examples of the above-mentioned payload include
(1) compound (I) wherein $B^1$ is a group represented by

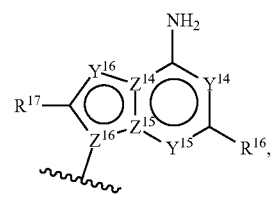

and
(2) compound (I) wherein $B^2$ is a group represented by

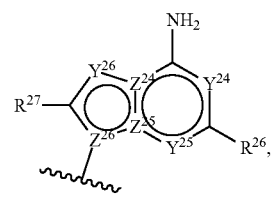

When compound (I) is used as a payload, compound (I) can be converted an antibody (or peptidic antigen recognition sequence)-drug conjugate, as follows.

(1) $B^1$ in the formula (I) is converted to a group represented by

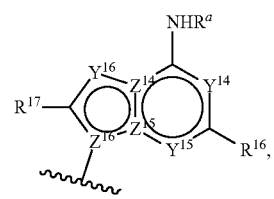

or
$B^2$ in the formula (I) is converted to a group represented by

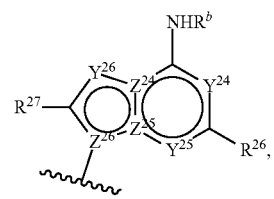

wherein
$R^a$ and $R^b$ are each independently
(i) a $C_{1-5}$ alkyl group,
(ii) an acyl group, or
(iii) a group represented by the formula:

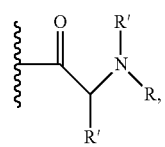

wherein

R is a linker bonding to an antibody or a peptidic antigen recognition sequence (the bond is a covalent bond between the linker and the functional group in the side chain of the antibody or peptidic antigen recognition sequence), and each R' is a hydrogen atom or a substituent.

(2) $R^1$ and $R^2$ in the formula (I) are each independently converted to a group represented by the formula: —$OR^3$ wherein $R^3$ is (i) a $C_{1-6}$ alkyl group, (ii) an acyl group (preferably a $C_{1-6}$ alkoxy-carbonyl group), (iii) a group represented by the formula:

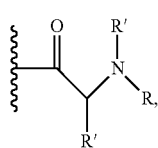

(iv) a group represented by the formula:

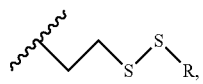

(v) a group represented by the formula:

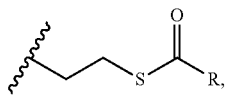

(vi) a group represented by the formula:

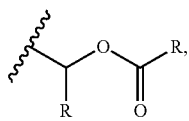

(vii) a group represented by the formula:

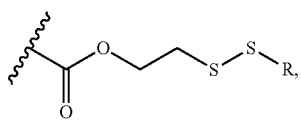

(viii) a group represented by the formula:

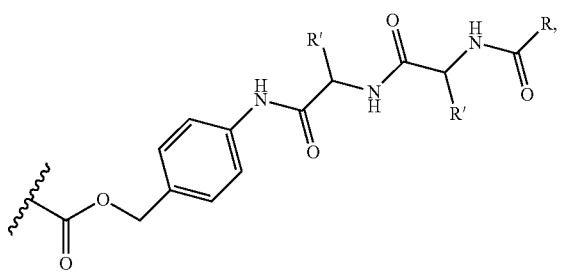

or (ix) a group represented by the formula:

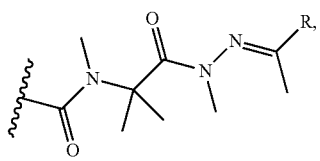

wherein each R and each R' in the formulas are each as defined above.

(3) $Q^2H$ and $Q^4H$ in the formula (I) are each independently converted to (i) a group represented by the formula: —$SR^4$ wherein $R^4$ is (a) a $C_{1-6}$ alkyl group,
(b) an acyl group,
(c) a group represented by the formula: —SR,
(d) a group represented by the formula:

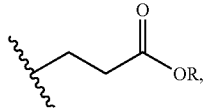

(e) a group represented by the formula:

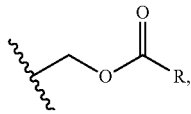

(f) a group represented by the formula:

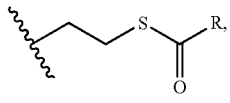

(g) a group represented by the formula:

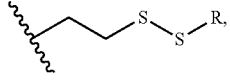

(h) a group represented by the formula:

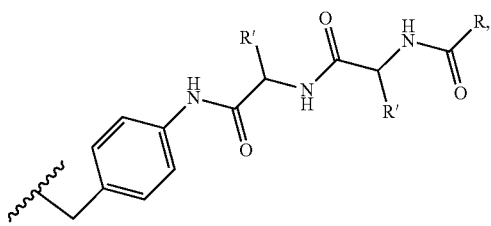

or (i) a group represented by the formula:

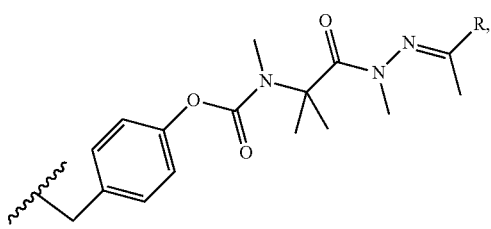

(ii) a group represented by the formula: —OR$^5$ wherein R$^5$ is
(a) a C$_{1-6}$ alkyl group,
(b) an acyl group,
(c) a group represented by the formula:

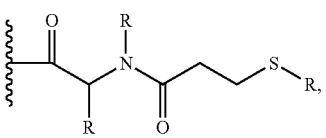

(d) a group represented by the formula:

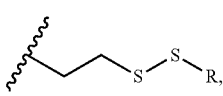

(e) a group represented by the formula:

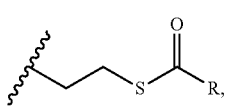

or (f) a group represented by the formula:

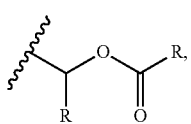

or (iii) a group represented by the formula: —NHR$^6$ wherein R$^6$ is
(a) a C$_{1-6}$ alkyl group,
(b) an acyl group,
(c) a group represented by the formula:

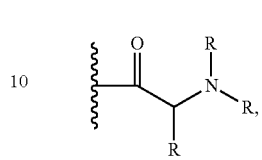

(d) a group represented by the formula:

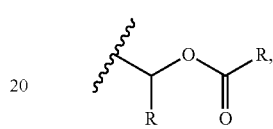

or (e) a group represented by the formula:

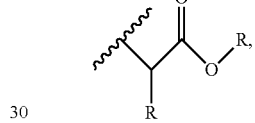

wherein each R and each R' in the formulas are each as defined above.

In addition, when compound (I) is used as a payload, the linker described in Chem. Rev., 114, 9154-9218 (2014), Pharma. Res. 32, 3526-3540 (2015), Bioconjugate Chem. 21, 5-13 (2010), The AAPS journal, 17, 339-351 (2015), WO 2011/005761 and the like may be used.

The disclosure also provides the following particular embodiments.

Embodiment 1. A compound having Formula (I):

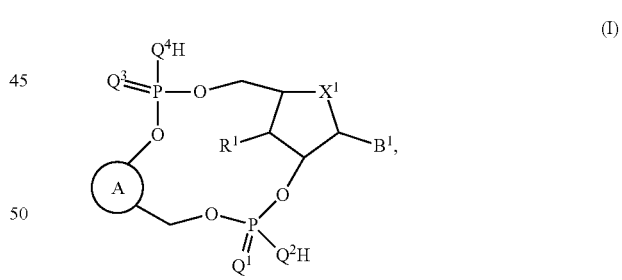

(I)

or a pharmaceutically acceptable salt thereof, wherein:
the partial structure represented by formula (A-1).

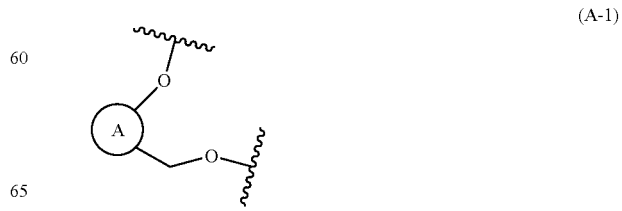

(A-1)

is a partial structure represented by formula (IIA), or formula (IIB):

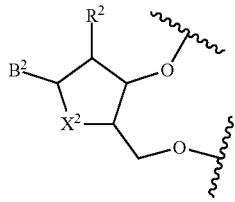
(IIA)

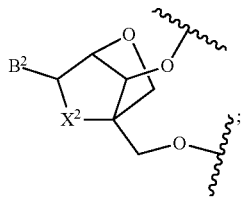
(IIB)

$R^1$ and $R^2$ are each independently a hydroxy group or a halogen atom;

$B^1$ is a group represented by formula ($B^1$-A) or formula ($B^1$-B):

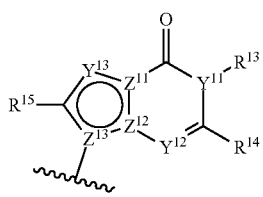
$B^1$-A or

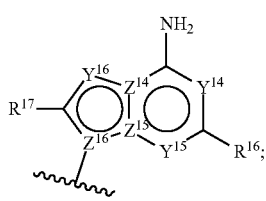
$B^1$-B $R^{13}$, $R^{14}$, $R^{15}$, $R^{16}$ and $R^{17}$ are each independently a hydrogen atom or a substituent;

$Y^{11}$, $Y^{12}$, $Y^{13}$, $Y^{14}$, $Y^{15}$ and $Y^{16}$ are each independently N or $CR^{1a}$;

$Z^{11}$, $Z^{12}$, $Z^{13}$, $Z^{14}$, $Z^{15}$ and $Z^{16}$ are each independently N or C;

$R^{1a}$ is a hydrogen atom or a substituent;

$B^2$ is a group represented by formula ($B^2$-A) or formula ($B^2$-B):

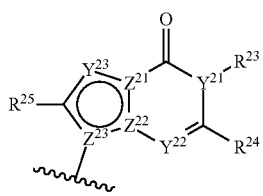
$B^2$-A or

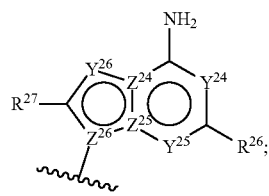
$B^2$-B $R^{23}$, $R^{24}$, $R^{25}$, $R^{26}$ and $R^{27}$ are each independently a hydrogen atom or a substituent;

$Y^{21}$, $Y^{22}$, $Y^{23}$, $Y^{24}$, $Y^{25}$ and $Y^{26}$ are each independently N or $CR^{2a}$;

$Z^{21}$, $Z^{22}$, $Z^{23}$, $Z^{24}$, $Z^{25}$ and $Z^{26}$ are each independently N or C;

$R^{2a}$ is a hydrogen atom or a substituent;

$X^1$ and $X^2$ are each independently an oxygen atom or a sulfur atom; and $Q^1$, $Q^2$, $Q^3$ and $Q^4$ are each independently an oxygen atom or a sulfur atom, provided that:

at least one of $B^1$ or $B^2$ is:

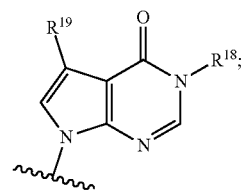

wherein:

$R^{18}$ is hydrogen or $C_{1-6}$ alkyl; and $R^{19}$ a halogen atom.

Embodiment 2. The compound of Embodiment 1, or a pharmaceutically acceptable salt thereof, wherein $R^{19}$ is fluoro or chloro.

Embodiment 3. The compound of Embodiments 1 or 2, or a pharmaceutically acceptable salt thereof, having formula (X):

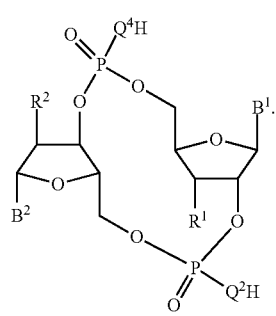
(X)

Embodiment 4. The compound of Embodiments 1 or 2, or a pharmaceutically acceptable salt thereof, having formula (XI).

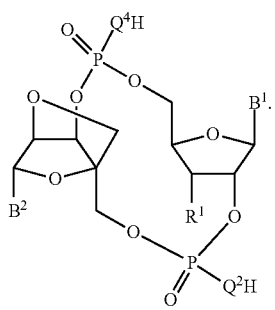
(XI)

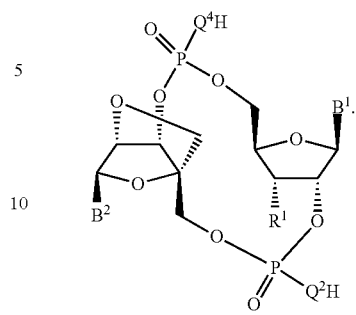
(XIII)

Embodiment 5. The compound of any one of Embodiments 1-4, or a pharmaceutically acceptable salt thereof, wherein $R^1$ is a hydroxy group.

Embodiment 6. The compound of any one of Embodiments 1-4, or a pharmaceutically acceptable salt thereof, wherein $R^1$ is fluoro atom.

Embodiment 7. The compound of any one of Embodiments 1-3, 5, or 6, or a pharmaceutically acceptable salt thereof, wherein $R^2$ is a hydroxyl group.

Embodiment 8. The compound of any one of Embodiments 1-3, 5, or 6, or a pharmaceutically acceptable salt thereof, wherein $R^2$ is a fluoro atom.

Embodiment 9. The compound of any one of Embodiments 1-8, or a pharmaceutically acceptable salt thereof, wherein $Q^4$ is a sulfur atom.

Embodiment 10. The compound of any one of Embodiments 1-9, or a pharmaceutically acceptable salt thereof, wherein $Q^2$ is an oxygen atom.

Embodiment 11. The compound of any one of Embodiments 1-9, or a pharmaceutically acceptable salt thereof, wherein $Q^2$ is a sulfur atom.

Embodiment 12. The compound of any one of Embodiments 1-3 or 5-11, or a pharmaceutically acceptable salt thereof, having the formula (XII):

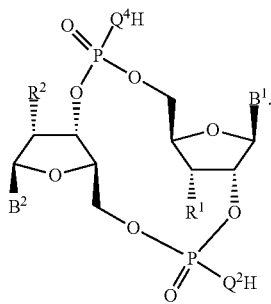
(XII)

Embodiment 13. The compound of any one of Embodiments 1, 2, 4-6, or 9-11, or a pharmaceutically acceptable salt thereof, having the formula (XIII):

Embodiment 14. The compound of any one of Embodiments 1-13, or a pharmaceutically acceptable salt thereof, wherein $B^1$ is:

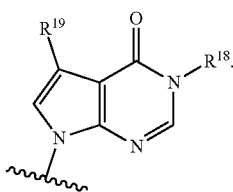

Embodiment 15. The compound of any one of Embodiments 1-13, or a pharmaceutically acceptable salt thereof, wherein B is:

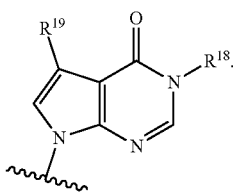

Embodiment 16. The compound of any one of Embodiments 2-15, or a pharmaceutically acceptable salt thereof, wherein $R^{19}$ is a fluoro atom.

Embodiment 17. The compound of any one of Embodiments 1-16, or a pharmaceutically acceptable salt thereof, wherein $R^{18}$ is hydrogen.

Embodiment 18. The compound of any one of Embodiments 1-16, or a pharmaceutically acceptable salt thereof, wherein $R^{18}$ is methyl.

Embodiment 19. The compound of any one of Embodiments 14 or 16-18, or a pharmaceutically acceptable salt thereof, wherein $B^2$ is selected from the group consisting of:

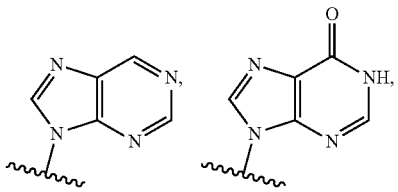

-continued

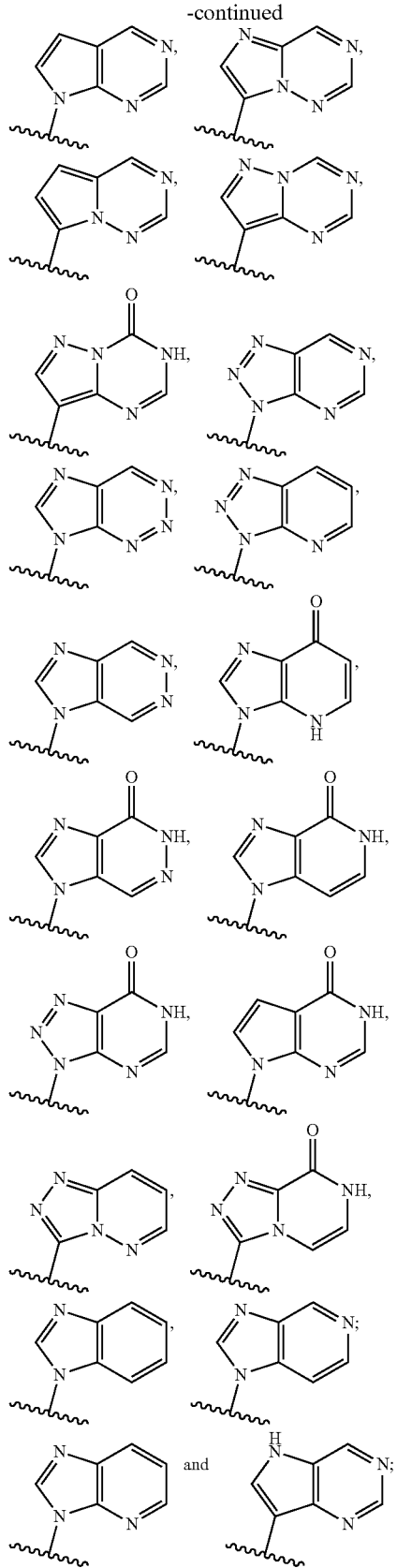

each of which is optionally and independently substituted at:

(i) any available carbon atom with a halo, $C_{1-6}$ alkyl, $C_{1-6}$ alkoxy, $C_{1-6}$ alkylthio, or amino group; and/or (ii) any available nitrogen atom with a $C_{1-6}$ alkyl group.

Embodiment 20. The compound of Embodiment 19, or a pharmaceutically acceptable salt thereof, wherein $B^2$ is selected from the group consisting of:

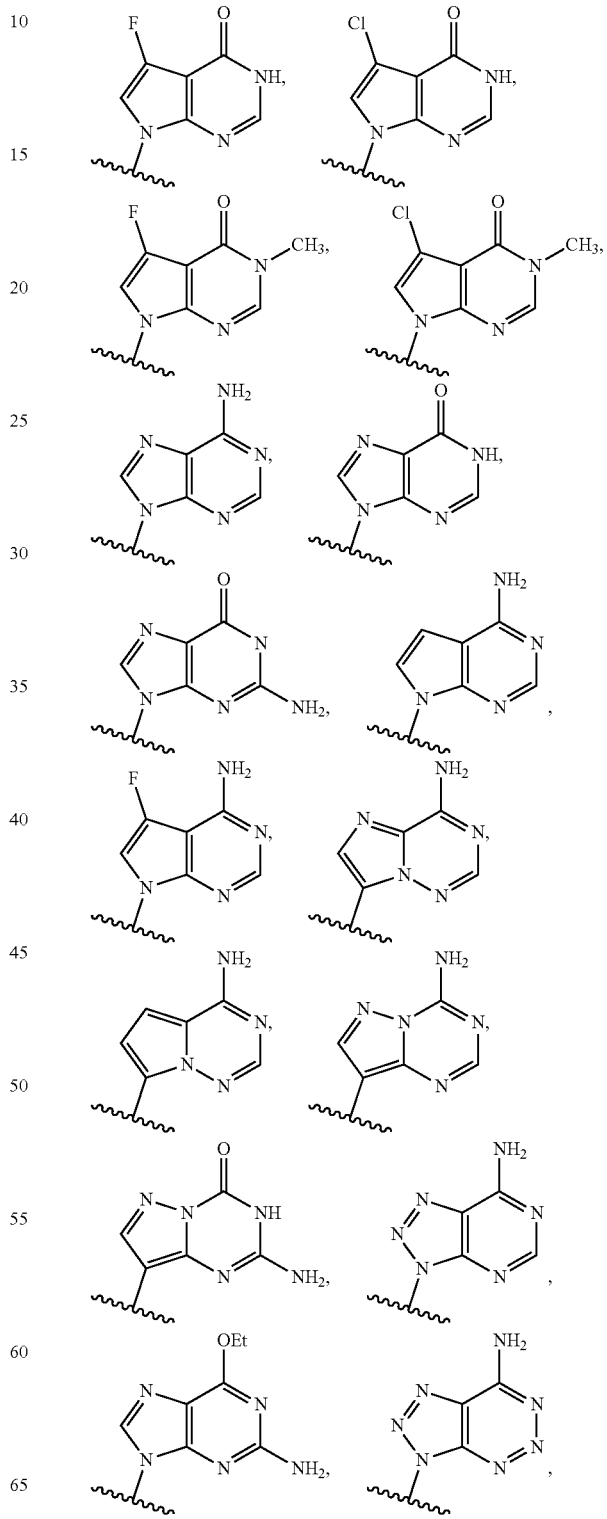

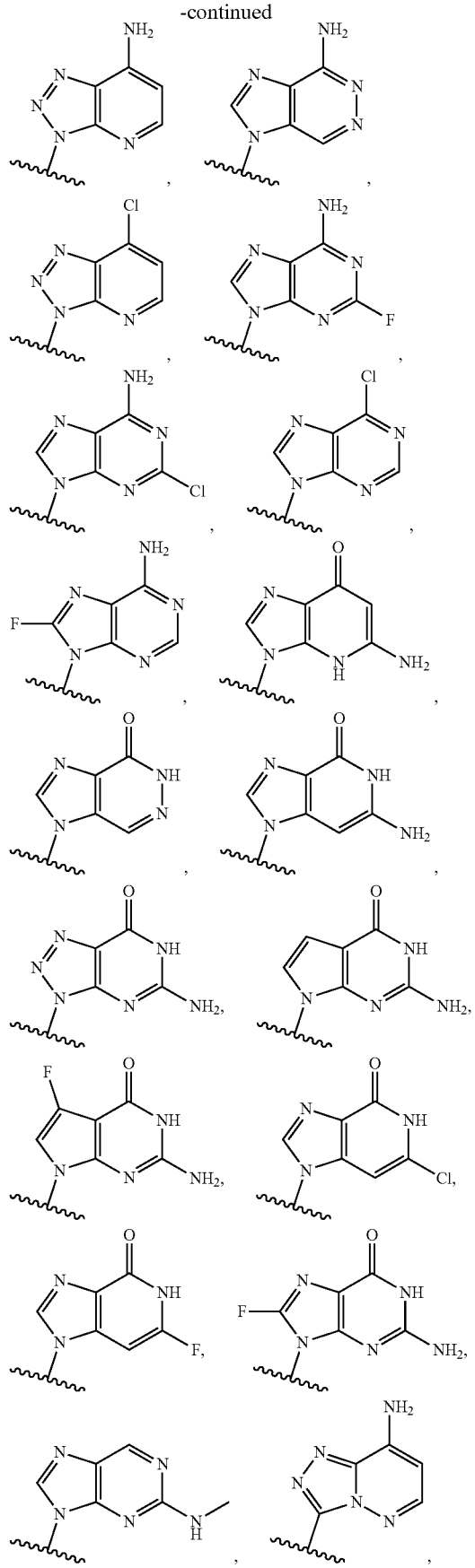
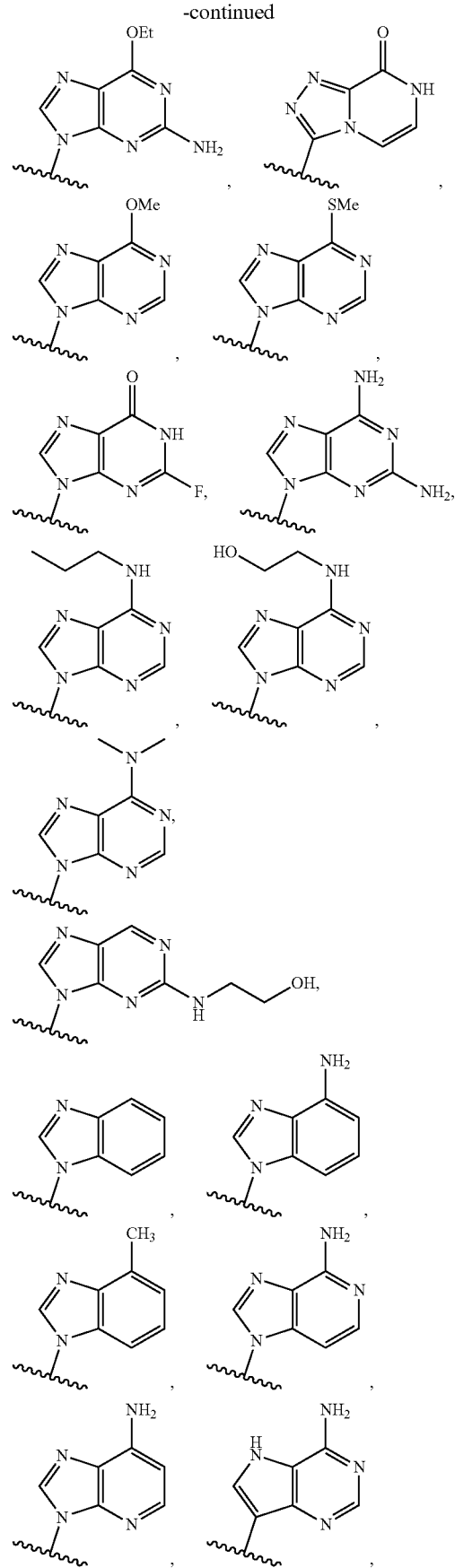

-continued

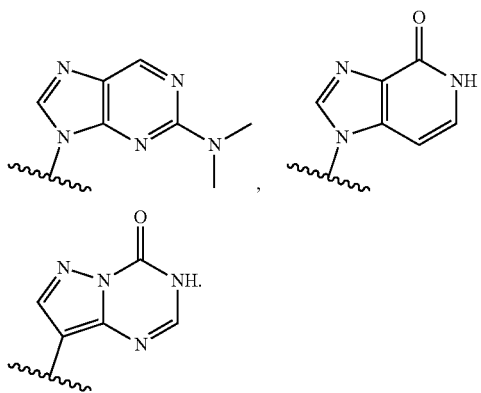

Embodiment 21. The compound of Embodiment 20, or a pharmaceutically acceptable salt thereof, wherein $B^2$ is selected from the group consisting of:

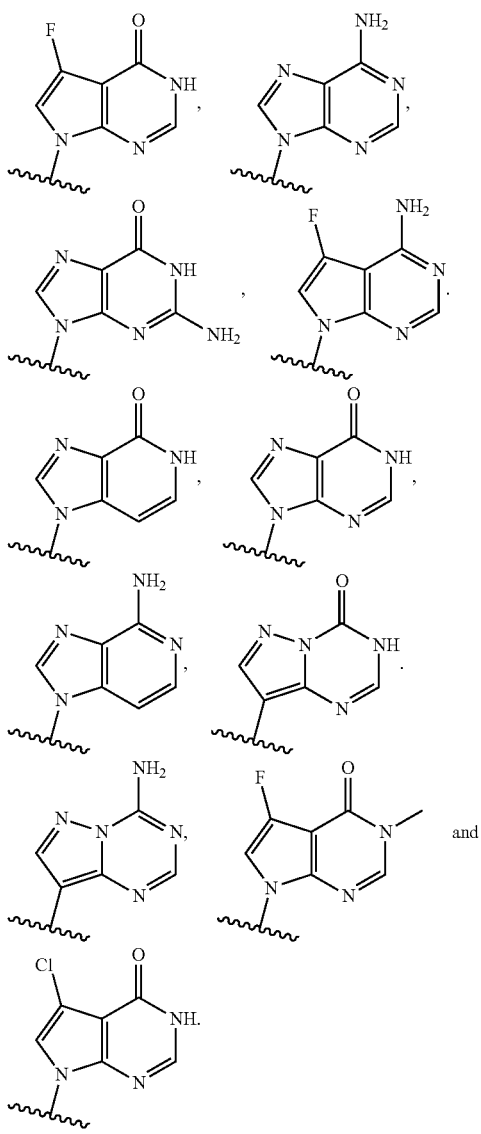

Embodiment 22. The compound of Embodiment 21, or a pharmaceutically acceptable salt thereof, wherein B is selected from the group consisting of:

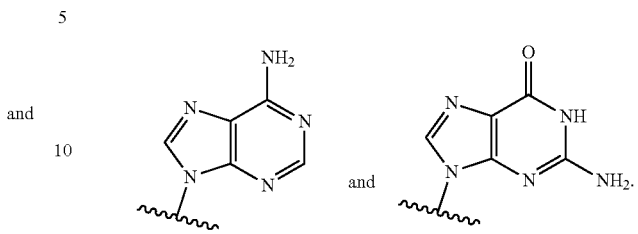

Embodiment 23. The compound of any one of Embodiments 15-18, or a pharmaceutically acceptable salt thereof, wherein $B^1$ is selected from the group consisting of:

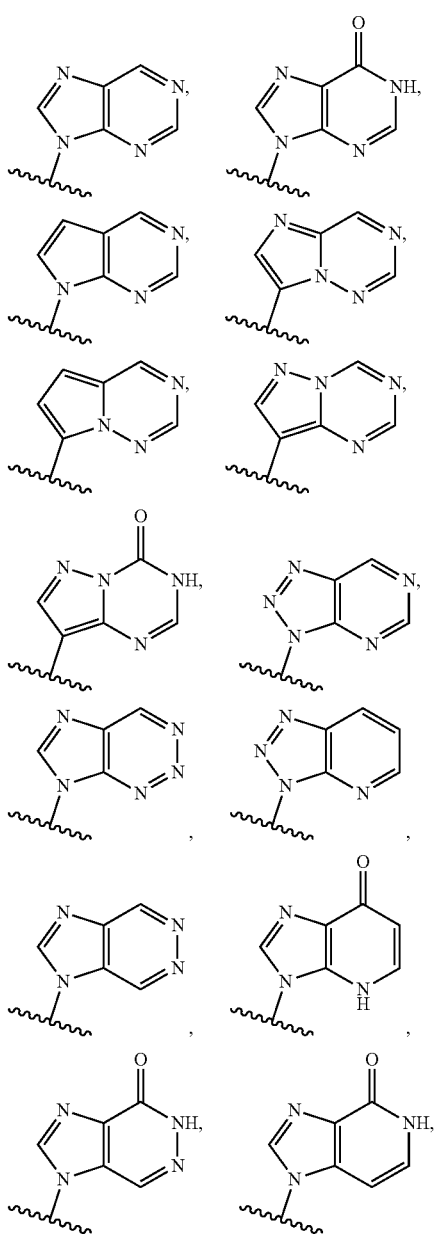

111

-continued

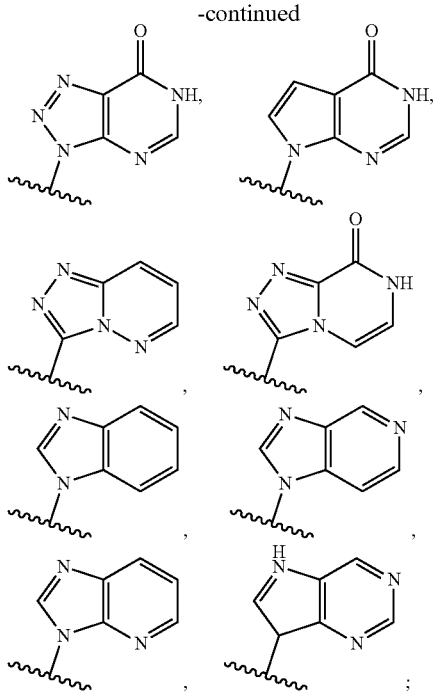

each of which is optionally and independently substituted at:
(i) any available carbon atom with a halo, $C_{1-6}$ alkyl, $C_{1-6}$ alkoxy, $C_{1-6}$ alkylthio, or amino group; and/or
(ii) any available nitrogen atom with a $C_{1-6}$ alkyl group.

Embodiment 24. The compound of Embodiment 23, or a pharmaceutically acceptable salt thereof, wherein $B^1$ is selected from the group consisting of:

112

-continued

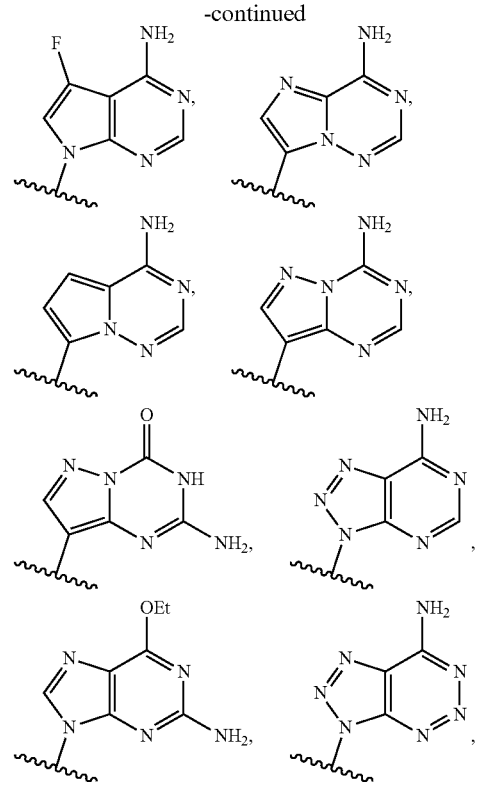

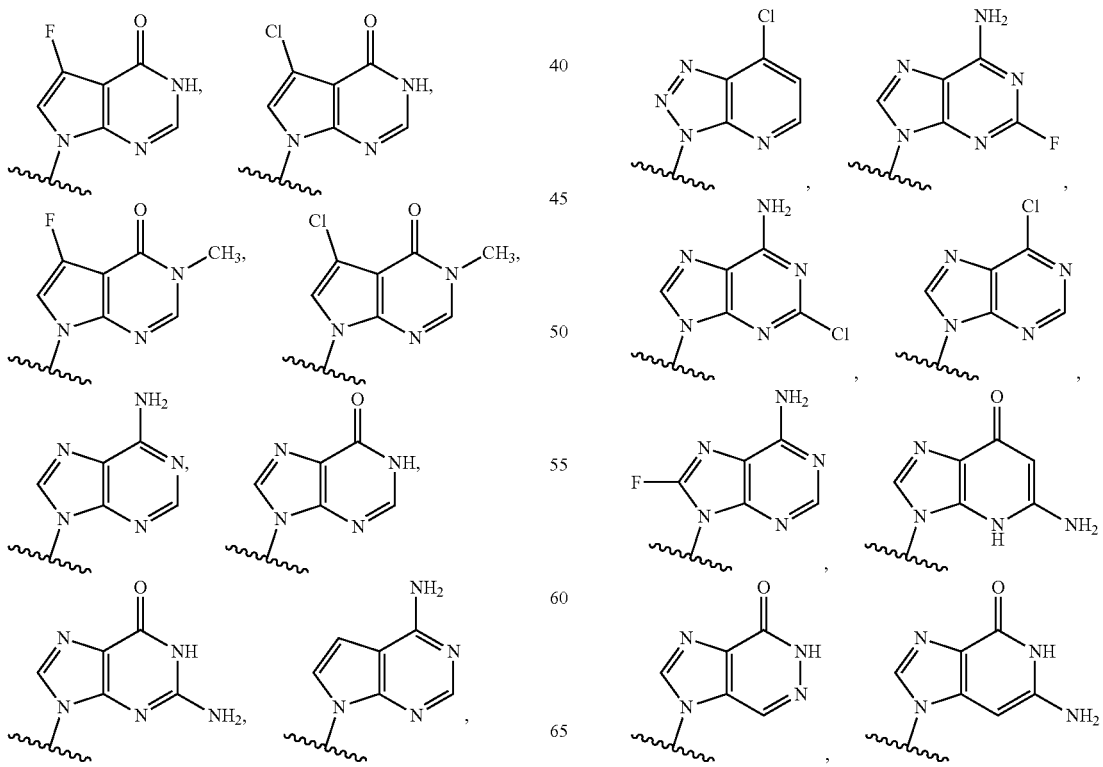

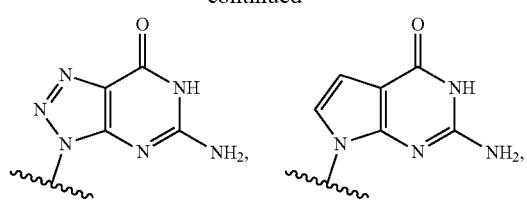
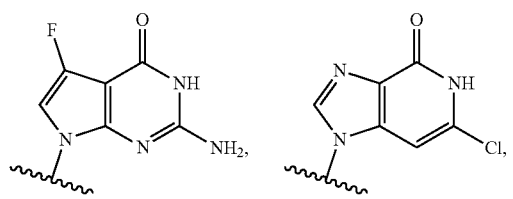
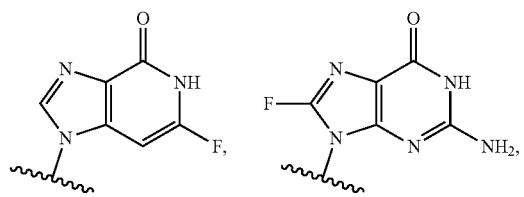
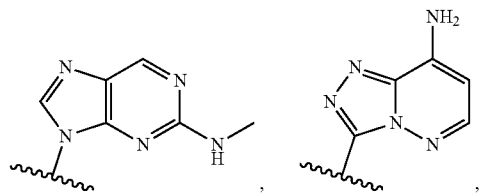
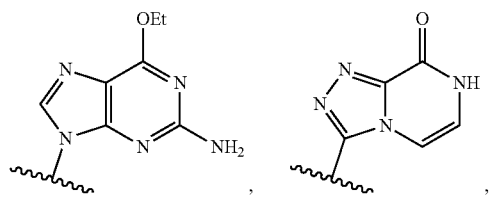
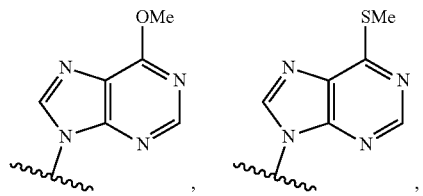
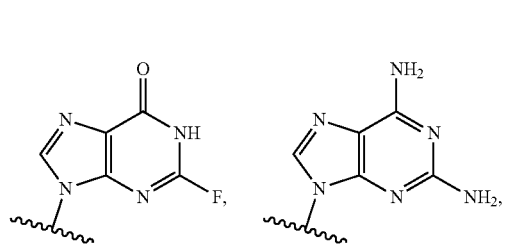
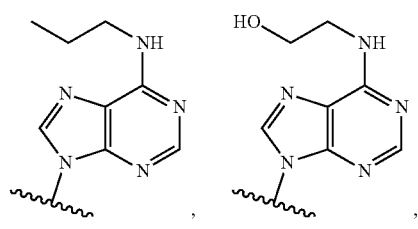
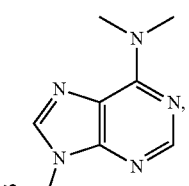
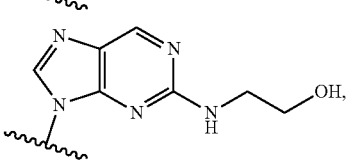
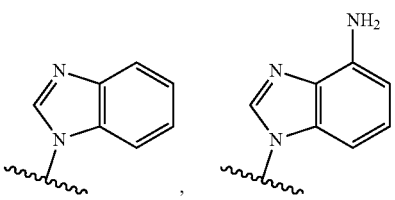
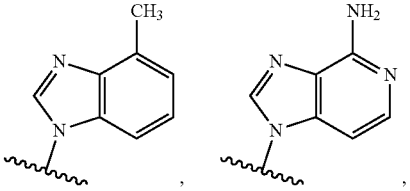
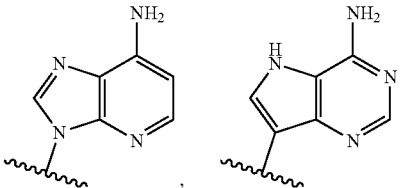
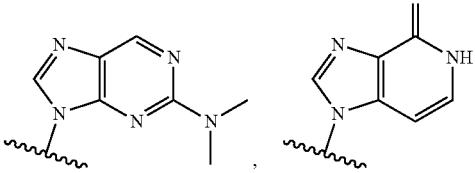
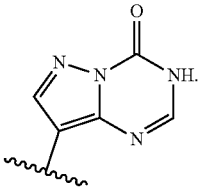
Embodiment 25. The compound of Embodiment 24, or a pharmaceutically acceptable salt thereof, wherein $B^1$ is selected from the group consisting of:
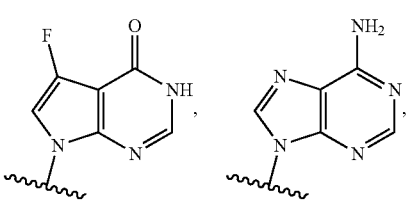

-continued
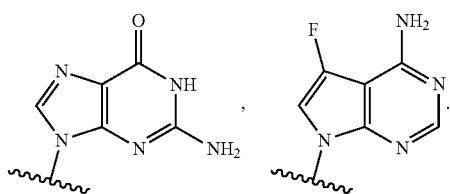
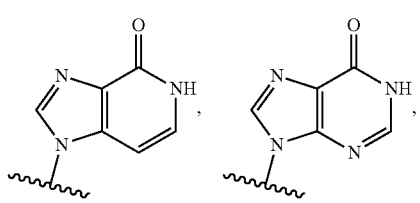
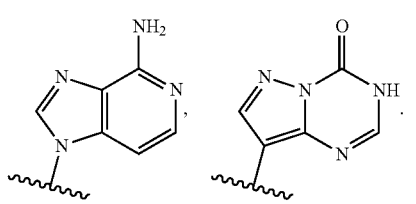
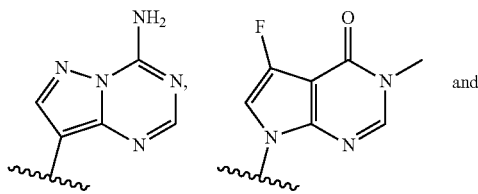
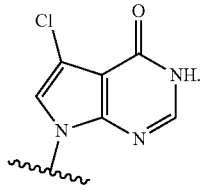
Embodiment 26. The compound of Embodiment 25, or a pharmaceutically acceptable salt thereof, wherein $B^1$ is selected from the group consisting of:
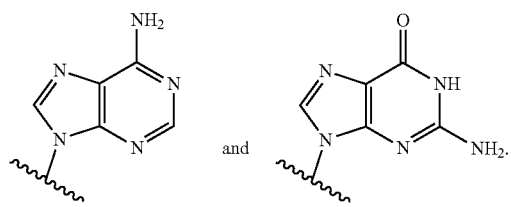 [SMILES: *n1cnc2c(N)ncnc21 ; *n1cnc2c(=O)[nH]c(N)nc21]
Embodiment 27. The compound of Embodiment 1, or a pharmaceutically acceptable salt thereof, selected from the group consisting of:
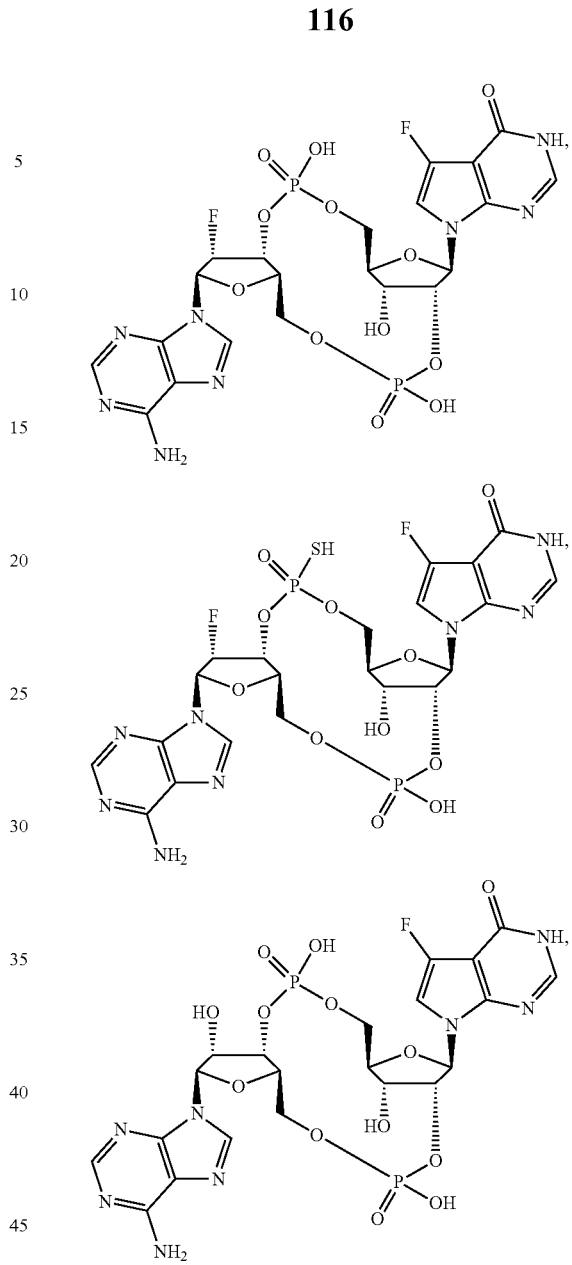
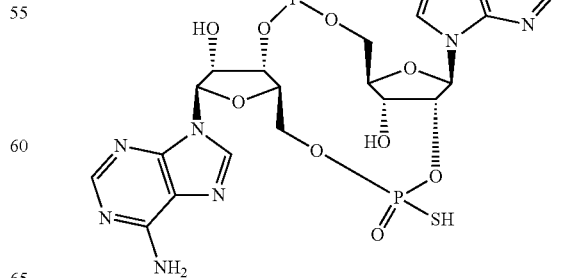

117
-continued
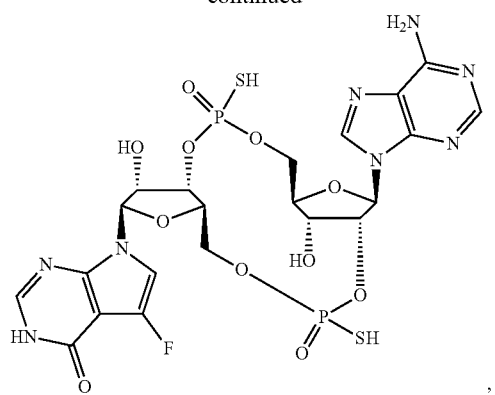
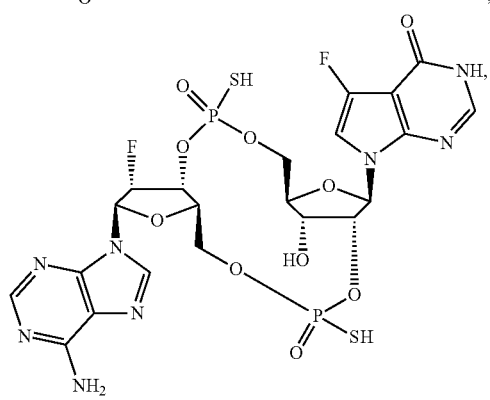
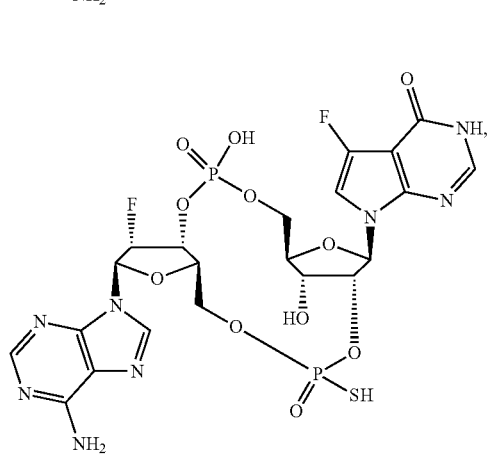
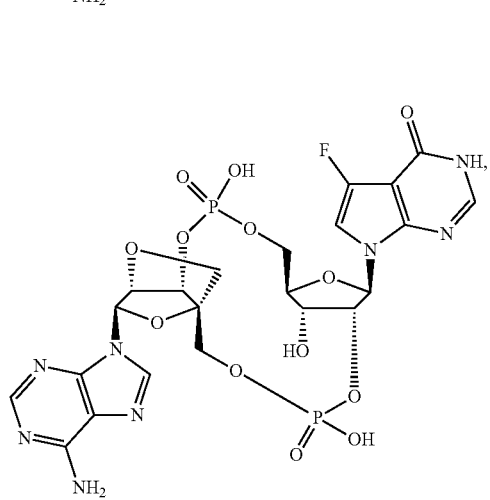
118
-continued
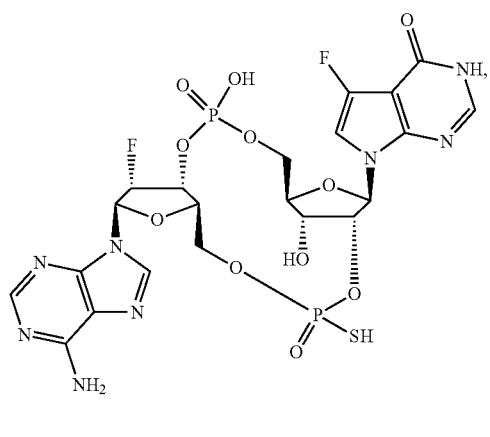
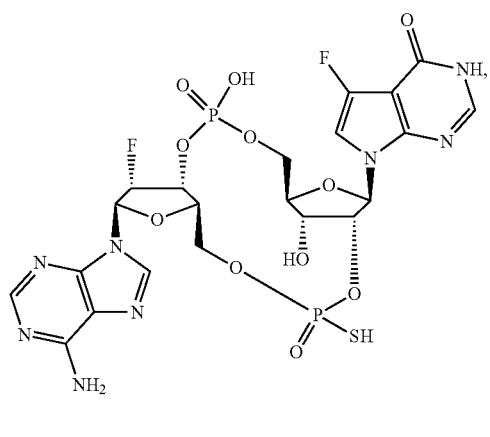
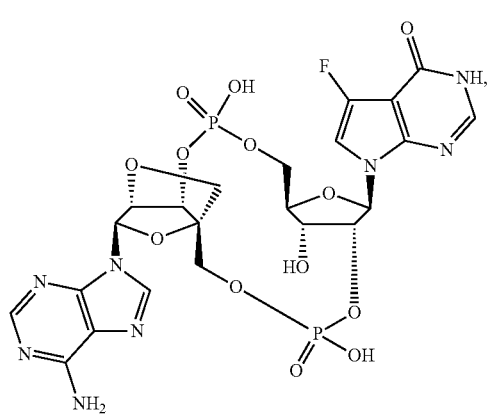
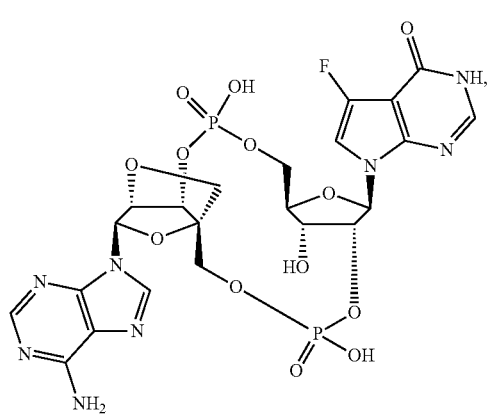

-continued
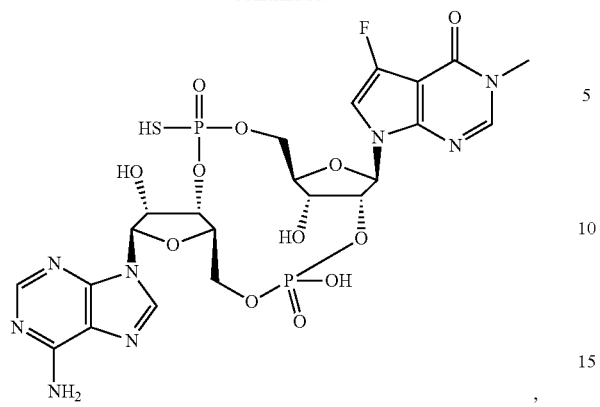
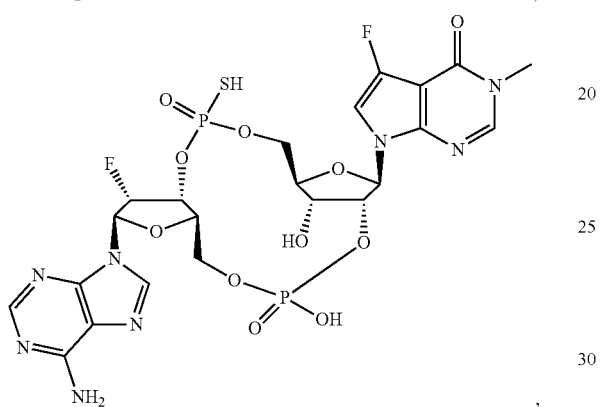
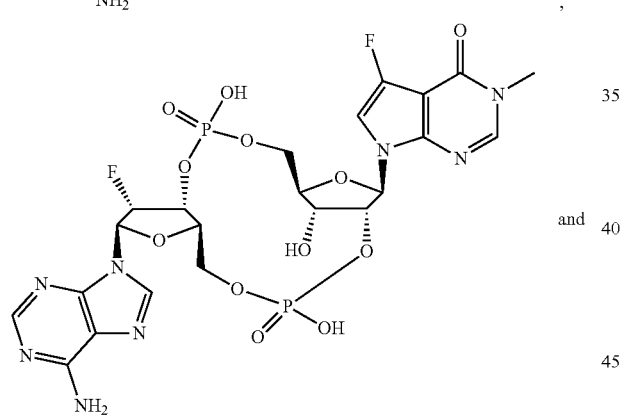
and
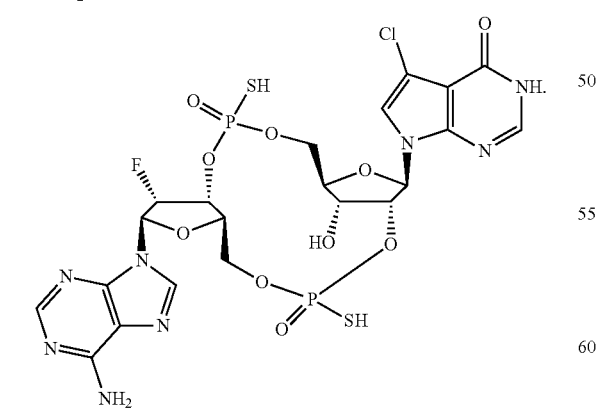
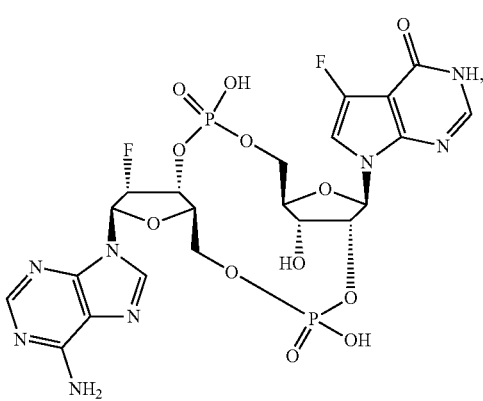
,
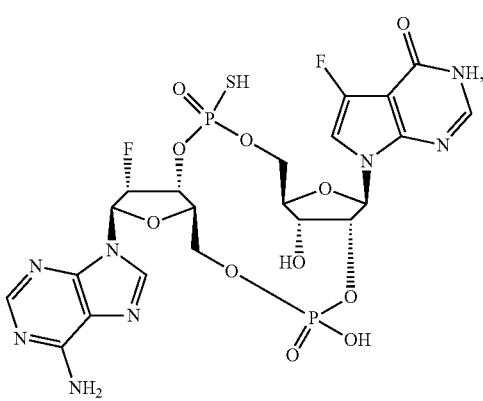
,
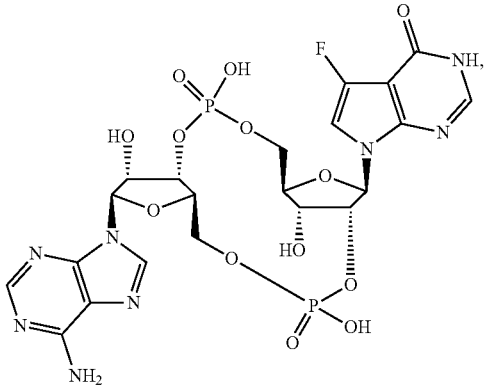
,
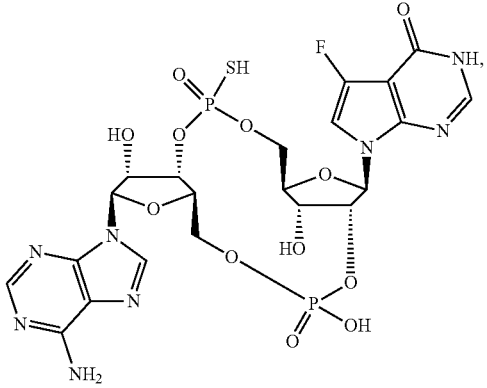
Embodiment 28. The compound of Embodiment 27, or a pharmaceutically acceptable salt thereof, selected from the group consisting of:

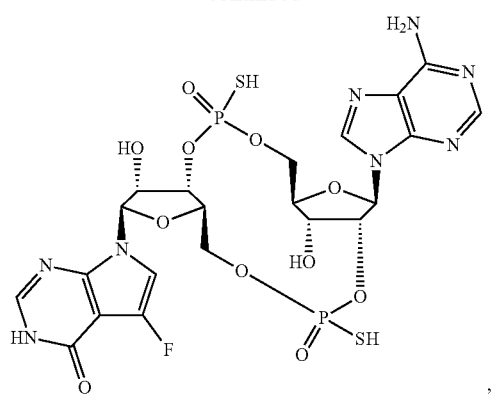
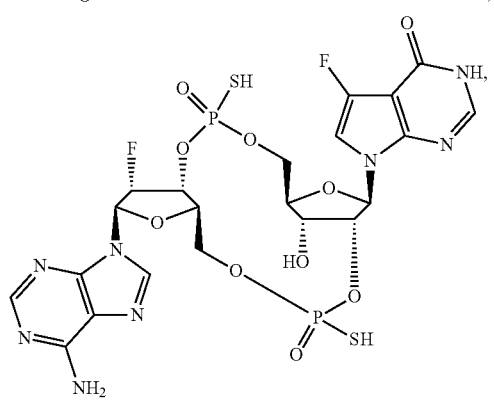
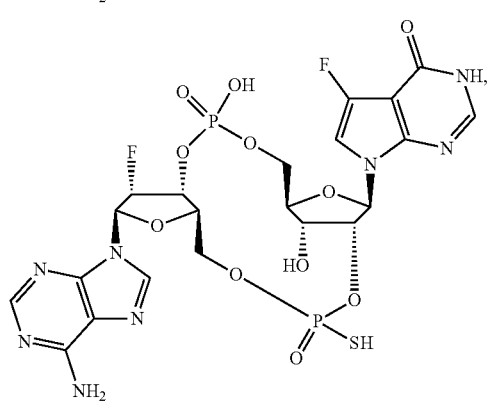
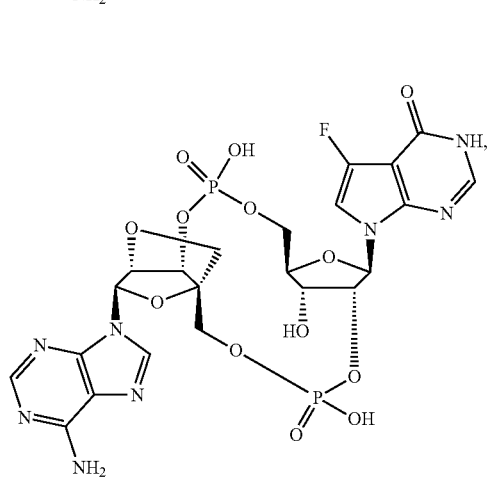
,
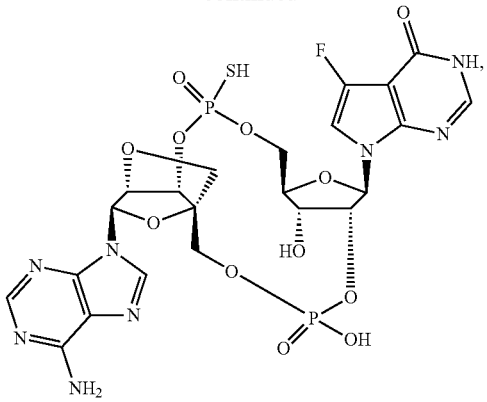
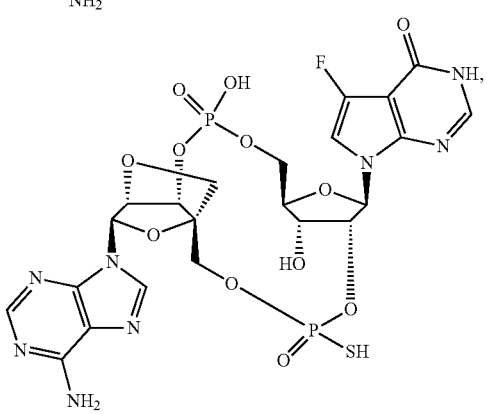
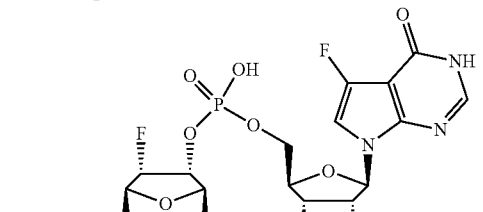
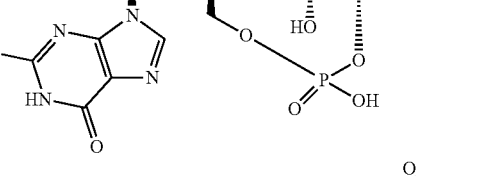
and
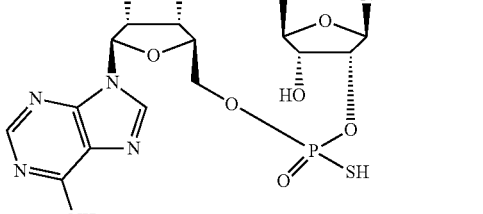
Embodiment 29. The compound of Embodiment 27, or a pharmaceutically acceptable salt thereof, selected from the group consisting of:

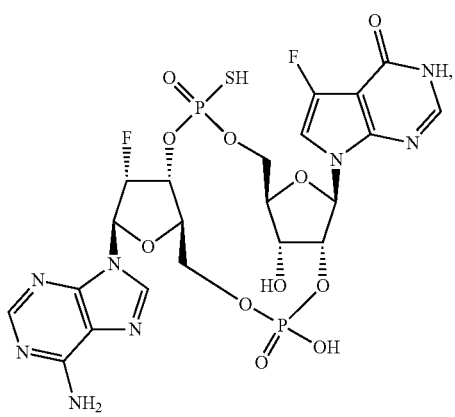

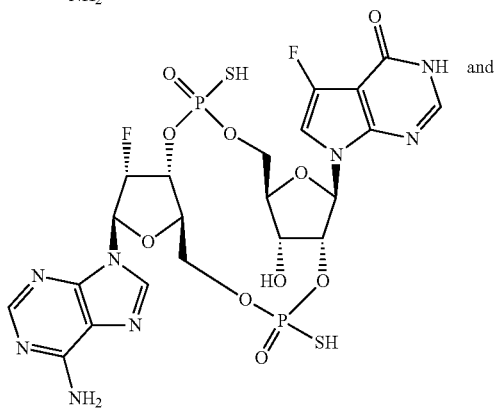

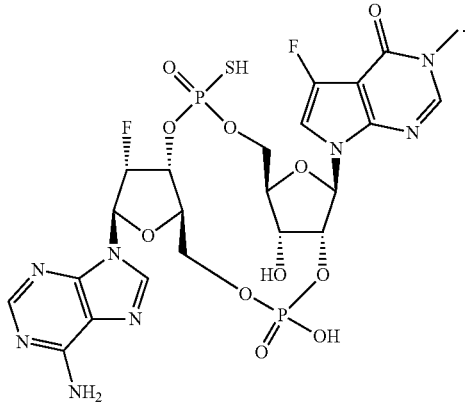

Embodiment 30. The compound of any one of Embodiments 1-29, wherein the pharmaceutically acceptable salt is the triethylamine salt or the sodium salt e.g., the di-triethylamine salt or di-sodium salt.

Embodiment 31. A pharmaceutical composition comprising the compound of any one of Embodiments 1-30, or a pharmaceutically acceptable salt thereof, and a pharmaceutically acceptable excipient.

Embodiment 32. A compound having Formula (XIV):

$$(CD-L)_n-A \qquad (XIV)$$

or a pharmaceutically acceptable salt thereof, wherein:

CD is a group represented by any one of Formula (XX)-(XXIX).

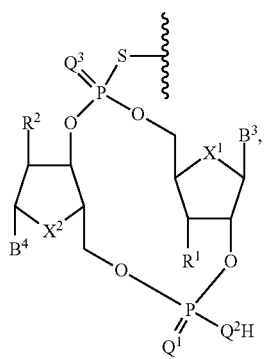

XX

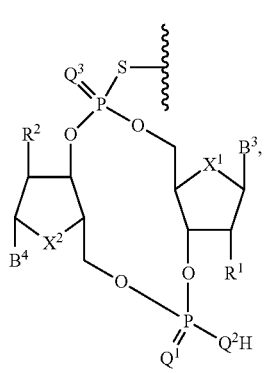

XXI

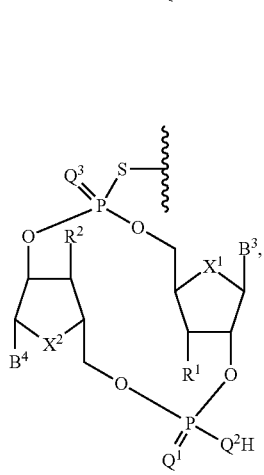

XXII

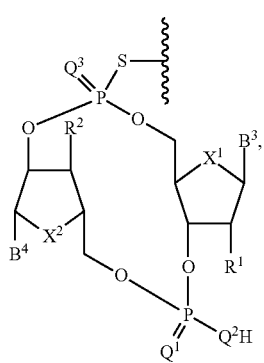

XXIII

XXIV
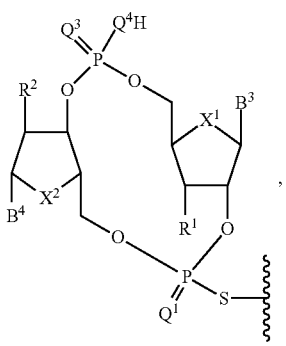,

XXV
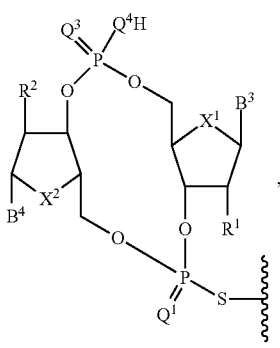,

XXVI
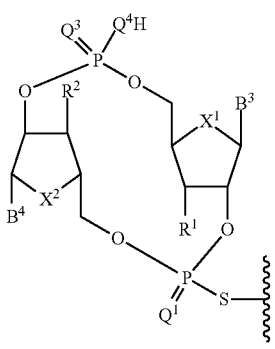,

XXVII
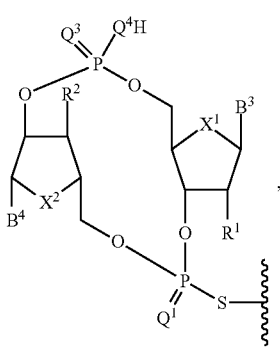,

XXVIII
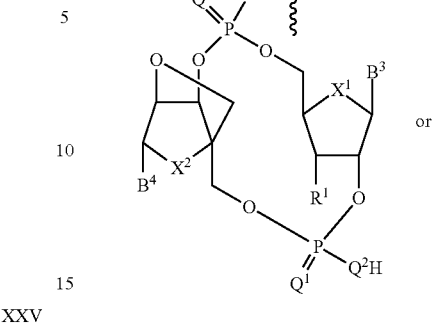

or

XXIX
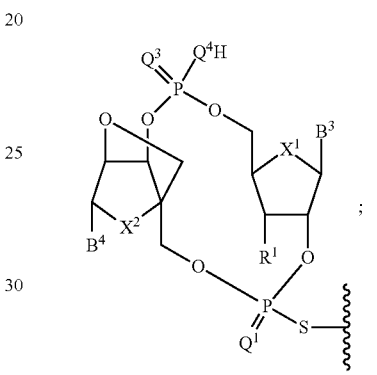;

$R^1$ and $R^2$ are each independently a hydroxy group, hydrogen, amino group, or a halogen atom;

$B^3$ and $B^4$ are independently an optionally substituted 5- to 14-membered aromatic heterocyclic group;

$X^1$ and $X^2$ are each independently an oxygen atom, $CH_2$, or a sulfur atom;

$Q^1$, $Q^2$, $Q^3$ and $Q^4$ are each independently an oxygen atom or a sulfur atom;

L is a linker;

A is an antibody, antibody fragment, or antigen-binding fragment; and n is 1-10.

Embodiment 33. The compound of Embodiment 32, or a pharmaceutically acceptable salt thereof, wherein $R^1$ and $R^2$ are each independently a hydroxy group or a halogen atom.

Embodiment 34. The compound of Embodiments 32 or 33, or a pharmaceutically acceptable salt thereof, wherein $X^1$ and X are each independently an oxygen atom or a sulfur atom.

Embodiment 35. The compound of any one of Embodiments 31-34, or a pharmaceutically acceptable salt thereof, wherein $Q^1$ and $Q^3$ are an oxygen atom.

Embodiment 36. The compound of Embodiment 32, or a pharmaceutically acceptable salt thereof, wherein CD is group represented by Formula (XX-A):

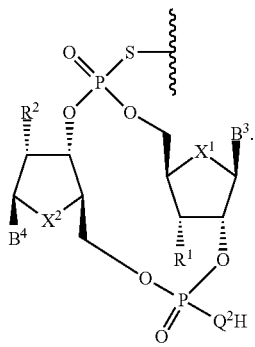

XX-A

Embodiment 37. The compound of Embodiment 32, or a pharmaceutically acceptable salt thereof, wherein CD is group represented by Formula (XXI-A):

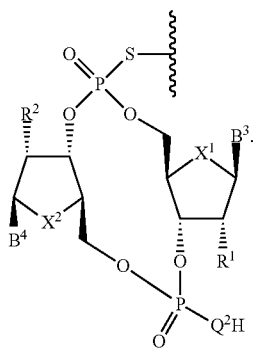

XXI-A

Embodiment 38. The compound of Embodiment 32, or a pharmaceutically acceptable salt thereof, wherein CD is group represented by Formula (XXII-A):

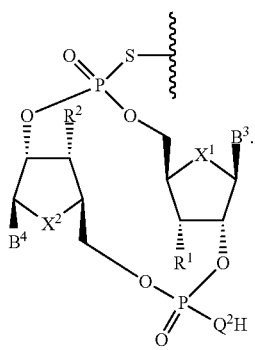

XXII-A

Embodiment 39. The compound of Embodiment 32, or a pharmaceutically acceptable salt thereof, wherein CD is group represented by Formula (XXIII-A):

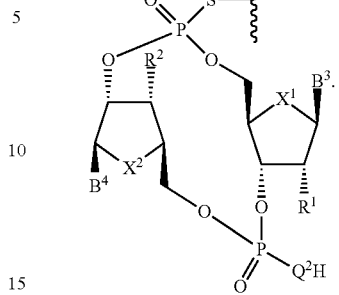

XXIII-A

Embodiment 40. The compound of Embodiment 32, or a pharmaceutically acceptable salt thereof, wherein CD is group represented by Formula (XX IV-A):

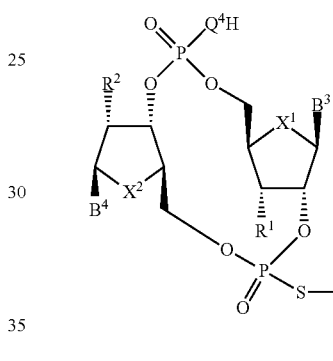

XXIV-A

Embodiment 41. The compound of Embodiment 32, or a pharmaceutically acceptable salt thereof, wherein CD is group represented by Formula (XXV-A):

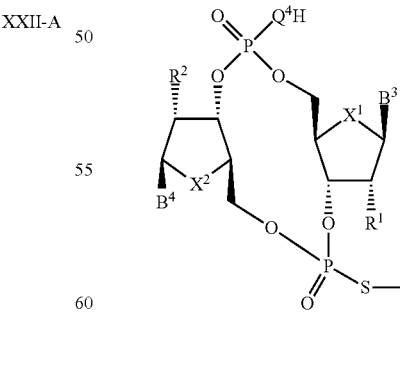

XXV-A

Embodiment 42. The compound of Embodiment 32, or a pharmaceutically acceptable salt thereof, wherein CD is group represented by Formula (XXVI-A):

XXVI-A

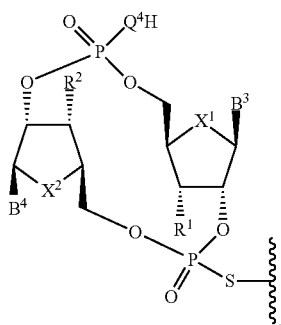

Embodiment 43. The compound of Embodiment 32, or a pharmaceutically acceptable salt thereof, wherein CD is group represented by Formula (XXVII-A):

XXVII-A

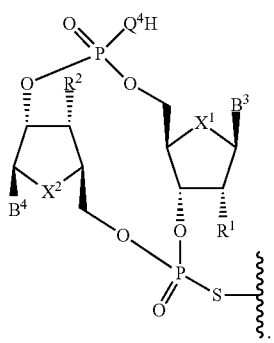

Embodiment 44. The compound of Embodiment 32, or a pharmaceutically acceptable salt thereof, wherein CD is group represented by Formula (XXVIII-A):

XXVIII-A

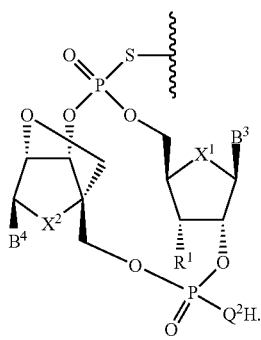

Embodiment 45. The compound of Embodiment 32, or a pharmaceutically acceptable salt thereof, wherein CD is group represented by Formula (XXIX-A):

XXIX-A

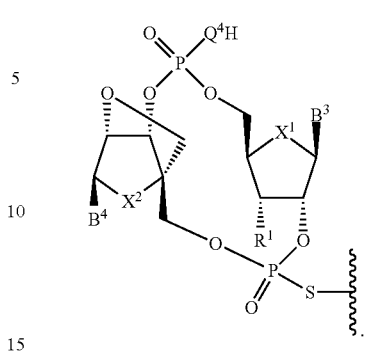

Embodiment 46. The compound of any one of Embodiments 32-45, or a pharmaceutically acceptable salt thereof, wherein.

L is —$X^3$-T-Z-Q-;

$X^3$ is —$(CH_2)_o$—,

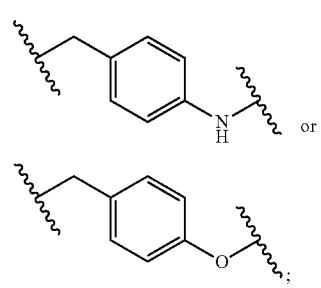

o is 1, 2, or 3; or $X^3$ is absent;

T is a peptide, or is absent;

Z is a spacer;

Q is a heterobifunctional group or heterotrifunctional group, or is absent.

Embodiment 47. The compound of Embodiment 46, or a pharmaceutically acceptable salt thereof, having the formula (XXX):

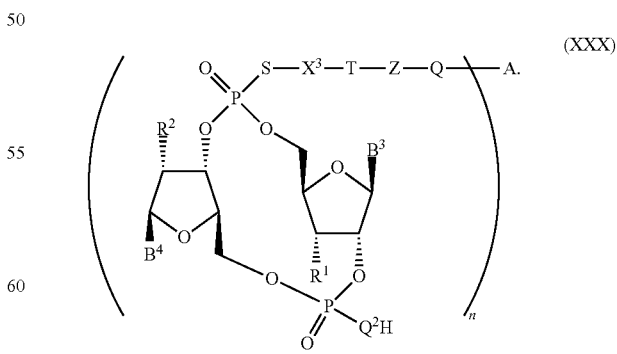

Embodiment 48. The compound of Embodiment 46, or a pharmaceutically acceptable salt thereof, having the formula (XXXI).

(XXXI)

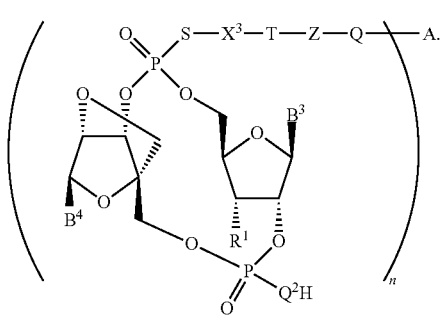

Embodiment 49. The compound of any one of Embodiments 46-48, or a pharmaceutically acceptable salt thereof, wherein:

$X^3$ is

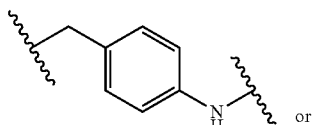

or

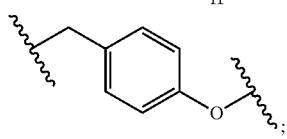

;

T is

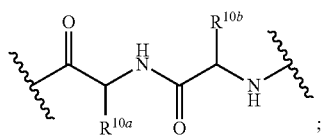

;

and $R^{10a}$ and $R^{10b}$ are independently selected from the group consisting of hydrogen and optionally substituted $C_{1-6}$ alkyl.

Embodiment 50. The compound of Embodiment 49, or a pharmaceutically acceptable salt thereof, wherein:

$X^3$ is

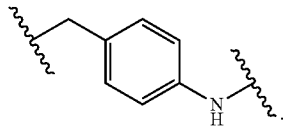 [SMILES: *Cc1ccc(N*)cc1]

.

Embodiment 51. The compound of any one of Embodiments 46-50, or a pharmaceutically acceptable salt thereof, wherein:

Z is

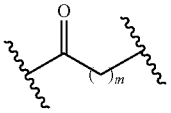

or $-(CH_2CH_2O)_s-$;

m is 1, 2, 3, 4, 5, or 6; and s is 1, 2, 3, 4, 5, 6, 7, 8, 9, or 10.

Embodiment 52. The compound of any one of Embodiments 46-48, or a pharmaceutically acceptable salt thereof, wherein:

$X^3$ is $-CH_2-$;

Z is

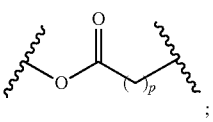

;

and p is 1, 2, 3, 4, 5, 6, 7, 8, 9, or 10.

Embodiment 53. The compound of any one of Embodiments 46-48, or a pharmaceutically acceptable salt thereof, wherein:

$X^3$ is $-CH_2CH_2-$;

Z is

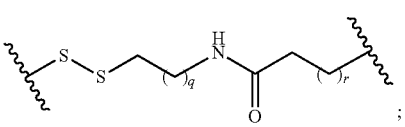

;

q is 1, 2, 3, 4, 5, or 6; and r is 1, 2, 3, 4, 5, or 6.

Embodiment 54. The compound of any one of Embodiments 46-53, or a pharmaceutically acceptable salt thereof, wherein:

Q is a heterobifunctional group selected from the group consisting of:

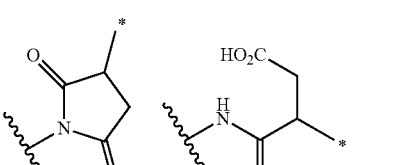

,

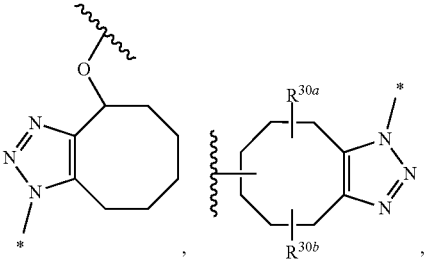

,

-continued

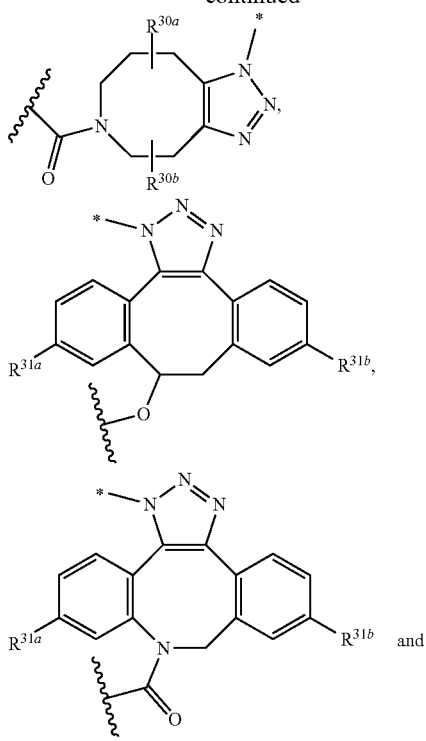

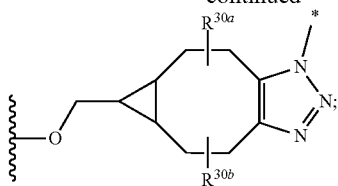

R[29] is hydrogen or $C_{1-6}$ alkyl;

R[30a] and R[30b] are independently selected from the group consisting of hydrogen, $C_{1-6}$ alkyl, halo, —C(=O)OR[29], —NH$_2$, $C_{1-6}$ alkoxy, —CN, —NO$_2$, and —OH;

R[31a] and R[31b] are independently selected from the group consisting of hydrogen, $C_{1-6}$ alkyl, halo, —C(=O)OR[29], —NH$_2$, —N(CH$_3$)$_2$, $C_{1-6}$ alkoxy, —CN, —NO$_2$, and —OH; and \* indicates the attachment point to any available carbon atom, nitrogen atom, oxygen atom, or sulfur atom attached to the antibody, antibody fragment, or antigen-binding fragment.

Embodiment 55. The compound of Embodiment 51, or a pharmaceutically acceptable salt thereof, having formula (XXXII):

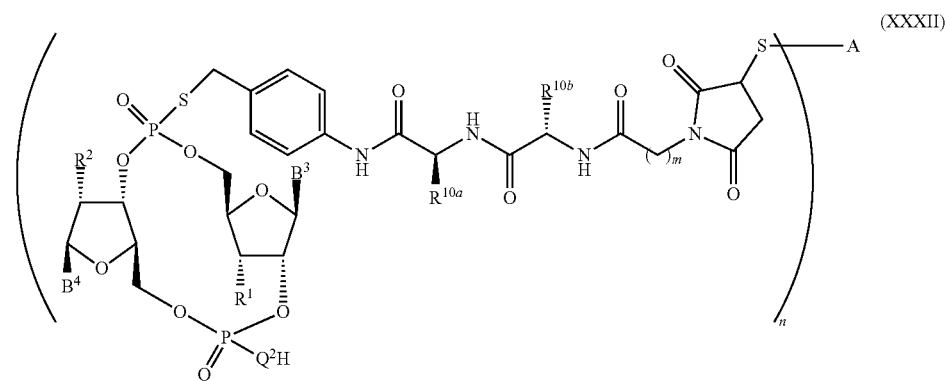

wherein:
R[10a] and R[10b] are independently $C_{1-3}$ alkyl; and
m is 2, 3, 4, or 5.

Embodiment 56. The compound of Embodiment 55, or a pharmaceutically acceptable salt thereof, having formula (XXXIII):

(XXXIII)

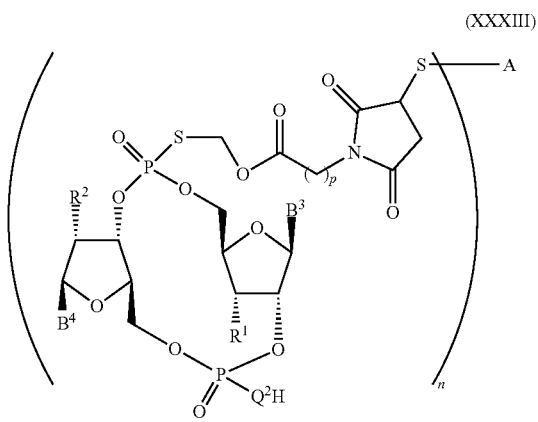

wherein p is 4, 5, or 6.

Embodiment 57. The compound of Embodiment 56, or a pharmaceutically acceptable salt thereof, having formula (XXXIV):

(XXXIV)

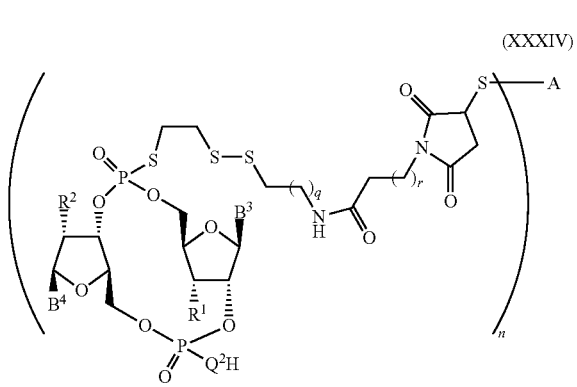

wherein:

q is 1, 2, or 3; and r is 1, 2, or 3.

Embodiment 58. The compound of any one of Embodiments 32-57, or a pharmaceutically acceptable salt thereof, wherein n is 2-8.

Embodiment 59. The compound of any one of Embodiments 32-58, or a pharmaceutically acceptable salt thereof, wherein $B^3$ and $B^4$ are independently an optionally substituted 8- to 14-membered fused bicyclic aromatic heterocyclic.

Embodiment 60. The compound of Embodiment 59, or a pharmaceutically acceptable salt thereof, wherein:

$B^3$ is a group represented by formula ($B^3$-A) or formula ($B^3$-B):

$B^3$-A

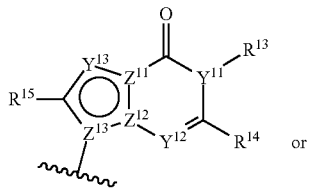

or $B^3$-B

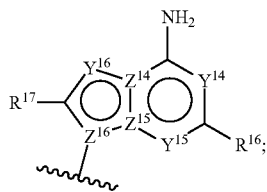

$R^{13}$, $R^{14}$, $R^{15}$, $R^{16}$ and $R^{17}$ are each independently a hydrogen atom or a substituent;

$Y^{11}$, $Y^{12}$, $Y^{13}$, $Y^{14}$, $Y^{15}$ and $Y^{16}$ are each independently N or $CR^{1a}$;

$Z^{11}$, $Z^{12}$, $Z^{13}$, $Z^{14}$, $Z^{15}$ and $Z^{16}$ are each independently N or C;

$R^{1a}$ is a hydrogen atom or a substituent;

$B^4$ is a group represented by formula ($B^4$-A) or formula ($B^4$-B):

$B^4$-A (structure with $R^{23}$, $R^{24}$, $R^{25}$, $Y^{21}$, $Y^{22}$, $Y^{23}$, $Z^{21}$, $Z^{22}$, $Z^{23}$)

or $B^4$-B

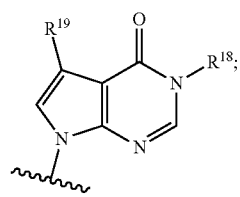

$R^{23}$, $R^{24}$, $R^{25}$, $R^{26}$ and $R^{27}$ are each independently a hydrogen atom or a substituent;

$Y^{21}$, $Y^{22}$, $X^{23}$, $Y^{24}$, $Y^{25}$ and $Y^{26}$ are each independently N or $CR^{2a}$;

$Z^{21}$, $Z^{22}$, $Z^{23}$, $Z^{24}$, $Z^{25}$ and $Z^{26}$ are each independently N or C;

$R^{2a}$ is a hydrogen atom or a substituent.

Embodiment 61. The compound of any one of Embodiments 32-60, or a pharmaceutically acceptable salt thereof, wherein at least one of $B^3$ or $B^4$ is:

(structure with $R^{18}$, $R^{19}$ on pyrrolopyrimidinone)

$R^{18}$ is hydrogen or $C_{1-6}$ alkyl, and $R^{19}$ is a halogen atom.

Embodiment 62. The compound of Embodiment 61, or a pharmaceutically acceptable salt thereof, wherein $B^3$ is:

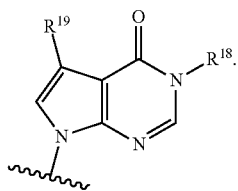

Embodiment 63. The compound of Embodiment 61, or a pharmaceutically acceptable salt thereof, wherein $B^4$ is:

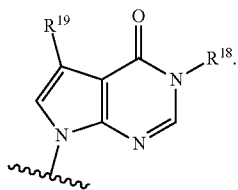

Embodiment 64. The compound of any one of Embodiments 61-63, or a pharmaceutically acceptable salt thereof, wherein $R^{19}$ is a fluoro atom.

Embodiment 65. The compound of any one of Embodiments 61-64, or a pharmaceutically acceptable salt thereof, wherein $R^{18}$ is hydrogen.

Embodiment 66. The compound of any one of Embodiments 61-64, or a pharmaceutically acceptable salt thereof, wherein $R^{18}$ is methyl.

Embodiment 67. The compound of any one of Embodiments 62 or 64-66, or a pharmaceutically acceptable salt thereof, wherein $B^4$ is selected from the group consisting of:

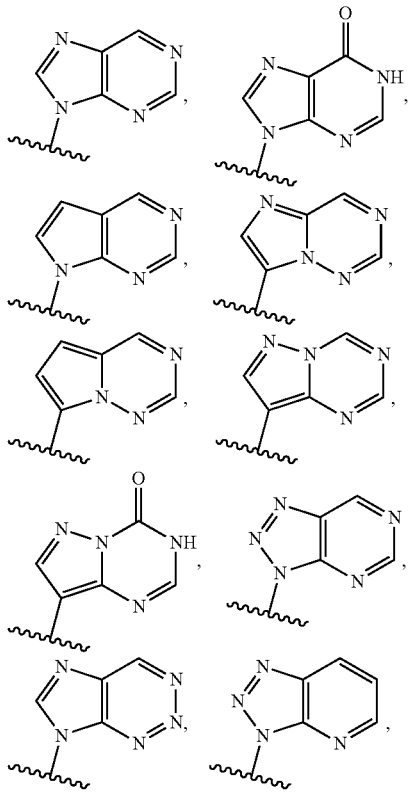

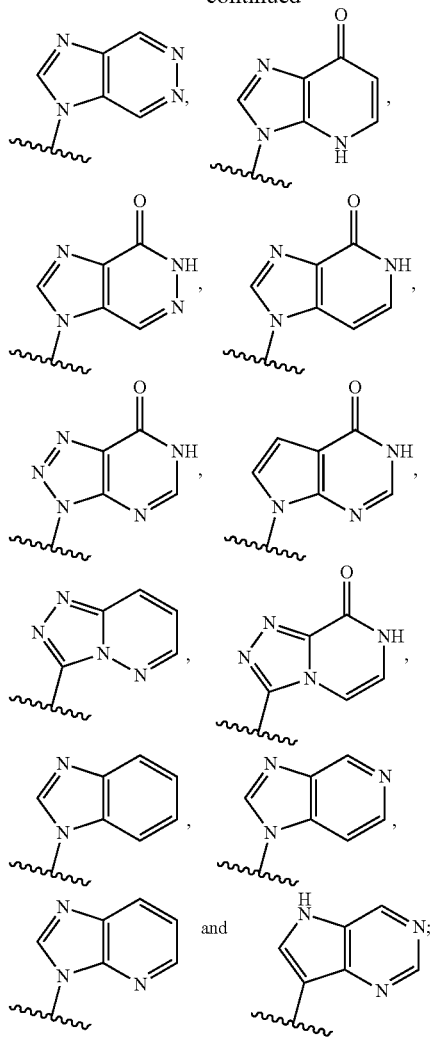

each of which is optionally and independently substituted at:
(i) any available carbon atom with a halo, $C_{1-6}$ alkyl, $C_t^*$, alkoxy, $C_{1-6}$ alkylthio, or amino group; and/or
(ii) any available nitrogen atom with a $C_{1-6}$ alkyl group.

Embodiment 68. The compound of Embodiment 67, or a pharmaceutically acceptable salt thereof, wherein $B^4$ is selected from the group consisting of:

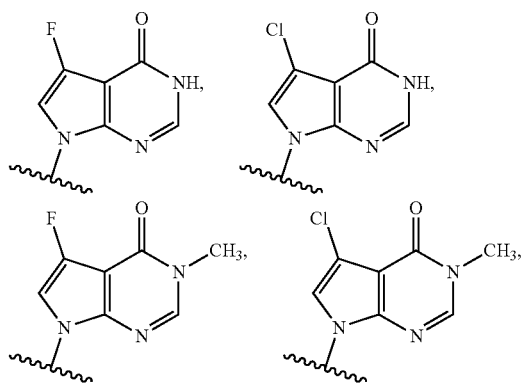

-continued
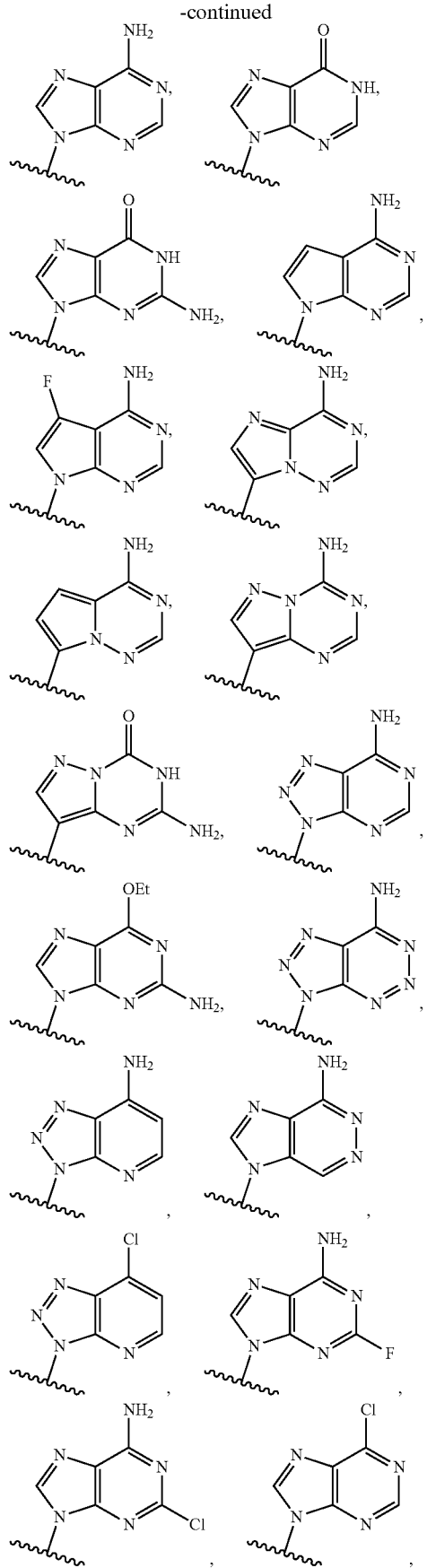
-continued
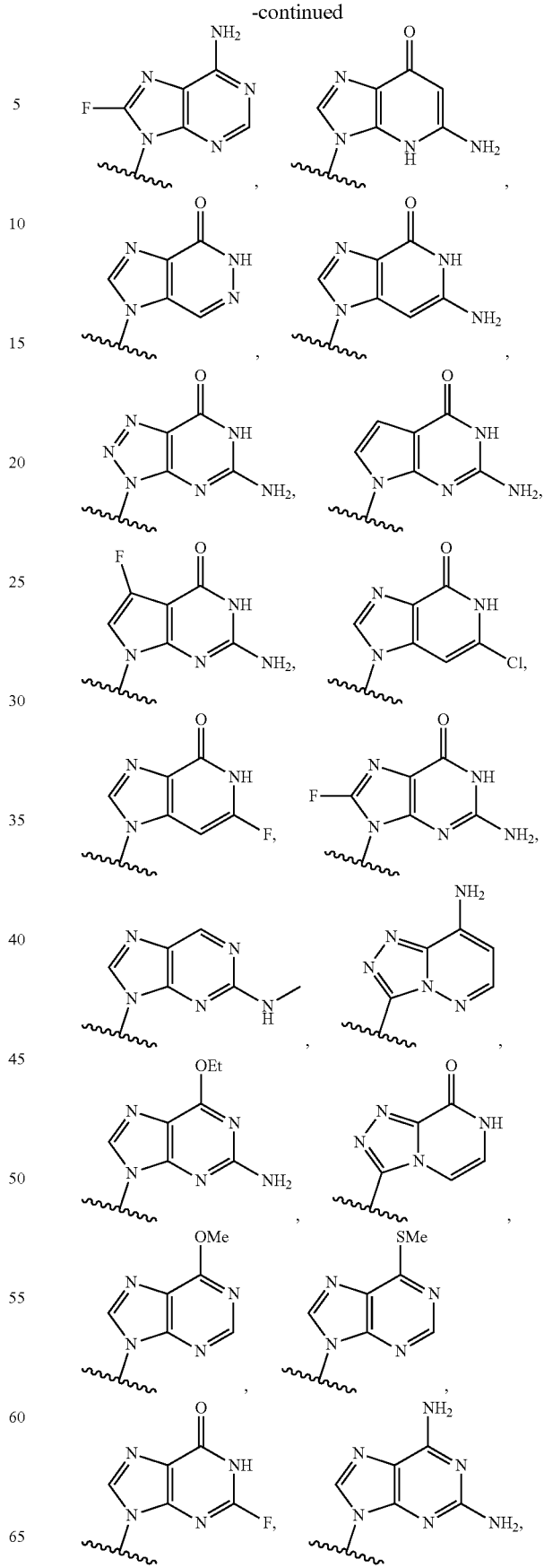

-continued

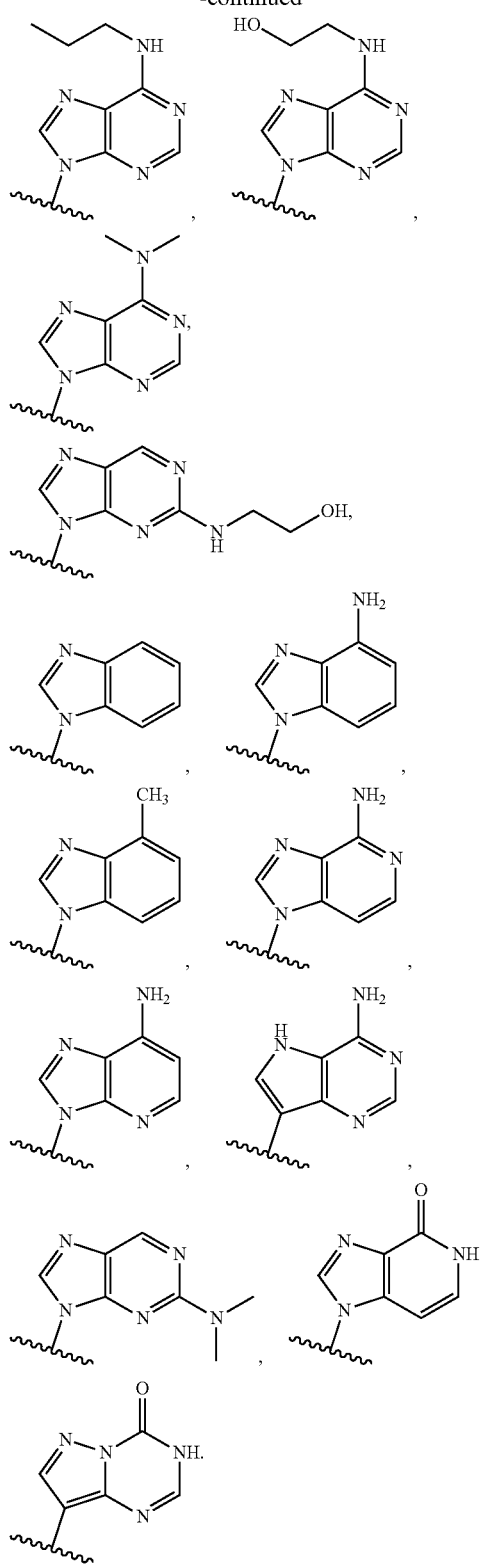
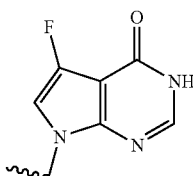 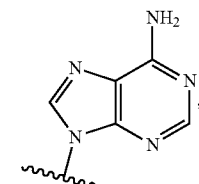
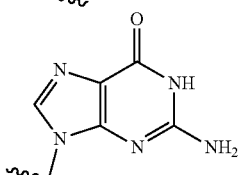 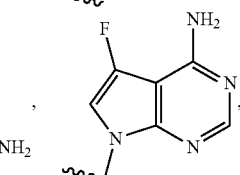
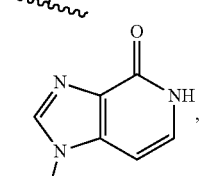 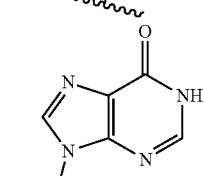
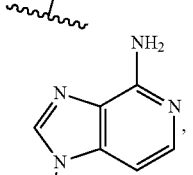 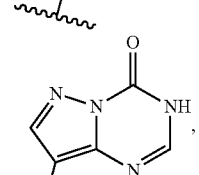
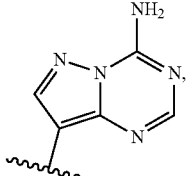 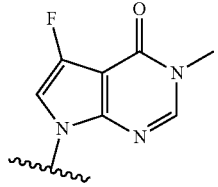
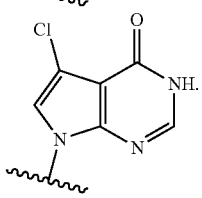 
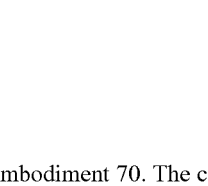 and
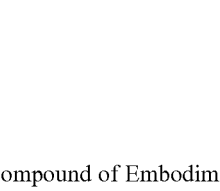

Embodiment 69. The compound of Embodiment 68, or a pharmaceutically acceptable salt thereof, wherein $B^4$ is selected from the group consisting of:

Embodiment 70. The compound of Embodiment 69, or a pharmaceutically acceptable salt thereof, wherein $B^4$ is selected from the group consisting of:

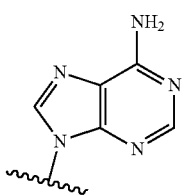 and 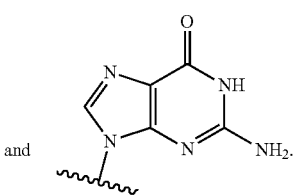

Embodiment 71. The compound of any one of Embodiments 63-66, or a pharmaceutically acceptable salt thereof, wherein $B^3$ is selected from the group consisting of:

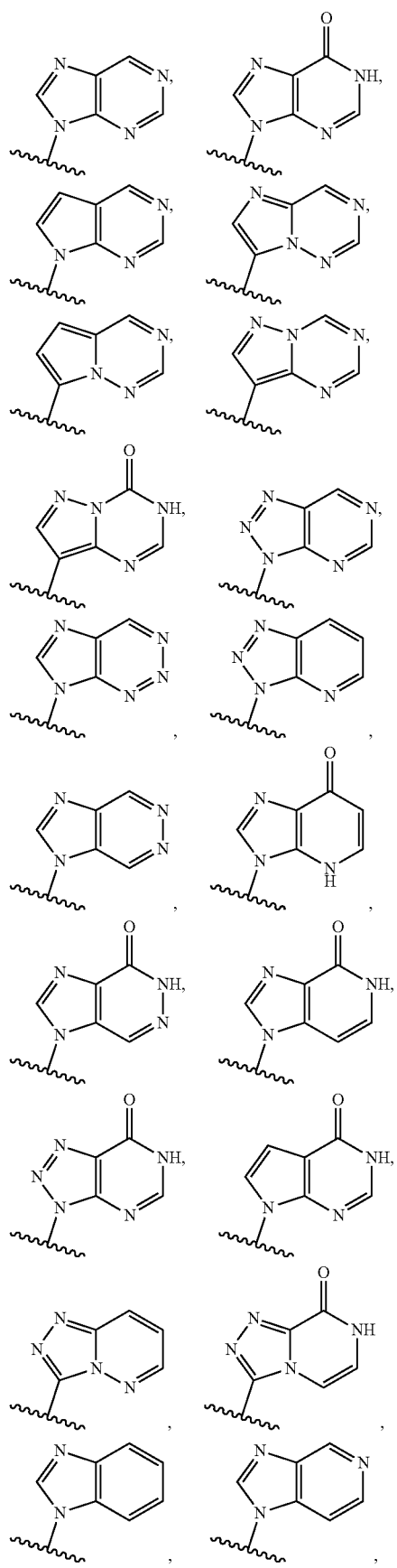
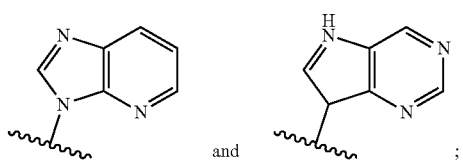
and
each of which is optionally and independently substituted at:
(i) any available carbon atom with a halo, $C_{1-6}$ alkyl, $C_{1-6}$ alkoxy, $C_{1-6}$ alkylthio, or amino group; and/or
(ii) any available nitrogen atom with a $C_{1-6}$ alkyl group.
Embodiment 72. The compound of Embodiment 71, or a pharmaceutically acceptable salt thereof, wherein $B^3$ is selected from the group consisting of:
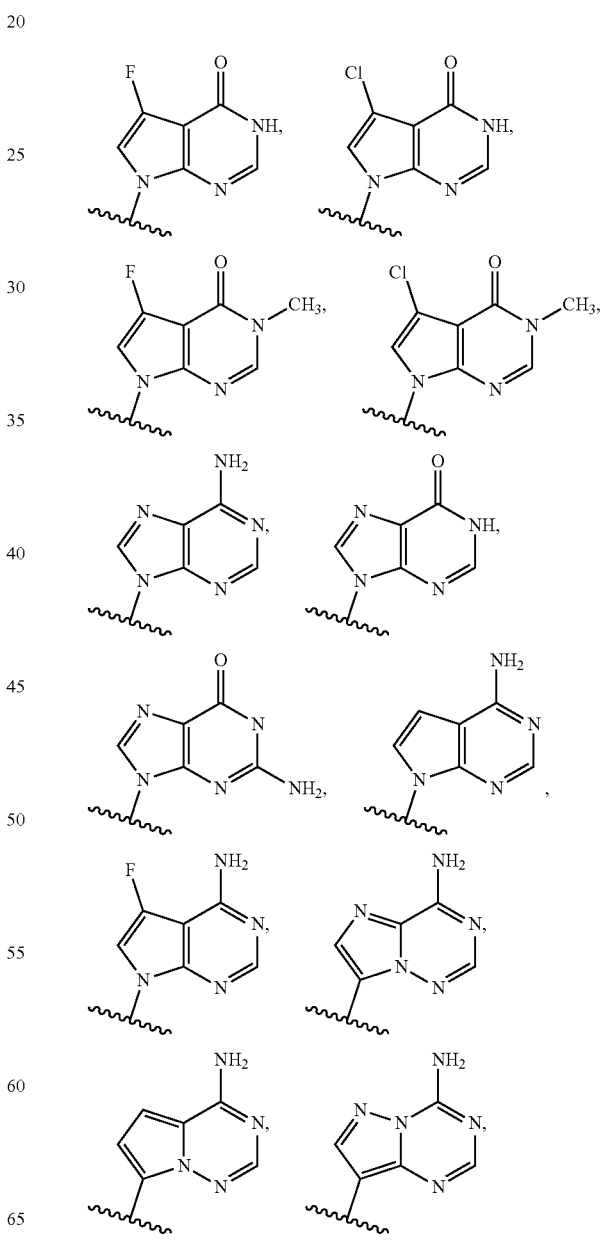

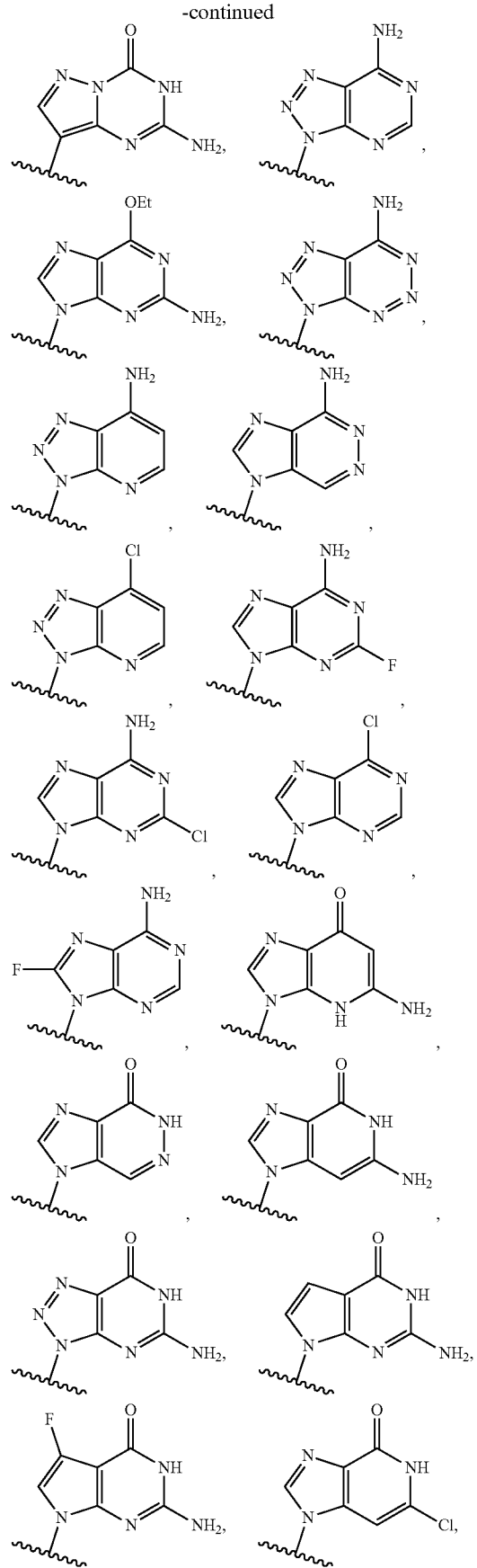
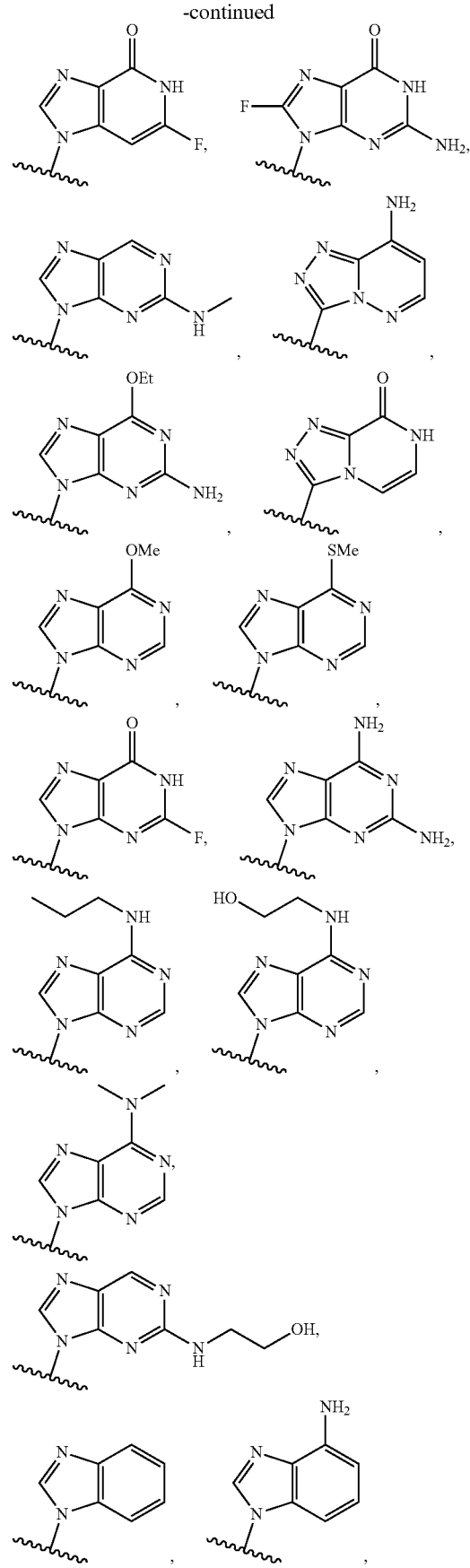

-continued

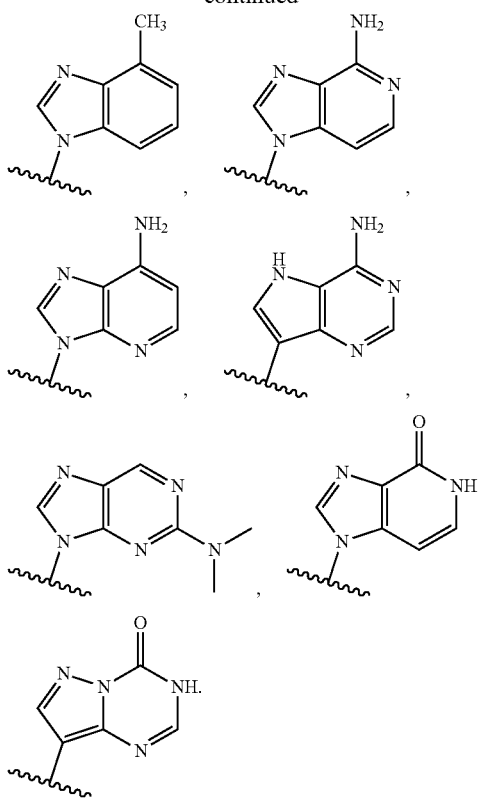

Embodiment 73. The compound of Embodiment 72, or a pharmaceutically acceptable salt thereof, wherein $B^3$ is selected from the group consisting of:

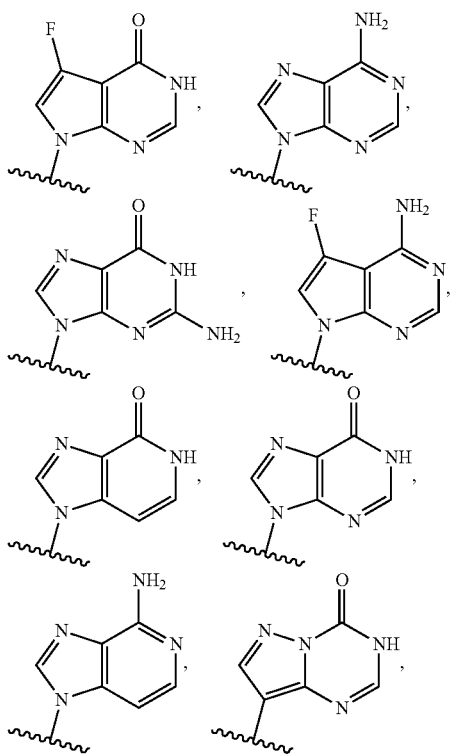

-continued

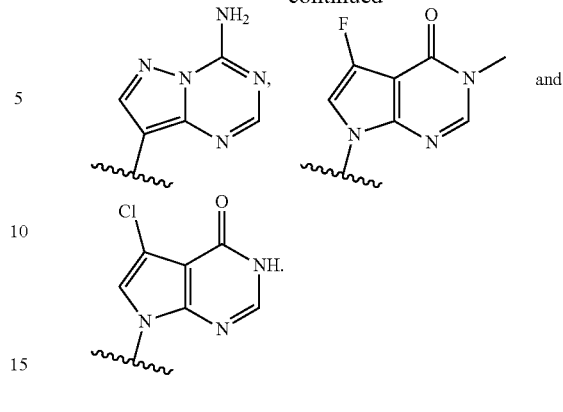

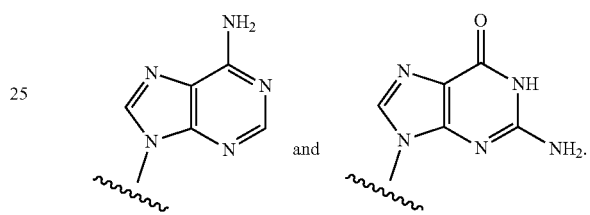

Embodiment 74. The compound of Embodiment 73, or a pharmaceutically acceptable salt thereof, wherein $B^3$ is selected from the group consisting of:

Embodiment 75. The compound of any one of Embodiments 32-39, 44, or 46-74, or a pharmaceutically acceptable salt thereof, wherein $Q^2$ is an oxygen atom.

Embodiment 76. The compound of any one of Embodiments 32-39, 44, or 46-74, or a pharmaceutically acceptable salt thereof, wherein $Q^2$ is a sulfur atom.

Embodiment 77. The compound of any one of Embodiments 32-35, 40-43, 45, 46, 49-54, or 58-74, or a pharmaceutically acceptable salt thereof, wherein $Q^4$ is an oxygen atom.

Embodiment 78. The compound of any one of Embodiments 32-35, 40-43, 45, 46, 49-54, or 58-74, or a pharmaceutically acceptable salt thereof, wherein $Q^4$ is a sulfur atom.

Embodiment 79. The compound of any one of Embodiments 32-78, or a pharmaceutically acceptable salt thereof, wherein $X^1$ and $X^2$ are an oxygen atom and $R^1$ and $R^2$ are independently a hydroxy group, a fluoro atom, or a chloro atom.

Embodiment 80. The compound of any one of Embodiments 32-79, or a pharmaceutically acceptable salt thereof, wherein the antibody is an anti-GCC antibody. Antibodies that bind to human guanylyl cyclase C (GCC) are disclosed, e.g., in US 20130315923 and WO 2011050242.

Embodiment 81. The compound of Embodiment 80, or a pharmaceutically acceptable salt thereof, wherein the antibody is an anti-GCC antibody comprising a heavy chain region comprising amino acid sequence SEQ. ID. No. 1.

Embodiment 82. The compound of Embodiments 80 or 81, or a pharmaceutically acceptable salt thereof, wherein the antibody is an anti-GCC antibody comprising a light chain region comprising amino acid sequence SEQ. ID. No. 2.

Embodiment 83. A pharmaceutical composition comprising the compound of any one of Embodiments 32-82, or a pharmaceutically acceptable salt thereof, and a pharmaceutically acceptable excipient.

Embodiment 84. A method of treating a patient comprising administering to the patient a therapeutically effective amount of the compound of any one of Embodiments 1-30 or 32-82, or a pharmaceutically acceptable salt thereof, wherein the patient has cancer.

Embodiment 85. The method of Embodiment 84, wherein the cancer is any one or more of the cancers of Table 7.

Embodiment 86. The method of Embodiment 85, wherein the cancer is selected from the group consisting of solid tumor and lymphoma.

Embodiment 87. The method of any one of Embodiments 84-86 further comprising administering a therapeutically effective amount of a second therapeutic agent useful in the treatment of cancer.

Embodiment 88. The pharmaceutical composition of Embodiments 31 or 83 for use in treating cancer.

Embodiment 89. The pharmaceutical composition of Embodiment 88, wherein the cancer is any one or more of the cancers of Table 7.

Embodiment 90. The pharmaceutical composition of Embodiment 88, wherein the cancer is selected from the group consisting of solid tumor and lymphoma.

Embodiment 91. A compound of any one of Embodiments 1-30 or 32-82, or a pharmaceutically acceptable salt thereof, for use in treatment of cancer.

Embodiment 92. The compound of Embodiment 91, wherein the cancer is any one or more of the cancers of Table 7.

Embodiment 93. The compound of Embodiment 91, wherein the cancer is selected from the group consisting of solid tumor and lymphoma.

Embodiment 94. Use of a compound of any one of Embodiments 1-30 or 32-82, or a pharmaceutically acceptable salt thereof, for the manufacture of a medicament for treatment of cancer.

Embodiment 95. The use of Embodiment 94, wherein the cancer is any one or more of the cancers of Table 7.

Embodiment 96. The use of Embodiment 94, wherein the cancer is selected from the group consisting of solid tumor and lymphoma.

Embodiment 97. A kit comprising the compound of any one of Embodiments 1-30 or 32-82, or a pharmaceutically acceptable salt, and instructions for administering the compound, or a pharmaceutically acceptable salt thereof, to a patient having cancer.

Embodiment 98. The kit of Embodiment 97, wherein the cancer is any one or more of the cancers of Table 7.

Embodiment 99. The kit of Embodiment 97, wherein the cancer is selected from the group consisting of solid tumor and lymphoma.

Embodiment 100. The kit of any one of Embodiments 97-99 further comprising one or more additional therapeutic agents.

Embodiment 101. A compound having Formula (XL):

$$CD\text{-}L^1\text{-}R^{28} \quad (XL)$$

or a pharmaceutically acceptable salt thereof, wherein:

CD is a group represented by any one of Formula (XX)-(XXIX):

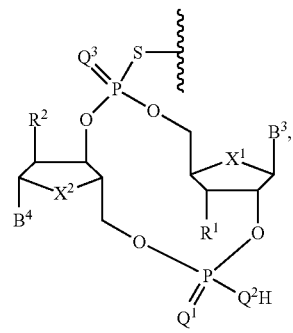

(XX)

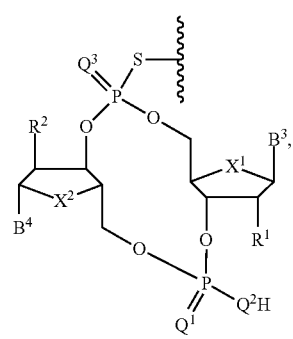

(XXI)

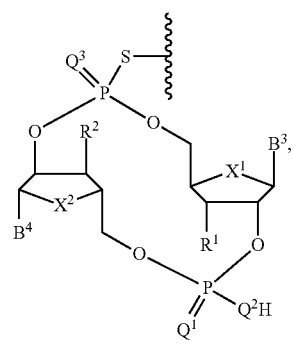

(XXII)

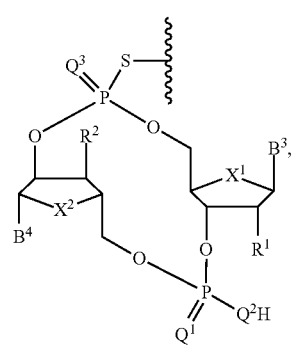

(XXIII)

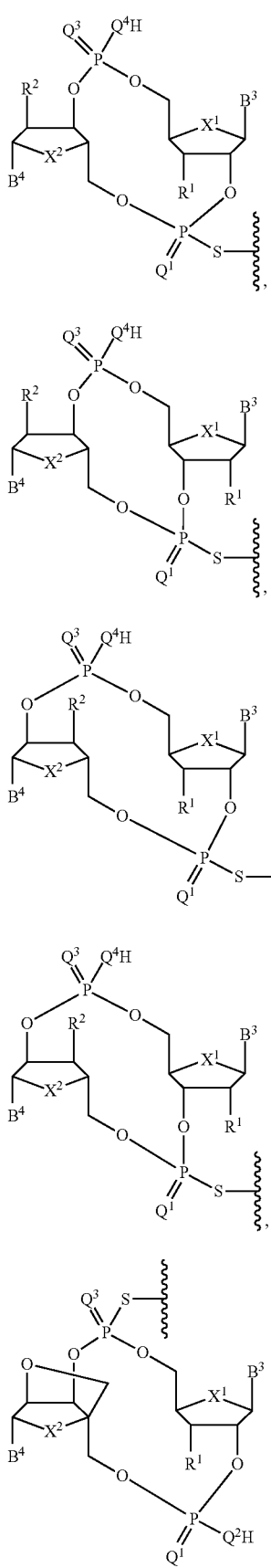

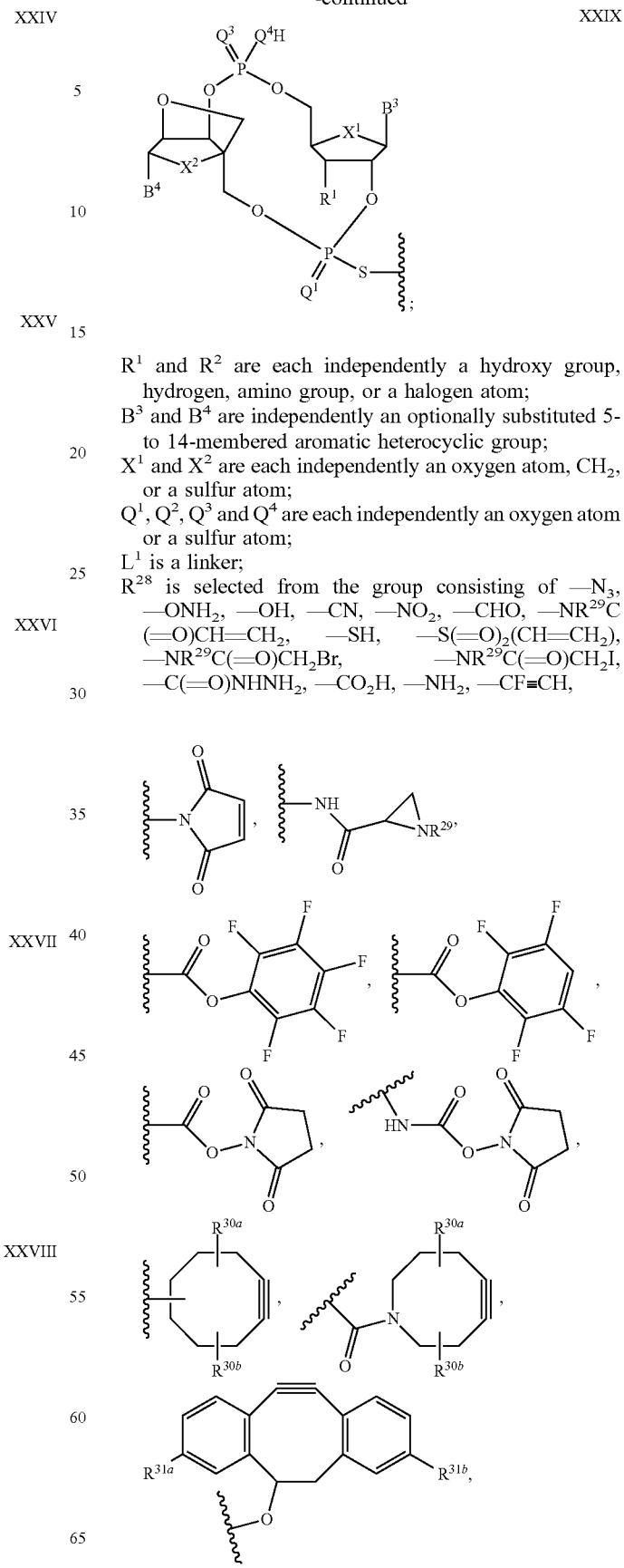

$R^1$ and $R^2$ are each independently a hydroxy group, hydrogen, amino group, or a halogen atom;

$B^3$ and $B^4$ are independently an optionally substituted 5- to 14-membered aromatic heterocyclic group;

$X^1$ and $X^2$ are each independently an oxygen atom, $CH_2$, or a sulfur atom;

$Q^1, Q^2, Q^3$ and $Q^4$ are each independently an oxygen atom or a sulfur atom;

$L^1$ is a linker;

$R^{28}$ is selected from the group consisting of —$N_3$, —$ONH_2$, —OH, —CN, —$NO_2$, —CHO, —$NR^{29}C(=O)CH=CH_2$, —SH, —$S(=O)_2(CH=CH_2)$, —$NR^{29}C(=O)CH_2Br$, —$NR^{29}C(=O)CH_2I$, —$C(=O)NHNH_2$, —$CO_2H$, —$NH_2$, —CF≡CH,

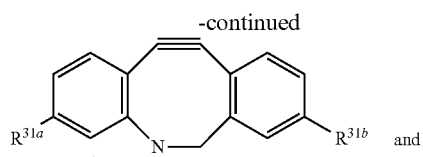

and

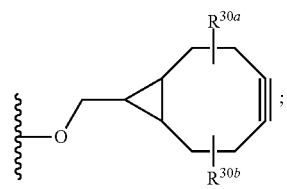

$R^{29}$ is hydrogen or $C_{1-6}$ alkyl;

$R^{30a}$ and $R^{30b}$ are independently selected from the group consisting of hydrogen, $C_{1-6}$ alkyl, halo, —C(=O)OR$^{29}$, —NH$_2$, $C_{1-6}$ alkoxy, —CN, —NO$_2$, and —OH;

$R^{31a}$ and $R^{31b}$ are independently selected from the group consisting of hydrogen, $C_{1-6}$ alkyl, halo, —C(=O)OR$^{29}$, —NH$_2$, —N(CH$_3$)$_2$, $C_{1-6}$ alkoxy, —CN, —NO$_2$, and —OH; and the linker is attached to cyclic dinucleotide through any available carbon, nitrogen, oxygen, or sulfur atom.

Embodiment 102. The compound of Embodiment 101, or a pharmaceutically acceptable salt thereof, wherein R$^1$ and R$^2$ are each independently a hydroxy group or a halogen atom.

Embodiment 103. The compound of Embodiments 101 or 102, or a pharmaceutically acceptable salt thereof, wherein X$^1$ and X$^2$ are each independently an oxygen atom or a sulfur atom Embodiment 104. The compound of any one of Embodiments 101-103, or a pharmaceutically acceptable salt thereof, wherein Q$^1$ and Q$^3$ are an oxygen atom.

Embodiment 105. The compound of Embodiment 101, or a pharmaceutically acceptable salt thereof, wherein CD is group represented by Formula (XX-A):

XX-A

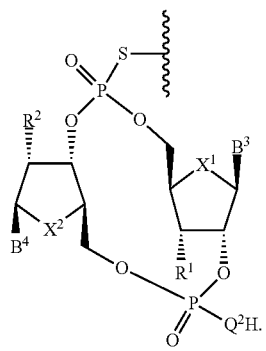

Embodiment 106. The compound of Embodiment 101, or a pharmaceutically acceptable salt thereof, wherein CD is group represented by Formula (XXI-A):

XXI-A

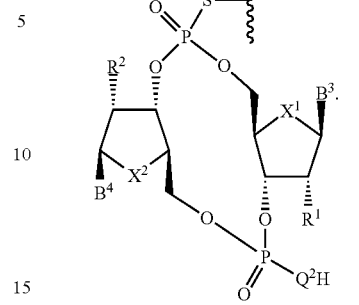

Embodiment 107. The compound of Embodiment 101, or a pharmaceutically acceptable salt thereof, wherein CD is group represented by Formula (XXII-A):

XXII-A

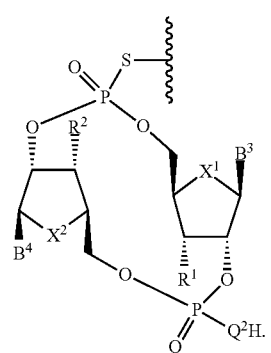

Embodiment 108. The compound of Embodiment 101, or a pharmaceutically acceptable salt thereof, wherein CD is group represented by Formula (XXIII-A):

XXIII-A

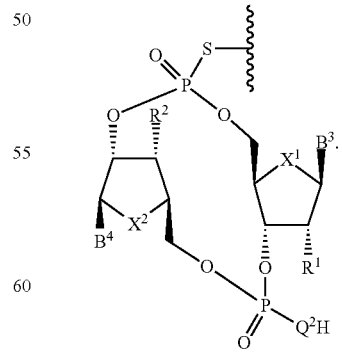

Embodiment 109. The compound of Embodiment 101, or a pharmaceutically acceptable salt thereof, wherein CD is group represented by Formula (XX IV-A):

XXIV-A

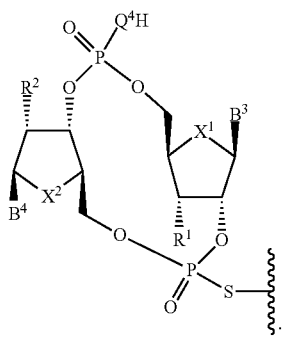

Embodiment 110. The compound of Embodiment 101, or a pharmaceutically acceptable salt thereof, wherein CD is group represented by Formula (XXV-A):

XXV-A

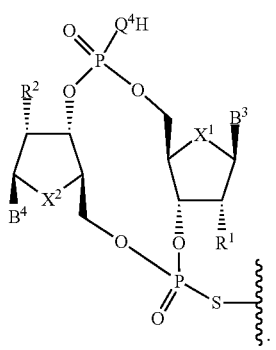

Embodiment 111. The compound of Embodiment 101, or a pharmaceutically acceptable salt thereof, wherein CD is group represented by Formula (XXVI-A):

XXVI-A

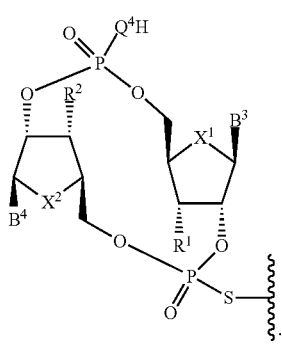

Embodiment 112. The compound of Embodiment 101, or a pharmaceutically acceptable salt thereof, wherein CD is group represented by Formula (XXVII-A):

XXVII-A

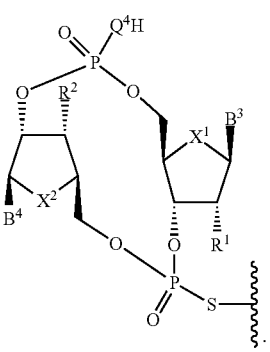

Embodiment 113. The compound of Embodiment 101, or a pharmaceutically acceptable salt thereof, wherein CD is group represented by Formula (XXVIII-A):

XXVIII-A

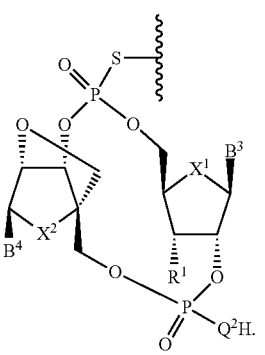

Embodiment 114. The compound of Embodiment 101, or a pharmaceutically acceptable salt thereof, wherein CD is group represented by Formula (XXIX-A):

XXIX-A

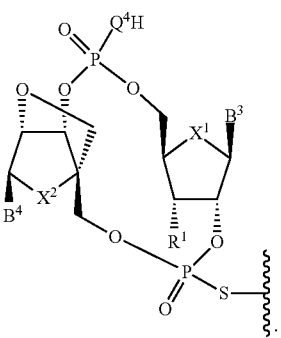

Embodiment 115. The compound of any one of Embodiments 101-114, or a pharmaceutically acceptable salt thereof, wherein:

$L^1$ is —$X^3$-T-Z—;

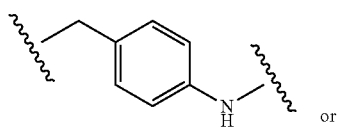

or

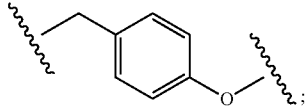

$X^3$ is —$(CH_2)_o$—,
o is 1, 2, or 3; or
$X^3$ is absent;
T is a peptide, or is absent; and
Z is a spacer.

Embodiment 116. The compound of Embodiment 115, or a pharmaceutically acceptable salt thereof, wherein:
$X^3$ is

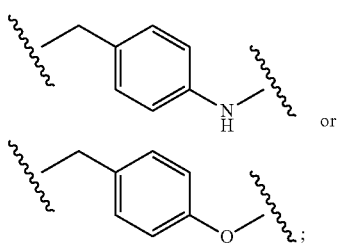

T is

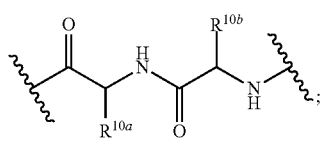

and
$R^{10a}$ and $R^{10b}$ are independently selected from the group consisting of hydrogen and optionally substituted $C_{1-6}$ alkyl.

Embodiment 117. The compound of Embodiment 116, or a pharmaceutically acceptable salt thereof, wherein:
$X^3$ is

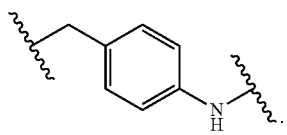 [SMILES: *Cc1ccc(N*)cc1]

Embodiment 118. The compound of any one of Embodiments 115-117, or a pharmaceutically acceptable salt thereof, wherein:

Z is

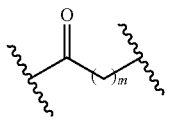

or —$(CH_2CH_2O)_s$—;
m is 1, 2, 3, 4, 5, or 6; and
s is 1, 2, 3, 4, 5, 6, 7, 8, 9, or 10.

Embodiment 119. The compound of Embodiment 115, or a pharmaceutically acceptable salt thereof, wherein:
$X^3$ is —$CH_2$—;
Z is

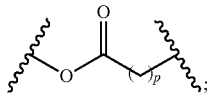

and
p is 1, 2, 3, 4, 5, 6, 7, 8, 9, or 10.

Embodiment 120. The compound of Embodiment 115, or a pharmaceutically acceptable salt thereof, wherein:
$X^3$ is —$CH_2CH_2$—;
Z is

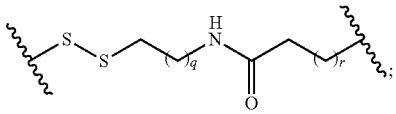

q is 1, 2, 3, 4, 5, or 6; and
r is 1, 2, 3, 4, 5, or 6.

Embodiment 121. The compound of any one of Embodiments 101-120, or a pharmaceutically acceptable salt thereof, wherein $B^3$ and $B^4$ are independently an optionally substituted 8- to 14-membered fused bicyclic aromatic heterocyclic.

Embodiment 122. The compound of Embodiment 121, or a pharmaceutically acceptable salt thereof, wherein:
$B^3$ is a group represented by formula ($B^3$-A) or formula ($B^3$-B):

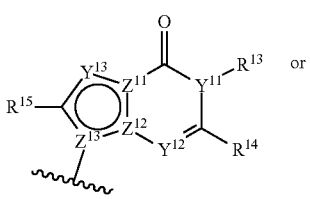

B³-A or

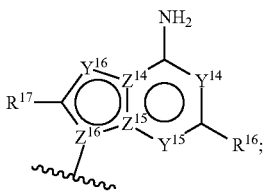

B³-B $R^{13}$, $R^{14}$, $R^{15}$, $R^{16}$ and $R^{17}$ are each independently a hydrogen atom or a substituent;

$Y^{11}, Y^{12}, Y^{13}, Y^{14}, Y^{15}$ and $Y^{16}$ are each independently N or $CR^{1a}$;

$Z^{11}, Z^{12}, Z^{13}, Z^{14}, Z^{15}$ and $Z^{16}$ are each independently N or C;

$R^{1a}$ is a hydrogen atom or a substituent;

$B^4$ is a group represented by formula ($B^4$-A) or formula ($B^4$-B):

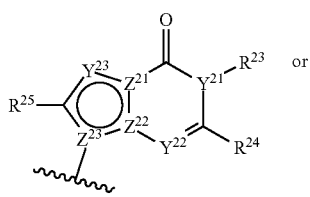
B⁴-A

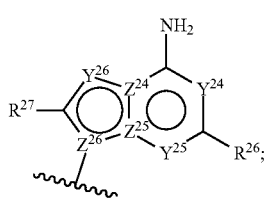
B⁴-B $R^{23}, R^{24}, R^{25}, R^{26}$ and $R^{27}$ are each independently a hydrogen atom or a substituent;

$Y^{21}, Y^{22}, Y^{23}, Y^{24}, Y^{25}$ and $Y^{26}$ are each independently N or $CR^{2a}$;

$Z^{21}, Z^{22}, Z^{23}, Z^{24}, Z^{25}$ and $Z^{26}$ are each independently N or C;

$R^{2a}$ is a hydrogen atom or a substituent.

Embodiment 123. The compound of any one of Embodiments 101-122, or a pharmaceutically acceptable salt thereof, wherein at least one of B3 or B4 is:

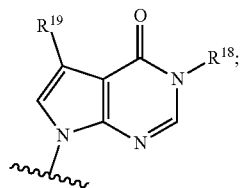

$R^{15}$ is hydrogen or $C_{1-6}$ alkyl; and
$R^{19}$ is a halogen atom.

Embodiment 124. The compound of Embodiment 123, or a pharmaceutically acceptable salt thereof, wherein B3 is:

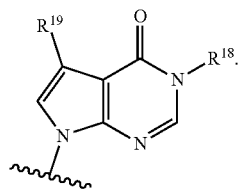

Embodiment 125. The compound of Embodiment 123, or a pharmaceutically acceptable salt thereof, wherein B4 is:

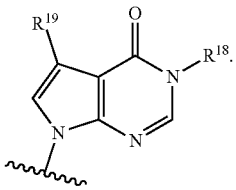

Embodiment 126. The compound of any one of Embodiments 123-125, or a pharmaceutically acceptable salt thereof, wherein $R^{19}$ is a fluoro atom.

Embodiment 127. The compound of any one of Embodiments 123-126, or a pharmaceutically acceptable salt thereof, wherein $R^{18}$ is hydrogen.

Embodiment 128. The compound of any one of Embodiments 123-126, or a pharmaceutically acceptable salt thereof, wherein $R^{18}$ is methyl.

Embodiment 129. The compound of any one of Embodiments 124 or 126-128, or a pharmaceutically acceptable salt thereof, wherein $B^4$ is selected from the group consisting of:

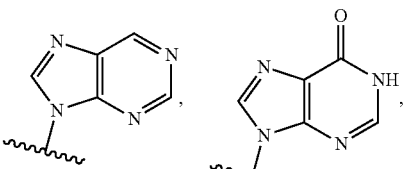

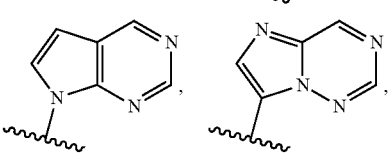

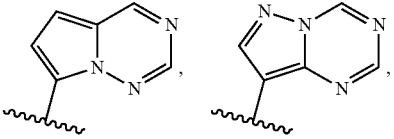

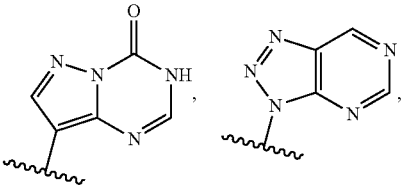

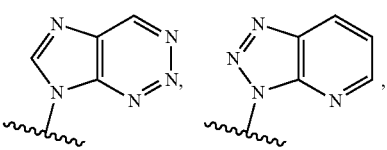

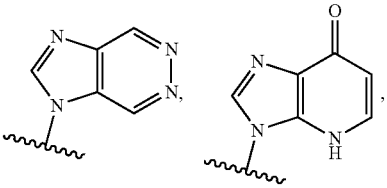

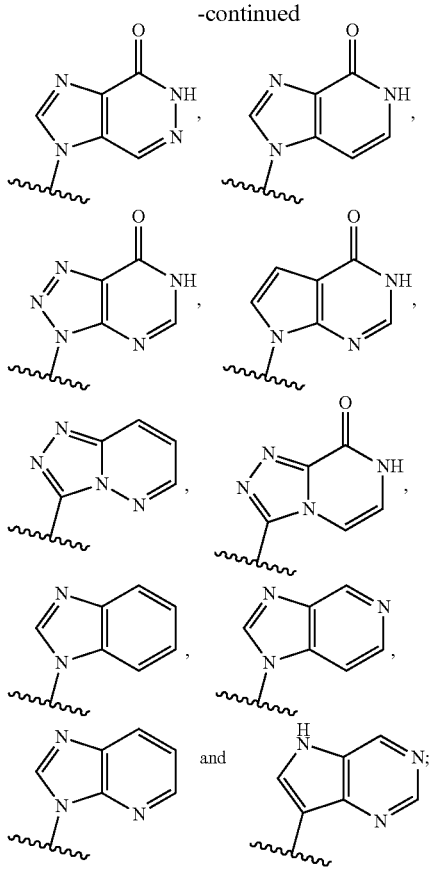
each of which is optionally and independently substituted at:
(i) any available carbon atom with a halo, $C_{1-6}$ alkyl, $C_{1-6}$ alkoxy, $C_{1-6}$ alkylthio, or amino group; and/or
(ii) any available nitrogen atom with a $C_{1-6}$ alkyl group.
Embodiment 130. The compound of Embodiment 129, or a pharmaceutically acceptable salt thereof, wherein $B^4$ is selected from the group consisting of:
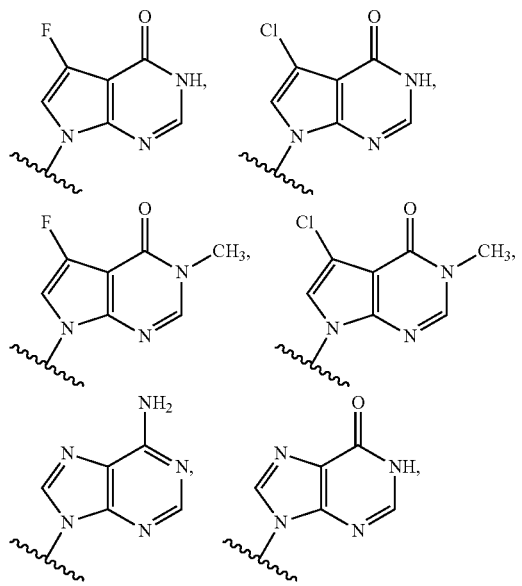
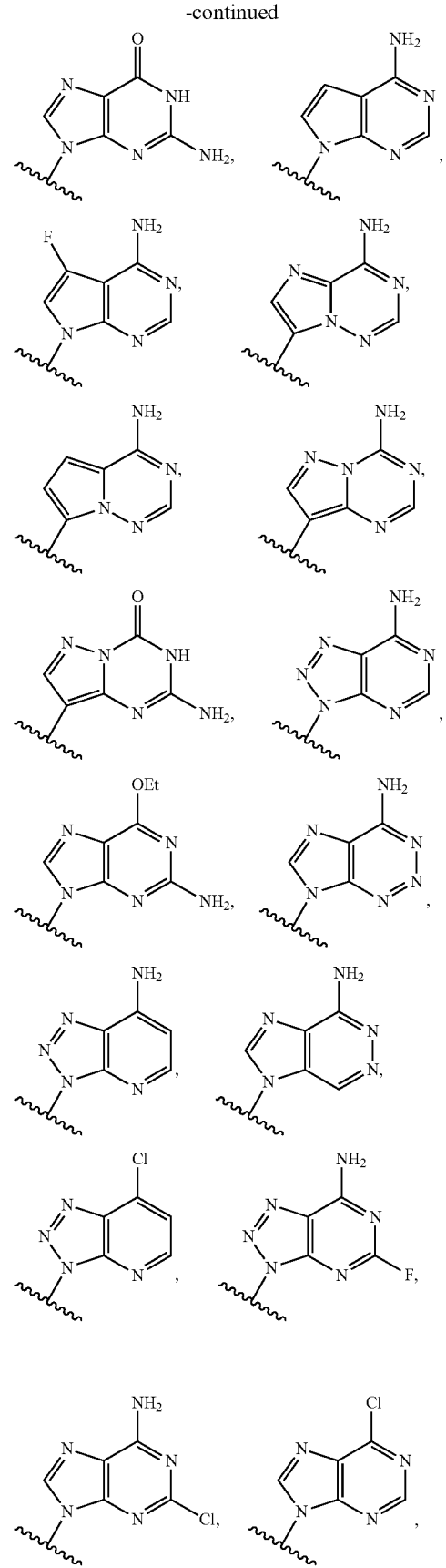

163
-continued
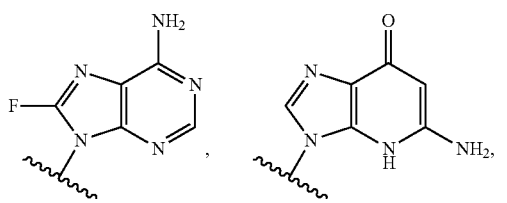
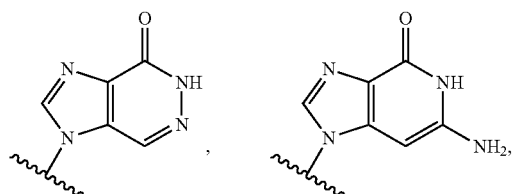
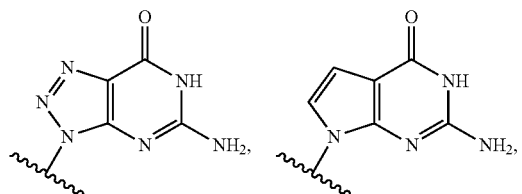
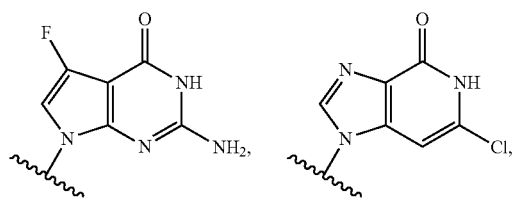
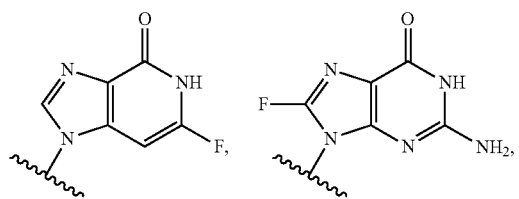
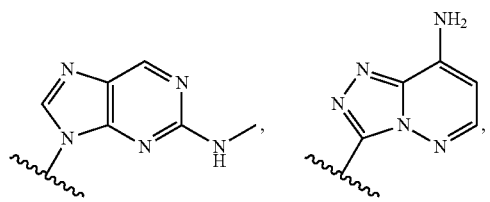
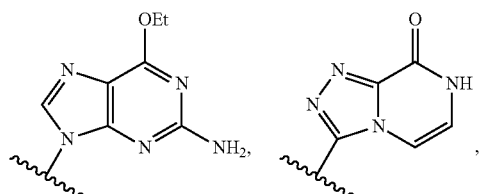
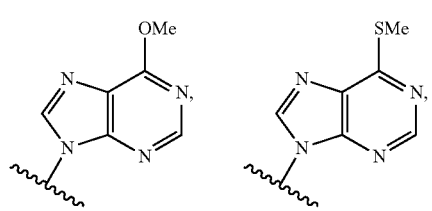
164
-continued
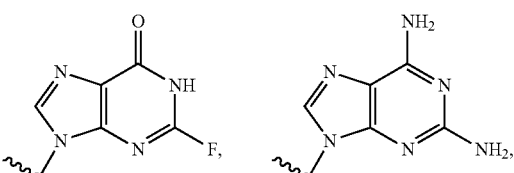
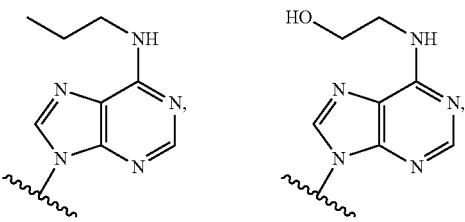
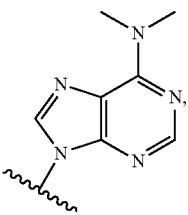
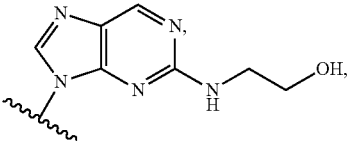
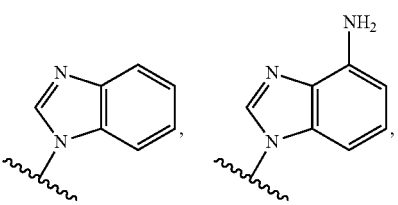
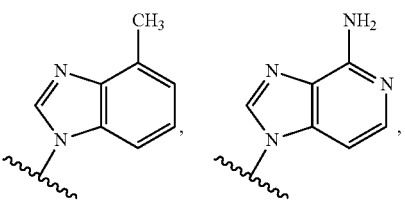
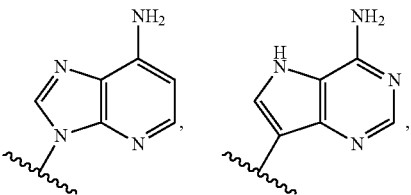
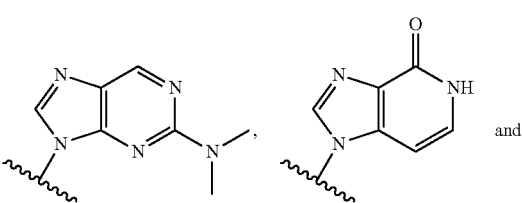

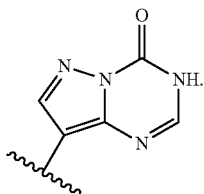

Embodiment 131. The compound of Embodiment 130, or a pharmaceutically acceptable salt thereof, wherein $B^4$ is selected from the group consisting of:

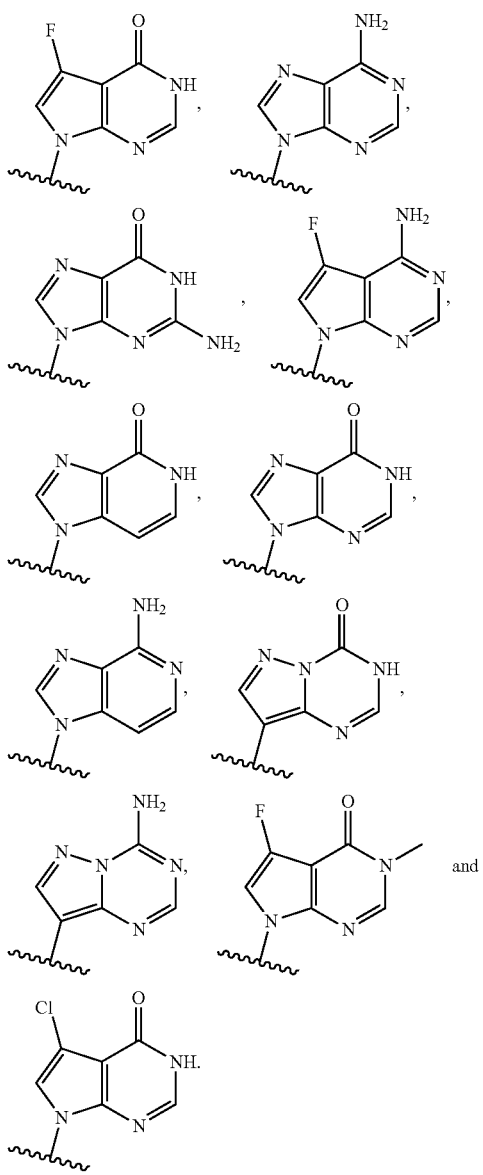

Embodiment 132. The compound of Embodiment 131, or a pharmaceutically acceptable salt thereof, wherein $B^4$ is selected from the group consisting of:

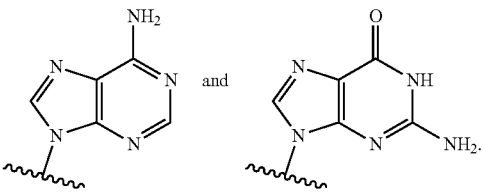 [SMILES: *n1cnc2c(N)ncnc21 ; "and" ; *n1cnc2c(=O)[nH]c(N)nc21]

Embodiment 133. The compound of any one of Embodiments 125-128, or a pharmaceutically acceptable salt thereof, wherein $B^3$ is selected from the group consisting of:

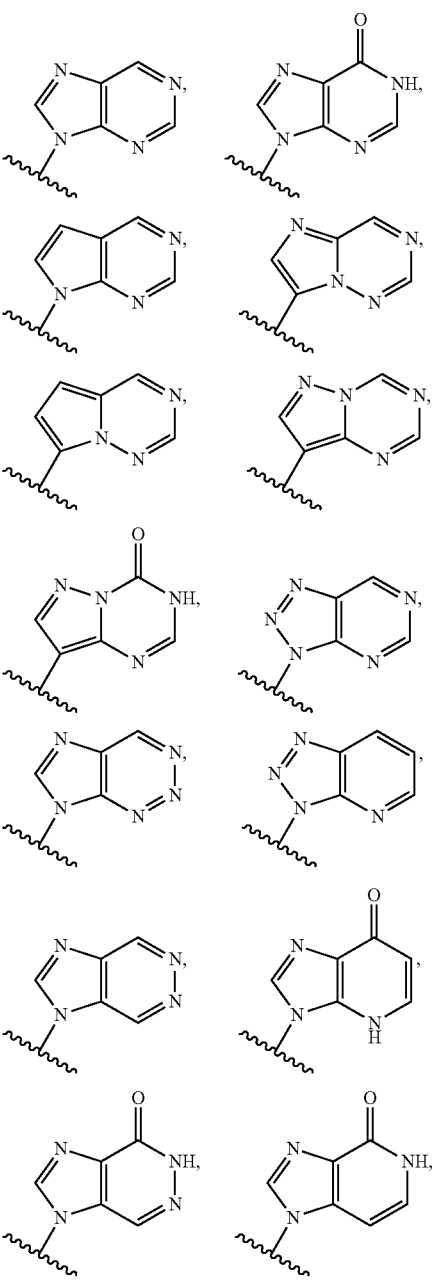

-continued

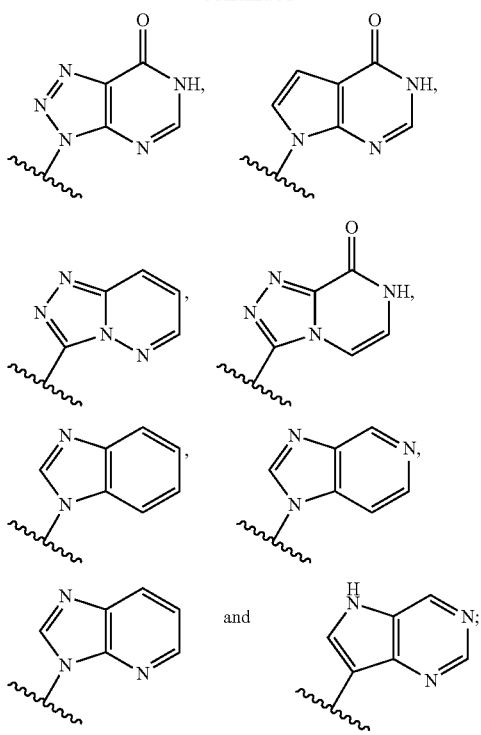

each of which is optionally and independently substituted at:
(i) any available carbon atom with a halo, $C_{1-6}$ alkyl, $C_{1-6}$ alkoxy, $C_{1-43}$ alkylthio, or amino group; and/or
(ii) any available nitrogen atom with a $C_{1-6}$ alkyl group.

Embodiment 134. The compound of Embodiment 133, or a pharmaceutically acceptable salt thereof, wherein $B^3$ is selected from the group consisting of:

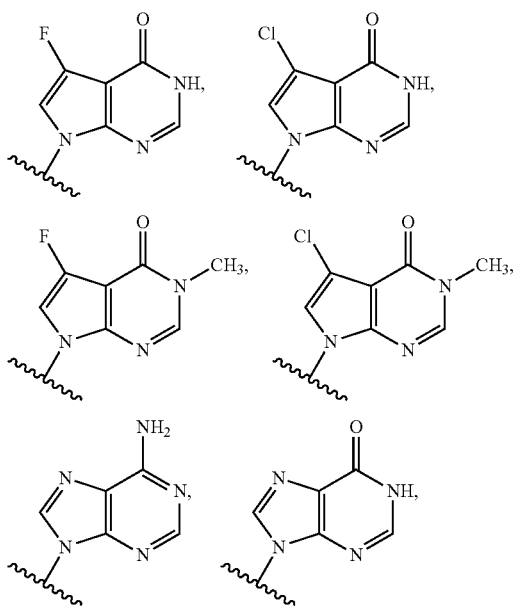

-continued

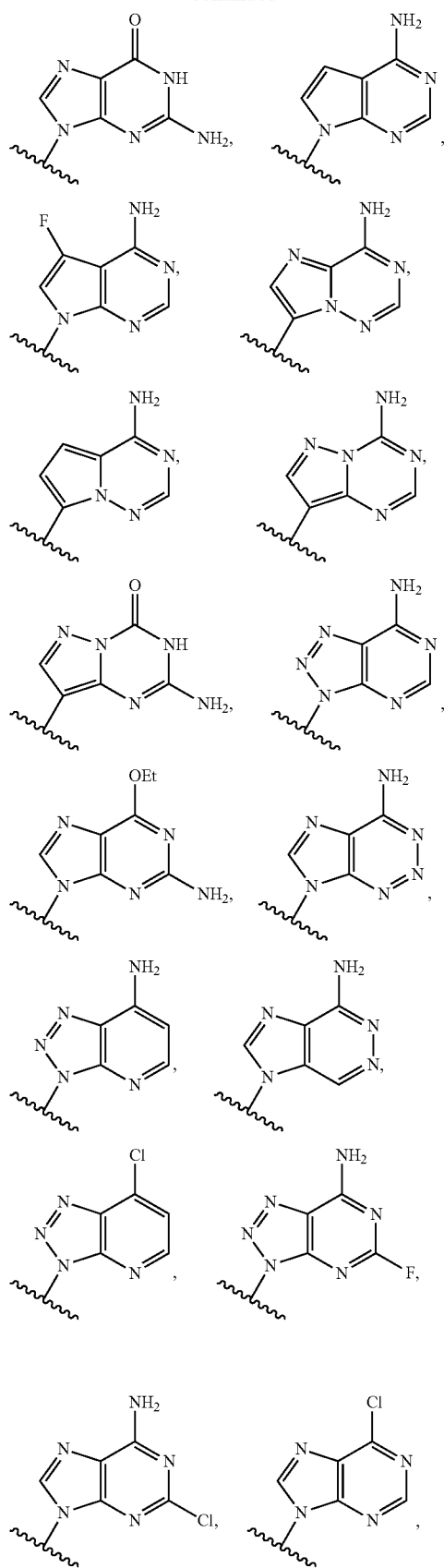

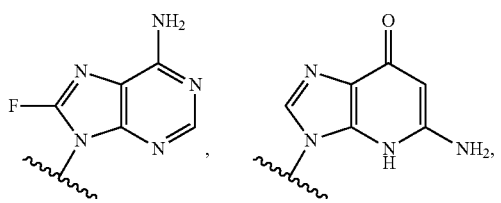
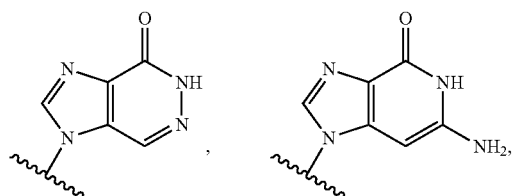
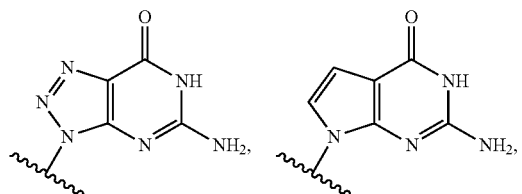
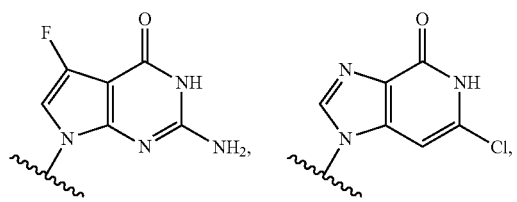
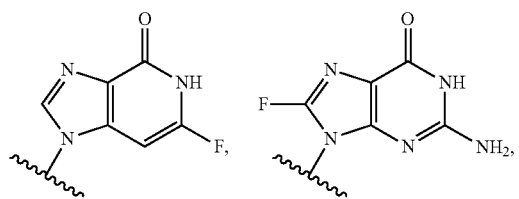
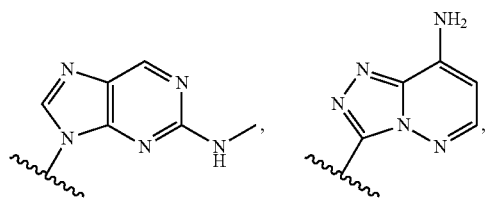
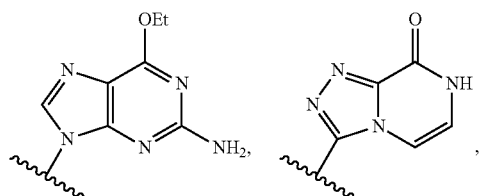
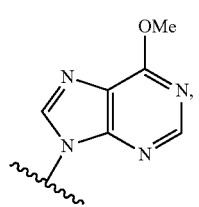 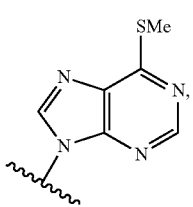
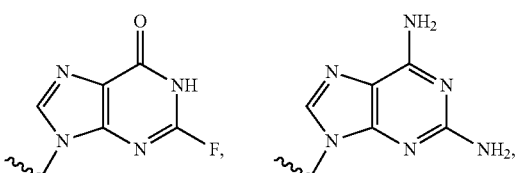
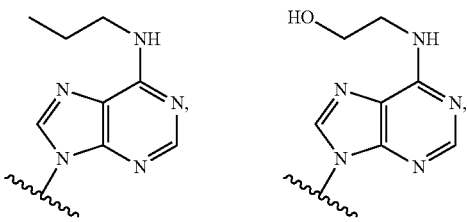
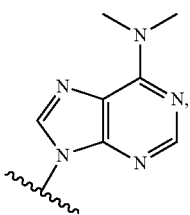
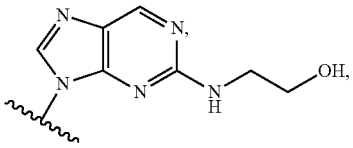
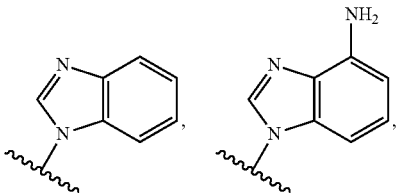
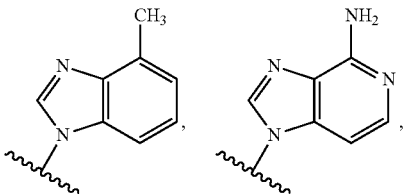
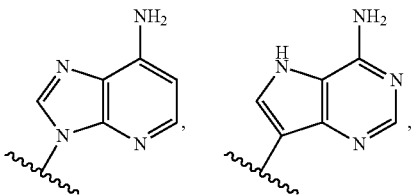
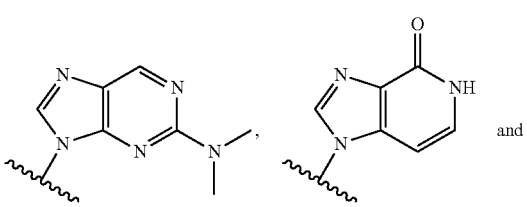 and -continued

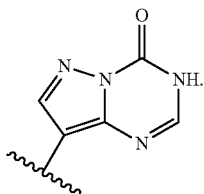

-continued

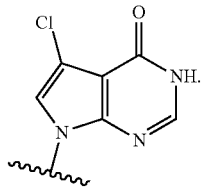

Embodiment 135. The compound of Embodiment 134, or a pharmaceutically acceptable salt thereof, wherein $B^3$ is selected from the group consisting of:

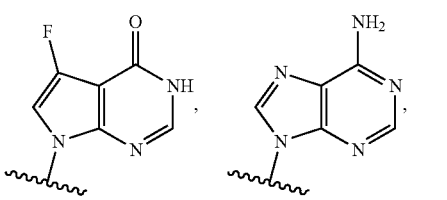

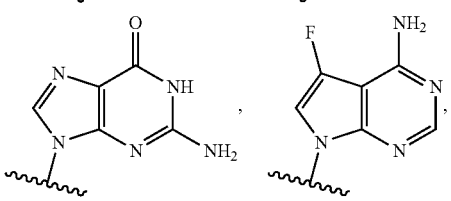

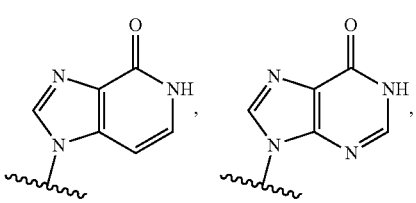

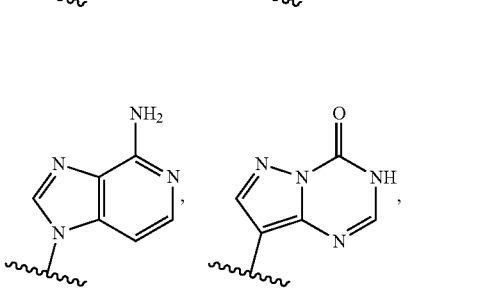

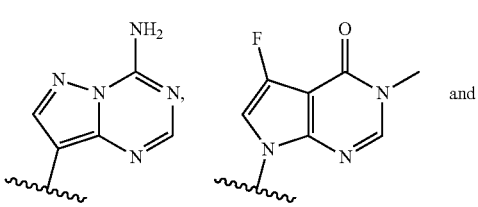 and

Embodiment 136. The compound of Embodiment 135, or a pharmaceutically acceptable salt thereof, wherein $B^3$ is selected from the group consisting of:

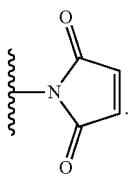

Embodiment 137. The compound of any one of Embodiments 101-108, 113, or 115-136, or a pharmaceutically acceptable salt thereof, wherein $Q^2$ is an oxygen atom.

Embodiment 138. The compound of any one of Embodiments 101-108, 113, or 115-136, or a pharmaceutically acceptable salt thereof, wherein $Q^2$ is a sulfur atom.

Embodiment 139. The compound of any one of Embodiments 101-104, 109-112, 114, or 115-136, or a pharmaceutically acceptable salt thereof, wherein $Q^4$ is an oxygen atom.

Embodiment 140. The compound of any one of Embodiments 101-04, 109-112, 114, or 115-136, or a pharmaceutically acceptable salt thereof, wherein $Q^4$ is a sulfur atom.

Embodiment 141. The compound of any one of Embodiments 101-142, or a pharmaceutically acceptable salt thereof, wherein $X^1$ and $X^2$ are an oxygen atom and $R^1$ and $R^2$ are independently a hydroxy group or a halogen atom.

Embodiment 142. The compound of any one of Embodiments 101-141, wherein $R^{28}$ is Embodiment 143. The compound of Embodiment 142, selected from the group consisting of:

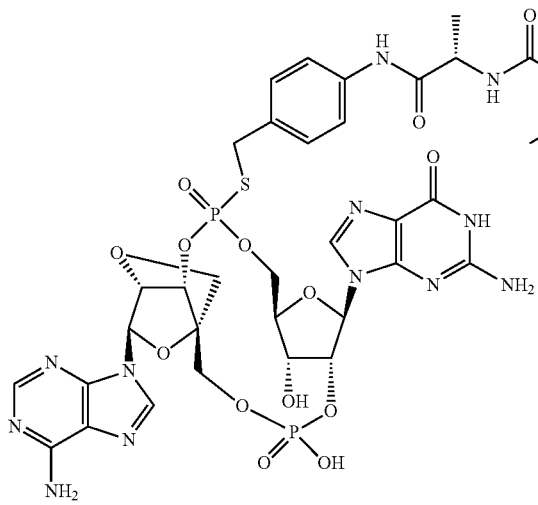
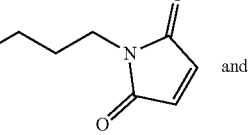
and
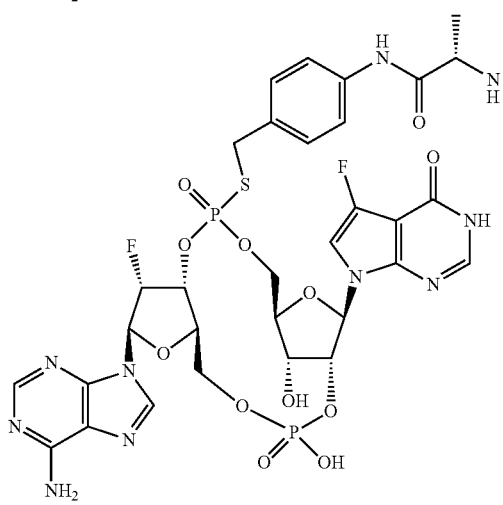
Embodiment 144. A compound having Formula (XLI):
(CD-L²)ᵤ-DA   (XLI)
or a pharmaceutically acceptable salt thereof, wherein:
CD is a group represented by any one of Formula (XX)-(XXIX):
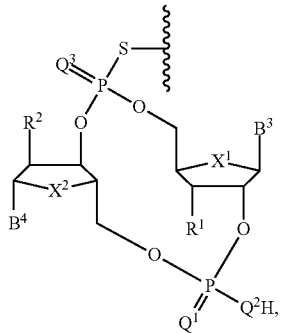
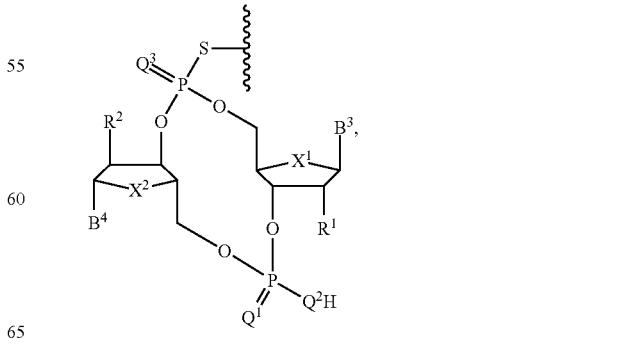

XXII 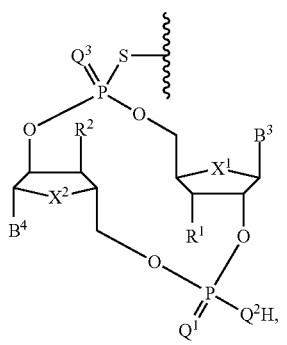

XXIII 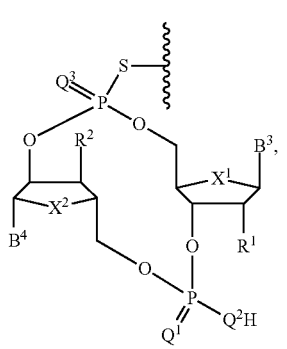

XXIV 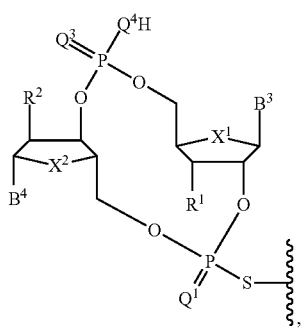

XXV 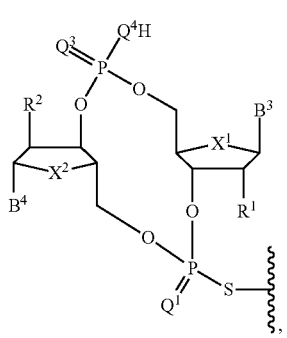

XXVI 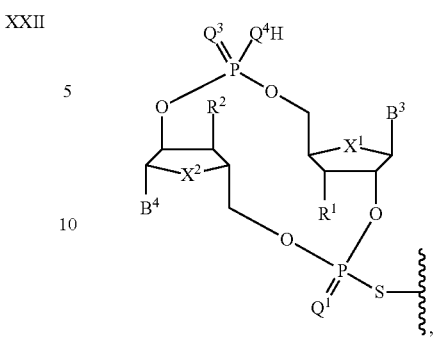

XXVII 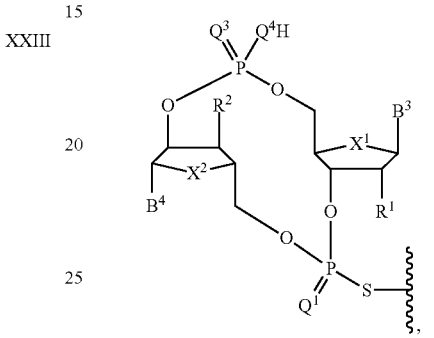

XXVIII 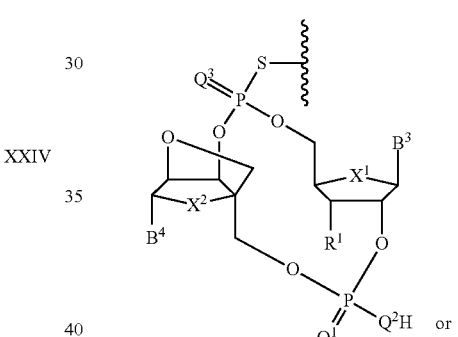

or

XXIX 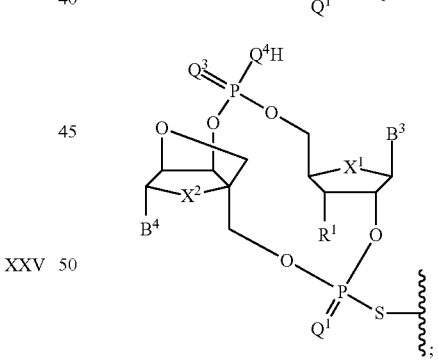

$R^1$ and $R^2$ are each independently a hydroxy group, hydrogen, amino group, or a halogen atom;

$B^3$ and $B^4$ are independently an optionally substituted 5- to 14-membered aromatic heterocyclic group;

$X^1$ and $X^2$ are each independently an oxygen atom, $CH_2$, or a sulfur atom;

$Q^1$, $Q^2$, $Q^3$, and $Q^4$ are each independently an oxygen atom or a sulfur atom;

$L^2$ is a linker; or $L^2$ is absent;

DA is a drug delivery agent; and u is 1-1000.

Embodiment 145. The compound of Embodiment 144, or a pharmaceutically acceptable salt thereof, wherein $R^1$ and $R^2$ are each independently a hydroxy group or a halogen atom.

Embodiment 146. The compound of Embodiments 144 or 145, or a pharmaceutically acceptable salt thereof, wherein $X^1$ and $X^2$ are each independently an oxygen atom or a sulfur atom.

Embodiment 147. The compound of any one of Embodiments 144-146, or a pharmaceutically acceptable salt thereof, wherein $Q^1$ and $Q^3$ are an oxygen atom.

Embodiment 148. The compound of Embodiment 144, or a pharmaceutically acceptable salt thereof, wherein CD is group represented by Formula (XX-A):

XX-A

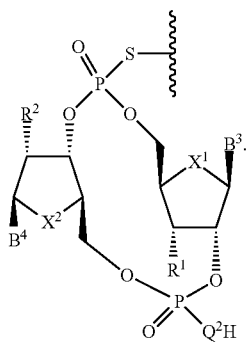

Embodiment 149. The compound of Embodiment 144, or a pharmaceutically acceptable salt thereof, wherein CD is group represented by Formula (XXI-A):

XXI-A

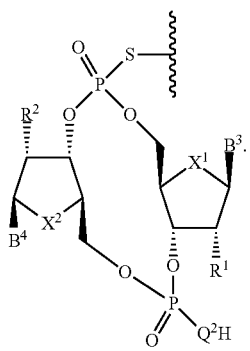

Embodiment 150. The compound of Embodiment 144, or a pharmaceutically acceptable salt thereof, wherein CD is group represented by Formula (XXII-A):

XXII-A

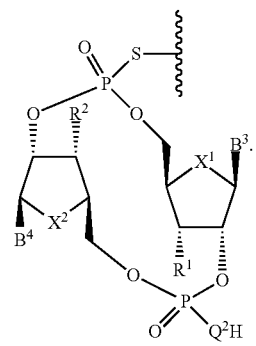

Embodiment 151. The compound of Embodiment 144, or a pharmaceutically acceptable salt thereof, wherein CD is group represented by Formula (XXIII-A):

XXIII-A

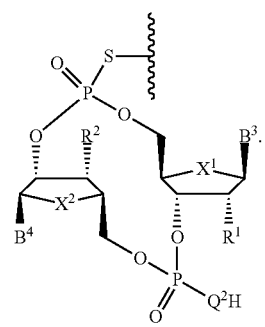

Embodiment 152. The compound of Embodiment 144, or a pharmaceutically acceptable salt thereof, wherein CD is group represented by Formula (XXIV-A):

XXIV-A

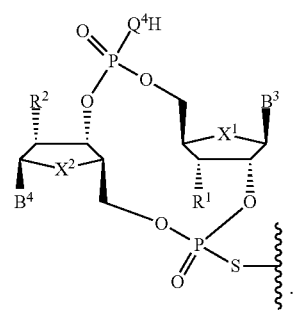

Embodiment 152. The compound of Embodiment 144, or a pharmaceutically acceptable salt thereof, wherein CD is group represented by Formula (XXV-A):

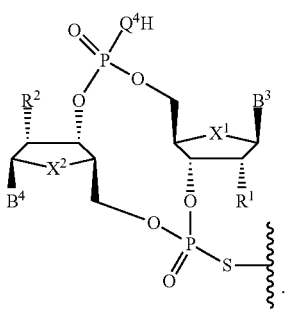

XXV-A

Embodiment 153. The compound of Embodiment 144, or a pharmaceutically acceptable salt thereof, wherein CD is group represented by Formula (XXVI-A):

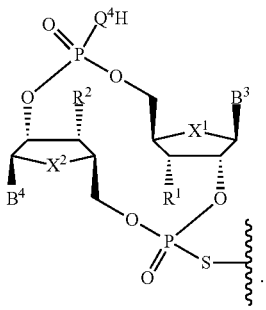

XXVI-A

Embodiment 154. The compound of Embodiment 144, or a pharmaceutically acceptable salt thereof, wherein CD is group represented by Formula (XXVII-A):

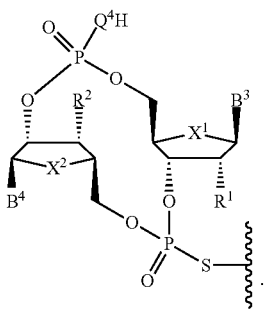

XXVII-A

Embodiment 155. The compound of Embodiment 144, or a pharmaceutically acceptable salt thereof, wherein CD is group represented by Formula (XXVIII-A):

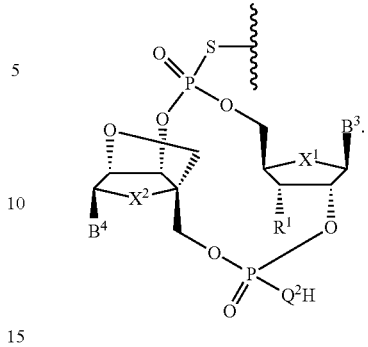

XXVIII-A

Embodiment 156. The compound of Embodiment 144, or a pharmaceutically acceptable salt thereof, wherein CD is group represented by Formula (XXIX-A):

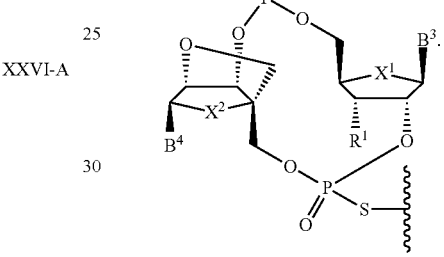

XXIX-A

Embodiment 157. The compound of any one of Embodiments 144-156, or a pharmaceutically acceptable salt thereof, wherein $B^3$ and $B^4$ are independently an optionally substituted 8- to 14-membered fused bicyclic aromatic heterocyclic.

Embodiment 158. The compound of Embodiment 157, or a pharmaceutically acceptable salt thereof, wherein:

$B^3$ is a group represented by formula ($B^3$-A) or formula ($B^3$-B):

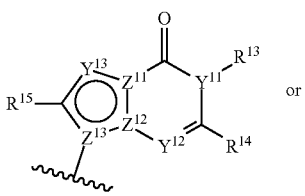

$B^3$-A

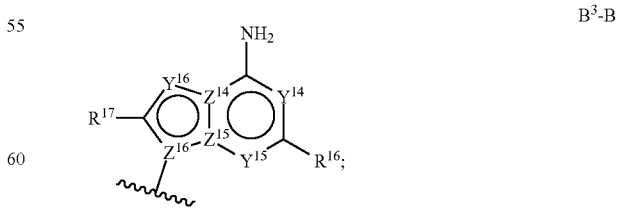

$B^3$-B $R^{13}$, $R^{14}$, $R^{15}$, $R^{16}$ and $R^{17}$ are each independently a hydrogen atom or a substituent;

$Y^{11}$, $Y^{12}$, $Y^{13}$, $Y^{14}$, $Y^{15}$ and $Y^{16}$ are each independently N or $CR^{1a}$;

$Z^{11}$, $Z^{12}$, $Z^{13}$, $Z^{14}$, $Z^{15}$ and $Z^{16}$ are each independently N or C;

$R^{1a}$ is a hydrogen atom or a substituent;

$B^4$ is a group represented by formula ($B^4$-A) or formula ($B^4$-B):

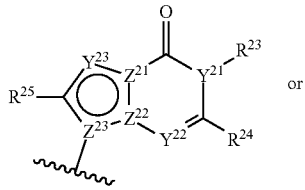
B⁴-A or

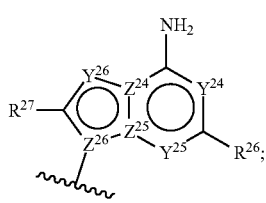
B⁴-B $R^{23}$, $R^{24}$, $R^{25}$, $R^{26}$ and $R^{27}$ are each independently a hydrogen atom or a substituent;

$Y^{21}$, $Y^{22}$, $Y^{23}$, $Y^{24}$, $Y^{25}$ and $Y^{26}$ are each independently N or $CR^{2a}$;

$Z^{21}$, $Z^{22}$, $Z^{23}$, $Z^{24}$, $Z^{25}$ and $Z^{26}$ are each independently N or C;

$R^{2a}$ is a hydrogen atom or a substituent.

Embodiment 159. The compound of any one of Embodiments 144-158, or a pharmaceutically acceptable salt thereof, wherein at least one of $B^3$ or $B^4$ is:

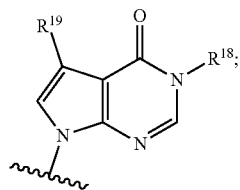

$R^{18}$ is hydrogen or $C_{1-6}$ alkyl; and $R^{19}$ is a halogen atom.

Embodiment 160. The compound of Embodiment 159, or a pharmaceutically acceptable salt thereof, wherein $B^3$ is:

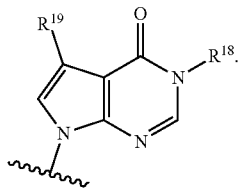

Embodiment 161. The compound of Embodiment 159, or a pharmaceutically acceptable salt thereof, wherein $B^4$ is:

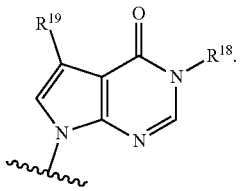

Embodiment 162. The compound of any one of Embodiments 159-161, or a pharmaceutically acceptable salt thereof, wherein $R^{19}$ is a fluoro atom.

Embodiment 163. The compound of any one of Embodiments 159-162, or a pharmaceutically acceptable salt thereof, wherein $R^{18}$ is hydrogen.

Embodiment 164. The compound of any one of Embodiments 159-162, or a pharmaceutically acceptable salt thereof, wherein $R^{18}$ is methyl.

Embodiment 165. The compound of any one of Embodiments 159 or 162-164, or a pharmaceutically acceptable salt thereof, wherein $B^4$ is selected from the group consisting of:

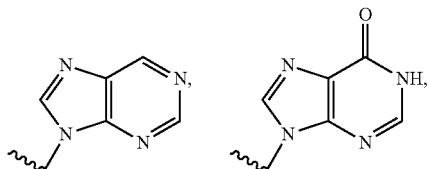

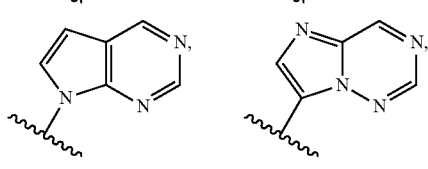

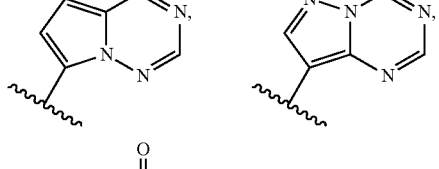

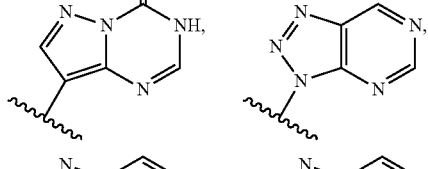

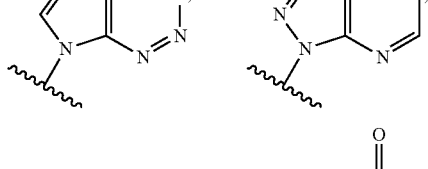

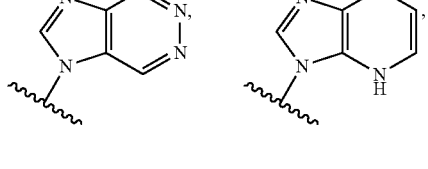

-continued

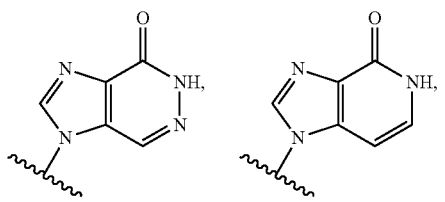

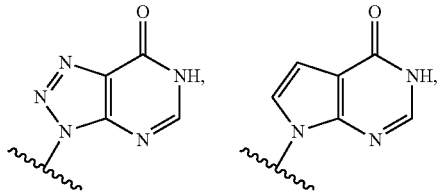

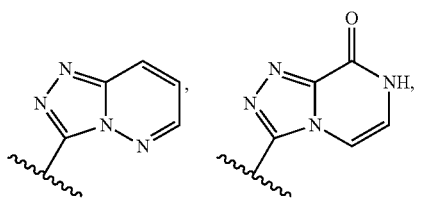

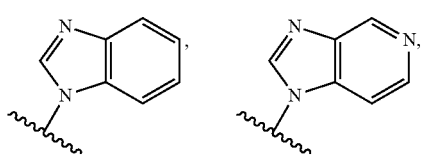

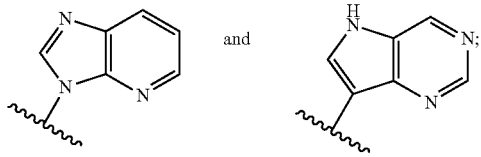

each of which is optionally and independently substituted at:
(i) any available carbon atom with a halo, $C_{1-6}$ alkyl, $C_{1-6}$ alkoxy, $C_{1-6}$ alkylthio, or amino group; and/or
(ii) any available nitrogen atom with a $C_{1-6}$ alkyl group.

Embodiment 166. The compound of Embodiment 165, or a pharmaceutically acceptable salt thereof, wherein $B^4$ is selected from the group consisting of:

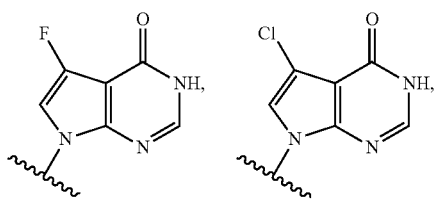

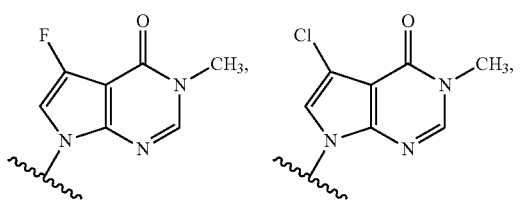

-continued

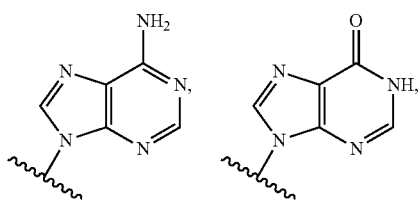

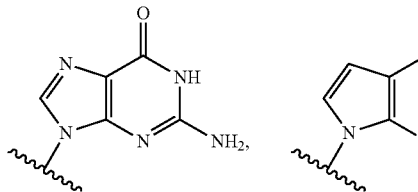

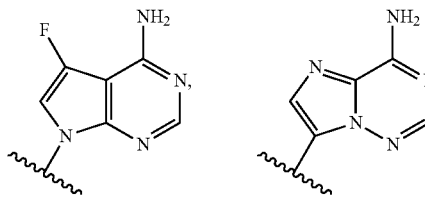

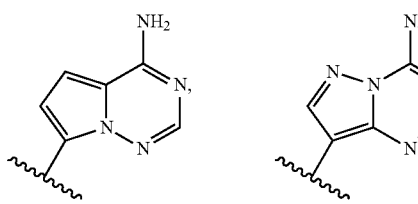

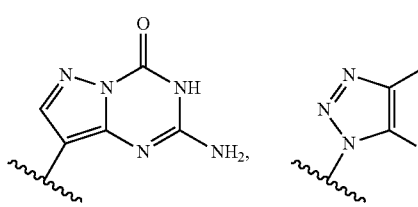

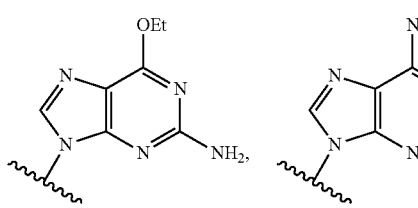

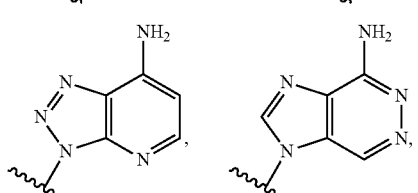

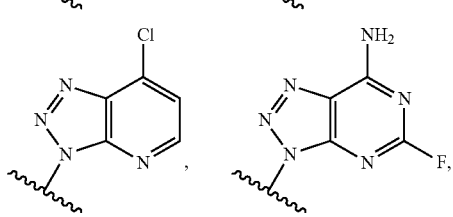

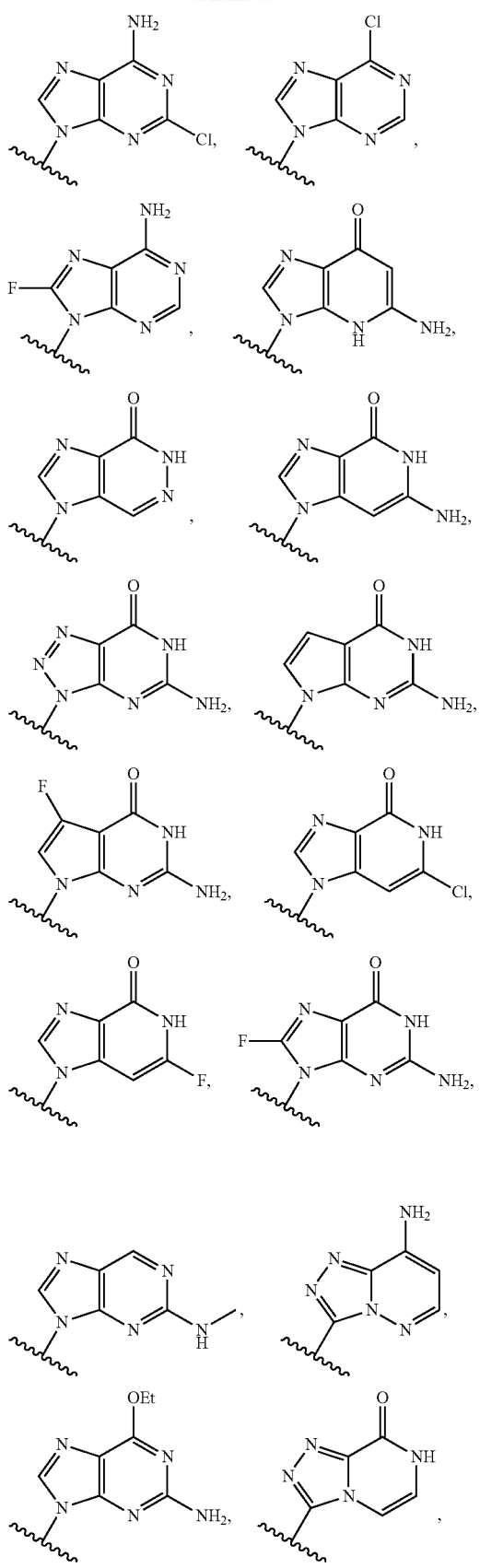
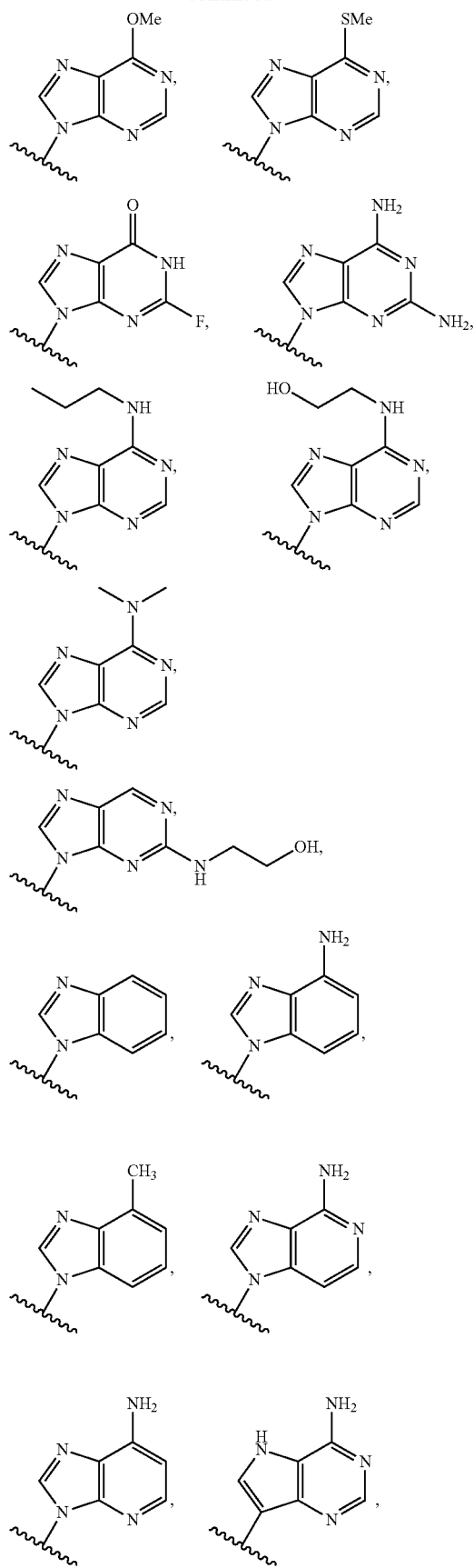

-continued

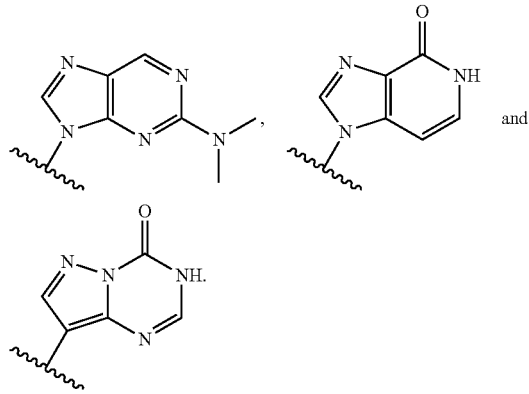

Embodiment 167. The compound of Embodiment 166, or a pharmaceutically acceptable salt thereof, wherein $B^4$ is selected from the group consisting of:

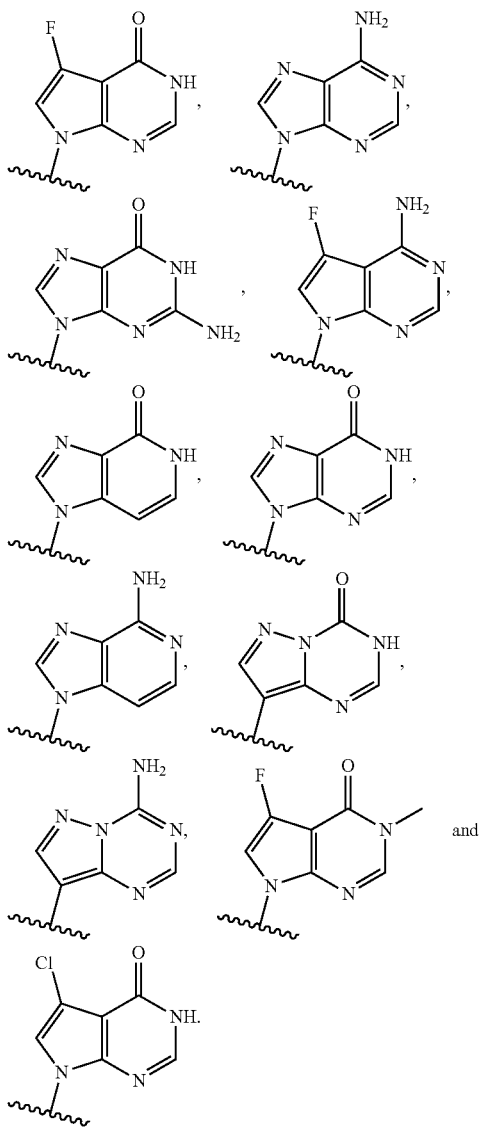

Embodiment 168. The compound of Embodiment 167, or a pharmaceutically acceptable salt thereof, wherein $B^4$ is selected from the group consisting of:

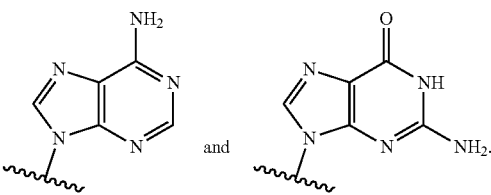 [SMILES: *n1cnc2c(N)ncnc21 ; "and" ; *n1cnc2c(=O)[nH]c(N)nc21]

Embodiment 169. The compound of any one of Embodiments 161-164, or a pharmaceutically acceptable salt thereof, wherein $B^3$ is selected from the group consisting of:

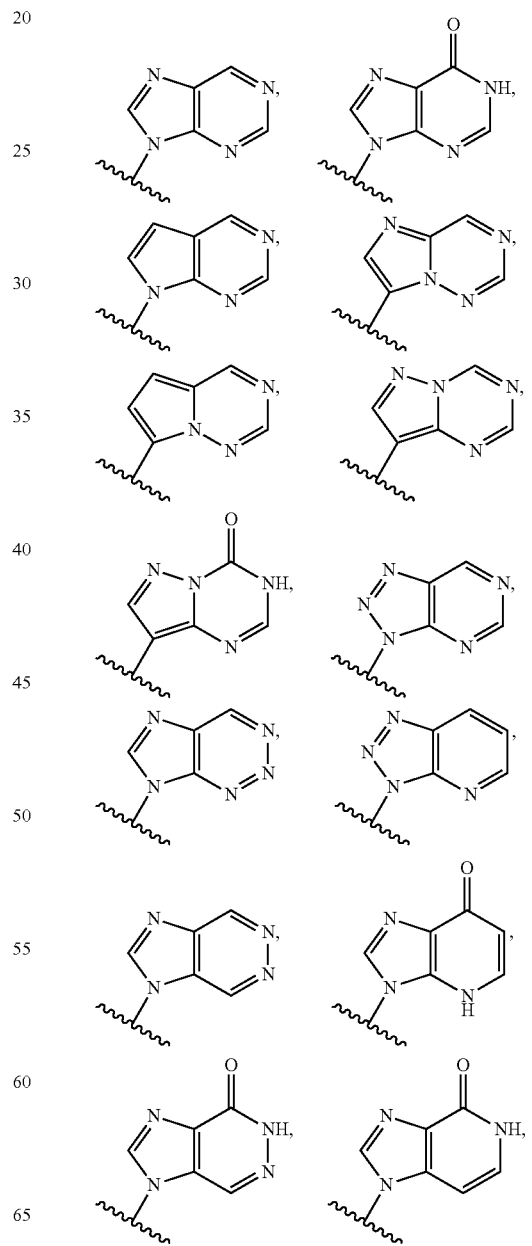

189
-continued

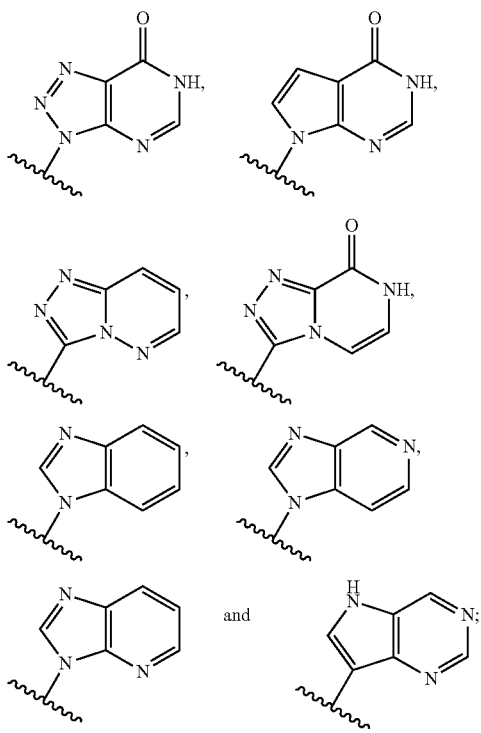

each of which is optionally and independently substituted at:

(i) any available carbon atom with a halo, $C_{1-6}$ alkyl, $C_{1-6}$ alkoxy, $C_{1-6}$ alkylthio, or amino group; and/or (ii) any available nitrogen atom with a $C_{1-6}$ alkyl group.

Embodiment 170. The compound of Embodiment 169, or a pharmaceutically acceptable salt thereof, wherein $B^3$ is selected from the group consisting of:

190
-continued

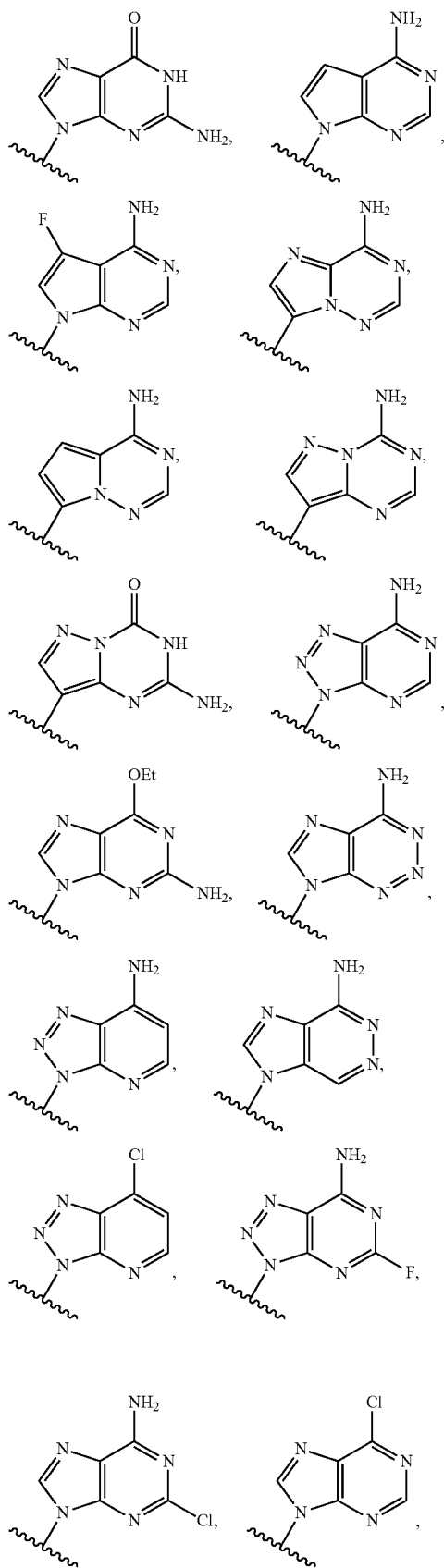

-continued
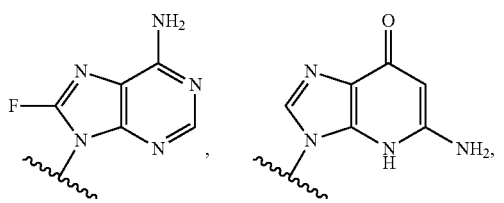
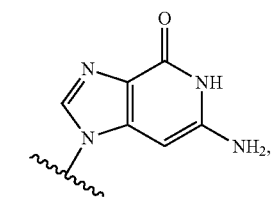
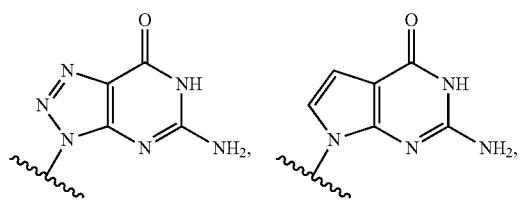
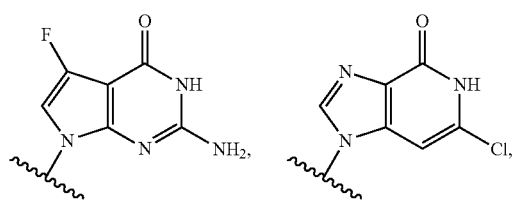
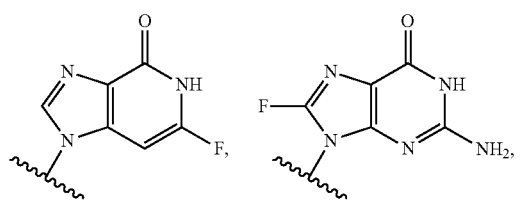
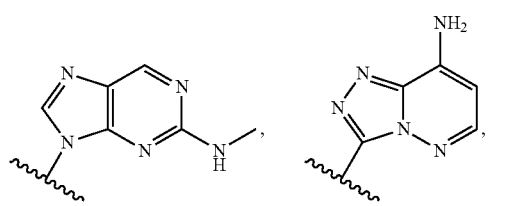
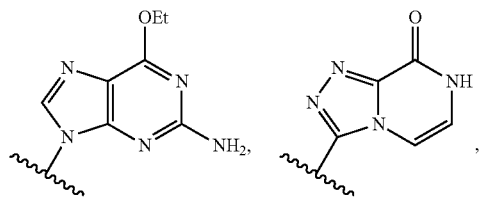
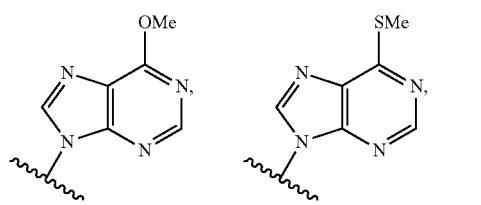
-continued
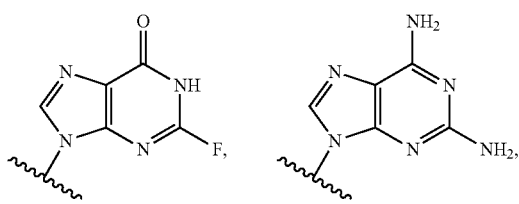
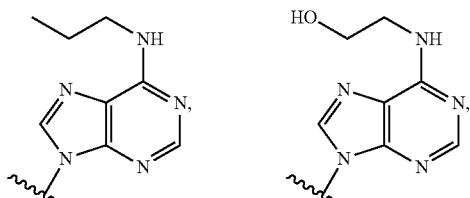
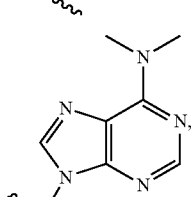
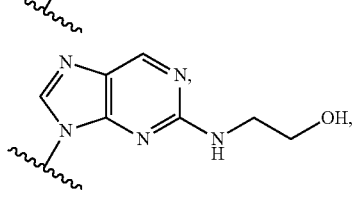
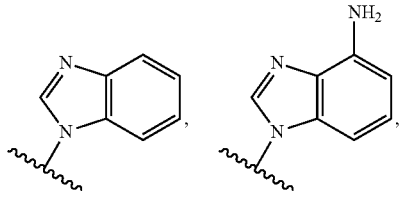
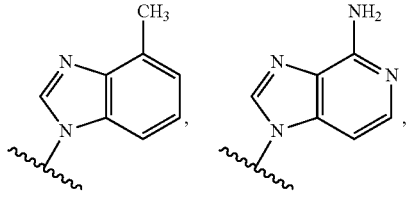
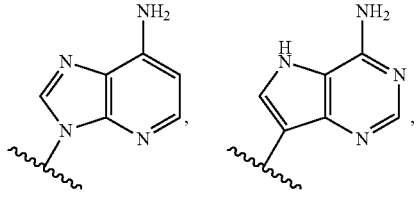
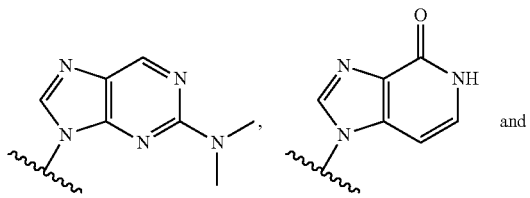 and

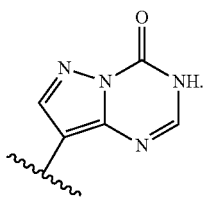

Embodiment 171. The compound of Embodiment 170, or a pharmaceutically acceptable salt thereof, wherein $B^3$ is selected from the group consisting of:

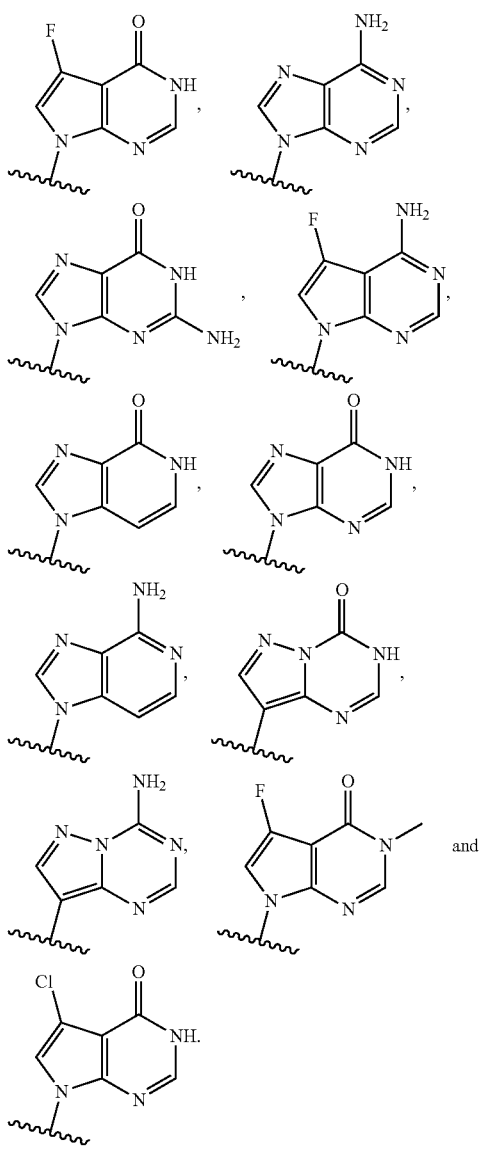

Embodiment 172. The compound of Embodiment 171, or a pharmaceutically acceptable salt thereof, wherein $B^3$ is selected from the group consisting of:

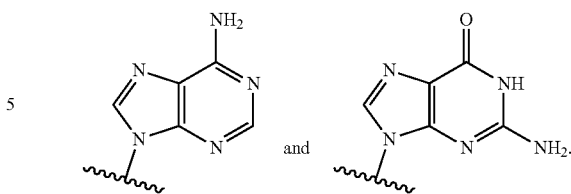

Embodiment 173. The compound of any one of Embodiments 144-151, 155, or 157-172, or a pharmaceutically acceptable salt thereof, wherein $Q^2$ is an oxygen atom.

Embodiment 174. The compound of any one of Embodiments 144-151, 155, or 157-172, or a pharmaceutically acceptable salt thereof, wherein $Q^2$ is a sulfur atom.

Embodiment 175. The compound of any one of Embodiments 144-147, 152-154, 156, or 157-172, or a pharmaceutically acceptable salt thereof, wherein $Q^4$ is an oxygen atom.

Embodiment 176. The compound of any one of Embodiments 144-147, 152-154, 156, or 157-172, or a pharmaceutically acceptable salt thereof, wherein $Q^4$ is a sulfur atom.

Embodiment 177. The compound of any one of Embodiments 144-176, or a pharmaceutically acceptable salt thereof, wherein $X^1$ and $X^2$ are an oxygen atom and $R^1$ and $R^2$ are independently a hydroxy group, a fluoro atom, or a chloro atom.

Embodiment 178. The compound of any one of Embodiments 144-177, or a pharmaceutically acceptable salt thereof, wherein u is 1-100.

Embodiment 179. The compound of Embodiment 178, or a pharmaceutically acceptable salt thereof, wherein u is 1-10.

Embodiment 180. The compound of Embodiment 179, or a pharmaceutically acceptable salt thereof, wherein u is 1-5.

Embodiment 181. The compound of Embodiment 180, or a pharmaceutically acceptable salt thereof, wherein u is 1.

Embodiment 182. The compound of any one of Embodiments 144-181, or a pharmaceutically acceptable salt thereof, wherein:

$L^2$ is —$X^4$-$T^1$-$Z^1$-$Q^4$-;

$X^4$ is —$(CH_2)_v$—,

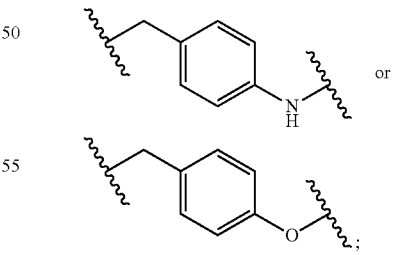

v is 1, 2, 3, 4, 5, 6, 7, 8, 9 or 10; or $X^4$ is absent;

$T^1$ is a peptide, or is absent;

$Z^1$ is a spacer;

$Q^4$ is a heterobifunctional group or heterotrifunctional group, or is absent.

Embodiment 183. The compound of Embodiment 182, or a pharmaceutically acceptable salt thereof, wherein:
$X^4$ is

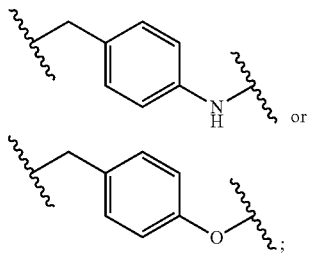

or $T^1$ is

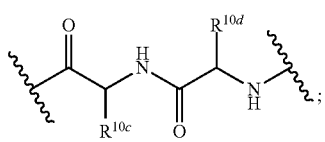

and
$R^{10c}$ and $R^{10d}$ are independently selected from the group consisting of hydrogen and optionally substituted $C_{1-6}$ alkyl.

Embodiment 184. The compound of Embodiment 183, or a pharmaceutically acceptable salt thereof, wherein:
$X^4$ is

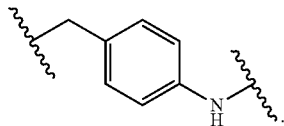 [SMILES: *Cc1ccc(N*)cc1]

Embodiment 185. The compound of any one of Embodiments 182-184, or a pharmaceutically acceptable salt thereof, wherein:
$Z^1$ is

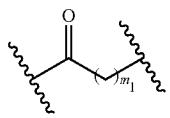

or —(CH2CH$_2$O)$_{s1}$—;
$m_1$ is 1, 2, 3, 4, 5, or 6; and
$s_1$ is 1, 2, 3, 4, 5, 6, 7, 8, 9, or 10.

Embodiment 186. The compound of Embodiment 182, or a pharmaceutically acceptable salt thereof, wherein:
$X^4$ is —CH$_2$—;
$Z^1$ is

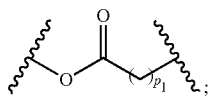

and
p1 is 1, 2, 3, 4, 5, 6, 7, 8, 9, or 10.

Embodiment 187. The compound of Embodiment 182, or a pharmaceutically acceptable salt thereof, wherein:
$X^4$ is —CH$_2$CH$_2$—;
$Z^1$ is

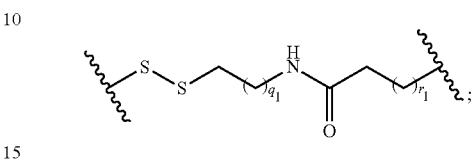

$q_1$ is 1, 2, 3, 4, 5, or 6; and
$r_1$ is 1, 2, 3, 4, 5, or 6.

Embodiment 188. The compound of any one of Embodiments 182, 186, or 187, or a pharmaceutically acceptable salt thereof, wherein $T^1$ is absent.

Embodiment 189. The compound of any one of Embodiments 182-188, or a pharmaceutically acceptable salt thereof, wherein $Q^A$ is a heterobifunctional group selected from the group consisting of:

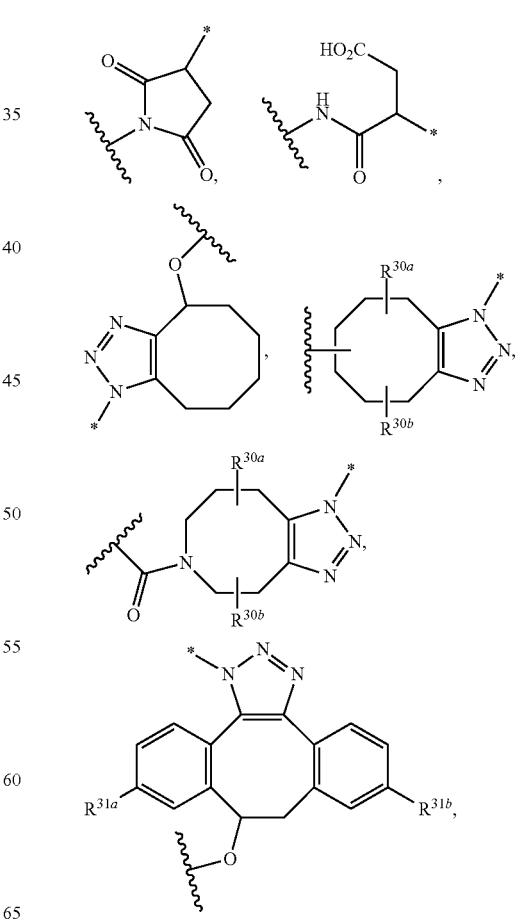

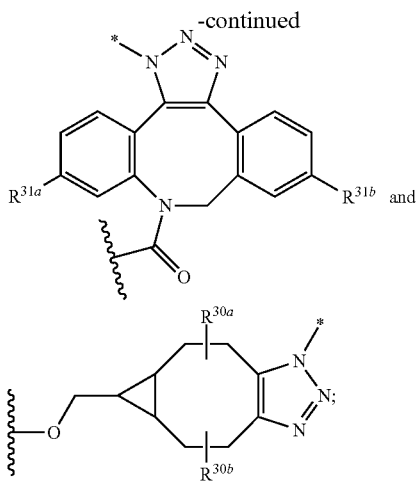

$R^{29}$ is hydrogen or $C_{1-6}$ alkyl;
$R^{30a}$ and $R^{30b}$ are independently selected from the group consisting of hydrogen, $C_{1-6}$ alkyl, halo, —C(=O)OR$^{29}$, —NH$_2$, $C_{1-6}$ alkoxy, —CN, —NO$_2$, and —OH;
$R^{31a}$ and $R^{31b}$ are independently selected from the group consisting of hydrogen, $C_{1-6}$ alkyl, halo, —C(=O)OR$^{29}$, —NH$_2$, —N(CH$_3$)$_2$, $C_{1-6}$ alkoxy, —CN, —NO$_2$, and —OH; and
* indicates the attachment point to any available carbon atom, nitrogen atom, oxygen atom, or sulfur atom attached to the drug delivery agent.

Embodiment 190. The compound of Embodiment 182, or a pharmaceutically acceptable salt thereof, wherein $X^4$, $T^1$, and $Q^4$ are absent.

Embodiment 191. The compound of any one of Embodiments 144-190, or a pharmaceutically acceptable salt thereof, wherein the drug delivery agent comprises lipids, steroids, vitamins, carbohydrates, proteins, peptides, polyamines, polyethylene glycols, or peptidomimetics, or any combinations thereof.

Embodiment 192. The compound of Embodiment 191, or a pharmaceutically acceptable salt thereof, wherein the drug delivery agent comprises lipids.

Embodiment 193. The compound of Embodiment 191, or a pharmaceutically acceptable salt thereof, wherein the drug delivery agent comprises steroids.

Embodiment 194. The compound of Embodiment 191, or a pharmaceutically acceptable salt thereof, wherein the drug delivery agent comprises vitamins.

Embodiment 195. The compound of Embodiment 191, or a pharmaceutically acceptable salt thereof, wherein the drug delivery agent comprises carbohydrates.

Embodiment 196. The compound of Embodiment 191, or a pharmaceutically acceptable salt thereof, wherein the drug delivery agent comprises proteins.

Embodiment 197. The compound of Embodiment 191, or a pharmaceutically acceptable salt thereof, wherein the drug delivery agent comprises peptides.

Embodiment 198. The compound of Embodiment 191, or a pharmaceutically acceptable salt thereof, wherein the drug delivery agent comprises polyamines.

Embodiment 199. The compound of Embodiment 191, or a pharmaceutically acceptable salt thereof, wherein the drug delivery agent comprises polyethylene glycols.

Embodiment 200. The compound of Embodiment 191, or a pharmaceutically acceptable salt thereof, wherein the drug delivery agent comprises peptidomimetics Since compound (I) or a prodrug thereof (in the present specification, sometimes to be collectively abbreviated as "the compound of the present disclosure") has a STING agonistic activity, it may be useful as an agent for the prophylaxis or treatment of cancer, a cancer growth inhibitor or a cancer metastasis inhibitor.

Since the compound of the present disclosure shows a STING agonistic activity, and is superior in terms of efficacy expression, pharmacokinetics (e.g., absorption, distribution, metabolism, excretion), solubility (e.g., water solubility), interaction with other medicaments (e.g., drug-metabolizing enzyme inhibitory action), safety (e.g., acute toxicity, chronic toxicity, genetic toxicity, reproductive toxicity, cardiotoxicity, carcinogenicity, central toxicity) and stability (e.g., chemical stability, stability to an enzyme), it may be useful as a medicament.

Therefore, the compound of the present disclosure may be used for increased STING activity in a mammal (e.g., mouse, rat, hamster, rabbit, cat, dog, cow, sheep, monkey, human).

The compound of the present disclosure may be used as a medicament such as an agent for the prophylaxis or treatment of diseases possibly influenced by STING (in the present specification, sometimes to be abbreviated as "STING-related diseases"), for example, cancers [e.g., colorectal cancers (e.g., colorectal cancer, rectal cancer, anus cancer, familial colorectal cancer, hereditary nonpolyposis colorectal cancer, gastrointestinal stromal tumor), lung cancers (e.g., non-small-cell lung cancer, small-cell lung cancer, malignant mesothelioma), mesothelioma, pancreatic cancers (e.g., pancreatic ductal carcinoma, pancreatic endocrine tumor), pharynx cancer, larynx cancer, esophageal cancer, stomach cancers (e.g., papillary adenocarcinoma, mucinous adenocarcinoma, adenosquamous carcinoma), duodenal cancer, small intestinal cancer, breast cancers (e.g., invasive ductal carcinoma, non-invasive ductal carcinoma, inflammatory breast cancer), ovarian cancers (e.g., ovarian epithelial cancer, extragonadal germ cell tumor, ovarian germ cell tumor, ovarian low-malignant potential tumor), testis tumor, prostate cancers (e.g., hormone-dependent prostate cancer, non-hormone dependent prostate cancer, castration-resistant prostate cancer), liver cancers (e.g., hepatocellular cancer, primary liver cancer, extrahepatic bile duct cancer), thyroid cancers (e.g., medullary thyroid carcinoma), renal cancers (e.g., renal cell cancers (e.g., clear cell renal cell cancer), transitional cell cancer of renal pelvis and ureter), uterine cancers (e.g., cervical cancer, uterine body cancer, uterus sarcoma), gestational choriocarcinoma, brain tumors (e.g., medulloblastoma, glioma, pineal astrocytic tumors, pilocytic astrocytoma, diffuse astrocytoma, anaplastic astrocytoma, pituitary adenoma), retinoblastoma, skin cancers (e.g., basalioma, malignant melanoma), sarcomas (e.g., rhabdomyosarcoma, leiomyosarcoma, soft tissue sarcoma, spindle cell sarcoma), malignant bone tumor, bladder cancer, blood cancers (e.g., multiple myeloma, leukemias (e.g., acute myelogenous leukemia), malignant lymphoma, Hodgkin's disease, chronic myeloproliferative disease), cancer of unknown primary], a cancer growth inhibitor, a cancer metastasis inhibitor, an apoptosis promoter, an agent for the treatment of precancerous lesions (e.g., myelodysplastic syndromes), and the like.

In another embodiment, the cancer is selected from any one or more of the cancers of Table 7.

TABLE 7 adrenal cancer
acinic cell carcinoma
acoustic neuroma
acral lentigious melanoma
acrospiroma
acute eosinophilic leukemia
acute erythroid leukemia
acute lymphoblastic leukemia
acute megakaryoblastic leukemia
acute monocytic leukemia
acute promyelocytic leukemia
adenocarcinoma
adenoid cystic carcinoma
adenoma
adenomatoid odontogenic tumor
adenosquamous carcinoma
adipose tissue neoplasm
adrenocortical carcinoma
adult T-cell leukemia/lymphoma
aggressive NK-cell leukemia
AIDS-related lymphoma
alveolar rhabdomyosarcoma
alveolar soft part sarcoma
ameloblastic fibroma
anaplastic large cell lymphoma
anaplastic thyroid cancer
angioimmunoblastic T-cell lymphoma,
angiomyolipoma
angiosarcoma
astrocytoma
atypical teratoid rhabdoid tumor
B-cell chronic lymphocytic leukemia
B-cell prolymphocytic leukemia
B-cell lymphoma
basal cell carcinoma
biliary tract cancer
bladder cancer
blastoma
bone cancer
Brenner tumor
Brown tumor
Burkitt's lymphoma
breast cancer
brain cancer
carcinoma
carcinoma in situ
carcinosarcoma
cartilage tumor
cementoma
myeloid sarcoma
chondroma
chordoma
choriocarcinoma
choroid plexus papilloma
clear-cell sarcoma of the kidney
craniopharyngioma
cutaneous T-cell lymphoma
cervical cancer
colorectal cancer
Degos disease
desmoplastic small round cell tumor
diffuse large B-cell lymphoma
dysembryoplastic neuroepithelial tumor,
dysgerminoma
embiyonal carcinoma
endocrine gland neoplasm
endodermal sinus tumor
enteropathy-associated T-cell lymphoma
esophageal cancer
fetus in fetu
fibroma
fibrosarcoma
follicular lymphoma
follicular thyroid cancer
ganglioneuroma
gastrointestinal cancer
germ cell tumor
gestational choriocarcinoma
giant cell fibroblastoma
giant cell tumor of the bone TABLE 7-continued glial tumor
glioblastoma multiforme
glioma
gliomatosis cerebri
glucagonoma
gonadoblastoma
granulosa cell tumor
gynandroblastoma
gallbladder cancer
gastric cancer
hairy cell leukemia
hemangioblastoma
head and neck cancer
hemangiopericytoma
hematological malignancy
hepatoblastoma
hepatosplenic T-cell lymphoma
Hodgkin's lymphoma
non-Hodgkin's lymphoma
invasive lobular carcinoma
intestinal cancer
kidney cancer
laryngeal cancer
lentigo maligna
lethal midline carcinoma
leukemia
leydig cell tumor
liposarcoma
lung cancer
lymphangioma
lymphangiosarcoma
lymphoepithelioma
lymphoma
acute lymphocytic leukemia
acute myelogeous leukemia
chronic lymphocytic leukemia
liver cancer
small cell lung cancer
non-small cell lung cancer
MALT lymphoma
malignant fibrous histiocytoma
malignant peripheral nerve sheath tumor
malignant triton tumor
mantle cell lymphoma
marginal zone B-cell lymphoma
mast cell leukemia
mediastinal germ cell tumor
medullary carcinoma of the breast
medullary thyroid cancer,
medulloblastoma
melanoma,
meningioma,
merkel cell cancer
mesothelioma
metastatic urothelial carcinoma
mixed Mullerian tumor
mucinous tumor
multiple myeloma
muscle tissue neoplasm
mycosis fungoides
myxoid liposarcoma
myxoma
myxosarcoma
nasopharyngeal carcinoma
neurinoma
neuroblastoma
neurofibroma
neuroma
nodular melanoma
ocular cancer
oligoastrocytoma
oligodendroglioma
oncocytoma
optic nerve sheath meningioma
optic nerve tumor
oral cancer
osteosarcoma
ovarian cancer
Pancoast tumor
papillary thyroid cancer TABLE 7-continued paraganglioma
pinealoblastoma
pineocytoma
pituicytoma
pituitary adenoma
pituitary tumor
plasmacytoma
polyembryoma
precursor T-lymphoblastic lymphoma
primary central nervous system lymphoma
primary effusion lymphoma
preimary peritoneal cancer
prostate cancer
pancreatic cancer
pharyngeal cancer
pseudomyxoma periotonei
renal cell carcinoma
renal medullary carcinoma
retinoblastoma
rhabdomyoma
rhabdomyosarcoma
Richter's transformation
rectal cancer
sarcoma
Schwannomatosis
seminoma
Sertoli cell tumor
sex cord-gonadal stromal tumor
signet ring cell carcinoma
skin cancer
small blue round cell tumors
small cell carcinoma
soft tissue sarcoma
somatostatinoma
soot wart
spinal tumor
splenic marginal zone lymphoma
squamous cell carcinoma
synovial sarcoma
Sezary's disease
small intestine cancer
squamous carcinoma
stomach cancer
T-cell lymphoma
testicular cancer
thecoma
thyroid cancer
transitional cell carcinoma
throat cancer
urachal cancer
urogenital cancer
urothelial carcinoma
uveal melanoma
uterine cancer
verrucous carcinoma
visual pathway glioma
vulvar cancer
vaginal cancer
Waldenstrom's macroglobulinemia
Warthin's tumor
Wilms' tumor In another embodiment, the cancer is a solid tumor or lymphoma.

Particularly, the compound of the present disclosure may be used as a medicament for colorectal cancer, breast cancer, skin cancer, malignant lymphoma or lung cancer.

The compound of the present disclosure may be administered orally or parenterally as it is or in a mixture with a pharmacologically acceptable carrier as a medicament, to a mammal (preferably humans).

The medicament containing the compound of the present disclosure (hereinafter sometimes to be abbreviated as "the medicament of the present disclosure") is explained in detail below. Examples of the dosage form of the medicament of the present disclosure include oral preparations such as tablet (e.g., sugar-coated tablet, film-coated tablet, sublingual tablet, buccal, orally disintegrating tablet), pill, granule, powder, capsule (e.g., soft capsule, microcapsule), syrup, emulsion, suspension, films (e.g., orally disintegrable films, oral mucosa-adhesive film) and the like. In addition, examples of the dosage form of the medicament of the present disclosure include parenteral preparations such as injection, drip infusion, transdermal absorption type preparation (e.g., iontophoresis transdermal absorption type preparation), suppository, ointment, nasal preparation, pulmonary preparation, eye drop and the like. Moreover, the medicament of the present disclosure may be a release control preparation such as an immediate-release preparation, a sustained-release preparation (e.g., a sustained-release microcapsule) and the like.

As the dosage form of the medicament of the present disclosure, a nanoparticle preparation and a preparation using a bacteria-derived membrane can also be used.

The medicament of the present disclosure may be prepared according to a method known per se (e.g., the method described in the Japanese Pharmacopoeia etc.) generally used in the field of preparation. In addition, the medicament of the present disclosure may contain a suitable amount of an additive such as a excipient, a binder, a disintegrant, a lubricant, a sweetening agent, a surfactant, a suspending agent, an emulsifier, a colorant, a preservative, an aromatic, a corrigent, a stabilizer, a thickening agent and the like generally used in the field of preparation as necessary. Examples of the pharmacologically acceptable carrier include these additives.

For example, tablet may be prepared using an excipient, a binder, a disintegrant, a lubricant and the like, and pill or granule may be prepared using an excipient, a binder and a disintegrant. Powder or capsule may be prepared using an excipient and the like, syrup may be prepared using a sweetening agent and the like, and emulsion or suspension may be prepared using a suspending agent, a surfactant, an emulsifier and the like.

Examples of the excipient include lactose, sucrose, glucose, starch, sucrose, crystalline cellulose, powdered *glycyrrhiza*, mannitol, sodium hydrogencarbonate, calcium phosphate and calcium sulfate.

Examples of the binder include 5 to 10 wt % starch liquid paste, 10 to 20 wt % gum arabic solution or gelatin solution, 1 to 5 wt % tragacanth solution, carboxymethyl cellulose solution, sodium alginate solution and glycerin.

Examples of the disintegrant include starch and calcium carbonate.

Examples of the lubricant include magnesium stearate, stearic acid, calcium stearate and purified talc.

Examples of the sweetener include glucose, fructose, invert sugar, sorbitol, xylitol, glycerin and simple syrup.

Examples of the surfactant include sodium lauryl sulfate, polysorbate 80, sorbitan monofatty acid ester and polyoxyl 40 stearate.

Examples of the suspending agent include gum arabic, sodium alginate, sodium carboxymethyl cellulose, methyl cellulose and bentonite.

Examples of the emulsifier include gum arabic, tragacanth, gelatin and polysorbate 80.

For example, when the medicament of present disclosure is a tablet, for example, an excipient (e.g., lactose, sucrose, starch), a disintegrant (e.g., starch, calcium carbonate), a binder (e.g., starch, gum arabic, carboxymethyl cellulose, polyvinyl pyrrolidone, hydroxypropyl cellulose) or a lubricant (e.g., talc, magnesium stearate, polyethylene glycol 6000) is added to the compound of the present disclosure, and the mixture is compression-molded, according to a method known per se, and then where necessary, the molded product is coated according to a method known per se for the purpose of masking of taste, enteric property or durability, to give a tablet. As the coating agent for the coating, for example, hydroxypropylmethyl cellulose, ethyl cellulose, hydroxymethyl cellulose, hydroxypropyl cellulose, polyoxyethylene glycol, Tween 80, Pluronic F68, cellulose acetate phthalate, hydroxypropylmethyl cellulose phthalate, hydroxymethyl cellulose acetate succinate, Eudragit (methacrylic acid-acrylic acid copolymer, manufactured by Rohm, DE) and pigment (e.g., iron oxide red, titanium dioxide) may be used.

Examples of the injection include intravenous injection as well as subcutaneous injection, intracutaneous injection, intramuscular injection, intraperitoneal injection, drip injection and the like.

Such injections are prepared according to a method known per se, or by dissolving, suspending or emulsifying the compound of the present disclosure in a sterilized aqueous or oily liquid. Examples of the aqueous liquid include physiological saline, isotonic solutions containing glucose or other auxiliary drugs (e.g., D-sorbitol, D-mannitol, sodium chloride) and the like. The aqueous liquid may contain a suitable solubilizing agent such as an alcohol (e.g., ethanol), a polyalcohol (e.g., propylene glycol, polyethylene glycol), a nonionic surfactant (e.g., polysorbate 80, HCO-50) and the like. Examples of the oily liquid include sesame oil, soybean oil and the like. The oily liquid may contain a solubilizing agent. Examples of the solubilizing agent include benzyl benzoate, benzyl alcohol and the like. In addition, the injection may be blended with a buffer (e.g., phosphate buffer, sodium acetate buffer), a soothing agent (e.g., benzalkonium chloride, procaine hydrochloride), a stabilizer (e.g., human serum albumin, polyethylene glycol), a preservative (e.g., benzyl alcohol, phenol) and the like. A prepared injection may be generally filled in an ampoule.

While the content of the compound of the present disclosure in the medicament of the present disclosure varies depending on the form of the pharmaceutical preparation, it is generally about 0.01 to about 100 wt %, preferably about 2 to about 85 wt %, more preferably about 5 to about 70 wt %, relative to the entire preparation.

While the content of the additive in the medicament of the present disclosure varies depending on the form of the pharmaceutical preparation, it is generally about 1 to about 99.9 wt %, preferably about 10 to about 90 wt %, relative to the entire preparation.

The compound of the present disclosure is stable and low toxic, and may be used safely. While the daily dose of the compound of the present disclosure varies depending on the condition and body weight of patients, the kind of compound, administration route and the like, in the case of, for example, oral administration to patients for the treatment of cancer, the daily dose to an adult (body weight about 60 kg) is about 1 to about 1000 mg, preferably about 3 to about 300 mg, more preferably about 10 to about 200 mg, as the compound of the present disclosure, which may be given in a single administration or administered in 2 or 3 portions a day.

When the compound of the present disclosure is administered parenterally, it is generally administered in the form of a liquid (e.g., injection). While the dose of the compound of the present disclosure varies depending on the subject of administration, target organ, symptom, administration method and the like, it is, for example, about 0.01 mg to about 100 mg, preferably about 0.01 to about 50 mg, more preferably about 0.01 to about 20 mg, relative to 1 kg body weight, which is preferably given by intravenous injection.

The compound of the present disclosure may be used concurrently with other drugs. To be specific, the compound of the present disclosure may be used together with medicaments such as hormonal therapeutic agents, chemotherapeutic agents, immunotherapeutic agents, medicaments inhibiting the action of cell growth factors or cell growth factor receptors and the like. In the following, the drugs that can be used in combination with the compound of the present disclosure are abbreviated as concomitant drugs.

Examples of the "hormonal therapeutic agents" include fosfestrol, diethylstylbestrol, chlorotrianisene, medroxyprogesterone acetate, megestrol acetate, chlormadinone acetate, cyproterone acetate, danazol, allylestrenol, gestrinone, mepartricin, raloxifene, ormeloxifene, levormeloxifene, anti-estrogens (e.g., tamoxifen citrate, toremifene citrate), pill preparations, mepitiostane, testrolactone, aminoglutethimide, LH-RH agonists (e.g., goserelin acetate, buserelin, leuprorelin, leuprorelin acetate), droloxifene, epitiostanol, ethinylestradiol sulfonate, aromatase inhibitors (e.g., fadrozole hydrochloride, anastrozole, retrozole, exemestane, vorozole, formestane), anti-androgens (e.g., flutamide, bicartamide, nilutamide, enzalutamide), 5α-reductase inhibitors (e.g., finasteride, epristeride, dutasteride), aderenal cortex hormone drugs (e.g., dexamethasone, prednisolone, betamethasone, triamcinolone), androgen synthesis inhibitors (e.g., abiraterone), retinoid and drugs that retard retinoid metabolism (e.g., liarozole), thyroid hormone, and DDS (Drug Delivery System) preparations thereof.

Examples of the "chemotherapeutic agents" include alkylating agents, antimetabolites, anticancer antibiotics and plant-derived anticancer agents.

Examples of the "alkylating agents" include nitrogen mustard, nitrogen mustard-N-oxide hydrochloride, chlorambutyl, cyclophosphamide, ifosfamide, thiotepa, carboquone, improsulfan tosylate, busulfan, nimustine hydrochloride, mitobronitol, melphalan, dacarbazine, ranimustine, sodium estramustine phosphate, triethylenemelamine, carmustine, lomustine, streptozocin, pipobroman, etoglucid, carboplatin, cisplatin, miboplatin, nedaplatin, oxaliplatin, altretamine, ambamustine, dibrospidium hydrochloride, fotemustine, prednimustine, pumitepa, ribomustin, temozolomide, treosulphan, trophosphamide, zinostatin stimalamer, adozelesin, cystemustine, bizelesin, and DDS preparations thereof.

Examples of the "antimetabolites" include mercaptopurine, 6-mercaptopurine riboside, thioinosine, methotrexate, pemetrexed, enocitabine, cytarabine, cytarabine ocfosfate, ancitabine hydrochloride, 5-FU drugs (e.g., fluorouracil, tegafur, UFT, doxifluridine, carmofur, gallocitabine, emitefur, capecitabine), aminopterine, nelzarabine, leucovorin calcium, tabloid, butocine, calcium folinate, levofolinate calcium, cladribine, emitefur, fludarabine, gemcitabine, hydroxycarbamide, pentostatin, piritrexim, idoxuridine, mitoguazone, thiazophrine, ambamustine, bendamustine, and DDS preparations thereof.

Examples of the "anticancer antibiotics" include actinomycin-D, actinomycin-C, mitomycin-C, chromomycin-A3, bleomycin hydrochloride, bleomycin sulfate, peplomycin sulfate, daunorubicin hydrochloride, doxorubicin hydrochloride, aclarubicin hydrochloride, pirarubicin hydrochloride, epirubicin hydrochloride, neocarzinostatin, mithramycin, sarcomycin, carzinophilin, mitotane, zorubicin hydrochloride, mitoxantrone hydrochloride, idarubicin hydrochloride, and DDS preparations thereof (e.g., doxorubicin-including PEG liposome).

Examples of the "plant-derived anticancer agents" include etoposide, etoposide phosphate, vinblastine sulfate, vincristine sulfate, vindesine sulfate, teniposide, paclitaxel, docetaxel, cabazitaxel, vinorelbine, and DDS preparations thereof.

Examples of the "immunotherapeutic agents (BRM)" include picibanil, krestin, sizofiran, lentinan, ubenimex, interferons, interleukins, macrophage colony-stimulating factor, granulocyte colony-stimulating factor, erythropoietin, lymphotoxin, BCG vaccine, *Corynebacterium parvum*, levamisole, polysaccharide K, procodazole, anti-CTLA4 antibodies (e.g., ipilimumab, tremelimumab), anti-PD-1 antibodies (e.g., nivolumab, pembrolizumab), and anti-PD-L1 antibody.

Example of the "cell growth factors" in the "medicaments inhibiting the action of cell growth factors or cell growth factor receptors" include any substances that promote cell proliferation, which are normally peptides having not more than 20,000 molecular weight that are capable of exhibiting their activity at low concentrations by binding to a receptor, including (1) EGF (epidermal growth factor) or substances possessing substantially the same activity as EGF [e.g., TGFα], (2) insulin or substances possessing substantially the same activity as insulin [e.g., insulin, IGF (insulin-like growth factor)-1, IGF-2], (3) FGF (fibroblast growth factor) or substances possessing substantially the same activity as FGF [e.g., acidic FGF, basic FGF, KGF (keratinocyte growth factor), FGF-10], and (4) other cell growth factors [e.g., CSF (colony stimulating factor), EPO (erythropoietin), IL-2 (interleukin-2), NGF (nerve growth factor), PDGF (platelet-derived growth factor), TGFβ (transforming growth factor β), HGF (hepatocyte growth factor), VEGF (vascular endothelial growth factor), heregulin, angiopoietin].

Examples of the "cell growth factor receptors" include any receptors capable of binding to the aforementioned cell growth factors, including EGF receptor, heregulin receptor (e.g., HER3), insulin receptor, IGF receptor-1, IGF receptor-2, FGF receptor-1 or FGF receptor-2, VEGF receptor, angiopoietin receptor (e.g., Tie2), PDGF receptor and the like.

Examples of the "medicaments inhibiting the action of cell growth factors or cell growth factor receptors" include EGF inhibitor, TGFα inhibitor, heregulin inhibitor, insulin inhibitor, IGF inhibitor, FGF inhibitor, KGF inhibitor, CSF inhibitor, EPO inhibitor, IL-2 inhibitor, NGF inhibitor, PDGF inhibitor, TGFβ inhibitor, HGF inhibitor, VEGF inhibitor, angiopoietin inhibitor, EGF receptor inhibitor, HER2 inhibitor, HER4 inhibitor, insulin receptor, IGF-1 receptor inhibitor, IGF-2 receptor inhibitor, FGF receptor-1 inhibitor, FGF receptor-2 inhibitor, FGF receptor-3 inhibitor, FGF receptor-4 inhibitor, VEGF receptor inhibitor, Tie-2 inhibitor, PDGF receptor inhibitor, Abl inhibitor, Raf inhibitor, FLT3 inhibitor, c-Kit inhibitor, Src inhibitor, PKC inhibitor, Smo inhibitor, ALK inhibitor, RORI inhibitor, Trk inhibitor, Ret inhibitor, mTOR inhibitor, Aurora inhibitor, PLK inhibitor, MEK (MEKI/2) inhibitor, MET inhibitor, CDK inhibitor, Akt inhibitor, ERK inhibitor, PI3K inhibitor and the like. More specifically, anti-VEGF antibody (e.g., Bevacizumab, Ramucurumab), anti-HER2 antibody (e.g., Trastuzumab, Pertuzumab), anti-EGFR antibody (e.g., Cetuximab, Panitumumab, Matuzumab, Nimotuzumab), anti-HGF antibody, Imatinib, Erlotinib, Gefitinib, Sorafenib, Sunitinib, Dasatinib, Lapatinib, Vatalanib, Ibrutinib, Bosutinib, Cabozantinib, Crizotinib, Alectinib, Vismodegib, Axitinib, Motesanib, Nilotinib, 6-[4-(4-ethylpiperazin-1-ylmethyl)phenyl]-N-[1(R)-phenylethyl]-7H-pyrrolo[2,3-d]pyrimidin-4-amine (AEE-788), Vandetanib, Temsirolimus, Everolimus, Enzastaurin, Tozasertib, 2-[N-[3-[4-[5-[N-(3-fluorophenyl)carbamoylmethyl]-1H-pyrazol-3-ylamino] quinazolin-7-yloxy]propyl]-N ethylamino]ethyl phosphate (AZD-1152), 4-[9-chloro-7-(2,6-difluorophenyl)-5H-pyrimido[5,4-d][2]benzazepin-2-ylamino]benzoic acid, N-[2-methoxy-5-[(E)-2-(2,4,6-trimethoxyphenyl)vinylsulfonyl methyl]phenyl]glycine sodium salt (ON-1910Na), Volasertib, Selumetinib, Trametinib, N-[2(R),3-dihydroxypropoxy]-3,4-di fluoro-2-(2-fluoro-4-iodophenylamino) benzamide (PD-0325901), Bosutinib, Regorafenib, Afatinib, Idelalisib, Ceritinib, Dabrafenib and the like may be used.

In addition to the aforementioned drugs, L-asparaginase, L-arginase, arginine deiminase, aceglatone, procarbazine hydrochloride, protoporphyrin-cobalt complex salt, mercuric hematoporphyrin-sodium, topoisomerase 1 inhibitors (e.g., irinotecan, topotecan, indotecan, Indimitecan), topoisomerase II inhibitors (e.g., sobuzoxane), differentiation inducers (e.g., retinoid, vitamin D), other angiogenesis inhibitors (e.g., humagillin, shark extract, COX-2 inhibitor), α-blockers (e.g., tamsulosin hydrochloride), bisphosphonic acids (e.g., pamidronate, zoledronate), thalidomide, lenalidomide, pomalidomide, azacytidine, decitabine, proteasome inhibitors (e.g., bortezomib, carfilzomib, ixazomib), NEDD8 inhibitors (e.g., Pevonedistat), UAE inhibitors, PARP inhibitors (e.g., Olaparib, Niraparib, Veliparib), antitumor antibodies such as anti-CD20 antibodies (e.g., Rituximab, Obinutuzumab), anti-CCR4 antibodies (e.g., Mogamulizumab) and the like, antibody-drug conjugates (e.g., trastuzumab emtansine, Brentuximab vedotin) and the like may also be used as a concomitant drug.

By combining the compound of the present disclosure and a concomitant drug, a superior effect such as (1) the dose may be reduced as compared to single administration of the compound of the present disclosure or a concomitant drug, (2) the drug to be combined with the compound of the present disclosure may be selected according to the condition of patients (mild case, severe case and the like), (3) the period of treatment may be set longer, (4) a sustained treatment effect may be designed, (5) a synergistic effect may be afforded by a combined use of the compound of the present disclosure and a concomitant drug, and the like, may be achieved.

In the present specification, the compound of the present disclosure and a concomitant drug used in combination are referred to as the "combination agent of the present disclosure".

For use of the combination agent of the present disclosure, the administration time of the compound of the present disclosure and the concomitant drug is not restricted, and the compound of the present disclosure and the concomitant drug can be administered to an administration subject simultaneously, or may be administered at different times. When administered at a time interval, the interval differs depending on the effective ingredient to be administered, dosage form and administration method, and for example, when the concomitant drug is administered first, the compound of the present disclosure may be administered within time range of from 1 min to 3 days, preferably from 10 min to 1 day, more preferably from 15 min to 1 hr after administration of the concomitant drug. When the compound of the present disclosure is administered first, the concomitant drug is administered within time range of from 1 min to 1 day, preferably from 10 min to 6 hrs, more preferably from 15 min to 1 hr after administration of the compound of the present disclosure. The dosage of the concomitant drug may be determined according to the dose clinically set, and may be appropriately selected depending on the administration subject, administration route, disease, combination and the like.

Examples of the administration mode of the combined use of the compound of the present disclosure and the concomitant drug include the following methods: (1) The compound of the present disclosure and the concomitant drug are simultaneously produced to give a single preparation, which is then administered. (2) The compound of the present disclosure and the concomitant drug are separately produced to give two kinds of preparations which are administered simultaneously by the same administration route. (3) The compound of the present disclosure and the concomitant drug are separately produced to give two kinds of preparations which are administered by the same administration route at different times. (4) The compound of the present disclosure and the concomitant drug are separately produced to give two kinds of preparations which are administered simultaneously by different administration routes. (5) The compound of the present disclosure and the concomitant drug are separately produced to give two kinds of preparations which are administered by different administration routes at different times (e.g., the compound of the present disclosure and the concomitant drug are administered in this order, or in the reverse order).

The dose of the concomitant drug may be appropriately determined in accordance with its clinical dose, and the ratio of the compound of the present disclosure and the concomitant drug may be appropriately determined depending on the administration subject, administration route, target disease, symptom, combination, and the like. For example, when the administration subject is human, the concomitant drug is used in 0.01 to 100 (parts by weight), relative to 1 part by weight of the compound of the present disclosure.

Furthermore, the compound of the present disclosure or the combination agent of the present disclosure may be used concurrently with a non-drug therapy. To be precise, the compound of the present disclosure or the combination agent of the present disclosure may be combined with a non-drug therapy such as (1) surgery, (2) hypertensive chemotherapy using angiotensin II etc., (3) gene therapy, (4) thermotherapy, (5) cryotherapy, (6) laser cauterization and (7) radiotherapy.

For example, by using the compound of the present disclosure or the combination agent of the present disclosure before or after the above-mentioned surgery and the like, or before or after a combined treatment of two or three kinds thereof, effects such as prevention of emergence of resistance, prolongation of Disease-Free Survival, suppression of cancer metastasis or recurrence, prolongation of life and the like may be afforded.

In addition, it is possible to combine a treatment with the compound of the present disclosure or the combination agent of the present disclosure with a supportive therapy [(i) administration of antibiotic (e.g., β-lactam type such as pansporin and the like, macrolide type such as clarithromycin and the like) for the complication with various infectious diseases, (ii) administration of high-calorie transfusion, amino acid preparation or general vitamin preparation for the improvement of malnutrition, (iii) administration of morphine for pain mitigation, (iv) administration of a pharmaceutical agent for ameliorating side effects such as nausea, vomiting, anorexia, diarrhea, leucopenia, thrombocytopenia, decreased hemoglobin concentration, hair loss, hepatopathy, renopathy, DIC, fever and the like and (v) administration of a pharmaceutical agent for suppressing multiple drug resistance of cancer and the like].

EXAMPLES

The present disclosure is explained in detail by referring to the following Examples, Experimental Examples and Formulation Examples, which are not to be construed as limitative, and the disclosure may be changed within the scope of the present disclosure.

In the following Examples, the "room temperature" generally means about 10° C. to about 35° C. The ratios indicated for mixed solvents are volume mixing ratios, unless otherwise specified. % means wt %, unless otherwise specified.

In silica gel column chromatography, "Diol" means use of 3-(2,3-dihydroxypropoxy)propylsilane-bound silica gel. In silica gel column chromatography and HPLC (high-performance liquid chromatography), "C18" means use of octadecyl-bound silica gel. The ratios of elution solvents are volume mixing ratios, unless otherwise specified.

The measurement by LC/MS was performed under the following conditions [column: L-Column2 ODS, 3.0 mmI.D.×50 mm, mobile phase: acetonitrile/5 mM ammonium acetate buffer solution=900/100)].

In Examples, the following abbreviations are used.

mp: melting point

MS: mass spectrum $[M+H]^+$, $[M-H]^-$: molecular ion peak

M: mol concentration

N: normal $CDCl_3$: deuterated chloroform

DMSO-$d_6$: deuterated dimethyl sulfoxide $D_2O$: deuterated water $^1$H NMR: proton nuclear magnetic resonance $^{31}$P NMR: phosphorus nuclear magnetic resonance LC/MS: liquid chromatograph mass spectrometer ESI: ElectroSpray Ionization APCI: Atomspheric Pressure Chemical Ionization THF: tetrahydrofuran DMF: N,N-dimethylformamide DCM: dichloromethane $^1$H NMR and $^{31}$P NMR was measured by Fourier-transform type NMR. For the analysis, ACD/SpecManager (trade name) and the like were used. Peaks with very mild protons such as a hydroxy group, an amino group and the like are not described.

MS was measured by LC/MS. As ionization method, ESI method or APCI method was used. The data indicates actual measured value (found). Generally, a molecular ion peak is observed. In the case of a compound having a tert-butoxycarbonyl group, a peak after elimination of a tert-butoxycarbonyl group or a tert-butyl group may be observed as a fragment ion. In the case of a compound having a hydroxy group, a peak after elimination of $H_2O$ may be observed as a fragment ion. In the case of a salt, a molecular ion peak or fragment ion peak of free form is generally observed.

Example 1
Synthesis of 7-((5R,7R,8R,12aR,14R,15R,15aR, 16R)-14-(6-amino-9H-purin-9-yl)-15-fluoro-2,10, 16-trihydroxy-2,10-dioxidooctahydro-12H-5,8-methanofuro[3,2-1][1,3,6,9,11,2,10]pentaoxadiphosphacyclotetradecin-7-yl)-5-fluoro-3, 7-dihydro-4H-pyrrolo[2,3-d]pyrimidin-4-one di-triethylamine salt
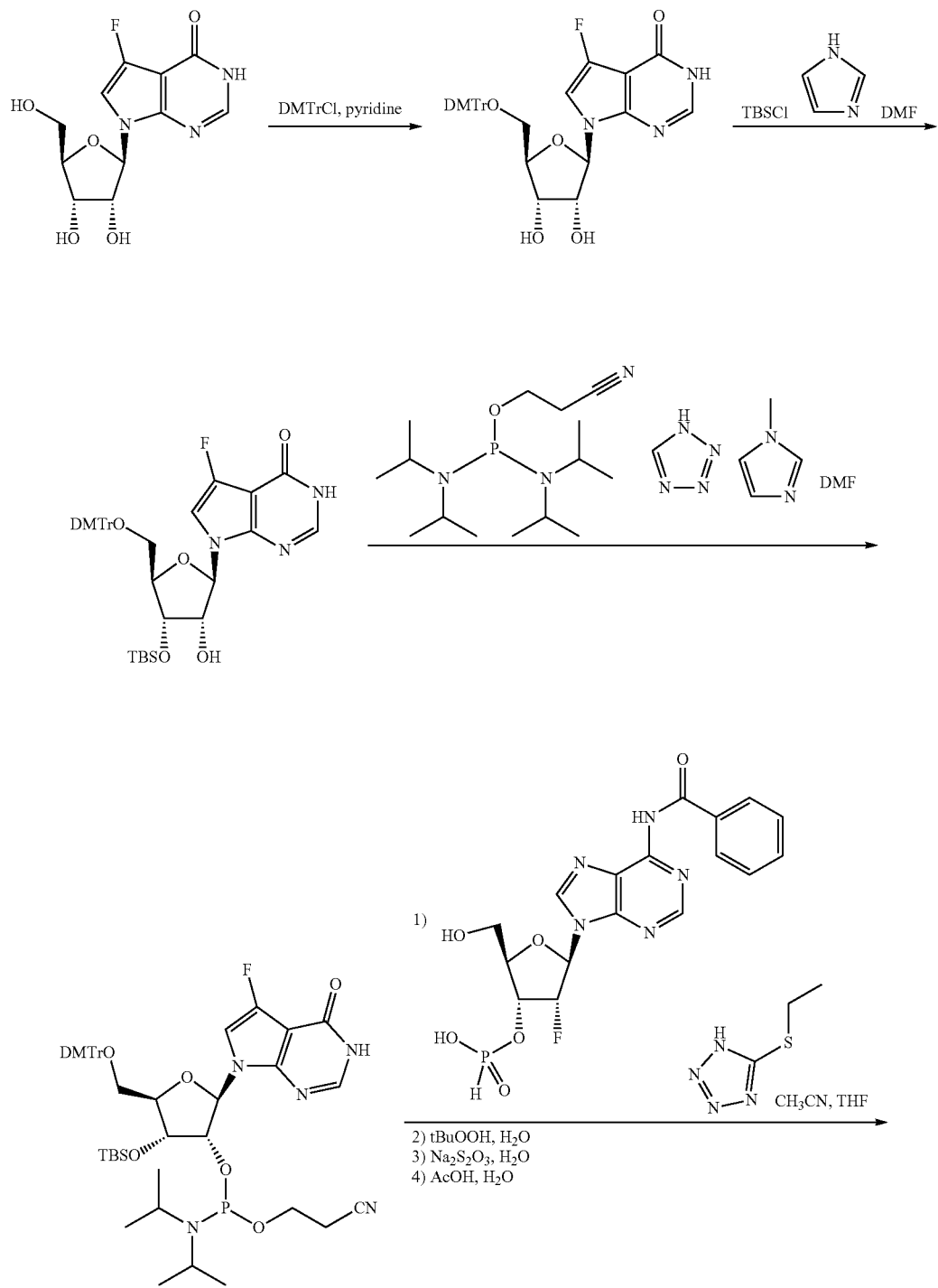

-continued
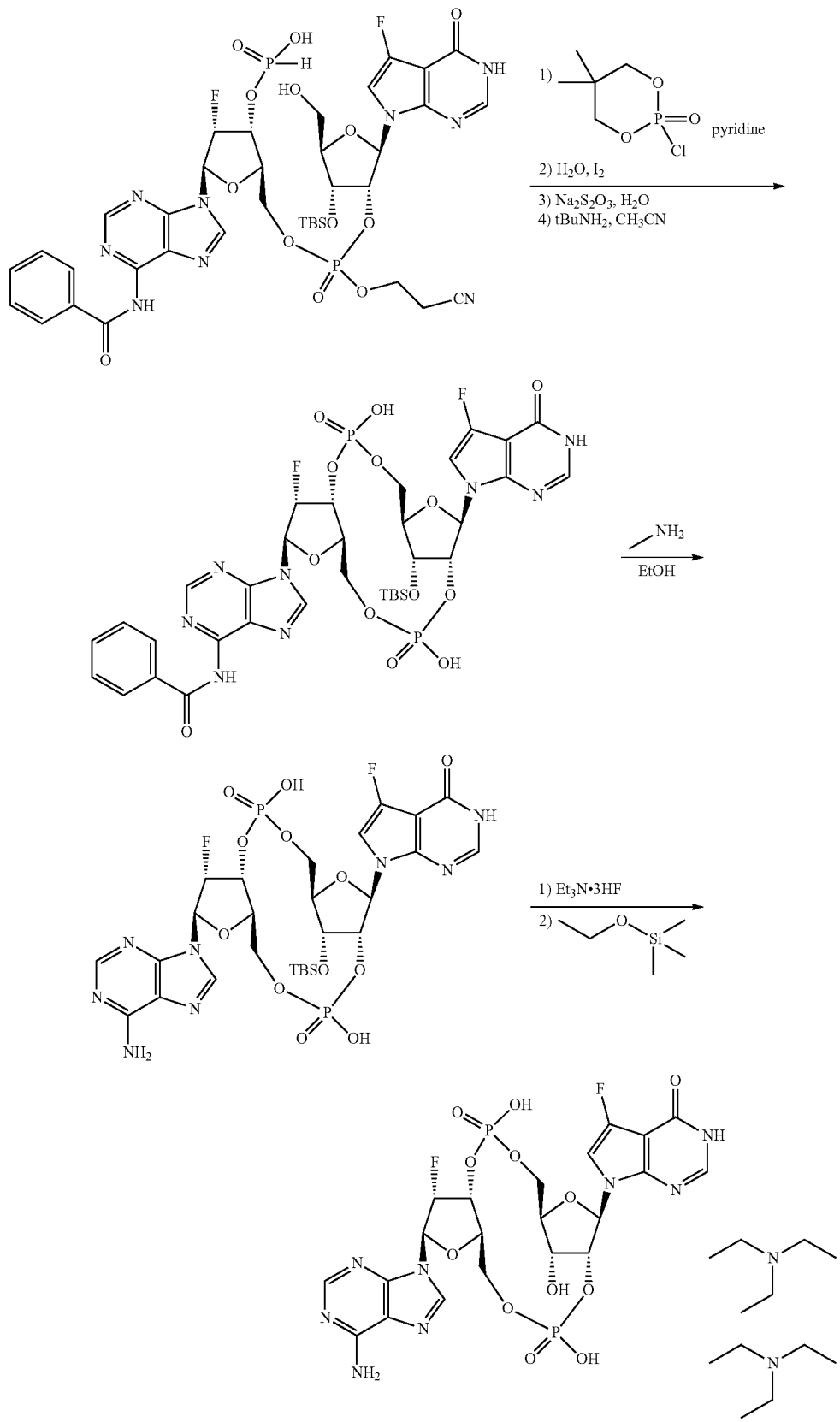

A) 7-((2R,3R,4S,5R)-5-((bis(4-methoxyphenyl)(phenyl)methoxy)methyl)-3,4-dihydroxytetrahydrofuran-2-yl)-5-fluoro-3H-pyrrolo[2,3-d]pyrimidin-4(7H)-one To a solution of 7-((2R,3R,4S,5R)-3,4-dihydroxy-5-(hydroxymethyl)tetrahydrofuran-2-yl)-5-fluoro-3H-pyrrolo[2,3-d]pyrimidin-4(7H)-one (6.26 g) in pyridine (100 mL) was added 4,4'-dimethoxytrityl chloride (8.92 g) at room temperature, and the mixture was stirred overnight under argon atmosphere at room temperature. To the reaction mixture was added saturated aqueous sodium hydrogencarbonate solution, and the mixture was extracted with ethyl acetate. The organic layer was washed successively with saturated aqueous sodium hydrogencarbonate solution and saturated brine, and dried over anhydrous sodium sulfate, and the solvent was evaporated under reduced pressure. The residue was purified by silica gel column chromatography (methanol/ethyl acetate) to give the title compound (8.65 g). MS: [M−H]⁻ 586.0.

B) 7-(5-O-(bis(4-methoxyphenyl)(phenyl)methyl)-3-O-(tert-butyl(dimethyl)silyl)-beta-D-ribofuranosyl)-5-fluoro-3,7-dihydro-4H-pyrrolo[2,3-d]pyrimidin-4-one To a solution of 74(2R,3R,4S,5R)-5-((bis(4-methoxyphenyl)(phenyl)methoxy)methyl)-3,4-dihydroxytetrahydrofuran-2-yl)-5-fluoro-3H-pyrrolo[2,3-d]pyrimidin-4(7H)-one (2.65 g) in DMF (20 mL) were added imidazole (0.614 g) and tert-butyldimethylchlorosilane (0.816 g), and the mixture was stirred overnight at room temperature. The reaction mixture was diluted with water, and extracted with ethyl acetate. The extract was washed with saturated brine, dried over anhydrous sodium sulfate, and concentrated under reduced pressure. The residue was purified by silica gel column chromatography (ethyl acetate/hexane) to give the title compound (1.1 g). MS: [M−H]⁻ 700.2.

C) 7-(5-O-(bis(4-methoxyphenyl)(phenyl)methyl)-3-O-(tert-butyl(dimethyl)silyl)-2-O-((2-cyanoethoxy)(diisopropylamino)phosphino)-beta-D-ribofuranosyl)-5-fluoro-3,7-dihydro-4H-pyrrolo[2,3-d]pyrimidin-4-one 7-(5-O-Bis(4-methoxyphenyl)(phenyl)methyl)-3-O-(tert-butyl(dimethyl)silyl)-beta-D-ribofuranosyl)-5-fluoro-3,7-dihydro-4H-pyrrolo[2,3-d]pyrimidin-4-one (5.43 g) was subjected to azeotropic dehydration three times with anhydrous toluene, and dissolved in anhydrous DMF (15 mL). To the solution were added 3-((bis(diisopropylamino)phosphino)oxy)propanenitrile (3.19 mL), 1H-tetrazole (0.542 g) and 1-methyl-1H-imidazole (0.306 mL), and the mixture was stirred overnight under argon atmosphere at room temperature, poured into saturated aqueous sodium hydrogencarbonate solution, and extracted with ethyl acetate. The organic layer was washed successively with saturated aqueous sodium hydrogencarbonate solution and saturated brine, and dried over anhydrous sodium sulfate, and the solvent was evaporated under reduced pressure. The residue was purified by silica gel column chromatography (DIOL, ethyl acetate/hexane). The obtained crude product was purified again by silica gel column chromatography (ethyl acetate/hexane, containing 0.5% triethylamine) to give the title compound (4.22 g) as a mixture of two diastereomers. MS: [M−H]⁻ 901.2.

D) (2R,3R,4R,5R)-5-(6-benzamido-9H-purin-9-yl)-2-(((((2R,3R,4R,5R)-4-((tert-butyldimethylsilyl)oxy)-2-(5-fluoro-4-oxo-3H-pyrrolo[2,3-d]pyrimidin-7(4H)-yl)-5-(hydroxymethyl)tetrahydrofuran-3-yl)oxy)(2-cyanoethoxy)phosphoryl)oxy)methyl)-4-fluorotetrahydrofuran-3-yl hydrogen phosphonate N-Benzoyl-2'-deoxy-2'-fluoro-3'-O-(hydroxy(oxido)phosphoranyl)adenosine (1.2 g) and 7-(5-O-([bis(4-methoxyphenyl)(phenyl)methyl)]-3-O-([tert-butyl(dimethyl)silyl)]-2-O-({(2-cyanoethoxy)([diisopropylamino)]phosphino)}-beta-D-ribofuranosyl)-5-fluoro-3,7-dihydro-4H-pyrrolo[2,3-d]pyrimidin-4-one (3.4 g) were subjected to azeotropic dehydration with anhydrous acetonitrile, and anhydrous acetonitrile (15 mL) and anhydrous THF (5 mL) were added thereto. To the mixture was added a mixture of 5-(ethylsulfanyl)-2H-tetrazole (1.07 g) (which was subjected to azeotropic dehydration with anhydrous acetonitrile) and anhydrous acetonitrile (10 mL), and the mixture was stirred under argon atmosphere at 55° C. for 2 hr. 70% tert-Butyl hydroperoxide aqueous solution (1.12 mL) was added thereto, and the mixture was stirred at room temperature for 20 min. To the reaction mixture was added a mixture of sodium thiosulfate (5920 mg) and water (3 mL), and the mixture was concentrated under reduced pressure. To the residue was added 80% acetic acid (30 mL), and the mixture was stirred at room temperature for 20 min. The reaction mixture was concentrated under reduced pressure, and the residue was purified by silica gel column chromatography (methanol/ethyl acetate) to give the title compound (1.1 g). MS: [M+H]⁺ 952.2

E) N-(9-((5R,7R,8R,12aR,14R,15R,15aR,16R)-16-((tert-butyl(dimethyl)silyl)oxy)-15-fluoro-7-(5-fluoro-4-oxo-3,4-dihydro-7H-pyrrolo[2,3-d]pyrimidin-7-yl)-2,10-dihydroxy-2,10-dioxidooctahydro-12H-5,8-methanofuro[3,2-1][1,3,6,9,11,2,10]pentaoxadiphosphacyclotetradecin-14-yl)-9H-purin-6-yl)benzamide (2R,3R,4R,5R)-5-(6-Benzamido-9H-purin-9-yl)-2-((((((2R,3R,4R,5R)-4-((tert-butyldimethylsilyl)oxy)-2-(5-fluoro-4-oxo-3H-pyrrolo[2,3-d]pyrimidin-7(4H)-yl)-5-(hydroxymethyl)tetrahydrofuran-3-yl)oxy)(2-cyanoethoxy)phosphoryl)oxy)methyl)-4-fluorotetrahydrofuran-3-yl hydrogen phosphonate (350 mg) was subjected to azeotropic dehydration with anhydrous acetonitrile and anhydrous pyridine, and anhydrous pyridine (15 mL) was added thereto. To the mixture was added 2-chloro-5,5-dimethyl-1,3,2-dioxaphosphinane 2-oxide (238 mg), and the mixture was stirred under argon atmosphere at room temperature for 1 hr. Water (232 μL) and iodine (121 mg) were added thereto, and the mixture was stirred at room temperature for additional 20 min. To the reaction mixture was added a mixture of sodium thiosulfate pentahydrate (91 mg) and water (1 mL), and the mixture was stirred at room temperature for 5 min. Toluene was added thereto, and the mixture was concentrated under reduced pressure. To the residue were added anhydrous acetonitrile (15 mL) and 2-methylpropan-2-amine (5.26 mL), and the mixture was stirred at room temperature for 2 hr, and concentrated under reduced pressure. The residue was purified by silica gel column chromatography (methanol/ethyl acetate) to give the title compound (332 mg). MS: [M+H]⁺ 897.1

215

F) 7-((5R,7R,8R,12aR,14R,15R,15aR,16R)-14-(6-amino-9H-purin-9-yl)-16-((tert-butyl(dimethyl)silyl)oxy)-15-fluoro-2,10-dihydroxy-2,10-dioxidooctahydro-12H-5,8-methanofuro[3,2-1][1,3,6,9,11,2,10]pentaoxadiphosphacyclotetradecin-7-yl)-5-fluoro-3,7-dihydro-4H-pyrrolo[2,3-d]pyrimidin-4-one To N-(9-((5R,7R,8R,12aR,14R,15R,15aR,16R)-16-((tert-butyl(dimethyl)silyl)oxy)-15-fluoro-7-(5-fluoro-4-oxo-3,4-dihydro-7H-pyrrolo[2,3-d]pyrimidin-7-yl)-2,10-dihydroxy-2,10-dioxidooctahydro-12H-5,8-methanofuro[3,2-1][1,3,6,9,11,2,10]pentaoxadiphosphacyclotetradecin-14-yl)-9H-purin-6-yl)benzamide (332 mg) was added 40% methylamine ethanol solution (7.6 mL), and the mixture was stirred under argon atmosphere at room temperature for 1 hr, and concentrated under reduced pressure. The residue was purified by silica gel column chromatography (methanol/ethyl acetate), and the obtained residue was purified by HPLC (L-column2 ODS, 50×150 mm, mobile phase: 5 mM aqueous ammonium acetate solution/acetonitrile) to give the title compound (106.4 mg). MS: [M+H]$^-$ 793.1

G) 7-((5R,7R,8R,12aR,14R,15R,15aR,16R)-14-(6-amino-9H-purin-9-yl)-15-fluoro-2,10,16-trihydroxy-2,10-dioxidooctahydro-12H-5,8-methanofuro[3,2-1][1,3,6,9,11,2,10]pentaoxadiphosphacyclotetradecin-7-yl)-5-fluoro-3,7-dihydro-4H-pyrrolo[2,3-d]pyrimidin-4-one di-triethylamine salt To 7-((5R,7R,8R,12aR,14R,15R,15aR,16R)-14-(6-amino-9H-purin-9-yl)-16-((tert-butyl(dimethyl)silyl)oxy)-15-fluoro-2,10-dihydroxy-2,10-dioxidooctahydro-12H-5,8-methanofuro[3,2-1][1,3,6,9,11,2,10]pentaoxadiphosphacyclotetradecin-7-yl)-5-fluoro-3,7-dihydro-4H-pyrrolo[2,3-d]pyrimidin-4-one (106.4 mg) was added triethylamine trihydrofluoride (1094 μL). The reaction mixture was stirred at 50° C. for 1 hr, and cooled to room temperature, ethoxy(trimethyl)silane (6266 μL) was added thereto, and the mixture was stirred at room temperature for 1 hr. The reaction mixture was concentrated under reduced pressure, and to the residue were added ethoxy(trimethyl)silane (6266 μL) and methanol (1 mL), and the mixture was stirred at room temperature for 1 hr. The reaction mixture was concentrated under reduced pressure, and the residue was purified by C18 column chromatography (acetonitrile/10 mM triethylammonium acetate buffer solution) to give the title compound (82 mg). $^1$H NMR (400 MHz, D$_2$O) δ 1.18 (18H, t, J=7.3 Hz), 3.11 (12H, q, J=7.4 Hz), 4.01-4.14 (2H, m), 4.17-4.26 (1H, m), 4.34 (2H, d, J=3.4 Hz), 4.42-4.50 (1H, m), 4.54 (1H, d, J=4.2 Hz), 4.86-4.99 (2H, m), 5.38-5.60 (1H, m), 6.30-6.45 (2H, m), 7.24 (1H, d, J=2.0 Hz), 7.91 (1H, s), 8.05 (1H, s), 8.17 (1H, s). $^{31}$P NMR (162 MHz, D$_2$O) δ 2.16, −1.66.

216

Example 1a

Synthesis of 7-((5R,7R,8R,12aR,14R,15R,15aR,16R)-14-(6-amino-9H-purin-9-yl)-15-fluoro-2,10,16-trihydroxy-2,10-dioxidooctahydro-12H-5,8-methanofuro[3,2-1][1,3,6,9,11,2,10]pentaoxadiphosphacyclotetradecin-7-yl)-5-fluoro-3,7-dihydro-4H-pyrrolo[2,3-d]pyrimidin-4-one disodium salt

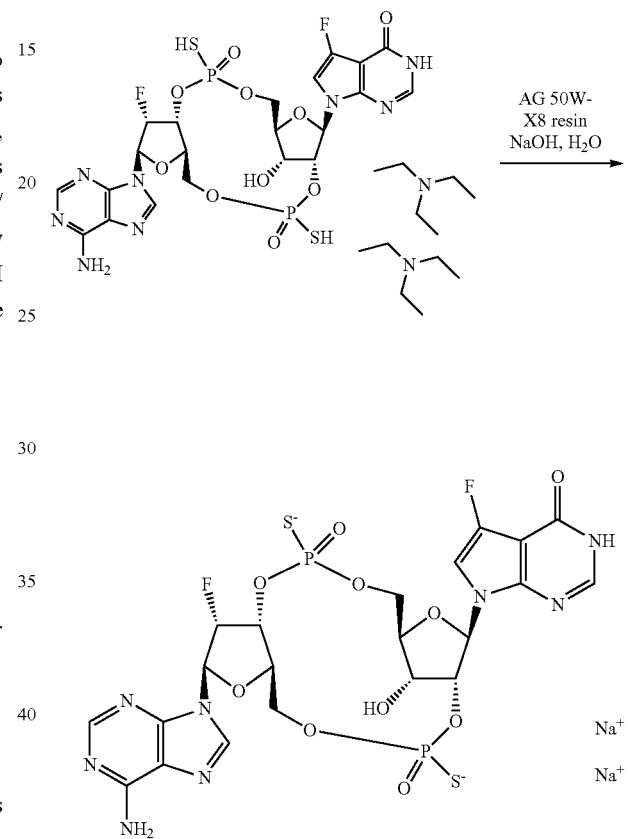

Deionized water (480 mL) was passed through a column prepared by packing AG (trade name) 50W-X8 cation-exchange resin (100-200 mesh, 30 g) in an empty column. Then, 1 M aqueous sodium hydroxide solution (288 mL) and deionized water (540 mL) were passed through the resin. Deionized water (54 mL) containing 7-((5R,7R,8R,12aR,14R,15R,15aR,16R)-14-(6-amino-9H-purin-9-yl)-15-fluoro-2,10,16-trihydroxy-2,10-dioxidooctahydro-12H-5,8-methanofuro[3,2-1][1,3,6,9,11,2,10]pentaoxadiphosphacyclotetradecin-7-yl)-5-fluoro-3,7-dihydro-4H-pyrrolo[2,3-d]pyrimidin-4-one di-triethylamine salt (1.53 g) was passed through the resin after the above-mentioned pre-treatment, and deionized water (72 mL) was passed through the resin, and the obtained aqueous solution was freeze-dried to give the title compound (1.28 g). $^1$H NMR (300 MHz, D$_2$O) δ 4.05-4.17 (2H, m), 4.20-4.28 (1H, m), 4.33-4.40 (2H, m), 4.44-4.51 (1H, m), 4.55 (1H, d, J=4.2 Hz), 4.84-5.01 (2H, m), 5.39-5.61 (1H, m), 6.31-6.40 (2H, m), 7.25 (1H, d, J=2.0 Hz), 7.91 (1H, s), 8.07 (1H, s), 8.18 (1H, s). $^{31}$P NMR (121 MHz, D$_2$O) δ −2.2, −1.6.

Example 2
Synthesis of 7-((5R,7R,8R,12aR,14R,15R,15aR, 16R)-14-(6-amino-9H-purin-9-yl)-15-fluoro-10,16-dihydroxy-2,10-dioxido-2-sulfanyloctahydro-12H-5, 8-methanofuro[3,2-1][1,3,6,9,11,2,10] pentaoxadiphosphacyclotetradecin-7-yl)-5-fluoro-3, 7-dihydro-4H-pyrrolo[2,3-d]pyrimidin-4-one di-triethylamine salt (Optical Isomer)
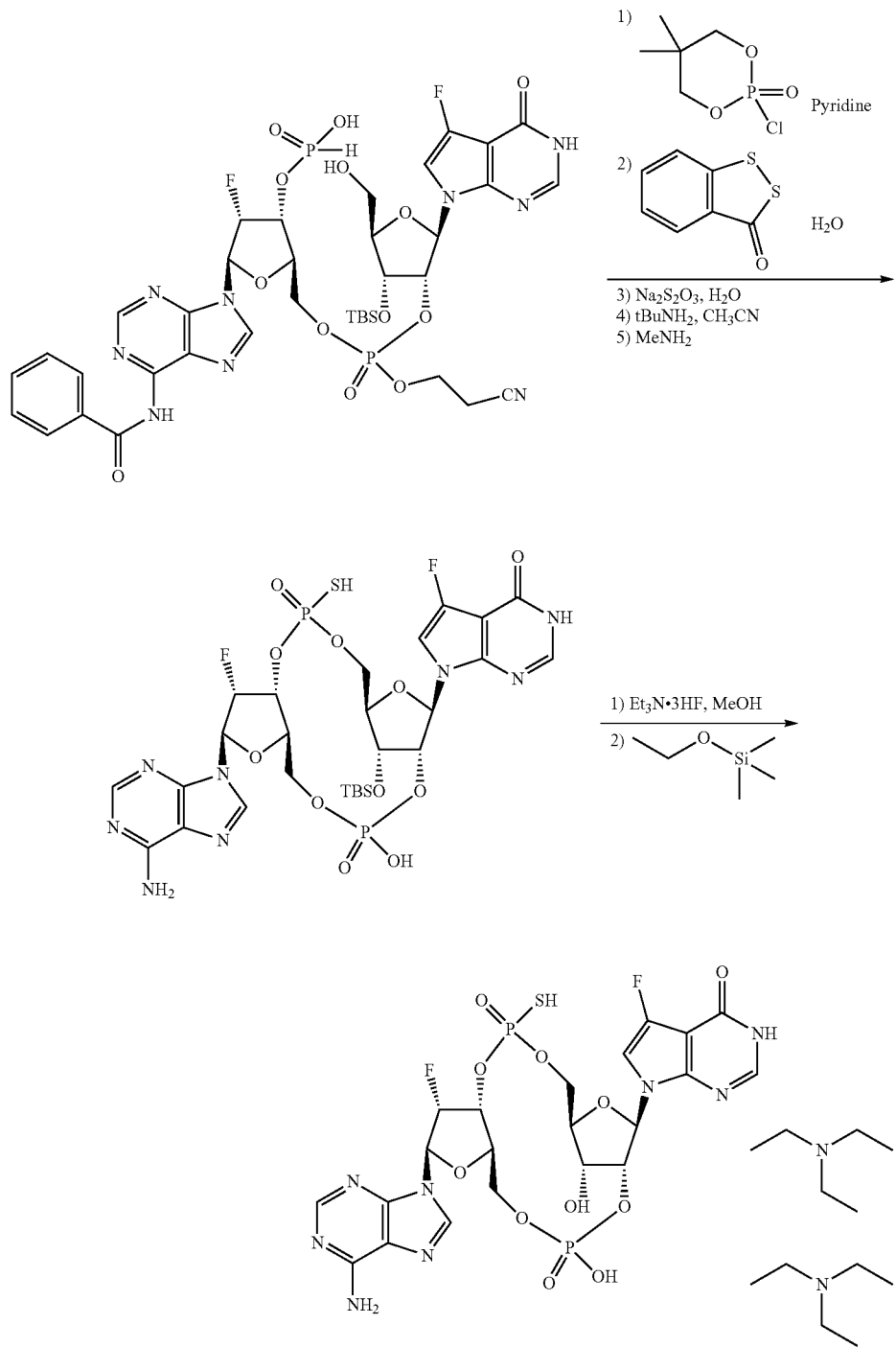

A) 7-((5R,7R,8R,12aR,14R,15R,15aR,16R)-14-(6-amino-9H-purin-9-yl)-16-((tert-butyl(dimethyl)silyl)oxy)-15-fluoro-10-hydroxy-2,10-dioxido-2-sulfanyloctahydro-12H-5,8-methanofuro[3,2-l][1,3,6,9,11,2,10]pentaoxadiphosphacyclotetradecin-7-yl)-5-fluoro-3,7-dihydro-4H-pyrrolo[2,3-d]pyrimidin-4-one (Optical Isomer)

(2R,3R,4R,5R)-5-(6-Benzamido-9H-purin-9-yl)-2-((((((2R,3R,4R,5R)-4-((tert-butyldimethylsilyl)oxy)-2-(5-fluoro-4-oxo-3H-pyrrolo[2,3-d]pyrimidin-7(4H)-yl)-5-(hydroxymethyl)tetrahydrofuran-3-yl)oxy)(2-cyanoethoxy)phosphoryl)oxy)methyl)-4-fluorotetrahydrofuran-3-yl hydrogen phosphonate (700 mg) was subjected to azeotropic dehydration with anhydrous acetonitrile and anhydrous pyridine, and anhydrous pyridine (50 mL) was added thereto. To the mixture was added 2-chloro-5,5-dimethyl-1,3,2-dioxaphosphinane 2-oxide (475 mg) at room temperature, and the mixture was stirred under argon atmosphere at room temperature for 1 hr. Water (464 μL) and 3H-benzo[c][1,2]dithiol-3-one (186 mg) were added thereto, and the mixture was stirred at room temperature for additional 30 min. To the reaction mixture was added a mixture of sodium thiosulfate (913 mg) and water (3 mL), and the mixture was concentrated under reduced pressure. To the residue were added anhydrous acetonitrile (30 mL) and 2-methylpropan-2-amine (10 mL), and the mixture was stirred at room temperature for 1 hr, and concentrated under reduced pressure. The residue was purified by silica gel column chromatography (methanol/ethyl acetate), and to the obtained residue was added 40% methylamine ethanol solution (7.3 mL). The mixture was stirred under argon atmosphere at room temperature for 30 min, and the reaction mixture was concentrated under reduced pressure. The residue was purified by silica gel column chromatography (methanol/ethyl acetate). The obtained residue was resolved into two diastereomers (tR1 and tR2, retention times of which by LC/MS are from shorter to longer in this order) by HPLC (L-column2 ODS, 50×150 mm, mobile phase: mM aqueous ammonium acetate solution/acetonitrile) to give the title compound (70 mg, tR1) and the title compound (150 mg, tR2). MS (tR1): [M+H]$^+$ 809.1. MS (tR2): [M+H]$^+$ 809.1

B) 7-((5R,7R,8R,12aR,14R,15R,15aR,16R)-14-(6-amino-9H-purin-9-yl)-15-fluoro-10,16-dihydroxy-2,10-dioxido-2-sulfanyloctahydro-12H-5,8-methanofuro[3,2-l][1,3,6,9,11,2,10]pentaoxadiphosphacyclotetradecin-7-yl)-5-fluoro-3,7-dihydro-4H-pyrrolo[2,3-d]pyrimidin-4-one di-triethylamine salt (Optical Isomer)

To 7-((5R,7R,8R,12aR,14R,15R,15aR,16R)-14-(6-amino-9H-purin-9-yl)-16-((tert-butyl(dimethyl)silyl)oxy)-15-fluoro-10-hydroxy-2,10-dioxido-2-sulfanyloctahydro-12H-5,8-methanofuro[3,2-l][1,3,6,9,11,2,10]pentaoxadiphosphacyclotetradecin-7-yl)-5-fluoro-3,7-dihydro-4H-pyrrolo[2,3-d]pyrimidin-4-one (optical isomer) (70 mg, derived from tR1) were added methanol (3.0 mL) and triethylamine trihydrofluoride (1.41 mL). The reaction mixture was concentrated to remove the methanol, and the residue was stirred at 55'C for 1 hr. The residue was cooled to room temperature, ethoxy(trimethyl)silane (7.8 mL) was added thereto, and the mixture was stirred at room temperature for 2 hr. The reaction mixture was concentrated under reduced pressure, and the residue was purified by C18 column chromatography (acetonitrile/10 mM triethylammonium acetate buffer solution) to give the title compound (56 mg). $^1$H NMR (400 MHz, D2O) δ 1.23 (18H, t, J=7.3 Hz), 3.15 (12H, q, J=7.3 Hz), 4.15-4.23 (3H, m), 4.37-4.50 (2H, m), 4.54 (1H, d, J=10.3 Hz), 4.61 (1H, d, J=3.9 Hz), 4.96 (2H, dt, J=7.9, 3.9 Hz), 5.77-5.95 (1H, m), 6.36 (1H, d, J=8.1 Hz), 6.40 (1H, d, J=15.4 Hz), 7.51 (1H, d, J=1.7 Hz), 7.99 (2H, d, J=13.7 Hz), 8.23 (1H, s). $^{31}$P NMR (162 MHz, D2O) δ−2.43, 54.03.

Example 3

Synthesis of 7-((2R,5R,7R,8R,12aR,14R,15R,15aR,16R)-14-(6-amino-9H-purin-9-yl)-15-fluoro-10,16-dihydroxy-2,10-dioxido-2-sulfanyloctahydro-12H-5,8-methanofuro[3,2-l][1,3,6,9,11,2,10]pentaoxadiphosphacyclotetradecin-7-yl)-5-fluoro-3,7-dihydro-4H-pyrrolo[2,3-d]pyrimidin-4-one 1.7 triethylamine salt

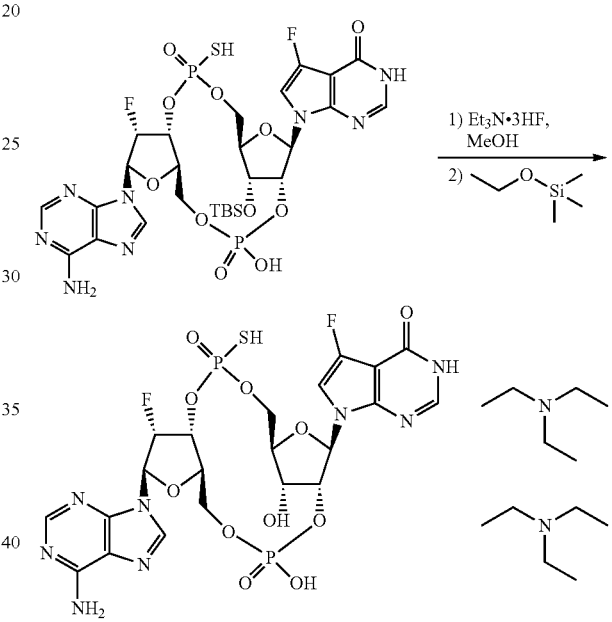

To 7-((5R,7R,8R,12aR,14R,15R,15aR,16R)-14-(6-amino-9H-purin-9-yl)-16-((tert-butyl(dimethyl)silyl)oxy)-15-fluoro-10-hydroxy-2,10-dioxido-2-sulfanyl octahydro-12H-5,8-methanofuro[3,2-l][1,3,6,9,11,2,10]pentaoxadiphosphacyclotetradecin-7-yl)-5-fluoro-3,7-dihydro-4H-pyrrolo[2,3-d]pyrimidin-4-one (optical isomer) (150 mg, derived from tR2) were added methanol (3.0 mL) and triethylamine trihydrofluoride (3.02 mL). The reaction mixture was concentrated to remove the methanol, and the residue was stirred at 55° C. for 1 hr. The residue was cooled to room temperature, ethoxy(trimethyl)silane (16.4 mL) was added thereto, and the mixture was stirred at room temperature for 2 hr. The reaction mixture was concentrated under reduced pressure, and the residue was purified by C18 column chromatography (acetonitrile/10 mM triethylammonium acetate buffer solution) to give the title compound (155 mg). $^1$H NMR (400 MHz, D2O) δ 1.23 (1514, t, J=7.3 Hz), 3.15 (10H, q, J=7.3 Hz), 4.06 (1H, dd, J=11.7, 4.9 Hz), 4.18 (1H, dd, J=11.6, 2.8 Hz), 4.29-4.47 (3H, m), 4.51 (1H, d, J=8.8 Hz), 4.58 (1H, d, J=3.9 Hz), 4.93-5.14 (2H, m), 5.44-5.64 (1H, m), 6.33-6.45 (2H, m), 7.32 (1H, d, J=1.5 Hz), 7.95 (1H, s), 8.06 (1H, s), 8.24 (1H, s). 71P NMR (162 MHz, D2O) δ−2.41, 55.33.

Example 3a

Synthesis of 7-((2R,5R,7R,8R,12aR,14R,15R,15aR,16R)-14-(6-amino-9H-purin-9-yl)-15-fluoro-10,16-dihydroxy-2,10-dioxido-2-sulfanyloctahydro-12H-5,8-methanofuro[3,2-1][1,3,6,9,11,2,10]pentaoxadiphosphacyclotetradecin-7-yl)-5-fluoro-3,7-dihydro-4H-pyrrolo[2,3-d]pyrimidin-4-one disodium salt

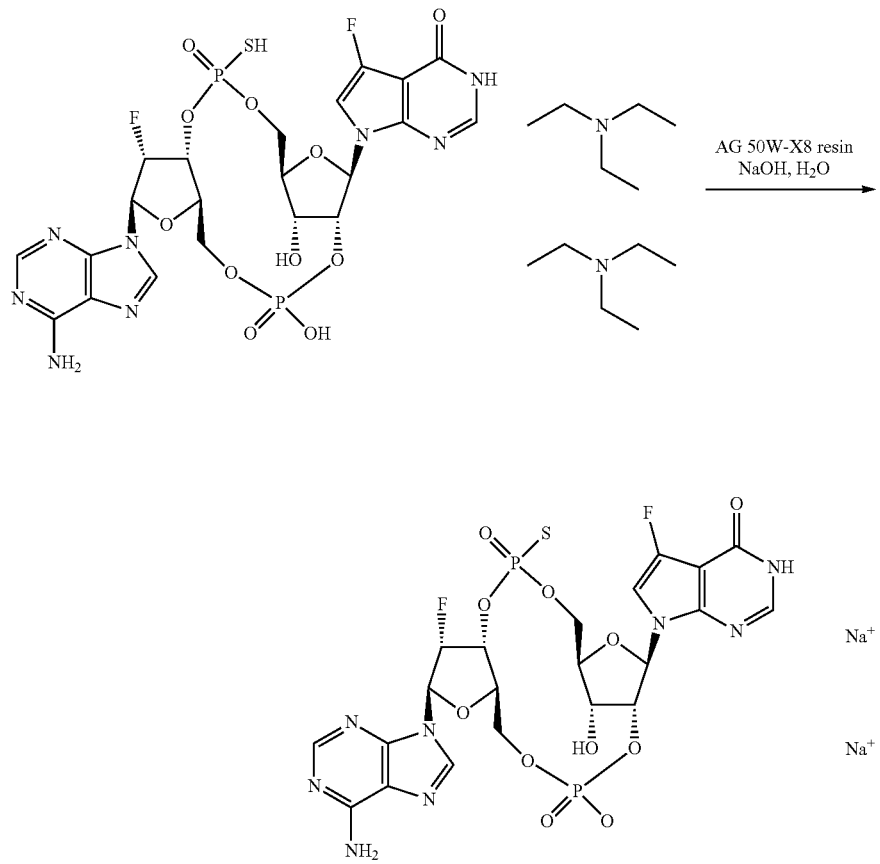

Deionized water (400 mL) was passed through a column prepared by packing AG (trade name) 50W-X8 cation-exchange resin (100-200 mesh, 25.3 g) in an empty column. Then, 1 M aqueous sodium hydroxide solution (240 mL) and deionized water (450 mL) were passed through the resin. Deionized water (45 mL) containing 7-((2R,5R,7R,8R,12aR,14R,15R,15aR,16R)-14-(6-amino-9H-purin-9-yl)-15-fluoro-10,16-dihydroxy-2,10-dioxido-2-sulfanyloctahydro-12H-5,8-methanofuro[3,2-1][1,3,6,9,11,2,10]pentaoxadiphosphacyclotetradecin-7-yl)-5-fluoro-3,7-dihydro-4H-pyrrolo[2,3-d]pyrimidin-4-one di-triethylamine salt (1.30 g) was passed through the resin after the above-mentioned pre-treatment, and deionized water (60 mL) was passed through the resin to give an aqueous solution containing the title compound.

Deionized water (400 mL) was passed through a column prepared by packing AG (trade name) 50W-X8 cation-exchange resin (100-200 mesh, 26.3 g) in an empty column. Then, 1 M aqueous sodium hydroxide solution (270 mL) and deionized water (540 mL) were passed through the resin. Deionized water (54 mL) containing 7-((2R,5R,7R,8R,12aR,14R,15R,15aR,16R)-14-(6-amino-9H-purin-9-yl)-15-fluoro-10,16-dihydroxy-2,10-dioxido-2-sulfanyl octahydro-12H-5,8-m ethanofuro[3,2-1][1,3,6,9,11,2,10]pentaoxadiphosphacyclotetradecin-7-yl)-5-fluoro-3,7-dihydro-4H-pyrrolo[2,3-d]pyrimidin-4-one di-triethylamine salt (1.18 g) was passed through the resin after the above-mentioned pre-treatment, and deionized water (63 mL) was passed through the resin to give an aqueous solution containing the title compound. The two aqueous solutions containing the title compound were combined, and freeze-dried to give the title compound (2.0 g). $^1$H NMR (300 MHz, D$_2$O) δ 3.97-4.07 (1H, m), 4.11-4.20 (1H, m), 4.27-4.42 (3H, m), 4.43-4.51 (1H, m), 4.55 (1H, d, J=3.8 Hz), 4.88-5.12 (2H, m), 5.34-5.59 (1H, m), 6.30-6.40 (2H, m), 7.28 (1H, d, J=1.9 Hz), 7.91 (1H, s), 8.01 (1H, S), 8.18 (1H, S). $^{31}$P NMR (121 MHz, D$_2$O) δ−2.38, 55.3.

Example 4
Synthesis of 7-((5R,7R,8R,12aR,14R,15R,15aS, 16R)-14-(6-amino-9H-purin-9-yl)-2,10,15,16-tetra-hydroxy-2,10-dioxidooctahydro-12H-5,8-methano-furo[3,2-1][1,3,6,9,11,2,10] pentaoxadiphosphacyclotetradecin-7-yl)-5-fluoro-3, 7-dihydro-4H-pyrrolo[2,3-d]pyrimidin-4-one di-triethylamine salt
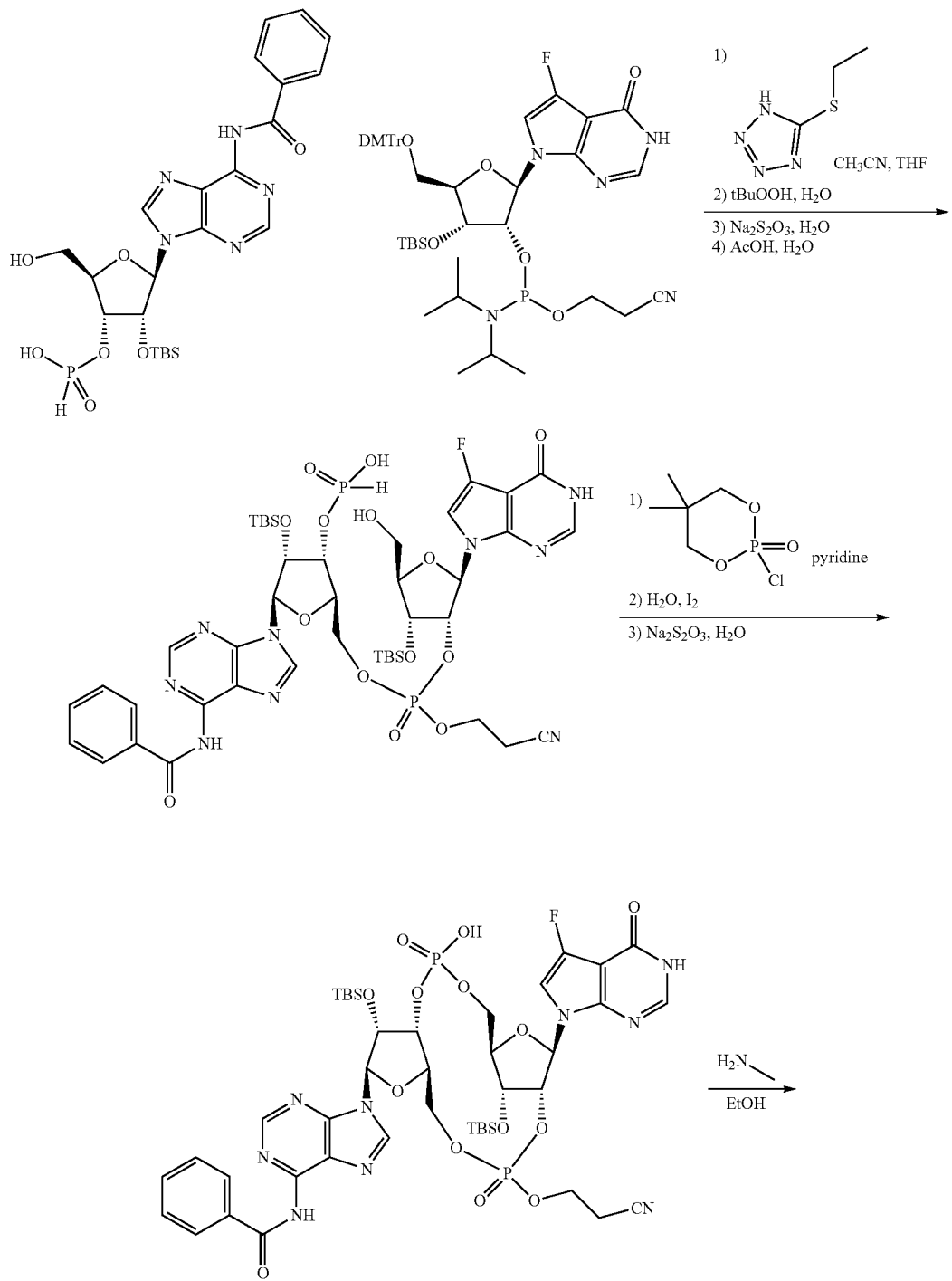

-continued

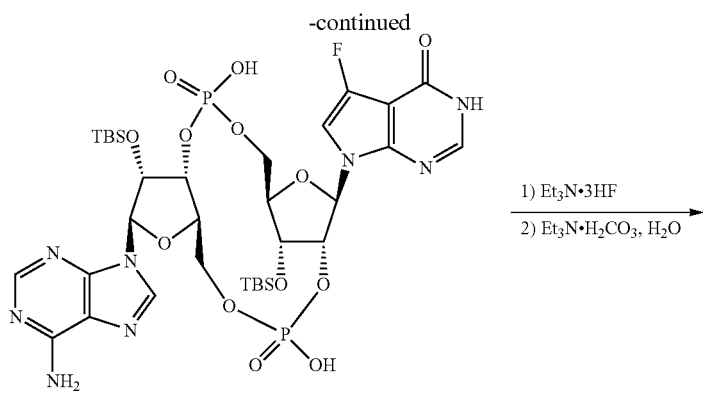

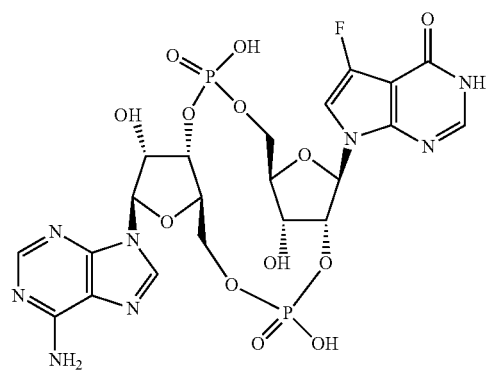

A) (2R,3R,4R,5R)-5-(6-benzamido-9H-purin-9-yl)-4-((tert-butyldimethylsilyl)oxy)-2-((((((2R,3R,4R,5R)-4-((tert-butyldimethylsilyl)oxy)-2-(5-fluoro-4-oxo-3H-pyrrolo[2,3-d]pyrimidin-7(4H)-yl)-5-(hydroxymethyl)tetrahydrofuran-3-yl)oxy)(2-cyanoethoxy)phosphoryl)oxy)methyl) tetrahydrofuran-3-yl hydrogen phosphonate N-Benzoyl-2'-O-(tert-butyl(dimethyl)silyl)-3'-O-(hydroxy(oxido)phosphoranyl)adenosine (369 mg) and 7-(5-O-(bis(4-methoxyphenyl)(phenyl)methyl)-3-O-(tert-butyl(dimethyl)silyl)-2-O-((2-cyanoethoxy)(diisopropylamino)phosphino)-beta-D-ribofuranosyl)-5-fluoro-3,7-dihydro-4H-pyrrolo[2,3-d]pyrimidin-4-one (817 mg) were subjected to azeotropic dehydration with anhydrous acetonitrile (three times), and suspended in anhydrous acetonitrile (3.6 mL) and anhydrous THF (1.2 mL). To the suspension was added a mixture of 5-(ethylsulfanyl)-2H-tetrazole (262 mg) (which was subjected to azeotropic dehydration with anhydrous acetonitrile) and anhydrous acetonitrile (2.4 mL), and the mixture was stirred under argon atmosphere at room temperature for 1.5 hr. To the reaction solution was added 70% tert-butyl hydroperoxide aqueous solution (0.276 mL), and the mixture was stirred at room temperature for additional 40 min. The reaction mixture was quenched with sodium thiosulfate (636 mg) and water (2 mL), and the solvent was evaporated under reduced pressure. The residue was dissolved in 80% acetic acid (5 mL), and the solution was stirred at room temperature for 2.5 hr. The reaction mixture was concentrated under reduced pressure, and the residue was subjected to azeotropic dehydration with anhydrous acetonitrile and toluene. The residue was purified by silica gel column chromatography (methanol/ethyl acetate) to give the title compound (538 mg). MS: [M+H]$^+$ 1064.3.

B) N-(9-((5R,7R,8R,12aR,14R,15R,15aR,16R)-15,16-bis((tert-butyl(dimethyl)silyl)oxy)-10-(2-cyanoethoxy)-7-(5-fluoro-4-oxo-3,4-dihydro-7H-pyrrolo[2,3-d]pyrimidin-7-yl)-2-hydroxy-2,10-dioxidooctahydro-12H-5,8-methanofuro[3,2-1][1,3,6,9,11,2,10]pentaoxadiphosphacyclotetradecin-14-yl)-9H-purin-6-yl)benzamide (2R,3R,4R,5R)-5-(6-Benzamido-9H-purin-9-yl)-4-((tert-butyldimethylsilyl)oxy)-2-((((((2R,3R,4R,5R)-4-((tert-butyldimethylsilyl)oxy)-2-(5-fluoro-4-oxo-3H-pyrrolo[2,3-d]pyrimidin-7(4H)-yl)-5-(hydroxymethyl)tetrahydrofuran-3-yl)oxy)(2-cyanoethoxy)phosphoryl)oxy)methyl)

tetrahydrofuran-3-yl hydrogen phosphonate (538 mg) was subjected to azeotropic dehydration with anhydrous acetonitrile and anhydrous pyridine, and suspended in anhydrous pyridine (12 mL). 2-Chloro-5,5-dimethyl-1,3,2-dioxaphosphinane 2-oxide (327 mg) was added thereto, and the mixture was stirred at room temperature for 1 hr. Water (0.319 mL) and iodine (167 mg) were added thereto, and the mixture was stirred at room temperature for additional 30 min. The reaction mixture was quenched with sodium thiosulfate (208 mg) and water (2 mL), and the solvent was evaporated under reduced pressure. The residue was purified by silica gel column chromatography (methanol/ethyl acetate) to give the title compound (509 mg). MS: [M+H]$^+$ 1062.3.

C) 7-((5R,7R,8R,12aR,14R,15R,15aR,16R)-14-(6-amino-9H-purin-9-yl)-15,16-bis((tert-butyl(dimethyl)silyl)oxy)-2,10-dihydroxy-2,10-dioxidooctahydro-12H-5,8-methanofuro[3,2-1][1,3,6,9,11,2,10]pentaoxadiphosphacyclotetradecin-7-yl)-5-fluoro-3,7-dihydro-4H-pyrrolo[2,3-d]pyrimidin-4-one N-(9-((5R,7R,8R,12aR,14R,15R,15aR,16R)-15,16-Bis((tert-butyl(dimethyl)silyl)oxy)-10-(2-cyanoethoxy)-7-(5-fluoro-4-oxo-3,4-dihydro-7H-pyrrolo[2,3-d]pyrimidin-7-yl)-2-hydroxy-2,10-dioxidooctahydro-12H-5,8-methanofuro[3,2-1][1,3,6,9,11,2,10]pentaoxadiphosphacyclotetradecin-14-yl)-9H-purin-6-yl)benzamide (509 mg) was dissolved in 33% methylamine ethanol solution (10 mL), the solution was stirred under argon atmosphere at room temperature for 1 hr, and the solvent was evaporated under reduced pressure. The residue was purified by silica gel column chromatography (methanol/ethyl acetate). The obtained residue was purified by HPLC (L-column2 ODS, 50×150 mm, mobile phase: 5 mM aqueous ammonium acetate solution/acetonitrile) to give the title compound (227 mg). MS: [M+H]+ 905.2.

D) 7-((5R,7R,8R,12aR,14R,15R,15aS,16R)-14-(6-amino-9H-purin-9-yl)-2,10,15,16-tetrahydroxy-2,10-dioxidooctahydro-12H-5,8-methanofuro[3,2-1][1,3,6,9,11,2,10]pentaoxadiphosphacyclotetradecin-7-yl)-5-fluoro-3,7-dihydro-4H-pyrrolo[2,3-d]pyrimidin-4-one di-triethylamine salt To 7-((5R,7R,8R,12aR,14R,15R,15aR,16R)-14-(6-amino-9H-purin-9-yl)-15,16-bis((tert-butyl(dimethyl)silyl)oxy)-2,10-dihydroxy-2,10-dioxidooctahydro-12H-5,8-methanofuro[3,2-1][1,3,6,9,11,2,10]pentaoxadiphosphacyclotetradecin-7-yl)-5-fluoro-3,7-dihydro-4H-pyrrolo[2,3-d]pyrimidin-4-one (227 mg) was added triethylamine trihydrofluoride (0.818 mL), and the mixture was stirred at 50° C. for 5 hr. The solvent was evaporated under reduced pressure, the residue was neutralized with 1 M aqueous triethylammonium bicarbonate solution, and the solvent was again evaporated under reduced pressure. The residue was purified by C18 silica gel column chromatography (10 mM triethylammonium acetate buffer solution/acetonitrile), and the obtained solid was freeze-dried to give the title compound (103 mg). $^1$H NMR (300 MHz, D$_2$O) δ1.26 (18H, t, J=7.4 Hz), 3.18 (12H, q, J=7.4 Hz), 4.06-4.29 (311, m), 4.34-4.52 (3H, m), 4.62 (1H, d, J=3.8 Hz), 4.69-4.83 (1H, m), 4.84-4.95 (1H, m), 4.98-5.09 (1H, m), 6.14 (1H, d, J=1.5 Hz), 6.41 (1H, dd, J=8.3, 1.5 Hz), 7.33 (1H, d, J=1.9 Hz), 7.99 (1H, s), 8.16 (1H, s), 8.25 (1H, s). $^{31}$P NMR (121 MHz, D2O) δ−1.96, −1.21.

Example 5

7-((5R,7R,8R,12aR,14R,15R,15aS,16R)-14-(6-amino-9H-purin-9-yl)-15,16-dihydroxy-2,10-di-oxido-2,10-disulfanyloctahydro-12H-5,8-methanofuro[3,2-1][1,3,6,9,11,2,10]pentaoxadiphosphacyclotetradecin-7-yl)-5-fluoro-3,7-dihydro-4H-pyrrolo[2,3-d]pyrimidin-4-one di-triethylamine salt (Optical Isomer)

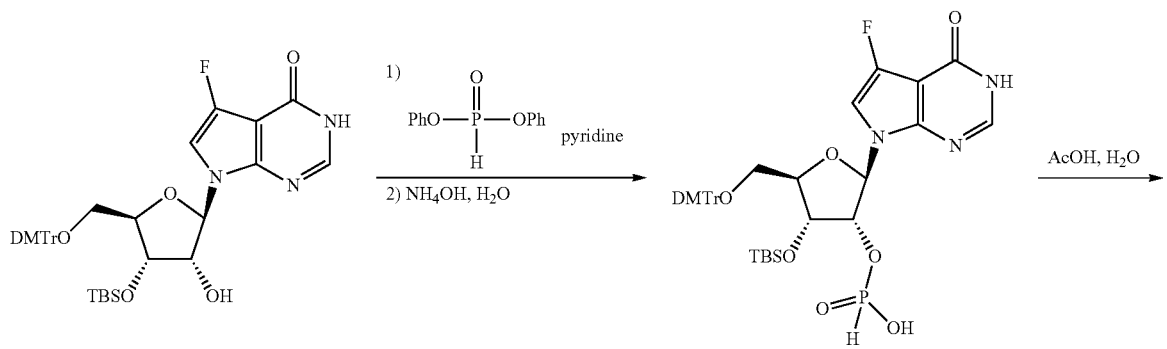

-continued
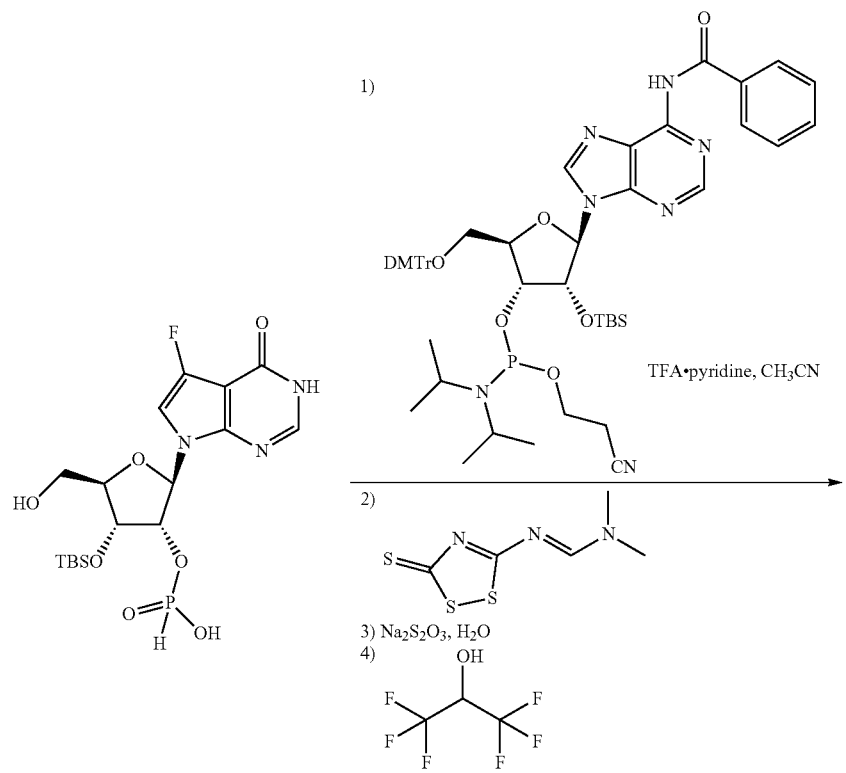
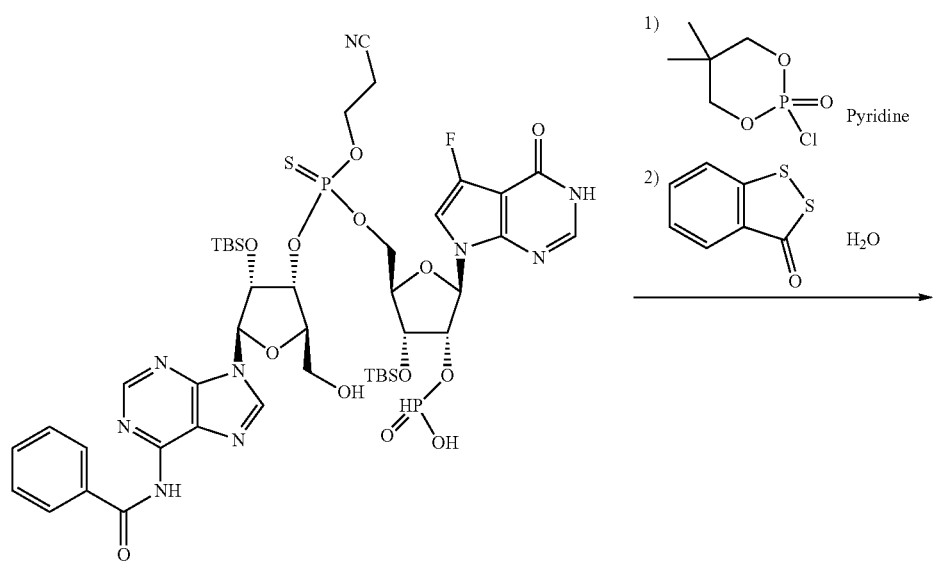

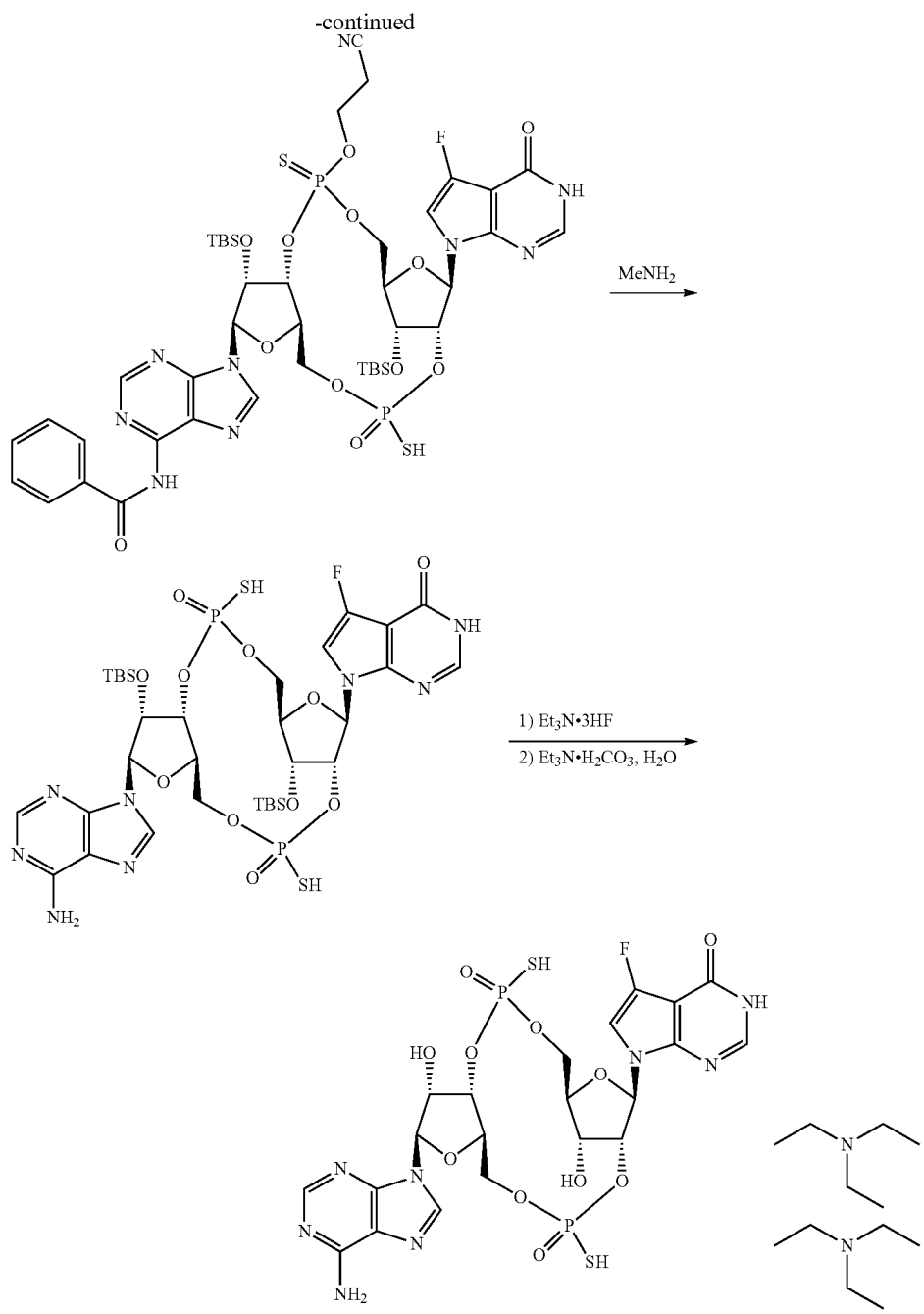

A) 7-(5-O-(bis(4-methoxyphenyl)(phenyl)methyl)-3-O-(tert-butyl(dimethyl)silyl)-2-O-(hydroxy(oxido) phosphoranyl)-beta-D-ribofuranosyl)-5-fluoro-3,7-dihydro-4H-pyrrolo[2,3-d]pyrimidin-4-one 7-(5-O-(Bis(4-methoxyphenyl)(phenyl)methyl)-3-O-(tert-butyl(dimethyl)silyl)-beta-D-ribofuranosyl)-5-fluoro-3,7-dihydro-4H-pyrrolo[2,3-d]pyrimidin-4-one (835 mg) was dissolved in pyridine (4 mL), and diphenyl phosphite (0.456 mL) was added thereto. The mixture was stirred at room temperature for 2 hr. Water (1 mL) and hydroxide ammonium (2 mL) were added thereto. The mixture was stirred at room temperature for 30 min, and the reaction mixture was diluted with water, and extracted with ethyl acetate. The extract was dried over anhydrous magnesium sulfate, and the solvent was evaporated under reduced pressure. The residue was purified by silica gel column chromatography (methanol/ethyl acetate) to give the title compound (611 mg). MS: [M−H]⁻ 764.1.

B) 7-(3-O-(tert-butyl(dimethyl)silyl)-2-O-(hydroxy (oxido)phosphoranyl)-beta-D-ribofuranosyl)-5-fluoro-3,7-dihydro-4H-pyrrolo[2,3-d]pyrimidin-4-one A mixture of 7-(5-O-(bis(4-methoxyphenyl)(phenyl) methyl)-3-O-(tert-butyl(dimethyl)silyl)-2-O-(hydroxy (oxido)phosphoranyl)-beta-D-ribofuranosyl)-5-fluoro-3,7- dihydro-4H-pyrrolo[2,3-d]pyrimidin-4-one (611 mg) and 80% acetic acid (4 mL) was stirred at room temperature for 2 hr. The reaction mixture was diluted with methanol, and the solvent was evaporated under reduced pressure. The residue was purified by silica gel column chromatography (methanol/ethyl acetate) to give the title compound (358 mg). MS: [M+H]$^+$ 464.1.

C) (2R,3R,4R,5R)-5-(((((2R,3R,4R,5R)-5-(6-benzamido-9H-purin-9-yl)-4-((tert-butyldimethylsilyl)oxy)-2-(hydroxymethyl)tetrahydrofuran-3-yl)oxy)(2-cyanoethoxy)phosphorothioyl)oxy)methyl)-4-((tert-butyldimethylsilyl)oxy)-2-(5-fluoro-4-oxo-3H-pyrrolo[2,3-d]pyrimidin-7(4H)-yl)tetrahydrofuran-3-yl hydrogen phosphonate A mixture of 7-(3-O-(tert-butyl(dimethyl)silyl)-2-O-(hydroxy(oxido)phosphoranyl)-beta-D-ribofuranosyl)-5-fluoro-3,7-dihydro-4H-pyrrolo[2,3-d]pyrimidin-4-one (358 mg) and N-benzoyl-5'-O-(bis(4-methoxyphenyl)(phenyl)methyl)-2'-O-(tert-butyl(dimethyl)silyl)-3'-O-((2-cyanoethoxy)(diisopropylamino)phosphino)adenosine (1.02 g) was subjected to azeotropic dehydration with anhydrous acetonitrile, and suspended in anhydrous acetonitrile (10 mL). Pyridine 2,2,2-trifluoroacetate (386 mg) was added thereto, and the mixture was stirred under argon atmosphere at room temperature for 1 hr. ((Dimethylamino-methylidene)amino)-3H-1,2,4-dithiazoline-3-thione (199 mg) was added thereto, and the mixture was stirred at room temperature for additional 30 min. The reaction mixture was quenched with a aqueous solution (2.5 mL) of sodium thiosulfate (250 mg), and the solvent was evaporated under reduced pressure. The residue was dissolved in 1,1,1,3,3,3-hexafluoropropan-2-ol (10 mL), the solution was stirred at room temperature for 30 min, and the solvent was evaporated under reduced pressure. The residue was purified by silica gel column chromatography (methanol/ethyl acetate) to give the title compound (328 mg). MS: [M+H]$^+$ 1080.3.

D) N-(9-((5R,7R,8R,12aR,14R,15R,15aR,16R)-15,16-bis((tert-butyl(dimethyl)silyl)oxy)-2-(2-cyanoethoxy)-7-(5-fluoro-4-oxo-3,4-dihydro-7H-pyrrolo[2,3-d]pyrimidin-7-yl)-10-oxido-10-sulfanyl-2-sulfidooctahydro-12H-5,8-methanofuro[3,2-1][1,3,6,9,11,2,10]pentaoxadiphosphacyclotetradecin-14-yl)-9H-purin-6-yl)benzamide (Optical Isomer)

To a mixture of (2R,3R,4R,5R)-5-(((((2R,3R,4R,5R)-5-(6-benzamido-9H-purin-9-yl)-4-((tert-butyldimethylsilyl)oxy)-2-(hydroxymethyl)tetrahydrofuran-3-yl)oxy)(2-cyanoethoxy)phosphorothioyl)oxy)methyl)-4-((tert-butyldimethylsilyl)oxy)-2-(5-fluoro-4-oxo-3H-pyrrolo[2,3-d]pyrimidin-7(4H)-yl)tetrahydrofuran-3-yl hydrogen phosphonate (328 mg) and anhydrous pyridine (10 mL) was added 2-chloro-5,5-dimethyl-1,3,2-dioxaphosphinane 2-oxide (196 mg). The mixture was stirred under argon atmosphere at room temperature for 30 min, water (0.5 mL) and 3H-benzo[c][1,2]dithiol-3-one (61 mg) were added thereto, and the mixture was stirred at room temperature for 1 hr. The reaction mixture was diluted with saturated aqueous sodium bicarbonate solution, and extracted with ethyl acetate. The extract was dried over anhydrous sodium sulfate, and the solvent was evaporated under reduced pressure. The residue was purified by silica gel column chromatography (methanol/ethyl acetate), and then purified by C18 silica gel column chromatography (10 mM triethylammonium acetate buffer solution/acetonitrile) to give the title compound (optical isomer) (92 mg, tR4). MS: [M+H]$^+$ 1094.3.

E) 7-((5R,7R,8R,12aR,14R,15R,15aR,16R)-14-(6-amino-9H-purin-9-yl)-15,16-bis((tert-butyl(dimethyl)silyl)oxy)-2,10-dioxido-2,10-disulfanyloctahydro-12H-5,8-methanofuro[3,2-1][1,3,6,9,11,2,10]pentaoxadiphosphacyclotetradecin-7-yl)-5-fluoro-3,7-dihydro-4H-pyrrolo[2,3-d]pyrimidin-4-one (Optical Isomer)

N-(9-((5R,7R,8R,12aR,14R,15R,15aR,16R)-15,16-Bis((tert-butyl(dimethyl)silyl)oxy)-2-(2-cyanoethoxy)-7-(5-fluoro-4-oxo-3,4-dihydro-7H-pyrrolo[2,3-d]pyrimidin-7-yl)-10-oxido-10-sulfanyl-2-sulfidooctahydro-12H-5,8-methanofuro[3,2-1][1,3,6,9,11,2,10]pentaoxadiphosphacyclotetradecin-14-yl)-9H-purin-6-yl)benzamide (optical isomer) (90 mg) was dissolved in 40% methylamine-methanol solution (3.0 mL), the solution was stirred under argon atmosphere at room temperature for 1 hr, and the solvent was evaporated under reduced pressure. The residue was purified by silica gel column chromatography (methanol/ethyl acetate) to give the title compound (32 mg). MS: [M+H]$^+$ 937.1.

F) 7-((5R,7R,8R,12aR,14R,15R,15aS,16R)-14-(6-amino-9H-purin-9-yl)-15,16-dihydroxy-2,10-dioxido-2,10-disulfanyloctahydro-12H-5,8-methanofuro[3,2-1][1,3,6,9,11,2,10]pentaoxadiphosphacyclotetradecin-7-yl)-5-fluoro-3,7-dihydro-4H-pyrrolo[2,3-d]pyrimidin-4-one di-triethylamine salt (Optical Isomer)

A mixture of 7-((5R,7R,8R,12aR,14R,15R,15aR,16R)-14-(6-amino-9H-purin-9-yl)-15,16-bis((tert-butyl(dimethyl)silyl)oxy)-2,10-dioxido-2,10-disulfanyloctahydro-12H-5,8-methanofuro[3,2-1][1,3,6,9,11,2,10]pentaoxadiphosphacyclotetradecin-7-yl)-5-fluoro-3,7-dihydro-4H-pyrrolo[2,3-d]pyrimidin-4-one (optical isomer) (32 mg) and triethylamine trihydrofluoride (0.12 mL) was stirred at 50° C. for 3 hr. The mixture was cooled to room temperature, and neutralized with 1 M aqueous triethylammonium bicarbonate solution, and the solvent was evaporated under reduced pressure. The residue was purified by C18 silica gel column chromatography (10 mM triethylammonium acetate buffer solution/acetonitrile). The obtained solid was freeze-dried to give the title compound (21 mg). $^1$H NMR (300 MHz, D$_2$O) δ1.23 (18H, t, J=7.3 Hz), 3.15 (12H, q, J=7.4 Hz), 3.99-4.09 (1H, m), 4.23-4.30 (2H, m), 4.30-4.41 (2H, m), 4.41-4.45 (1H, m), 4.47-4.54 (1H, m), 4.83-4.88 (2H, m), 4.96-5.13 (3H, m), 6.11 (1H, d, J=1.1 Hz), 6.36 (1H, d, J=7.4 Hz), 7.31 (1H, d, J=1.9 Hz), 7.95 (1H, s), 8.11 (1H, s), 8.22 (1H, s). $^{31}$P NMR (121 MHz, D$_2$O) δ52.25, 54.88.

Example 6
Synthesis of 7-((5R,7R,8R,12aR,14R,15R,15aS,16R)-7-(6-amino-9H-purin-9-yl)-15,16-dihydroxy-2,10-dioxido-2,10-disulfanyloctahydro-12H-5,8-methanofuro[3,2-1][1,3,6,9,11,2,10]pentaoxadiphosphacyclotetradecin-14-yl)-5-fluoro-3,7-dihydro-4H-pyrrolo[2,3-d]pyrimidin-4-one di-triethylamine salt (Optical Isomer)
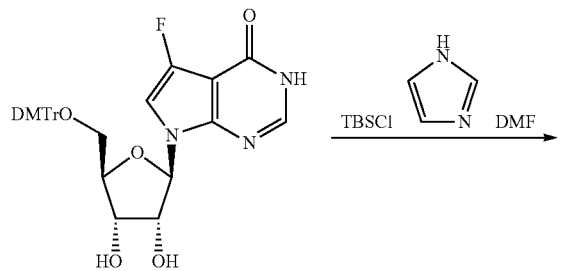
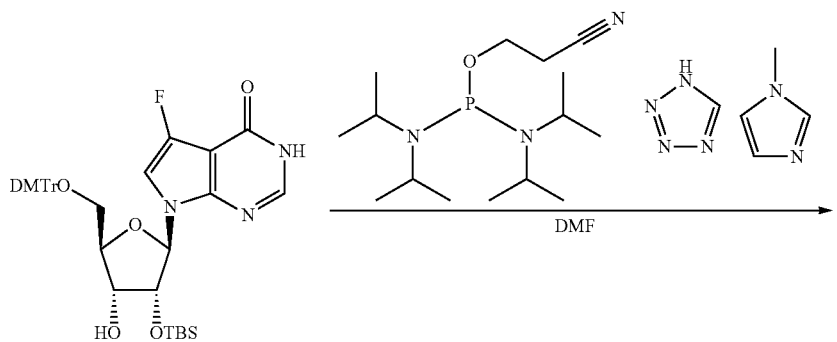
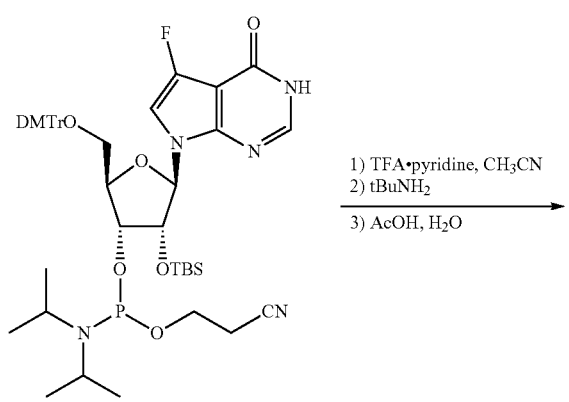

-continued
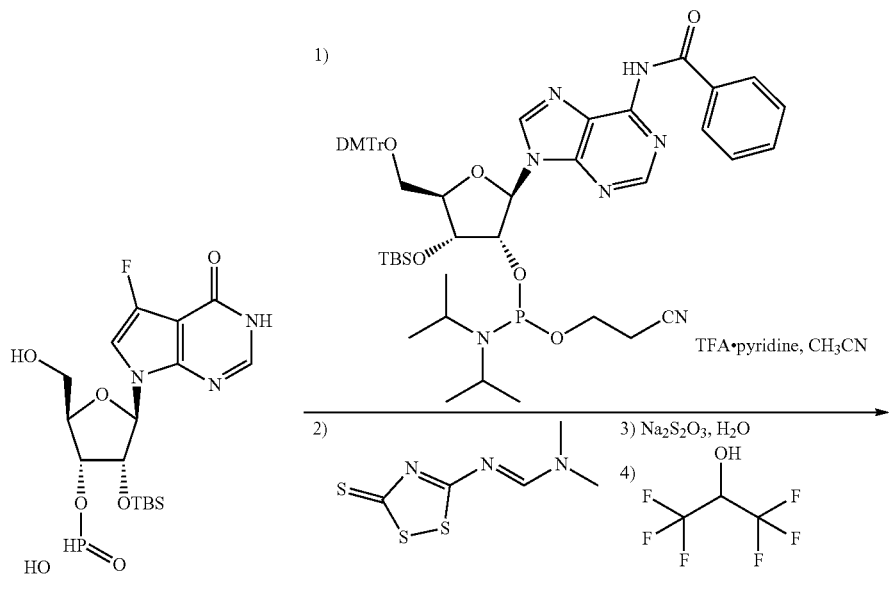
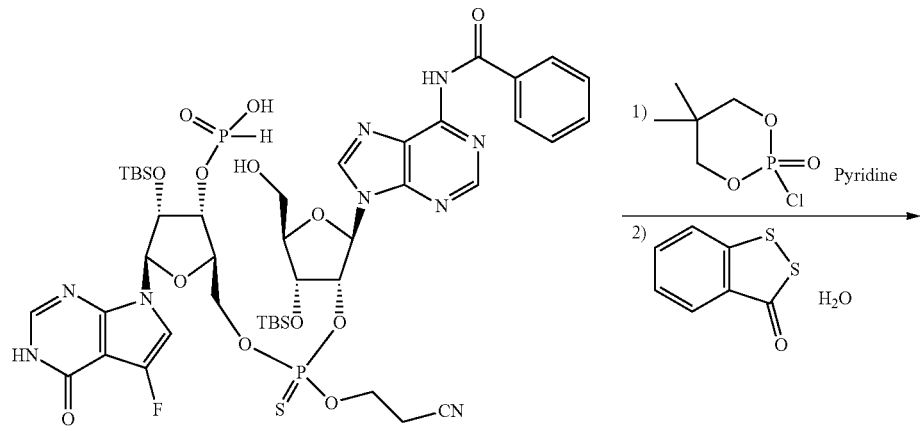
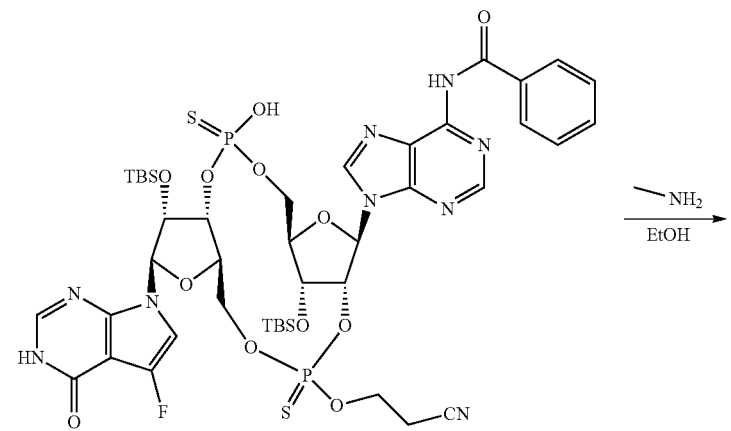

-continued

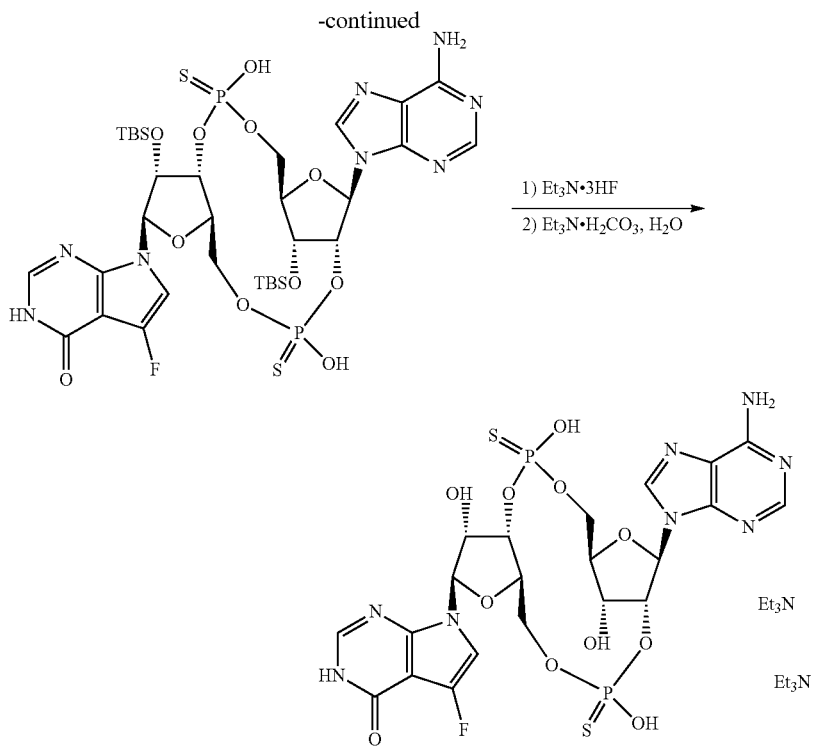

1) Et₃N•3HF
2) Et₃N•H₂CO₃, H₂O

A) 7-(5-O-(bis(4-methoxyphenyl)(phenyl)methyl)-2-O-(tert-butyl(dimethyl)silyl)-beta-D-ribofuranosyl)-5-fluoro-3,7-dihydro-4H-pyrrolo[2,3-d]pyrimidin-4-one To a solution of 7-((2R,3R,4S,5R)-5-((bis(4-methoxyphenyl)(phenyl)methoxy)methyl)-3,4-dihydroxytetrahydrofuran-2-yl)-5-fluoro-3H-pyrrolo[2,3-d]pyrimidin-4(7H)-one (2.65 g) in DMF (20 mL) were added imidazole (0.614 g) and tert-butyldimethylchlorosilane (0.816 g), and the mixture was stirred overnight at room temperature. The reaction mixture was diluted with water, and extracted with ethyl acetate. The extract was washed with saturated brine, dried over anhydrous sodium sulfate, and concentrated under reduced pressure. The residue was purified by silica gel column chromatography (ethyl acetate/hexane) to give the title compound (1.2 g). MS: [M−H]⁻ 700.3.

B) 7-(5-O-(bis(4-methoxyphenyl)(phenyl)methyl)-2-O-(tert-butyl(dimethyl)silyl)-3-O-((2-cyanoethoxy)(diisopropylamino)phosphino)-beta-D-ribofuranosyl)-5-fluoro-3,7-dihydro-4H-pyrrolo[2,3-d]pyrimidin-4-one 7-(5-O-(Bis(4-methoxyphenyl)(phenyl)methyl)-2-O-(tert-butyl(dimethyl)silyl)-beta-D-ribofuranosyl)-5-fluoro-3,7-dihydro-4H-pyrrolo[2,3-d]pyrimidin-4-one (2.37 g) was dissolved in DMF (6.75 mL), and to the solution were added 3-((bis(diisopropylamino)phosphino)oxy)propanenitrile (2.15 mL), 1H-tetrazole (0.237 g) and 1-methyl-1H-imidazole (0.134 mL), and the mixture was stirred under argon atmosphere at room temperature for 20.5 hr. To the reaction solution was added saturated aqueous sodium bicarbonate solution, and the mixture was extracted with ethyl acetate. The extract was washed with saturated brine, and dried over anhydrous magnesium sulfate, and the solvent was evaporated under reduced pressure. The residue was purified by silica gel column chromatography (ethyl acetate/hexane, containing 0.5% triethylamine) to give the title compound (2.67 g). MS: [M−H]⁺ 900.2.

C) 7-(2-O-(tert-butyl(dimethyl)silyl)-3-O-(hydroxy(oxido)phosphoranyl)-beta-D-ribofuranosyl)-5-fluoro-3,7-dihydro-4H-pyrrolo[2,3-d]pyrimidin-4-one 7-(5-O-(Bis(4-methoxyphenyl)(phenyl)methyl)-2-O-(tert-butyl(dimethyl)silyl)-3-O-((2-cyanoethoxy)(diisopropylamino)phosphino)-beta-D-ribofuranosyl)-5-fluoro-3,7-dihydro-4H-pyrrolo[2,3-d]pyrimidin-4-one (1.54 g) was dissolved in acetonitrile (15 mL), pyridine 2,2,2-trifluoroacetate (0.396 g) and water (0.062 mL) were added thereto at room temperature, and the mixture was stirred at room temperature for 50 min. To the reaction solution was added 2-methylpropan-2-amine (8.07 mL) at room temperature, and the mixture was stirred at room temperature for 30 min. The reaction mixture was concentrated under reduced pressure, to the residue was added 80% acetic acid (8.54 mL), and the mixture was stirred at room temperature for 1 hr.

Similarly, 7-(5-O-(bis(4-methoxyphenyl)(phenyl)methyl)-2-O-(tert-butyl(dimethyl)silyl)-3-O-((2-cyanoethoxy)(diisopropylamino)phosphino)-beta-D-ribofuranosyl)-5-fluoro-3,7-dihydro-4H-pyrrolo[2,3-d]pyrimidin-4-one (1.13 g) was dissolved in acetonitrile (10 mL), and pyridine 2,2,2-trifluoroacetate (0.290 g) and water (0.045 mL) were added thereto at room temperature, and the mixture was stirred at room temperature for 50 min. To the reaction solution was added 2-methylpropan-2-amine (5.92 mL) at room temperature, and the mixture was stirred at room temperature for 30 min. The reaction mixture was concentrated under reduced pressure, to the residue was added 80% acetic acid (6.27 mL), and the mixture was stirred at room temperature for 1 hr.

The reaction mixtures were combined, and concentrated under reduced pressure, and the residue was purified by silica gel column chromatography (methanol/ethyl acetate) to give the title compound (961 mg). MS: [M+H]$^+$ 464.0.

D) (2R,3R,4R,5R)-2-((((((2R,3R,4R,5R)-2-(6-benzamido-9H-purin-9-yl)-4-((tert-butyldimethylsilyl)oxy)-5-(hydroxymethyl)tetrahydrofuran-3-yl)oxy)(2-cyanoethoxy)phosphorothioyl)oxy)methyl)-4-((tert-butyldimethylsilyl)oxy)-5-(5-fluoro-4-oxo-3H-pyrrolo[2,3-d]pyrimidin-7(4H)-yl)tetrahydrofuran-3-yl hydrogen phosphonate 7-(2-O-(tert-Butyl(dimethyl)silyl)-3-O-(hydroxy(oxido)phosphoranyl)-beta-D-ribofuranosyl)-5-fluoro-3,7-dihydro-4H-pyrrolo[2,3-d]pyrimidin-4-one (400 mg) and N-benzoyl-5'-O-(bis(4-methoxyphenyl)(phenyl)methyl)-3'-O-tert-butyl(dimethyl)silyl)-2'-O-((2-cyanoethoxy)(diisopropylamino)phosphino)adenosine (1.02 g) were subjected to azeotropic dehydration with anhydrous acetonitrile (three times), and was suspended in anhydrous acetonitrile (6 mL). Pyridine 2,2,2-trifluoroacetate (333 mg) was added thereto, and the mixture was stirred under argon atmosphere at room temperature for 1 hr. (Dimethylaminomethylidene)amino)-3H-1,2,4-dithiazoline-3-thione (195 mg) was added thereto, and the mixture was stirred at room temperature for additional 30 min. The reaction mixture was quenched with sodium thiosulfate (316 mg) and water (0.5 mL), and the solvent was evaporated under reduced pressure. The residue was dissolved in 1,1,1,3,3,3-hexafluoropropan-2-ol (5 mL), and the solution was stirred at room temperature for 1 hr.

The reaction mixture was concentrated under reduced pressure, and the residue was subjected to azeotropic dehydration with anhydrous acetonitrile and toluene. The residue was purified by silica gel column chromatography (methanol/ethyl acetate) to give the title compound (556 mg). MS: [M+H]$^+$ 1080.3.

E) N-(9-((5R,7R,8R,12aR,14R,15R,15aR,16R)-15,16-bis((tert-butyl(dimethyl)silyl)oxy)-10-(2-cyanoethoxy)-14-(5-fluoro-4-oxo-3,4-dihydro-7H-pyrrolo[2,3-d]pyrimidin-7-yl)-2-hydroxy-2,10-disulfidooctahydro-12H-5,8-methanofuro[3,2-1][1,3,6,9,11,2,10]pentaoxadiphosphacyclotetradecin-7-yl)-9H-purin-6-yl)benzamide (Optical Isomer)

((2R,3R,4R,5R)-2-((((((2R,3R,4R,5R)-2-(6-Benzamido-9H-purin-9-yl)-4-((tert-butyldimethylsilyl)oxy)-5-(hydroxymethyl)tetrahydrofuran-3-yl)oxy)(2-cyanoethoxy)phosphorothioyl)oxy)methyl)-4-((tert-butyldimethylsilyl)oxy)-5-(5-fluoro-4-oxo-3H-pyrrolo[2,3-d]pyrimidin-7(4H)-yl)tetrahydrofuran-3-yl hydrogen phosphonate (556 mg) was subjected to azeotropic dehydration with anhydrous acetonitrile and anhydrous pyridine, and dissolved in anhydrous pyridine (15 mL). To the solution was added 2-chloro-5,5-dimethyl-1,3,2-dioxaphosphinane 2-oxide (332 mg) at room temperature, and the mixture was stirred under argon atmosphere at room temperature for 30 min. Water (1 mL) and 3H-1,2-benzodithiol-3-one (108 mg) were added thereto, and the mixture was stirred at room temperature for additional 1 hr. To the reaction mixture was added saturated aqueous sodium bicarbonate solution, and the mixture was extracted with ethyl acetate. The extract was washed with saturated brine, and dried over anhydrous sodium sulfate, and the solvent was evaporated under reduced pressure. The residue was purified by silica gel column chromatography (ethyl acetate/methanol). The obtained residue was resolved into four diastereomers (tR1, tR2, tR3 and tR4, retention times of which by LC/MS are from shorter to longer in this order) by HPLC (L-column2 ODS, 50×150 mm, mobile phase: 5 mM aqueous ammonium acetate solution/acetonitrile) to give the title compound (120 mg, tR2) and the title compound (183 mg, tR4). tR2 MS: [M+H]$^+$ 1094.3. tR4 MS: [M+H]$^+$ 1094.3.

F) 7-((5R,7R,8R,12aR,14R,15R,15aR,16R)-7-(6-amino-9H-purin-9-yl)-15,16-bis((tert-butyl(dimethyl)silyl)oxy)-2,10-dioxido-2,10-disulfanyloctahydro-12H-5,8-methanofuro[3,2-1][1,3,6,9,11,2,10]pentaoxadiphosphacyclotetradecin-14-yl)-5-fluoro-3,7-dihydro-4H-pyrrolo[2,3-d]pyrimidin-4-one (Optical Isomer)

N-(9-((5R,7R,8R,12aR,14R,15R,15aR,16R)-15,16-Bis((tert-butyl(dimethyl)silyl)oxy)-10-(2-cyanoethoxy)-14-(5-fluoro-4-oxo-3,4-dihydro-7H-pyrrolo[2,3-d]pyrimidin-7-yl)-2-oxido-2-sulfanyl-10-sulfidooctahydro-12H-5,8-methanofuro[3,2-1][1,3,6,9,11,2,10]pentaoxadiphosphacyclotetradecin-7-yl)-9H-purin-6-yl)benzamide (optical isomer, derived from tR2) (120 mg) was dissolved in 33% methylamine ethanol solution (5.0 mL), the solution was stirred under argon atmosphere at room temperature for 1.5 hr, and the solvent was evaporated under reduced pressure. The residue was purified by silica gel column chromatography (methanol/ethyl acetate) to give the title compound (84.4 mg). MS: [M+H]$^+$ 937.2.

G) 7-((5R,7R,8R,12aR,14R,15R,15aS,16R)-7-(6-amino-9H-purin-9-yl)-15,16-dihydroxy-2,10-dioxido-2,10-disulfanyloctahydro-12H-5,8-methanofuro[3,2-1][1,3,6,9,11,2,10]pentaoxadiphosphacyclotetradecin-14-yl)-5-fluoro-3,7-dihydro-4H-pyrrolo[2,3-d]pyrimidin-4-one di-triethylamine salt (Optical Isomer)

To 7-((5R,7R,8R,12aR,14R,15R,15aR,16R)-7-(6-amino-9H-purin-9-yl)-15,16-bis((tert-butyl(dimethyl)silyl)oxy)-2,10-dioxido-2,10-disulfanyloctahydro-12H-5,8-methanofuro[3,2-1][1,3,6,9,11,2,10]pentaoxadiphosphacyclotetradecin-14-yl)-5-fluoro-3,7-dihydro-4H-pyrrolo[2,3-d]pyrimidin-4-one (optical isomer, derived from tR2) (84.4 mg) was added triethylamine trihydrofluoride (0.294 mL), and the mixture was stirred at 50° C. for 2 hr. The reaction solution was cooled to room temperature, and neutralized with 1 M aqueous triethylammonium bicarbonate solution, and the solvent was evaporated under reduced pressure. The residue was purified by C18 silica gel column chromatography (10 mM triethylammonium acetate buffer solution/acetonitrile), and the obtained solid was freeze-dried to give the title compound (58.4 mg). $^1$H NMR (300 MHz, D$_2$O) δ 1.26 (18H, t, J=7.4 Hz), 3.18 (12H, q, J=7.3 Hz), 3.94-4.05 (1H, m), 4.10-4.20 (1H, m), 4.28-4.45 (2H, m), 4.50 (2H, brs), 4.59 (1H, d, J=4.2 Hz), 4.71-4.81 (1H, m), 5.32 (2H, d, J=10.6 Hz), 6.23-6.32 (2H, m), 7.17 (1H, d, J=2.3 Hz), 8.05 (1H, S), 8.20 (1H, s), 8.66 (1H, s). $^{31}$P NMR (121 MHz, D$_2$O) δ55.8, 59.2.

Example 7

Synthesis of 7-((5R,7R,8R,12aR,14R,15R,15aS,16R)-7-(6-amino-9H-purin-9-yl)-15,16-dihydroxy-2,10-dioxido-2,10-disulfanyloctahydro-12H-5,8-methanofuro[3,2-1][1,3,6,9,11,2,10]pentaoxadiphosphacyclotetradecin-14-yl)-5-fluoro-3,7-dihydro-4H-pyrrolo[2,3-d]pyrimidin-4-one di-triethylamine salt (Optical Isomer)

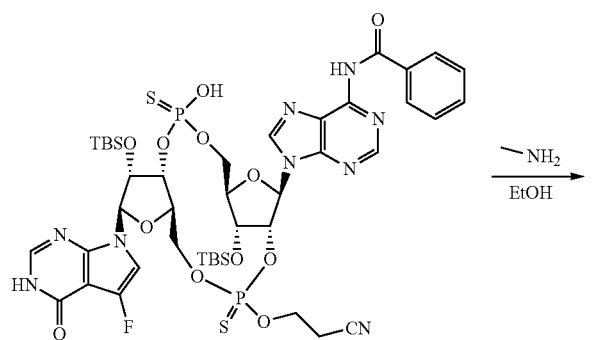

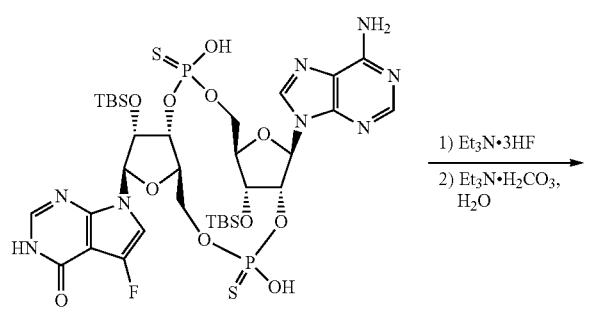

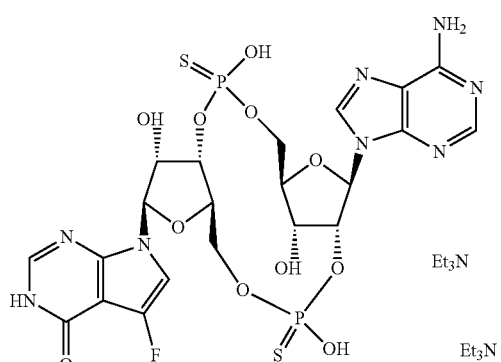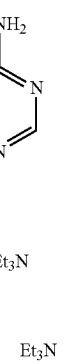

A) 7-((5R,7R,8R,12aR,14R,15R,15aR,16R)-7-(6-amino-9H-purin-9-yl)-15,16-bis((tert-butyl(dimethyl)silyl)oxy)-2,10-dioxido-2,10-disulfanyloctahydro-12H-5,8-methanofuro[3,2-1][1,3,6,9,11,2,10]pentaoxadiphosphacyclotetradecin-14-yl)-5-fluoro-3,7-dihydro-4H-pyrrolo[2,3-d]pyrimidin-4-one (Optical Isomer)

N-(9-((5R,7R,8R,12aR,14R,15R,15aR,16R)-15,16-Bis((tert-butyl(dimethyl)silyl)oxy)-10-(2-cyanoethoxy)-14-(5-fluoro-4-oxo-3,4-dihydro-7H-pyrrolo[2,3-d]pyrimidin-7-yl)-2-oxido-2-sulfanyl-10-sulfidooctahydro-12H-5,8-methanofuro[3,2-1][1,3,6,9,11,2,10]pentaoxadiphosphacyclotetradecin-7-yl)-9H-purin-6-yl)benzamide (optical isomer, derived from tR4) (183 mg) was dissolved in 33% methylamine ethanol solution (5.0 mL), the solution was stirred under argon atmosphere at room temperature for 1 hr, and the solvent was evaporated under reduced pressure. The residue was purified by silica gel column chromatography (methanol/ethyl acetate) to give the title compound (107 mg). MS: $[M+H]^+$ 937.1.

B) 7-((5R,7R,8R,12aR,14R,15R,15aS,16R)-7-(6-amino-9H-purin-9-yl)-15,16-dihydroxy-2,10-dioxido-2,10-disulfanyloctahydro-12H-5,8-methanofuro[3,2-1][1,3,6,9,11,2,10]pentaoxadiphosphacyclotetradecin-14-yl)-5-fluoro-3,7-dihydro-4H-pyrrolo[2,3-d]pyrimidin-4-one di-triethylamine salt (Optical Isomer)

To 7-((5R,7R,8R,12aR,14R,15R,15aR,16R)-7-(6-amino-9H-purin-9-yl)-15,16-bis((tert-butyl(dimethyl)silyl)oxy)-2,10-dioxido-2,10-disulfanyloctahydro-12H-5,8-methanofuro[3,2-1][1,3,6,9,11,2,10]pentaoxadiphosphacyclotetradecin-14-yl)-5-fluoro-3,7-dihydro-4H-pyrrolo[2,3-d]pyrimidin-4-one (optical isomer, derived from tR4) (107 mg) was added triethylamine trihydrofluoride (0.372 mL), and the mixture was stirred at 50° C. for 2.5 hr. The reaction solution was cooled to room temperature, and neutralized with 1 M aqueous triethylammonium bicarbonate solution, and the solvent was evaporated under reduced pressure. The residue was purified by C18 silica gel column chromatography (10 mM triethylammonium acetate buffer solution/acetonitrile), and the obtained solid was freeze-dried to give the title compound (78 mg). $^1$H NMR (300 MHz, $D_2O$) δ 1.26 (18H, t, J=7.4 Hz), 3.18 (12H, q, J=7.2 Hz), 4.09-4.18 (1H, m), 4.21-4.29 (2H, m), 4.33-4.43 (1H, m), 4.51 (2H, brs), 4.65-4.71 (1H, m), 4.89 (1H, d, J=4.2 Hz), 4.99-5.11 (1H, m), 5.29-5.42 (1H, m), 6.23-6.31 (2H, m), 7.00 (1H, d, J=1.9 Hz), 8.03 (1H, s), 8.17 (1H, s), 8.56 (1H, s). $^{31}$P NMR (121 MHz, $D_2O$) δ52.8, 55.1.

Example 8
Synthesis of 2-amino-9-((5R,7R,8R,12aR,14R,15R, 15aS,16R)-14-(4-amino-5-fluoro-7H-pyrrolo[2,3-d] pyrimidin-7-yl)-2,10,15,16-tetrahydroxy-2,10-dioxidooctahydro-12H-5,8-methanofuro[3,2-1][1,3,6,9, 11,2,10]pentaoxadiphosphacyclotetradecin-7-yl)-1,9-dihydro-6H-purin-6-one di-triethylamine salt
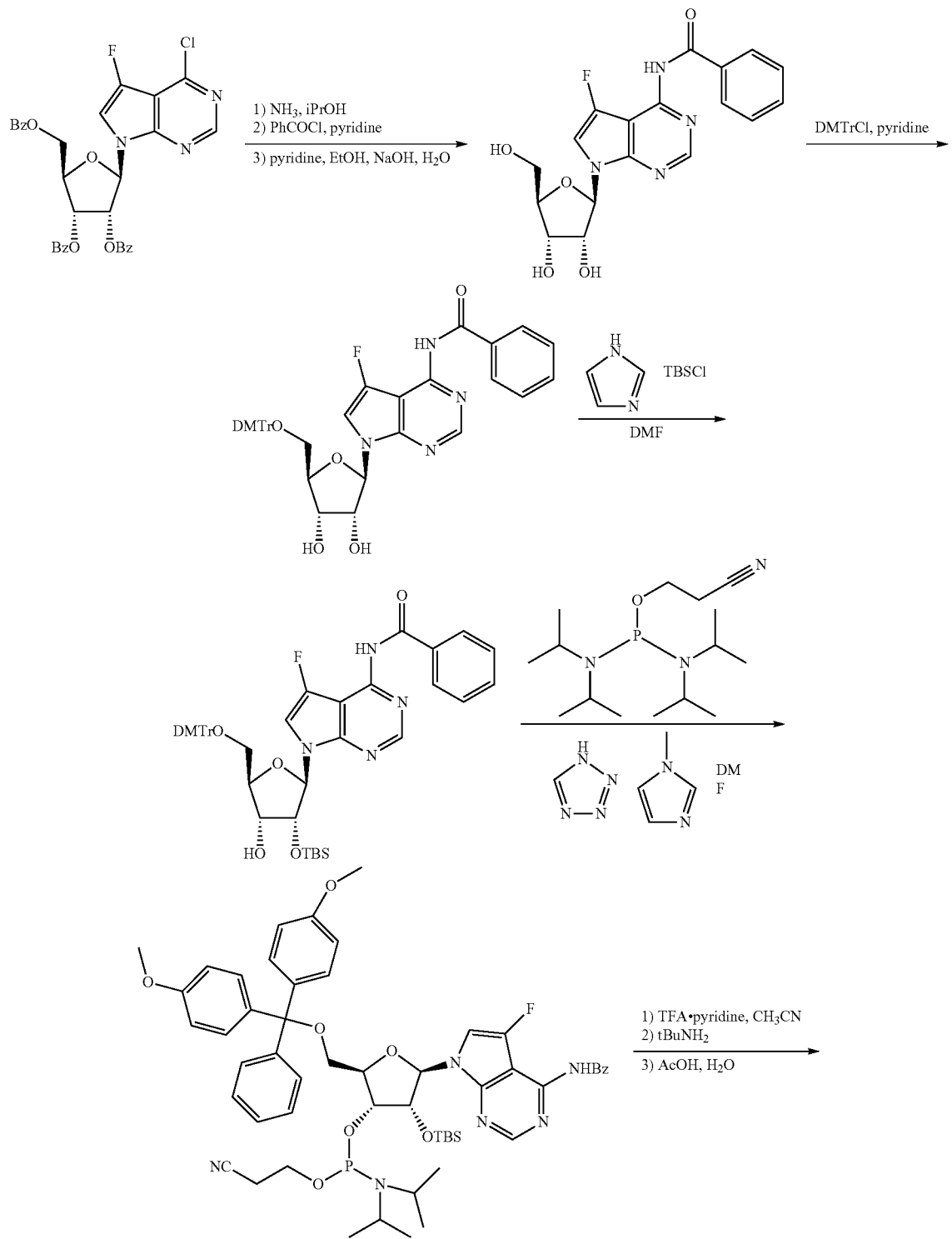

-continued
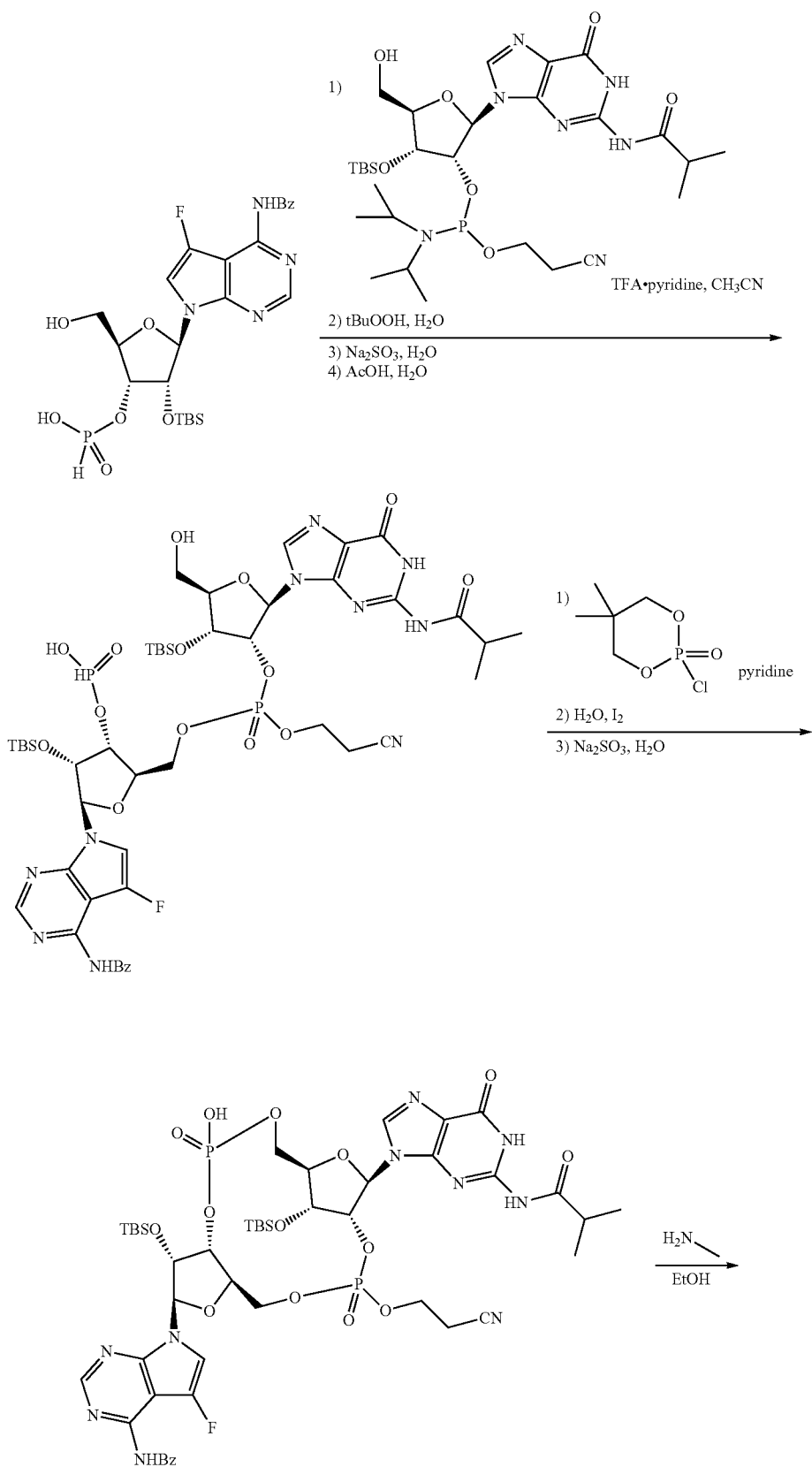

-continued

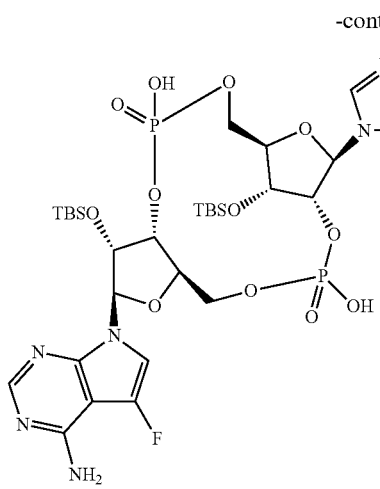

1) Et₃N·3HF
2) Et₃N H₂CO₃, H₂O

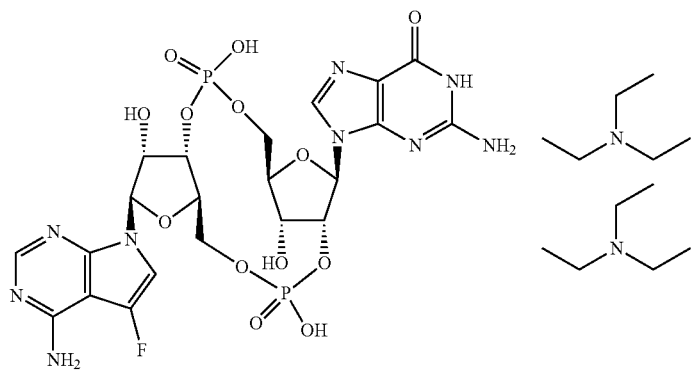

A) N-(7-((2R,3R,4S,5R)-5-((bis(4-methoxyphenyl)(phenyl)methoxy)methyl)-3,4-dihydroxytetrahydrofuran-2-yl)-5-fluoro-7H-pyrrolo[2,3-d]pyrimidin-4-yl)benzamide (2R,3R,4R,5R)-2-((Benzoyloxy)methyl)-5-(4-chloro-5-fluoro-7H-pyrrolo[2,3-d]pyrimidin-7-yl)tetrahydrofuran-3,4-diyl dibenzoate (14.09 g) was charged into 17 seal tube containers in 17 parts, and 2 M ammonia isopropanol solution (20 mL) was added thereto, respectively. Each mixture was stirred with microwave irradiation at 130° C. for 5 hr. The obtained mixtures were combined, and concentrated under reduced pressure. The obtained residue was subjected to azeotropic evaporation twice with toluene to remove the solvent, pyridine (100 mL) was added thereto, and the mixture was cooled to 0° C. Benzoyl chloride (26.6 mL) was added thereto at 0° C., and the mixture was stirred overnight at room temperature. To the reaction mixture was added water, and the mixture was extracted with ethyl acetate. The extract was concentrated under reduced pressure, and the residue was purified by silica gel column chromatography (ethyl acetate/hexane). To the obtained compound were added pyridine (350 mL) and ethanol (100 mL), and the mixture was cooled to 0° C. 1 M Aqueous sodium hydroxide solution (103 mL) was added thereto, and the mixture was stirred at 0° C. for 1 hr. 1 M Aqueous sodium hydroxide solution (45.7 mL) was added again thereto, and the mixture was stirred at 0° C. for 1 hr. To the reaction mixture was added strong acidic cation-exchange resin DOWEX™ 50Wx4 100-200 (95 g) at room temperature, the solid was removed by filtration, and the filtrate was concentrated under reduced pressure. The residue was purified by silica gel column chromatography (methanol/ethyl acetate). To the obtained product (5.71 g) were added pyridine (60 mL) and 4,4'-dimethoxytrityl chloride (5.98 g), and the mixture was stirred at room temperature for 4 hr. 4,4'-Dimethoxytrityl chloride (5.98 g) was added again thereto, and the mixture was stirred at room temperature for 1 hr. The mixture was concentrated under reduced pressure, water was added thereto, and the mixture was extracted with ethyl acetate. The extract was washed with water and saturated brine, and dried over anhydrous sodium sulfate, and the solvent was evaporated under reduced pressure. The residue was purified by silica gel column chromatography (ethyl acetate/hexane) to give the title compound (8.50 g). MS: [M+H]⁺ 691.2.

B) N-(7-((2R,3R,4R,5R)-5-((bis(4-methoxyphenyl)(phenyl)methoxy)methyl)-3-((tert-butyldimethylsilyl)oxy)-4-hydroxytetrahydrofuran-2-yl)-5-fluoro-7H-pyrrolo[2,3-d]pyrimidin-4-yl)benzamide To a mixture of N-(7-((2R,3R,4S,5R)-5-((bis(4-methoxyphenyl)(phenyl)methoxy)methyl)-3,4-dihydroxytetrahydrofuran-2-yl)-5-fluoro-7H-pyrrolo[2,3-d]pyrimidin-4-yl)benzamide (7.51 g) and DMF (30 mL) were added imidazole (1.924 g) and tert-butyldimethylchlorosilane (2.13 g), and the mixture was stirred overnight at room temperature. To the reaction mixture was added water, and the mixture was extracted with ethyl acetate. The extract was washed with water and saturated brine, and dried over anhydrous sodium sulfate, and the solvent was evaporated under reduced pressure. The residue was purified by silica gel column chromatography (ethyl acetate/hexane) to give the title compound (2.94 g). MS, found: 501.2.

C) N-benzoyl-7-(5-O-(bis(4-methoxyphenyl)(phenyl)methyl)-2-O-(tert-butyl(dimethyl)silyl)-3-O-((2-cyanoethoxy)(diisopropylamino)phosphino)-beta-D-ribofuranosyl)-5-fluoro-7H-pyrrolo[2,3-d]pyrimidin-4-amine N-(7-((2R,3R,4R,5R)-5-((Bis(4-methoxyphenyl)(phenyl)methoxy)methyl)-3-((tert-butyldimethylsilyl)oxy)-4-hydroxytetrahydrofuran-2-yl)-5-fluoro-7H-pyrrolo[2,3-d]pyrimidin-4-yl)benzamide (1.03 g) was subjected to azeotropic dehydration with anhydrous toluene, and anhydrous DMF (5 mL) was added thereto under argon atmosphere. 3-((Bis(diisopropylamino)phosphino)oxy)propanenitrile (0.771 g), 1H-tetrazole (0.090 g) and 1-methyl-1H-imidazole (0.051 mL) were added thereto, and the mixture was stirred for 6 hr. To the reaction mixture was added saturated aqueous sodium hydrogencarbonate solution, and the mixture was extracted with ethyl acetate. The extract was washed with saturated aqueous sodium hydrogencarbonate solution and saturated brine, and dried over anhydrous sodium sulfate, and the solvent was evaporated under reduced pressure. The residue was purified by silica gel column chromatography (ethyl acetate containing 0.5% triethylamine/hexane) to give the title compound (1.12 g). $^1$H NMR (300 MHz, CDCl$_3$) δ 0.17 (3H, d, J=2.6 Hz), −0.04-0.00 (3H, m), 0.78 (9H, s), 1.04 (3H, d, J=6.8 Hz), 1.13-1.23 (9H, m), 2.32 (1H, t, J=6.6 Hz), 2.68 (1H, td, J=6.4, 1.9 Hz), 3.21-3.36 (1H, m), 3.42-3.71 (4H, m), 3.79 (6H, d, J=1.1 Hz), 3.85-4.05 (1H, m), 4.25-4.45 (2H, m), 4.64-4.82 (1H, m), 6.39 (1H, dd, J=14.2, 5.9 Hz), 6.74-6.89 (4H, m), 7.19-7.41 (8H, m), 7.43-7.67 (5H, m), 7.98 (2H, d, J=7.6 Hz), 8.50 (1H, s), 8.64 (1H, d, J=5.3 Hz).

D) (2R,3R,4R,5R)-5-(4-benzamido-5-fluoro-7H-pyrrolo[2,3-d]pyrimidin-7-yl)-4-((tert-butyldimethylsilyl)oxy)-2-(hydroxymethyl)tetrahydrofuran-3-yl hydrogen phosphonate To N-benzoyl-7-(5-O-(bis(4-methoxyphenyl)(phenyl)methyl)-2-O-(tert-butyl(dimethyl)silyl)-3-O-((2-cyanoethoxy)(diisopropylamino)phosphino)-beta-D-ribofuranosyl)-5-fluoro-7H-pyrrolo[2,3-d]pyrimidin-4-amine (1.12 g) were added acetonitrile (5 mL), water (40 μL) and pyridine 2,2,2-trifluoroacetate (258 mg). The mixture was stirred at room temperature for 10 min, tert-butylamine (5.43 mL) was added thereto, and the mixture was stirred at room temperature for 1 hr. The reaction mixture was concentrated under reduced pressure, 80% acetic acid (5.5 mL) was added thereto, and the mixture was stirred at room temperature for additional 1 hr. The solvent was evaporated under reduced pressure, and the residue was purified by silica gel column chromatography (methanol/ethyl acetate) to give the title compound (527 mg). MS: [M+H]$^Y$ 567.2.

E) (2R,3R,4R,5R)-5-(4-benzamido-5-fluoro-7H-pyrrolo[2,3-d]pyrimidin-7-yl)-4-((tert-butyldimethylsilyl)oxy)-2-((((((2R,3R,4R,5R)-4-((tert-butyldimethylsilyl)oxy)-5-(hydroxymethyl)-2-(2-isobutylamido-6-oxo-1H-purin-9(6H)-yl)tetrahydrofuran-3-yl)oxy)(2-cyanoethoxy)phosphoryl)oxy)methyl)tetrahydrofuran-3-yl hydrogen phosphonate (2R,3R,4R,5R)-5-(4-Benzamido-5-fluoro-7H-pyrrolo[2,3-d]pyrimidin-7-yl)-4-((tert-butyldimethylsilyl)oxy)-2-(hydroxymethyl)tetrahydrofuran-3-yl hydrogen phosphonate (527 mg) and 3'-O-(tert-butyl(dimethyl)silyl)-2'-O-((2-cyanoethoxy)(diisopropylamino)phosphino)-N-isobutyrylguanosine (1.083 g) were subjected to azeotropic dehydration three times with anhydrous acetonitrile, and anhydrous acetonitrile (10 mL) was added thereto. Pyridine 2,2,2-trifluoroacetate (359 mg) was added thereto, and the mixture was stirred at room temperature for 30 min. 70% tert-Butyl hydroperoxide aqueous solution (382 μL) was added thereto, and the mixture was stirred at room temperature for additional 20 min. To the reaction mixture were added sodium thiosulfate (693 mg) and water (1 mL), and the mixture was concentrated under reduced pressure. To the residue was added 80% acetic acid (5 mL), and the mixture was stirred at room temperature for 1 hr. The reaction mixture was concentrated under reduced pressure, and the residue was subjected to azeotropic dehydration three times with toluene. The residue was purified by silica gel column chromatography (methanol/ethyl acetate) to give the title compound (175 mg). MS: [M+H]$^+$ 1149.4.

F) N-(7-((5R,7R,8R,12aR,14R,15R,15aR,16R)-15,16-bis((tert-butyl(dimethyl)silyl)oxy)-10-(2-cyanoethoxy)-2-hydroxy-7-(2-((2-methylpropanoyl)amino)-6-oxo-1,6-dihydro-9H-purin-9-yl)-2,10-dioxidooctahydro-12H-5,8-methanofuro[3,2-1][1,3,6,9,11,2,10]pentaoxadiphosphacyclotetradecin-14-yl)-5-fluoro-7H-pyrrolo[2,3-d]pyrimidin-4-yl)benzamide (2R,3R,4R,5R)-5-(4-Benzamido-5-fluoro-7H-pyrrolo[2,3-d]pyrimidin-7-yl)-4-((tert-butyldimethylsilyl)oxy)-2-((((((2R,3R,4R,5R)-4-((tert-butyldimethylsilyl)oxy)-5-(hydroxymethyl)-2-(2-isobutylamido-6-oxo-1H-purin-9(6H)-yl)tetrahydrofuran-3-yl)oxy)(2-cyanoethoxy)phosphoryl)oxy)methyl)tetrahydrofuran-3-yl hydrogen phosphonate (175 mg) was subjected to azeotropic dehydration three times with anhydrous acetonitrile, and anhydrous pyridine (3 mL) and 2-chloro-5,5-dimethyl-1,3,2-dioxaphosphinane 2-oxide (98 mg) were added thereto. The mixture was stirred under argon atmosphere at room temperature for 10 min, water (96 μL) and iodine (50 mg) were added thereto, and the mixture was stirred at room temperature for additional 20 min. The reaction mixture was added to a mixture of sodium thiosulfate (98 mg) and water (0.4 mL), and the mixture was stirred for 5 min, and concentrated under reduced pressure. The residue was purified twice by silica gel column chromatography (methanol/ethyl acetate) to give the title compound (48 mg). MS: [M+H]$^+$ 1147.6.

G) 2-amino-9-((5R,7R,8R,12aR,14R,15R,15aR,16R)-14-(4-amino-5-fluoro-7H-pyrrolo[2,3-d]pyrimidin-7-yl)-15,16-bis((test-butyl(dimethyl)silyl)oxy)-2,10-dihydroxy-2,10-dioxidooctahydro-12H-5,8-methanofuro[3,2-1][1,3,6,9,11,2,10]pentaoxadiphosphacyclotetradecin-7-yl)-1,9-dihydro-6H-purin-6-one N-(7-((5R,7R,8R,12aR,14R,15R,15aR,16R)-15,16-Bis((tert-butyl(dimethyl)silyl)oxy)-10-(2-cyanoethoxy)-2-hydroxy-7-(2-((2-methylpropanoyl)amino)-6-oxo-1,6-dihydro-9H-purin-9-yl)-2,10-dioxidooctahydro-12H-5,8-methanofuro[3,2-1][1,3,6,9,11,2,10]pentaoxadiphosphacyclotetradecin-14-yl)-5-fluoro-7H-pyrrolo[2,3-d]pyrimidin-4-yl)benzamide (48 mg) was subjected to azeotropic dehydration twice with anhydrous acetonitrile, 33% methylamine ethanol solution (2 mL) was added thereto, and the mixture was stirred overnight under argon atmosphere at room temperature. The obtained mixture was concentrated under reduced pressure, and the residue was purified by silica gel column chromatography (methanol/ethyl acetate). The obtained residue was purified by HPLC (L-column2 ODS, 50×150 mm, mobile phase: 5 mM aqueous ammonium acetate solution/acetonitrile), the obtained fraction was concentrated under reduced pressure, and the obtained product was freeze-dried to give the title compound (5 mg). MS: [M+H]$^+$ 920.3.

H) 2-amino-9-((5R,7R,8R,12aR,14R,15R,15aS, 16R)-14-(4-amino-5-fluoro-7H-pyrrolo[2,3-d]pyrimidin-7-yl)-2,10,15,16-tetrahydroxy-2,10-dioxidooctahydro-12H-5,8-methanofuro[3,2-1][1,3,6,9,11,2,10]pentaoxadiphosphacyclotetradecin-7-yl)-1,9-dihydro-6H-purin-6-one di-triethylamine salt A mixture of 2-amino-9-((5R,7R,8R,12aR,14R,15R,15aR,16R)-14-(4-amino-5-fluoro-7H-pyrrolo[2,3-d]pyrimidin-7-yl)-15,16-bis((tert-butyl(dimethyl)silyl)oxy)-2,10-dihydroxy-2,10-dioxidooctahydro-12H-5,8-methanofuro[3,2-1][1,3,6,9,11,2,10]pentaoxadiphosphacyclotetradecin-7-yl)-1,9-dihydro-6H-purin-6-one (5 mg) and triethylamine trihydrofluoride (200 μL) was stirred at 50° C. for 1 hr. The reaction mixture was cooled to room temperature, and neutralized with 1 M aqueous triethylammonium hydrogen carbonate solution. The reaction mixture was purified by C18 column chromatography (acetonitrile/10 mM triethylammonium acetate buffer solution), the objective fraction was concentrated under reduced pressure, and the obtained product was freeze-dried to give the title compound (3.2 mg). $^1$H NMR (600 MHz, D$_2$O) δ 1.23 (18H, t, J=7.3 Hz), 3.15 (12H, q, J=7.3 Hz), 4.06-4.11 (1H, m), 4.14-4.19 (1-1, m), 4.21-4.26 (1H, m), 4.31-4.37 (2H, m), 4.40 (1H, d, J=1.5 Hz), 4.56 (1H, dd, J=15.2, 4.3 Hz), 4.61-4.68 (1H, m), 5.00 (1H, ddd, J=8.5, 6.6, 4.5 Hz), 5.60 (1H, td, J=7.9, 4.1 Hz), 5.93 (1H, d, J=8.5 Hz), 6.26 (1H, s), 7.14 (1H, d, J=1.6 Hz), 7.87 (1H, s), 8.10 (1H, s).

Example 10

Synthesis of 1-((5R,7R,8R,12aR,14R,15R,15aS, 16R)-14-(6-amino-9H-purin-9-yl)-2,10,15,16-tetrahydroxy-2,10-dioxidooctahydro-12H-5,8-methanofuro[3,2-1][1,3,6,9,11,2,10] pentaoxadiphosphacyclotetradecin-7-yl)-1,5-dihydro-4H-imidazo[4,5-c]pyridin-4-one

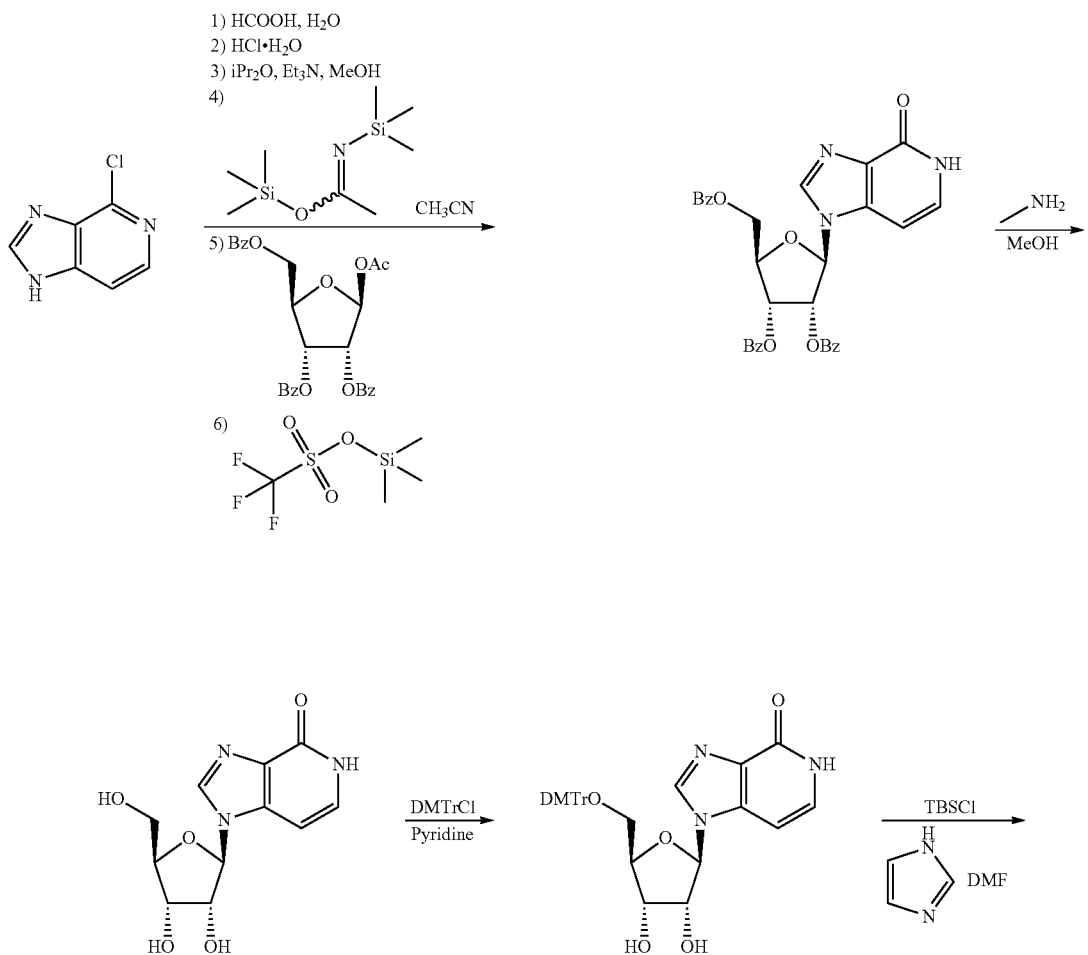

-continued
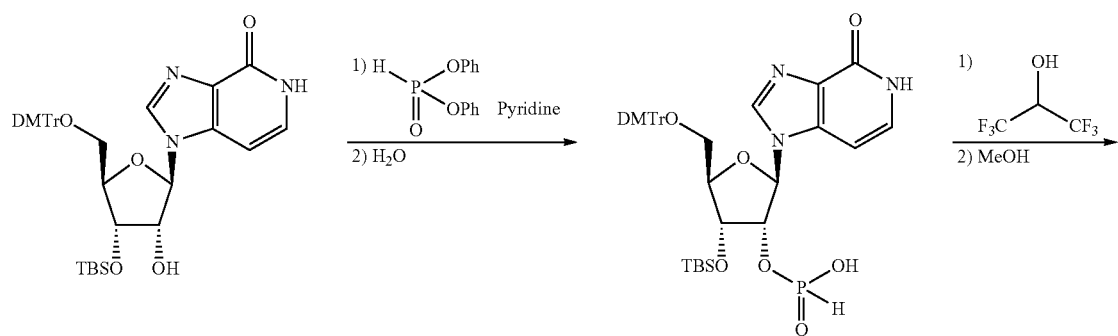
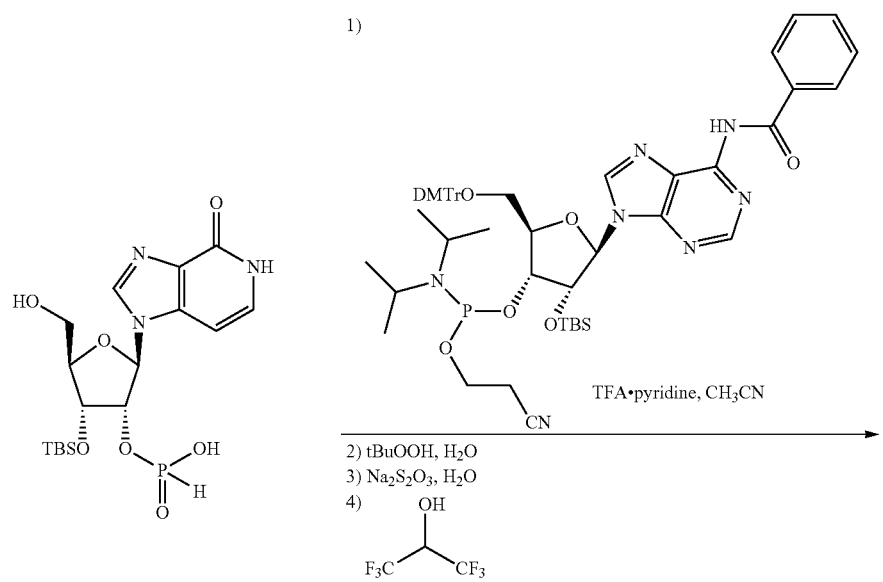
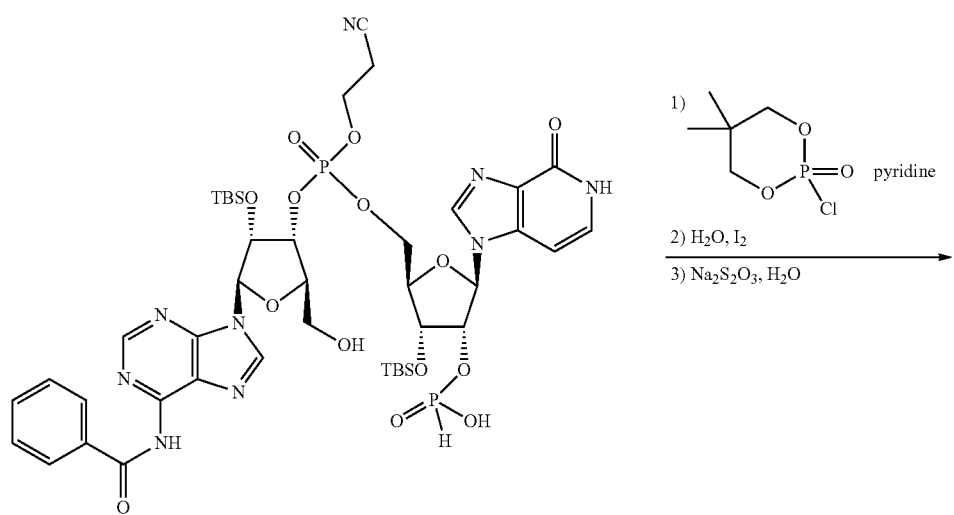

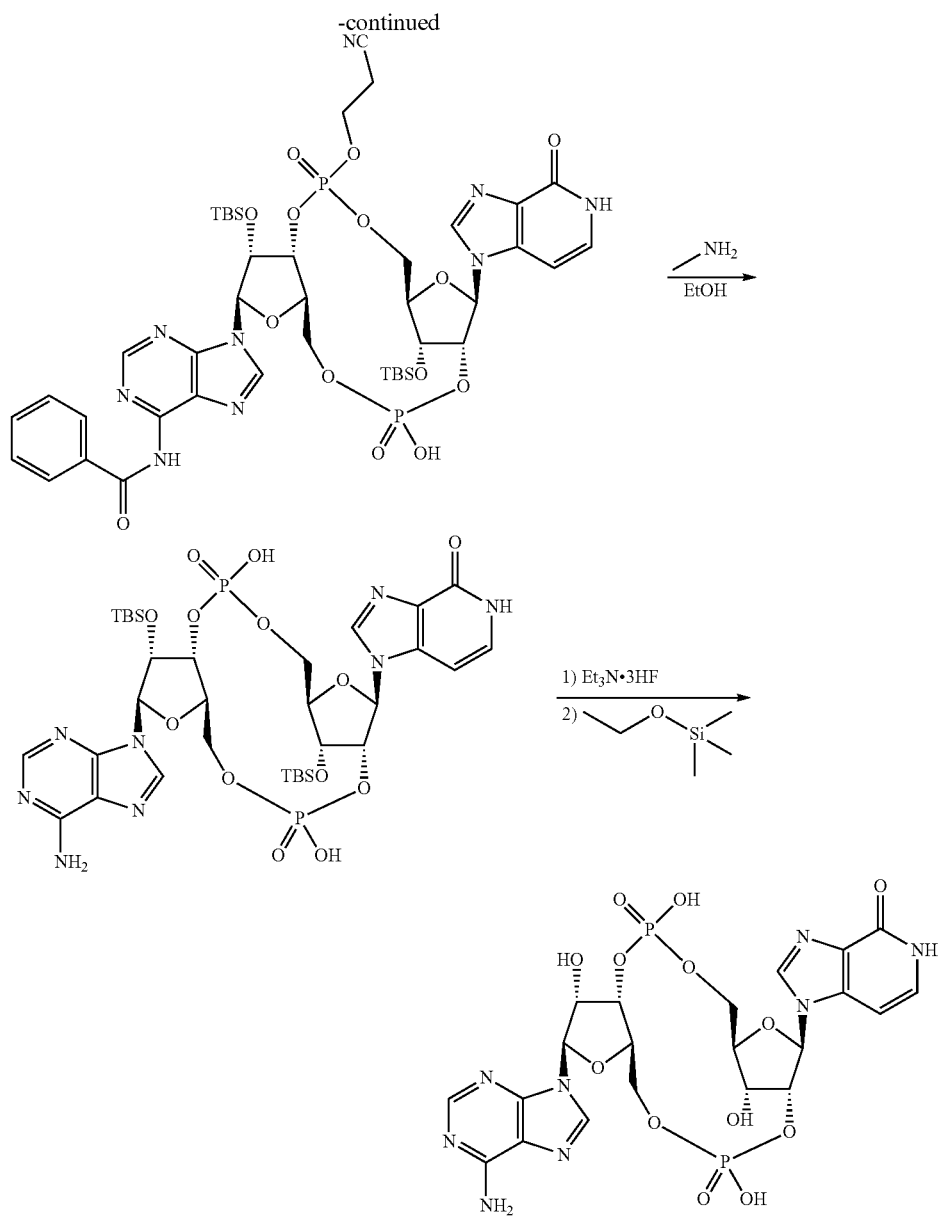

A) (2R,3R,4R,5R)-2-((benzoyloxy)methyl)-5-(4-oxo-4,5-dihydro-1H-imidazo[4,5-c]pyridin-1-yl)tetrahydrofuran-3,4-diyl dibenzoate To 4-chloro-1H-imidazo[4,5-c]pyridine (20 g) were added formic acid (123 mL) and water (30 mL) at room temperature, and the mixture was stirred at 100° C. for 2 hr. The mixture was cooled to room temperature, and concentrated under reduced pressure. To the residue was added conc. hydrochloric acid (100 mL), and the mixture was stirred at 100° C. for 1 hr. The mixture was concentrated under reduced pressure, the residue was suspended in MeOH (100 mL) and diisopropyl ether (100 mL), and triethylamine (50 mL) was added thereto. The resulting solid was collected by filtration, and dissolved in acetonitrile (600 mL). Trimethylsilyl N-(trimethylsilyl)acetimidate (38.2 mL) was added thereto at room temperature, and the mixture was stirred for 10 min. To the reaction mixture was added (2S,3R,4R,5R)-2-acetoxy-5-((benzoyloxy)methyl)tetrahydrofuran-3,4-diyl dibenzoate (79.0 g) at room temperature, and the mixture was heated to 80° C. To the reaction solution was added trimethylsilyl trifluoromethanesulfonate (28.2 mL), and the mixture was stirred under argon atmosphere overnight at 80° C. The mixture was cooled to room temperature, water (500 mL) was added thereto, and the resulting solid was collected by filtration. The solid was purified by silica gel column chromatography (methanol/ethyl acetate) to give the title compound (25.9 g). $^1$H NMR (400 MHz, CDCl$_3$) δ 4.65-4.96 (3H, m), 5.91 (2H, brs), 6.23-6.42 (1H, m), 6.64 (1H, brs), 7.15 (1H, brs), 7.32-7.56 (9H, m), 7.92-8.15 (7H, m), 12.11-12.50 (1H, m). MS: [M+H]$^+$ 580.1

B) 1-((2R,3R,4S,5R)-3,4-dihydroxy-5-(hydroxymethyl)tetrahydrofuran-2-yl)-1H-imidazo[4,5-c]pyridin-4(5H)-one To (2R,3R,4R,5R)-2-((benzoyloxy)methyl)-5-(4-oxo-4,5-dihydro-1H-imidazo[4,5-c]pyridin-1-yl)tetrahydrofuran-3,4-diyl dibenzoate (30.0 g) was added 40% methylamine methanol solution (200 mL), and the mixture was stirred under argon atmosphere at room temperature for 1 hr, and concentrated under reduced pressure. The residue was recrystallized from hexane-ethyl acetate to give the title compound (11.2 g). MS: [M+H]$^+$268.1

C) 1-((2R,3R,4S,5R)-5-((bis(4-methoxyphenyl)(phenyl)methoxy)methyl)-3,4-dihydroxytetrahydrofuran-2-yl)-1H-imidazo[4,5-c]pyridin-4(5H)-one To a solution of 1-((2R,3R,4S,5R)-3,4-dihydroxy-5-(hydroxymethyl)tetrahydrofuran-2-yl)-1H-imidazo[4,5-c]pyridin-4(5H)-one (18.0 g) in pyridine (140 mL) was added 4,4'-dimethoxytrityl chloride (18.46 g) at room temperature, and the mixture was stirred at room temperature for 1 hr. The reaction mixture was concentrated under reduced pressure, to the residue was added water, and the mixture was extracted with ethyl acetate. The obtained extract was washed with saturated brine, dried over anhydrous sodium sulfate, and concentrated under reduced pressure. The residue was purified by silica gel column chromatography (methanol/ethyl acetate) to give the title compound (18.2 g). MS: [M+H]$^+$ 570.2

D) 1-((2R,3R,4S,5R)-5-((bis(4-methoxyphenyl)(phenyl)methoxy)methyl)-4-((tert-butyldimethylsilyl)oxy)-3-hydroxytetrahydrofuran-2-yl)-1H-imidazo[4,5-c]pyridin-4(5H)-one To a solution of 1-((2R,3R,4S,5R)-5-((bis(4-methoxyphenyl)(phenyl)methoxy)methyl)-3,4-dihydroxytetrahydrofuran-2-yl)-1H-imidazo[4,5-c]pyridin-4(5H)-one (18.02 g) in DMF (158 mL) were added imidazole (4.30 g) and tert-butyldimethylchlorosilane (5.72 g), and the mixture was stirred at room temperature for 3 hr. tert-Butyldimethylchlorosilane (2.38 g) was added again thereto, and the mixture was stirred for 3 hr. The reaction mixture was diluted with water, and extracted with ethyl acetate. The extract was washed with saturated brine, dried over anhydrous sodium sulfate, and concentrated under reduced pressure. The residue was purified by silica gel column chromatography (ethyl acetate/hexane). The isolated regioisomer of the title compound was dissolved in MeOH and triethylamine, and the solution was stirred overnight at room temperature. The reaction solution was concentrated, and the residue was purified by silica gel column chromatography (ethyl acetate/hexane) to give the title compound (11.5 g). MS: [M+H]$^+$ 684.2

E) (2R,3R,4R,5R)-5-((bis(4-methoxyphenyl)(phenyl)meth oxy)methyl)-4-((tert-butyldimethylsilyl)oxy)-2-(4-oxo-4,5-dihydro-1H-imidazo[4,5-c]pyridin-1-yl)tetrahydrofuran-3-yl hydrogen phosphonate To a mixture of 1-((2R,3R,4S,5R)-5-((bis(4-methoxyphenyl)(phenyl)methoxy)methyl)-4-((tert-butyldimethylsilyl)oxy)-3-hydroxytetrahydrofuran-2-yl)-1H-imidazo[4,5-c]pyridin-4(5H)-one (8.0 g) and pyridine (117 mL) was added diphenyl phosphite (4.5 mL). The mixture was stirred at room temperature for 1 hr. Water (20 mL) was added to the reaction mixture. The mixture was stirred at room temperature for 30 min, and the reaction mixture was diluted with water, and extracted with ethyl acetate. The extract was washed with saturated brine, and dried over anhydrous magnesium sulfate, and the solvent was evaporated under reduced pressure. The residue was purified by silica gel column chromatography (methanol/ethyl acetate) to give the title compound (8.5 g). MS: [M+H]$^+$ 748.3

F) (2R,3R,4R,5R)-4-((tert-butyldimethylsilyl)oxy)-5-(hydroxymethyl)-2-(4-oxo-4,5-dihydro-1H-imidazo[4,5-c]pyridin-1-yl)tetrahydrofuran-3-yl hydrogen phosphonate A mixture of (2R,3R,4R,5R)-5-((bis(4-methoxyphenyl)(phenyl)methoxy)methyl)-4-((tert-butyldimethylsilyl)oxy)-2-(4-oxo-4,5-dihydro-1H-imidazo[4,5-c]pyridin-1-yl)tetrahydrofuran-3-yl hydrogen phosphonate (8.2 g) and 1,1,1,3,3,3-hexafluoropropan-2-ol (30 mL) was stirred at room temperature for 2 hr. Methanol (10 mL) was added thereto, the mixture was stirred at 60° C. for 1 hr, and the solvent was evaporated under reduced pressure. The residue was recrystallized from ethyl acetate and diisopropyl ether to give the title compound (4.3 g). MS: [M+H]$^+$ 446.1

G) (2R,3R,4R,5R)-5-((((((2R,3R,4R,5R)-5-(6-benzamido-9H-purin-9-yl)-4-((tert-butyldimethylsilyl)oxy)-2-(hydroxymethyl)tetrahydrofuran-3-yl)oxy)(2-cyanoethoxy)phosphoryl)oxy)methyl)-4-((tert-butyldimethylsilyl)oxy)-2-(4-oxo-4,5-dihydro-1H-imidazo[4,5-c]pyridin-1-yl)tetrahydrofuran-3-yl hydrogen phosphonate (2R,3R,4R,5R)-4-((tert-Butyldimethylsilyl)oxy)-5-(hydroxymethyl)-2-(4-oxo-4,5-dihydro-1H-imidazo[4,5-c]pyridin-1-yl)tetrahydrofuran-3-yl hydrogen phosphonate (250 mg) and N-benzoyl-5'-O-(bis(4-methoxyphenyl)(phenyl)methyl)-2'-O-(tert-butyl(dimethyl)silyl)-3'-O-((2-cyanoethoxy)(diisopropylamino)phosphino)adenosine (776 mg) were subjected to azeotropic dehydration with anhydrous acetonitrile, and anhydrous acetonitrile (5.61 mL) was added thereto. To the mixture was added pyridine 2,2,2-trifluoroacetate (271 mg), and the mixture was stirred at room temperature for 40 min. 70% tert-Butyl hydroperoxide aqueous solution (231 µL) was added thereto, and the mixture was stirred at room temperature for 20 min. To the reaction mixture was added a mixture of sodium thiosulfate (1.3 g) and water (3 mL), and the mixture was concentrated under reduced pressure. To the residue was added 1,1,1,3,3,3-hexafluoropropan-2-ol (15 mL), and the mixture was stirred at room temperature for 1 hr. The reaction mixture was concentrated under reduced pressure, and the residue was purified by silica gel column chromatography (ethyl acetate/hexane and methanol/ethyl acetate) to give the title compound (170 mg). MS: [M+H]$^+$ 1046.3

H) N-(9-((5R,7R,8R,12aR,14R,15R,15aR,16R)-15,16-bis((tert-butyl(dimethyl)silyl)oxy)-2-(2-cyanoethoxy)-10-hydroxy-2,10-dioxido-7-(4-oxo-4,5-dihydro-1H-imidazo[4,5-c]pyridin-1-yl)octahydro-12H-5,8-methanofuro[3,2-l][1,3,6,9,11,2,10]pentaoxadiphosphacyclotetradecin-14-yl)-9H-purin-6-yl)benzamide (2R,3R,4R,5R)-5-((((((2R,3R,4R,5R)-5-(6-Benzamido-9H-purin-9-yl)-4-((tert-butyldimethylsilyl)oxy)-2-(hydroxymethyl)tetrahydrofuran-3-yl)oxy)(2-cyanoethoxy)

phosphoryl)oxy)methyl)-4-((tert-butyldimethylsilyl)oxy)-2-(4-oxo-4,5-dihydro-1H-imidazo[4,5-c]pyridin-1-yl)tetrahydrofuran-3-yl hydrogen phosphonate (160 mg) was subjected to azeotropic dehydration with anhydrous pyridine, and anhydrous pyridine (3.0 mL) was added thereto. To the mixture was added 2-chloro-5,5-dimethyl-1,3,2-dioxaphosphinane 2-oxide (99 mg) at room temperature, and the mixture was stirred at room temperature for 1 hr. Water (96 μL) and iodine (50.5 mg) were added thereto, and the mixture was stirred at room temperature for additional 20 min. To the reaction mixture was added a mixture of sodium thiosulfate (190 mg) and water (0.4 mL), and the mixture was concentrated under reduced pressure. The residue was purified by silica gel column chromatography (methanol/ethyl acetate) to give the title compound (10.6 mg). MS: [M+H]$^+$1044.3

I) 1-((5R,7R,8R,12aR,14R,15R,15aR,16R)-14-(6-amino-9H-purin-9-yl)-15,16-bis((tert-butyl(dimethyl)silyl)oxy)-2,10-dihydroxy-2,10-dioxidooctahydro-12H-5,8-methanofuro[3,2-1][1,3,6,9,11,2,10]pentaoxadiphosphacyclotetradecin-7-yl)-1,5-dihydro-4H-imidazo[4,5-c]pyridin-4-one To N-(9-((5R,7R,8R,12aR,14R,15R,15aR,16R)-15,16-bis((tert-butyl(dimethyl)silyl)oxy)-2-(2-cyanoethoxy)-10-hydroxy-2,10-dioxido-7-(4-oxo-4,5-dihydro-1H-imidazo[4,5-c]pyridin-1-yl)octahydro-12H-5,8-methanofuro[3,2-1][1,3,6,9,11,2,10]pentaoxadiphosphacyclotetradecin-14-yl)-9H-purin-6-yl)benzamide (10.6 mg) was added 40% methylamine ethanol solution (5.0 mL), and the mixture was stirred under argon atmosphere at room temperature for 1 hr, and concentrated under reduced pressure. The residue was purified by silica gel column chromatography (methanol/ethyl acetate) to give the title compound (9.0 mg). MS: [M+H]$^+$ 887.2

J) 1-((5R,7R,8R,12aR,14R,15R,15aS,16R)-14-(6-amino-9H-purin-9-yl)-2,10,15,16-tetrahydroxy-2,10-dioxidooctahydro-12H-5,8-methanofuro[3,2-1][1,3,6,9,11,2,10]pentaoxadiphosphacyclotetradecin-7-yl)-1,5-dihydro-4H-imidazo[4,5-c]pyridin-4-one To 1-((5R,7R,8R,12aR,14R,15R,15aR,16R)-14-(6-amino-9H-purin-9-yl)-15,16-bis((tert-butyl(dimethyl)silyl)oxy)-2,10-dihydroxy-2,10-dioxidooctahydro-12H-5,8-methanofuro[3,2-1][1,3,6,9,11,2,10]pentaoxadiphosphacyclotetradecin-7-yl)-1,5-dihydro-4H-imidazo[4,5-c]pyridin-4-one (9.0 mg) were added methanol (1.0 mL) and triethylamine trihydrofluoride (165 μL). The reaction mixture was concentrated to remove the methanol, and the residue was stirred at 55° C. for 1 hr. The mixture was cooled to room temperature, ethoxy(trimethyl)silane (0.90 mL) was added thereto, and the mixture was stirred at room temperature for 1 hr. The reaction mixture was concentrated under reduced pressure, and the residue was purified by C18 column chromatography (acetonitrile/10 mM triethylammonium acetate buffer solution) to give the title compound (0.3 mg). $^1$H NMR (400 MHz, D$_2$O) a 4.15 (2H, d, J=11.5 Hz), 4.46 (4H, brs), 4.56-4.62 (1H, m), 4.98-4.99 (21-1, m), 6.05-6.20 (2H, m), 6.79-6.87 (1H, m), 7.06-7.12 (1H, m), 8.00 (1H, s), 7.96-8.10 (1H, m), 8.23 (2H, s). $^{31}$P NMR (162 MHz, D$_2$O) δ−2.36, −1.94.

Example 11

Synthesis of 2-amino-9-((5R,7R,8R,12aR,14R,15R,15aS,16R)-14-(4-amino-1H-imidazo[4,5-c]pyridin-1-yl)-2,10,15,16-tetrahydroxy-2,10-dioxidooctahydro-12H-5,8-methanofuro[3,2-1][1,3,6,9,11,2,10]pentaoxadiphosphacyclotetradecin-7-yl)-1,9-dihydro-6H-purin-6-one di-triethylamine salt

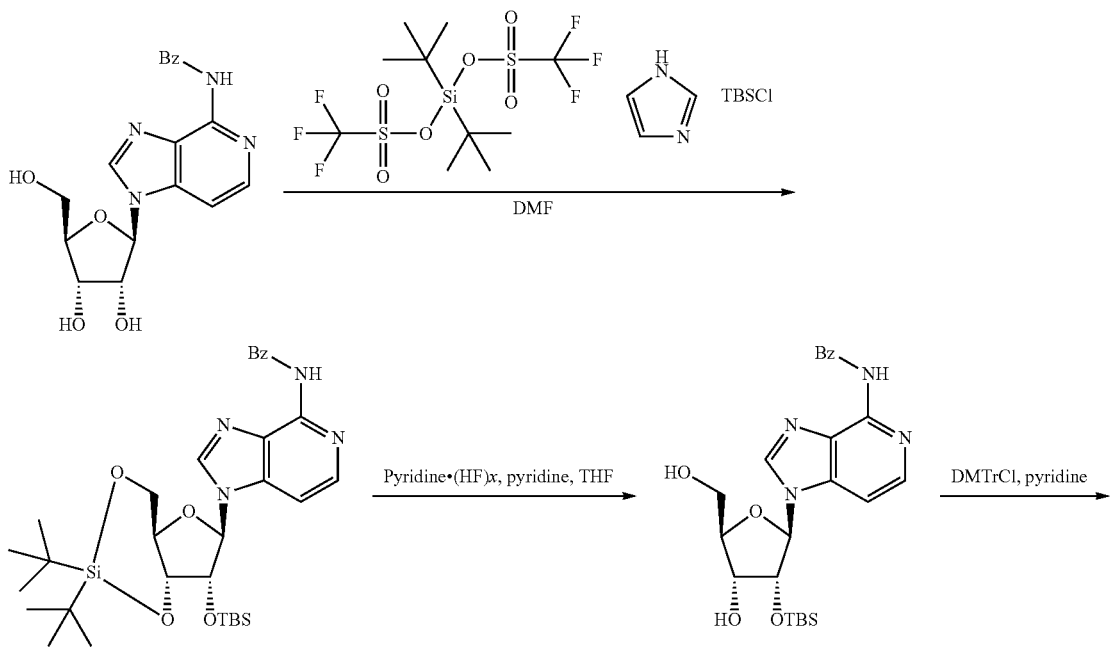

-continued
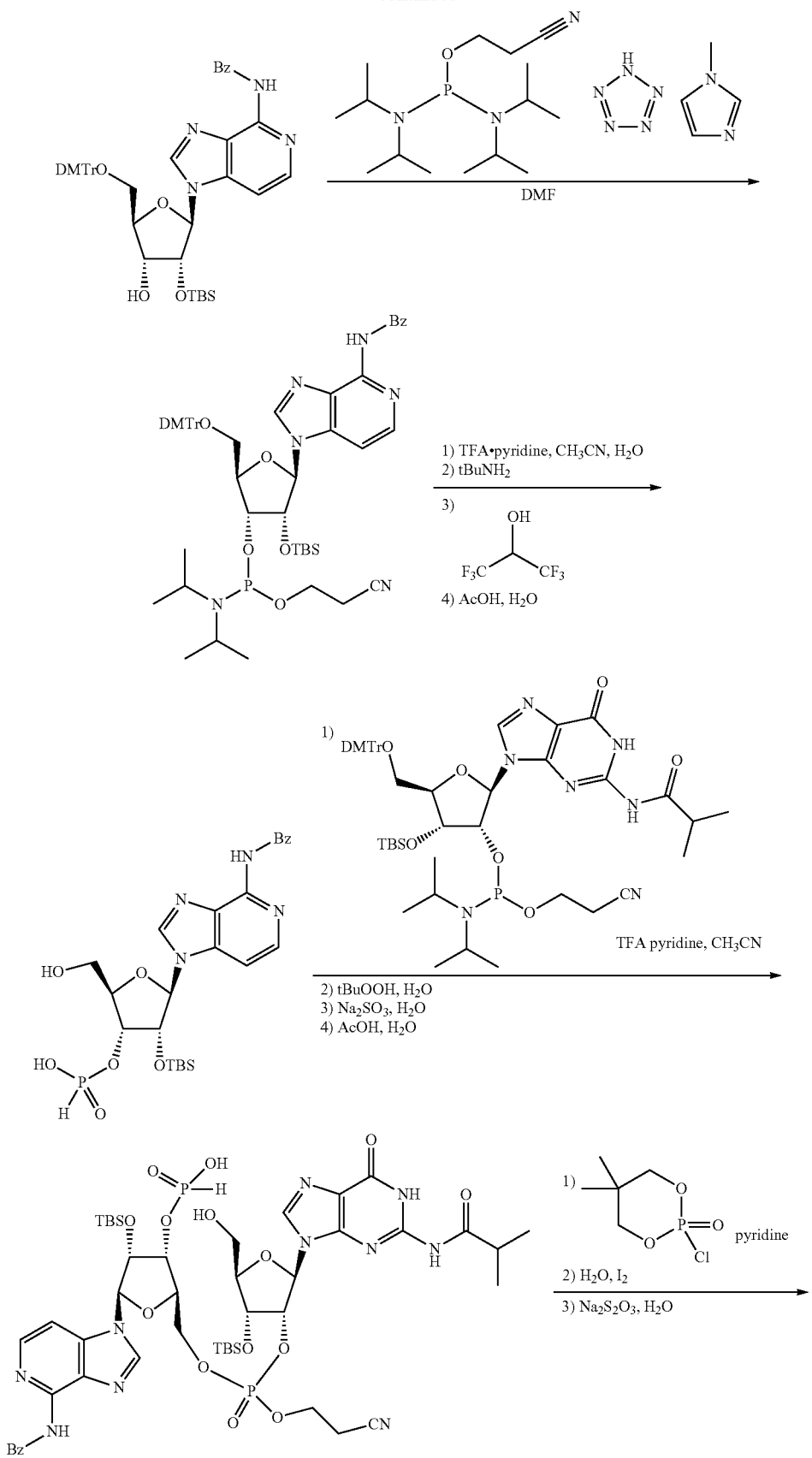

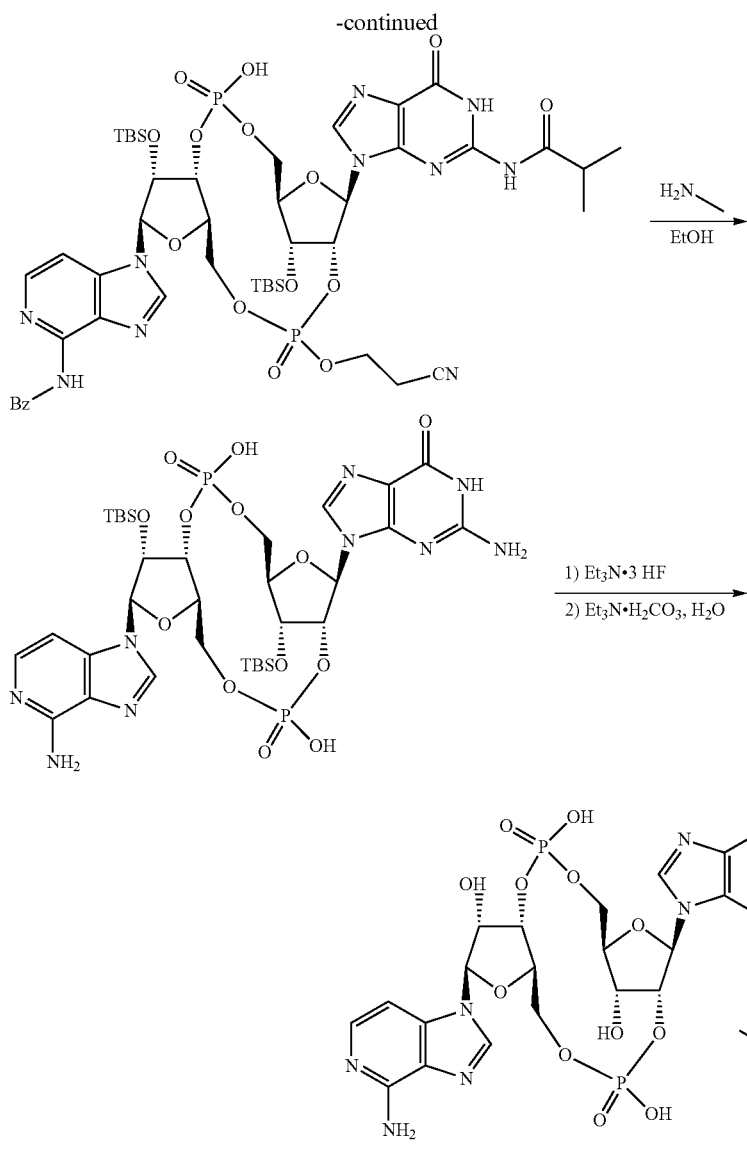

A) N-benzoyl-1-(2-O-(tert-butyl(dimethyl)silyl)-3,5-O-(di-tert-butylsilylene)-beta-D-ribofuranosyl)-1H-imidazo[4,5-c]pyridin-4-amine N-Benzoyl-1-(beta-D-ribofuranosyl)-1H-imidazo[4,5-c]pyridin-4-amine (2.41 g) was dissolved in DMF (25 mL), di-tert-butylsilanediyl bis(trifluoromethanesulfonate) (2.32 mL) was added thereto at 0° C., and the mixture was stirred at 0° C. for 75 min. Di-tert-butylsilanediyl bis(trifluoromethanesulfonate) (0.63 mL) was added thereto at 0° C., and the mixture was stirred at 0° C. for additional 30 min. Di-tert-butylsilanediyl bis(trifluoromethanesulfonate) (0.63 mL) was added thereto at 0° C., and the mixture was stirred at 0° C. for additional 35 min. To the reaction mixture was added 1H-imidazole (2.22 g), and the mixture was stirred at room temperature for 10 min. tert-Butyldimethylchlorosilane (1.18 g) was added thereto, and the mixture was stirred at 60° C. for 1.5 hr. tert-Butyldimethylchlorosilane (0.294 g) was added thereto, and the mixture was stirred at 60° C. for 14.5 hr. The reaction mixture was diluted with water, and extracted with ethyl acetate. The extract was washed with saturated brine, and dried over anhydrous sodium sulfate, and the solvent was evaporated under reduced pressure. The residue was purified by silica gel column chromatography (ethyl acetate/hexane) to give the title compound (3.28 g). MS: [M+H]$^+$ 625.2.

B) N-benzoyl-1-(2-O-(tert-butyl(dimethyl)silyl)-beta-D-ribofuranosyl)-1H-imidazo[4,5-c]pyridin-4-amine Pyridinium poly(hydrogen fluoride) (1.86 mL) was dissolved in pyridine (10 mL) at 0° C., the solution was added to a solution of N-benzoyl-1-(2-O-(tert-butyl(dimethyl)silyl)-3,5-O-(di-tert-butylsilylene)-beta-D-ribofuranosyl)-1H-imidazo[4,5-c]pyridin-4-amine (1.64 g) in THF (13 mL) at 0° C., and the mixture was stirred at 0° C. for 8 min. This reaction was repeated twice. The reaction solutions were combined, diluted with water, and extracted with ethyl acetate. The extract was washed with saturated brine, and dried over anhydrous sodium sulfate, and the solvent was evaporated under reduced pressure. The residue was purified by silica gel column chromatography (ethyl acetate/hexane and methanol/ethyl acetate) to give the title compound (2.24 g). MS: [M+H]⁺ 485.1.

C) N-benzoyl-1-(5-O-(bis(4-methoxyphenyl)(phenyl)methyl)-2-O-(tert-butyl(dimethyl)silyl)-beta-D-ribofuranosyl)-1H-imidazo[4,5-c]pyridin-4-amine N-Benzoyl-1-(2-O-(tert-butyl(dimethyl)silyl)-beta-D-ribofuranosyl)-1H-imidazo[4,5-c]pyridin-4-amine (2.24 g) was dissolved in pyridine (25 mL), 4,4'-dimethoxytrityl chloride (2.04 g) was added thereto at room temperature, and the mixture was stirred at room temperature for 4.5 hr. The reaction mixture was concentrated under reduced pressure, to the residue was added water, and the mixture was extracted with ethyl acetate. The extract was washed with saturated brine, and dried over anhydrous sodium sulfate, and the solvent was evaporated under reduced pressure. The residue was purified by silica gel column chromatography (ethyl acetate/hexane) to give the title compound (3.29 g). MS: [M+H]⁺787.3.

D) N-benzoyl-1-(5-O-(bis(4-methoxyphenyl)(phenyl)methyl)-2-O-(tert-butyl(dimethyl)silyl)-3-O-((2-cyanoethoxy)(diisopropylamino)phosphino)-beta-D-ribofuranosyl)-1H-imidazo[4,5-c]pyridin-4-amine N-Benzoyl-1-(5-O-(bis(4-methoxyphenyl)(phenyl)methyl)-2-O-(tert-butyl(dimethyl)silyl)-beta-D-ribofuranosyl)-1H-imidazo[4,5-c]pyridin-4-amine (3.29 g) was dissolved in anhydrous DMF (9.5 mL), to the solution were added 3-((bis(diisopropylamino)phosphino)oxy)propanenitrile (2.98 mL), 1H-tetrazole (0.328 g) and 1-methyl-1H-imidazole (0.185 mL), and the mixture was stirred under argon atmosphere at room temperature for 2.5 hr. To the reaction solution was added saturated aqueous sodium bicarbonate solution, and the mixture was extracted with ethyl acetate. The extract was washed with saturated brine, and dried over anhydrous sodium sulfate, and the solvent was evaporated under reduced pressure. The residue was purified by silica gel column chromatography (ethyl acetate/hexane, containing 0.5% triethylamine) to give the title compound (3.85 g). MS: [M+H]987.4.

E) N-benzoyl-1-(2-O-(tert-butyl(dimethyl)silyl)-3-O-(hydroxy(oxido)phosphoranyl)-beta-D-ribofuranosyl)-1H-imidazo[4,5-c]pyridin-4-amine N-Benzoyl-1-(5-O-(bis(4-methoxyphenyl)(phenyl)methyl)-2-O-(tert-butyl(dimethyl)silyl)-3-O-((2-cyanoethoxy)(diisopropylamino)phosphino)-beta-D-ribofuranosyl)-1H-imidazo[4,5-c]pyridin-4-amine (3.85 g) was dissolved in acetonitrile (30 mL), pyridine 2,2,2-trifluoroacetate (0.904 g) and water (0.141 mL) were added thereto at room temperature, and the mixture was stirred at room temperature for 30 min. To the reaction solution was added 2-methylpropan-2-amine (9 mL) at room temperature, and the mixture was stirred at room temperature for 40 min. The reaction mixture was concentrated under reduced pressure, and to the residue was added 1,1,1,3,3,3-hexafluoropropan-2-ol (25 mL), and the mixture was stirred at room temperature for 3.5 hr. The reaction mixture was concentrated under reduced pressure, acetic acid (20 mL) and water (5 mL) were added thereto, and the mixture was stirred at room temperature for 1 hr. The reaction mixture was concentrated under reduced pressure, and the residue was purified by silica gel column chromatography (methanol/ethyl acetate) to give the title compound (1.85 g). MS: [M+H]⁺549.1.

F) (2R,3R,4R,5R)-5-(4-benzamido-1H-imidazo[4,5-c]pyridin-1-yl)-4-((tert-butyldimethylsilyl)oxy)-2-((((((2R,3R,4R,5R)-4-((tert-butyldimethylsilyl)oxy)-5-(hydroxymethyl)-2-(2-isobutyl amido-6-oxo-1H-purin-9(6H)-yl)tetrahydrofuran-3-yl)oxy)(2-cyanoethoxy)phosphoryl)oxy)methyl)tetrahydrofuran-3-yl hydrogen phosphonate N-Benzoyl-1-(2-O-(tert-butyl(dimethyl)silyl)-3-O-(hydroxy(oxido)phosphoranyl)-beta-D-ribofuranosyl)-1H-imidazo[4,5-c]pyridin-4-amine (300 mg) and 5'-O-(bis(4-methoxyphenyl)(phenyl)methyl)-3'-O-(tert-butyl(dimethyl)silyl)-2'-O-((2-cyanoethoxy)(diisopropylamino)phosphino)-N-isobutyrylguanosine (637 mg) were subjected to azeotropic dehydration with anhydrous acetonitrile (three times), and suspended in anhydrous acetonitrile (6 mL). Pyridine 2,2,2-trifluoroacetate (264 mg) was added thereto, and the mixture was stirred under argon atmosphere at room temperature for 1 hr. 70% tert-Butyl hydroperoxide aqueous solution (0.225 mL) was added thereto, and the mixture was stirred at room temperature for additional 1 hr. The reaction mixture was quenched with sodium thiosulfate (400 mg) and water (1.5 mL), and the solvent was evaporated under reduced pressure. The residue was dissolved in 80% acetic acid (5 mL), and the solution was stirred at room temperature for 45 min. The reaction mixture was concentrated under reduced pressure, and the residue was subjected to azeotropic dehydration with anhydrous acetonitrile and toluene. The residue was purified by silica gel column chromatography (methanol/ethyl acetate) to give the title compound (469 mg). MS: [M+H]⁺ 1131.4.

G) N-(1-((5R,7R,8R,12aR,14R,15R,15aR,16R)-15,16-bis((tert-butyl(dimethyl)silyl)oxy)-10-(2-cyanoethoxy)-2-hydroxy-7-(2-(isobutyrylamino)-6-oxo-1,6-dihydro-9H-purin-9-yl)-2,10-dioxidooctahydro-12H-5,8-methanofuro[3,2-1][1,3,6,9,11,2,10]pentaoxadiphosphacyclotetradecin-14-yl)-1H-imidazo[4,5-c]pyridin-4-yl)benzamide (2R,3R,4R,5R)-5-(4-Benzamido-1H-imidazo[4,5-c]pyridin-1-yl)-4-((tert-butyldimethylsilyl)oxy)-2-((((((2R,3R,4R,5R)-4-((tert-butyldimethylsilyl)oxy)-5-(hydroxymethyl)-2-(2-isobutylamido-6-oxo-1H-purin-9(6H)-yl)tetrahydrofuran-3-yl)oxy)(2-cyanoethoxy)phosphoryl)oxy)methyl)tetrahydrofuran-3-yl hydrogen phosphonate (469 mg) was subjected to azeotropic dehydration with anhydrous acetonitrile and anhydrous pyridine, and suspended in anhydrous pyridine (10 mL). 2-Chloro-5,5-dimethyl-1,3,2-dioxaphosphinane 2-oxide (268 mg) was added thereto, and the mixture was stirred under argon atmosphere at room temperature for 15 min. Water (1 mL) and iodine (158 mg) were added thereto, and the mixture was stirred at room temperature for additional 13 min. The reaction mixture was quenched with sodium thiosulfate (170 mg) and water (0.5 mL), the solvent was evaporated under reduced pressure, and the residue was subjected to azeotropic dehydration with toluene. The residue was purified by silica gel column chromatography (methanol/ethyl acetate) to give the title compound (419 mg). MS: [M+H]⁺ 1129.3

H) 2-amino-9-((5R,7R,8R,12aR,14R,15R,15aR, 16R)-14-(4-amino-1H-imidazo[4,5-c]pyridin-1-yl)-15,16-bis((tert-butyl(dimethyl)silyl)oxy)-2,10-dihydroxy-2,10-dioxidooctahydro-12H-5,8-methanofuro [3,2-1][1,3,6,9,11,2,10] pentaoxadiphosphacyclotetradecin-7-yl)-1,9-dihydro-6H-purin-6-one N-(1-((5R,7R,8R,12aR,14R,15R,15aR,16R)-15,16-Bis((tert-butyl(dimethyl)silyl)oxy)-10-(2-cyanoethoxy)-2-hydroxy-7-(2-(isobutyrylamino)-6-oxo-1,6-dihydro-9H-purin-9-yl)-2,10-dioxidooctahydro-12H-5,8-methanofuro[3,2-1][1,3,6,9,11,2,10]pentaoxadiphosphacyclotetradecin-14-yl)-1H-imidazo[4,5-c]pyridin-4-yl)benzamide (419 mg) was dissolved in 33% methylamine ethanol solution (10.0 mL), and the solution was stirred under argon atmosphere at room temperature for 18.5 hr. 33% Methylamine ethanol solution (5 mL) was added thereto, the mixture was stirred for additional 3 hr, and the solvent was evaporated under reduced pressure. The residue was dissolved in 33% methylamine ethanol solution (10.0 mL), the solution was stirred at room temperature for 1 hr, and the solvent was evaporated under reduced pressure. The residue was purified by silica gel column chromatography (methanol/ethyl acetate) to give the title compound (173 mg). MS: [M+H]⁺ 902.3.

I) 2-amino-9-((5R,7R,8R,12aR,14R,15R,15aS,16R)-14-(4-amino-1H-imidazo[4,5-c]pyridin-1-yl)-2,10,15,16-tetrahydroxy-2,10-dioxidooctahydro-12H-5,8-methanofuro[3,2-1][1,3,6,9,11,2,10] pentaoxadiphosphacyclotetradecin-7-yl)-1,9-dihydro-6H-purin-6-one di-triethylamine salt To 2-amino-9-((5R,7R,8R,12aR,14R,15R,15aR,16R)-14-(4-amino-1H-imidazo[4,5-c]pyridin-1-yl)-15,16-bis((tert-butyl(dimethyl)silyl)oxy)-2,10-dihydroxy-2,10-dioxidooctahydro-12H-5,8-methanofuro[3,2-1][1,3,6,9,11,2,10] pentaoxadiphosphacyclotetradecin-7-yl)-1,9-dihydro-6H-purin-6-one (173 mg) was added triethylamine trihydrofluoride (0.625 mL), and the mixture was stirred at 50° C. for 3 hr. The mixture was cooled to room temperature, and neutralized with 1 M aqueous triethylammonium bicarbonate solution, and the solvent was evaporated under reduced pressure. The residue was purified by C18 silica gel column chromatography (10 mM triethylammonium acetate buffer solution/acetonitrile), and the obtained solid was freeze-dried to give the title compound (123 mg). ¹H NMR (300 MHz, D₂O) δ 1.25 (18H, t, J=7.4 Hz), 3.17 (12H, q, J=7.2 Hz), 3.87-4.10 (1H, m), 4.11-4.30 (3H, m), 4.32-4.45 (2H, m), 4.52 (1H, d, J=3.8 Hz), 4.65 (1H, d, J=4.2 Hz), 4.97-5.10 (1H, m), 5.79 (1H, brs), 5.94 (2H, d, J=8.3 Hz), 7.10 (1H, d, J=6.8 Hz), 7.68-7.78 (1H, m), 7.83 (1H, S), 7.94-8.26 (1H, m). ³¹P NMR (121 MHz, D₂O) δ −1.36.

Example 12

Synthesis of 8-((5R,7R,8R,12aR,14S,15S,15aS,16R)-7-(6-amino-9H-purin-9-yl)-15,16-dihydroxy-2,10-dioxido-2,10-disulfanyloctahydro-12H-5,8-methanofuro[3,2-1][1,3,6,9,11,2,10] pentaoxadiphosphacyclotetradecin-14-yl)pyrazolo[1,5-a][1,3,5]triazin-4(3H)-one di-triethylamine salt (Optical Isomer)

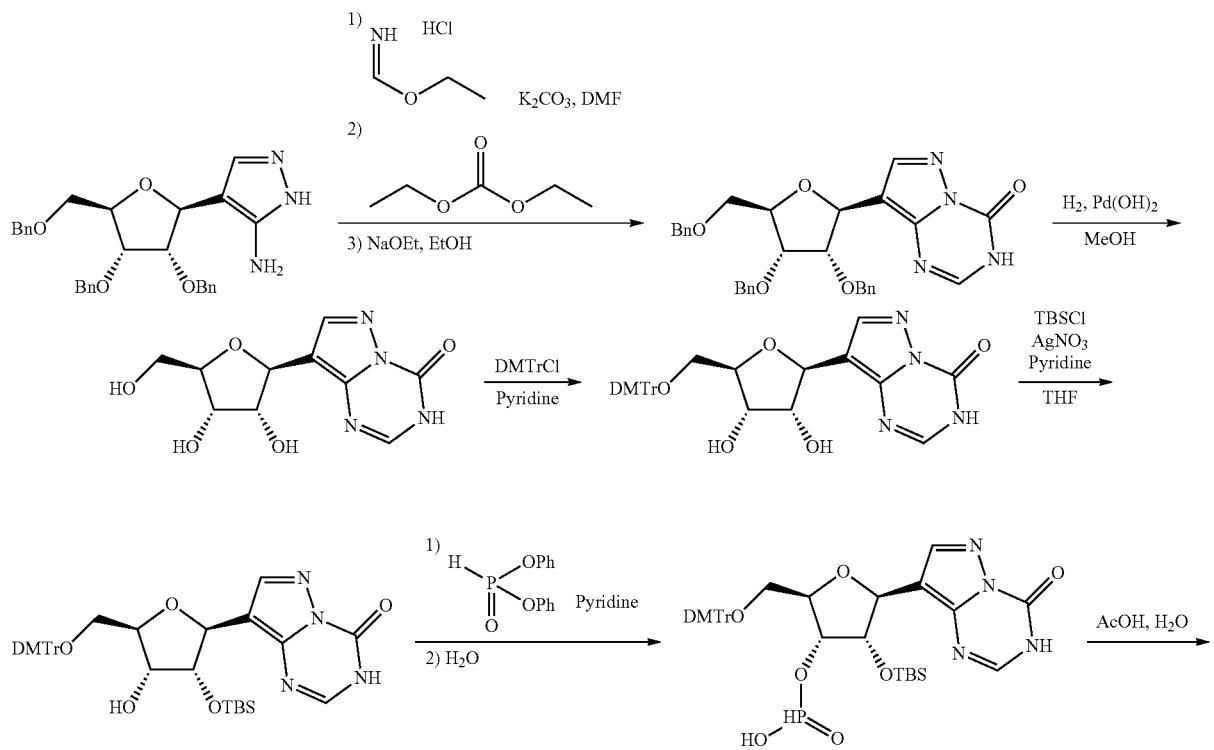

-continued
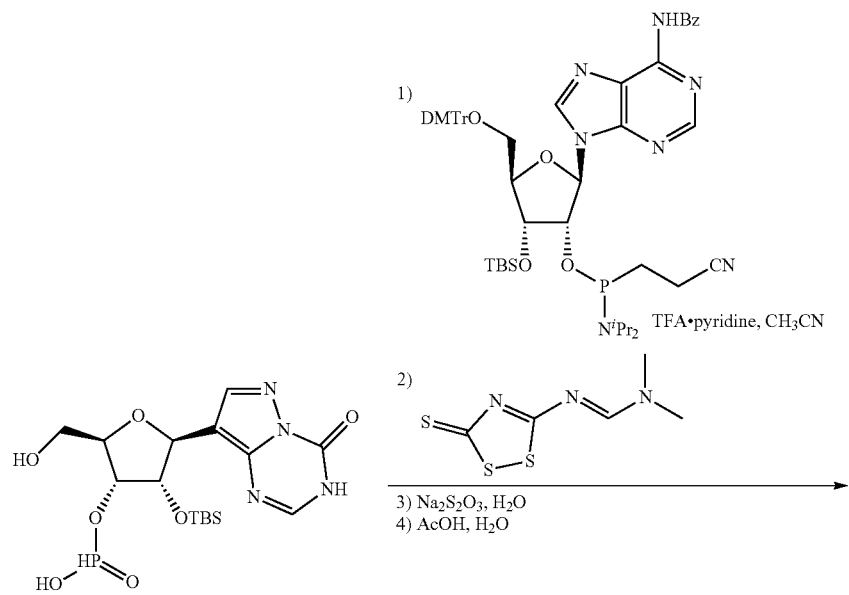
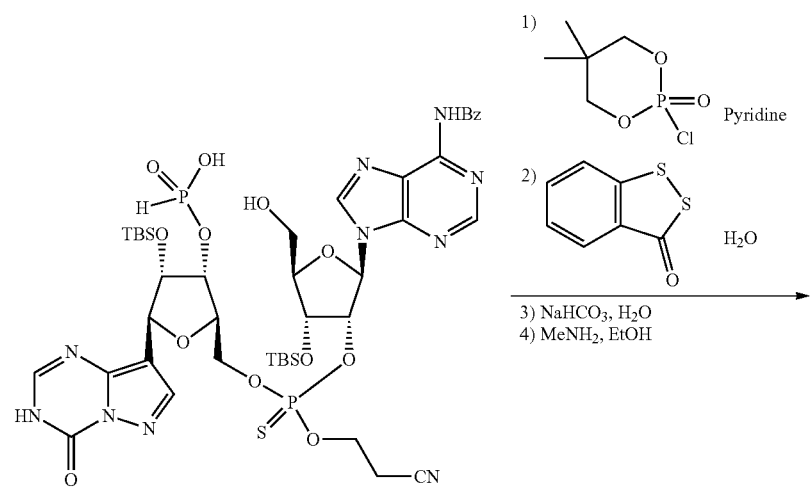
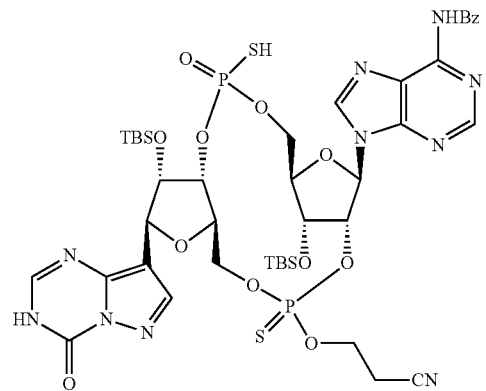

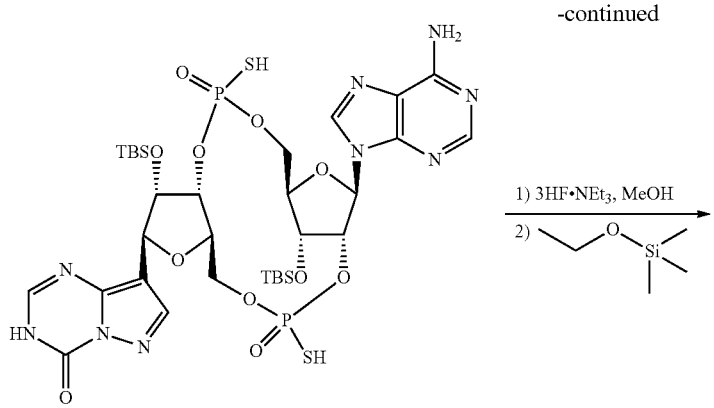 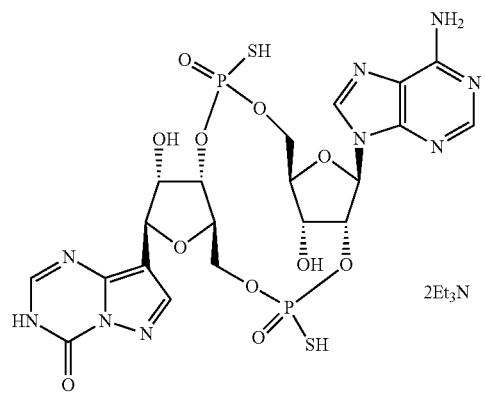

1) 3HF·NEt₃, MeOH
2) [TMS-O-ethyl reagent]

A) 8-((2S,3S,4R,5R)-3,4-bis(benzyloxy)-5-((benzyloxy)methyl)tetrahydrofuran-2-yl)pyrazolo[1,5-a][1,3,5]triazin-4(3H)-one To a solution of 4-((2S,3S,4R,5R)-3,4-bis(benzyloxy)-5-((benzyloxy)methyl)tetrahydrofuran-2-yl)-1H-pyrazol-5-amine (17.3 g) and potassium carbonate (24.6 g) in DMF (200 mL) was added ethyl formimidate hydrochloride (19.5 g) at room temperature. The reaction mixture was stirred overnight at room temperature. To the reaction mixture was added diethyl carbonate (126 g) at room temperature, and the reaction mixture was stirred at 100° C. for 1 hr. To the reaction mixture was added 20% sodium ethoxide ethanol solution (60.6 g) at room temperature. The reaction mixture was stirred at 100° C. for 30 min. The reaction mixture was neutralized with acetic acid at room temperature, and extracted with ethyl acetate. The extract was washed with water and saturated brine, dried over anhydrous sodium sulfate, and concentrated under reduced pressure. The residue was purified by silica gel column chromatography (ethyl acetate/hexane) to give the title compound (5.79 g). MS: [M+H]⁺ 539.1.

B) 8-((2S,3R,4S,5R)-3,4-dihydroxy-5-(hydroxymethyl)tetrahydrofuran-2-yl)pyrazolo[1,5-a][1,3,5]triazin-4(3H)-one A solution of 8-((2S,3S,4R,5R)-3,4-bis(benzyloxy)-5-((benzyloxy)methyl)tetrahydrofuran-2-yl)pyrazolo[1,5-a][1,3,5]triazin-4(3H)-one (3.49 g) and palladium hydroxide (1.37 g, 10% Pd) in methanol (30 mL) was stirred under hydrogen atmosphere overnight at room temperature. The catalyst was removed by filtration, and the filtrate was concentrated under reduced pressure to give the title compound (1.72 g). MS: [M+H]⁺ 269.0.

C) 8-((2S,3R,4S,5R)-5-((bis(4-methoxyphenyl)(phenyl)methoxy)methyl)-3,4-dihydroxytetrahydrofuran-2-yl)pyrazolo[1,5-a][1,3,5]triazin-4(3H)-one To a solution of 8-((2S,3R,4S,5R)-3,4-dihydroxy-5-(hydroxymethyl)tetrahydrofuran-2-yl)pyrazolo[1,5-a][1,3,5]triazin-4(3H)-one (1.72 g) in dehydrated pyridine (30 mL) was added 4,4'-dimethoxytrityl chloride (2.39 g) under ice-cooling. The reaction mixture was stirred under argon atmosphere at room temperature for 2 hr. To the reaction mixture was added 4,4'-dimethoxytrityl chloride (0.217 g) under ice-cooling. The reaction mixture was stirred under argon atmosphere at room temperature for 3 hr. To the reaction mixture was added 4,4'-dimethoxytrityl chloride (0.217 g) at room temperature. The reaction mixture was stirred under argon atmosphere at room temperature for 30 min. To the reaction mixture was added saturated aqueous sodium hydrogencarbonate solution at room temperature, and the mixture was extracted with ethyl acetate. The extract was washed with water and saturated brine, dried over anhydrous sodium sulfate, and concentrated under reduced pressure. The residue was purified by silica gel column chromatography (methanol/ethyl acetate) to give the title compound (1.62 g). MS: [M–H]⁻ 569.1.

D) 8-((2S,3R,4R,5R)-5-((bis(4-methoxyphenyl)(phenyl)methoxy)methyl)-3-((tert-butyldimethylsilyl)oxy)-4-hydroxytetrahydrofuran-2-yl)pyrazolo[1,5-a][1,3,5]triazin-4(3H)-one tert-Butyldimethylchlorosilane (536 mg) and silver(I) nitrate (604 mg) were added to a solution of 8-((2S,3R,4S,5R)-5-((bis(4-methoxyphenyl)(phenyl)methoxy)methyl)-3,4-dihydroxytetrahydrofuran-2-yl)pyrazolo[1,5-a][1,3,5]triazin-4(3H)-one (1.69 g) and dehydrated pyridine (1.20 mL) in dehydrated THF (20 mL) at room temperature under argon atmosphere. The reaction mixture was stirred at room temperature for 8 hr, and to the reaction mixture were added tert-butyldimethylchlorosilane (89 mg) and silver(I) nitrate (101 mg) at room temperature. The reaction mixture was stirred overnight at room temperature. The insoluble substance was removed by filtration, and washed with ethyl acetate. To the filtrate was added saturated aqueous sodium hydrogencarbonate solution, and the mixture was extracted with ethyl acetate. The extract was washed with saturated brine, dried over anhydrous sodium sulfate, and concentrated under reduced pressure. The residue was purified by silica gel column chromatography (methanol/ethyl acetate) to give the title compound (740 mg). MS: [M–H]⁻ 683.1.

E) (2R,3R,4S,5S)-2-((bis(4-methoxyphenyl)(phenyl)methoxy)methyl)-4-((tert-butyldimethylsilyl)oxy)-5-(4-oxo-3,4-dihydropyrazolo[1,5-a][1,3,5]triazin-8-yl)tetrahydrofuran-3-yl hydrogen phosphonate Diphenyl phosphite (0.41 mL) was added to a solution of 8-((2S,3R,4R,5R)-5-((bis(4-methoxyphenyl)(phenyl)methoxy)methyl)-3-((tert-butyldimethylsilyl)oxy)-4-hydroxytetrahydrofuran-2-yl)pyrazolo[1,5-a][1,3,5]triazin-4(3H)-one (740 mg) in pyridine (10 mL) at room temperature. The reaction mixture was stirred under argon atmosphere at room temperature for 1 hr. To the reaction mixture was added water (20 mL), and the mixture was stirred for 1 hr. The reaction mixture was poured into water at room temperature, and extracted with ethyl acetate. The extract was washed with water and saturated brine, dried over anhydrous sodium sulfate, and concentrated under reduced pressure. The residue was purified by silica gel column chromatography (methanol/ethyl acetate) to give the title compound (300 mg). MS: [M−H]⁻ 747.1.

F) (2R,3R,4S,5S)-4-((tert-butyldimethylsilyl)oxy)-2-(hydroxymethyl)-5-(4-oxo-3,4-dihydropyrazolo[1,5-a][1,3,5]triazin-8-yl)tetrahydrofuran-3-yl hydrogen phosphonate To (2R,3R,4S,5S)-2-((bis(4-methoxyphenyl)(phenyl)methoxy)methyl)-4-((tert-butyldimethylsilyl)oxy)-5-(4-oxo-3,4-dihydropyrazolo[1,5-a][1,3,5]triazin-8-yl)tetrahydrofuran-3-yl hydrogen phosphonate (300 mg) was added 80% aqueous acetic acid solution (10 mL), and the mixture was stirred at room temperature for 1 hr. The reaction mixture was concentrated under reduced pressure, and the residue was purified by silica gel column chromatography (methanol/ethyl acetate) to give the title compound (170 mg). MS: [M+H]⁺ 447.0.

G) (2R,3R,4S,5S)-2-((((((2R,3R,4R,5R)-2-(6-benzamido-9H-purin-9-yl)-4-((tert-butyldimethylsilyl)oxy)-5-(hydroxymethyl)tetrahydrofuran-3-yl)oxy)(2-cyanoethoxy)phosphorothioyl)oxy)methyl)-4-((tert-butyldimethylsilyl)oxy)-5-(4-oxo-3,4-dihydropyrazolo[1,5-a][1,3,5]triazin-8-yl)tetrahydrofuran-3-yl hydrogen phosphonate (2R,3R,4S,5S)-4-((tert-Butyldimethylsilyl)oxy)-2-(hydroxymethyl)-5-(4-oxo-3,4-dihydropyrazolo[1,5-a][1,3,5]triazin-8-yl)tetrahydrofuran-3-yl hydrogen phosphonate (190 mg) and N-benzoyl-5'-O-(bis(4-methoxyphenyl)(phenyl)methyl)-3'-O-(tert-butyl(dimethyl)silyl)-2'-O-((2-cyanoethyl)(diisopropylamino)phosphino)adenosine (505 mg) were subjected to azeotropic process three times with dehydrated acetonitrile. To the residue were added dehydrated acetonitrile (5 mL) and pyridine 2,2,2-trifluoroacetate (164 mg). The reaction mixture was stirred under argon atmosphere at room temperature for 10 min, ((dimethylaminomethylidene)amino)-3H-1,2,4-dithiazoline-3-thione (96 mg) was added to the reaction mixture, and the mixture was stirred at room temperature for 20 min. To the reaction mixture was added an aqueous solution (0.2 mL) of sodium thiosulfate (0.2 g), and the mixture was concentrated under reduced pressure. To the residue was added 80% aqueous acetic acid solution (5 mL), the mixture was stirred at room temperature for 1 hr, and the reaction mixture was subjected to azeotropic process twice with acetonitrile. The residue was purified by silica gel column chromatography (methanol/ethyl acetate) to give the title compound (260 mg). MS: [M+H]⁺ 1063.2.

H) 8-((5R,7R,8R,12aR,14S,15S,15aR,16R)-7-(6-amino-9H-purin-9-yl)-15,16-bis((tert-butyl(dimethyl)silyl)oxy)-2,10-dioxido-2,10-disulfanyloctahydro-12H-5,8-methanofuro[3,2-l][1,3,6,9,11,2,10]pentaoxadiphosphacyclotetradecin-14-yl)pyrazolo[1,5-a][1,3,5]triazin-4(3H)-one (Optical Isomer)

(2R,3R,4S,5S)-2-((((((2R,3R,4R,5R)-2-(6-Benzamido-9H-purin-9-yl)-4-((tert-butyldimethylsilyl)oxy)-5-(hydroxymethyl)tetrahydrofuran-3-yl)oxy)(2-cyanoethoxy)phosphorothioyl)oxy)methyl)-4-((tert-butyldimethylsilyl)oxy)-5-(4-oxo-3,4-dihydropyrazolo[1,5-a][1,3,5]triazin-8-yl)tetrahydrofuran-3-yl hydrogen phosphonate (260 mg) was subjected to azeotropic process twice with dehydrated acetonitrile. The residue was subjected to azeotropic process once with dehydrated pyridine. To a solution of the residue in dehydrated pyridine (5 mL) was added 2-chloro-5,5-dimethyl-1,3,2-dioxaphosphinane 2-oxide (158 mg), and the mixture was stirred under argon atmosphere at room temperature for 20 min. To the reaction mixture were added water (0.15 mL) and 3H-benzo[c][1,2]dithiol-3-one (49.4 mg) at room temperature. The reaction mixture was stirred at room temperature for 1 hr. To the reaction mixture was added saturated aqueous sodium hydrogencarbonate solution at room temperature, and the mixture was extracted with ethyl acetate. The extract was washed with saturated aqueous sodium thiosulfate solution and saturated brine, dried over anhydrous sodium sulfate, and concentrated under reduced pressure. The residue was purified by silica gel column chromatography (methanol/ethyl acetate), and then purified by HPLC (L-column2 ODS, 50×150 mm, mobile phase: 5 mM aqueous ammonium acetate solution/acetonitrile) to give fractions, and the fraction having the longest retention time was concentrated under reduced pressure. To the residue was added 33% methylamine ethanol solution (5 mL), and the mixture was stirred at room temperature for 1 hr. The reaction mixture was concentrated under reduced pressure. The residue was purified by silica gel column chromatography (methanol/ethyl acetate) to give the title compound (25 mg). MS: [M+H]⁺ 920.2.

I) 8-((5R,7R,8R,12aR,14S,15S,15aS,16R)-7-(6-amino-9H-purin-9-yl)-15,16-dihydroxy-2,10-dioxido-2,10-disulfanyloctahydro-12H-5,8-methanofuro[3,2-l][1,3,6,9,11,2,10]pentaoxadiphosphacyclotetradecin-14-yl)pyrazolo[1,5-a][1,3,5]triazin-4(3H)-one di-triethylamine salt (Optical Isomer)

To a solution of 8-((5R,7R,8R,12aR,14S,15S,15aR,16R)-7-(6-amino-9H-purin-9-yl)-15,16-bis((tert-butyl(dimethyl)silyl)oxy)-2,10-dioxido-2,10-disulfanyloctahydro-12H-5,8-methanofuro[3,2-l][1,3,6,9,11,2,10]pentaoxadiphosphacyclotetradecin-14-yl)pyrazolo[1,5-a][1,3,5]triazin-4(3H)-one (optical isomer) (25 mg) in methanol (2 mL) was added triethylamine trihydrofluoride (0.177 mL) at room temperature, and the mixture was stirred at 50° C. for 2 hr. To the reaction mixture was added ethoxytrimethylsilane (5 mL) at room temperature, and the mixture was stirred for 10 min. The reaction mixture was concentrated under reduced pressure, the residue was purified by C18 silica gel column chromatography (10 mM triethylammonium acetate buffer solution/acetonitrile), and the obtained product was freeze-dried to give the title compound (13 mg). ¹H NMR (300 MHz, D₂O) δ 4.02-4.19 (3H, m), 4.32-4.42 (2H, m), 4.44-4.49 (1H, m), 4.59-4.64 (1H, m), 4.76-4.80 (1H, m), 4.95-5.04 (1H, m), 5.16 (1H, d, J=4.9 Hz), 5.31 (1H, ddd, J=9.8, 8.7, 4.2 Hz), 6.22 (1H, d, J=8.3 Hz), 7.99 (1H, s), 8.00 (1H, s), 8.14 (1H, s), 8.49 (1H, s).

Example 13
Synthesis of 2-amino-9-((5R,7R,8R,12aR,14S,15S,15aS,16R)-14-(4-aminopyrazolo[1,5-a][1,3,5]triazin-8-yl)-2,10,15,16-tetrahydroxy-2,10-dioxidooctahydro-12H-5,8-methanofuro[3,2-1][1,3,6,9,11,2,10]pentaoxadiphosphacyclotetradecin-7-yl)-1,9-dihydro-6H-purin-6-one di-triethylamine salt
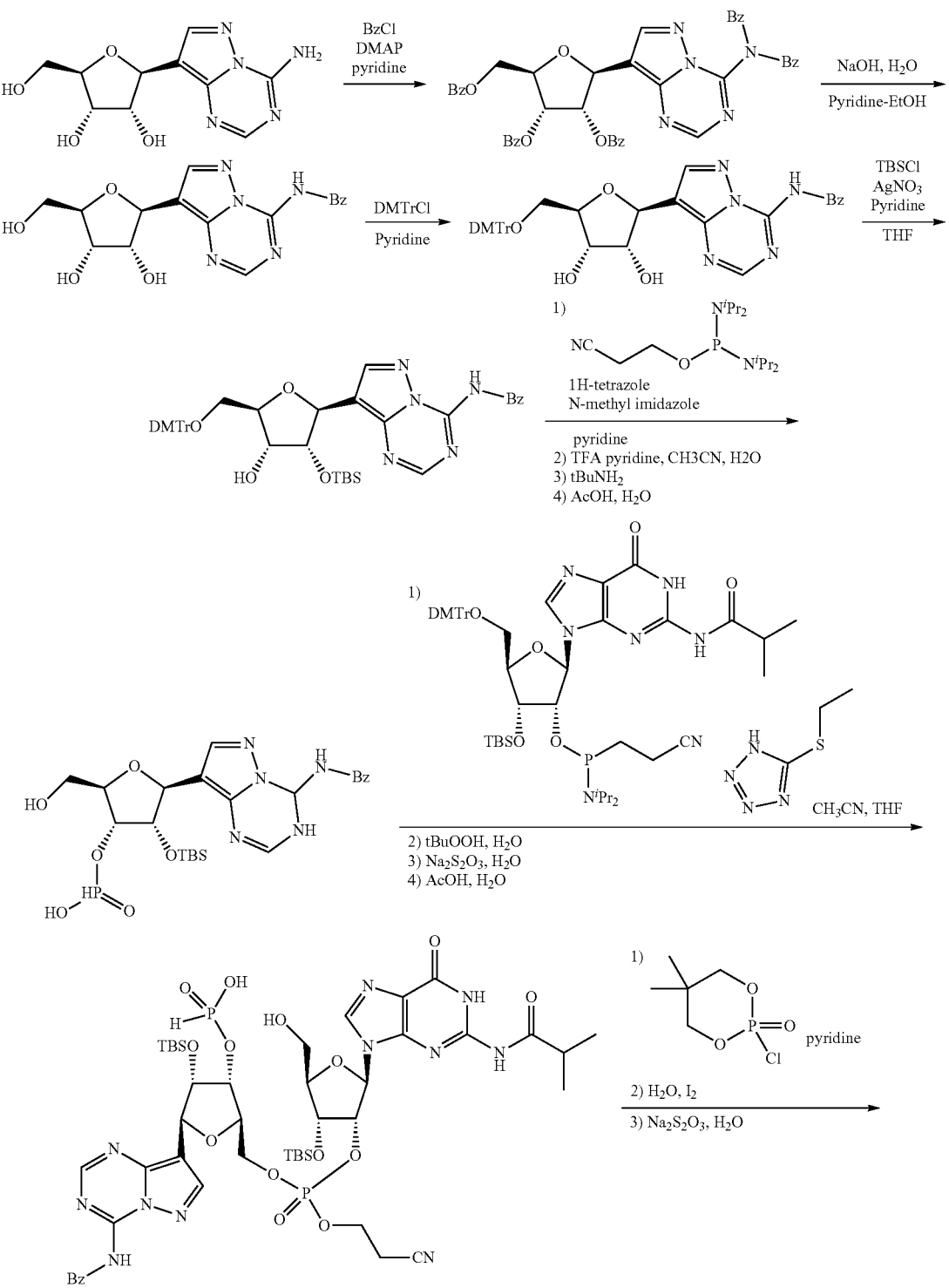

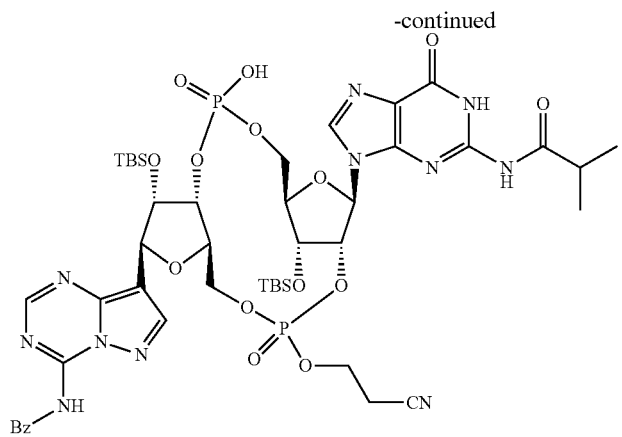

-continued

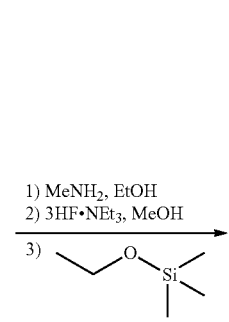

1) MeNH$_2$, EtOH
2) 3HF·NEt$_3$, MeOH
3)

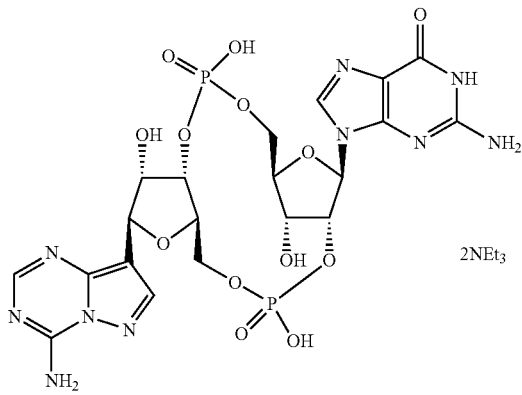

2NEt$_3$

A) (2S,3S,4R,5R)-2-(4-(N-benzoylbenzamido)pyrazolo[1,5-a][1,3,5]triazin-8-yl)-5-((benzoyloxy)methyl)tetrahydrofuran-3,4-diyl dibenzoate To a solution of (2S,3R,4S,5R)-2-(4-aminopyrazolo[1,5-a][1,3,5]triazin-8-yl)-5-(hydroxymethyl)tetrahydrofuran-3,4-diol (2.98 g) and N,N-dimethyl-4-aminopyridine (1.36 g) in dehydrated pyridine (50 mL) was added benzoyl chloride (12.5 g) under ice-cooling. The reaction mixture was stirred under argon atmosphere for 1 hr. To the reaction mixture was added benzoyl chloride (3.13 g) under ice-cooling. The reaction mixture was stirred under argon atmosphere at room temperature for 2 hr. To the reaction mixture was added water, and the mixture was extracted with ethyl acetate. The extract was washed with water and saturated brine, dried over anhydrous sodium sulfate, and concentrated under reduced pressure. The residue was purified by silica gel column chromatography (ethyl acetate/hexane) to give the title compound (6.51 g). MS: [M+H]$^+$ 788.2.

B) N-(8-((2S,3R,4S,5R)-3,4-dihydroxy-5-(hydroxymethyl)tetrahydrofuran-2-yl)pyrazolo[1,5-a][1,3,5]triazin-4-yl)benzamide To a solution of (2S,3S,4R,5R)-2-(4-(N-benzoylbenzamido)pyrazolo[1,5-a][1,3,5]triazin-8-yl)-5-((benzoyloxy)methyl)tetrahydrofuran-3,4-diyl di benzoate (6.51 g) in a mixed solvent of pyridine (50 mL) and ethanol (25 mL) was added 1M aqueous sodium hydroxide solution (49.6 mL) under ice-cooling, and the mixture was stirred at room temperature for 2 hr. To the reaction mixture was added strong acidic cation-exchange resin DOWEX™ 50Wx4 100-200 (40 g) at room temperature, and the mixture was stirred at room temperature for 15 min. The solid was removed by filtration, and the filtrate was concentrated under reduced pressure. To the residue was added methanol, and the obtained solid was collected by filtration to give the title compound (1.82 g). MS: [M+H]$^+$ 372.1.

C) N-(8-((2S,3R,4S,5R)-5-((bis(4-methoxyphenyl)(phenyl)methoxy)methyl)-3,4-dihydroxytetrahydrofuran-2-yl)pyrazolo[1,5-a][1,3,5]triazin-4-yl)benzamide To a solution of N-(8-((2S,3R,4S,5R)-3,4-dihydroxy-5-(hydroxymethyl)tetrahydrofuran-2-yl)pyrazolo[1,5-a][1,3,5]triazin-4-yl)benzamide (1.89 g) in dehydrated pyridine (30 mL) was added 4,4'-dimethoxytrityl chloride (517 mg) under ice-cooling. The reaction mixture was stirred under argon atmosphere at room temperature for 3 hr. To the reaction mixture was added 4,4'-dimethoxytrityl chloride (517 mg) at room temperature, and the mixture was stirred overnight under argon atmosphere at room temperature. To the reaction mixture was added 4,4'-dimethoxytrityl chloride (1035 mg) at room temperature, and the mixture was stirred under argon atmosphere at room temperature for 1 hr. To the reaction mixture was added saturated aqueous sodium hydrogencarbonate solution at room temperature, and the mixture was extracted with ethyl acetate. The extract was washed with saturated brine, dried over anhydrous sodium sulfate, and concentrated under reduced pressure. The residue was purified by silica gel column chromatography (methanol/ethyl acetate) to give the title compound (2160 mg). MS: [M−H]$^−$ 672.1.

D) N-(8-((2S,3R,4R,5R)-5-((bis(4-methoxyphenyl) (phenyl)methoxy)methyl)-3-((tert-butyldimethylsilyl)oxy)-4-hydroxytetrahydrofuran-2-yl)pyrazolo[1,5-a][1,3,5]triazin-4-yl)benzamide To a solution of N-(8-((2S,3R,4S,5R)-5-((bis(4-methoxyphenyl)(phenyl)methoxy)methyl)-3,4-dihydroxytetrahydrofuran-2-yl)pyrazolo[1,5-a][1,3,5]triazin-4-yl)benzamide (2.16 g) in dehydrated THF (30 mL) were added silver(I) nitrate (708 mg) and dehydrated pyridine (1.22 g). The reaction mixture was stirred under argon atmosphere for 15 min, and tert-butyldimethylchlorosilane (628 mg) was added thereto. The reaction mixture was stirred under argon atmosphere at room temperature for 2 hr. To the reaction mixture were added silver(I) nitrate (163 mg), tert-butyldimethylchlorosilane (145 mg) and dehydrated pyridine (507 mg) at room temperature. The reaction mixture was stirred overnight under argon atmosphere at room temperature. To the reaction mixture were added silver(I) nitrate (436 mg), tert-butyldimethylchlorosilane (387 mg) and dehydrated pyridine (761 mg) at room temperature. The reaction mixture was stirred under argon atmosphere at room temperature for 2 hr. To the reaction mixture was added saturated aqueous sodium hydrogencarbonate solution at room temperature, and the mixture was extracted with ethyl acetate. The extract was washed with saturated brine, dried over anhydrous sodium sulfate, and concentrated under reduced pressure. The residue was purified by silica gel column chromatography (ethyl acetate/hexane) to give the title compound (980 mg). MS: [M–H]⁻ 786.2.

E) (2R,3R,4S,5S)-5-(4-benzamidopyrazolo[1,5-a][1,3,5]triazin-8-yl)-4-((tert-butyldimethylsilyl)oxy)-2-(hydroxymethyl)tetrahydrofuran-3-yl hydrogen phosphonate N-(8-((2S,3R,4R,5R)-5-((Bis(4-methoxyphenyl)(phenyl)methoxy)methyl)-3-((tert-butyldimethylsilyl)oxy)-4-hydroxytetrahydrofuran-2-yl)pyrazolo[1,5-a][1,3,5]triazin-4-yl)benzamide (980 mg) was subjected to azeotropic process twice with dehydrated toluene, and dissolved in dehydrated DMF (10 mL). To the reaction mixture were added 3-((bis(diisopropylamino)phosphino)oxy)propanenitrile (487 mg), 1H-tetrazole (87 mg) and 1-methyl-1H-imidazole (51 mg). The reaction mixture was stirred under argon atmosphere at room temperature for 5 hr. To the reaction mixture was added saturated aqueous sodium hydrogencarbonate solution at room temperature, and the mixture was extracted with ethyl acetate. The extract was washed with saturated brine, dried over anhydrous sodium sulfate, and concentrated under reduced pressure. The residue was purified by silica gel column chromatography (ethyl acetate containing 0.5% triethylamine/hexane). To a solution of the obtained mixture in acetonitrile (10 mL) were added water (0.04 mL) and pyridine 2,2,2-trifluoroacetate (256 mg) at room temperature. The reaction mixture was stirred at room temperature for 30 min, tert-butylamine (5.38 mL) was added thereto, and the mixture was stirred at room temperature for 45 min. The solvent was evaporated under reduced pressure. To the residue was added 80% aqueous acetic acid solution (5.4 mL), the mixture was stirred at room temperature for 1 hr, and the solvent was evaporated under reduced pressure. The residue was purified by silica gel column chromatography (methanol/ethyl acetate) to give the title compound (530 mg). MS: [M+H]⁺ 550.2.

F) (2R,3R,4S,5S)-5-(4-benzamidopyrazolo[1,5-a][1,3,5]triazin-8-yl)-4-((tert-butyldimethylsilyl)oxy)-2-((((((2R,3R,4R,5R)-4-((tert-butyldimethylsilyl)oxy)-5-(hydroxymethyl)-2-(2-isobutylamido-6-oxo-1H-purin-9(6H)-yl)tetrahydrofuran-3-yl)oxy)(2-cyanoethoxy)phosphoryl)oxy)methyl) tetrahydrofuran-3-yl hydrogen phosphonate A mixture of (2R,3R,4S,5S)-5-(4-benzamidopyrazolo[1,5-a][1,3,5]triazin-8-yl)-4-((tert-butyldimethylsilyl)oxy)-2-(hydroxymethyl)tetrahydrofuran-3-yl hydrogen phosphonate (240 mg) and 5'-O-(bis(4-methoxyphenyl)(phenyl)methyl)-3'-O-(tert-butyl(dimethyl)silyl)-2'-O-((2-cyanoethyl)(diisopropylamino)phosphino)-N-isobutyrylguanosine (635 mg) was subjected to azeotropic process three times with dehydrated acetonitrile. To the residue was added a solution of dehydrated acetonitrile (5 mL), dehydrated THF (2.5 mL) and 5-(ethylthio)-2H-tetrazole (171 mg) (which was in advance subjected to azeotropic process with dehydrated acetonitrile) in dehydrated acetonitrile (2.5 mL). The reaction mixture was stirred under argon atmosphere at room temperature for 2 hr. 70% Aqueous tert-butyl hydroperoxide solution (0.179 mL) was added thereto, and the mixture was stirred at room temperature for 20 min. To the reaction mixture was added an aqueous solution (0.12 mL) of sodium thiosulfate pentahydrate (0.12 g), and the reaction mixture was concentrated under reduced pressure. To the residue was added 80% aqueous acetic acid solution (3 mL), and the mixture was stirred at room temperature for 1 hr. The residue was subjected to azeotropic process twice with acetonitrile. The residue was purified by silica gel column chromatography (methanol/ethyl acetate) to give a crude product (420 mg) containing the title compound. MS: [M+H]⁺ 1132.3.

G) N-(8-((5R,7R,8R,12aR,14S,15S,15aR,16R)-15,16-bis((tert-butyl(dimethyl)silyl)oxy)-10-(2-cyanoethoxy)-2-hydroxy-7-(2-((2-methylpropanoyl)amino)-6-oxo-1,6-dihydro-9H-purin-9-yl)-2,10-dioxidooctahydro-12H-5,8-methanofuro[3,2-1][1,3,6,9,11,2,10]pentaoxadiphosphacyclotetradecin-14-yl)pyrazolo[1,5-a][1,3,5]triazin-4-yl)benzamide The crude product (430 mg) containing (2R,3R,4S,5S)-5-(4-benzamidopyrazolo[1,5-a][1,3,5]triazin-8-yl)-4-((tert-butyldimethylsilyl)oxy)-2-((((((2R,3R,4R,5R)-4-((tert-butyldimethylsilyl)oxy)-5-(hydroxymethyl)-2-(2-isobutylamido-6-oxo-1H-purin-9(6H)-yl)tetrahydrofuran-3-yl)oxy)(2-cyanoethoxy)phosphoryl)oxy)methyl) tetrahydrofuran-3-yl hydrogen phosphonate was subjected to azeotropic process twice with dehydrated acetonitrile. The obtained residue was subjected to azeotropic process once with dehydrated pyridine. To a solution of the obtained residue in dehydrated pyridine (3 mL) was added 2-chloro-5,5-dimethyl-1,3,2-dioxaphosphinane 2-oxide (245 mg), and the mixture was stirred at room temperature under argon atmosphere for 10 min. To the reaction mixture were added water (0.239 mL) and iodine (125 mg), and the mixture was stirred at room temperature for 20 min. To the reaction mixture was added an aqueous solution (0.4 mL) of sodium thiosulfate pentahydrate (245 mg), and the mixture was stirred at room temperature for 5 min. Toluene was added thereto, and the mixture was concentrated under reduced pressure. The residue was purified by silica gel column chromatography (methanol/ethyl acetate) to give a crude product (553 mg) containing the title compound. MS: [M+H]+ 1130.4.

H) 2-amino-9-((5R,7R,8R,12aR,14S,15S,15aS, 16R)-14-(4-aminopyrazolo[1,5-a][1,3,5]triazin-8-yl)-2,10,15,16-tetrahydroxy-2,10-dioxidooctahydro-12H-5,8-methanofuro[3,2-1][1,3,6,9,11,2,10]pentaoxadiphosphacyclotetradecin-7-yl)-1,9-dihydro-6H-purin-6-one di-triethylamine salt A mixture of N-(8-((5R,7R,8R,12aR,14S,15S,15aR, 16R)-15,16-bis((tert-butyl(dimethyl)silyl)oxy)-10-(2-cyanoethoxy)-2-hydroxy-7-(2-((2-methylpropanoyl)amino)-6-oxo-1,6-dihydro-9H-purin-9-yl)-2,10-dioxidooctahydro-12H-5,8-methanofuro[3,2-1][1,3,6,9,11,2,10]pentaoxadiphosphacyclotetradecin-14-yl)pyrazolo[1,5-a][1,3,5]triazin-4-yl)benzamide (553 mg) and 33% methylamine ethanol solution (20 mL) was stirred overnight at room temperature. The reaction mixture was concentrated under reduced pressure, the residue was purified by silica gel column chromatography (methanol/ethyl acetate), and then purified by HPLC (ODS, mobile phase: water/acetonitrile (containing 5 mM ammonium acetate)) to give a fraction, and the obtained fraction was concentrated under reduced pressure. To a solution of the obtained residue in methanol (3 mL) was added triethylamine trihydrofluoride (0.072 mL) at room temperature, and the mixture was stirred at 50° C. for 4 hr. To the reaction mixture was added triethylamine trihydrofluoride (0.181 mL) at room temperature, and the mixture was stirred overnight at 50° C. To the reaction mixture was added triethylamine trihydrofluoride (0.181 mL) at room temperature, and the mixture was stirred at 50° C. for 5 hr. To the reaction mixture was added ethoxytrimethylsilane (1.034 mL) at room temperature, and the mixture was stirred for 5 min. The reaction mixture was concentrated under reduced pressure, the residue was purified by C18 silica gel column chromatography (10 mM triethylammonium acetate buffer solution/acetonitrile), and the obtained product was freeze-dried to give the title compound (10 mg). $^1$H NMR (300 MHz, D$_2$O) δ 3.99-4.08 (1H, m), 4.11-4.31 (4H, m), 4.34-4.42 (1H, m), 4.52-4.60 (2.1-1, m), 4.94-5.05 (1H, m), 5.27-5.35 (1H, m), 5.51-5.62 (1H, m), 5.94 (1H, d, J=8.3 Hz), 7.89 (1H, s), 8.07 (1H, s), 8.08 (1H, s).

Example 14

7-((2R,5R,7R,8R,10R,12aR,14R,15R,15aR,16R)-14-(6-amino-9H-purin-9-yl)-15-fluoro-16-hydroxy-2,10-dioxido-2,10-disulfanyloctahydro-12H-5,8-methanofuro[3,2-1][1,3,6,9,11,2,10]pentaoxadiphosphacyclotetradecin-7-yl)-5-fluoro-3,7-dihydro-4H-pyrrolo[2,3-d]pyrimidin-4-one di sodium salt

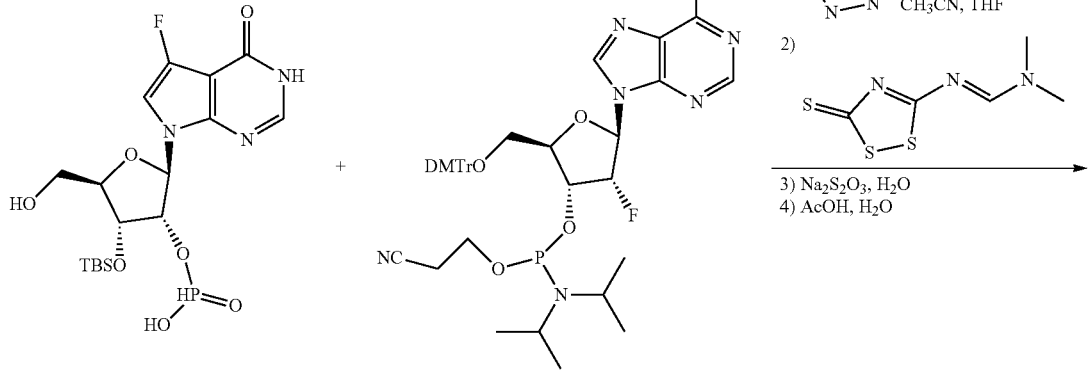

285 286
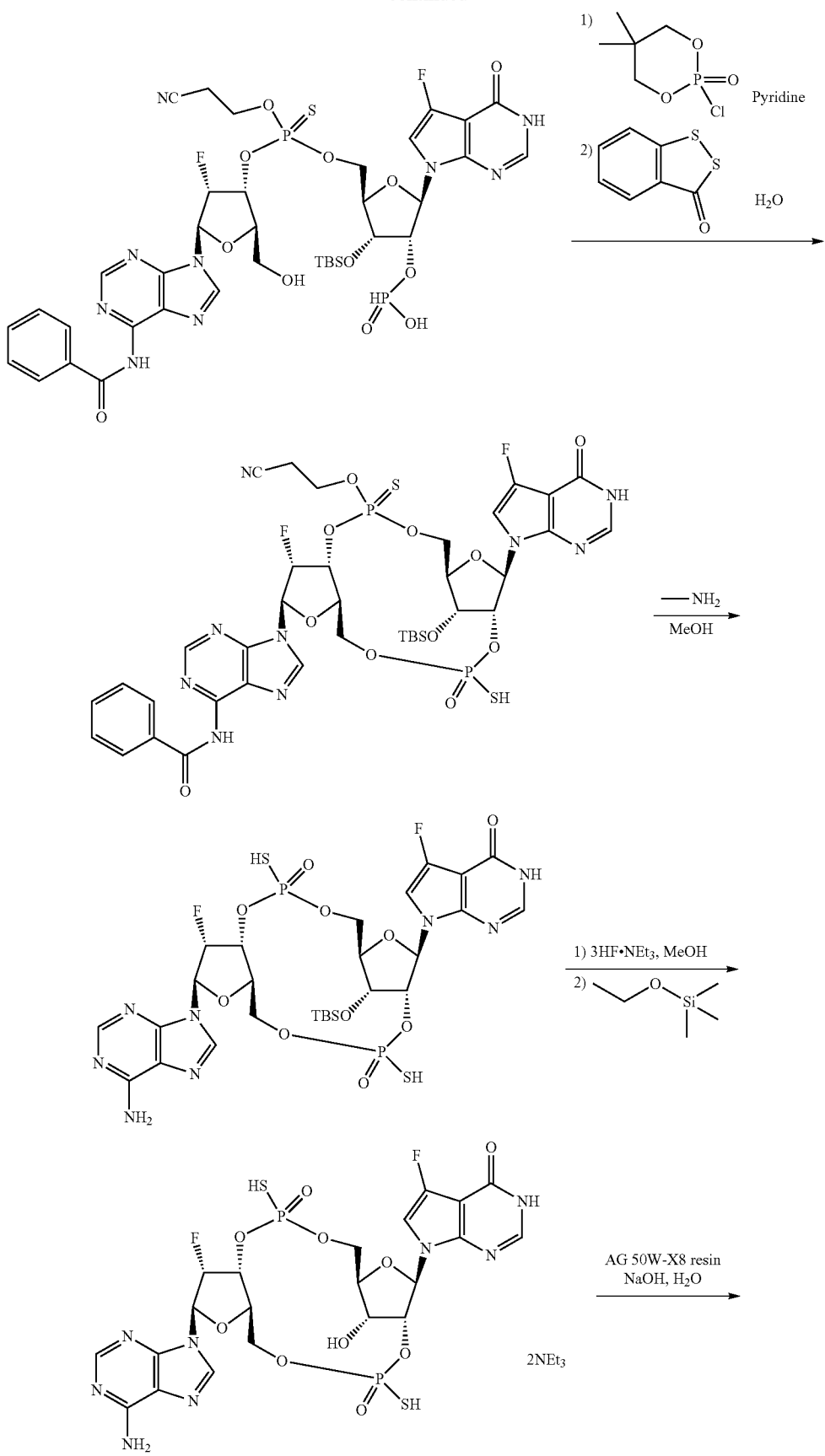

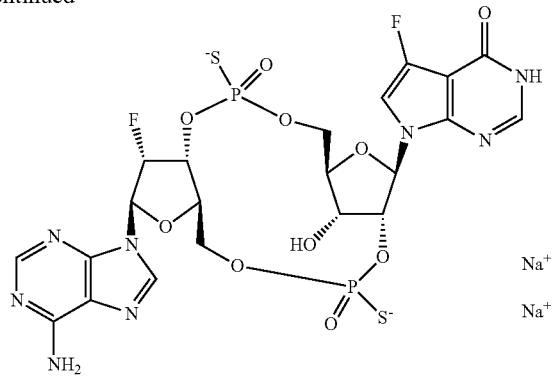

A) (2R,3R,4R,5R)-5-((((((2R,3R,4R,5R)-5-(6-benzamido-9H-purin-9-yl)-4-fluoro-2-(hydroxymethyl)tetrahydrofuran-3-yl)oxy)(2-cyanoethoxy)phosphorothioyl)oxy)methyl)-4-((tert-butyldimethylsilyl)oxy)-2-(5-fluoro-4-oxo-3H-pyrrolo[2,3-d]pyrimidin-7(4H)-yl)tetrahydrofuran-3-yl hydrogen phosphonate 7-(3-O-(tert-Butyl(dimethyl)silyl)-2-O-(hydroxy(oxido)phosphoranyl)-beta-D-ribofuranosyl)-5-fluoro-3,7-dihydro-4H-pyrrolo[2,3-d]pyrimidin-4-one (8.89 g) and N-benzoyl-5'-O-(bis(4-methoxyphenyl)(phenyl)methyl)-3'-O-((2-cyanoethoxy)(diisopropylamino]phosphino)-2'-deoxy-2'-fluoroadenosine (18.5 g) were subjected to azeotropic process three times with dehydrated acetonitrile. To the residue were added anhydrous acetonitrile (40 mL), anhydrous THF (20 mL) and an anhydrous acetonitrile solution (40 mL) of 5-(ethylsulfanyl)-2H-tetrazole (7.49 g). The reaction mixture was stirred at room temperature for 30 min under argon atmosphere, ((dimethylaminomethylidene)amino)-3H-1,2,4-dithiazoline-3-thione (4.33 g) was added to the reaction mixture, and the mixture was stirred at room temperature for 30 min. To the reaction mixture was added an aqueous solution (5 mL) containing sodium thiosulfate (5.24 g), and the mixture was concentrated under reduced pressure. To the residue was added 80% aqueous acetic acid solution (100 mL), the mixture was stirred at room temperature for 1 hr, and the reaction mixture was subjected to azeotropic process with toluene. The residue was purified by silica gel column chromatography (methanol/ethyl acetate) to give the title compound (14.3 g). MS: [M+H]⁻ 968.3.

B) N-(9-((5R,7R,8R,12aR,14R,15R,15aR,16R)-16-((tert-butyl(dimethyl)silyl)oxy)-2-(2-cyanoethoxy)-15-fluoro-7-(5-fluoro-4-oxo-3,4-dihydro-7H-pyrrolo[2,3-d]pyrimidin-7-yl)-10-oxido-10-sulfanyl-2-sulfidooctahydro-12H-5,8-methanofuro[3,2-1][1,3,6,9,11,2,10]pentaoxadiphosphacyclotetradecin-14-yl)-9H-purin-6-yl)benzamide (Optical Isomer)

(2R,3R,4R,5R)-5-((((((2R,3R,4R,5R)-5-(6-Benzamido-9H-purin-9-yl)-4-fluoro-2-(hydroxymethyl)tetrahydrofuran-3-yl)oxy)(2-cyanoethoxy)phosphorothioyl)oxy)methyl)-4-((tert-butyldimethylsilyl)oxy)-2-(5-fluoro-4-oxo-3H-pyrrolo[2,3-d]pyrimidin-7(4H)-yl)tetrahydrofuran-3-yl hydrogen phosphonate (1.07 g) was subjected to azeotropic process three times with dehydration pyridine. To a solution of the residue in anhydrous pyridine (150 mL) was added 2-chloro-5,5-dimethyl-1,3,2-dioxaphosphinane 2-oxide (4.66 g), and the mixture was stirred at room temperature for 30 min under argon atmosphere. To the reaction mixture were added 3H-benzo[c][1,2]dithiol-3-one (1.46 g) and water (4.55 mL) at room temperature, and the reaction mixture was stirred for 30 min. LCMS analysis of the reaction mixture showed four peaks with the same mass ([M+H]⁺ 971.1), indicating four diastereomers being formed. The reaction mixture was concentrated under reduced pressure, and the residue was purified by silica gel column chromatography (methanol/ethyl acetate), and then purified by HPLC (L-column2 ODS, 50×150 mm, mobile phase: 5 mM aqueous ammonium acetate solution/acetonitrile). The fraction having the longest retention time was concentrated under reduced pressure to give the title compound (379 mg). MS: [M+H]⁺ 982.1.

C) 7-((5R,7R,8R,12aR,14R,15R,15aR,16R)-14-(6-amino-9H-purin-9-yl)-16-((tert-butyl(dimethyl)silyl)oxy)-15-fluoro-2,10-dioxido-2,10-disulfanyloctahydro-12H-5,8-methanofuro[3,2-1][1,3,6,9,11,2,10]pentaoxadiphosphacyclotetradecin-7-yl)-5-fluoro-3,7-dihydro-4H-pyrrolo[2,3-d]pyrimidin-4-one (Optical Isomer)

40% Methylamine methanol solution (10 mL) of N-(9-((5R,7R,8R,12aR,14R,15R,15aR,16R)-16-((tert-butyl(dimethyl)silyl)oxy)-2-(2-cyanoethoxy)-15-fluoro-7-(5-fluoro-4-oxo-3,4-dihydro-7H-pyrrolo[2,3-d]pyrimidin-7-yl)-10-oxido-10-sulfanyl-2-sulfidooctahydro-12H-5,8-methanofuro[3,2-1][1,3,6,9,11,2,10]pentaoxadiphosphacyclotetradecin-14-yl)-9H-purin-6-yl)benzamide (optical isomer) (379 mg) was stirred at room temperature for 3 hr under argon atmosphere. The reaction mixture was concentrated under reduced pressure, and the residue was purified by silica gel column chromatography (methanol/ethyl acetate) to give the title compound (319 mg). MS: [M+H]⁺ 825.1.

D) 7-((2R,5R,7R,8R,10R,12aR,14R,15R,15aR,16R)-14-(6-amino-9H-purin-9-yl)-15-fluoro-16-hydroxy-2,10-dioxido-2,10-disulfanyloctahydro-12H-5,8-methanofuro[3,2-1][1,3,6,9,11,2,10]pentaoxadiphosphacyclotetradecin-7-yl)-5-fluoro-3,7-dihydro-4H-pyrrolo[2,3-d]pyrimidin-4-one di-triethylamine salt To a solution of 7-((5R,7R,8R,12aR,14R,15R,15aR,16R)-14-(6-amino-9H-purin-9-yl)-16-((tert-butyl(dimethyl)silyl)oxy)-15-fluoro-2,10-dioxido-2,10-disulfanyloctahydro- 12H-5,8-methanofuro[3,2-l][1,3,6,9,11,2,10]pentaoxadiphosphacyclotetradecin-7-yl)-5-fluoro-3,7-dihydro-4H-pyrrolo[2,3-d]pyrimidin-4-one (optical isomer) (319 mg) in methanol (1 mL) was added triethylamine trihydrofluoride (2.52 mL) at room temperature, and the mixture was stirred at 50° C. for 3 hr, and diluted with methanol (10 mL). To the reaction mixture was added ethoxytrimethylsilane (12 mL) at room temperature, and the mixture was stirred for 10 min. The reaction mixture was concentrated under reduced pressure, the residue was diluted with methanol, and the mixture was concentrated again under reduced pressure. To the residue was added triethylammonium acetate buffer solution, and the solid was collected by filtration, and washed with acetonitrile to give a white solid. The obtained white solid was purified by silica gel column chromatography (ODS, 10 mM triethylammonium acetate buffer solution/acetonitrile). On the other hand, the filtrate was concentrated under reduced pressure, and the residue was purified by silica gel column chromatography (methanol/ethyl acetate) and silica gel column chromatography (ODS, 10 mM triethylammonium acetate buffer solution/acetonitrile). The fraction containing the title compound obtained by silica gel column chromatography (ODS, 10 mM triethylammonium acetate buffer solution/acetonitrile) was concentrated under reduced pressure, and the residue was freeze-dried to give the title compound (195 mg). MS: [M+H]$^+$ 711.0.

E) 7-((2R,5R,7R,8R,10R,12aR,14R,15R,15aR,16R)-14-(6-amino-9H-purin-9-yl)-15-fluoro-16-hydroxy-2,10-dioxido-2,10-disulfanyloctahydro-12H-5,8-methanofuro[3,2-l][1,3,6,9,11,2,10]pentaoxadiphosphacyclotetradecin-7-yl)-5-fluoro-3,7-dihydro-4H-pyrrolo[2,3-d]pyrimidin-4-one disodium salt Deionized water (60 mL) was passed through a column prepared by packing AG (trade name) 50W-X8 cation-exchange resin (100-200 mesh, 3.9 g) in an empty column. Then, 1 M aqueous sodium hydroxide solution (36 mL) and deionized water (68 mL) were passed through the resin. Deionized water (15 mL) containing 7-((2R,5R,7R,8R,10R,12aR,14R,15R,15aR,16R)-14-(6-amino-9H-purin-9-yl)-15-fluoro-16-hydroxy-2,10-dioxido-2,10-disulfanyloctahydro-12H-5,8-methanofuro[3,2-l][1,3,6,9,11,2,10]pentaoxadiphosphacyclotetradecin-7-yl)-5-fluoro-3,7-dihydro-4H-pyrrolo[2,3-d]pyrimidin-4-one di-triethylamine salt (195 mg) was passed through the resin after the above-mentioned pre-treatment, and deionized water (19 mL) was passed through the resin, and the obtained aqueous solution was freeze-dried to give the title compound (165 mg). $^1$H NMR (300 MHz, D$_2$O) δ 4.00-4.08 (1H, m), 4.22-4.45 (4H, m), 4.50-4.57 (1H, m), 4.81-4.84 (1H, m), 4.98-5.14 (2H, m), 5.40-5.61 (1H, m), 6.33-6.43 (2H, m), 7.28 (1H, d, J=1.9 Hz), 7.94 (1H, s), 8.05 (1H, s), 8.21 (1H, s). $^{31}$P NMR (121 MHz, D$_2$O) δ 52.1, 55.3.

Example 15

Synthesis of 7-((5R,7R,8R,12aR,14R,15R,15aR,16R)-14-(6-amino-9H-purin-9-yl)-15-fluoro-2,16-dihydroxy-2,10-dioxido-10-sulfanyl octahydro-12H-5,8-methanofuro[3,2-l][1,3,6,9,11,2,10]pentaoxadiphosphacyclotetradecin-7-yl)-5-fluoro-3,7-dihydro-4H-pyrrolo[2,3-d]pyrimidin-4-one di-triethylamine salt (optical isomer)

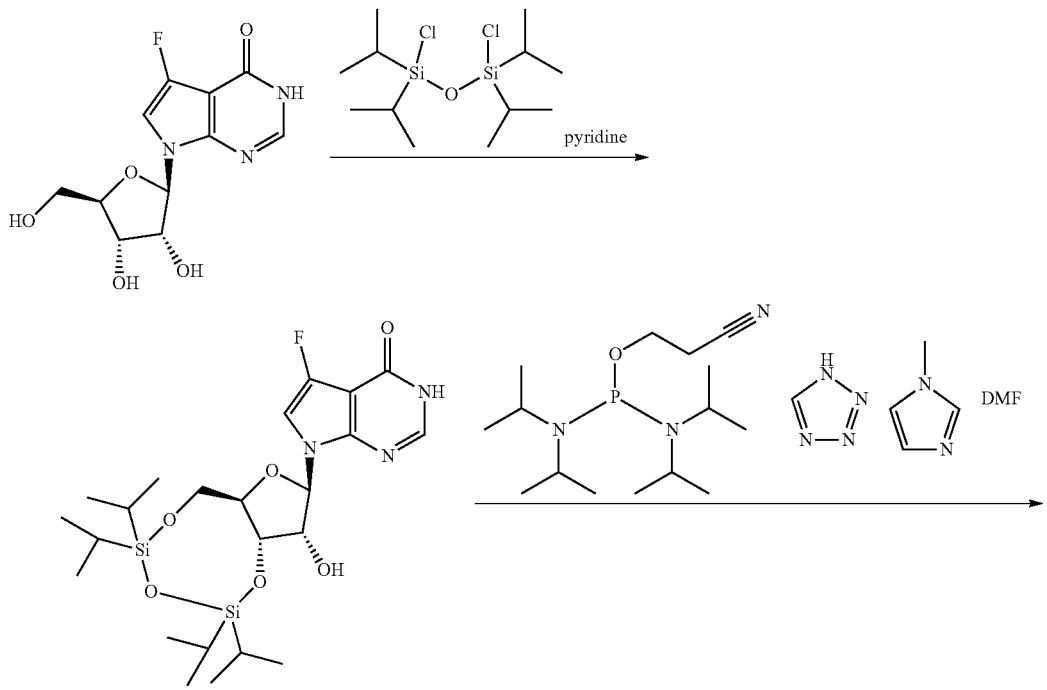

-continued
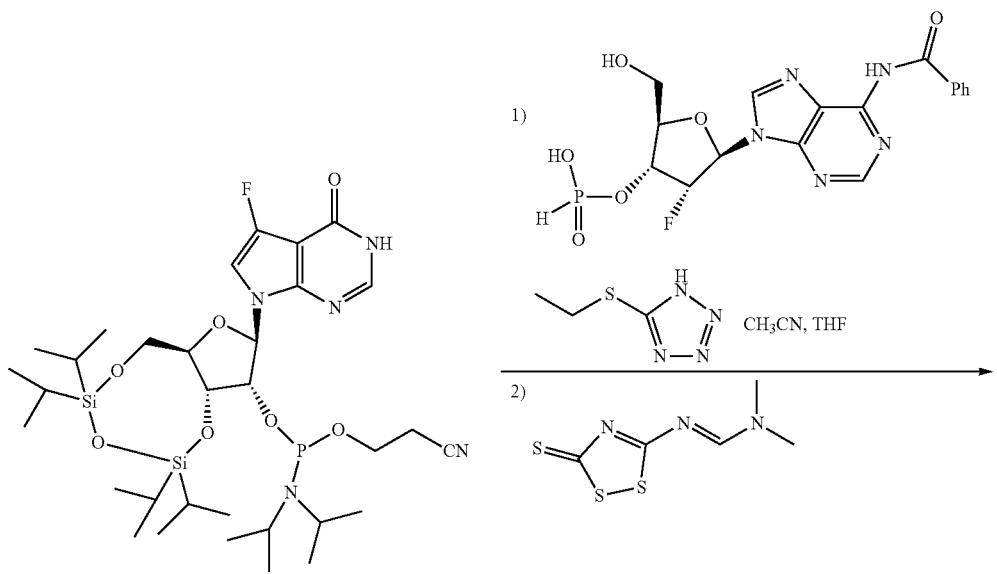
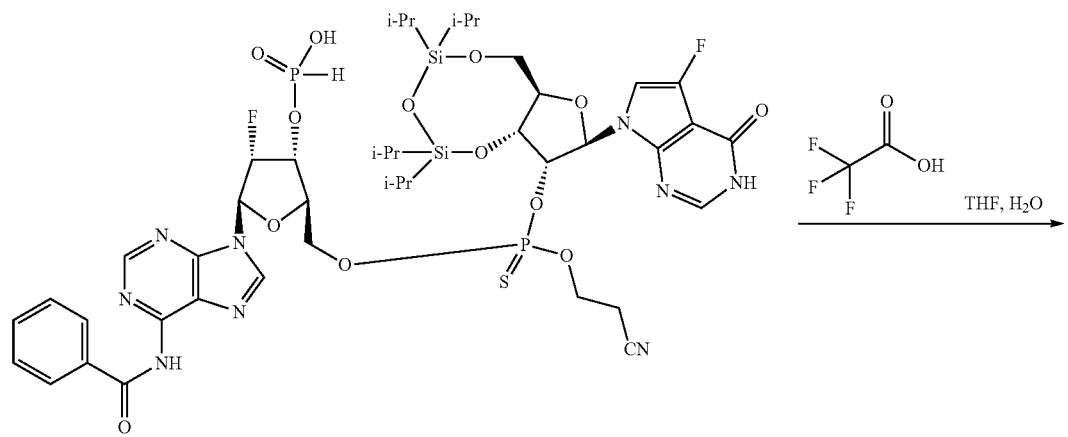
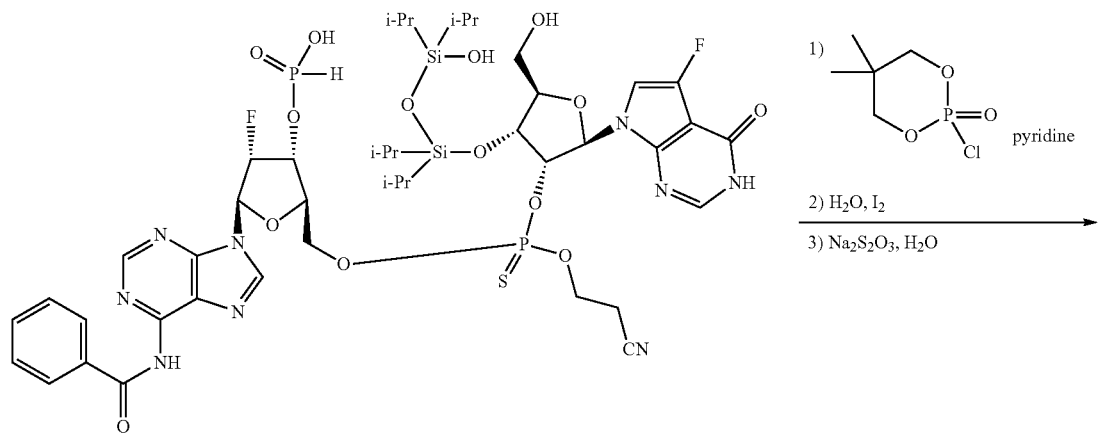

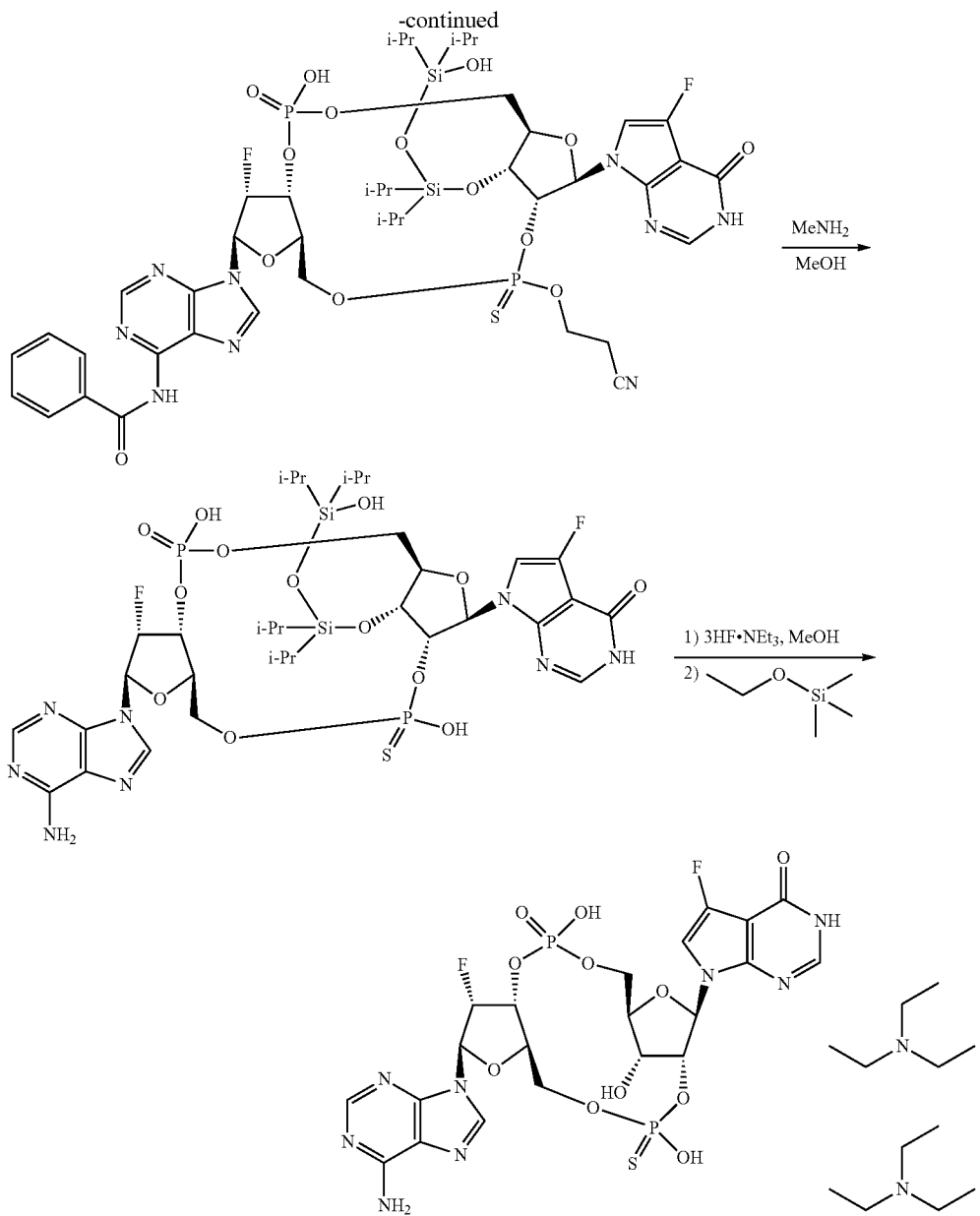

A) 5-fluoro-7-((6aR,8R,9R,9aS)-9-hydroxy-2,2,4,4-tetraisopropyltetrahydro-6H-furo[3,2-f][1,3,5,2,4]trioxadisilocin-8-yl)-3,7-dihydro-4H-pyrrolo[2,3-d]pyrimidin-4-one To a solution of 7-((2R,3R,4S,5R)-3,4-dihydroxy-5-(hydroxymethyl)tetrahydrofuran-2-yl)-5-fluoro-3H-pyrrolo[2,3-d]pyrimidin-4(7H)-one (37.9 g) in pyridine (760 mL) was added 1,3-dichloro-1,1,3,3-tetraisopropyldisiloxane (44.4 mL), and the mixture was stirred at room temperature for 3 hr under argon atmosphere. The solvent was evaporated under reduced pressure, and to the residue were added ethyl acetate and water. The organic layer was washed with water and saturated brine, and dried over anhydrous sodium sulfate, and the solvent was evaporated under reduced pressure. The residue was diluted with isopropyl ether (WE), and the mixture was stirred overnight at room temperature. The solid was collected by filtration to give the title compound (32.3 g). The mother liquor was concentrated under reduced pressure, and the residue was purified by silica gel column chromatography (hexane/ethyl acetate) to give the title compound (13.3 g). MS: [M+H]$^+$ 528.2.

B) 2-cyanoethyl (6aR,8R,9R,9aR)-8-(5-fluoro-4-oxo-3H-pyrrolo[2,3-d]pyrimidin-7(4H)-yl)-2,2,4,4-tetraisopropyltetrahydro-6H-furo[3,2-f][1,3,5,2,4]trioxadisilocin-9-yl diisopropylphosphoramidite 5-Fluoro-7-((6aR,8R,9R,9aS)-9-hydroxy-2,2,4,4-tetraisopropyltetrahydro-6H-furo[3,2-f][1,3,5,2,4]trioxadisilocin-8-yl)-3,7-dihydro-4H-pyrrolo[2,3-d]pyrimidin-4-one (20 g) was subjected to azeotropic dehydration three times with anhydrous acetonitrile, and dissolved in anhydrous DMF (100 mL). To this solution were added 1H-tetrazole (2.79 g), 1-methyl-1H-imidazole (1.65 mL), and 3-((bis(diisopropylamino)phosphino)oxy)propanenitrile (24.1 mL), and the mixture was stirred overnight at room temperature under argon atmosphere, poured into saturated aqueous sodium hydrogencarbonate solution, and extracted with ethyl acetate. The organic layer was washed successively with saturated aqueous sodium hydrogencarbonate solution and saturated brine, and dried over anhydrous sodium sulfate, and the solvent was evaporated under reduced pressure. The residue was purified by silica gel column chromatography (ethyl acetate/hexane, containing 0.5% triethylamine) to give the title compound (20.8 g) as a mixture of two diastereomers. $^1$H NMR (300 MHz, DMSO-$d_6$) δ 0.91-1.19 (40H, m), 2.69-2.82 (2H, m), 3.46-3.73 (2H, m), 3.78-4.12 (5H, m), 4.47-4.61 (2H, m), 6.02-6.12 (1H, m), 7.14-7.23 (1H, m), 7.84-7.91 (1H, m), 12.00-12.40 (1H, br).

C) (2R,3R,4R,5R)-S-(6-benzamido-9H-purin-9-yl)-2-((((2-cyanoethoxy)(((6aR,8R,9R,9aR)-8-(5-fluoro-4-oxo-3H-pyrrolo[2,3-d]pyrimidin-7(4H)-yl)-2,2,4,4-tetraisopropyltetrahydro-6H-furo[3,2-f][1,3,5,2,4]trioxadisilocin-9-yl)oxy)phosphorothioyl)oxy)methyl)-4-fluorotetrahydrofuran-3-yl hydrogen phosphonate A mixture of (2R,3R,4R,5R)-5-(6-benzamido-9H-purin-9-yl)-4-fluoro-2-(hydroxymethyl)tetrahydrofuran-3-yl hydrogen phosphonate (3.48 g) and 2-cyanoethyl (6aR,8R,9R,9aR)-8-(5-fluoro-4-oxo-3H-pyrrolo[2,3-d]pyrimidin-7(4H)-yl)-2,2,4,4-tetraisopropyltetrahydro-6H-furo[3,2-f][1,3,5,2,4]trioxadisilocin-9-yl diisopropylphosphoramidite (7.82 g) was subjected to azeotropic dehydration with anhydrous acetonitrile, and suspended in anhydrous acetonitrile (25 mL) and anhydrous THF (15 mL). 5-(Ethylsulfanyl)-2H-tetrazole (3.11 g), which was subjected in advance to azeotropic dehydration with anhydrous acetonitrile, was dissolved in anhydrous acetonitrile (6 mL), the solution was added to the above-mentioned suspension, and the mixture was stirred at room temperature for 1 hr under argon atmosphere. ((Dimethylaminomethylidene)amino)-3H-1,2,4-dithiazoline-3-thione (3.27 g) was added thereto, and the mixture was stirred at room temperature for additional 30 min. The solvent was evaporated under reduced pressure, and the residue was purified by silica gel column chromatography (methanol/ethyl acetate) to give the title compound (6.73 g). MS: [M+H]$^+$ 1096.2.

D) (2R,3R,4R,5R)-5-(6-benzamido-9H-purin-9-yl)-2-((((2-cyanoethoxy)(((2R,3R,4R,5R)-2-(5-fluoro-4-oxo-3H-pyrrolo[2,3-d]pyrimidin-7(4H)-yl)-4-((3-hydroxy-1,1,3,3-tetraisopropyldisilanyl)oxy)-5-(hydroxymethyl)tetrahydrofuran-3-yl)oxy)phosphorothioyl)oxy)methyl)-4-fluorotetrahydrofuran-3-yl hydrogen phosphonate (2R,3R,4R,5R)-5-(6-Benzamido-9H-purin-9-yl)-2-((((2-cyanoethoxy)(((6aR,8R,9R,9aR)-8-(5-fluoro-4-oxo-3H-pyrrolo[2,3-d]pyrimidin-7(4H)-yl)-2,2,4,4-tetraisopropyltetrahydro-6H-furo[3,2-f][1,3,5,2,4]trioxadisilocin-9-yl)oxy)phosphorothioyl)oxy)methyl)-4-fluorotetrahydrofuran-3-yl hydrogen phosphonate (6.73 g) was dissolved in a mixed solvent of THF (74.8 mL) and water (16.6 mL), and the solution was ice-cooled. Trifluoroacetic acid (16.6 mL) was added thereto, and the mixture was stirred 0° C. for 2 hr. The reaction mixture was quenched with an aqueous solution of sodium bicarbonate (25.8 g), and extracted with ethyl acetate. The organic layer was washed with saturated brine, and dried over anhydrous magnesium sulfate, and the sol-vent was evaporated under reduced pressure. The residue was purified by silica gel column chromatography (methanol/ethyl acetate) to give the title compound (6.43 g). MS: [M+H]$^+$ 1114.2.

E) N-(9-((5R,7R,8R,12aR,14R,15R,15aR,16R)-10-(2-cyanoethoxy)-15-fluoro-7-(5-fluoro-4-oxo-3,4-dihydro-7H-pyrrolo[2,3-d]pyrimidin-7-yl)-2-hydroxy-16-((3-hydroxy-1,1,3,3-tetra(propan-2-yl)disiloxanyl)oxy)-2-oxido-10-sulfidooctahydro-12H-5,8-methanofuro[3,2-1][1,3,6,9,11,2,10]pentaoxadiphosphacyclotetradecin-14-yl)-9H-purin-6-yl)benzamide (2R,3R,4R,5R)-5-(6-Benzamido-9H-purin-9-yl)-2-((((2-cyanoethoxy)(((2R,3R,4R,5R)-2-(5-fluoro-4-oxo-3H-pyrrolo[2,3-d]pyrimidin-7(4H)-yl)-4-((3-hydroxy-1,1,3,3-tetraisopropyldisilanyl)oxy)-5-(hydroxymethyl)tetrahydrofuran-3-yl)oxy)phosphorothioyl)oxy)methyl)-4-fluorotetrahydrofuran-3-yl hydrogen phosphonate (6.43 g) was subjected to azeotropic dehydration with anhydrous acetonitrile and anhydrous pyridine, and suspended in anhydrous pyridine (130 mL). 2-Chloro-5,5-dimethyl-1,3,2-dioxaphosphinane 2-oxide (3.73 g) was added thereto, and the mixture was stirred at room temperature for 1 hr under argon atmosphere. Water (5.17 mL) and iodine (1.90 g) were added thereto, and the mixture was stirred at room temperature for additional 1 hr. The reaction mixture was quenched with sodium thiosulfate (7.16 g) and water (3.6 mL), and extracted with ethyl acetate. The organic layer was washed with water and saturated brine, and dried over anhydrous magnesium sulfate, and the solvent was evaporated under reduced pressure. The residue was purified by silica gel column chromatography (methanol/ethyl acetate) to give the title compound (4.60 g). MS: [M+H]$^+$ 1112.2.

F) 7-((5R,7R,8R,12aR,14R,15R,15aR,16R)-14-(6-amino-9H-purin-9-yl)-15-fluoro-2-hydroxy-16-((3-hydroxy-1,1,3,3-tetraisopropyldisiloxanyl)oxy)-2,10-dioxido-10-sulfanyloctahydro-12H-5,8-methanofuro[3,2-1][1,3,6,9,11,2,10]pentaoxadiphosphacyclotetradecin-7-yl)-5-fluoro-3,7-dihydro-4H-pyrrolo[2,3-d]pyrimidin-4-one (Optical Isomer)

To N-(9-((5R,7R,8R,12aR,14R,15R,15aR,16R)-10-(2-cyanoethoxy)-15-fluoro-7-(5-fluoro-4-oxo-3,4-dihydro-7H-pyrrolo[2,3-d]pyrimidin-7-yl)-2-hydroxy-16-((3-hydroxy-1,1,3,3-tetra(propan-2-yl)disilanyl)oxy)-2-oxido-10-sulfidooctahydro-12H-5,8-methanofuro[3,2-1][1,3,6,9,11,2,10]pentaoxadiphosphacyclotetradecin-14-yl)-9H-purin-6-yl)benzamide (6.42 g) was added 40% methylamine methanol solution (30 mL), and the mixture was stirred at room temperature for 1 hr under argon atmosphere. The obtained mixture was concentrated under reduced pressure, and the residue was purified by silica gel column chromatography (methanol/ethyl acetate). The obtained residue was purified by HPLC (L-column2 ODS, 50×150 mm, mobile phase: 5 mM aqueous ammonium acetate solution/acetonitrile), the obtained fraction was concentrated under reduced pressure, and the residue was freeze-dried to give the title compound (420 mg). MS: [M+H]$^+$ 955.2.

G) 7-((5R,7R,8R,12aR,14R,15R,15aR,16R)-14-(6-amino-9H-purin-9-yl)-15-fluoro-2,16-dihydroxy-2,10-dioxido-10-sulfanyloctahydro-12H-5,8-methanofuro[3,2-l][1,3,6,9,11,2,10]pentaoxadiphosphacyclotetradecin-7-yl)-5-fluoro-3,7-dihydro-4H-pyrrolo[2,3-d]pyrimidin-4-one di-trimethyl amine salt (Optical Isomer)

To 7-((5R,7R,8R,12aR,14R,15R,15aR,16R)-14-(6-amino-9H-purin-9-yl)-15-fluoro-2-hydroxy-16-((3-hydroxy-1,1,3,3-tetraisopropyldisiloxanyl)oxy)-2,10-dioxido-10-sulfanyloctahydro-12H-5,8-methanofuro[3,2-l][1,3,6,9,11,2,1 0]pentaoxadiphosphacyclotetradecin-7-yl)-5-fluoro-3,7-dihydro-4H-pyrrolo[2,3-d]pyrimidin-4-one (optical isomer, derived from tR2) (420 mg) was added triethylamine trihydrofluoride (9.68 mL), and the mixture was stirred at 50° C. for 7.5 hr. To the reaction mixture was added ethoxytrimethylsilane (36.3 mL) at room temperature, and the mixture was stirred for 30 min. The reaction mixture was concentrated under reduced pressure, and the residue was purified by C18 silica gel column chromatography (10 mM triethylammonium acetate buffer solution/acetonitrile), and freeze-dried to give the title compound (298 mg). $^1$H NMR (300 MHz, D$_2$O) δ1.13-1.29 (16H, m), 3.12 (11H, q, J=7.2 Hz), 3.99-4.29 (4H, m), 4.31-4.43 (2H, m), 4.50 (1H, d, J=9.1 Hz), 4.81-5.08 (3H, m), 5.39-5.61 (1H, m), 6.30-6.42 (2H, m), 7.24 (1H, d, J=1.9 Hz), 7.92 (1H, s), 8.09 (1H, s), 8.19 (1H, s). $^{31}$P NMR (121 MHz, D$_2$O) δ52.2, 1.63.

Example 16

Synthesis of 7-((5R,7R,8R,12aR,14R,15R,15aS,18R)-14-(6-amino-9H-purin-9-yl)-2,10,18-trihydroxy-2,10-dioxidohexahydro-14H-15,12a-(epoxymethano)-5,8-methanofuro[3,2-l][1,3,6,9,11,2,10]pentaoxadiphosphacyclotetradecin-7(12H)-yl)-5-fluoro-3,7-dihydro-4H-pyrrolo[2,3-d]pyrimidin-4-one di-triethylamine salt (optical isomer)

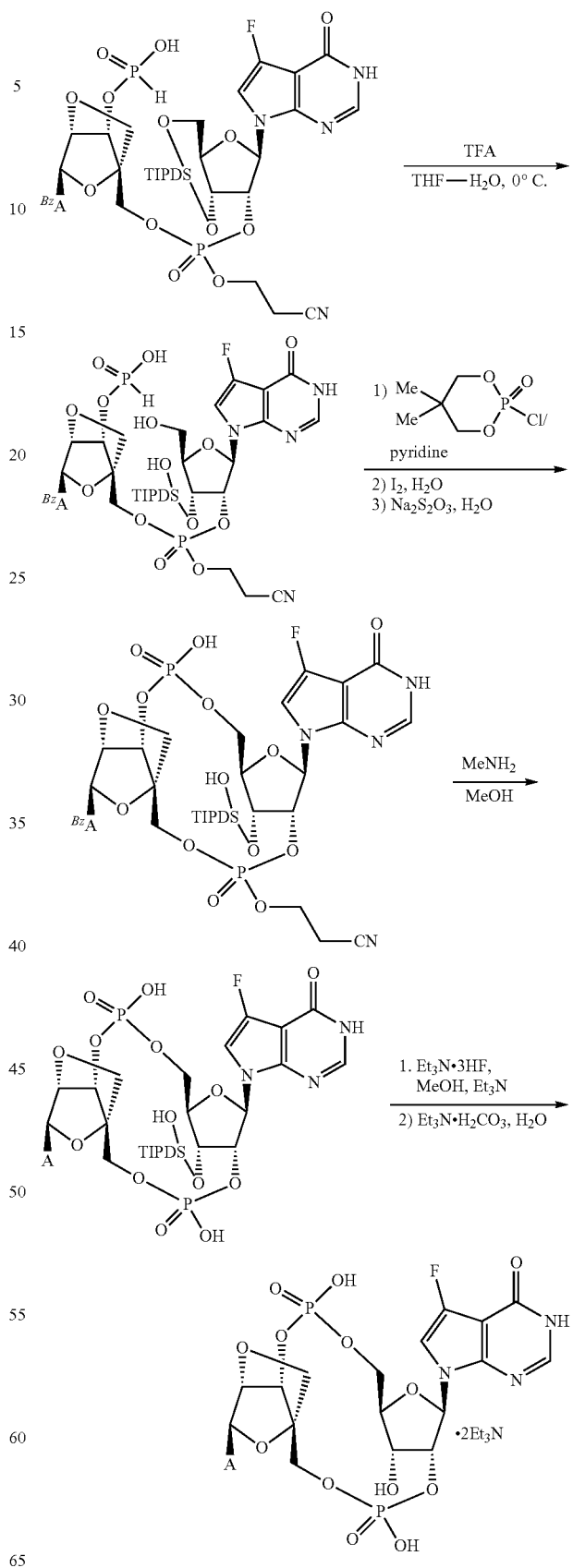

A) (1R,3R,4R,7S)-3-(6-benzamido-9H-purin-9-yl)-1-(((((2-cyanoethoxy)(((6aR,8R,9R,9aR)-8-(5-fluoro-4-oxo-3H-pyrrolo[2,3-d]pyrimidin-7(4H)-yl)-2,2,4,4-tetraisopropyltetrahydro-6H-furo[3,2-f][1,3,5,2,4]trioxadisilocin-9-yl)oxy)phosphoryl)oxy)methyl)-2,5-dioxabicyclo[2.2.1]heptan-7-yl hydrogen phosphonate (1S,3R,4R,7S)-3-(6-Benzamido-9H-purin-9-yl)-1-(hydroxymethyl)-2,5-dioxabicyclo[2.2.1]heptan-7-yl hydrogen phosphonate (2.00 g) and 2-cyanoethyl (6aR,8R,9R,9aR)-8-(5-fluoro-4-oxo-3H-pyrrolo[2,3-d]pyrimidin-7(4H)-yl)-2,2,4,4-tetraisopropyltetrahydro-6H-furo[3,2-f][1,3,5,2,4]trioxadisilocin-9-yl diisopropylphosphoramidite (4.23 g) were subjected to azeotropic dehydration with anhydrous acetonitrile (about 50 mL, three times), and suspended in anhydrous THF (16 mL). 5-(Ethylsulfanyl)-2H-tetrazole (1.75 g), which was subjected in advance to azeotropic dehydration with anhydrous acetonitrile (about 30 mL, three times), was dissolved in anhydrous acetonitrile (16 mL), the solution was added to the above-mentioned suspension, and the mixture was stirred at room temperature for 15 hr under argon stream. 70% tert-Butyl hydroperoxide aqueous solution (1.86 mL) was added thereto, and the mixture was stirred at room temperature for additional 30 min. The reaction mixture was quenched with 10% aqueous sodium thiosulfate solution (13 mL), and concentrated under reduced pressure. The residue was subjected successively to azeotropic dehydration with acetonitrile (about 80 mL) and toluene (about 80 mL), the residue was subjected to silica gel column chromatography (methanol/ethyl acetate), and the objective fraction was concentrated under reduced pressure to give the title compound (5.36 g) as a white amorphous solid (a mixture of two diastereomers). MS: [M+H]⁺ 1090.2.

B) (1R,3R,4R,7S)-3-(6-benzamido-9H-purin-9-yl)-1-(((((2-cyanoethoxy)(((2R,3R,4R,5R)-2-(5-fluoro-4-oxo-3H-pyrrolo[2,3-d]pyrimidin-7(4H)-yl)-4-((3-hydroxy-1,1,3,3-tetraisopropyldisilanyl)oxy)-5-(hydroxymethyl)tetrahydrofuran-3-yl)oxy)phosphoryl)oxy)methyl)-2,5-dioxabicyclo[2.2.1]heptan-7-yl hydrogen phosphonate (1R,3R,4R,7S)-3-(6-Benzamido-9H-purin-9-yl)-1-(((((2-cyanoethoxy)(((6aR,8R,9R,9aR)-8-(5-fluoro-4-oxo-3H-pyrrolo[2,3-d]pyrimidin-7(4H)-yl)-2,2,4,4-tetraisopropyltetrahydro-6H-furo[3,2-f][1,3,5,2,4]trioxadisilocin-9-yl)oxy)phosphoryl)oxy)methyl)-2,5-dioxabicyclo[2.2.1]heptan-7-yl hydrogen phosphonate (5.36 g) was dissolved in a mixed solvent of THF (60 mL) and water (13 mL), and the solution was ice-cooled. Trifluoroacetic acid (13.18 mL) was added thereto, and the mixture was stirred at 0° C. for 4 hr. The reaction mixture was quenched with a solution of sodium bicarbonate (20.65 g) in water (250 mL) little by little, saturated with NaCl, and extracted with ethyl acetate-THF (3:1). The organic layer was washed with saturated brine, and dried over anhydrous magnesium sulfate, and the solvent was evaporated under reduced pressure. The residue was subjected to silica gel column chromatography (methanol/ethyl acetate), and the objective fraction was concentrated under reduced pressure to give the title compound (3.06 g) as a white amorphous solid (a mixture of two diastereomers). MS: [M+H]⁺ 1108.3.

C) N-(9-((5R,7R,8R,12aR,14R,15K,15aS,18R)-10-(2-cyanoethoxy)-7-(5-fluoro-4-oxo-3,4-dihydro-7H-pyrrolo[2,3-d]pyrimidin-7-yl)-2-hydroxy-18-((3-hydroxy-1,1,3,3-tetra(propan-2-yl)disiloxanyl)oxy)-2,10-dioxidohexahydro-14H-15,12a-(epoxymethano)-5,8-methanofuro[3,2-l][1,3,6,9,11,2,10]pentaoxadiphosphacyclotetradecin-14(12H)-yl)-9H-purin-6-yl)benzamide (1R,3R,4R,7S)-3-(6-Benzamido-9H-purin-9-yl)-1-(((((2-cyanoethoxy)(((2R,3R,4R,5R)-2-(5-fluoro-4-oxo-3H-pyrrolo[2,3-d]pyrimidin-7(4H)-yl)-4-((3-hydroxy-1,1,3,3-tetraisopropyldisilanyl)oxy)-5-(hydroxymethyl)tetrahydrofuran-3-yl)oxy)phosphoryl)oxy)methyl)-2,5-dioxabicyclo[2.2.1]heptan-7-yl hydrogen phosphonate (3.06 g) was subjected successively to azeotropic dehydration with anhydrous acetonitrile (about 100 mL) and anhydrous pyridine (about 100 mL), and dissolved in anhydrous pyridine (75 mL). 2-Chloro-5,5-dimethyl-1,3,2-dioxaphosphinane 2-oxide (1.78 g) was added thereto, and the mixture was stirred at room temperature for 1 hr under argon stream. Water (1.74 mL) and iodine (911 mg) were added thereto, and the mixture was stirred at room temperature for additional 15 min. The reaction mixture was quenched with 10% aqueous sodium thiosulfate solution (7.5 mL), and concentrated under reduced pressure. The residue was diluted with water (100 mL), and the mixture was extracted with ethyl acetate-THF (3:1). The organic layer was washed with saturated brine, and dried over anhydrous magnesium sulfate, and the solvent was evaporated under reduced pressure. Toluene (about 100 mL) was added thereto, and the mixture was concentrated again under reduced pressure. The residue was subjected to silica gel column chromatography (methanol/ethyl acetate), and the objective fraction was concentrated under reduced pressure to give the title compound (2.38 g) as a white amorphous solid (a mixture of two diastereomers). MS: [M+H]⁺ 1106.3.

D) 7-((5R,7R,8R,12aR,14R,15R,15aS,18R)-14-(6-amino-9H-purin-9-yl)-2,10-dihydroxy-18-((3-hydroxy-1,1,3,3-tetra(propan-2-yl)disiloxanyl)oxy)-2,10-dioxidohexahydro-14H-15,12a-(epoxymethano)-5,8-methanofuro[3,2-l][1,3,6,9,11,2,10]pentaoxadiphosphacyclotetradecin-7(12H)-yl)-5-fluoro-3,7-dihydro-4H-pyrrolo[2,3-d]pyrimidin-4-one N-(9-((5R,7R,8R,12aR,14R,15R,15aS,18R)-10-(2-Cyanoethoxy)-7-(5-fluoro-4-oxo-3,4-dihydro-7H-pyrrolo[2,3-d]pyrimidin-7-yl)-2-hydroxy-18-((3-hydroxy-1,1,3,3-tetra(propan-2-yl)disiloxanyl)oxy)-2,10-dioxidohexahydro-14H-15,12a-(epoxymethano)-5,8-methanofuro[3,2-l][1,3,6,9,11,2,10]pentaoxadiphosphacyclotetradecin-14(12H)-yl)-9H-purin-6-yl)benzamide (2.38 g) was dissolved in 40% methylamine methanol solution (40 mL), the solution was stirred at room temperature for 1 hr, and the reaction mixture was concentrated under reduced pressure. Toluene (about 80 mL) was added thereto, and the mixture was concentrated again under reduced pressure. The residue was subjected to silica gel column chromatography (methanol/ethyl acetate), and the objective fraction was concentrated under reduced pressure to give the title compound (756 mg) as a white solid. MS: [M+H]⁺ 949.2.

E) 7-((5R,7R,8R,12aR,14R,15R,15aS,18R)-14-(6-amino-9H-purin-9-yl)-2,10,18-trihydroxy-2,10-dioxidohexahydro-14H-15,12a-(epoxymethano)-5,8-methanofuro[3,2-l][1,3,6,9,11,2,10]pentaoxadiphosphacyclotetradecin-7(12H)-yl)-5-fluoro-3,7-dihydro-4H-pyrrolo[2,3-d]pyrimidin-4-one di-triethylamine salt (Optical Isomer)

7-((5R,7R,8R,12aR,14R,15R,15aS,18R)-14-(6-Amino-9H-purin-9-yl)-2,10-dihydroxy-18-((3-hydroxy-1,1,3,3-tetra(propan-2-yl)disiloxanyl)oxy)-2,10-dioxidohexahydro-14H-15,12a-(epoxymethano)-5,8-methanofuro[3,2-l][1,3,6,9,11,2,10]pentaoxadiphosphacyclotetradecin-7(12H)-yl)-5-fluoro-3,7-dihydro-4H-pyrrolo[2,3-d]pyrimidin-4-one (756 mg) was dissolved in methanol (2 mL) and triethylamine (0.8 mL), triethylamine trihydrofluoride (3.90 mL) was added thereto, and the mixture was stirred at 50° C. for 2 hr. The reaction mixture was allowed to cool to room temperature, neutralized with 1 M aqueous triethylammonium hydrogencarbonate solution (110 mL), and stirred at room temperature for 15 min. The reaction mixture was concentrated under reduced pressure, and the residue was subjected to ODS column chromatography (acetonitrile/10 mM triethylammonium acetate buffer solution). The objective fraction was concentrated under reduced pressure, and the residue was freeze-dried to give the title compound (504 mg) as a white solid. $^1$H NMR (300 MHz, D$_2$O) δ 1.20 (18H, t, J=7.4 Hz), 3.12 (12H, q, J=7.2 Hz), 4.02-4.16 (4H, m), 4.23-4.37 (3H, m), 4.55 (1H, d, J=4.5 Hz), 4.82-4.93 (3H, m), 6.12 (1H, s), 6.39 (1H, dd, J=8.3, 1.5 Hz), 7.19 (1H, d, J=1.9 Hz), 7.96 (1H, s), 8.11 (1H, s), 8.17 (1H, s). $^{31}$P NMR (121 MHz, D$_2$O) δ −1.91, −1.80.

Example 17

Synthesis of 7-((5R,7R,8R,12aR,14R,15R,15aS,18R)-14-(6-amino-9H-purin-9-yl)-10,18-dihydroxy-2,10-dioxido-2-sulfanylhexahydro-14H-15,12a-(epoxymethano)-5,8-methanofuro[3,2-l][1,3,6,9,11,2,10]pentaoxadiphosphacyclotetradecin-7(12H)-yl)-5-fluoro-3,7-dihydro-4H-pyrrolo[2,3-d]pyrimidin-4-one di-trimethylamine salt (Optical Isomer)

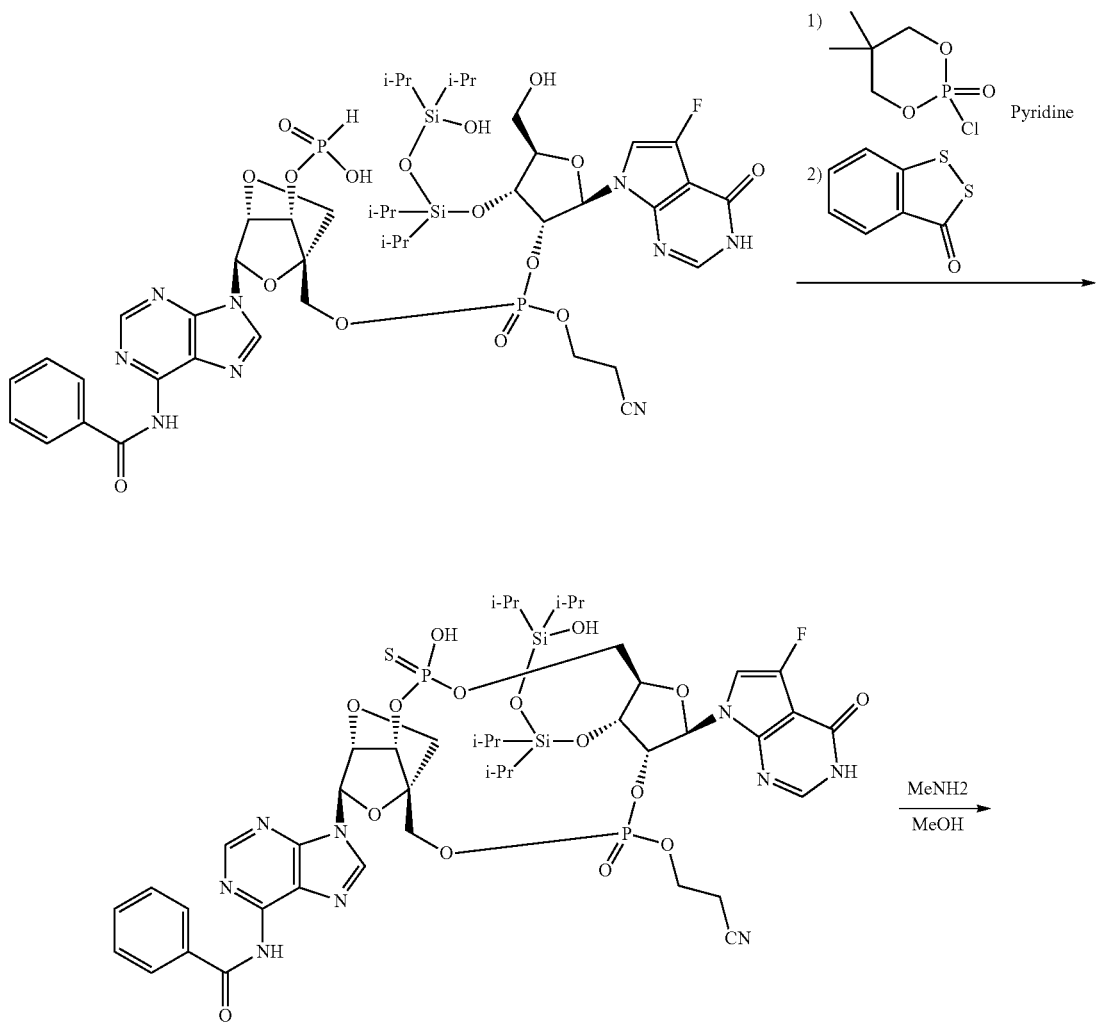

-continued

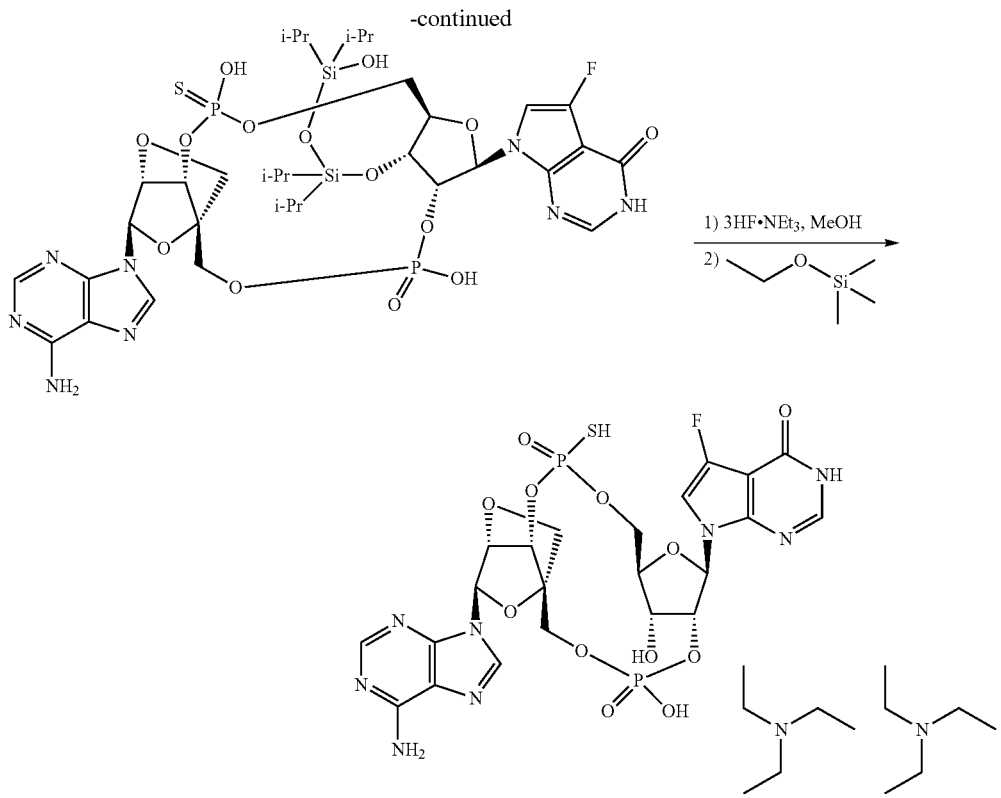

A) N-(9-((5R,7R,8R,12aR,14R,15R,15aS,18R)-10-(2-cyanoethoxy)-7-(5-fluoro-4-oxo-3,4-dihydro-7H-pyrrolo[2,3-d]pyrimidin-7-yl)-18-((3-hydroxy-1,1,3,3-tetraisopropyldisiloxanyl)oxy)-2,10-dioxido-2-sulfanylhexahydro-14H-15,12a-(epoxymethano)-5,8-methanofuro[3,2-1][1,3,6,9,11,2,10]pentaoxadiphosphacyclotetradecin-14(12H)-yl)-9H-purin-6-yl)benzamide (1R,3R,4R,7S)-3-(6-Benzamido-9H-purin-9-yl)-1-((((2-cyanoethoxy)(((2R,3R,4R,5R)-2-(5-fluoro-4-oxo-3H-pyrrolo[2,3-d]pyrimidin-7(4H)-yl)-4-((3-hydroxy-1,1,3,3-tetraisopropyldisiloxanyl)oxy)-5-(hydroxymethyl)tetrahydrofuran-3-yl)oxy)phosphoryl)oxy)methyl)-2,5-dioxabicyclo[2.2.1]heptan-7-yl hydrogen phosphonate (3.71 g) was subjected to azeotropic dehydration with anhydrous acetonitrile and anhydrous pyridine, and suspended in anhydrous pyridine (70 mL). 2-Chloro-5,5-dimethyl-1,3,2-dioxaphosphinane 2-oxide (2.15 g) was added thereto, and the mixture was stirred at room temperature for 1 hr under argon atmosphere. 3H-Benzo[c][1,2]dithiol-3-one (674 mg) was added thereto, and the mixture was stirred at room temperature for additional 1 hr. To the reaction mixture was added saturated aqueous sodium hydrogencarbonate solution, and the mixture was extracted with ethyl acetate. The organic layer was washed with saturated brine, and dried over sodium sulfate, and the solvent was evaporated under reduced pressure. The residue was purified by silica gel column chromatography (methanol/ethyl acetate) to give the title compound (2.78 g). MS: [M+H]$^+$ 1122.2

B) 7-((5R,7R,8R,12aR,14R,15R,15aS,18R)-14-(6-amino-9H-purin-9-yl)-10-hydroxy-18-((3-hydroxy-1,1,3,3-tetraisopropyldisiloxanyl)oxy)-2,10-dioxido-2-sulfanylhexahydro-14H-15,12a-(epoxymethano)-5,8-methanofuro[3,2-1][1,3,6,9,11,2,10]pentaoxadiphosphacyclotetradecin-7(12H)-yl)-5-fluoro-3,7-dihydro-4H-pyrrolo[2,3-d]pyrimidin-4-one (Optical Isomer)

N-(9-((5R,7R,8R,12aR,14R,15R,15aS,18R)-10-(2-Cyanoethoxy)-7-(5-fluoro-4-oxo-3,4-dihydro-7H-pyrrolo[2,3-d]pyrimidin-7-yl)-184(3-hydroxy-1,1,3,3-tetraisopropyldisiloxanyl)oxy)-2,10-dioxido-2-sulfanylhexahydro-14H-15,12a-(epoxymethano)-5,8-methanofuro[3,2-1][1,3,6,9,11,2,10]pentaoxadiphosphacyclotetradecin-14(12H)-yl)-9H-purin-6-yl)benzamide (2.78 g) was dissolved in 40% methylamine methanol solution (50 mL), the solution was stirred at room temperature for 1 hr under argon atmosphere, and the solvent was evaporated under reduced pressure. The residue was purified by silica gel column chromatography (methanol/ethyl acetate). The obtained residue was purified by HPLC (L-column2 ODS, 50×150 mm, mobile phase: 5 mM aqueous ammonium acetate solution/acetonitrile) to give the title compound (30 mg). MS: [M+H]$^+$965.3.

C) 7-((5R,7R,8R,12aR,14R,15R,15aS,18R)-14-(6-amino-9H-purin-9-yl)-10,18-dihydroxy-2,10-dioxido-2-sulfanylhexahydro-14H-15,12a-(epoxymethano)-5,8-methanofuro[3,2-1][1,3,6,9,11,2,10]pentaoxadiphosphacyclotetradecin-7(12H)-yl)-5-fluoro-3,7-dihydro-4H-pyrrolo[2,3-d]pyrimidin-4-one di-triethylamine salt (Optical Isomer)

To 7-((5R,7R,8R,12aR,14R,15R,15aS,18R)-14-(6-amino-9H-purin-9-yl)-10-hydroxy-18-((3-hydroxy-1,1,3,3- tetraisopropyldisiloxanyl)oxy)-2,10-dioxido-2-sulfanyl-hexahydro-14H-15,12a-(epoxymethano)-5,8-methanofuro[3,2-1][1,3,6,9,11,2,10]pentaoxadiphosphacyclotetradecin-7(12H)-yl)-5-fluoro-3,7-dihydro-4H-pyrrolo[2,3-d]pyrimidin-4-one (optical isomer) (30 mg) were added triethylamine trihydrofluoride (0.70 mL) and methanol (1 mL), and the mixture was stirred at 50° C. for 3 hr. To the reaction solution was added ethoxy(trimethyl)silane (2.5 mL), the mixture was stirred at room temperature for 30 min, and the solvent was evaporated under reduced pressure. The residue was purified by C18 silica gel column chromatography (10 mM triethylammonium acetate buffer solution/acetonitrile), and the obtained solid was freeze-dried to give the title compound (25 mg). $^1$H NMR (300 MHz, D$_2$O) δ1.19 (18H, t, J=7.4 Hz), 3.11 (12H, q, J=7.2 Hz), 3.99-4.09 (3H, m), 4.09-4.17 (2H, m), 4.22-4.29 (1H, m), 4.34-4.38 (1H, m), 4.50-4.54 (2H, m), 4.90-4.96 (1H, m), 5.06 (1H, s), 6.11 (1H, s), 6.35 (1H, dd, J=8.3, 1.1 Hz), 7.19 (1H, d, J=2.3 Hz), 7.94 (1H, s), 8.08 (1H, s), 8.16 (1H, s). $^{31}$P NMR (121 MHz, D$_2$O) δ 55.76, −1.56.

Example 18

Synthesis of 7-((5R,7R,8R,12aR,14R,15R,15aS,18R)-14-(6-amino-9H-purin-9-yl)-2,18-dihydroxy-2,10-dioxido-10-sulfanylhexahydro-14H-15,12a-(epoxymethano)-5,8-methanofuro[3,2-1][1,3,6,9,11,2,10]pentaoxadiphosphacyclotetradecin-7(12H)-yl)-5-fluoro-3,7-dihydro-4H-pyrrolo[2,3-d]pyrimidin-4-one di-triethylamine salt (Optical Isomer)

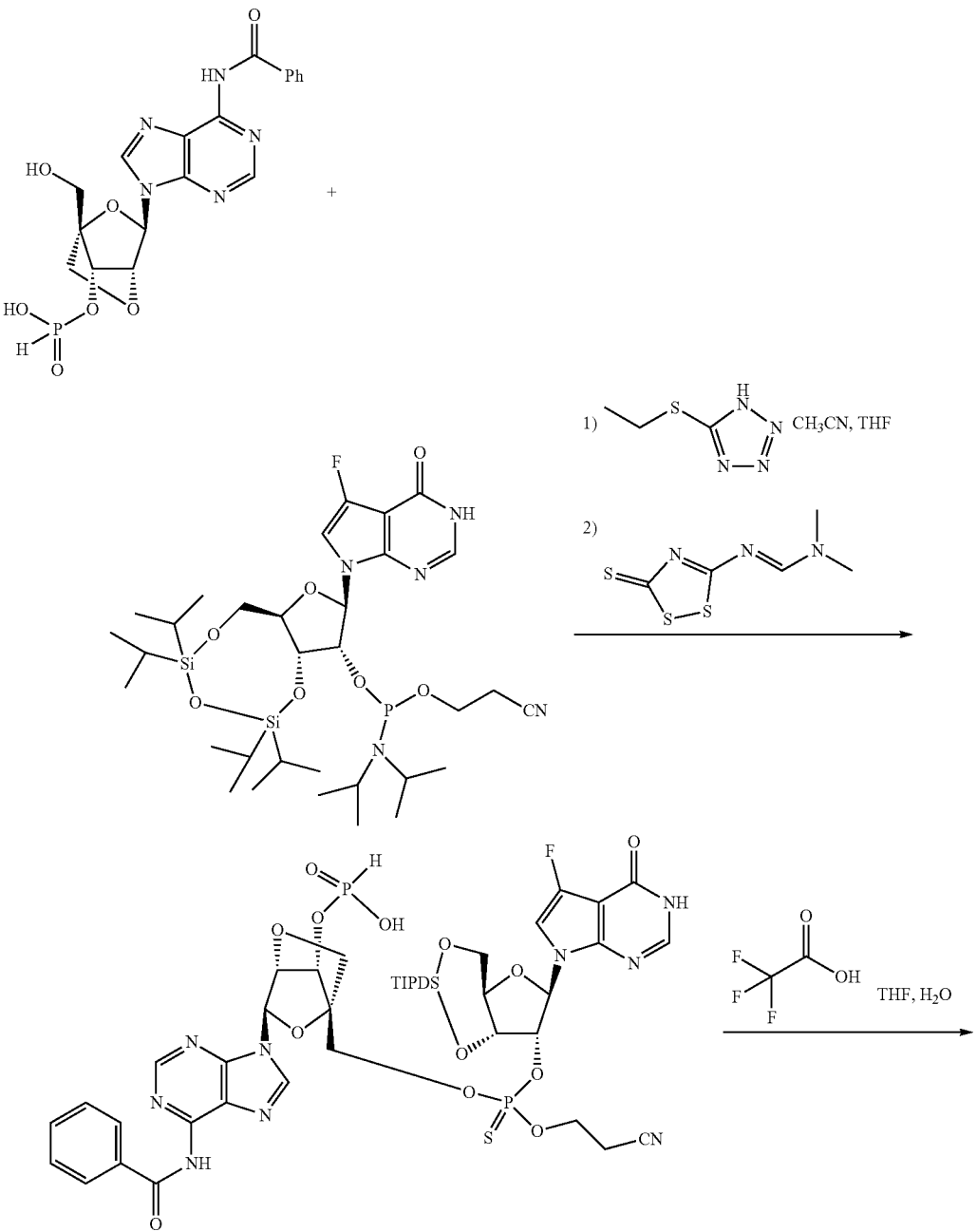

307                                    308
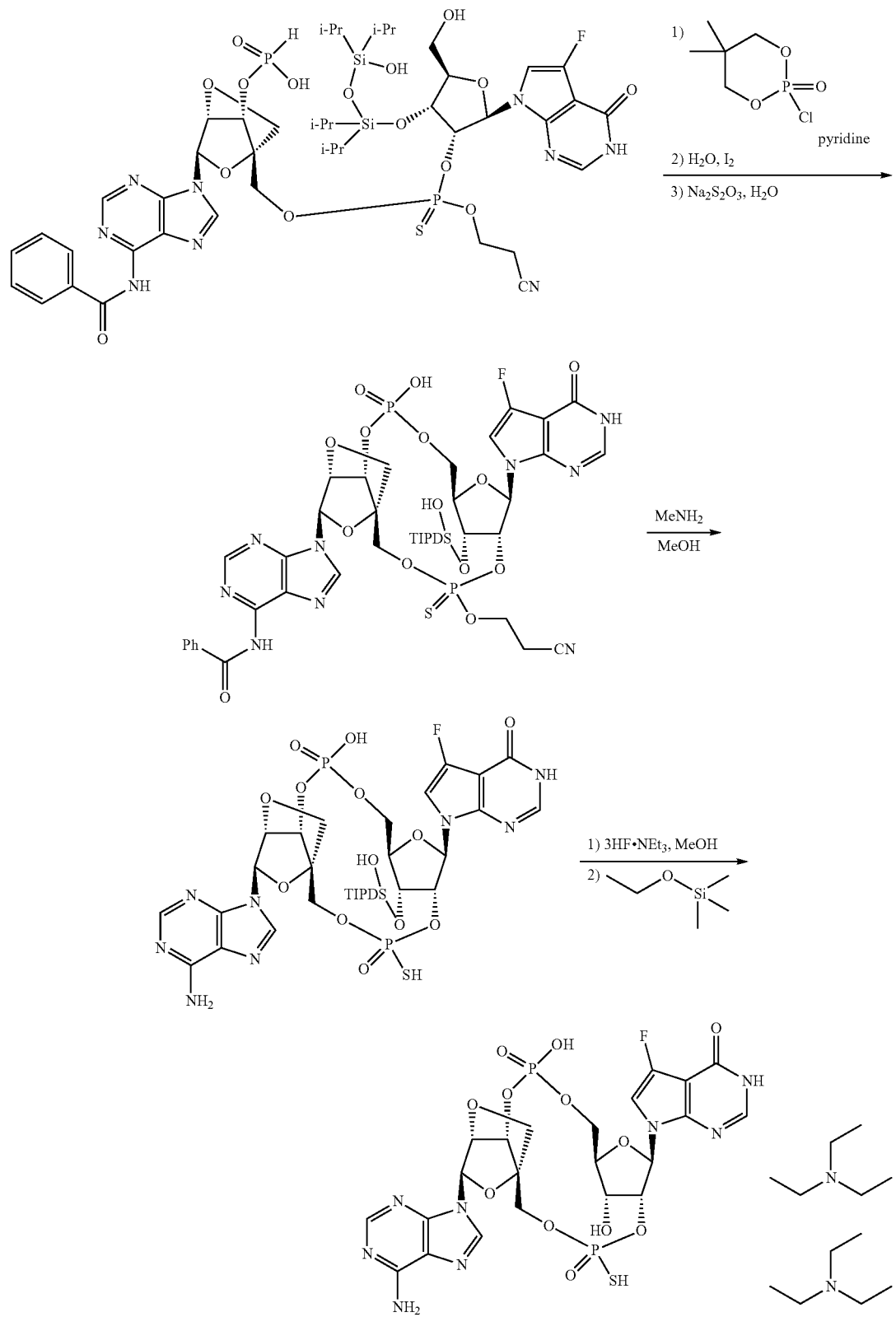

A) (1R,3R,4R,7S)-3-(6-benzamido-9H-purin-9-yl)-1-((((2-cyanoethoxy)(((6aR,8R,9R,9aR)-8-(5-fluoro-4-oxo-3H-pyrrolo[2,3-d]pyrimidin-7(4H)-yl)-2,2,4,4-tetraisopropyltetrahydro-6H-furo[3,2-f][1,3,5,2,4]trioxadisilocin-9-yl)oxy)phosphorothioyl)oxy)methyl)-2,5-dioxabicyclo[2.2.1]heptan-7-yl hydrogen phosphonate A mixture of (1 S,3R,4R,7S)-3-(6-benzamido-9H-purin-9-yl)-1-(hydroxymethyl)-2,5-dioxabicyclo[2.2.1]heptan-7-yl hydrogen phosphonate (3.0 g) and 2-cyanoethyl (6aR,8R,9R,9aR)-8-(5-fluoro-4-oxo-3H-pyrrolo[2,3-d]pyrimidin-7(4H)-yl)-2,2,4,4-tetraisopropyltetrahydro-6H-furo[3,2-f][1,3,5,2,4]trioxadisilocin-9-yl diisopropylphosphoramidite (5.86 g) was subjected to azeotropic dehydration with anhydrous acetonitrile, and suspended in anhydrous THF (25 mL). 5-(Ethylsulfanyl)-2H-tetrazole (2.62 g), which was subjected in advance to azeotropic dehydration with anhydrous acetonitrile, was dissolved in anhydrous acetonitrile (25 mL), the solution was added to the above-mentioned suspension, and the mixture was stirred overnight at room temperature under argon atmosphere. ((Dimethylaminomethylidene)amino)-3H-1,2,4-dithiazoline-3-thione (2.75 g) was added thereto, and the mixture was stirred at room temperature for additional 30 min. The solvent was evaporated under reduced pressure, and the residue was purified by silica gel column chromatography (methanol/ethyl acetate) to give the title compound (4.96 g). MS: [M+H]⁺ 1106.3.

B) (1R,3R,4R,7S)-3-(6-benzamido-9H-purin-9-yl)-1-((((2-cyanoethoxy)(((2R,3R,4R,5R)-2-(5-fluoro-4-oxo-3H-pyrrolo[2,3-d]pyrimidin-7(4H)-yl)-4-((3-hydroxy-1,1,3,3-tetraisopropyldisiloxanyl)oxy)-5-(hydroxymethyl)tetrahydrofuran-3-yl)oxy)phosphorothioyl)oxy)methyl)-2,5-dioxabicyclo[2.2.1]heptan-7-yl hydrogen phosphonate (1R,3R,4R,7S)-3-(6-Benzamido-9H-purin-9-yl)-1-((((2-cyanoethoxy)(((6aR,8R,9R,9aR)-8-(5-fluoro-4-oxo-3H-pyrrolo[2,3-d]pyrimidin-7(4H)-yl)-2,2,4,4-tetraisopropyltetrahydro-6H-furo[3,2-f][1,3,5,2,4]trioxadisilocin-9-yl)oxy)phosphorothioyl)oxy)methyl)-2,5-dioxabicyclo[2.2.1]heptan-7-yl hydrogen phosphonate (4.96 g) was dissolved in a mixed solvent of THF (60 mL) and water (12 mL), and the solution was ice-cooled. Trifluoroacetic acid (12.1 mL) was added thereto, and the mixture was stirred at 0° C. for 3 hr. The reaction mixture was quenched with a solution of sodium bicarbonate (18.8 g) in water (100 mL), and extracted with ethyl acetate-THF (3:1). The organic layer was dried over sodium sulfate, and the solvent was evaporated under reduced pressure. The residue was purified by silica gel column chromatography (methanol/ethyl acetate) to give the title compound (3.77 g). MS: [M+H]⁺ 1124.2.

C) N-(9-((5R,7R,8R,12aR,14R,15R,15aS,18R)-10-(2-cyanoethoxy)-7-(5-fluoro-4-oxo-3,4-dihydro-7H-pyrrolo[2,3-d]pyrimidin-7-yl)-2-hydroxy-18-((3-hydroxy-1,1,3,3-tetraisopropyldisiloxanyl)oxy)-2-oxido-10-sulfidohexahydro-14H-15,12a-(epoxymethano)-5,8-methanofuro[3,2-1][1,3,6,9,11,2,10]pentaoxadiphosphacyclotetradecin-14(12H)-yl)-9H-purin-6-yl)benzamide (1R,3R,4R,7S)-3-(6-Benzamido-9H-purin-9-yl)-1-((((2-cyanoethoxy)(((2R,3R,4R,5R)-2-(5-fluoro-4-oxo-3H-pyrrolo[2,3-d]pyrimidin-7(4H)-yl)-4-((3-hydroxy-1,1,3,3-tet-raisopropyldisiloxanyl)oxy)-5-(hydroxymethyl)tetrahydrofuran-3-yl)oxy)phosphorothioyl)oxy)methyl)-2,5-dioxabicyclo[2.2.1]heptan-7-yl hydrogen phosphonate (3.77 g) was subjected to azeotropic dehydration with anhydrous acetonitrile and anhydrous pyridine, and suspended in anhydrous pyridine (70 mL). 2-Chloro-5,5-dimethyl-1,3,2-dioxaphosphinane 2-oxide (2.17 g) was added thereto, and the mixture was stirred at room temperature for 1 hr under argon atmosphere. Water (2.12 mL) and iodine (1.11 g) were added thereto, and the mixture was stirred at room temperature for additional 1 hr. The reaction mixture was quenched with 10% aqueous sodium thiosulfate solution (15 mL), and the solvent was evaporated under reduced pressure. The residue was diluted with water (100 mL), and the mixture was extracted with ethyl acetate-THF (3:1). The organic layer was dried over sodium sulfate, and the solvent was evaporated under reduced pressure. The residue was purified by silica gel column chromatography (methanol/ethyl acetate) to give the title compound (2.21 g). MS: [M+H]⁺ 1122.2.

D) 74(5R,7R,8R,12aR,14R,15R,15aS,18R)-14-(6-amino-9H-purin-9-yl)-2-hydroxy-18-((3-hydroxy-1,1,3,3-tetra(propan-2-yl)disiloxanyl)oxy)-2,10-dioxido-10-sulfanyl-hexahydro-14H-15,12a-(epoxymethano)-5,8-methanofuro[3,2-1][1,3,6,9,11,2,10]pentaoxadiphosphacyclotetradecin-7(12H)-yl)-5-fluoro-3,7-dihydro-4H-pyrrolo[2,3-d]pyrimidin-4-one (Optical Isomer)

To N-(9-((5R,7R,8R,12aR,14R,15R,15aS,18R)-10-(2-cyanoethoxy)-7-(5-fluoro-4-oxo-3,4-dihydro-7H-pyrrolo[2,3-d]pyrimidin-7-yl)-2-hydroxy-18-((3-hydroxy-1,1,3,3-tetraisopropyldisiloxanyl)oxy)-2-oxido-10-sulfidohexahydro-14H-15,12a-(epoxymethano)-5,8-methanofuro[3,2-1][1,3,6,9,11,2,10]pentaoxadiphosphacyclotetradecin-14(12H)-yl)-9H-purin-6-yl)benzamide (2.38 g) was added 40% methylamine methanol solution (40 mL), and the mixture was stirred at room temperature for 1 hr under argon atmosphere. The obtained mixture was concentrated under reduced pressure, and the residue was purified by silica gel column chromatography (methanol/ethyl acetate). The obtained residue was purified by HPLC (L-column2 ODS, 50×150 mm, mobile phase: 5 mM aqueous ammonium acetate solution/acetonitrile), the obtained fraction was concentrated under reduced pressure, and the residue was freeze-dried to give the title compound (710 mg). MS: [M+H]⁺ 965.2.

E) 7-((5R,7R,8R,12aR,14R,15R,15aS,18R)-14-(6-amino-9H-purin-9-yl)-2,18-dihydroxy-2,10-dioxido-10-sulfanylhexahydro-14H-15,12a-(epoxymethano)-5,8-methanofuro[3,2-1][1,3,6,9,11,2,10]pentaoxadiphosphacyclotetradecin-7(12H)-yl)-5-fluoro-3,7-dihydro-4H-pyrrolo[2,3-d]pyrimidin-4-one di-triethylamine salt (Optical Isomer)

To a solution of 7-((5R,7R,8R,12aR,14R,15R,15aS,18R)-14-(6-amino-9H-purin-9-yl)-2-hydroxy-18-((3-hydroxy-1,1,3,3-tetra(propan-2-yl)disiloxanyl)oxy)-2,10-dioxido-10-sulfanylhexahydro-14H-15,12a-(epoxymethano)-5,8-methanofuro[3,2-1][1,3,6,9,11,2,10]pentaoxadiphosphacyclotetradecin-7(12H)-yl)-5-fluoro-3,7-dihydro-4H-pyrrolo[2,3-d]pyrimidin-4-one (optical isomer, derived from tR2) (710 mg) in methanol (20 mL) was added triethylamine trihydrofluoride (4.80 mL), and the mixture was stirred at 50° C. for 3 hr. To the reaction mixture was added ethoxytrimethylsilane (2.29 mL) at room temperature, and the mixture was stirred for 30 min. The reaction mixture was concentrated under reduced pressure, and the residue was purified by C18 silica gel column chromatography (10 mM triethylammonium acetate buffer solution/acetonitrile), and freeze-dried to give the title compound (530 mg). $^1$H NMR (300 MHz, D$_2$O) δ1.22 (18H, t, J=7.2 Hz), 3.14 (12H, q, J=7.6 Hz), 4.03-4.19 (4H, m), 4.25-4.41 (3H, m), 4.65 (1H, d, J=4.5 Hz), 4.84 (1H, d, J=4.5 Hz), 4.91 (1H, s), 4.99 (1H, ddd, J=10.1, 8.2, 4.3 Hz), 6.14 (1H, s), 6.39 (1H, d, J=7.9 Hz), 7.17 (1H, d, J=2.3 Hz), 7.97 (1H, s), 8.11 (1H, s), 8.19 (1H, s). $^{31}$P NMR (121 MHz, D$_2$O) δ52.5, 1.74.

Example 19

Synthesis of 2-amino-9-((5R,7R,8R,12aR,14R,15R,15aR,16R)-15-fluoro-7-(5-fluoro-4-oxo-3,4-dihydro-7H-pyrrolo[2,3-d]pyrimidin-7-yl)-2,10,16-trihydroxy-2,10-dioxidooctahydro-12H-5,8-methanofuro[3,2-l][1,3,6,9,11,2,10]pentaoxadiphosphacyclotetradecin-14-yl)-1,9-dihydro-6H-purin-6-one di-triethylamine salt
(Optical Isomer)

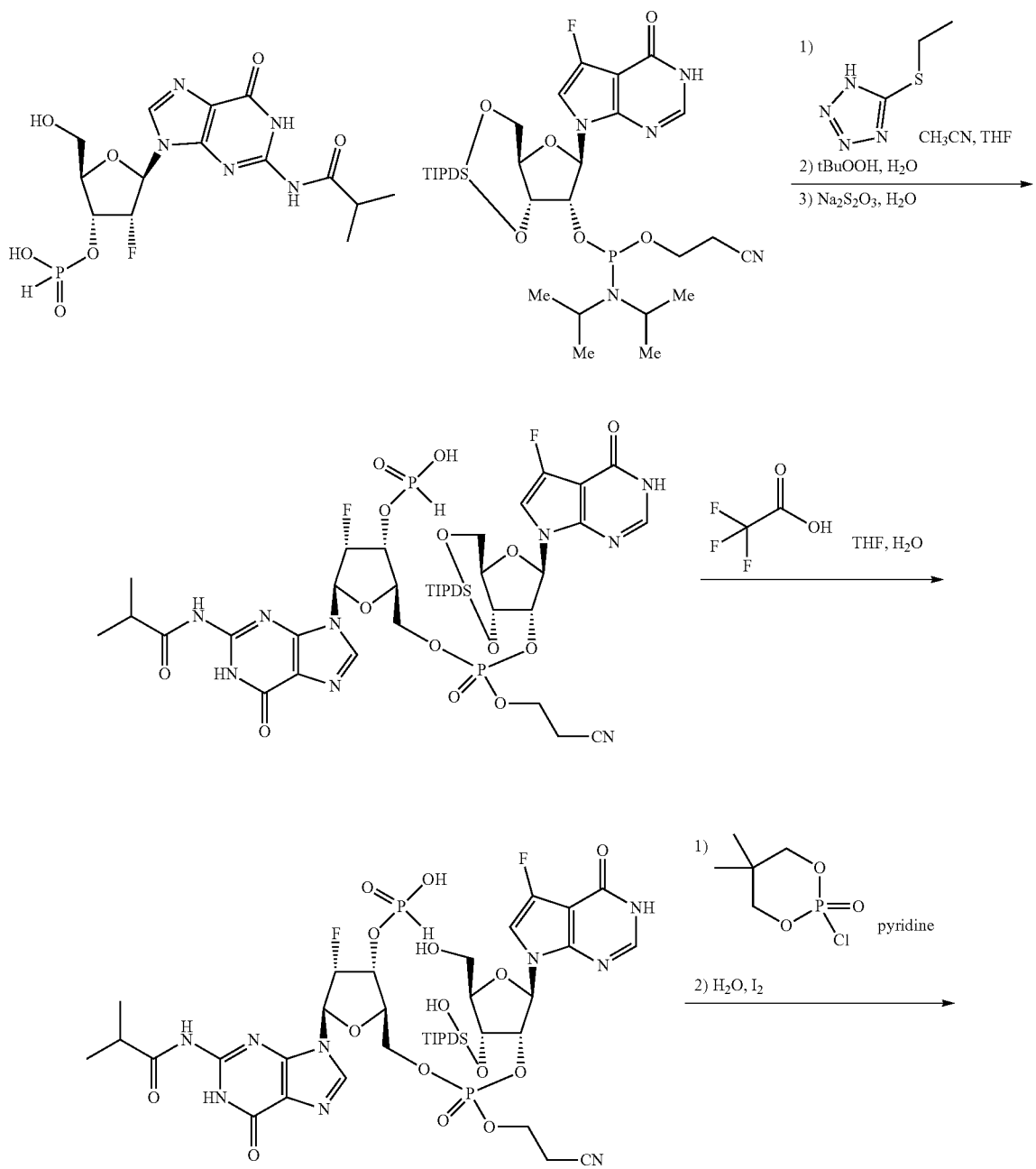

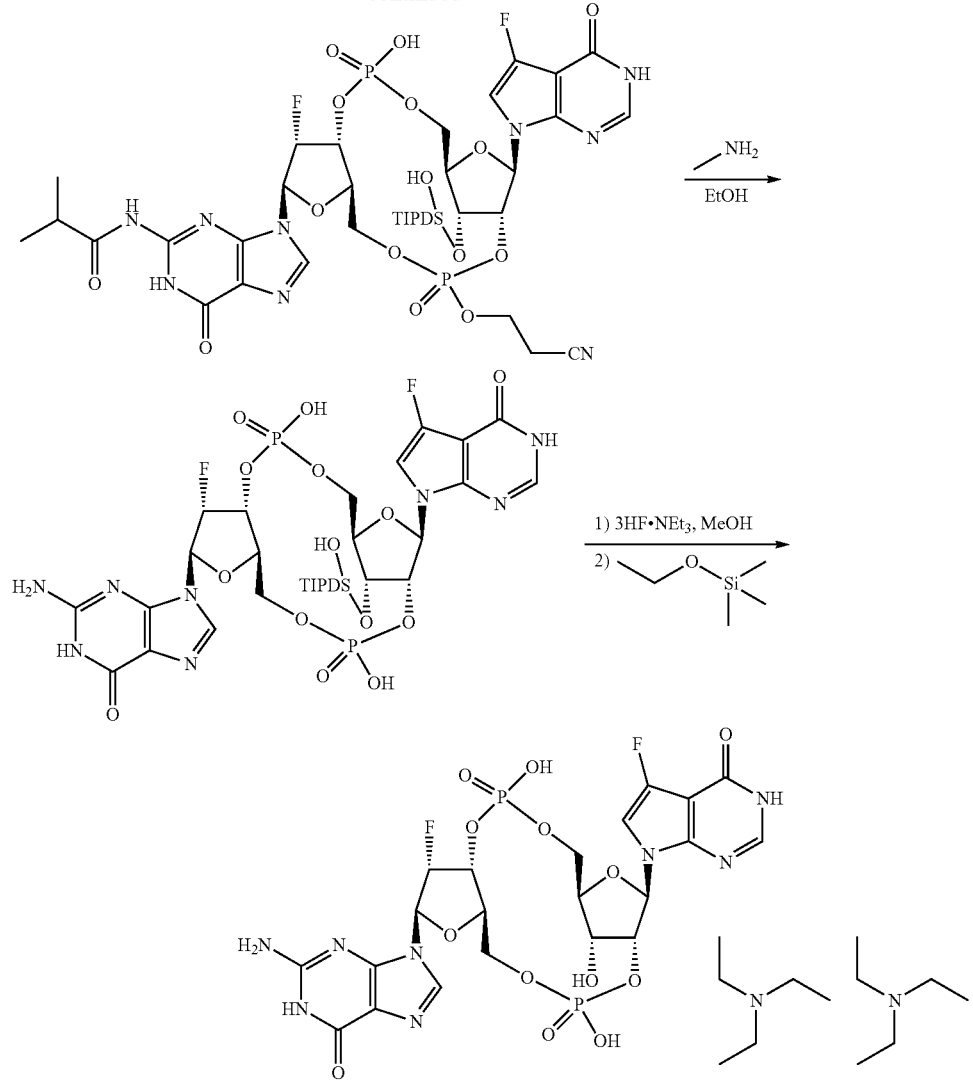

A) (2R,3R,4R,5R)-2-((((2-cyanoethoxy)(((6aR,8R, 9R,9aR)-8-(5-fluoro-4-oxo-3H-pyrrolo[2,3-d]pyrimidin-7(4H)-yl)-2,2,4,4-tetraisopropyltetrahydro-6H-furo[3,2-f][1,3,5,2,4]trioxadisilocin-9-yl)oxy) phosphoryl)oxy)methyl)-4-fluoro-5-(2-isobutylamido-6-oxo-1H-purin-9(6H)-yl) tetrahydrofuran-3-yl hydrogen phosphonate 2'-Deoxy-2'-fluoro-3'-O-(hydroxy(oxido)phosphoranyl)-N-isobutyrylguanosine (680 mg) and 2-cyanoethyl (6aR,8R, 9R,9aR)-8-(5-fluoro-4-oxo-3H-pyrrolo[2,3-d]pyrimidin-7(4H)-yl)-2,2,4,4-tetraisopropyltetrahydro-6H-furo[3,2-f][1, 3,5,2,4]trioxadisilocin-9-yl diisopropylphosphoramidite (1535 mg) were subjected to azeotropic dehydration with anhydrous acetonitrile (three times), and suspended in anhydrous THF (10.00 ml). To the suspension was added a mixture of 5-(ethylsulfanyl)-2H-tetrazole (633 mg) (which was subjected to azeotropic dehydration with anhydrous acetonitrile) and anhydrous acetonitrile (10 ml), and the mixture was stirred at room temperature for 7 hr under argon atmosphere. To the mixture were added a mixture of 2-cyanoethyl (6aR,8R,9R,9aR)-8-(5-fluoro-4-oxo-3H-pyrrolo[2, 3-d]pyrimidin-7(4H)-yl)-2,2,4,4-tetraisopropyltetrahydro-6H-furo[3,2-f][1,3,5,2,4]trioxadisilocin-9-yl diisopropylphosphoramidite (1181 mg, 1.62 mmol) (which was subjected to azeotropic dehydration with anhydrous acetonitrile) and anhydrous acetonitrile (3 ml), and a mixture of 5-(ethylsulfanyl)-2H-tetrazole (633 mg) (which was subjected to azeotropic dehydration with anhydrous acetonitrile) and anhydrous acetonitrile (3 ml), and the mixture was stirred overnight at room temperature under argon atmosphere. To the reaction mixture was added 70% tert-butyl hydroperoxide aqueous solution (0.674 mL), and the mixture was stirred at room temperature for additional 30 min. To the reaction mixture was added a mixture of sodium thiosulfate pentahydrate (2817 mg) and water (4 mL), and the solvent was evaporated under reduced pressure. The residue was purified by silica gel column chromatography (methanol/ethyl acetate) to give the title compound (1260 mg). MS: [M+H]$^+$ 1062.3.

B) (2R,3R,4R,5R)-24 ((((2-cyanoethoxy)(((2R,3R, 4R,5R)-2-(5-fluoro-4-oxo-3H-pyrrolo[2,3-d]pyrimidin-7(4H)-yl)-4-((3-hydroxy-1,1,3,3-tetraisopropyldisiloxanyl)oxy)-5-(hydroxymethyl)tetrahydrofuran-3-yl)oxy)phosphoryl)oxy)methyl)-4-fluoro-5-(2-isobutylamido-6-oxo-1H-purin-9(6H)-yl) tetrahydrofuran-3-yl hydrogen phosphonate To a mixture of (2R,3R,4R,5R)-2-((((2-cyanoethoxy) (((6aR,8R,9R,9aR)-8-(5-fluoro-4-oxo-3H-pyrrolo[2,3-d]pyrimidin-7(4H)-yl)-2,2,4,4-tetraisopropyltetrahydro-6H-furo[3,2-f][1,3,5,2,4]trioxadisilocin-9-yl)oxy)phosphoryl)oxy) methyl)-4-fluoro-5-(2-isobutylamido-6-oxo-1H-purin-9 (6H)-yl)tetrahydrofuran-3-yl hydrogen phosphonate (1.26 g), THF (16 ml) and water (4 ml) was added trifluoroacetic acid (3.18 ml) at 0° C., and the mixture was stirred for 4 hr. To the mixture was added an aqueous solution of sodium hydrogencarbonate (4.98 g), and the mixture was saturated with sodium chloride. The mixture was extracted with ethyl acetate/THF, and the solvent was evaporated under reduced pressure. The residue was purified by silica gel column chromatography (methanol/ethyl acetate) to give the title compound (1000 mg). MS: [M+H]$^+$ 1080.3.

C) N-(9-((5R,7R,8R,12aR,14R,15R,15aR,16R)-10-(2-cyanoethoxy)-15-fluoro-7-(5-fluoro-4-oxo-3,4-dihydro-7H-pyrrolo[2,3-d]pyrimidin-7-yl)-2-hydroxy-16-((3-hydroxy-1,1,3,3-tetraisopropyldisiloxanyl)oxy)-2,10-dioxidooctahydro-12H-5,8-methanofuro[3,2-1][1,3,6,9,11,2,10]pentaoxadiphosphacyclotetradecin-14-yl)-6-oxo-6,9-dihydro-1H-purin-2-yl)-2-methylpropanamide (2R,3R,4R,5R)-2-((((2-Cyanoethoxy)(((2R,3R,4R,5R)-2-(5-fluoro-4-oxo-3H-pyrrolo[2,3-d]pyrimidin-7(4H)-yl)-4-((3-hydroxy-1,1,3,3-tetraisopropyldisiloxanyl)oxy)-5-(hydroxymethyl)tetrahydrofuran-3-yl)oxy)phosphoryl)oxy) methyl)-4-fluoro-5-(2-isobutylamido-6-oxo-1H-purin-9 (6H)-yl)tetrahydrofuran-3-yl hydrogen phosphonate (1 g) was subjected to azeotropic dehydration with anhydrous acetonitrile and anhydrous pyridine, and suspended in anhydrous pyridine (24 mL). 2-Chloro-5,5-dimethyl-1,3,2-dioxaphosphinane 2-oxide (598 mg) was added thereto, and the mixture was stirred at room temperature for 15 min under argon atmosphere. Water (0.584 mL) and iodine (305 mg) were added thereto, and the mixture was stirred at room temperature for additional 25 min. The reaction mixture was concentrated under reduced pressure, and the residue was purified by silica gel column chromatography (methanol/ethyl acetate) to give the title compound (800 mg). MS: [M+H]$^+$ 1078.2

D) 2-amino-9-((5R,7R,8R,12aR,14R,15R,15aR, 16R)-15-fluoro-7-(5-fluoro-4-oxo-3,4-dihydro-7H-pyrrolo[2,3-d]pyrimidin-7-yl)-2,10-dihydroxy-16-((3-hydroxy-1,1,3,3-tetraisopropyldisiloxanyl)oxy)-2,10-dioxidooctahydro-12H-5,8-methanofuro[3,2-1] [1,3,6,9,11,2,10]pentaoxadiphosphacyclotetradecin-14-yl)-1,9-dihydro-6H-purin-6-one (Optical Isomer)

To N-(9-((5R,7R,8R,12aR,14R,15R,15aR,16R)-10-(2-cyanoethoxy)-15-fluoro-7-(5-fluoro-4-oxo-3,4-dihydro-7H-pyrrolo[2,3-d]pyrimidin-7-yl)-2-hydroxy-16-((3-hydroxy-1,1,3,3-tetraisopropyldisiloxanyl)oxy)-2,10-dioxidooctahydro-12H-5,8-methanofuro[3,2-1][1,3,6,9,11,2,10]pentaoxadiphosphacyclotetradecin-14-yl)-6-oxo-6,9-dihydro-1H-purin-2-yl)-2-methylpropanamide (800 mg, 0.74 mmol) was added 33% methylamine ethanol solution (30 mL), the mixture was stirred overnight at room temperature under argon atmosphere, and the solvent was evaporated under reduced pressure. The residue was purified by silica gel column chromatography (methanol/ethyl acetate). The obtained residue was purified by HPLC (L-column2 ODS, 50×150 mm, mobile phase: 5 mM aqueous ammonium acetate solution/acetonitrile) to give the title compound (163.4 mg). MS: [M+H]$^+$ 955.3.

E) 2-amino-9-((5R,7R,8R,12aR,14R,15R,15aR, 16R)-15-fluoro-7-(5-fluoro-4-oxo-3,4-dihydro-7H-pyrrolo[2,3-d]pyrimidin-7-yl)-2,10,16-trihydroxy-2, 10-dioxidooctahydro-12H-5,8-methanofuro[3,2-1][1, 3,6,9,11,2,10]pentaoxadiphosphacyclotetradecin-14-yl)-1,9-dihydro-6H-purin-6-one di-triethylamine salt (Optical Isomer)

A mixture of 2-amino-9-((5R,7R,8R,12aR,14R,15R, 15aR,16R)-15-fluoro-7-(5-fluoro-4-oxo-3,4-dihydro-7H-pyrrolo[2,3-d]pyrimidin-7-yl)-2,10-dihydroxy-16-((3-hydroxy-1,1,3,3-tetraisopropyldisiloxanyl)oxy)-2,10-dioxidooctahydro-12H-5,8-methanofuro[3,2-1][1,3,6,9,11, 2,10]pentaoxadiphosphacyclotetradecin-14-yl)-1,9-dihydro-6H-purin-6-one (optical isomer) (21.4 mg), triethylamine trihydrofluoride (0.183 mL) and methanol (0.07 mL) was stirred at 50° C. for 1 hr under argon atmosphere. To the reaction mixture was added ethoxy (trimethyl)silane (1.046 mL), the mixture was stirred at room temperature for additional 1 hr, and the solvent was evaporated under reduced pressure. The residue was purified by C18 silica gel column chromatography (10 mM triethylammonium acetate buffer solution/acetonitrile), and freeze-dried to give the title compound (4.6 mg). $^1$H NMR (300 MHz, D$_2$O) δ 1.20 (18H, t, J=7.3 Hz), 3.13 (12H, q, J=7.3 Hz), 4.07 (2H, d, J=11.1 Hz), 4.25 (2H, d, J=7.6 Hz), 4.33-4.99 (4H, m), 5.04-5.25 (1H, m), 5.41-5.70 (1H, m), 6.17 (1H, d, J=19.0 Hz), 6.38 (1H, d, J=9.2 Hz), 7.32 (1H, S), 7.79 (1H, brs), 7.95 (1H, S). $^{31}$P NMR (121 MHz, D$_2$O) δ−1.61, −1.52.

Example 20
Synthesis of 7-((5R,7R,8R,12aR,14R,15R,15aS, 16R)-14-(6-amino-9H-purin-9-yl)-2,10,15,16-tetra-hydroxy-2-oxido-10-sulfanyloctahydro-12H-5,8-methanofuro[3,2-1][1,3,6,9,11,2,10]pentaoxadiphosphacyclotetradecin-7-yl)-5-fluoro-3,7-dihydro-4H-pyrrolo[2,3-d]pyrimidin-4-one di-triethylamine salt (Optical Isomer)
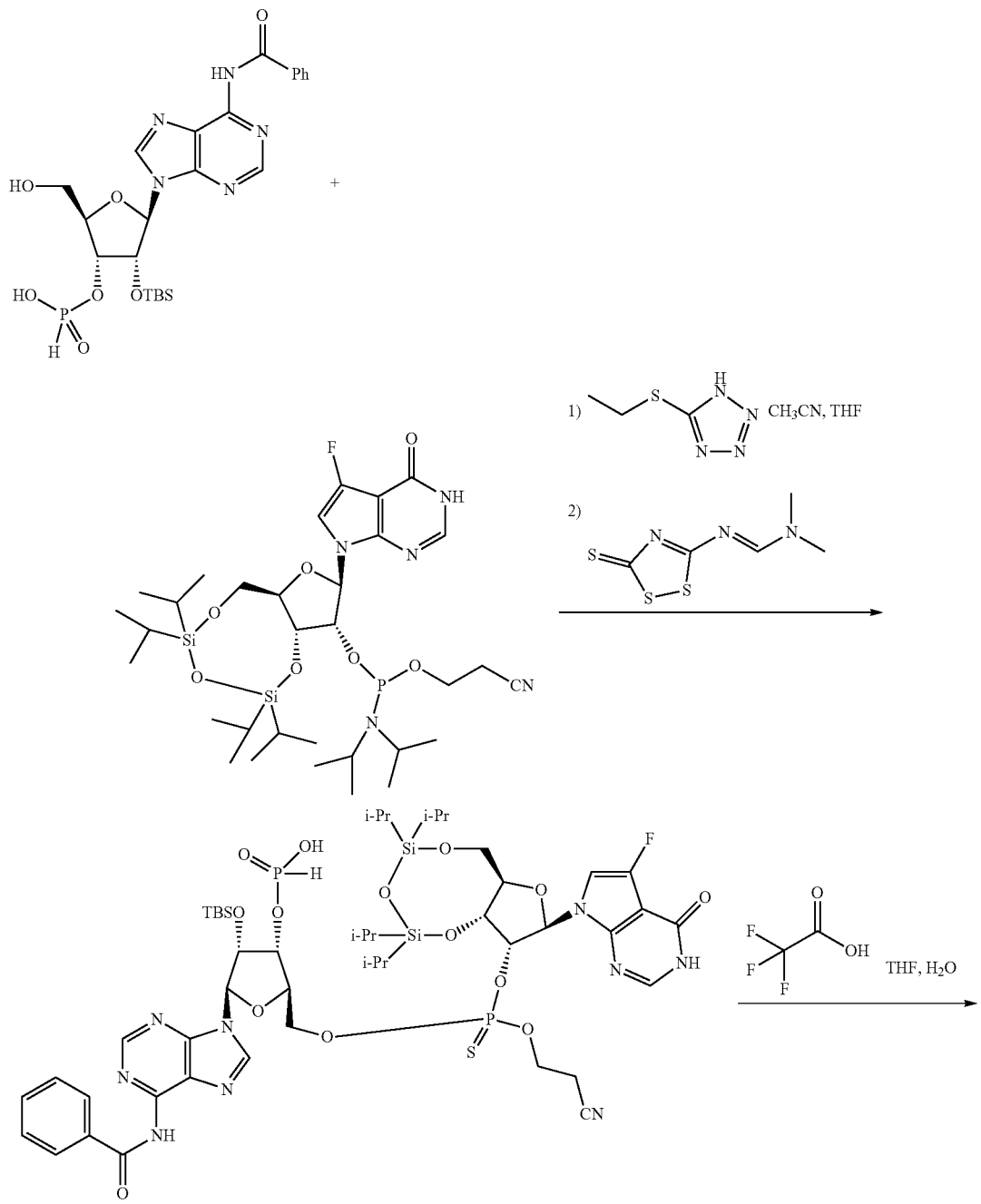

319 320
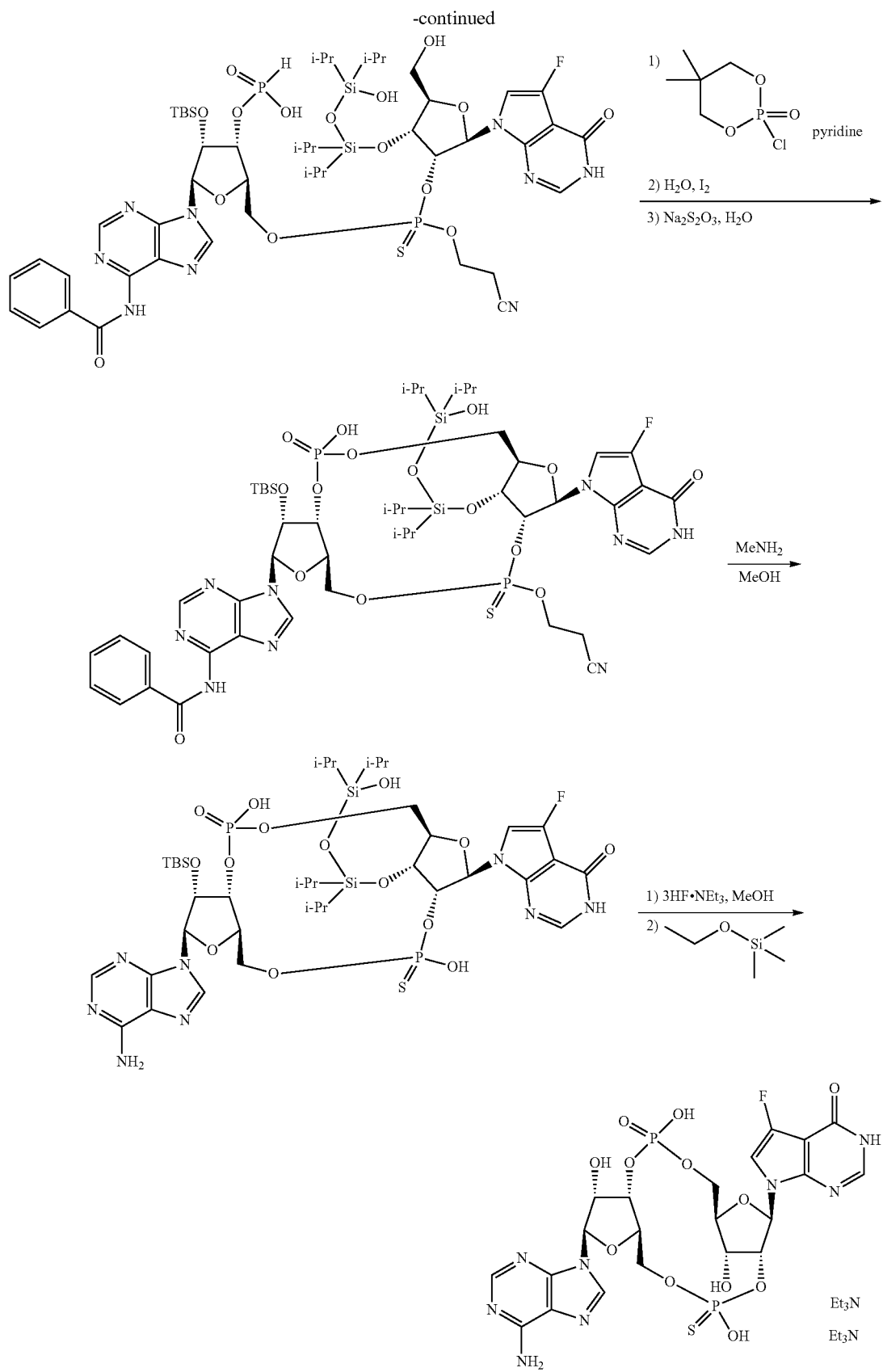
-continued

A) (2R,3R,4R,5R)-5-(6-benzamido-9H-purin-9-yl)-4-((tert-butyldimethylsilyl)oxy)-2-(((((2-cyanoethoxy)(((6aR,8R,9R,9aR)-8-(5-fluoro-4-oxo-3H-pyrrolo[2,3-d]pyrimidin-7(4H)-yl)-2,2,4,4-tetraisopropyltetrahydro-6H-furo[3,2-f][1,3,5,2,4]trioxadisilocin-9-yl)oxy)phosphorothioyl)oxy)methyl)tetrahydrofuran-3-yl hydrogen phosphonate A mixture of (2R,3R,4R,5R)-5-(6-benzamido-9H-purin-9-yl)-4-((tert-butyldimethylsilyl)oxy)-2-(hydroxymethyl)tetrahydrofuran-3-yl hydrogen phosphonate (3.0 g) and 2-cyanoethyl (6aR,8R,9R,9aR)-8-(5-fluoro-4-oxo-3H-pyrrolo[2,3-d]pyrimidin-7(4H)-yl)-2,2,4,4-tetraisopropyltetrahydro-6H-furo[3,2-f][1,3,5,2,4]trioxadisilocin-9-yl diisopropylphosphoramidite (5.36 g) was subjected to azeotropic dehydration with anhydrous acetonitrile, and suspended in anhydrous acetonitrile (25 mL) and anhydrous THF (15 mL). 5-(Ethylsulfanyl)-2H-tetrazole (2.13 g), which was subjected in advance to azeotropic dehydration with anhydrous acetonitrile, was dissolved in anhydrous acetonitrile (15 mL), the solution was added to the above-mentioned suspension, and the mixture was stirred overnight at room temperature under argon atmosphere. ((Dimethylaminomethylidene)amino)-3H-1,2,4-dithiazoline-3-thione (2.24 g) was added thereto, and the mixture was stirred at room temperature for additional 1 hr. The solvent was evaporated under reduced pressure, and the residue was purified by silica gel column chromatography (methanol/ethyl acetate) to give the title compound (5.15 g). MS: [M+H]⁺ 1208.3.

B) (2R,3R,4R,5R)-5-(6-benzamido-9H-purin-9-yl)-4-((tert-butyldimethylsilyl)oxy)-2-(((((2-cyanoethoxy)(((2R,3R,4R,5R)-2-(5-fluoro-4-oxo-3H-pyrrolo[2,3-d]pyrimidin-7(4H)-yl)-4-((3-hydroxy-1,1,3,3-tetraisopropyldisiloxanyl)oxy)-5-(hydroxymethyl)tetrahydrofuran-3-yl)oxy)phosphorothioyl)oxy)methyl)tetrahydrofuran-3-yl hydrogen phosphonate (2R,3R,4R,5R)-5-(6-Benzamido-9H-purin-9-yl)-4-((tert-butyldimethylsilyl)oxy)-2-(((((2-cyanoethoxy)(((6aR,8R,9R,9aR)-8-(5-fluoro-4-oxo-3H-pyrrolo[2,3-d]pyrimidin-7(4H)-yl)-2,2,4,4-tetraisopropyltetrahydro-6H-furo[3,2-f][1,3,5,2,4]trioxadisilocin-9-yl)oxy)phosphorothioyl)oxy)methyl)tetrahydrofuran-3-yl hydrogen phosphonate (5.15 g) was dissolved in a mixed solvent of THF (48 mL) and water (10 mL), and the solution was ice-cooled. Trifluoroacetic acid (11.5 mL) was added thereto, and the mixture was stirred at 0° C. for 3 hr. The reaction mixture was quenched with a solution of sodium bicarbonate (12.5 g) in water (100 mL), and extracted with ethyl acetate-THF. The organic layer was washed with saturated brine, and dried over sodium sulfate, and the solvent was evaporated under reduced pressure. The residue was purified by silica gel column chromatography (methanol/ethyl acetate) to give the title compound (5.13 g). MS: [M+H]⁺ 1226.4.

C) N-(9-((5R,7R,8R,12aR,14R,15R,15aR,16R)-15-((tert-butyl(dimethyl)silyl)oxy)-10-(2-cyanoethoxy)-7-(5-fluoro-4-oxo-3,4-dihydro-7H-pyrrolo[2,3-d]pyrimidin-7-yl)-2-hydroxy-16-((3-hydroxy-1,1,3,3-tetra(propan-2-yl)disiloxanyl)oxy)-2-oxido-10-sulfidooctahydro-12H-5,8-methanofuro[3,2-1][1,3,6,9,11,2,10]pentaoxadiphosphacyclotetradecin-14-yl)-9H-purin-6-yl)benzamide (2R,3R,4R,5R)-5-(6-Benzamido-9H-purin-9-yl)-4-((tert-butyldimethylsilyl)oxy)-2-(((((2-cyanoethoxy)(((2R,3R,5R)-2-(5-fluoro-4-oxo-3H-pyrrolo[2,3-d]pyrimidin-7(4H)-yl)-4-((3-hydroxy-1,1,3,3-tetraisopropyldisiloxanyl)oxy)-5-(hydroxymethyl)tetrahydrofuran-3-yl)oxy)phosphorothioyl)oxy)methyl)tetrahydrofuran-3-yl hydrogen phosphonate (5.13 g) was subjected to azeotropic dehydration with anhydrous acetonitrile and anhydrous pyridine, and suspended in anhydrous pyridine (100 mL). 2-Chloro-5,5-dimethyl-1,3,2-dioxaphosphinane 2-oxide (2.70 g) was added thereto, and the mixture was stirred at room temperature for 1 hr under argon atmosphere. Water (2.64 g) and iodine (1.38 g) were added thereto, and the mixture was stirred at room temperature for additional 1 hr. The reaction mixture was quenched with sodium thiosulfate (5.19 g) and water (2.64 g), and extracted with ethyl acetate. The organic layer was washed with water and saturated brine, and dried over anhydrous magnesium sulfate, and the solvent was evaporated under reduced pressure. The residue was purified by silica gel column chromatography (methanol/ethyl acetate) to give the title compound (3.53 g). MS: [M+H]⁺ 1224.4.

D) 7-((5R,7R,8R,12aR,14R,15R,15aR,16R)-14-(6-amino-9H-purin-9-yl)-15-(((1,1-dimethylethyl)dimethylsilyl)oxy)octahydro-2,10-dihydroxy-16-((3-hydroxy-1,1,3,3-tetrakis(1-methylethyl)disiloxanyl)oxy)-2-oxido-10-sulfanyl-5,8-methano-12H-furo[3,2-1][1,3,6,9,11,2,10]pentaoxadiphosphacyclotetradecin-7-yl)-5-fluoro-3,7-dihydro-4H-pyrrolo[2,3-d]pyrimidin-4-one (Optical Isomer)

To N-(9-((5R,7R,8R,12aR,14R,15R,15aR,16R)-15-((tert-butyl(dimethyl)silyl)oxy)-10-(2-cyanoethoxy)-7-(5-fluoro-4-oxo-3,4-dihydro-7H-pyrrolo[2,3-d]pyrimidin-7-yl)-2-hydroxy-16-((3-hydroxy-1,1,3,3-tetra(propan-2-yl)disiloxanyl)oxy)-2-oxido-10-sulfidooctahydro-12H-5,8-methanofuro[3,2-1][1,3,6,9,11,2,10]pentaoxadiphosphacyclotetradecin-14-yl)-9H-purin-6-yl)benzamide (3.5 g) was added 40% methylamine methanol solution (50 mL), and the mixture was stirred at room temperature for 1 hr under argon atmosphere. The obtained mixture was concentrated under reduced pressure, and the residue was purified by silica gel column chromatography (methanol/ethyl acetate). The obtained residue was purified by HPLC (L-column2 ODS, 50×150 mm, mobile phase: 5 mM aqueous ammonium acetate solution/acetonitrile), the obtained fraction was concentrated under reduced pressure, and the residue was freeze-dried to give the title compound (210 mg). MS: [M+H]⁺ 1067.4.

E) 7-((5R,7R,8R,12aR,14R,15R,15aS,16R)-14-(6-amino-9H-purin-9-yl)-2,10,15,16-tetrahydroxy-2-oxido-10-sulfanyloctahydro-12H-5,8-methanofuro[3,2-1][1,3,6,9,11,2,10]pentaoxadiphosphacyclotetradecin-7-yl)-5-fluoro-3,7-dihydro-4H-pyrrolo[2,3-d]pyrimidin-4-one di-triethylamine salt (Optical Isomer)

To a solution of 7-((5R,7R,8R,12aR,14R,15R,15aR,16R)-14-(6-amino-9H-purin-9-yl)-15-(((1,1-dimethylethyl)dimethylsilyl)oxy)octahydro-2,10-dihydroxy-16-((3-hydroxy-1,1,3,3-tetrakis(1-methylethyl)disiloxanyl)oxy)-2-oxido-10-sulfanyl-5,8-methano-12H-furo[3,2-1][1,3,6,9,11,2,10]pentaoxadiphosphacyclotetradecin-7-yl)-5-fluoro-3,7-dihydro-4H-pyrrolo[2,3-d]pyrimidin-4-one (optical isomer, derived from tR2) (210 mg) in methanol (1.0 mL)-triethylamine (0.4 mL) was added triethylamine trihydrofluoride (0.962 mL), and the mixture was stirred at 50° C. for 2.5 hr.

To the reaction mixture was added ethoxytrimethylsilane (4.59 mL) at room temperature, and the mixture was stirred for 30 min. The reaction mixture was concentrated under reduced pressure, and the residue was purified by C18 silica gel column chromatography (10 mM triethylammonium acetate buffer solution/acetonitrile), and freeze-dried to give the title compound (125 mg).

$^1$H NMR (300 MHz, D$_2$O) δ1.13-1.28 (18H, m), 3.12 (12H, q, J=7.2 Hz), 4.02-4.11 (1H, m), 4.13-4.25 (2H, m), 4.27-4.40 (2H, m), 4.46 (1H, d, J=6.4 Hz), 4.73-4.79 (2H, m), 4.80-4.91 (1H, m), 5.02 (1H, td, J=8.8, 4.2 Hz), 6.08 (1H, d, J=1.7 Hz), 6.35 (1H, d, J=8.1 Hz), 7.27 (1H, d, J=1.7 Hz), 7.93 (1H, s), 8.14 (1H, s), 8.18 (1H, s). $^{31}$P NMR (121 MHz, D$_2$O) δ52.4, 1.21.

Example 23

Synthesis of 7-[(5R,7R,8R,12aR,14R,15R,15aS,16R)-14-(6-amino-9H-purin-9-yl)-10,15,16-trihydroxy-2,10-dioxido-2-sulfanyl octahydro-12H-5,8-methanofuro[3,2-l][1,3,6,9,11,2,10]pentaoxadiphosphacyclotetradecin-7-yl]-5-fluoro-3-methyl-3,7-dihydro-4H-pyrrolo[2,3-d]pyrimidin-4-one di-triethylamine salt (optical isomer 1 and 2)

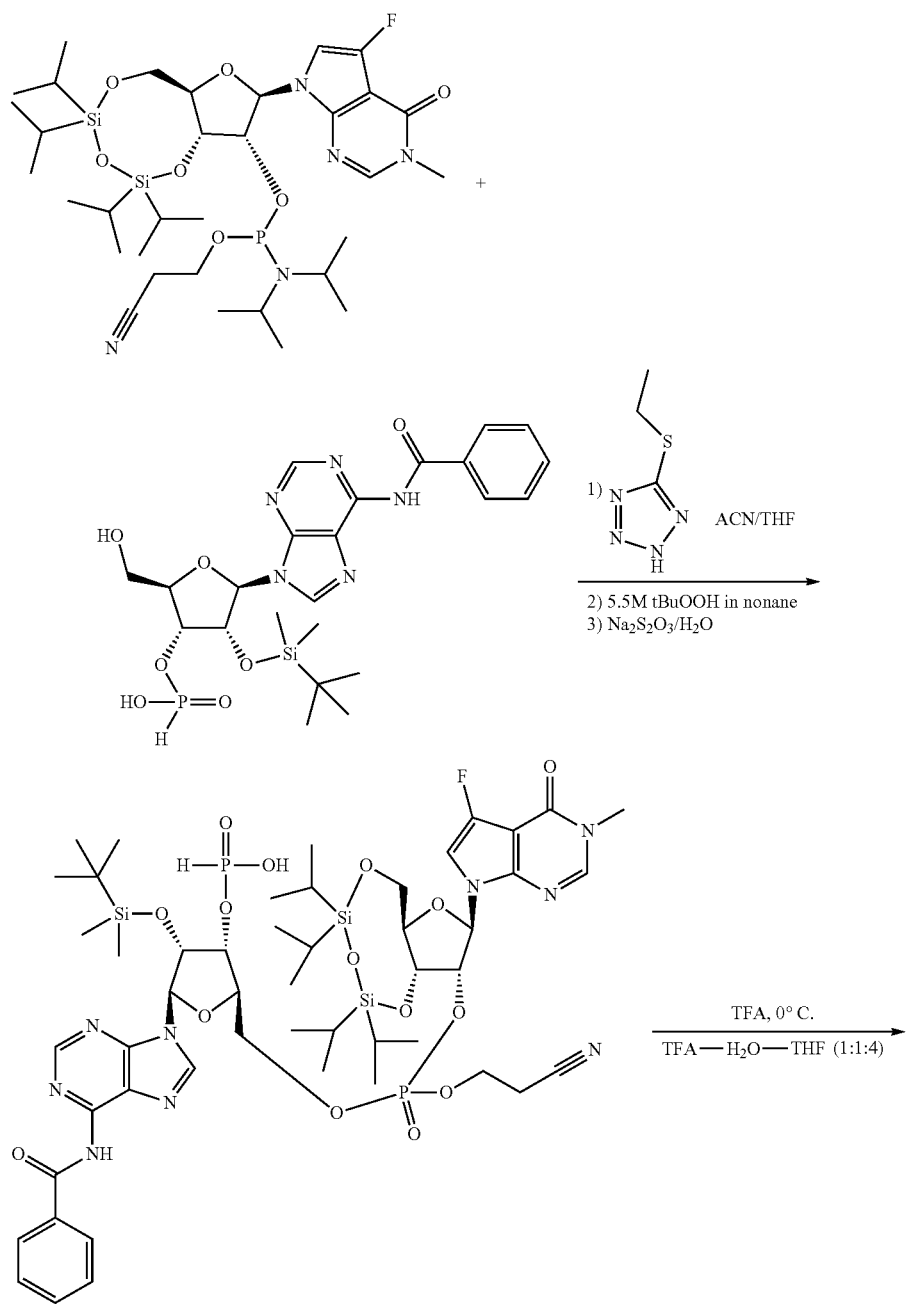

-continued
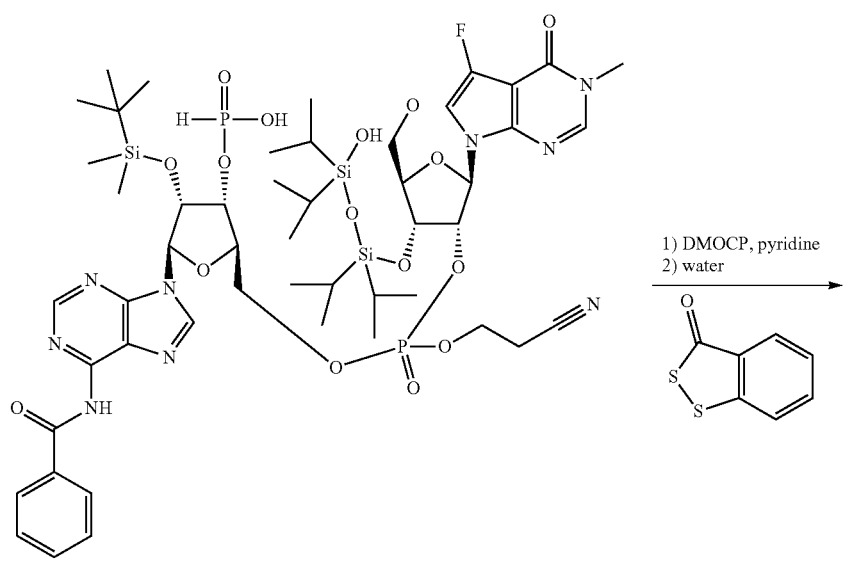
1) DMOCP, pyridine
2) water
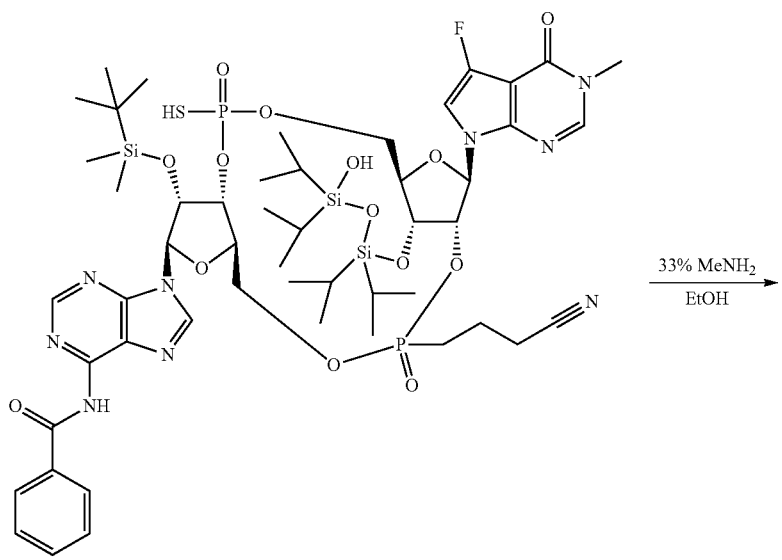
33% MeNH₂
EtOH
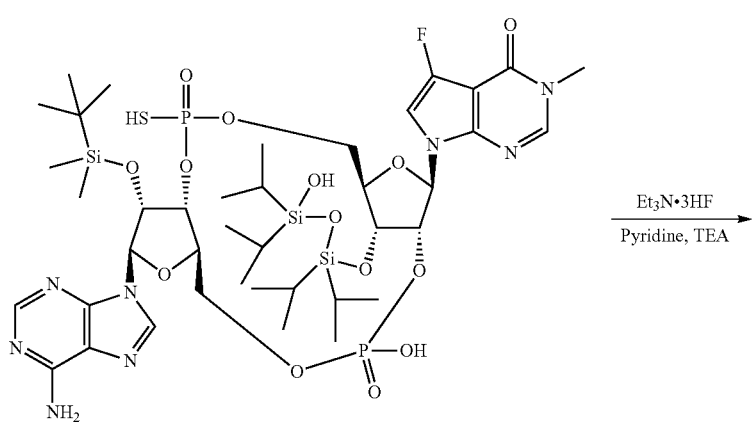
Et₃N•3HF
Pyridine, TEA

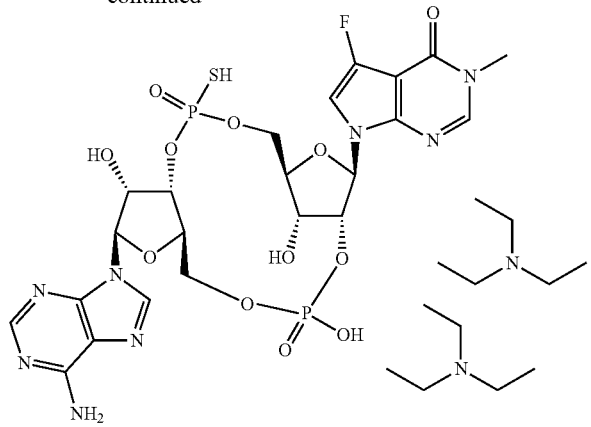

A) (2R,3R,4R,5R)-5-[6-(benzoylamino)-9H-purin-9-yl]-4-{[tert-butyl(dimethyl)silyl]oxy}-2-({[(2-cyanoethoxy) {[(6aR,8R,9R,9aR)-8-(5-fluoro-3-methyl-4-oxo-3,4-dihydro-7H-pyrrolo[2,3-d]pyrimidin-7-yl)-2,2,4,4-tetraisopropyltetrahydro-6H-furo[3,2-f][1,3,5,2,4]trioxadisilocin-9-yl]oxy}phosphoryl]oxy}methyl)tetrahydrofuran-3-yl hydrogen phosphonate (2R,3R,4R,5R)-5-[6-(benzoylamino)-9H-purin-9-yl]-4-{[tert-butyl(dimethyl)silyl]oxy}-2-(hydroxymethyl)tetrahydrofuran-3-yl hydrogen phosphonate (250 mg) and 2-cyanoethyl (6aR,8R,9R,9aR)-8-(5-fluoro-3-methyl-4-oxo-3,4-dihydro-7H-pyrrolo[2,3-d]pyrimidin-7-yl)-2,2,4,4-tetraisopropyltetrahydro-6H-furo[3,2-f][1,3,5,2,4]trioxadisilocin-9-yl diisopropylphosphoramidoite (359 mg) (Example 24 step C) were subjected to azeotropic dehydration with anhydrous acetonitrile, and anhydrous acetonitrile (1.1 mL) and anhydrous tetrahydrofuran (0.7 mL) were added thereto. To the mixture was added a solution of 5-(ethylsulfanyl)-2H-tetrazole (175 mg) (which was subjected to azeotropic dehydration with anhydrous acetonitrile) in anhydrous acetonitrile (0.75 mL), and the mixture was stirred under argon atmosphere at room temperature for 2 hr. Tert-butyl hydroperoxide (5.5 mol/L) in nonane (0.25 mL) was added thereto, and the mixture was stirred at room temperature for 40 min. The reaction mixture was cooled in ice bath and a solution of sodium thiosulfate (345 mg) in water (0.275 mL) was added. The mixture was allowed to stir at room temperature for 15 min and was concentrated under reduced pressure. The crude product was purified by silica gel column chromatography (methanol/dichloromethane) to give the title compound (318 mg) as a mixture of diastereomers. MS: [M+H]$^+$ 1206.3

B) (2R,3R,4R,5R)-5-[6-(benzoylamino)-9H-purin-9-yl]-4-{[tert-butyl(dimethyl)silyl]oxy}-2-({[(2-cyanoethoxy)({(2R,3R,4R,5R)-2-(5-fluoro-3-methyl-4-oxo-3,4-dihydro-7H-pyrrolo[2,3-d]pyrimidin-7-yl)-5-(hydroxymethyl)-4-[(3-hydroxy-1,1,3,3-tetraisopropyldisiloxanyl)oxy]tetrahydrofuran-3-yl}oxy)phosphoryl]oxy}methyl)tetrahydrofuran-3-yl hydrogen phosphonate (2R,3R,4R,5R)-5-[6-(benzoylamino)-9H-purin-9-yl]-4-{[tert-butyl(dimethyl)silyl]oxy}-2-({[(2-cyanoethoxy){[(6aR,8R,9R,9aR)-8-(5-fluoro-3-methyl-4-oxo-3,4-dihydro-7H-pyrrolo[2,3-d]pyrimidin-7-yl)-2,2,4,4-tetraisopropyltetrahydro-6H-furo[3,2-f][1,3,5,2,4]trioxadisilocin-9-yl]oxy}phosphoryl]oxy}methyl)tetrahydrofuran-3-yl hydrogen phosphonate (315 mg) was dissolved in a mixture of tetrahydrofuran (2.8 mL) and water (0.71 mL) and the solution was allowed to stir and cooled in ice bath. Trifluoroacetic acid (0.71 mL) was added drop wise and the mixture was allowed to stir at 0-5° C. for 2 hr 15 min. Sodium bicarbonate (1.14 g) was added gradually to the reaction mixture while maintaining good stirring followed by addition of water (3 mL) and ethyl acetate (10 mL). Separated aqueous layer was extracted with ethyl acetate (10 mL). Combined organics was washed with brine (3 mL), dried over anhydrous sodium sulfate, filtered, and the solvent was evaporated under reduced pressure. The residue was purified by silica gel column chromatography (methanol/methylene chloride) to give the title compound (145 mg). MS: [M+H]$^+$ 1224.3

C) N-(9-{(5R,7R,8R,12aR,14R,15R,15aR,16R)-15-{[tert-butyl(dimethyl)silyl]oxy}-10-(2-cyanoethoxy)-7-(5-fluoro-3-methyl-4-oxo-3,4-dihydro-7H-pyrrolo[2,3-d]pyrimidin-7-yl)-16-[(3-hydroxy-1,1,3,3-tetraisopropyldisiloxanyl)oxy]-2,10-dioxido-2-sulfanyloctahydro-12H-5,8-methanofuro[3,2-1][1,3,6,9,11,2,10]pentaoxadiphosphacyclotetradecin-14-yl}-9H-purin-6-yl)benzamide (2R,3R,4R,5R)-5-[6-(benzoylamino)-9H-purin-9-yl]-4-{[tert-butyl(dimethyl)silyl]oxy}-2-({[(2-cyanoethoxy)({(2R,3R,4R,5R)-2-(5-fluoro-3-methyl-4-oxo-3,4-dihydro-7H-pyrrolo[2,3-d]pyrimidin-7-yl)-5-(hydroxymethyl)-4-[(3-hydroxy-1,1,3,3-tetraisopropyldisiloxanyl)oxy]tetrahydrofuran-3-yl}oxy)phosphoryl]oxy}methyl) tetrahydrofuran-3-yl hydrogen phosphonate (143 mg) was subjected to azeotropic dehydration with anhydrous acetonitrile and anhydrous pyridine (2.3 mL) was added thereto. To the mixture was added 2-chloro-5,5-dimethyl-1,3,2-dioxaphosphinane 2-oxide (75 mg), and the mixture was stirred under argon atmosphere at room temperature for 45 min. Water (75 µL) and 3H-1,2-benzodithiol-3-one 1,1-dioxide (29 mg) were added thereto, and the mixture was stirred at room temperature for additional 40 min. To the reaction mixture was added a solution of sodium thiosulfate pentahydrate (150 mg) in water (0.35 mL), and the mixture was stirred at room temperature for 5 min. The mixture was concentrated, toluene was added thereto, and the mixture was concentrated under reduced pressure (repeat 4×). The crude product was purified by silica gel column chromatography (methanol/dichloromethane) to give the title compound (84 mg) as a mixture of diastereomers. MS: [M+H]+ 1238.3

D) 7-{(5R,7R,8R,12aR,14R,15R,15aR,16R)-14-(6-amino-9H-purin-9-yl)-15-{[tert-butyl(dimethyl)silyl]oxy}-10-hydroxy-16-[(3-hydroxy-1,1,3,3-tetraisopropyldisiloxanyl)oxy]-2,10-dioxido-2-sulfanyloctahydro-12H-5,8-methanofuro[3,2-1][1,3,6,9,11,2,10]pentaoxadiphosphacyclotetradecin-7-yl}-5-fluoro-3-methyl-3,7-dihydro-4H-pyrrolo[2,3-d]pyrimidin-4-one To N-(9-{(5R,7R,8R,12aR,14R,15R,15aR,16R)-15-{[tert-butyl(dimethyl)silyl]oxy}-10-(2-cyanoethoxy)-7-(5-fluoro-3-methyl-4-oxo-3,4-dihydro-7H-pyrrolo[2,3-d]pyrimidin-7-yl)-16-[(3-hydroxy-1,1,3,3-tetraisopropyldisiloxanyl)oxy]-2,10-dioxido-2-sulfanyloctahydro-12H-5,8-methanofuro[3,2-1][1,3,6,9,11,2,10]pentaoxadiphosphacyclotetradecin-14-yl}-9H-purin-6-yl) benzamide (83 mg) was added 33% methylamine ethanol solution (2.0 mL), and the mixture was stirred under argon atmosphere at room temperature for 1 hr, and concentrated under reduced pressure. The crude product was purified by reverse phase chromatography (ISCO RediSepRf Gold HP C18 15.5 g column) eluted with 0 to 70% ACN in 10 mM aq NH$_4$OAc to give two isolated single isomers of the title compounds: peak 1 (early fraction, 11 mg) and peak 2 (late fraction, 44.5 mg). MS: [M+H]+ 1081.3

E) 7-[(5R,7R,8R,12aR,14R,15R,15aS,16R)-14-(6-amino-9H-purin-9-yl)-10,15,16-trihydroxy-2,10-dioxido-2-sulfanyl octahydro-12H-5,8-m ethanofuro[3,2-1][1,3,6,9,11,2,10]pentaoxadiphosphacyclotetradecin-7-yl]-5-fluoro-3-methyl-3,7-dihydro-4H-pyrrolo[2,3-d]pyrimidin-4-one di-triethylamine salt (Optical Isomer 1)

To 7-{(5R,7R,8R,12aR,14R,15R,15aR,16R)-14-(6-amino-9H-purin-9-yl)-15-{[tert-butyl(dimethyl)silyl]oxy}-10-hydroxy-16-[(3-hydroxy-1,1,3,3-tetraisopropyldisiloxanyl)oxy]-2,10-dioxido-2-sulfanyloctahydro-12H-5,8-methanofuro[3,2-1][1,3,6,9,11,2,10]pentaoxadiphosphacyclotetradecin-7-yl}-5-fluoro-3-methyl-3,7-dihydro-4H-pyrrolo[2,3-d]pyrimidin-4-one (324 mg, peak 2/late fraction from step D) were added pyridine (6.0 mL) and triethylamine trihydrofluoride (0.303 mL). The reaction mixture was stirred at 55° C. for 16 hr. LCMS analysis showed some of monoprotected intermediate. Methanol (2.0 mL) was added and the reaction mixture was stirred at 55° C. for 3 hr. LCMS then showed completed reaction. The reaction mixture was concentrated under reduced pressure and water (6.7 mL) and calcium chloride (700 mg) were added. The resulting suspension was stirred for 1 hr and was filtered on a pad of Celite®. The filtrate was concentrated under reduce pressure, and the residue was purified by reverse phase chromatography (ISCO RediSepRf Gold HP C18Aq column) eluted with 0 to 15% ACN in 10 mM aq triethylammonium acetate to give the title compound (195 mg). MS: [M+H]+ 707.1 $^1$H NMR (400 MHz, D$_2$O) δ1.27 (18H, t, J=7.3 Hz), 3.19 (12H, q, J=7.3 Hz), 3.35 (3H, s), 4.06-4.10 (1H, m), 4.18-4.26 (1H, m), 4.32-4.37 (1H, m), 4.39-4.54 (3H, m), 4.63 (1H, d, J=4.0 Hz), 4.80-4.82 (1H, m), 5.03-5.12 (2H, m), 6.15-6.17 (1H, m), 6.35-6.39 (1H, m), 7.33-7.37 (1H, m), 8.13 (1H, s), 8.15 (1H, s), 8.27 (1H, s). $^{31}$P NMR (162 MHz, D$_2$O) δ−2.22, 54.80. $^{19}$F NMR (376 MHz, D$_2$O) δ−164.6.

F) 7-[(5R,7R,8R,12aR,14R,15R,15aS,16R)-14-(6-amino-9H-purin-9-yl)-10,15,16-trihydroxy-2,10-dioxido-2-sulfanyloctahydro-12H-5,8-methanofuro[3,2-1][1,3,6,9,11,2,10]pentaoxadiphosphacyclotetradecin-7-yl]-5-fluoro-3-methyl-3,7-dihydro-4H-pyrrolo[2,3-d]pyrimidin-4-one di-triethylamine salt (Optical Isomer 2)

Optical isomer 2 was prepared by using the same procedure as for optical isomer 1. 7-{(5R,7R,8R,12aR,14R,15R,15aR,16R)-14-(6-amino-9H-purin-9-yl)-15-{[tert-butyl(dimethyl)silyl]oxy}-10-hydroxy-16-[(3-hydroxy-1,1,3,3-tetraisopropyldisiloxanyl)oxy]-2,10-dioxido-2-sulfanyloctahydro-12H-5,8-methanofuro[3,2-1][1,3,6,9,11,2, 1 0]pentaoxadiphosphacyclotetradecin-7-yl}-5-fluoro-3-methyl-3,7-dihydro-4H-pyrrolo[2,3-d]pyrimidin-4-one (24.5 mg, peak 1/early fraction from step D) give the title compound (11.8 mg). MS: [M+H]+ 707.1. $^1$H NMR (400 MHz, D$_2$O) δ ppm 1.25 (18H, t, J=7.22 Hz), 3.17 (q, J=7.24 Hz, 12H), 3.35 (3H, s), 4.12-4.22 (3H, m), 4.40-4.53 (3H, m), 4.62 (1H, m), 4.83-4.90 OH, m), 4.93-4.98 (1H, m), 5.09-5.15 (1H, m), 6.16 (1H, s), 6.28-6.36 (1H, m), 7.50 (1H, s), 8.12 (1H, s), 8.15 (1H, s), 8.31 (1H, s). $^{31}$P NMR (162 MHz, D$_2$O) δ−2.42, 54.11. $^{19}$F NMR (376 MHz, D$_2$O) δ−165.54

Example 24

Synthesis of 7-[(5R,7R,8R,12aR,14R,15R,15aR,16R)-14-(6-amino-9H-purin-9-yl)-15-fluoro-10,16-dihydroxy-2,10-dioxido-2-sulfanyloctahydro-12H-5,8-methanofuro[3,2-1][1,3,6,9,11,2,10]pentaoxadiphosphacyclotetradecin-7-yl]-5-fluoro-3-methyl-3,7-dihydro-4H-pyrrolo[2,3-d]pyrimidin-4-one di-triethylamine salt (Optical Isomer 1 and 2)

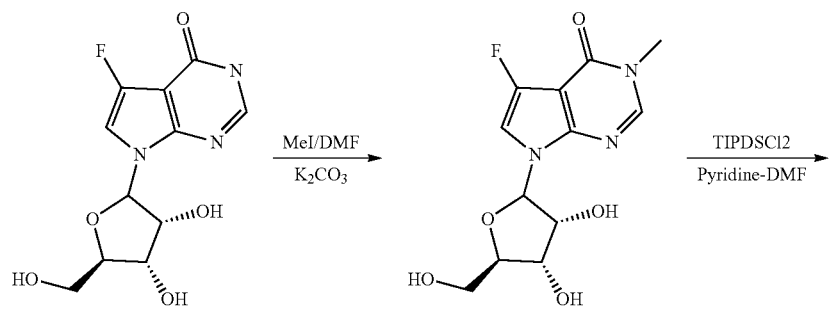

-continued
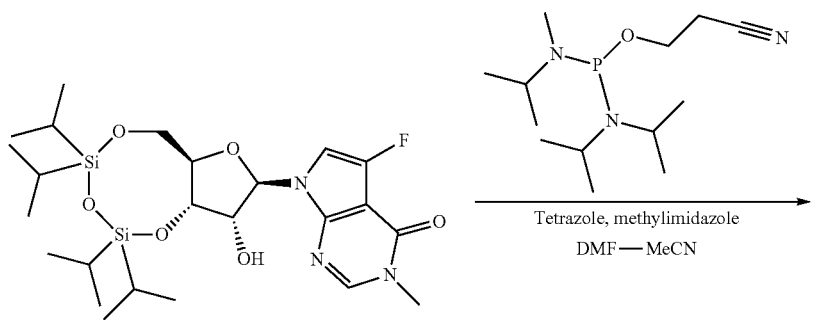
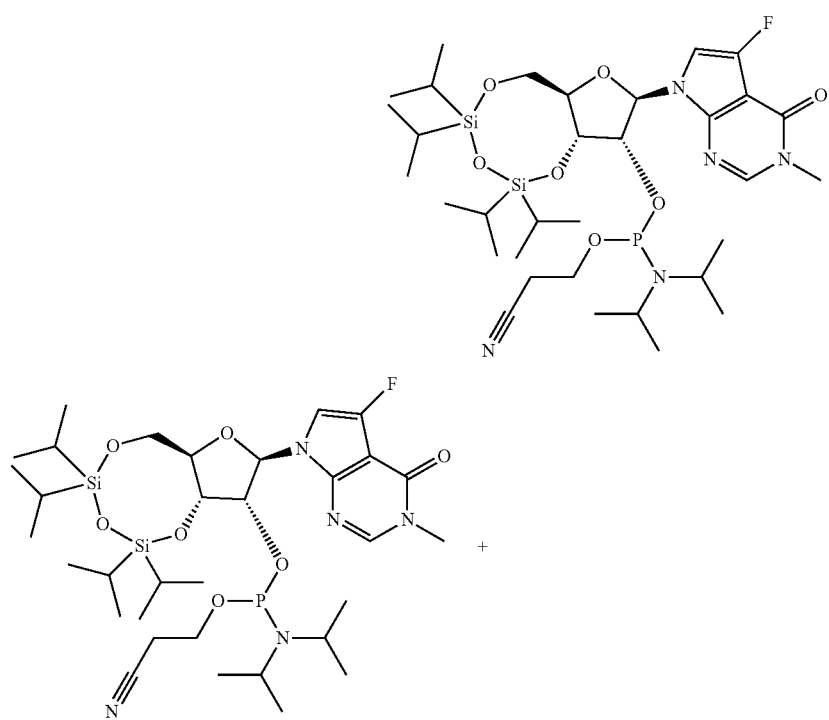
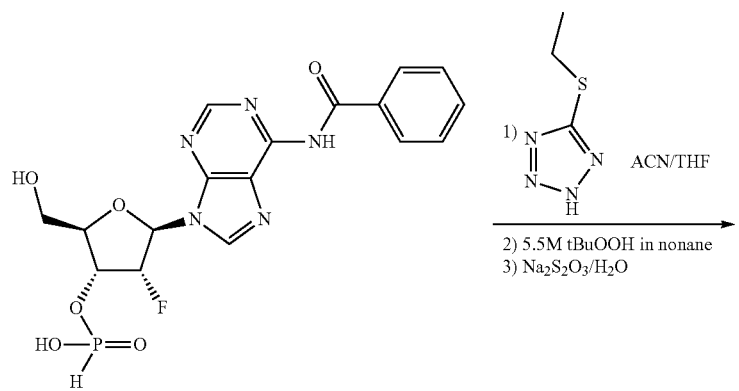

-continued
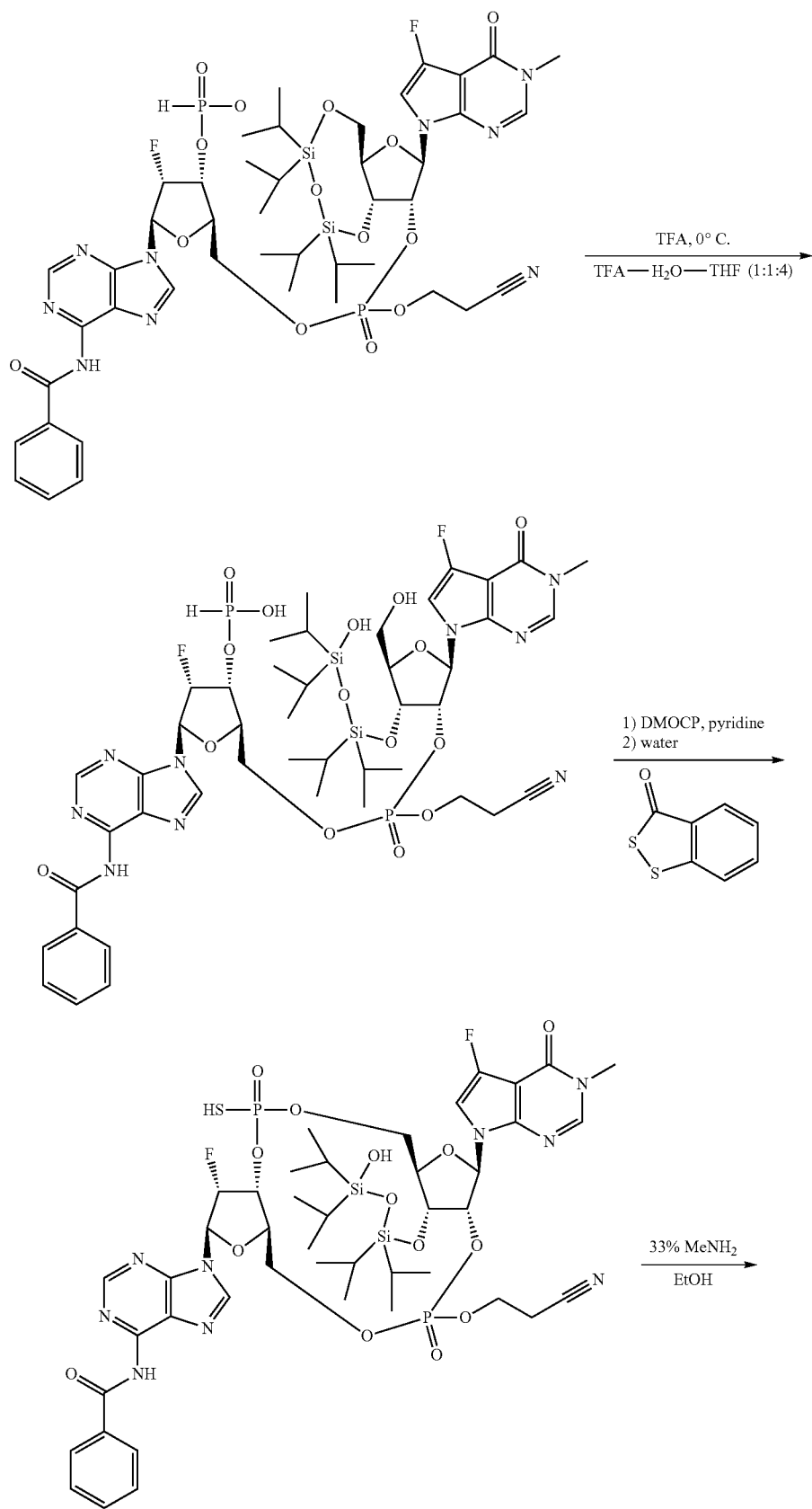

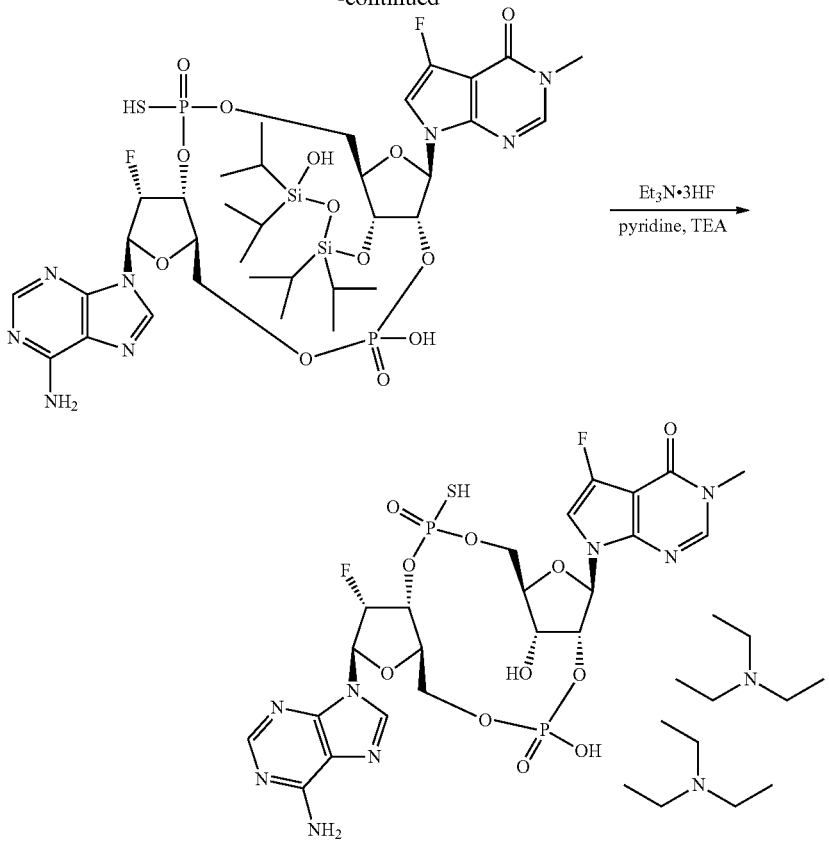

A) 7-[(2R,3R,4S,5R)-3,4-dihydroxy-5-(hydroxymethyl)tetrahydrofuran-2-yl]-5-fluoro-3-methyl-pyrrolo[2,3-d]pyrimidin-4-one 7-[(2R,3R,4S,5R)-3,4-dihydroxy-5-(hydroxymethyl)tetrahydrofuran-2-yl]-5-fluoro-3,7-dihydro-4H-pyrrolo[2,3-d]pyrimidin-4-one (300 mg) was dissolved in N,N-dimethylformamide (3.30 mL) and potassium carbonate (192 mg) was added. The suspension was cooled in ice bath. Iodomethane (0.080 mL) was added. The mixture was stirred with cooling for 5 min and then stirred at room temperature overnight. The mixture was concentrated and water was added, neutralized with 1M HCl to pH ~6. The resulted solid was collected by filtration and dried under vacuum overnight to give the title compound (266 mg). MS: [M+H]+ 300.1.

B) 5-fluoro-7-[(6aR,8R,9R,9aS)-9-hydroxy-2,2,4,4-tetraisopropyltetrahydro-6H-furo[3,2-f][1,3,5,2,4]trioxadisilocin-8-yl]-3-methyl-3,7-dihydro-4H-pyrrolo[2,3-d]pyrimidin-4-one 7-[(2R,3R,4S,5R)-3,4-dihydroxy-5-(hydroxymethyl)tetrahydrofuran-2-yl]-5-fluoro-3-methyl-pyrrolo[2,3-d]pyrimidin-4-one (985 mg) (pre-azeotroped with acetonitrile 3 times and dried in vacuum for 5 hours) was dissolved in pyridine (9.75 mL) and N,N-dimethylformamide (4.80 mL). After stirring for 15 min 1,3-dichloro-1,1,3,3-tetraisopropyldisiloxane (1.02 mL) was added drop wise. The mixture was stirred at room temperature overnight. The mixture was concentrated under reduced pressure and azeotroped with toluene. The residue was partitioned between EtOAc (120 mL) and water (50 mL). Separated organic layer was washed with water (2×50 mL) and brine (50 mL), dried over Na$_2$SO$_4$, filtered and concentrated under reduced pressure. The residue was purified by chromatography using EtOAc/hexane to give the title compound (1.41 g). MS: [M+H]+ 542.3.

C) 2-cyanoethyl (6aR,8R,9R,9aR)-8-(5-fluoro-3-methyl-4-oxo-3,4-dihydro-7H-pyrrolo[2,3-d]pyrimidin-7-yl)-2,2,4,4-tetraisopropyltetrahydro-6H-furo[3,2-f][1,3,5,2,4]trioxadisilocin-9-yl diisopropylphosphoramidoite In a 15 mL round bottom flask 5-fluoro-7-[(6aR,8R,9R,9aS)-9-hydroxy-2,2,4,4-tetraisopropyltetrahydro-6H-furo[3,2-f][1,3,5,2,4]trioxadisilocin-8-yl]-3-methyl-3,7-dihydro-4H-pyrrolo[2,3-d]pyrimidin-4-one (1.41 g) was azeotroped with dry acetonitrile (3×5 mL), dissolved in dry N,N-dimethylformamide (6.17 mL) under Argon. 1H-tetrazole 0.45M in acetonitrile (7.05 mL), 1-methyl-1H-imidazole (123 μL) and 2-cyanoethyl N,N,N,N-tetraisopropylphosphorodiamidite (1.86 mL) were added. The mixture was stirred at room temperature for 1 hour. The mixture was diluted with 70 ml of EtOAc, washed with saturated NaHCO$_3$(×2) and brine, dried over Na$_2$SO$_4$, filtered and concentrated under reduced pressure. The crude residue was purified by silica gel chromatography using EtOAc/hexane (0.5% Et$_3$N) to give the title compound (1.87 g). MS: [M+H]+ 742.4.

D) (2R,3R,4R,5R)-5-[6-(benzoylamino)-9H-purin-9-yl]-2-(([(2-cyanoethoxy){[(6aR,8R,9R,9aR)-8-(5-fluoro-3-methyl-4-oxo-3,4-dihydro-7H-pyrrolo[2,3-d]pyrimidin-7-yl)-2,2,4,4-tetraisopropyltetrahydro-6H-furo[3,2-f][1,3,5,2,4]trioxadisilocin-9-yl]oxy}phosphoryl]oxy)methyl)-4-fluorotetrahydrofuran-3-yl hydrogen phosphonate In a 100 mL round bottom flask 2-cyanoethyl (6aR,8R,9R,9aR)-8-(5-fluoro-3-methyl-4-oxo-3,4-dihydro-7H-pyrrolo[2,3-d]pyrimidin-7-yl)-2,2,4,4-tetraisopropyltetrahydro-6H-furo[3,2-f][1,3,5,2,4]trioxadisilocin-9-yl diisopropylphosphoramidoite (937 mg) and (2R,3R,4R,5R)-5-[6-(benzoylamino)-9H-purin-9-yl]-4-fluoro-2-(hydroxymethyl)tetrahydrofuran-3-yl hydrogen phosphonate (425 mg) were azeotroped with dry CH₃CN (3×5 mL), suspended in dry tetrahydrofuran (1.80 mL) and acetonitrile (2.95 mL) under Argon. A solution of 5-(ethylthio)-1H-tetrazole (380 mg) (pre-azeotroped with acetonitrile 3×5 mL) in dry acetonitrile (1.80 mL) was added. The mixture was allowed to stir at room temperature for 1 hour. Tert-butyl hydroperoxide (5.5 mol/L) in nonane (425 µL) was added. The mixture was stirred for 40 min at room temperature then cooled in an ice bath. A solution of sodium thiosulfate (500.0 mg) in water (700 µL as added and the mixture was stirred for 10 min. The mixture was concentrated under reduced pressure and the residue was purified by silica gel column chromatography (methanol/DCM). The title compound (1.10 g) as a mixture of two optical isomers was afforded. MS: [M+H]⁺ 1094.3.

E) (2R,3R,4R,5R)-5-[6-(benzoylamino)-9H-purin-9-yl]-2-({[(2-cyanoethoxy)({(2R,3R,4R,5R)-2-(5-fluoro-3-methyl-4-oxo-3,4-dihydro-7H-pyrrolo[2,3-d]pyrimidin-7-yl)-5-(hydroxymethyl)-4-[(3-hydroxy-1,1,3,3-tetraisopropyldisiloxanyl)oxy]tetrahydrofuran-3-yl}oxy)phosphoryl]oxy}methyl)-4-fluorotetrahydrofuran-3-yl hydrogen phosphonate To a solution of (2R,3R,4R,5R)-5-[6-(benzoylamino)-9H-purin-9-yl]-2-({[(2-cyanoethoxy){[(6aR,8R,9R,9aR)-8-(5-fluoro-3-methyl-4-oxo-3,4-dihydro-7H-pyrrolo[2,3-d]pyrimidin-7-yl)-2,2,4,4-tetraisopropyltetrahydro-6H-furo[3,2-f][1,3,5,2,4]trioxadisilocin-9-yl]oxy}phosphoryl]oxy}methyl)-4-fluorotetrahydrofuran-3-yl hydrogen phosphonate (1.10 g) in tetrahydrofuran (11.0 mL) and water (2.50 mL) cooled with an ice bath was slowly added trifluoroacetic acid (2.50 mL). The mixture was stirred with cooling for 4 hours.

Sodium bicarbonate (3800 mg) was added, followed by 8 ml of water. The mixture was stirred for 5 min, brought to room temperature and extracted with EtOAc twice. The combined organic layer was washed with brine, dried over Na₂SO₄, filtered and the filtrate was evaporated under reduced pressure to give a crude product. Chromatography using silica gel column (methanol/DCM) afforded the title compound (1.14 g). MS: [M+H]⁺ 1112.3.

F) N-(9-{(5R,7R,8R,12aR,14R,15R,15aR,16R)-10-(2-cyanoethoxy)-15-fluoro-7-(5-fluoro-3-methyl-4-oxo-3,4-dihydro-7H-pyrrolo[2,3-d]pyrimidin-7-yl)-16-[(3-hydroxy-1,1,3,3-tetraisopropyldisiloxanyl)oxy]-2,10-dioxido-2-sulfanyloctahydro-12H-5,8-methanofuro[3,2-1][1,3,6,9,11,2,10]pentaoxadiphosphacyclotetradecin-14-yl}-9H-purin-6-yl)benzamide In a 100 mL round bottom flask (2R,3R,4R,5R)-5-[6-(benzoylamino)-9H-purin-9-yl]-2-({[(2-cyanoethoxy)({(2R,3R,4R,5R)-2-(S-fluoro-3-methyl-4-oxo-3,4-dihydro-7H-pyrrolo[2,3-d]pyrimidin-7-yl)-5-(hydroxymethyl)-4-[(3-hydroxy-1,1,3,3-tetraisopropyldisiloxanyl)oxy]tetrahydrofuran-3-yl}oxy)phosphoryl]oxy}methyl)-4-fluorotetrahydrofuran-3-yl hydrogen phosphonate (149 mg) was azeotroped with acetonitrile (3×4 mL) and dried under vacuum, dissolved in dry pyridine (2.35 mL) and cooled in an ice bath. 2-Chloro-5,5-dimethyl-1,3,2-dioxaphosphorinane 2-oxide (180 mg) in pyridine (0.120 ml) was added. The mixture was allowed to stir at room temperature for 1.5 hour. Water (70.3 µL) was added, followed by 3H-1,2-benzodithiol-3-one (56.2 mg). The mixture was allowed to stir at room temperature for 40 min. Sodium thiosulfate (135 mg) in 1 mL of water was added. The mixture was stirred for 10 min, concentrated under reduced pressure, azeotroped with toluene to remove the pyridine. The residue was purified by silica gel column chromatography (methanol/DCM) to give the title compound as a mixture of two optical isomers (63.6 mg). MS: [M+H]⁺ 1126.3.

G) 7-{(5R,7R,8R,12aR,14R,15R,15aR,16R)-14-(6-amino-9H-purin-9-yl)-15-fluoro-10-hydroxy-16-[(3-hydroxy-1,1,3,3-tetraisopropyldisiloxanyl)oxy]-2,10-dioxido-2-sulfanyloctahydro-12H-5,8-methanofuro[3,2-1][1,3,6,9,11,2,10]pentaoxadiphosphacyclotetradecin-7-yl}-5-fluoro-3-methyl-3,7-dihydro-4H-pyrrolo[2,3-d]pyrimidin-4-one The mixture of two isomers N-(9-{(5R,7R,8R,12aR,14R,15R,15aR,16R)-10-(2-cyanoethoxy)-15-fluoro-7-(5-fluoro-3-methyl-4-oxo-3,4-dihydro-7H-pyrrolo[2,3-d]pyrimidin-7-yl)-16-[(3-hydroxy-1,1,3,3-tetraisopropyldisiloxanyl)oxy]-2,10-dioxido-2-sulfanyloctahydro-12H-5,8-methanofuro[3,2-1][1,3,6,9,11,2,10]pentaoxadiphosphacyclotetradecin-14-yl}-9H-purin-6-yl)benzamide (60.7 mg) was stirred in methylamine (33% wt.) in ethanol (3.00 mL) at room temperature for 1 hour. The volatile substance was evaporated off under reduced pressure. The crude product was purified by reverse phase chromatography (ISCO RediSepRf Gold HP C18 column) eluted with 0 to 50% ACN in 10 mM aq NH₄OAc to give two isolated single isomers of the title compounds: peak 1 (early fraction, 12 mg) and peak 2 (late fraction, 35.6 mg). MS: [M+H]⁺ 969.3.

H) 7-[(5R,7R,8R,12aR,14R,15R,15aR,16R)-14-(6-amino-9H-purin-9-yl)-15-fluoro-10,16-dihydroxy-2,10-dioxido-2-sulfanyloctahydro-12H-5,8-methanofuro[3,2-1][1,3,6,9,11,2,10]pentaoxadiphosphacyclotetradecin-7-yl]-5-fluoro-3-methyl-3,7-dihydro-4H-pyrrolo[2,3-d]pyrimidin-4-one di-triethylamine salt (Optical Isomer 1)

15 mL polypropylene conical tube was loaded with 7-{(5R,7R,8R,12aR,14R,15R,15aR,16R)-14-(6-amino-9H-purin-9-yl)-15-fluoro-10-hydroxy-16-[(3-hydroxy-1,1,3,3-tetraisopropyldisiloxanyl)oxy]-2,10-dioxido-2-sulfanyloctahydro-12H-5,8-methanofuro[3,2-1][1,3,6,9,11,2,10]pentaoxadiphosphacyclotetradecin-7-yl}-5-fluoro-3-methyl-3,7-dihydro-4H-pyrrolo[2,3-d]pyrimidin-4-one (35.6 mg, peak2/late fraction from step G). Pyridine (273 µL) was added, followed by triethylamine trihydrofluoride (27.3 µL) and triethylamine (414 µL). The mixture was allowed to stir at room temperature overnight and at 50° C. for 2 hours. The reaction mixture was cooled in ice bath and diluted with water (1.3 mL). A solution of calcium chloride (146.0 mg) in water (1.0 mL) was added slowly. The mixture was stirred for 30 min then filtered through a plug of Celite®. The filtrate was concentrated under reduced pressure and the residue was purified by reverse phase chromatography (ISCO RediSepRf Gold HP C18Aq column) eluted with 0 to 10% ACN in 10 mM aq triethylammonium acetate to give the title compound (23.9 mg). MS: [M+H]$^+$ 709.2. $^1$H NMR (400 MHz, METHANOL-d4) δ 8.29-8.24 (m, 1H), 8.22 (s, 1H), 8.08-8.04 (m, 1H), 7.46-7.40 (m, 1H), 6.48 (d, 1H, J=12 Hz), 6.37 (d, 1H, J=16 Hz), 5.80-5.57 (m, 1H), 5.33-5.12 (m, 1H), 5.05-4.95 (m, 1H), 4.50-4.42 (m, 2H), 4.41-4.34 (m, 1H), 4.34-4.24 (m, 2H), 4.08-3.96 (m, 1H), 3.57 (s, 3H), 3.52-3.48 (m, 1H), 3.25-3.11 (m, 12H), 1.39-1.24 (m, 18H). $^{31}$P NMR (162 MHz, D$_2$O) δ−2.45, 55.32. $^{19}$F NMR (376.5 MHz, D$_2$O) δ−164.60, −200.71.

I) 7-[(5R,7R,8R,12aR,14R,15R,15aR,16R)-14-(6-amino-9H-purin-9-yl)-15-fluoro-10,16-dihydroxy-2,10-dioxido-2-sulfanyloctahydro-12H-5,8-methanofuro[3,2-l][1,3,6,9,11,2,10]pentaoxadiphosphacyclotetradecin-7-yl]-5-fluoro-3-methyl-3,7-dihydro-4H-pyrrolo[2,3-d]pyrimidin-4-one di-triethylamine salt (Optical Isomer 2)

15 mL polypropylene conical tube was loaded with 7 {(5R,7R,8R,12aR,14R,15R,15aR,16R)-14-(6-amino-9H-purin-9-yl)-15-fluoro-10-hydroxy-16-[(3-hydroxy-1,1,3,3-tetraisopropyldisiloxanyl)oxy]-2,10-dioxido-2-sulfanyloctahydro-12H-5,8-methanofuro[3,2-l][1,3,6,9,11,2,10]pentaoxadiphosphacyclotetradecin-7-yl}-5-fluoro-3-methyl-3,7-dihydro-4H-pyrrolo[2,3-d]pyrimidin-4-one (12.0 mg, peak 1/early fraction from step G). Pyridine (92 µL) was added, followed by triethylamine trihydrofluoride (9.2 µL) and triethylamine (140 µL). The mixture was allowed to stir at 50° C. for 2 hours. The reaction mixture was cooled with an ice bath and diluted with water (1.0 mL). A solution of calcium chloride (6.98 mg) in water (1.0 mL) was added slowly. The mixture was stirred for 30 min then filtered through a plug of Celite®. The filtrate was concentrated under reduced pressure and the residue was purified by reverse phase chromatography (ISCO RediSepRf Gold HP C18Aq column) eluted with 0 to 10% ACN in 10 mM aq triethylammonium acetate to give the title compound (1.94 mg). MS: [M+H]$^+$ 709.3. NMR (400 MHz, DEUTERIUM OXIDE) δ 8.20 (s, 1H), 8.06 (s, 1H), 7.99 (s, 1H), 7.46-7.40 (m, 1H), 6.37 (d, 1H, J=16 Hz), 6.27 (d, 1H, J=8 Hz), 5.83 (dd, 1H, J1=52 Hz, J2=4 Hz), 4.98-4.84 (m, 2H), 4.57 (brd, J=3.9 Hz, 2H), 4.54-4.48 (m, 2H), 4.46-4.36 (m, 3H), 4.20-4.11 (m, 3H), 3.55-3.47 (m, 3H), 3.20-3.06 (dd, 12H), 1.28-1.12 (t, 18H). $^{31}$P NMR (162 MHz, D$_2$O) 6-2.52, 53.94. $^{19}$F NMR (376.5 MHz, D$_2$O) δ−165.55, 202.45.

Example 25

Synthesis of 7-[(5R,7R,8R,12aR,14R,15R,15aR,16R)-14-(6-amino-9H-purin-9-yl)-15-fluoro-2,10,16-trihydroxy-2,10-dioxidooctahydro-12H-5,8-methanofuro[3,2-l][1,3,6,9,11,2,10]pentaoxadiphosphacyclotetradecin-7-yl]-5-fluoro-3-methyl-3,7-dihydro-4H-pyrrolo[2,3-d]pyrimidin-4-one di-triethylamine salt

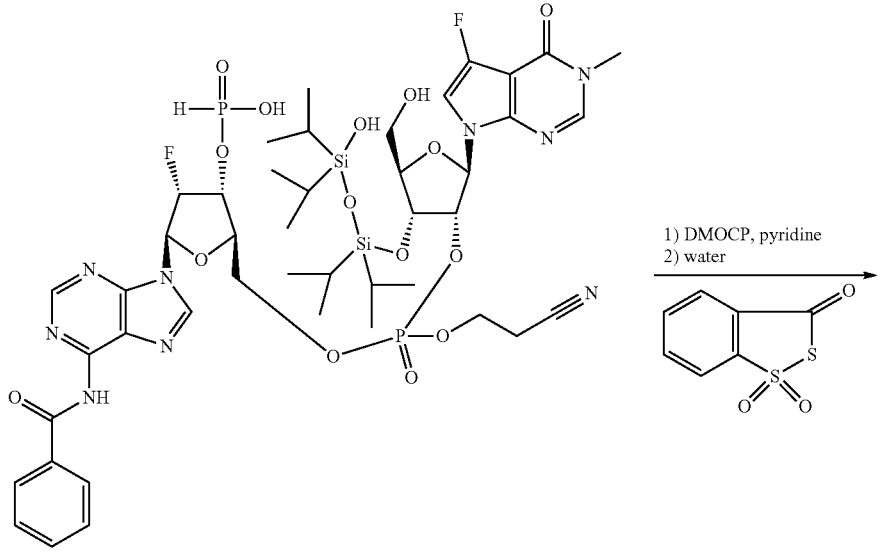

-continued
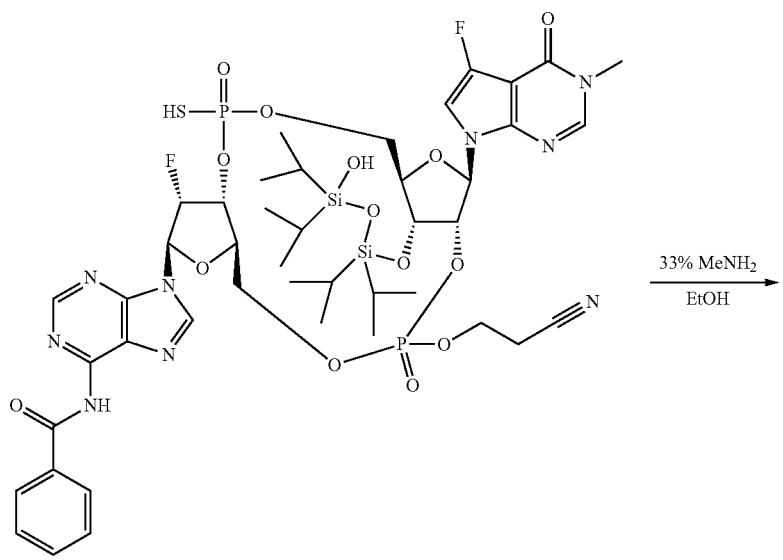
33% MeNH₂
EtOH
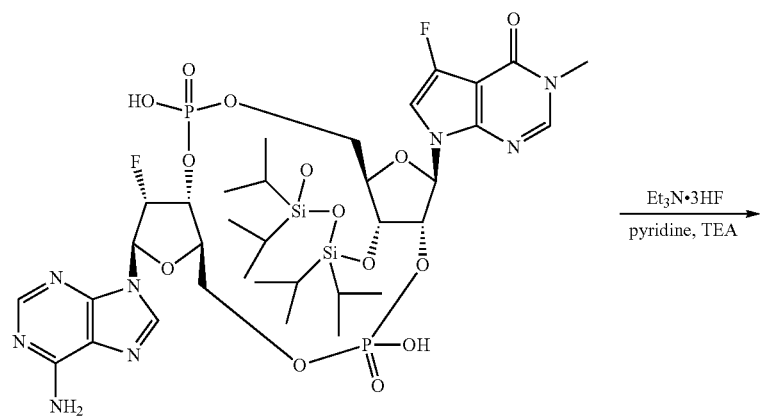
Et₃N•3HF
pyridine, TEA
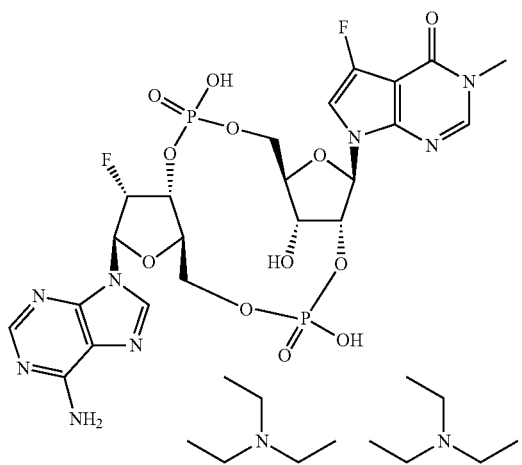

343

A) N-(9-{(5R,7R,8R,12aR,14R,15R,15aR,16R)-10-(2-cyanoethoxy)-15-fluoro-7-(5-fluoro-3-methyl-4-oxo-3,4-dihydro-7H-pyrrolo[2,3-d]pyrimidin-7-yl)-2-hydroxy-16-[(3-hydroxy-1,1,3,3-tetraisopropyldisiloxanyl)oxy]-2,10-dioxidooctahydro-12H-5,8-methanofuro[3,2-1][1,3,6,9,11,2,10]pentaoxadiphosphacyclotetradecin-14-yl}-9H-purin-6-yl)benzamide In a 100 mL round bottom flask (2R,3R,4R,5R)-5-[6-(benzoylamino)-9H-purin-9-yl]-2-({[(2-cyanoethoxy)({(2R,3R,4R,5R)-2-(5-fluoro-3-methyl-4-oxo-3,4-dihydro-7H-pyrrolo[2,3-d]pyrimidin-7-yl)-5-(hydroxymethyl)-4-[(3-hydroxy-1,1,3,3-tetraisopropyldisiloxanyl)oxy]tetrahydrofuran-3-yl}oxy)phosphoryl]oxy}methyl)-4-fluorotetrahydrofuran-3-yl hydrogen phosphonate (1.14 g) was azeotroped with acetonitrile (3×4 mL) and dried under vacuum, dissolved in pyridine (18.0 mL) and cooled in an ice bath. 2-Chloro-5,5-dimethyl-1,3,2-dioxaphosphorinane 2-oxide (586 mg) was added in 2 portions. The mixture was allowed to stir at room temperature for 40 min. Water (0.554 mL) was added, followed by 3H-1,2-benzodithiol-3-one 1,1-dioxide (251 mg). The mixture was allowed to stir at room temperature for 40 min. A solution of sodium thiosulfate (810 mg) in 2 mL of water was added. The mixture was concentrated under reduced pressure and azeotroped with toluene to remove the pyridine. The residue was purified by silica gel column chromatography (methanol/DCM) to give the title compound (650 mg). MS: [M+H]$^+$ 1111.3

B) 7-{(5R,7R,8R,12aR,14R,15R,15aR,16R)-14-(6-amino-9H-purin-9-yl)-15-fluoro-2,10-dihydroxy-16-[(3-hydroxy-1,1,3,3-tetraisopropyldisiloxanyl)oxy]-2,10-dioxidooctahydro-12H-5,8-methanofuro[3,2-1][1,3,6,9,11,2,10]pentaoxadiphosphacyclotetradecin-7-yl}-5-fluoro-3-methyl-3,7-dihydro-4H-pyrrolo[2,3-d]pyrimidin-4-one To a 25 mL round-bottom flask was added N-(9-{(5R,7R,8R,12aR,14R,15R,15aR,16R)-10-(2-cyanoethoxy)-15-fluoro-7-(5-fluoro-3-methyl-4-oxo-3,4-dihydro-7H-pyrrolo[2,3-d]pyrimidin-7-yl)-2-hydroxy-16-[(3-hydroxy-1,1,3,3-tetraisopropyldisiloxanyl)oxy]-2,10-dioxidooctahydro-12H-5,8-methanofuro[3,2-1][1,3,6,9,11,2,10]pentaoxadiphosphacyclotetradecin-14-yl}-9H-purin-6-yl)benzamide (650 mg) and methylamine (33 mass %) in absolute ethanol (22.7 mL). The mixture was stirred at room temperature for 3 hours. The reaction mixture was concentrated under reduced pressure and the residue was purified by by reverse phase chromatography (ISCO RediSepRf Gold HP C18 column) eluted with 0 to 60% ACN in 10 mM aq NH$_4$OAc to give the title compound (32.0 mg). MS: [M+H]$^+$ 953.3.

C) 7-[(5R,7R,8R,12aR,14R,15R,15aR,16R)-14-(6-amino-9H-purin-9-yl)-15-fluoro-2,10,16-trihydroxy-2,10-dioxidooctahydro-12H-5,8-methanofuro[3,2-1][1,3,6,9,11,2,10]pentaoxadiphosphacyclotetradecin-7-yl]-5-fluoro-3-methyl-3,7-dihydro-4H-pyrrolo[2,3-d]pyrimidin-4-one di-triethylamine salt 15 mL polypropylene conical tube was loaded with 7{(5R,7R,8R,12aR,14R,15R,15aR,16R)-14-(6-amino-9H-purin-9-yl)-15-fluoro-2,10-dihydroxy-16-[(3-hydroxy-1,1,3,3-tetraisopropyldisiloxanyl)oxy]-2,10-dioxidooctahydro-12H-5,8-methanofuro[3,2-1][1,3,6,9,11,2,10]pentaoxadiphosphacyclotetradecin-7-yl}-5-fluoro-3-methyl-3,7-dihydro-4H-pyrrolo[2,3-d]pyrimidin-4-one (32.0 mg) and pyridine (246 μL) was added. To the suspension was added triethylamine trihydrofluoride (24.6 μL), followed by triethylamine (372 μL). The mixture was allowed to stir at room temperature overnight. The reaction mixture was cooled in ice bath and diluted with water (1 mL). A solution of calcium chloride (18.6 mg) in water (1 mL) was added slowly. The mixture was stirred for 30 min then filtered through a plug of Celite®. The filtrate was concentrated under reduced pressure and the residue was purified by reverse phase chromatography (ISCO RediSepRf Gold HP C18Aq column) eluted with 0 to 5% ACN in 10 mM aq triethylammonium acetate to give the title compound (8.3 mg). MS: [M+H]$^+$ 693.2. $^1$H NMR (400 MHz, METHANOL-d4) δ 8.36 (br, 1H), 8.22 (s, 1H), 8.05 (s, 1H), 7.38 (d, 1H, j=2), 6.48 (d, 1H, j=8), 6.37 (d, 1H, J=16 Hz), 5.70 (dd, 1H, J1=52 Hz, J2=4 Hz), 5.20-5.07 (m, 1H), 4.98-4.92 (m, 1H), 4.53 (d, 1H, J=4 Hz), 4.45-4.33 (m, 2H), 4.33-4.19 (m, 3H), 4.09-4.03 (m, 1H), 3.45 (s, 3H), 3.17 (qt, 12H), 1.28 (t, 18H). $^{31}$P NMR (162 MHz, D$_2$O) δ 1.66, −2.26. $^{19}$F NMR (376.5 MHz, D$_2$O) 6-164.5, −201.7.

Example 26

Synthesis of 7-[(5R,7R,8R,12aR,14R,15R,15aR,16R)-14-(6-amino-9H-purin-9-yl)-15-fluoro-16-hydroxy-2,10-dioxido-2,10-disulfanyloctahydro-12H-5,8-methanofuro[3,2-1][1,3,6,9,11,2,10]pentaoxadiphosphacyclotetradecin-7-yl]-5-chloro-3,7-dihydro-4H-pyrrolo[2,3-d]pyrimidin-4-one di-triethylamine salt (Optical Isomer 1 and Optical Isomer 2)

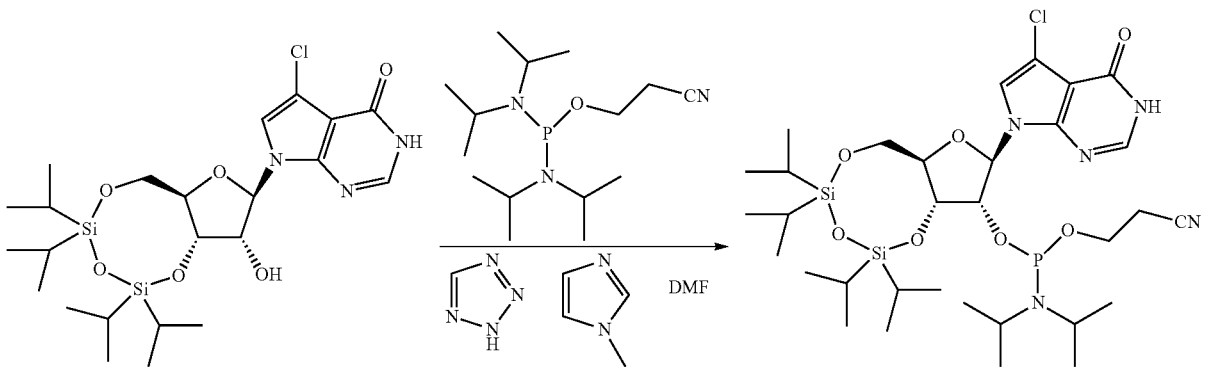

-continued
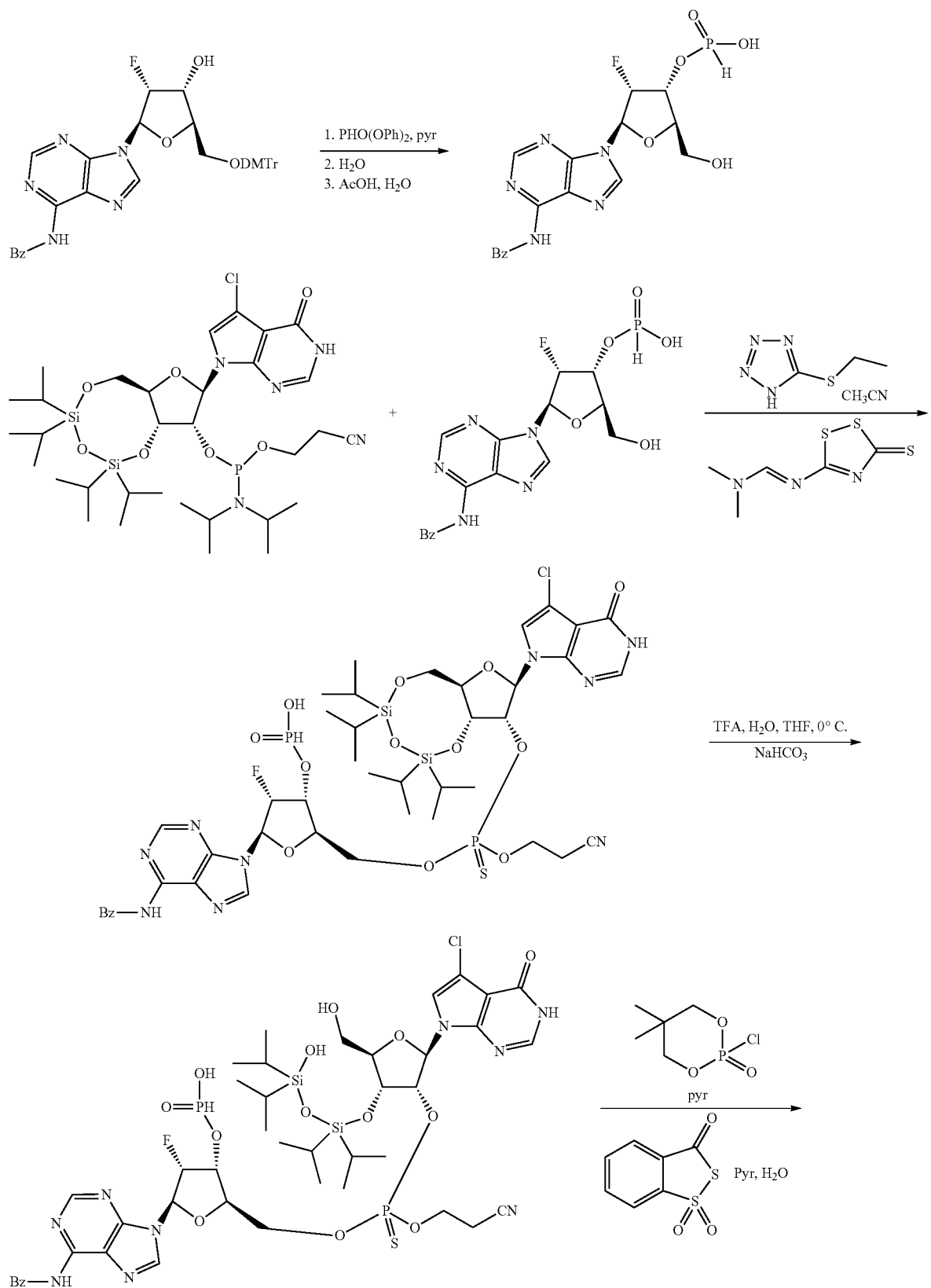

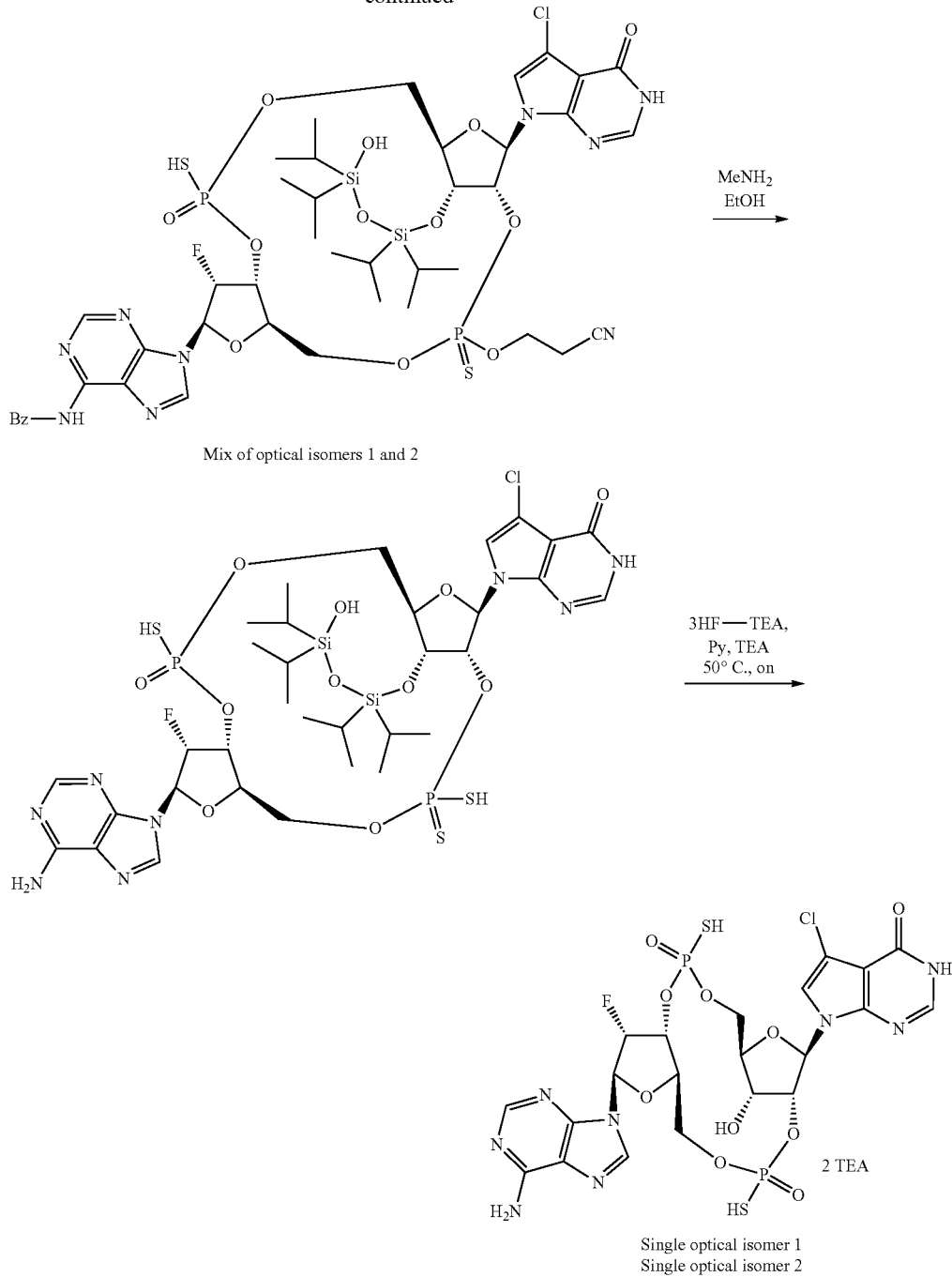

Mix of optical isomers 1 and 2

Single optical isomer 1
Single optical isomer 2

A) (6aR,8R,9R,9aR)-8-(5-chloro-4-oxo-3,4-dihydro-7H-pyrrolo[2,3-d]pyrimidin-7-yl)-2,2,4,4-tetraisopropyltetrahydro-6H-furo[3,2-f][1,3,5,2,4]trioxadisilocin-9-yl 2-cyanoethyl diisopropylphosphoramidoite In a 100 mL round bottom flask 5-chloro-7-[(6aR,8R,9R,9aS)-9-hydroxy-2,2,4,4-tetraisopropyltetrahydro-6H-furo[3,2-f][1,3,5,2,4]trioxadisilocin-8-yl]-3,7-dihydro-4H-pyrrolo[2,3-d]pyrimidin-4-one (1.469 g) (synthesized in the same manner as in the method of Example 15 A)) was azeotroped with toluene (3×) and dried in vacuum. The round bottom flask was evacuated and back filled with argon (3×). Anhydrous N,N-dimethylformamide (5.00 mL) was added to dissolve the starting material with sonication for a minute, followed by 2-cyanoethyl N,N,N',N'-tetraisopropylphosphorodiamidite (2.50 mL), 1-methylimidazole (0.13 mL) and then 1H-tetrazole (0.45M in acetonitrile, 6.70 mL). The mixture was stirred under atmosphere of argon at room temperature for 3 hours. The mixture was diluted with EtOAc (200 mL). Saturated NaHCO$_3$ solution was added. The aqueous layer was extracted with EtOAc twice. The combined EtOAc layer was washed with water then brine, dried over anhydrous Na$_2$SO$_4$, filtered. The filtrate was concentrated under reduced pressure to give a crude oily product. The crude material was purified by column chromatography (ISCO RediSepRf DIOL HP Gold 100 g column) eluted with EtOAc:hexanes (1:9 to 1:1) to give the title compound (1.77 g). MS: [M+H]$^+$ 661.3 for the hydrolyzed fragment of the product.

B) (2R,3R,4R,5R)-5-[6-(benzoylamino)-9H-purin-9-yl]-4-fluoro-2-(hydroxymethyl)tetrahydrofuran-3-yl hydrogen phosphonate N-{9-[(2R,3R,4R,5R)-5-{[bis(4-methoxyphenyl)(phenyl)methoxy]methyl}-3-fluoro-4-hydroxytetrahydrofuran-2-yl]-9H-purin-6-yl}benzamide (2.64 g) was dissolved in anhydrous pyridine (18.0 mL) under argon, cooled with an ice bath. Diphenyl phosphite (1.60 mL) was added slowly over 1 min. The reaction solution was allowed to warm to room temperature and stirred for 1 hour. The second portion of diphenyl phosphite (0.35 mL) was added slowly and the mixture was kept stirring for 30 more min. The mixture was cooled with an ice bath. Water (2.0 mL) was added and the mixture was stirred at room temperature for 30 min. The mixture was concentrated under reduced pressure and azeotroped with toluene to further remove pyridine and water. The residue was dried on vacuum pump. To the residue was added acetic acid (10.0 mL) and water (2.0 mL). The mixture was stirred at room temperature for 30 min. The mixture was concentrated under reduced pressure and azeotroped with toluene, then dried on vacuum pump to give a crude oil, which was chromatographed on a silica column using MeOH/DCM (0/100 to 50/50) to afford 1.33 g of the title product as a white solid. MS: [M+H]$^+$ 438.1.

C) (2R,3R,4R,5R)-5-[6-(benzoylamino)-9H-purin-9-yl]-2-({[{[(6aR,8R,9R,9aR)-8-(5-chloro-4-oxo-3,4-dihydro-7H-pyrrolo[2,3-d]pyrimidin-7-yl)-2,2,4,4-tetraisopropyltetrahydro-6H-furo[3,2-f][1,3,5,2,4]trioxadisilocin-9-yl]oxy}(2-cyanoethoxy)phosphorothioyl]oxy}methyl)-4-fluorotetrahydrofuran-3-yl hydrogen phosphonate In a 250 mL round bottom flask a mixture of (6aR,8R,9R,9aR)-8-(5-chloro-4-oxo-3,4-dihydro-7H-pyrrolo[2,3-d]pyrimidin-7-yl)-2,2,4,4-tetraisopropyltetrahydro-6H-furo[3,2-f][1,3,5,2,4]trioxadisilocin-9-yl 2-cyanoethyl diisopropylphosphoramidoite (2.23 g) and (2R,3R,4R,5R)-5-[6-(benzoylamino)-9H-purin-9-yl]-4-fluoro-2-(hydroxymethyl)tetrahydrofuran-3-yl hydrogen phosphonate (1.17 g) was azeotroped with dry acetonitrile (25 mL×3), dried on vacuum pump for 1 hour. To the mixture was added anhydrous acetonitrile (20.0 mL) under argon, followed by a solution of 5-(ethylthio)-1H-tetrazole (1.00 g) (pre-azeotroped with dry acetonitrile, 10 mL×3 and dried on vacuum pump) in anhydrous acetonitrile (10.0 mL). The mixture was stirred at room temperature for 1 hour 20 min. ((Dimethylamino-methylidene)amino)-3H-1,2,4-dithiazoline-3-thione (655 mg) was added and the mixture was stirred at room temperature for 40 min. The mixture was concentrated under reduced pressure. Chromatography on silica column using MeOH/DCM (0/100 to 40/60) afforded the title compound (1.78 g) as a mixture of 2 optical isomers. MS: [M+H]$^+$ 1112.4.

E) (2R,3R,4R,5R)-5-[6-(benzoylamino)-9H-purin-9-yl]-2-({[(({(2R,3R,4R,5R)-2-(5-chloro-4-oxo-3,4-dihydro-7H-pyrrolo[2,3-d]pyrimidin-7-yl)-5-(hydroxymethyl)-4-[(3-hydroxy-1,1,3,3-tetraisopropyldisiloxanyl)oxy]tetrahydrofuran-3-yl}oxy)(2-cyanoethoxy)phosphorothioyl]oxy}methyl)-4-fluorotetrahydrofuran-3-yl hydrogen phosphonate In a round bottom flask (2R,3R,4R,5R)-5-[6-(benzoylamino)-9H-purin-9-yl]-2-({[{[(6aR,8R,9R,9aR)-8-(5-chloro-4-oxo-3,4-dihydro-7H-pyrrolo[2,3-d]pyrimidin-7-yl)-2,2,4,4-tetraisopropyltetrahydro-6H-furo[3,2-f][1,3,5,2,4]trioxadisilocin-9-yl]oxy}(2-cyanoethoxy)phosphorothioyl]oxy}methyl)-4-fluorotetrahydrofuran-3-yl hydrogen phosphonate (1.73 g) was dissolved in tetrahydrofuran (16 mL) and water (4.0 mL). The solution was cooled with an ice bath. Triflouroacetic acid (4.0 mL) was dropwise added. The mixture was stirred with cooling for 4 hours. At 0° C. sodium bicarbonate (7.00 g) was portion wise added, followed by water and EtOAc. The mixture was stirred for 3 min then brought to room temperature. The layers were separated. The aqueous layer was extracted with EtOAc (3×). The combined EtOAc solution was washed with brine, dried over anhydrous Na$_2$SO$_4$, filtered. The filtrate was concentrated under reduce pressure and dried on vacuum pump to give the crude product. The crude material was purified on a silica column using MeOH/DCM (0/100 to 40/60) to afford the title product (1.43 g) as a mixture of 2 optical isomers. MS: [M+H]$^+$ 1130.3.

F) N-(9-{(5R,7R,8R,12aR,14R,15R,15aR,16R)-7-(5-chloro-4-oxo-3,4-dihydro-7H-pyrrolo[2,3-d]pyrimidin-7-yl)-10-(2-cyanoethoxy)-15-fluoro-16-[(3-hydroxy-1,1,3,3-tetraisopropyldisiloxanyl)oxy]-2-oxido-2-sulfanyl-10-sulfidooctahydro-12H-5,8-methanofuro[3,2-1][1,3,6,9,11,2,10]pentaoxadiphosphacyclotetradecin-14-yl}-9H-purin-6-yl)benzamide (Mixture of Two Major Optical Isomers)

In a round bottom flask (2R,3R,4R,5R)-5-[6-(benzoylamino)-9H-purin-9-yl]-2-({[(({(2R,3R,4R,5R)-2-(5-chloro-4-oxo-3,4-dihydro-7H-pyrrolo[2,3-d]pyrimidin-7-yl)-5-(hydroxymethyl)-4-[(3-hydroxy-1,1,3,3-tetraisopropyldisiloxanyl)oxy]tetrahydrofuran-3-yl}oxy)(2-cyanoethoxy)phosphorothioyl]oxy}methyl)-4-fluorotetrahydrofuran-3-yl hydrogen phosphonate (1.20 g) was azeotroped with dry pyridine (fresh bottle)/acetonitrile (×2) then dry acetonitrile. The resulting white solid was dried under vacuum. Under an atmosphere of argon anhydrous pyridine (20.0 mL) (fresh bottle) was added, followed by 2-chloro-5,5-dimethyl-1,3,2-dioxaphosphinane 2-oxide (0.700 g). The clear solution was allowed to stir at room temperature for 1 hour 10 min. Water (0.70 mL) was added, followed by 3H-1,2-benzodithiol-3-one 1,1-dioxide (0.300 g). The mixture was stirred at room temperature for 20 min. The mixture was concentrated under reduced pressure, azeotroped with toluene (×2), dried on vacuum pump to give a crude residue. The crude residue was chromatographed on a silica column using MeOH/DCM (0/100 to 20/80). The title products (590 mg) from the early fraction was afforded and identified as the mixture of major isomers of peaks 2 and 4 from LCMS; while the second crop of products (389 mg) from the late fraction was a mixture of all 4 isomers. MS: [M+H]$^+$ 1144.2.

G) 7-{(5R,7R,8R,12aR,14R,15R,15aR,16R)-14-(6-amino-9H-purin-9-yl)-15-fluoro-16-[(3-hydroxy-1,1,3,3-tetraisopropyldisiloxanyl)oxy]-2,10-dioxido-2,10-disulfanyloctahydro-12H-5,8-methanofuro[3,2-1][1,3,6,9,11,2,10]pentaoxadiphosphacyclotetradecin-7-yl}-5-chloro-3,7-dihydro-4H-pyrrolo[2,3-d]pyrimidin-4-one (single optical isomers 1 and 2)

Under N$_2$ atmosphere N-(9-{(5R,7R,8R,12aR,14R,15R,15aR,16R)-7-(5-chloro-4-oxo-3,4-dihydro-7H-pyrrolo[2,3-d]pyrimidin-7-yl)-10-(2-cyanoethoxy)-15-fluoro-16-[(3-hydroxy-1,1,3,3-tetraisopropyldisiloxanyl)oxy]-2-oxido-2-sulfanyl-10-sulfidooctahydro-12H-5,8-methanofuro[3,2-l][1,3,6,9,11,2,10]pentaoxadiphosphacyclotetradecin-14-yl}-9H-purin-6-yl)benzamide (0.584 g, mixture of 2 major isomers, early fraction of column chromatograph) was stirred in methylamine (33 mass %) in absolute ethanol (15.0 mL) at room temperature for 2 hours. The mixture was concentrated under reduced pressure and dried on vacuum pump to give crude solid. Two subsequent purifications on silica gel columns, using MeOH/EtOAc (0/100 to 40/60) afforded 2 single optical isomers of the title compounds: isomer 1 (early fraction/peak 1, 73 mg) and isomer 2 (late fraction/peak 2, 304 mg), and a mix fraction of peak 1 and 2 (0.30 g). MS (optical isomer 1): [M+H]+ 987.2. MS (optical isomer 2): [M+H]+ 987.2.

H) 7-[(5R,7R,8R,12aR,14R,15R,15aR,16R)-14-(6-amino-9H-purin-9-yl)-15-fluoro-16-hydroxy-2,10-dioxido-2,10-disulfanyloctahydro-12H-5,8-methanofuro[3,2-l][1,3,6,9,11,2,10] pentaoxadiphosphacyclotetradecin-7-yl]-5-chloro-3,7-dihydro-4H-pyrrolo[2,3-d]pyrimidin-4-one di-triethylamine salt (Optical Isomer 1)

To a polypropylene tube was added 7-{(5R,7R,8R,12aR,14R,15R,15aR,16R)-14-(6-amino-9H-purin-9-yl)-15-fluoro-16-[(3-hydroxy-1,1,3,3-tetraisopropyldisiloxanyl)oxy]-2,10-dioxido-2,10-disulfanyloctahydro-12H-5,8-methanofuro[3,2-l][1,3,6,9,11,2,10]pentaoxadiphosphacyclotetradecin-7-yl}-5-chloro-3,7-dihydro-4H-pyrrolo[2,3-d]pyrimidin-4-one (optical isomer 1, 69.2 mg, early fraction from column chromatography), pyridine (0.40 mL), followed by triethylamine trihydrofluoride (0.060 mL), then triethylamine (0.90 mL). The reaction mixture in the sealed propylene tube was stirred at 50° C. overnight. The reaction mixture was cooled to room temperature, diluted with water (1.30 mL). A solution of calcium chloride (92.5 mg) in water (1.30 mL) was added. The cloudy white mixture was stirred at room temperature for 1 hour, and then filtered through Celite® using a plastic filter funnel, washed with water (1 mL×4). The clear aqueous filtrate was concentrated under reduced pressure, azeotroped with toluene for multiple times, dried on vacuum for 10 min to give a crude residue. The crude residue was purified by C18 column chromatography (water-acetonitrile/10 mM triethylammonium acetate buffer solution). The product fraction was concentrated under reduced pressure, azeotroped with toluene (×4), then with endotoxin-free water (×5). The final residue was dissolved in endotoxin-free water and lyophilized to afford the title product (optical isomer 1, 29.0 mg). MS [M+H]+ 727.0. $^1$H NMR (400 MHz, deuterium oxide) δ=8.19 (s, 1H), 8.16 (s, 1H), 7.96 (s, 1H), 7.63 (s, 1H), 6.39 (br d, J=15.7 Hz, 1H), 6.34 (br d, J=8.0 Hz, 1H), 5.60-5.41 (m, 1H), 5.22-5.14 (m, 1H), 5.14-5.02 (m, 1H), 4.55 (br d, J=3.8 Hz, 1H), 4.51 (br d, J=8.2 Hz, 1H), 4.42 (br s, 1H), 4.40 (br s, 1H), 4.35-4.28 (m, 1H), 4.16-4.10 (m, 1H), 4.06 (br dd, J=4.3, 11.5 Hz, 1H), 3.13 (q, J=7.3 Hz, 12H), 1.21 (t, J=7.3 Hz, 18H). $^{31}$P NMR (162 MHz, deuterium oxide) δ 55.29, 54.54. $^{19}$F NMR (376 MHz, deuterium oxide) δ−200.90.

I) 7-[(5R,7R,8R,12aR,14R,15R,15aR,16R)-14-(6-amino-9H-purin-9-yl)-15-fluoro-16-hydroxy-2,10-dioxido-2,10-disulfanyloctahydro-12H-5,8-methanofuro[3,2-l][1,3,6,9,11,2,10] pentaoxadiphosphacyclotetradecin-7-yl]-5-chloro-3,7-dihydro-4H-pyrrolo[2,3-d]pyrimidin-4-one di-triethylamine salt (Optical Isomer 2)

To a polypropylene tube was added 7-{(5R,7R,8R,12aR,14R,15R,15aR,16R)-14-(6-amino-9H-purin-9-yl)-15-fluoro-16-[(3-hydroxy-1,1,3,3-tetraisopropyldisiloxanyl)oxy]-2,10-dioxido-2,10-disulfanyloctahydro-12H-5,8-methanofuro[3,2-l][1,3,6,9,11,2,10]pentaoxadiphosphacyclotetradecin-7-yl}-5-chloro-3,7-dihydro-4H-pyrrolo[2,3-d]pyrimidin-4-one (optical isomer 2, 186 mg, late fraction from chromatograph). Pyridine (1.1 mL) was added, followed by triethylamine trihydrofluoride (0.161 mL), then triethylamine (2.4 mL). The reaction mixture in the sealed propylene tube was stirred at 50° C. overnight. The reaction mixture was cooled to room temperature, diluted with water (3.50 mL). A solution of calcium chloride (250 mg) in water (3.50 mL) was added. The cloudy white mixture was stirred at room temperature for 1 hour. The mixture was filtered through Celite® using a plastic filter funnel, washed with water (3 mL×4). The clear aqueous filtrate was concentrated under reduced pressure, azeotroped with toluene multiple times, dried on vacuum for 10 min to give a crude residue. The crude residue was purified by C18 column chromatography (water-acetonitrile/10 mM triethylammonium acetate buffer solution). The product fraction was concentrated under reduced pressure, azeotroped with toluene (×4), then with endotoxin-free water (×5). The final residue was dissolved in endotoxin-free water and lyophilized to afford the title product (optical isomer 2, 109 mg). MS [M+H]+ 727.0.

1H NMR (400 MHz, deuterium oxide) δ 8.10 (s, 1H), 7.89 (s, 1H), 7.86 (s, 1H), 7.55 (s, 1H), 6.30 (d, J=15.9 Hz, 1H), 6.24 (d, J=8.2 Hz, 1H), 5.49-5.27 (m, 1H), 5.07-4.86 (m, 2H), 4.85 (d, J=3.9 Hz, 1H), 4.44 (br d, J=9.0 Hz, 1H), 4.33 (br d, J=14.7 Hz, 2H), 4.28-4.16 (m, 2H), 3.98 (br dd, J=5.0, 11.8 Hz, 1H), 3.04 (q, J=7.4 Hz, 12H), 1.12 (t, J=7.3 Hz, 18H). $^{31}$P NMR (162 MHz, deuterium oxide) δ 55.12, 52.04. $^{19}$F NMR (376 MHz, deuterium oxide) δ−200.43.

Example 27

Linker-Payload 1

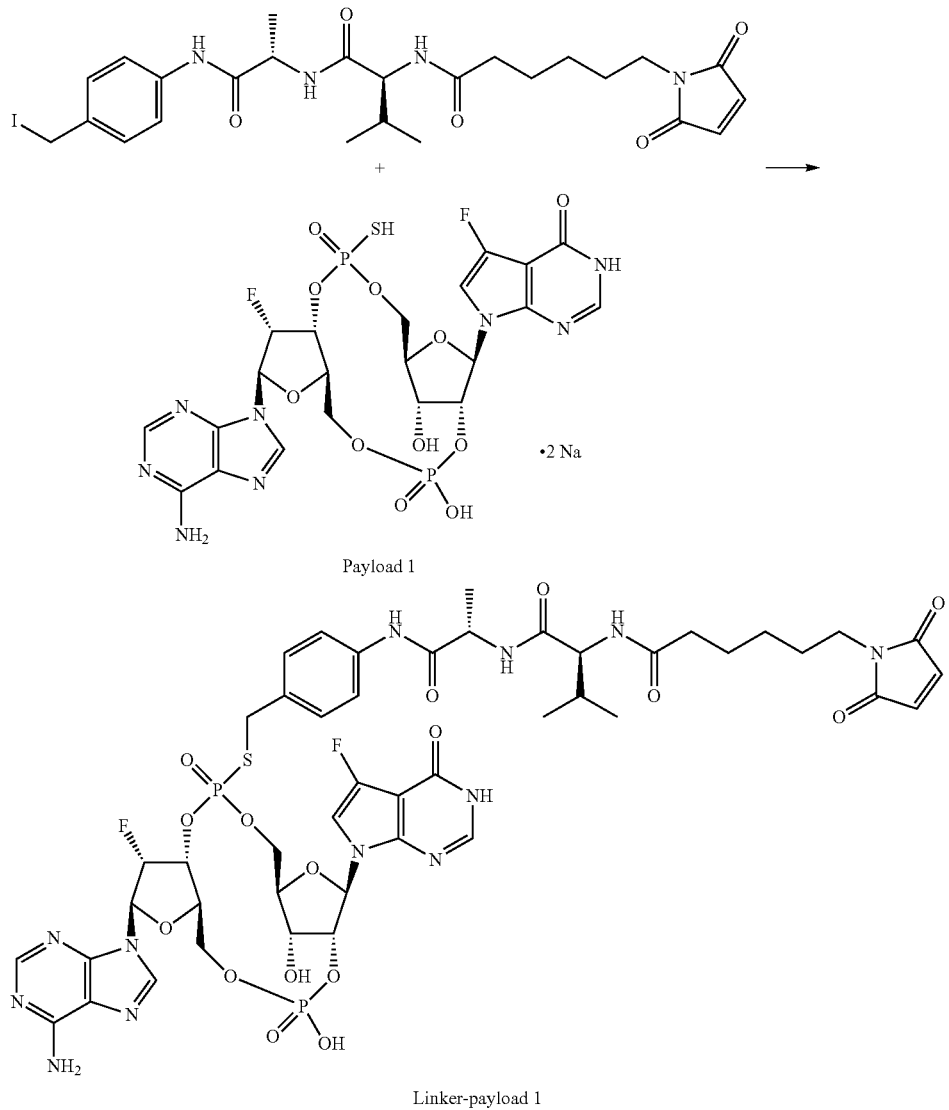

Payload 1

Linker-payload 1

To a mixture of 6-(2,5-dioxopyrrol-1-yl)-N-[(1S)-1-[[(1S)-2-[4-(hydroxymethyl)anilino]-1-methyl-2-oxo-ethyl]carbamoyl]-2-methyl-propyl]hexanamide (mc-Val-Ala-PAB-OH, Synchem, Elk Grove Village, IL, 0.0822 mmol, 40.0 mg) in anhydrous acetonitrile (19.1 mmol, 1.00 mL, 783 mg) was added cesium iodide (0.0986 mmol, 25.6 mg) and boron trifluoride diethyl etherate (0.0986 mmol, 0.0125 mL, 14.0 mg). The reaction was stirred at room temperature overnight. After 18 h of stirring the mixture was diluted with ~10 mL of DCM and filtered over a Celite® pad. The solid was washed with DCM. The filtrate was concentrated to provide an orange solid. The crude product (mc-Val-Ala-PAB-1) was used without further purification.

A vial charged with a solution of disodium (5R,7R,8R,12aR,14R,15R,15aR,16R)-14-(6-amino-9H-purin-9-yl)-15-fluoro-7-(5-fluoro-4-oxo-3,4-dihydro-7H-pyrrolo[2,3-d]pyrimidin-7-yl)-16-hydroxy-2-sulfidooctahydro-12H-5,8-methanofuro[3,2-l][1,3,6,9,11,2,10]pentaoxadiphosphacyclotetradecin-10-olate 2,10-dioxide (Payload 1, also "compound Ex. 3a", 0.0106 mmol, 7.80 mg) and 6-(2,5-dioxopyrrol-1-yl)-N-[(1S)-1-[[(1S)-2-[4-(iodomethyl)anilino]-1-methyl-2-oxo-ethyl]carbamoyl]-2-methyl-propyl]hexanamide (mc-Val-Ala-PAB-I, 0.0208 mmol, 12.4 mg, crude) in N,N-dimethylformamide (5.17 mmol, 0.400 mL, 378 mg) was sealed and heated to 60° C. In 2 h the reaction was cooled to room temperature and purified by chromatography on C18 column (continuous gradient from 20-60% CH3CN/water with 0.1% formic acid) to provide N-[(2S)-1-{[(2S)-1-{[4-({[[(5R,7R,8R,12aR,14R,15R,15aR,16R)-14-(6-amino-9H-purin-9-yl)-15-fluoro-7-(5-fluoro-4-oxo-3,4-dihydro-7H-pyrrolo[2,3-d]pyrimidin-7-yl)-10,16-dihydroxy-2,10-dioxidooctahydro-12H-5,8-methanofuro[3,2-l][1,3,6,9,11,2,10]pentaoxadiphosphacyclotetradecin-2-yl]sulfanyl}methyl)

phenyl]amino}-1-oxopropan-2-yl]amino}-3-methyl-1-oxobutan-2-yl]-6-(2,5-dioxo-2,5-dihydro-1H-pyrrol-1-yl)hexanamide (5.5 mg, 45% yield) as a white solid. $^1$H NMR (400 MHz, METHANOL-d4) δ 8.23-8.35 (m, 2H), 8.10 (s, 1H), 7.89-8.02 (m, 1H), 7.84 (s, 1H), 7.52-7.64 (m, 2H), 7.41 (br d, J=8.53 Hz, 2H), 7.22-7.38 (m, 2H), 6.75-6.83 (m, 2H), 6.32-6.43 (m, 2H), 5.71-5.90 (m, 2H), 4.54-4.59 (m, 2H), 4.42-4.51 (m, 2H), 4.07-4.35 (m, 8H), 3.46 (br t, J=7.03 Hz, 2H), 2.27 (br t, J=7.34 Hz, 21-1), 2.03-2.15 (m, 2H), 1.53-1.70 (m, 4H), 1.39-1.47 (m, 3H), 1.23-1.37 (m, 2H), 0.92-1.02 (m, 6H). LCMS: m/z 1163, 1164 [M+H].

Example 28

Linker-Payload 2

Linker-payload 2 was generated according to the procedure in Example 27, using 2-amino-9-[(5R,7R,8R,12aR,14R,15R,15aS,18R)-14-(6-amino-9H-purin-9-yl)-10,18-dihydroxy-2,10-dioxido-2-sulfanylhexahydro-14H-15,12a-(epoxymethano)-5,8-methanofuro[3,2-l][1,3,6,9,11,2,10]pentaoxadiphosphacyclotetradecin-7(12H)-yl]-1,9-dihydro-6H-purin-6-one sesqui-triethylamine salt (Payload 2) in place of Payload 1.

Payload 2 was prepared according to the method below.

2-amino-9-((5R,7R,8R,12aR,14R,15R,15aS,18R)-14-(6-amino-9H-purin-9-yl)-10,18-dihydroxy-2,10-oxido-2-sulfanylhexahydro-14H-15,12a-(epoxymethano)-5,8-methanofuro[3,2-l][1,3,6,9,11,2,10]pentaoxadiphosphacyclotetradecin-7(12H)-yl)-1,9-dihydro-6H-purin-6-one sesqui-triethylamine salt (Optical Isomer)

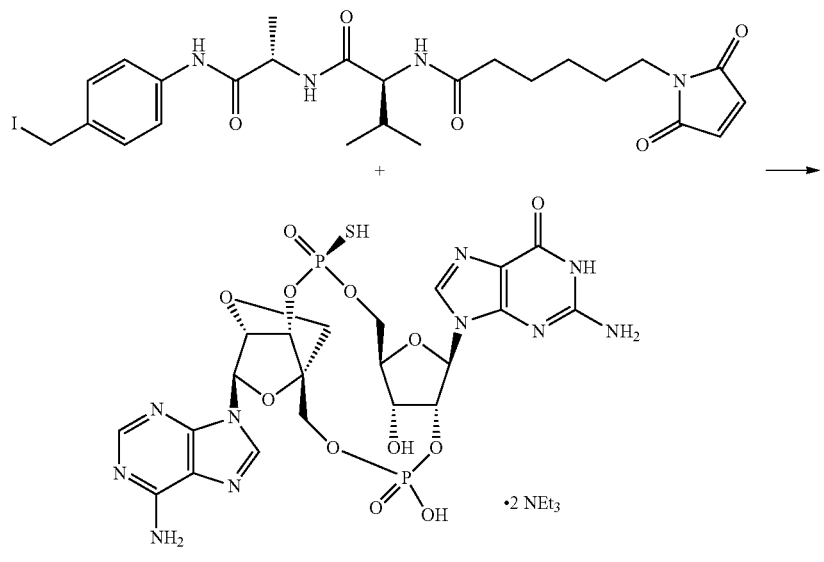

Payload 2

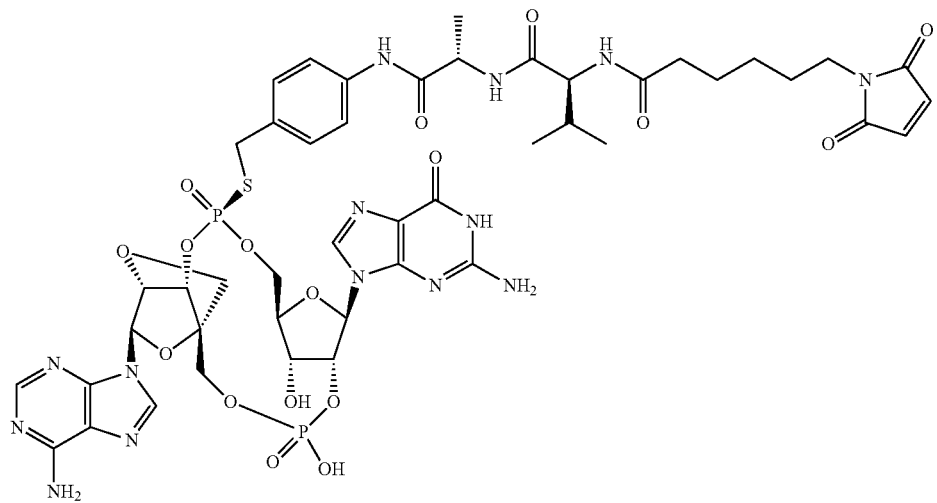

Linker-payload 2

A) (1R,3R,4R,7S)-3-(6-benzamido-9H-purin-9-yl)-1-((((((2R,3R,4R,5R)-4-((tert-butyldimethylsilyl)oxy)-5-(hydroxymethyl)-2-(2-isobutylamido-6-oxo-1H-purin-9(6H)-yl)tetrahydrofuran-3-yl)oxy)(2-cyanoethoxy)phosphoryl)oxy)methyl)-2,5-dioxabicyclo[2.2.1]heptan-7-yl hydrogen phosphonate (1 S,3R,4R,7S)-3-(6-Benzamido-9H-purin-9-yl)-1-(hydroxymethyl)-2,5-dioxabicyclo[2.2.1]heptan-7-yl hydrogen phosphonate (700 mg) and 5'-O-[bis(4-methoxyphenyl)(phenyl)methyl]-3'-O-[tert-butyl(dimethyl)silyl]-2'-O-{(2-cyanoethoxy)[diisopropylamino]phosphanyl}-N-(2-methylpropanoyl)guanosine (2280 mg) were subjected to azeotropic dehydration with anhydrous acetonitrile, and anhydrous acetonitrile (15 mL) and anhydrous tetrahydrofuran (5 mL) were added thereto. To the mixture was added a mixture of 5-(ethylsulfanyl)-2H-tetrazole (611 mg) (which was subjected to azeotropic dehydration with anhydrous acetonitrile) and anhydrous acetonitrile (10 mL), and the mixture was stirred overnight under argon atmosphere at room temperature. 70% tert-Butyl hydroperoxide (643 µL) was added thereto, and the mixture was stirred at room temperature for 20 min. To the reaction mixture was added a mixture of sodium thiosulfate (5920 mg) and water (3 mL), and the mixture was concentrated under reduced pressure. To the residue was added 80% acetic acid (30 mL), and the mixture was stirred at room temperature for 20 min. The reaction mixture was concentrated under reduced pressure, and the residue was purified by silica gel column chromatography (methanol/ethyl acetate) to give the title compound (980 mg). MS: [M+H]$^+$ 1030.2

B) 2-amino-9-[(5R,7R,8R,12aR,14R,15R,15aS,18R)-14-(6-amino-9H-purin-9-yl)-18-{[tert-butyl(dimethyl)silyl]oxy}-2,10-dihydroxy-10-oxido-2-sulfidohexahydro-14H-15,12a-(epoxymethano)-5,8-methanofuro[3,2-1][1,3,6,9,11,2,10]pentaoxadiphosphacyclotetradecin-7(12H)-yl]-1,9-dihydro-6H-purin-6-one (Optical Isomer)

(1R,3R,4R,7S)-3-(6-Benzamido-9H-purin-9-yl)-1-((((((2R,3R,4R,5R)-4-((tert-butyldimethylsilyl)oxy)-5-(hydroxymethyl)-2-(2-isobutyl amido-6-oxo-1H-purin-9(6H)-yl)tetrahydrofuran-3-yl)oxy)(2-cyanoethoxy)phosphoryl)oxy)methyl)-2,5-dioxabicyclo[2.2.1]heptan-7-yl hydrogen phosphonate (980 mg) was subjected to azeotropic dehydration with anhydrous acetonitrile and anhydrous pyridine, and anhydrous pyridine (50 mL) was added thereto. To the mixture was added 2-chloro-5,5-dimethyl-1,3,2-dioxaphosphinane 2-oxide (615 mg) at room temperature, and the mixture was stirred under argon atmosphere at room temperature for 1 hr. Water (600 µL) and 3H-benzo[c][1,2]dithiol-3-one (240 mg) were added thereto, and the mixture was stirred at room temperature for additional 30 min. To the reaction mixture was added a mixture of sodium thiosulfate (1180 mg) and water (3 mL), and the mixture was concentrated under reduced pressure. To the residue were added anhydrous acetonitrile (15 mL) and 2-methylpropan-2-amine (5.0 mL), and the mixture was stirred at room temperature for 1.5 hr, and concentrated under reduced pressure. The residue was purified by silica gel column chromatography (methanol/ethyl acetate), and to the obtained residue was added 40% methylamine ethanol solution (30 mL). The mixture was stirred overnight under argon atmosphere at room temperature, and the reaction mixture was concentrated under reduced pressure. The residue was purified by silica gel column chromatography (methanol/ethyl acetate). The obtained residue was resolved into two diastereomers (tR1 and tR2, retention times of which by LC/MS are from shorter to longer in this order) by HPLC (L-column2 ODS, 50×150 mm, mobile phase: 5 mM aqueous ammonium acetate solution/acetonitrile) to give the title compound (38 mg, tR1) and the title compound (322 mg, tR2). MS (tR2): [M+H]$^+$ 817.1. MS (tR2): [M+H]$^+$ 817.1

C) 2-amino-9-[(5R,7R,8R,12aR,14R,15R,15aS,18R)-14-(6-amino-9H-purin-9-yl)-2,10,18-trihydroxy-10-oxido-2-sulfidohexahydro-14H-15,12a-(epoxymethano)-5,8-methanofuro[3,2-1][1,3,6,9,11,2,10]pentaoxadiphosphacyclotetradecin-7(12H)-yl]-1,9-dihydro-6H-purin-6-one sesqui-triethylamine salt (Optical Isomer)

To 2-amino-9-[(5R,7R,8R,12aR,14R,15R,15aS,18R)-14-(6-amino-9H-purin-9-yl)-18-{[tert-butyl(dimethyl)silyl]oxy}-2,10-dihydroxy-10-oxido-2-sulfidohexahydro-14H-15,12a-(epoxymethano)-5,8-methanofuro[3,2-1][1,3,6,9,11,2,10]pentaoxadiphosphacyclotetradecin-7(12H)-yl]-1,9-dihydro-6H-purin-6-one (optical isomer) (38 mg, tR1) were added methanol (3.0 mL) and triethylamine trihydrofluoride (0.76 mL). The reaction mixture was concentrated to remove the methanol, and the residue was stirred at 55° C. for 1 hr. The mixture was cooled to room temperature, ethoxy(trimethyl)silane (4.2 mL) was added thereto, and the mixture was stirred at room temperature for 2 hr. The reaction mixture was concentrated under reduced pressure, and the residue was purified by C18 column chromatography (acetonitrile/10 mM triethylammonium acetate buffer solution) to give the title compound (27 mg). $^1$H NMR (400 MHz, D$_2$O) δ 1.23 (13H, t, J=7.3 Hz), 3.15 (9H, q, J=7.3 Hz), 4.04 (1H, d, J=8.3 Hz), 4.08-4.19 (3H, m), 4.28 (1H, d, J=12.2 Hz), 4.37-4.52 (2H, m), 4.65 (1H, d, J=4.2 Hz), 4.90 (1H, d, J=4.6 Hz), 5.36 (1H, s), 5.55 (1H, td, J=8.5, 4.0 Hz), 5.98 (1H, d, J=8.3 Hz), 6.16 (1H, s), 7.94 (1H, s), 8.21 (1H, s), 8.25 (1H, S). $^{31}$P NMR (162 MHz, D$_2$O) δ−1.45, 53.78.

Synthesis of 2-amino-9-[(5R,7R,8R,12aR,14R,15R,15aS,18R)-14-(6-amino-9H-purin-9-yl)-10,18-dihydroxy-2,10-dioxido-2-sulfanylhexahydro-14H-15,12a-(epoxymethano)-5,8-methanofuro[3,2-1][1,3,6,9,11,2,10]pentaoxadiphosphacyclotetradecin-7(12H)-yl]-1,9-dihydro-6H-purin-6-one sesqui-triethylamine salt (Optical Isomer; Payload 2)

To 2-amino-9-[(5R,7R,8R,12aR,14R,15R,15aS,18R)-14-(6-amino-9H-purin-9-yl)-18-{[tert-butyl(dimethyl)silyl]oxy}-2,10-dihydroxy-10-oxido-2-sulfidohexahydro-14H-15,12a-(epoxymethano)-5,8-methanofuro[3,2-1][1,3,6,9,11,2,10]pentaoxadiphosphacyclotetradecin-7(12H)-yl]-1,9-dihydro-6H-purin-6-one (optical isomer) (322 mg, tR2) were added methanol (3.0 mL) and triethylamine trihydrofluoride (3.2 mL). The reaction mixture was concentrated to remove the methanol, and the residue was stirred at 55° C. for 1 hr. The mixture was cooled to room temperature, ethoxy(trimethyl)silane (14 mL) was added thereto, and the mixture was stirred at room temperature for 2 hr. The reaction mixture was concentrated under reduced pressure, and the residue was purified by C18 column chromatography (acetonitrile/10 mM triethylammonium acetate buffer solution) to give the title compound (266 mg). $^1$H NMR (400 MHz, D$_2$O) δ 1.23 (14H, t, J=7.3 Hz), 3.15 (10H, q, J=7.3 Hz), 4.02 (1H, d, J=8.1 Hz), 4.13-4.24 (2H, m), 4.27-4.42 (4H, m), 4.59 (1H, d, J=4.4 Hz), 5.01 (1H, s), 5.11 (1H, d, J=4.2 Hz), 5.61-5.73 (1H, m), 5.95 (1H, d, J=8.3 Hz), 6.15 (1H, s), 7.87 (1H, s), 8.00 (1H, s), 8.25 (1H, s). $^{31}$P NMR (162 MHz, D$_2$O) δ−1.93, 55.44.

Example 29

General ADC Conjugation Procedure

A solution of antibody was diluted to the desired reaction concentration with an appropriate buffer. The pH was adjusted to 7 by addition of 0.5 M tris, 25 mM EDTA solution in water (pH 8.0). TCEP (2.2 equiv, 5 mM in water) was added with stirring. After 1 hour of incubation at room temperature, 5 equiv of linker-payload (5 mM in DMA) was added. After 2 additional hours of gentle stirring at room temperature the mixture was purified twice over 3 mL spinOUT desalting columns (G-Bioscience, pre-equilibrated with a buffer containing 10 mM histidine, 7.5% sucrose (w/v) and 0.08% polysorbate 20 (w/v) at pH 5.2), and then buffer exchanged to Dulbecco's PBS and concentrated to 1-3 mg/mL (as determined by UV absorption using a standard IgG1 extinction coefficient) using a Vivaspin6 column (GE Healthcare). Sample was then characterized for drug-antibody-ratio (DAR) by QTOF mass spectrometry. The monomer composition of the ADC was determined by size exclusion chromatography (SEC).

Size Exclusion Chromatography (SEC) Protocol

Sample Preparation

Prepare a water blank by adding HPLC water to an HPLC vial. Naked antibody controls and ADC samples are obtained from the chemists. The controls and samples are diluted with 1×PBS if the concentration is above 5 mg/mL, or injected neat if the concentration is 5 mg/mL or below.
HPLC System Setup An Agilent 1100 HPLC system is used for analysis. The system is set up with system wash (5% Acetonitrile in HPLC water) on one pump channel, and the mobile phase (as described above) on a different pump channel. The column used is Tosoh Biosep TSK Gel, G3000SWxl; P/N 8541; 250A; 5 um; 7.8 mm×300 mm. The flow rate is set to 1 mL/min, and each run is isocratic with 100% mobile phase [100 mM sodium phosphate, 300 mM sodium chloride, pH 6.8, 10% acetonitrile (v/v)] for 20 minutes. The DAD is set to 280 nm. The injection volume for each control, sample, and blank is typically 10 uL, but can be adjusted depending on UV absorbance. Data Analysis: All peaks at 280 nm within appropriate time window (typically 2-10 minutes) are integrated.

Example 30

Preparation of ADC1

The synthesis was performed according to the General ADC Conjugation Procedure.

Antibody: Antibody 1, an anti-GCC antibody (5F9), 100 uL of a 60 mg/mL solution in a buffer of 50 mM histidine and 100 mM arginine at pH 6.0, receptor target guanylyl cyclase C (GCC)

Antibody 1 heavy chain:
(SEQ. ID No. 1)
QVQLQQWGAGLLKPSETLSLTCAVFGGSFSGYYWSWIRQPPGKGLEWIGE

INHRGNTNDNPSLKSRVTISVDTSKNQFALKLSSVTAADTAVYYCARERG

-continued

YTYGNFDHWGQGTLVTVSSASTKGPSVFPLAPSSKSTSGGTAALGCLVKD

YFPEPVTVSWNSGALTSGVHTFPAVLQSSGLYSLSSVVTVPSSSLGTQTY

ICNVNHKPSNTKVDKKVEPKSCDKTHTCPPCPAPELLGGPSVFLFPPKPK

DTLMISRTPEVTCVVVDVSHEDPEVKFNWYVDGVEVHNAKTKPREEQYNS

TYRVVSVLTVLHQDWLNGKEYKCKVSNKALPAPIEKTISKAKGQPREPQV

YTLPPSRDELTKNQVSLTCLVKGFYPSDIAVEWESNGQPENNYKTTPPVL

DSDGSFFLYSKLTVDKSRWQQGNVFSCSVMHEALHNHYTQKSLSLSPGK

Antibody 1 light chain:
(SEQ. ID No. 2)
EIVMTQSPATLSVSPGERATLSCRASQSVSRNLAWYQQKPGQAPRLLIYG

ASTRATGIPARFSGSGSGTEFTLTIGSLQSEDFAVYYCQQYKTWPRTFGQ

GTNVEIKRTVAAPSVFIFPPSDEQLKSGTASVVCLLNNFYPREAKVQWKV

DNALQSGNSQESVTEQDSKDSTYSLSSTLTSKADYEKHKVYACEVTHQGL

SSPVTKSFNRGEC

Buffer: 50 mM histidine and 100 mM arginine at pH 6.0, 200 uL, final concentration 20 mg/mL Linker-payload: N-[(2S)-1-{[(2S)-1-{[4-({[(5R,7R,8R,12aR,14R,15R,15aR,16R)-14-(6-amino-9H-purin-9-yl)-15-fluoro-7-(5-fluoro-4-oxo-3,4-dihydro-7H-pyrrolo[2,3-d]pyrimidin-7-yl)-10,16-dihydroxy-2,10-dioxidooctahydro-12H-5,8-methanofuro[3,2-l][1,3,6,9,11,2,10]pentaoxadiphosphacyclotetradecin-2-yl]sulfanyl}methyl)phenyl]amino}-1-oxopropan-2-yl]amino}-3-methyl-1-oxobutan-2-yl]-6-(2,5-dioxo-2,5-dihydro-1H-pyrrol-1-yl)hexanamide (Linker-payload 1)

Product ADC: ADC1, yield=1.9 ml at 2.5 mg/mL (79%), DAR 3.5, 99% monomer (i.e., not aggregated)

Example 31

Preparation of ADC2

The synthesis was performed according to the General ADC Conjugation Procedure.

Antibody: Antibody 2, a non-GCC targeting antibody directed to a membrane-anchored protein over expressed in certain solid tumors including lung and breast, 100 uL at 11.8 mg/mL in 25 mM sodium acetate, pH 5.5.

Buffer: Dulbecco's PBS, pH 7.4, 200 uL, final concentration 4 mg/mL

Linker-payload: N-[(2S)-1-{[(2S)-1-{[4-({[(5R,7R,8R,12aR,14R,15R,15aR,16R)-14-(6-amino-9H-purin-9-yl)-15-fluoro-7-(5-fluoro-4-oxo-3,4-dihydro-7H-pyrrolo[2,3-d]pyrimidin-7-yl)-10,16-dihydroxy-2,10-dioxidooctahydro-12H-5,8-methanofuro[3,2-l][1,3,6,9,11,2,10]pentaoxadiphosphacyclotetradecin-2-yl]sulfanyl}methyl)phenyl]amino}-1-oxopropan-2-yl]amino}-3-methyl-1-oxobutan-2-yl]-6-(2,5-dioxo-2,5-dihydro-1H-pyrrol-1-yl)hexanamide (Linker-payload 1)

Product ADC: ADC2, yield=0.6 ml at 1.4 mg/mL (70%), DAR 2.6, 99% monomer

Example 32

Preparation of ADC3

The synthesis was performed according to the General ADC Conjugation Procedure.

Antibody: Antibody 1, 33 uL at 60 mg/mL in a buffer of 50 mM histidine and 100 mM arginine at pH 6.0

Buffer: 50 mM histidine and 100 mM arginine at pH 6.0, 66 uL final concentration of antibody solution 20 mg/mL Linker-payload: N-[(2S)-1-{[(2S)-1-{[4-({[(5R,7R,8R,12aR,14R,15R,15aS,18R)-7-(2-amino-6-oxo-1,6-dihydro-9H-purin-9-yl)-14-(6-amino-9H-purin-9-yl)-10,18-dihydroxy-2,10-dioxidohexahydro-14H-15,12a-(epoxymethano)-5,8-methanofuro[3,2-1][1,3,6,9,11,2,10]pentaoxadiphosphacyclotetradecin-2(12H)-yl]sulfanyl}methyl)phenyl]amino}-1-oxopropan-2-yl]amino}-3-methyl-1-oxobutan-2-yl]-6-(2,5-dioxo-2,5-dihydro-1H-pyrrol-1-yl)hexanamide (Linker-payload 2)

Product ADC: ADC3, yield=1.9 ml at 1.0 mg/mL (95%), DAR 4.3, 98% monomer

Example 33

Tritosomal Payload Release Assay—Measurement of Payload Release from Linker-Payload Systems or ADCs in an In Vitro Lysosome Model Materials:
Buffer: 47.9 mg/ml of Potassium Phosphate Monobasic (Sigma-Aldrich Product Number P5379); 6.8 mg/ml of Sodium Phosphate Dibasic (Sigma-Aldrich Product Number S0876), 1.7 mg/ml of Ethylenediaminetetraacetic Acid (Sigma-Aldrich Product Number ED4SS) in purified water. pH was adjusted to 6.0 using 1N HCl or 1N KOH.

Rat Liver Tritosomes purchased from XenoTech
Linker-payload (10 mM DMSO)
ADC (1-40 uM in the storage buffer used for production).

Procedure:
For evaluation of payload release from linker-payload compounds, a 120.95 uM DMSO working solution was prepared from 10 mM stock solution of linker-payload compounds. Then, the 120.95 uM DMSO working solution was diluted to 1 uM in 225 uL tritosome buffer solution containing 22.4% rat liver tritosomes.

For evaluation of ADC molecules, 1.86 uL of ADC solution was diluted with 223.1 uL of mixture of rat liver tritosomes in tritosome buffer.

The solutions thus prepared were incubated for 24 hours at 37° C. 40 uL aliquots were removed at 0.5, 1, 3, 5, and 24 hours and diluted with 160 uL of 0.1% formic acid in methanol solution in a 96-well plate, which was stored in −80° C. freezer until the completion of the experiment. After collecting the last time point, a fresh 200 uL of 0.1% formic acid in methanol solution and spiked with 150 nM carbutamide which is an internal standard solution was added into the samples. The samples were mixed well and centrifuged at 4000 g for 10 minute, and the 96-well plate was submitted for analysis of payload concentration by LC/MS/MS.

LC/MS/MS System:
5 uL of samples were injection into the LC/MS/MS with a Waters Xselect C18 CSH 3.5u 2.1 mmID×30 mm length column. Mobile phase aqueous solvent contained 0.1% formic acid in water, and mobile phase organic solvent contained 0.1% formic acid in 5% water and 95% acetonitrile. The samples were running in 3 minutes gradient at 1.5 mL/min flow rate. Initially, the instrument was running 100% aqueous mobile phase solvent for 0.5 minutes, and then it was increasing to 100% organic solvent in next 1.5 minutes. The system will hold at 100% organic solvent for another 0.5 minutes, and then it would change to 100% aqueous phase solvent in next 0.5 minutes.

Analysis:
To monitor and calculate the release of linker-payload and payload from ADC, a peak area or concentration versus time curve was plotted. The data would be analyzed by using Excel-Fit program to calculate linear range rate and t½ of formation payload from the tested molecules.

Figure 2:
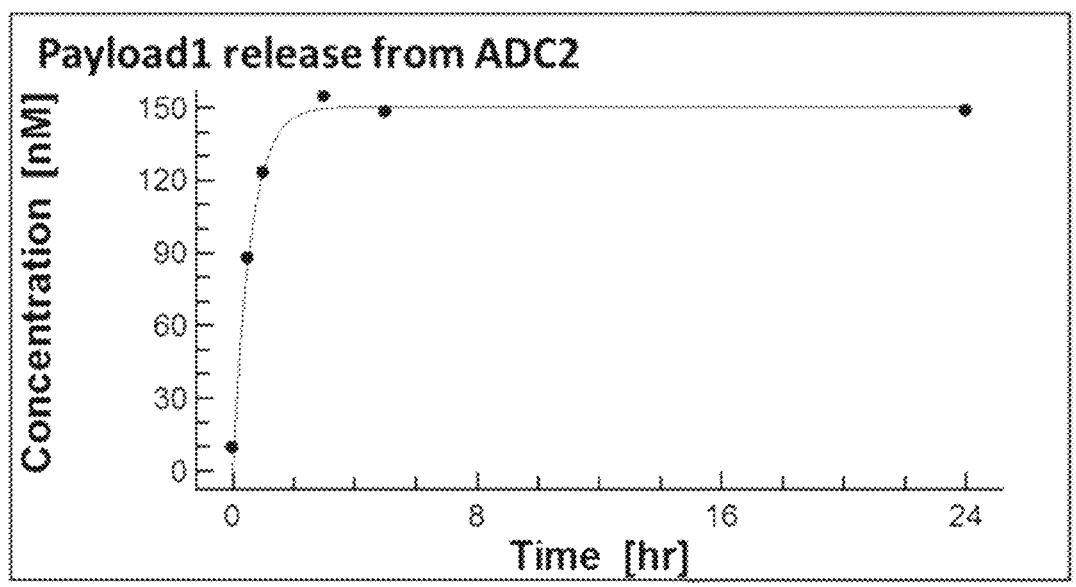
FIG. 2 is a line graph showing Payload 1 release from ADC2.
Figure 3:
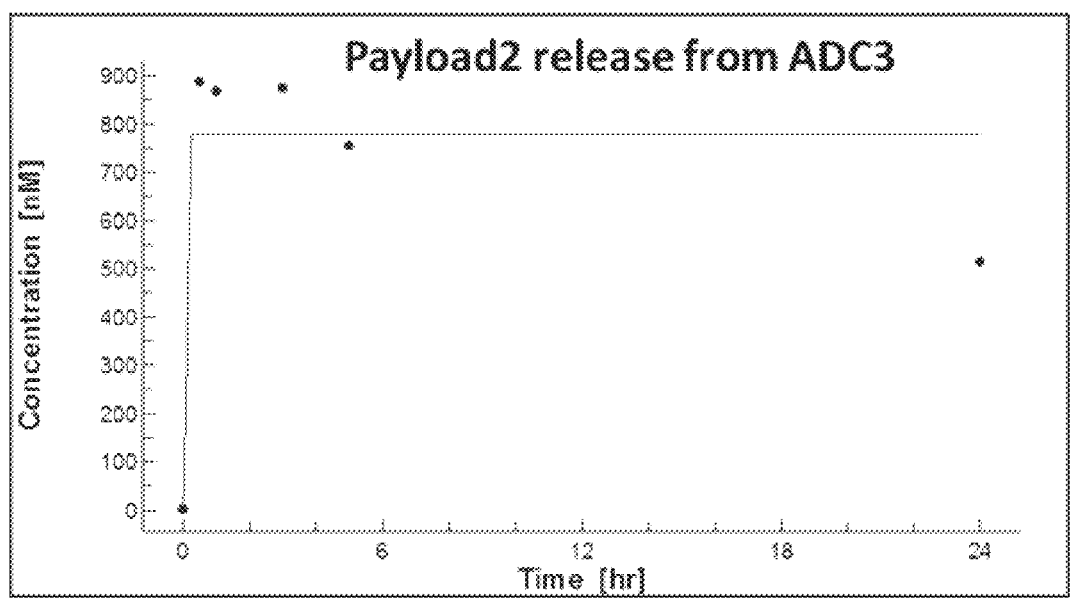
FIG. 3 is a line graph showing Payload 2 release from ADC3.

Tritosomal Payload Release Data:
As shown in FIG. 1, FIG. 2, and FIG. 3, when subjected to the above protocol ADC1, ADC2, and ADC3 release the expected payloads.

Phospho-IRF3 Assay Protocol
HEK293 cells engineered to express the tumor-associated cell surface targets for mAbs Antibody 1 (ADC1 and ADC3) and Antibody 2 (ADC2), as well as target non-expressing HEK293 cells (HEK293-Vect), were seeded at 1.5×10E5 cells/well (500 uL/well) in Poly-D-Lysine-coated 24-well plates (Corning) and were cultured overnight. After overnight serum deprivation, the cells were treated with various concentrations of ADCs for 6 hours and then lysed in RIPA buffer (ThermoFisher Scientific) with protease and phosphatase inhibitos (ThermoFisher Scientific). The cell lysates were subjected to Western blotting analysis for phospho-IRF3 (CST) and IRF3 (BD Biosciences). The level of phospho-IRF3 was normalized to its total IRF3.

Figure 4:
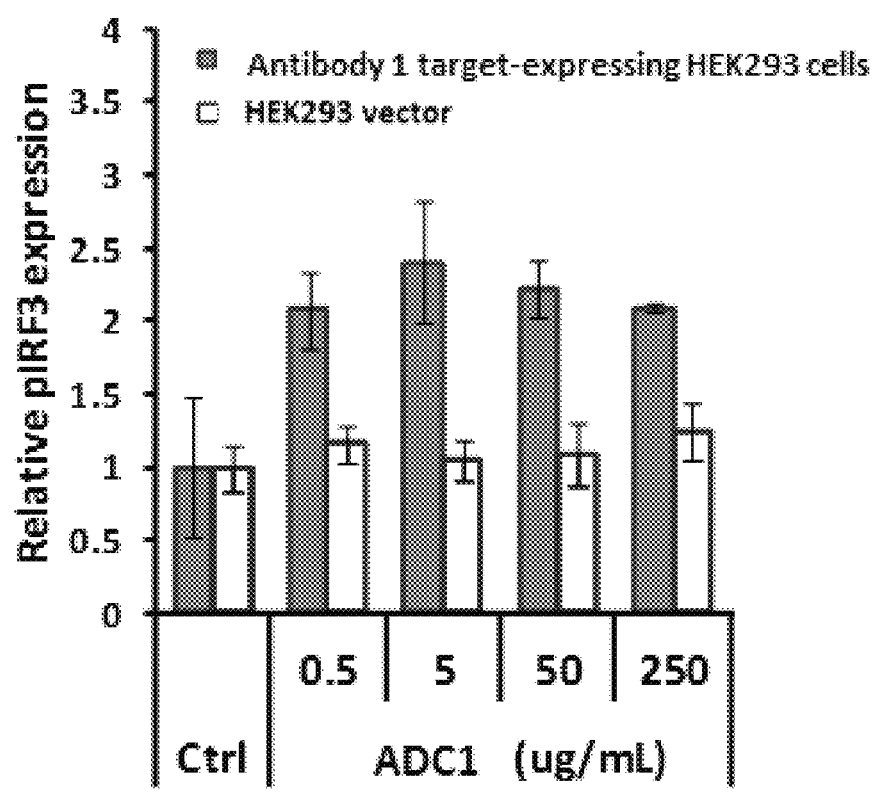
FIG. 4 is a bar graph showing that HEK293 cells that express the surface receptor targets for ADC1 exhibit the expected increase in the STING pathway marker phospho-IRF3 (pIRF3) when treated with the ADC1.
Figure 5:
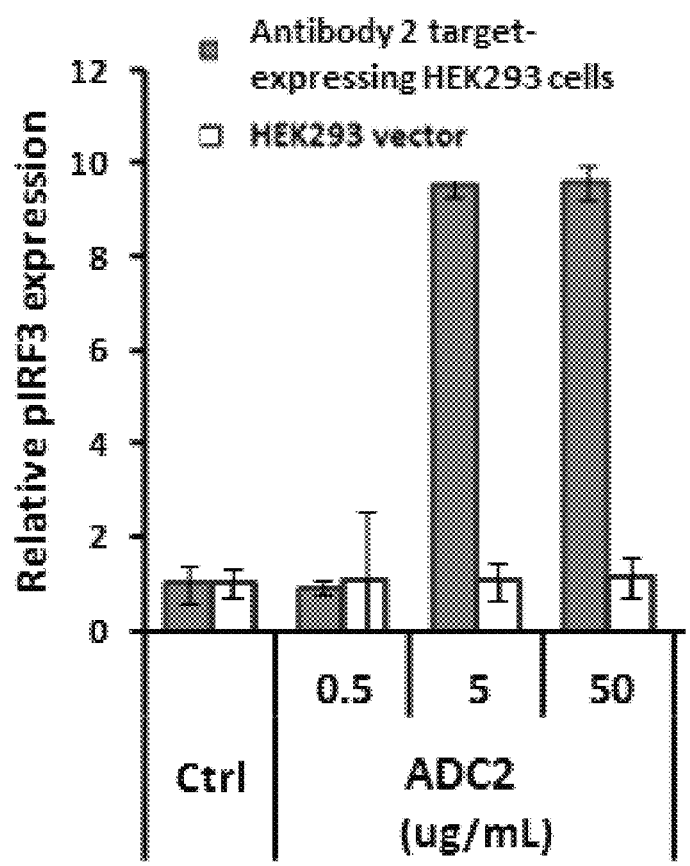
FIG. 5 is a bar graph showing that HEK293 cells that express the surface receptor targets for ADC2 exhibit the expected increase in the STING pathway marker phospho-IRF3 (pIRF3) when treated with the ADC2.
Figure 6:
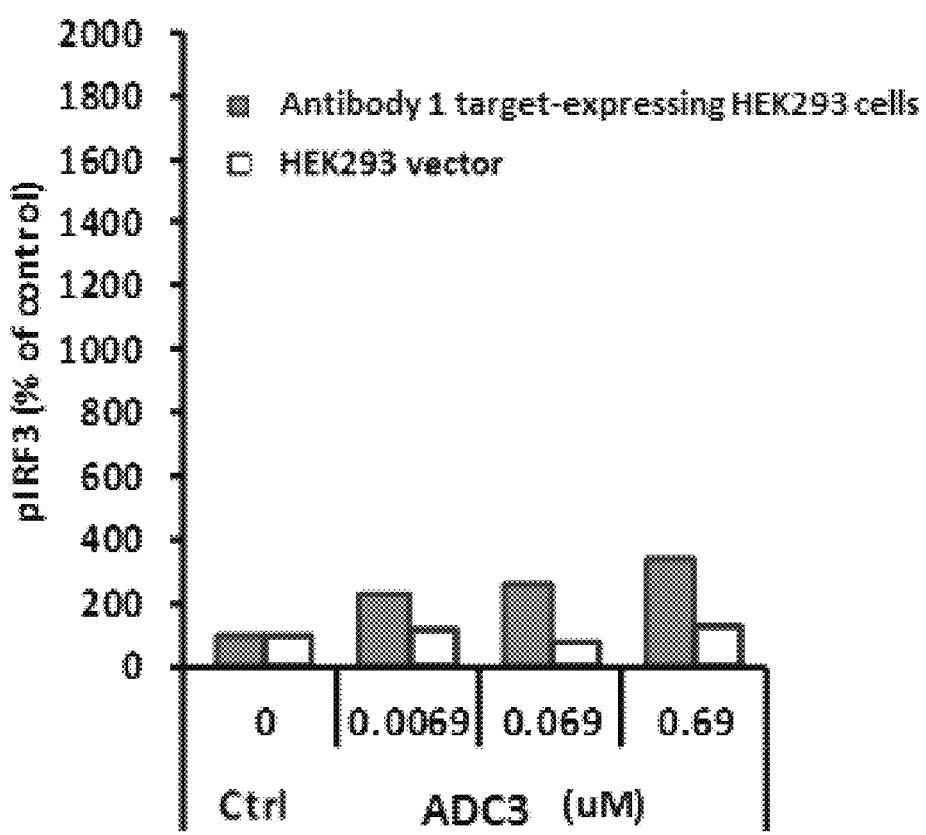
FIG. 6 is a bar graph showing that HEK293 cells that express the surface receptor targets for ADC3 exhibit the expected increase in the STING pathway marker phospho-IRF3 (pIRF3) when treated with the ADC3.

Phospho-IRF3 Assay Results
As shown in FIG. 4, FIG. 5, and FIG. 6, HEK293 cells that express the surface receptor targets for ADC1, ADC2, and ADC3 exhibit the expected increase in the STING pathway marker phospho-IRF3 (pIRF3) when treated with the ADC1, ADC2, and ADC3, respectively. Conversely, the pIRF3 response is not upregulated upon ADC treatment in vector HEK293 cells that do not express the corresponding surface receptor targets.

Example 34

Pharmacological Profiles of Selected Cyclic Dinucleotides

The pharmacological profiles of selected cyclic dinucleotides are shown in Table 6.

| Ex | STING binding ($\mu M$) | STING-293T cell $EC_{50}$ ($\mu M$) Reporter without digitonin (A) | STING-293T cell $EC_{50}$ ($\mu M$) Reporter with digitonin (B) | Cellular permeability Ratio $EC_{50}$s (A)/(B) | THP-1 Dual cell $EC_{50}$ ($\mu M$) Reporter | Human plasma stability (/h) |
|---|---|---|---|---|---|---|
| Ex3a | 0.015 | 2.9 | 0.13 | 22.3 | 5.6 | 0.58 |
| Ex5 | 0.050 | 3.6 | 0.19 | 18.9 | N.D. | <0.01 |
| Ex14 | 0.013 | 0.34 | 0.13 | 2.6 | 2.3 | <0.01 |
| cGAMP | 0.015 | 21 | 0.039 | 539 | 18 | 1.39 |

THP1-Dual™ cells (InvivoGen #thpd-nfis) were derived from the human THP-1 monocyte cell line by stable integration of the Lucia luciferase gene, a secreted luciferase reporter gene, under the control of an ISG54 (interferon-stimulated gene) minimal promoter in conjunction with five interferon (IFN)-stimulated response elements. On the day of experiment, the cells were plated to a black, 384-well plate (Corning 356697) at 7500 cells/25 µL per well density in growth media (RPMI 1640, 2 mM L-glutamine, 25 mM HEPES, 10% heat-inactivated fetal bovine serum, 100 µg/mL Normocin™, 100 U/mL-100 µg/mL Pen-Strep, 10 µg/mL of blasticidin, and 100 µg/mL of Zeocin). The cell plates were dosed with 62.5 nL of the testing compounds, and then incubated at 37° C. for 20 hours. At the end of the incubation, 15 µL/well of the QUANTI-Luc™ (InvivoGen #rep-qlc1) were added, and luminescence was measured immediately using the LeadSeeker.

Protocol of Western Blot Analyses of Downstream Signaling Pathway Activation (TBK1 and IRF3)

$1.5 \times 10^6$ THP-1-Dual Cells (Invivogen catalog #thpd-nfis) were treated with DMSO or the indicated concentrations of Ex14 for 3 hours. After stimulation, cells were collected on ice, centrifuged at 800 RCF for 5 minutes, and washed once in ice-cold PBS.

Cell pellets were lysed in 1% Triton X-100 whole cell lysis buffer (10% glycerol, 20 mM Tris-HCl pH 7.5, 150 mM NaCl, 1 µM EDTA, and 1 µM DTT) containing protease and phosphatase inhibitor cocktails (Sigma #P8340 and CalBiochem #524629, respectively). Cell lysates were cleared of insoluble debris by centrifuging at 16,000 RCF for 10 minutes. The protein concentrations of the lysates were determined by Bradford assay using BSA standards.

Lysates were denatured in NuPAGE™ LDS Sample Buffer (4X, catalog #NP0008) containing DTT as a reducing agent. Denatured lysates were resolved on NuPAGE™ 4-12% Bis-Tris gels in MES/SDS running buffer and transferred to PVDF membranes using a semi dry blotting method. Membranes were probed overnight at 4° C. for phospho-TBK1 S172, phospho-IRF3 S396, and GAPDH using antibodies from Cell Signaling Technology (#5483, #4947, and #5174, respectively).

After an overnight primary probe, membranes were washed extensively, then probed with secondary antibody (Alexa Fluor® 680 goat anti-rabbit IgG, Life Technologies #A21109) in Odyssey® Blocking Buffer (catalog #927-400000) at room temperature. After extensive washing, membranes were developed using a LI-COR ODYSSEY CLx.

Figure 7:
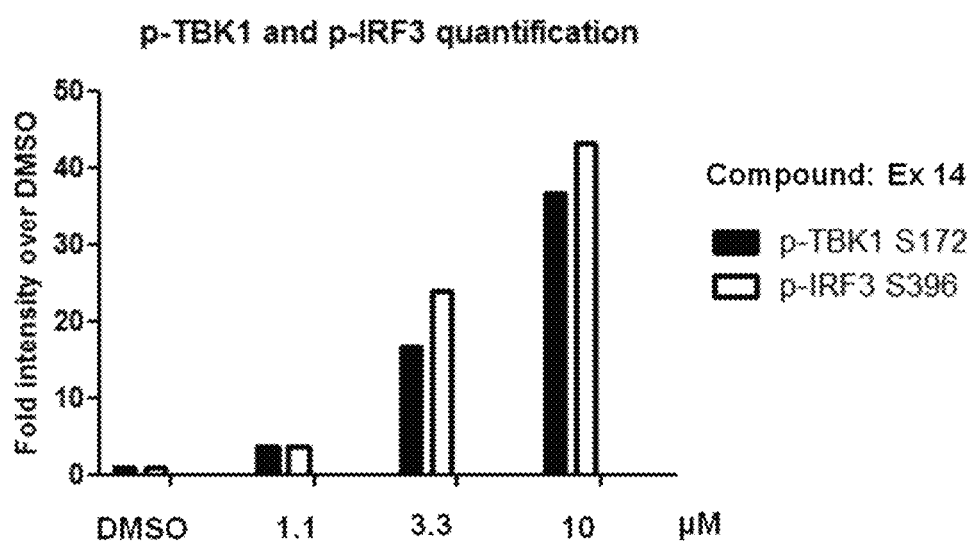
FIG. 7 is a bar graph showing the Western blot analyses of downstream signaling pathway activation (TBK1 and IRF3) for compound Ex. 14.

The relative intensities of the phospho-TBK1 and phospho-IRF3 bands were quantified and normalized to the levels of GAPDH. GAPDH-normalized phospho-TBK1 and phospho-IRF3 values were graphed as fold intensity over the non-stimulated (DMSO) control. See FIG. 7.

Protocol of Human Plasma Stability Assay

The compound was incubated in heparinized human plasma at 37° C. for 0, 1, 2, 4, 8 and 24 hours, and the change in compound concentration was measured by LC/MS/MS method. The elimination rate constant (=k(/h)) was calculated based on the fitted curve assuming the exponential decrease of concentration as follows; concentration at time x=initial concentration*exp(-k*x).

Syngeneic Tumor Model Testing

Figure 8:
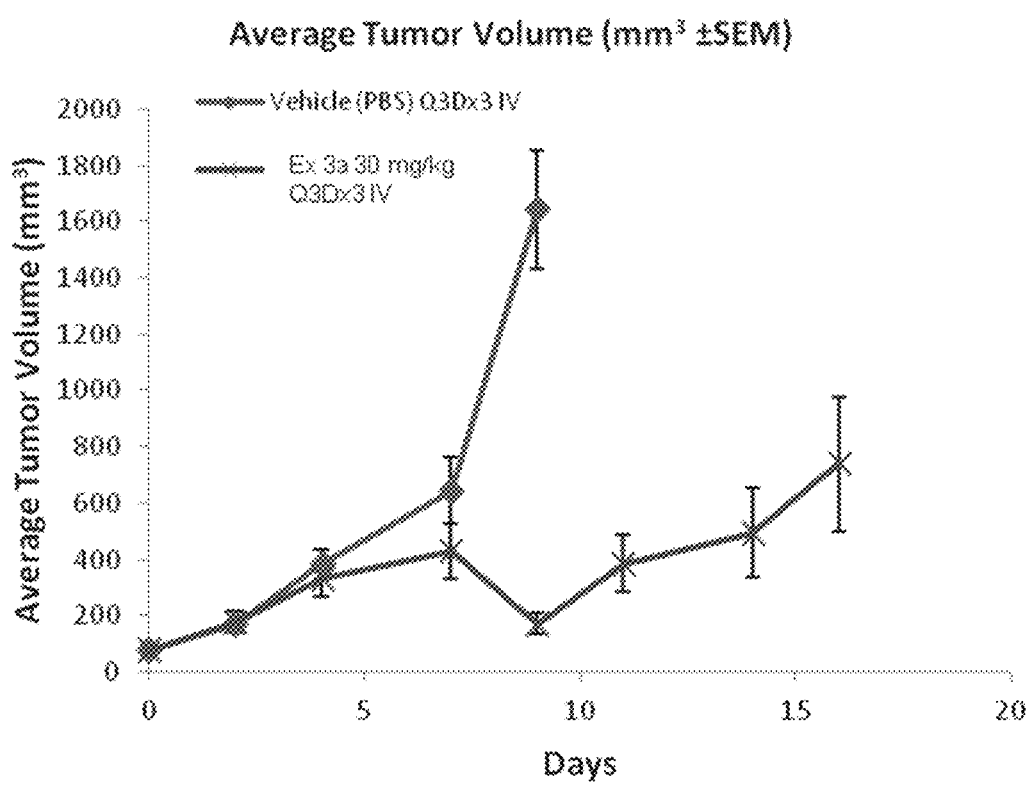
FIG. 8 is line graph showing the anti-tumor activity of compound Ex. 3a in the colon carcinoma CT-26 syngeneic mice model.
Figure 9:
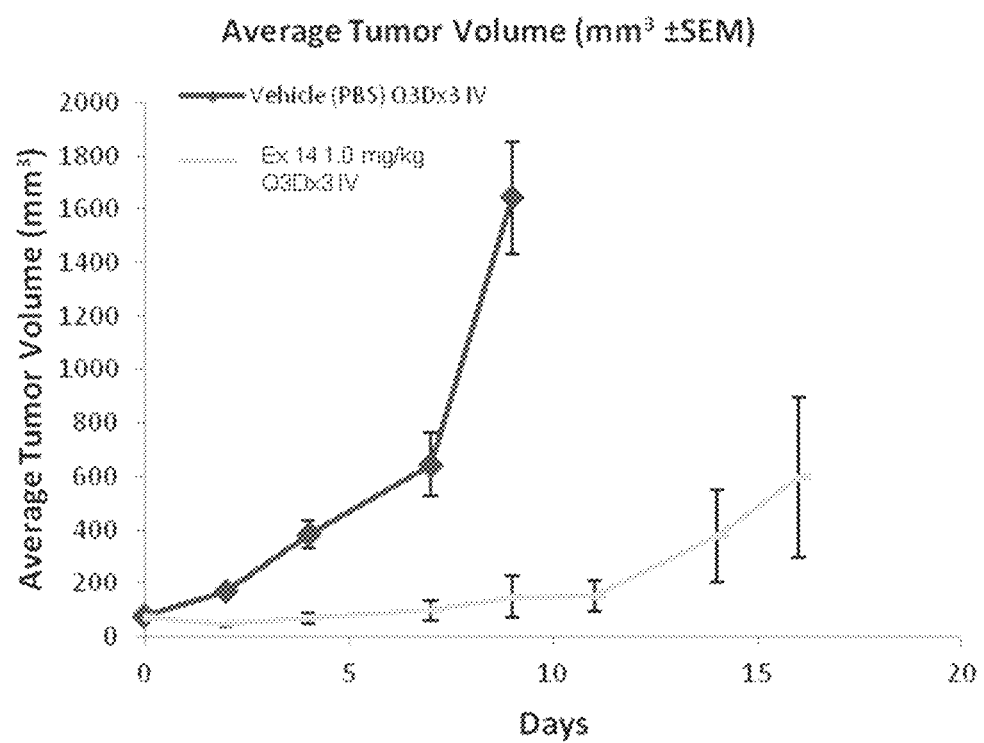
FIG. 9 is line graph showing the anti-tumor activity of compound Ex. 14 in the colon carcinoma CT-26 syngeneic mice model.
Figure 10:
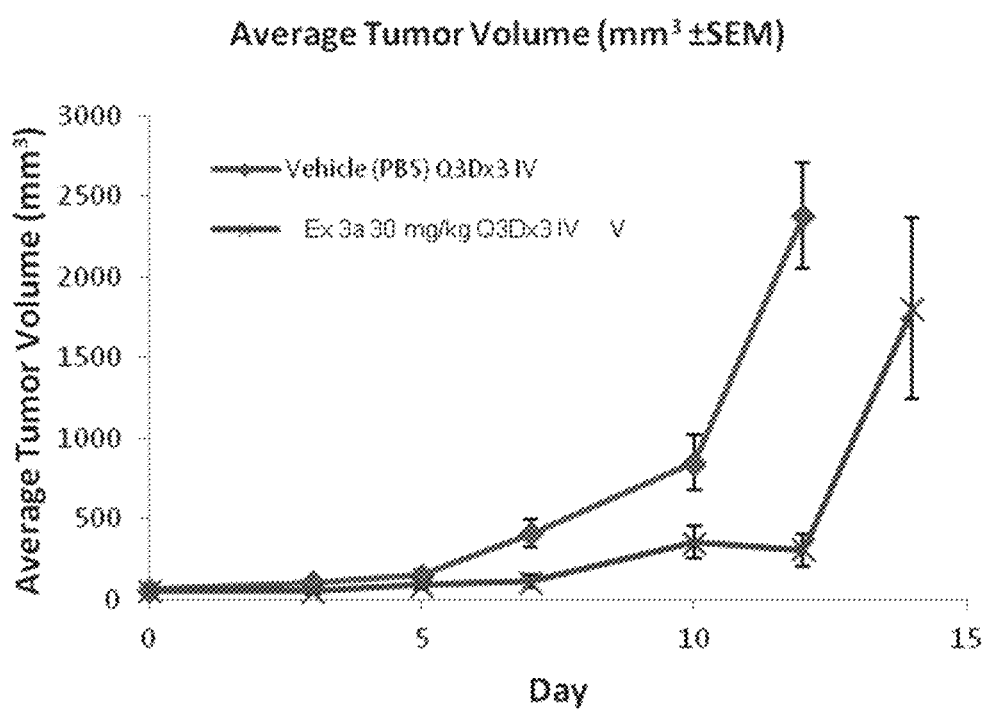
FIG. 10 is line graph showing the anti-tumor activity of compound Ex. 3a in the colon carcinoma B16F10 syngeneic mice model.
Figure 11:
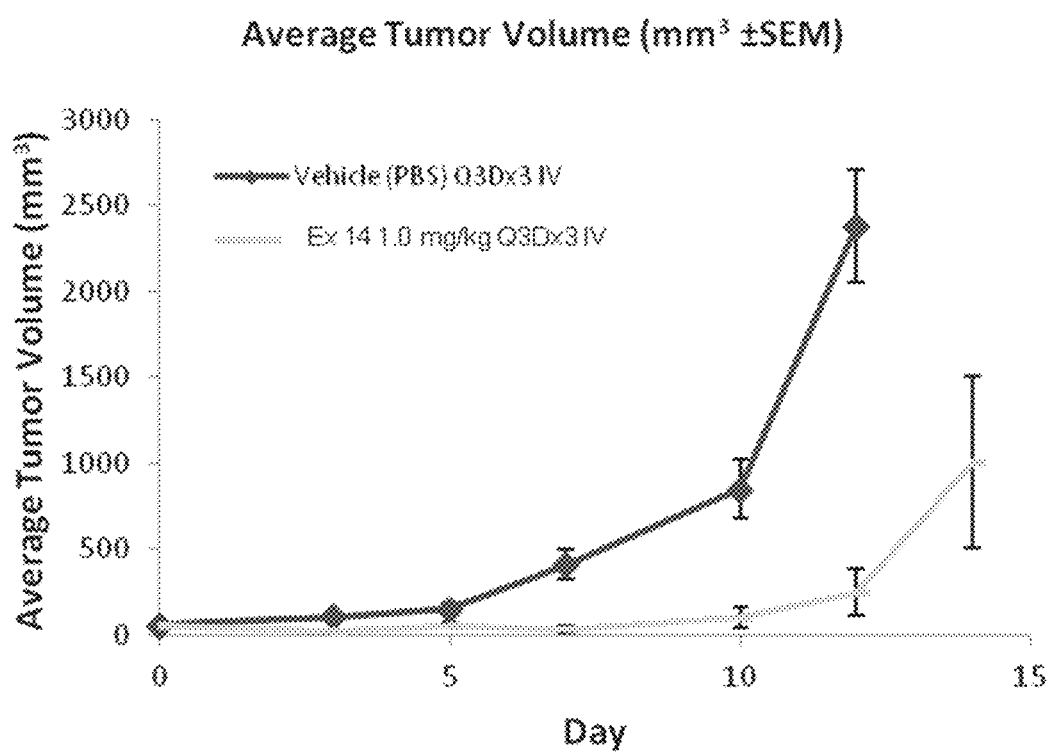
FIG. 11 is line graph showing the anti-tumor activity of compound Ex. 14 in the colon carcinoma B16F10 syngeneic mice model.

Ex14 and Ex3a were tested in syngeneic tumor models in mice. When Ex14 and Ex3a were administered intravenously (every 3 days, 3 times), anti-tumor effects were observed. See FIG. 8 and FIG. 9 for the anti-tumor effect colon carcinoma CT-26 syngeneic mice model, and FIG. 10 and FIG. 11 for the anti-tumor effect in the colon carcinoma B16F10 syngeneic mice model.

The Protocol for the Anti-Tumor Effect Evaluation $8 \times 10^4$ B16F10 and $2 \times 10^5$ CT-26 mouse tumor cells were subcutaneously implanted in the flank of female C57BL/6 (B16F10) and Balb/C (CT-26) mice (n=7 per group). Vehicle (1×PBS), compound Ex3a (30 mg/kg) or Ex14 (1.0 mg/kg) were intravenously administered (final volume of 100 µL) to tumor-bearing mice once the tumor volume has reached 100 mm$^3$ (Day 0). Vehicle, Ex3a or Ex14 were given every 3 days for a total of 3 doses (q3dx3). Tumor and body weight measurements were taken three times per week using vernier calipers and mettler scale, respectively. Tumor volumes were determined by multiplying the square of the width ('W'), measured along the short axis of the tumor, by one-half the length ('L') measured along the short axis of the tumor (V=W$^2$×0.5L)

The compounds of the Examples are shown in the following tables. MS in the tables means actual measured value. The compound example 9 was synthesized in the same manner as in the method of Example 5.

TABLE 1-1

| Ex. No. | IUPAC NAME | Structure | Additive | MS |
|---|---|---|---|---|
| 1 | 7-((5R,7R,8R,12aR,14R,15R,15aR,16R)-14-(6-amino-9H-purin-9-yl)-15-fluoro-2,10,16-trihydroxy-2,10-dioxidooctahydro-12H-5,8-methanofuro[3,2-l][1,3,6,9,11,2,10]pentaoxadiphosphacyclotetradecin-7-yl)-5-fluoro-3,7-dihydro-4H-pyrrolo[2,3-d]pyrimidin-4-one | 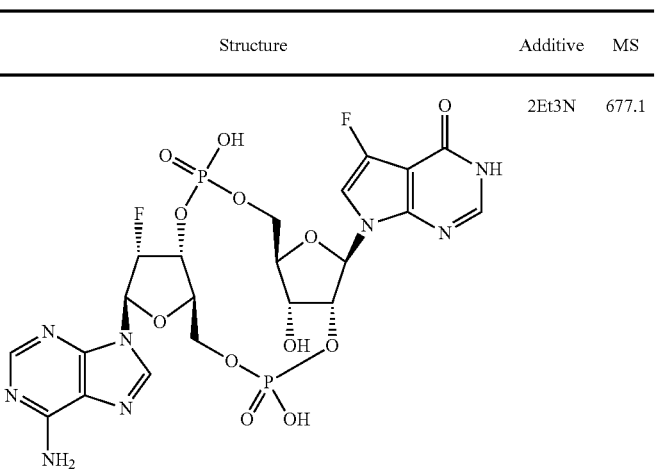 | 2Et3N | 677.1 |

TABLE 1-1-continued

| Ex. No. | IUPAC NAME | Structure | Additive | MS |
|---|---|---|---|---|
| 1a | 7-((5R,7R,8R,12aR,14R,15R,15aR,16R)-14-(6-amino-9H-purin-9-yl)-15-fluoro-2,10,16-trihydroxy-2,10-dioxidooctahydro-12H-5,8-methanofuro[3,2-l][1,3,6,9,11,2,10]pentaoxadiphosphacyclotetradecin-7-yl)-5-fluoro-3,7-dihydro-4H-pyrrolo[2,3-d]pyrimidin-4-one | 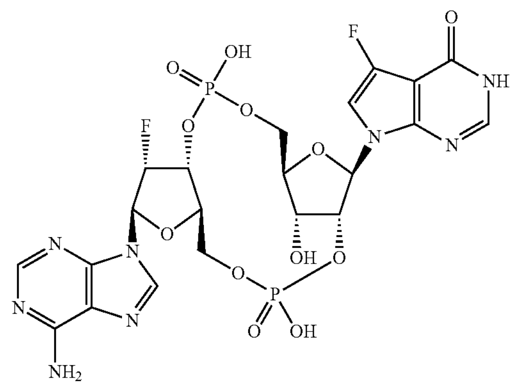 [SMILES: Nc1ncnc2c1ncn2[C@@H]1O[C@@H]2COP(=O)(O)O[C@@H]3[C@H](O)[C@@H](COP(=O)(O)O[C@H]2[C@H]1F)O[C@H]3n1cc(F)c2c(=O)[nH]cnc21] | 2Na | 678.9 |
| 2 | 7-((5R,7R,8R,12aR,14R,15R,15aR,16R)-14-(6-amino-9H-purin-9-yl)-15-fluoro-10,16-dihydroxy-2,10-dioxido-2-sulfanyloctahydro-12H-5,8-methanofuro[3,2-l][1,3,6,9,11,2,10]pentaoxadiphosphacyclotetradecin-7-yl)-5-fluoro-3,7-dihydro-4H-pyrrolo[2,3-d]pyrimidin-4-one (optical isomer) | 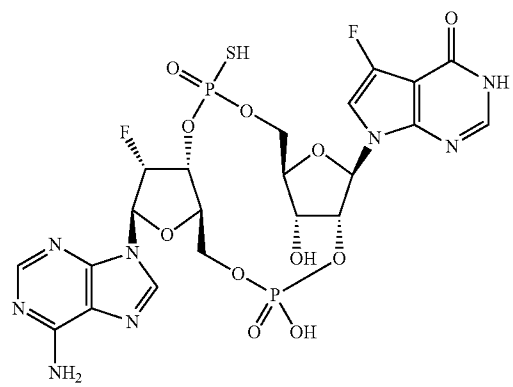 | 2Et3N | 695.0 |
| 3 | 7-((2R,5R,7R,8R,12aR,14R,15R,15aR,16R)-14-(6-amino-9H-purin-9-yl)-15-fluoro-10,16-dihydroxy-2,10-dioxido-2-sulfanyloctahydro-12H-5,8-methanofuro[3,2-l][1,3,6,9,11,2,10]pentaoxadiphosphacyclotetradecin-7-yl)-5-fluoro-3,7-dihydro-4H-pyrrolo[2,3-d]pyrimidin-4-one | 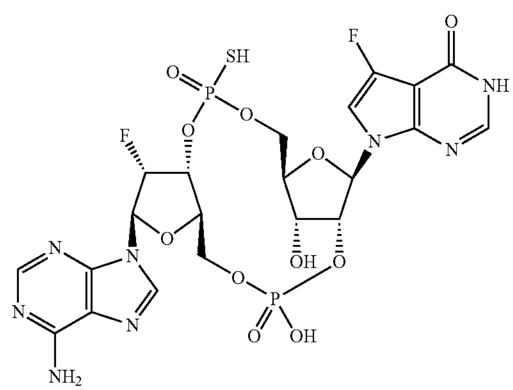 | 1.7Et3N | 693.1 |
| 3a | 7-((2R,5R,7R,8R,12aR,14R,15R,15aR,16R)-14-(6-amino-9H-purin-9-yl)-15-fluoro-10,16-dihydroxy-2,10-dioxido-2-sulfanyloctahydro-12H-5,8-methanofuro[3,2-l][1,3,6,9,11,2,10]pentaoxadiphosphacyclotetradecin-7-yl)-5-fluoro-3,7-dihydro-4H-pyrrolo[2,3-d]pyrimidin-4-one | 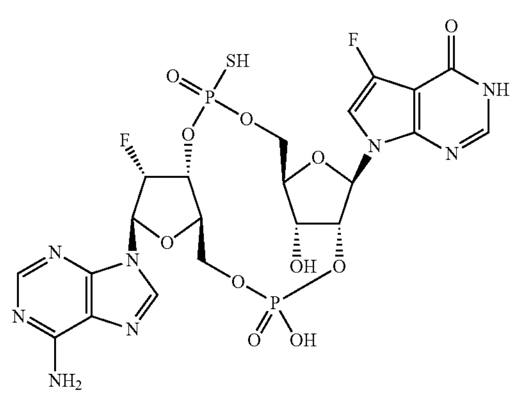 | 2Na | 695.0 |

TABLE 1-1-continued

| Ex. No. | IUPAC NAME | Structure | Additive | MS |
|---|---|---|---|---|
| 4 | 7-((5R,7R,8R,12aR,14R,15R,15aS,16R)-14-(6-amino-9H-purin-9-yl)-2,10,15,16-tetrahydroxy-2,10-dioxidooctahydro-12H-5,8-methanofuro[3,2-l][1,3,6,9,11,2,10]pentaoxadiphosphacyclotetradecin-7-yl)-5-fluoro-3,7-dihydro-4H-pyrrolo[2,3-d]pyrimidin-4-one | 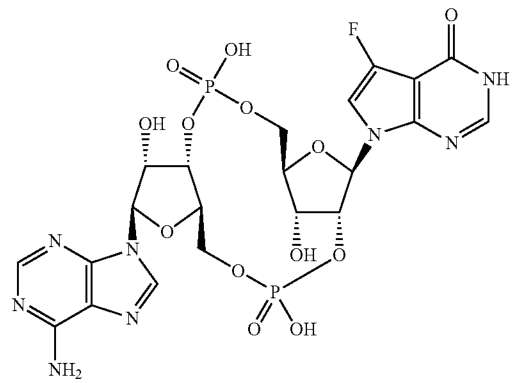 | 2Et3N | 677.1 |
| 5 | 7-((5R,7R,8R,12aR,14R,15R,15aS,16R)-14-(6-amino-9H-purin-9-yl)-15,16-dihydroxy-2,10-dioxido-2,10-disulfanyloctahydro-12H-5,8-methanofuro[3,2-l][1,3,6,9,11,2,10]pentaoxadiphosphacyclotetradecin-7-yl)-5-fluoro-3,7-dihydro-4H-pyrrolo[2,3-d]pyrimidin-4-one (optical isomer) | 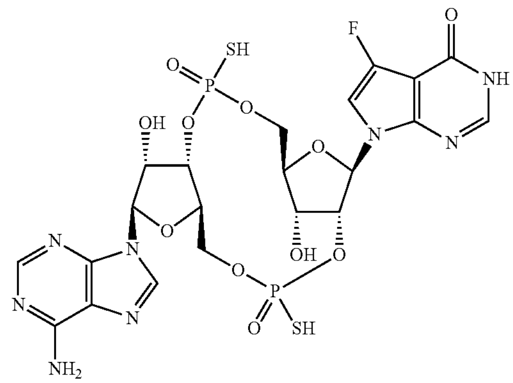 [SMILES: Nc1ncnc2c1ncn2[C@@H]1O[C@@H]2COP(=O)(S)O[C@@H]3[C@H](O)[C@@H](COP(=O)(S)O[C@H]2[C@H]1O)O[C@H]3n1cc(F)c2c(=O)[nH]cnc21] | 2Et3N | 707.1 |

TABLE 1-2

| Ex. No. | IUPAC NAME | Structure | Additive | MS |
|---|---|---|---|---|
| 6 | 7-((5R,7R,8R,12aR,14R,15R,15aS,16R)-7-(6-amino-9H-purin-9-yl)-15,16-dihydroxy-2,10-dioxido-2,10-disulfanyloctahydro-12H-5,8-methanofuro[3,2-l][1,3,6,9,11,2,10]pentaoxadiphosphacyclotetradecin-14-yl)-5-fluoro-3,7-dihydro-4H-pyrrolo[2,3-d]pyrimidin-4-one (optical isomer) | 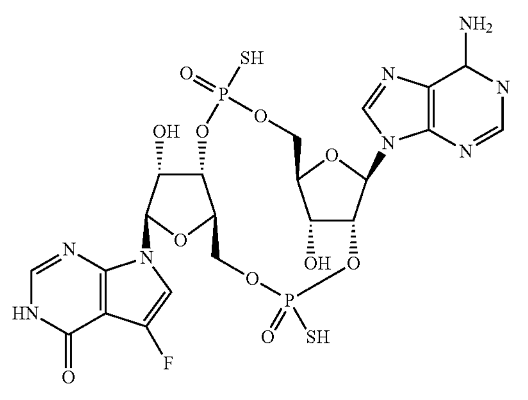 [SMILES: NC1NC=Nc2c1ncn2[C@@H]1O[C@@H]2COP(=O)(S)O[C@H]3[C@@H](O)[C@H](n4cc(F)c5c(=O)[nH]cnc54)O[C@@H]3COP(=O)(S)O[C@@H]1[C@@H]2O] | 2Et3N | 707.1 |

TABLE 1-2-continued

| Ex. No. | IUPAC NAME | Structure | Additive | MS |
|---|---|---|---|---|
| 7 | 7-((5R,7R,8R,12aR,14R,15R,15aS,16R)-7-(6-amino-9H-purin-9-yl)-15,16-dihydroxy-2,10-dioxido-2,10-disulfanyloctahydro-12H-5,8-methanofuro[3,2-l][1,3,6,9,11,2,10]pentaoxadiphosphacyclotetradecin-14-yl)-5-fluoro-3,7-dihydro-4H-pyrrolo[2,3-d]pyrimidin-4-one (optical isomer) | 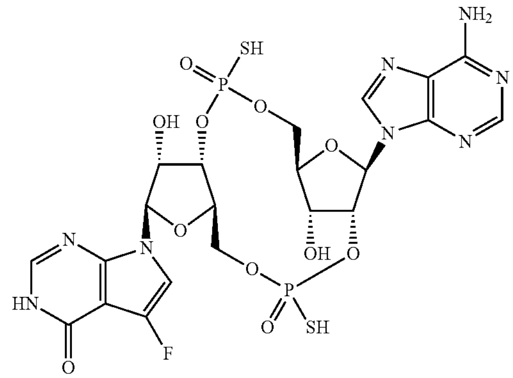 [SMILES: Nc1ncnc2c1ncn2[C@@H]1O[C@@H]2COP(=O)(S)O[C@H]3[C@@H](O)[C@H](n4cc(F)c5c(=O)[nH]cnc54)O[C@@H]3COP(=O)(S)O[C@@H]1[C@@H]2O] | 2Et3N | 709.0 |
| 8 | 2-amino-9-((5R,7R,8R,12aR,14R,15R,15aS,16R)-14-(4-amino-5-fluoro-7H-pyrrolo[2,3-d]pyrimidin-7-yl)-2,10,15,16-tetrahydroxy-2,10-dioxidooctahydro-12H-5,8-methanofuro[3,2-l][1,3,6,9,11,2,10]pentaoxadiphosphacyclotetradecin-7-yl)-1,9-dihydro-6H-purin-6-one | 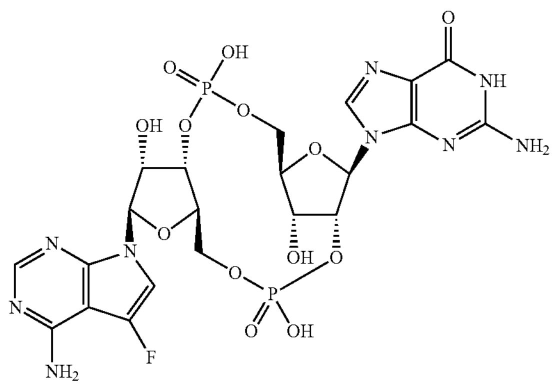 [SMILES: Nc1nc2c(ncn2[C@@H]2O[C@@H]3COP(=O)(O)O[C@H]4[C@@H](O)[C@H](n5cc(F)c6c(N)ncnc65)O[C@@H]4COP(=O)(O)O[C@@H]2[C@@H]3O)c(=O)[nH]1] | 2Et3N | 692.2 |
| 9 | 9-((5R,7R,8R,12aR,14R,15R,15aS,16R)-7-(4-amino-5-fluoro-7H-pyrrolo[2,3-d]pyrimidine-7-yl)-15,16-dihydroxy-2,10-dioxide-2,10-disulfanyloctahydro-12H-5,8-methanofuro[3,2-l][1,3,6,9,11,2,10]pentaoxadiphosphacyclotetradecin-14-yl)-1,9-dihydro-6H-purine-6-one | 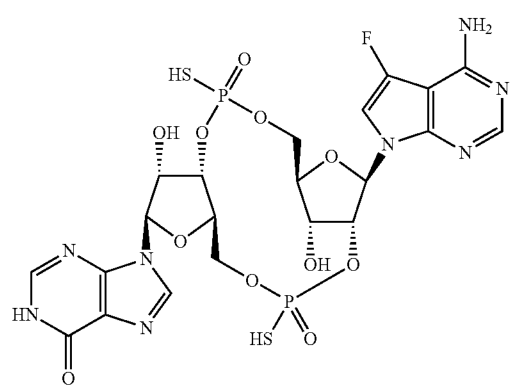 [SMILES: Nc1ncnc2c1c(F)cn2[C@@H]1O[C@@H]2COP(=O)(S)O[C@H]3[C@@H](O)[C@H](n4cnc5c(=O)[nH]cnc54)O[C@@H]3COP(=O)(S)O[C@@H]1[C@@H]2O] | 2Et3N | 707.1 |
| 10 | 1-((5R,7R,8R,12aR,14R,15R,15aS,16R)-14-(6-amino-9H-purin-9-yl)-2,10,15,16-tetrahydroxy-2,10-dioxidooctahydro-12H-5,8-methanofuro[3,2-l][1,3,6,9,11,2,10]pentaoxadiphosphacyclotetradecin-7-yl)-1,5-dihydro-4H-imidazo[4,5-c]pyridin-4-one | 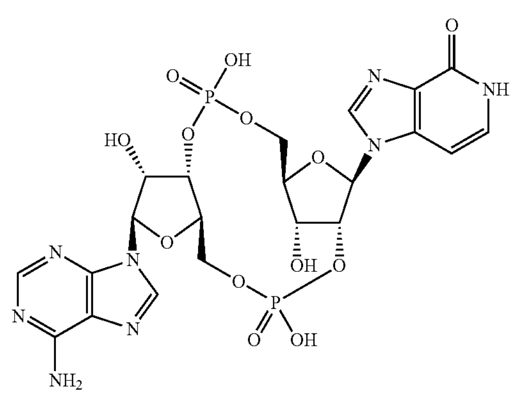 [SMILES: Nc1ncnc2c1ncn2[C@@H]1O[C@@H]2COP(=O)(O)O[C@@H]3[C@H](O)[C@@H](COP(=O)(O)O[C@H]2[C@H]1O)O[C@H]3n1cnc2c(=O)[nH]ccc21] | | 659.1 |

TABLE 1-3

| Ex. No. | IUPAC NAME | Structure | Additive | MS |
|---|---|---|---|---|
| 11 | 2-amino-9-((5R,7R,8R,12aR,14R,15R,15aS,16R)-14-(4-amino-1H-imidazo[4,5-c]pyridin-1-yl)-2,10,15,16-tetrahydroxy-2,10-dioxidooctahydro-12H-5,8-methanofuro[3,2-l][1,3,6,9,11,2,10]pentaoxadiphosphacyclotetradecin-7-yl)-1,9-dihydro-6H-purin-6-one | 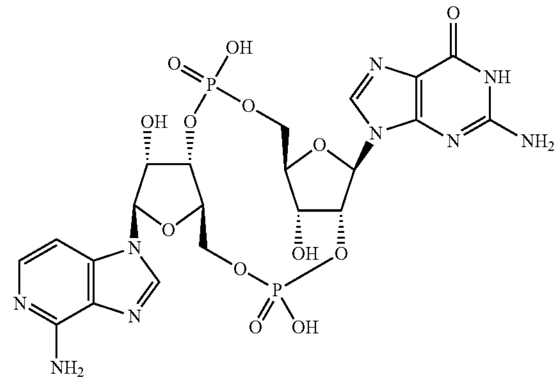 [SMILES: Nc1nc2c(ncn2[C@@H]2O[C@@H]3COP(=O)(O)O[C@H]4[C@@H](O)[C@H](n5cnc6c(N)nccc65)O[C@@H]4COP(=O)(O)O[C@@H]2[C@@H]3O)c(=O)[nH]1] | 2Et3N | 674.2 |
| 12 | 8-((5R,7R,8R,12aR,14S,15S,15aS,16R)-7-(6-amino-9H-purin-9-yl)-15,16-dihydroxy-2,10-dioxido-2,10-disulfanyloctahydro-12H-5,8-methanofuro[3,2-l][1,3,6,9,11,2,10]pentaoxadiphosphacyclotetradecin-14-yl)pyrazolo[1,5-a][1,3,5]triazin-4(3H)-one (optical isomer) | 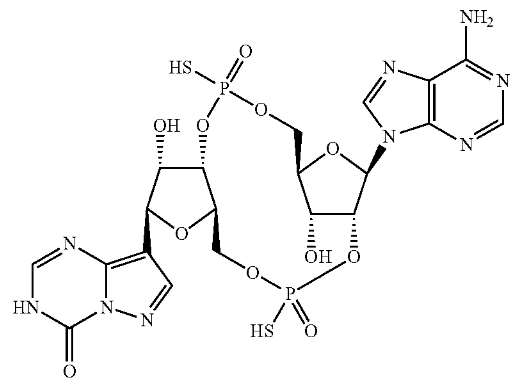 [SMILES: Nc1ncnc2c1ncn2[C@@H]1O[C@@H]2COP(=O)(S)O[C@H]3[C@@H](O)[C@H](c4cnn5c(=O)[nH]cnc45)O[C@@H]3COP(=O)(S)O[C@@H]1[C@@H]2O] | 2Et3N | 692.2 |
| 13 | 2-amino-9-((5R,7R,8R,12aR,14S,15S,15aS,16R)-14-(4-aminopyrazolo[1,5-a][1,3,5]triazin-8-yl)-2,10,15,16-tetrahydroxy-2,10-dioxidooctahydro-12H-5,8-methanofuro[3,2-l][1,3,6,9,11,2,10]pentaoxadiphosphacyclotetradecin-7-yl)-1,9-dihydro-6H-purin-6-one | 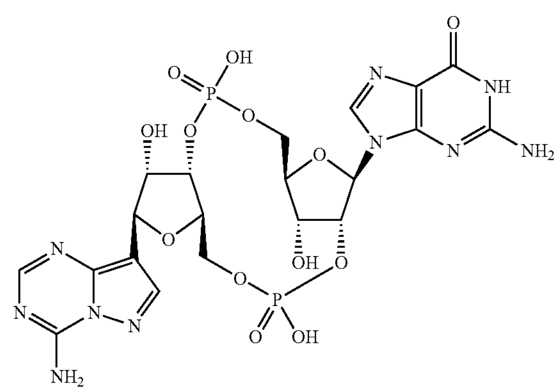 [SMILES: Nc1nc2c(ncn2[C@@H]2O[C@@H]3COP(=O)(O)O[C@H]4[C@@H](O)[C@H](c5cnn6c(N)ncnc56)O[C@@H]4COP(=O)(O)O[C@@H]2[C@@H]3O)c(=O)[nH]1] | 2Et3N | 675.1 |
| 14 | 7-((2R,5R,7R,8R,12aR,14R,15R,15aR,16R)-14-(6-amino-9H-purin-9-yl)-15-fluoro-16-hydroxy-2,10-dioxido-2,10-disulfanyloctahydro-12H-5,8-methanofuro[3,2-l][1,3,6,9,11,2,10]pentaoxadiphosphacyclotetradecin-7-yl)-5-fluoro-3,7-dihydro-4H-pyrrolo[2,3-d]pyrimidin-4-one | 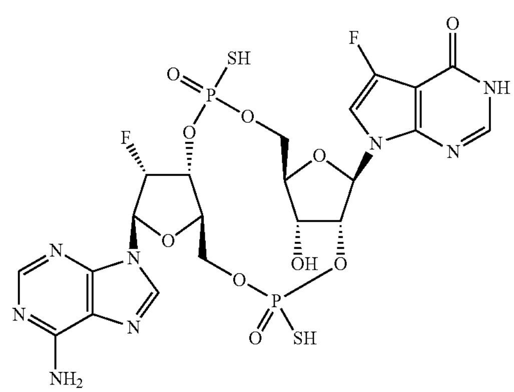 [SMILES: Nc1ncnc2c1ncn2[C@@H]1O[C@@H]2COP(=O)(S)O[C@@H]3[C@H](O)[C@@H](COP(=O)(S)O[C@H]2[C@H]1F)O[C@H]3n1cc(F)c2c(=O)[nH]cnc21] | 2Na | 711.0 |

TABLE 1-3-continued

| Ex. No. | IUPAC NAME | Structure | Additive | MS |
|---|---|---|---|---|
| 15 | 7-((5R,7R,8R,12aR,14R,15R,15aR,16R)-14-(6-amino-9H-purin-9-yl)-15-fluoro-2,16-dihydroxy-2,10-dioxido-10-sulfanyloctahydro-12H-5,8-methanofuro[3,2-l][1,3,6,9,11,2,10]pentaoxadiphosphacyclotetradecin-7-yl)-5-fluoro-3,7-dihydro-4H-pyrrolo[2,3-d]pyrimidin-4-one (optical isomer) | 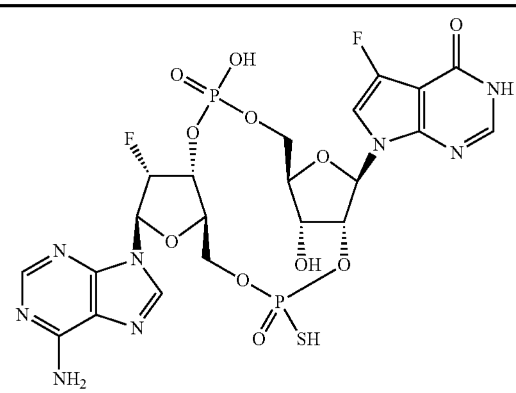 | 2Et3N | 695.0 |

TABLE 1-4

| Ex. No. | IUPAC NAME | Structure | Additive | MS |
|---|---|---|---|---|
| 16 | 7-((5R,7R,8R,12aR,14R,15R,15aS,18R)-14-(6-amino-9H-purin-9-yl)-2,10,18-trihydroxy-2,10-dioxidohexahydro-14H-15,12a-(epoxymethano)-5,8-methanofuro[3,2-l][1,3,6,9,11,2,10]pentaoxadiphosphacyclotetradecin-7(12H)-yl)-5-fluoro-3,7-dihydro-4H-pyrrolo[2,3-d]pyrimidin-4-one (optical isomer) | 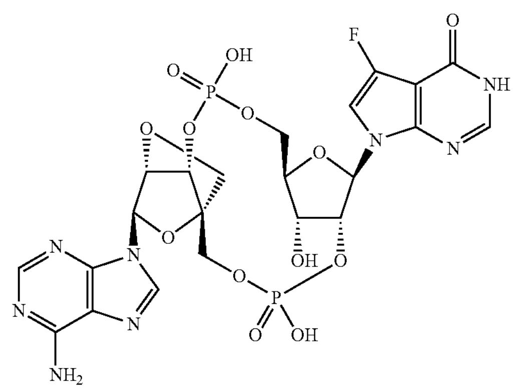 [SMILES: Nc1ncnc2c1ncn2[C@@H]1O[C@@]23CO[C@@H]1[C@@H]2OP(=O)(O)OC[C@H]1O[C@@H](n2cc(F)c4c(=O)[nH]cnc42)[C@H](OP(=O)(O)OC3)[C@@H]1O] | 2Et3N | 687.0 |
| 17 | 7-((5R,7R,8R,12aR,14R,15R,15aS,18R)-14-(6-amino-9H-purin-9-yl)-10,18-dihydroxy-2,10-dioxido-2-sulfanylhexahydro-14H-15,12a-(epoxymethano)-5,8-methanofuro[3,2-l][1,3,6,9,11,2,10]pentaoxadiphosphacyclotetradecin-7(12H)-yl)-5-fluoro-3,7-dihydro-4H-pyrrolo[2,3-d]pyrimidin-4-one (optical isomer) | 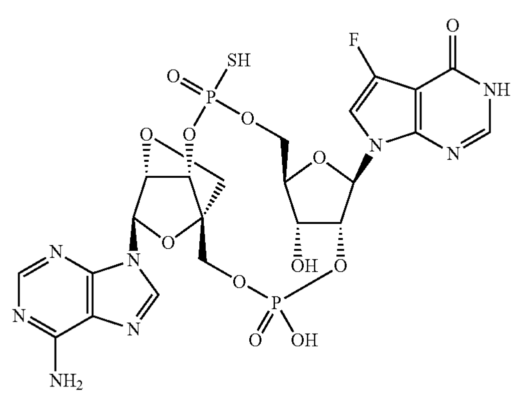 | 2Et3N | 702.9 |

TABLE 1-4-continued

| Ex. No. | IUPAC NAME | Structure | Additive | MS |
|---|---|---|---|---|
| 18 | 7-((5R,7R,8R,12aR,14R,15R,15aS,18R)-14-(6-amino-9H-purin-9-yl)-2,18-dihydroxy-2,10-dioxido-10-sulfanylhexahydro-14H-15,12a-(epoxymethano)-5,8-methanofuro[3,2-l][1,3,6,9,11,2,10]pentaoxadiphosphacyclotetradecin-7(12H)-yl)-5-fluoro-3,7-dihydro-4H-pyrrolo[2,3-d]pyrimidin-4-one (optical isomer) | 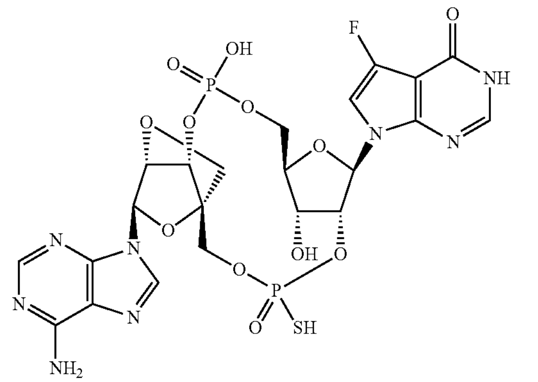 [SMILES: Nc1ncnc2c1ncn2[C@@H]1O[C@@]23CO[C@@H]1[C@@H]2OP(=O)(O)OC[C@H]1O[C@@H](n2cc(F)c4c(=O)[nH]cnc42)[C@H](OP(=O)(S)OC3)[C@@H]1O] | 2Et3N | 702.9 |
| 19 | 2-amino-9-((5R,7R,8R,12aR,14R,15R,15aR,16R)-15-fluoro-7-(5-fluoro-4-oxo-3,4-dihydro-7H-pyrrolo[2,3-d]pyrimidin-7-yl)-2,10,16-trihydroxy-2,10-dioxidooctahydro-12H-5,8-methanofuro[3,2-l][1,3,6,9,11,2,10]pentaoxadiphosphacyclotetradecin-14-yl)-1,9-dihydro-6H-purin-6-one (optical isomer) | 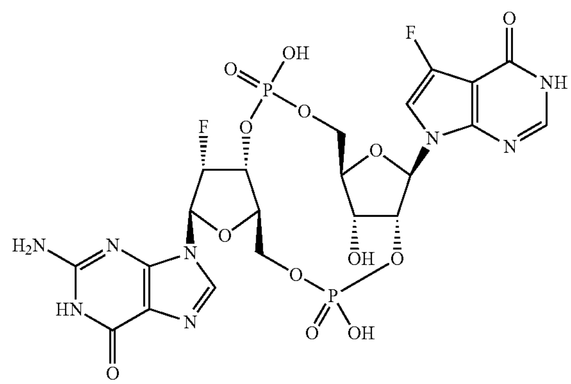 [SMILES: Nc1nc2c(ncn2[C@@H]2O[C@@H]3COP(=O)(O)O[C@@H]4[C@H](O)[C@@H](COP(=O)(O)O[C@H]3[C@H]2F)O[C@H]4n2cc(F)c3c(=O)[nH]cnc32)c(=O)[nH]1] | 2Et3N | 692.9 |
| 20 | 7-((5R,7R,8R,12aR,14R,15R,15aS,16R)-14-(6-amino-9H-purin-9-yl)-2,10,15,16-tetrahydroxy-2-oxido-10-sulfanyloctahydro-12H-5,8-methanofuro[3,2-l][1,3,6,9,11,2,10]pentaoxadiphosphacyclotetradecin-7-yl)-5-fluoro-3,7-dihydro-4H-pyrrolo[2,3-d]pyrimidin-4-one (optical isomer) | 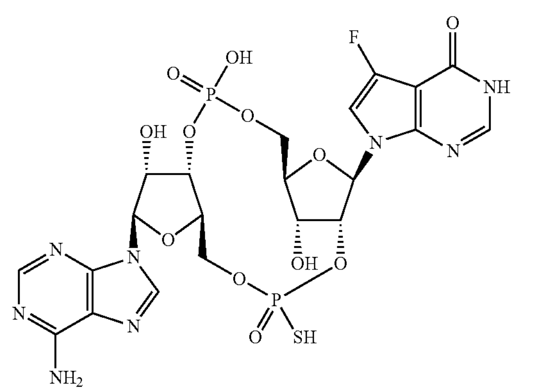 [SMILES: Nc1ncnc2c1ncn2[C@@H]1O[C@@H]2COP(=O)(S)O[C@@H]3[C@H](O)[C@@H](COP(=O)(O)O[C@H]2[C@H]1O)O[C@H]3n1cc(F)c2c(=O)[nH]cnc21] | 2Et3N | 693.3 |

TABLE 1-5

| Ex. No. | IUPAC Name | Structure | Additive | MS |
|---|---|---|---|---|
| 23 (optical isomer 1) | 7-[(5R,7R,8R,12aR,14R,15R,15aS,16R)-14-(6-amino-9H-purin-9-yl)-10,15,16-trihydroxy-2,10-dioxido-2-sulfanyloctahydro-12H-5,8-methanofuro[3,2-l][1,3,6,9,11,2,10]pentaoxadiphosphacyclotetradecin-7-yl]-5-fluoro-3-methyl-3,7-dihydro-4H-pyrrolo[2,3-d]pyrimidin-4-one di-triethylamine salt | 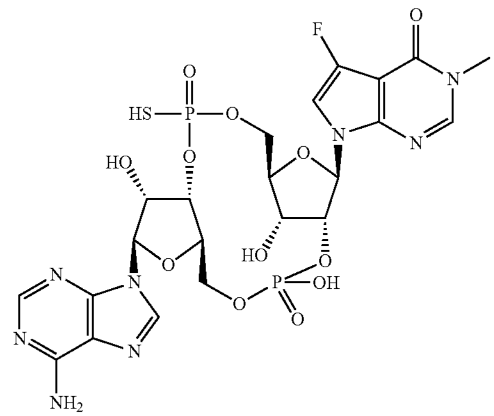 [SMILES: Cn1cnc2c(c(F)cn2[C@@H]2O[C@@H]3COP(=O)(S)O[C@H]4[C@@H](O)[C@H](n5cnc6c(N)ncnc65)O[C@@H]4COP(=O)(O)O[C@@H]2[C@@H]3O)c1=O] | 2 Et$_3$N | 707.1 |
| 23 (optical isomer 2) | 7-[(5R,7R,8R,12aR,14R,15R,15aS,16R)-14-(6-amino-9H-purin-9-yl)-10,15,16-trihydroxy-2,10-dioxido-2-sulfanyloctahydro-12H-5,8-methanofuro[3,2-l][1,3,6,9,11,2,10]pentaoxadiphosphacyclotetradecin-7-yl]-5-fluoro-3-methyl-3,7-dihydro-4H-pyrrolo[2,3-d]pyrimidin-4-one di-triethylamine salt | 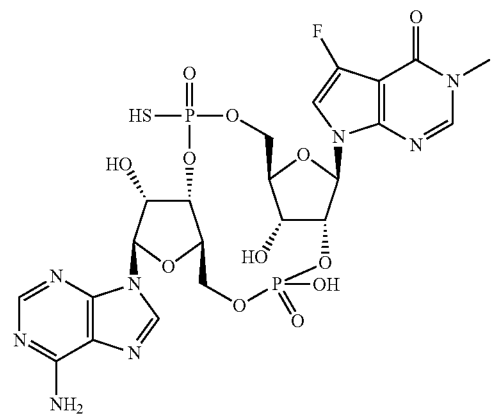 [SMILES: Cn1cnc2c(c(F)cn2[C@@H]2O[C@@H]3COP(=O)(S)O[C@H]4[C@@H](O)[C@H](n5cnc6c(N)ncnc65)O[C@@H]4COP(=O)(O)O[C@@H]2[C@@H]3O)c1=O] | 2 Et$_3$N | 707.1 |
| 24 (optical isomer 1) | 7-[(5R,7R,8R,12aR,14R,15R,15aR,16R)-14-(6-amino-9H-purin-9-yl)-15-fluoro-10,16-dihydroxy-2,10-dioxido-2-sulfanyloctahydro-12H-5,8-methanofuro[3,2-l][1,3,6,9,11,2,10]pentaoxadiphosphacyclotetradecin-7-yl]-5-fluoro-3-methyl-3,7-dihydro-4H-pyrrolo[2,3-d]pyrimidin-4-one di-triethylamine salt | 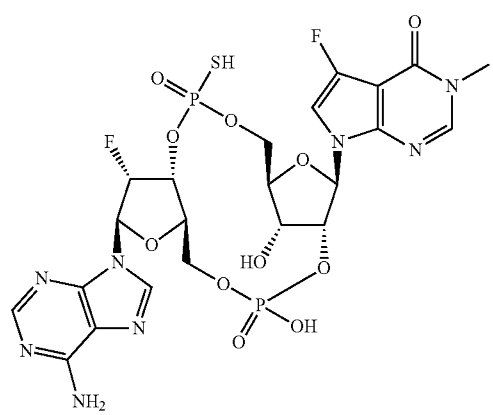 [SMILES: Cn1cnc2c(c(F)cn2[C@@H]2O[C@@H]3COP(=O)(S)O[C@H]4[C@@H](F)[C@H](n5cnc6c(N)ncnc65)O[C@@H]4COP(=O)(O)O[C@@H]2[C@@H]3O)c1=O] | 2 Et$_3$N | 709.2 |

TABLE 1-5-continued

| Ex. No. | IUPAC Name | Structure | Additive | MS |
|---|---|---|---|---|
| 24 (optical isomer 2) | 7-[(5R,7R,8R,12aR,14R,15R,15aR,16R)-14-(6-amino-9H-purin-9-yl)-15-fluoro-10,16-dihydroxy-2,10-dioxido-2-sulfanyloctahydro-12H-5,8-methanofuro[3,2-l][1,3,6,9,11,2,10]pentaoxadiphosphacyclotetradecin-7-yl]-5-fluoro-3-methyl-3,7-dihydro-4H-pyrrolo[2,3-d]pyrimidin-4-one di-triethylamine salt | 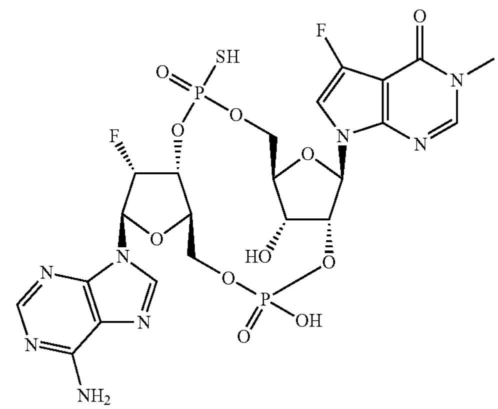 [SMILES: Cn1cnc2c(c(F)cn2[C@@H]2O[C@@H]3COP(=O)(S)O[C@H]4[C@@H](F)[C@H](n5cnc6c(N)ncnc65)O[C@@H]4COP(=O)(O)O[C@@H]2[C@@H]3O)c1=O] | 2 Et$_3$N | 709.3 |
| 25 | 7-[(5R,7R,8R,12aR,14R,15R,15aR,16R)-14-(6-amino-9H-purin-9-yl)-15-fluoro-2,10,16-trihydroxy-2,10-dioxidooctahydro-12H-5,8-methanofuro[3,2-l][1,3,6,9,11,2,10]pentaoxadiphosphacyclotetradecin-7-yl]-5-fluoro-3-methyl-3,7-dihydro-4H-pyrrolo[2,3-d]pyrimidin-4-one di-triethylamine salt | 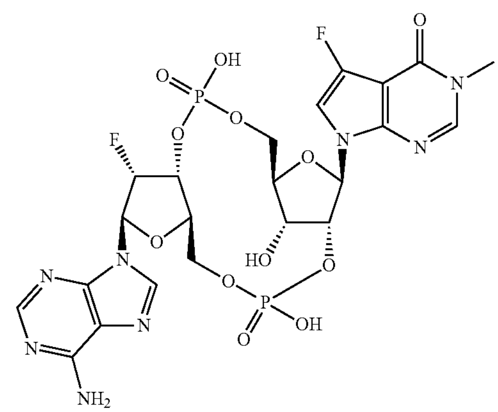 | 2 Et$_3$N | 693.2 |
| 26 (optical isomer 1) | 7-[(5R,7R,8R,12aR,14R,15R,15aR,16R)-14-(6-amino-9H-purin-9-yl)-15-fluoro-16-hydroxy-2,10-dioxido-2,10-disulfanyloctahydro-12H-5,8-methanofuro[3,2-l][1,3,6,9,11,2,10]pentaoxadiphosphacyclotetradecin-7-yl]-5-chloro-3,7-dihydro-4H-pyrrolo[2,3-d]pyrimidin-4-one di-triethylamine salt | 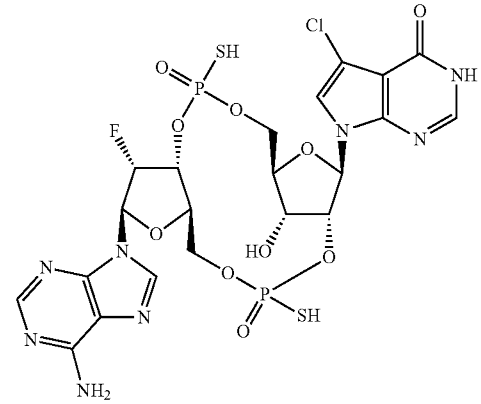 [SMILES: Nc1ncnc2c1ncn2[C@@H]1O[C@@H]2COP(=O)(S)O[C@@H]3[C@H](O)[C@@H](COP(=O)(S)O[C@H]2[C@H]1F)O[C@H]3n1cc(Cl)c2c(=O)[nH]cnc21] | 2 Et$_3$N | 727.0 |

TABLE 1-5-continued

| Ex. No. | IUPAC Name | Structure | Additive | MS |
|---|---|---|---|---|
| 26 (optical isomer 2) | 7-[(5R,7R,8R,12aR,14R,15R,15aR,16R)-14-(6-amino-9H-purin-9-yl)-15-fluoro-16-hydroxy-2,10-dioxido-2,10-disulfanyloctahydro-12H-5,8-methanofuro[3,2-l][1,3,6,9,11,2,10]pentaoxadiphosphacyclotetradecin-7-yl]-5-chloro-3,7-dihydro-4H-pyrrolo[2,3-d]pyrimidin-4-one di-triethylamine salt | 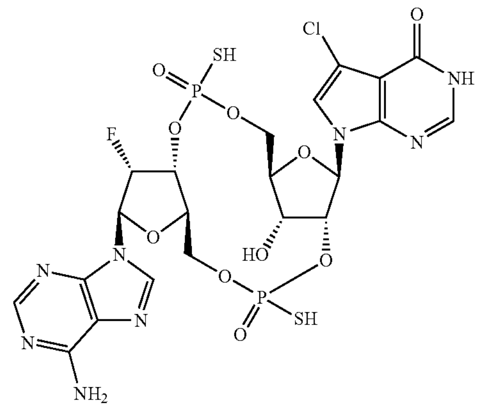 [SMILES: Nc1ncnc2c1ncn2[C@@H]1O[C@@H]2COP(=O)(S)O[C@@H]3[C@H](O)[C@@H](COP(=O)(S)O[C@H]2[C@H]1F)O[C@H]3n1cc(Cl)c2c(=O)[nH]cnc21] | 2 Et$_3$N | 727.0 |

Example 35

STING-Binding Test

Test compound (2 μL), Streptavidin-Terbium (4 μL, Cisbio), Fluorescein-labeled 2',3'-cGAMP (c[G(2',5')p-2'-Fluo-AHC-A(3',5')p]) (Biolog, Germany) and biotinylated STING protein (2 μL, wild-type, WT) were mixed using assay buffer (Dulbecco's Phosphate-Buffered Saline (Wako Pure Chemical Industries, Ltd.) containing 0.01% bovine serum albumin free of fatty acid (Wako Pure Chemical Industries, Ltd.)), and the mixture was left to stand at room temperature for 3 hr (The final concentration. Streptavidin-Terbium; diluted by 1/1000, FITC-cGAMP; 1 μM, biotinylated STING protein; 100 nM). The time-resolved fluorescence resonance energy transfer (TR-FRET) was measured at the wavelength of 520 nm and 486 nm by EnVision (PerkinElmer, Waltham, MA, US). The inhibition rate of the binding of wild-type STING protein and 2',3'-cGAMP of the test compound was calculated using the ratio of the count at 520 nm divided by the count at 486 nm. The results are shown in Tables 2 and 2A.

The above-mentioned biotinylated STING protein (wild-type (WT)) was prepared by the following method.

Preparation Method of Biotinylated Wild-Type STING Protein

ECOS (trade name) Competent E. coli BL21(DE3) was purchased from Nippon Gene Co., Ltd. Ampicillin, kanamycin, NaCl, glycerol, isopropylthiogalactoside, (+)-biotin, imidazole, SEM nuclease recombinant and BCA protein assay kit were purchased from Wako Pure Chemical Industries, Ltd. Tryptone, Bacto, and Yeast Extract, Bacto were purchased from Difco Laboratories, tris buffered saline (TBS) tablets, pH7.6 was purchased from Takara Bio Inc., Lysozyme (Egg White), 6× Cryst was purchased from Seikagaku Corporation, and cOmplet (trade name) and EDTA-free protease inhibitor cocktail were purchased from Roche. Ni-NTA Superflow Cartridge manufactured by QIAGEN was used, and HiLoad 26/60 Superdex 200 pg manufactured by GE Healthcare was used.

Into pRSF1b (Novagen) having altered multiple cloning site was inserted Escherichia coli BirA, and transfected to ECOS JM109, whereby pRH8/FLAG-BirA was constructed. pET21HH/His-Avi-SUMO-FLAG-hTMEM173(139-379XH232R) (which was constructed by the method mentioned in the EXAMPLE 36) and pRH8/FLAG-BirA for Avi tag biotinylation were simultaneously transformed to ECO (trade name) Competent E. coli BL21(DE3) to prepare His-Avi-SUMO-FLAG-hSTING (139-379, H232R)-expressing cell line. The expressing cell line was added to LB medium (10 g/L Tryptone, 5 g/L Yeast Extract, 5 g/L NaCl) containing ampicillin (100 μg/L) and kanamycin (50 μg/L), and the mixture was pre-cultured at 30° C., and expanded to TB medium (12 g/L Tryptone, 24 g/L Yeast Extract, 4 mL/L Glycerol, 2.3 g/L KH$_2$PO$_4$, 12.5 g/L K$_2$HPO$_4$) containing the same antibiotics, and the mixture was cultured at 37° C. When the turbidity of the culture solution reached 500 KU, the culture temperature was reduced to 16° C., 0.1 mM isopropylthiogalactoside and 50 μM (+)-biotin were added thereto, and the mixture was cultured for additional 16 hr.

The culture solution was centrifuged, the obtained fungus bodies were suspended in Lysis Buffer (50 mM TrisHCl, 150 mM NaCl, 20 mM Imidazole, 1 mg/mL Lysozyme, 5 U/mL SEM Nuclease, recombinant, Complete EDTA-free, pH7.6), and the protein was extracted by ultrasonic fragmentation. The reagent was added thereto so that the salt concentration of the extract was adjusted to 300 mM NaCl, and the supernatant was collected by centrifugation. The obtained supernatant was passed through NiNTA superflow Cartridge equilibrated with Wash Buffer (50 mM TrisHCl, 300 mM NaCl, 20 mM Imidazole, pH7.6), and the Cartridge was washed with Wash Buffer, and eluted with Elution Buffer (50 mM TrisHCl, 300 mM NaCl, 250 mM Imidazole, pH7.6). The eluate was passed through HiLoad 26/60 Superdex 200 pg column equilibrated with Storage Buffer (50 mM TrisHCl, 150 mM NaCl, pH7.6), and the eluted fraction was collected as biotinylated His-Avi-SUMO-FLAG-hSTING (139-379, H232R). The protein concentration was measured using BCA protein assay kit, and the fraction was cryopreserved at −80° C. until used.

TABLE 2

STING-binding test

| Example No. | binding inhibition rate of test compound (30 μM) |
|---|---|
| 1 | 76% |
| 2 | 79% |
| 3 | 64% |

TABLE 2-continued

STING-binding test

| Example No. | binding inhibition rate of test compound (30 μM) |
|---|---|
| 3a | 93% |
| 5 | 71% |
| 8 | 90% |
| 13 | 68% |
| 14 | 89% |
| 15 | 89% |
| 16 | 91% |
| 17 | 86% |
| 18 | 94% |
| 19 | 93% |
| 20 | 98% |

TABLE 2A

STING-binding test

| Example No. | IC$_{50}$ (μM) |
|---|---|
| 23 (optical isomer 1) | 0.17 |
| 23 (optical isomer 2) | 20 |
| 24 (optical isomer 1) | 0.029 |
| 24 (optical isomer 2) | 0.29 |
| 25 | 0.083 |
| 26 (optical isomer 1) | 0.53 |
| 26 (optical isomer 2) | 0.075 |

As is clear from the above-mentioned results, the compound of the present disclosure inhibits the binding of wild-type STING protein and the natural ligand 2',3'-cGAMP, that is, the compound of the present disclosure binds to wild-type STING protein.

Example 36

Reporter Gene Assay
Preparation of Various Plasmids
(i) Expression Plasmid Construction of Human TMEM173 and the Like Expression plasmid of human STING (in the present specification, sometimes to be referred to as human TMEM 173) in *E. coli* was obtained by overlap extension PCR for introduction of mutation using human TMEM173 cDNA Clone (GeneCopoeia) as a template. First, PCRs were performed using two kinds of Primer (5'-CCTGGCCCCAGCTGAGATCTCTG-3' (C-hTMEM(139aa)-F) (SEQ. ID No. 3) and 5'-GTAAACCCGATCCTTGATGCCAGCACGGTCACCGGTC-3' (hTMEM173 (H232R)-R)) (SEQ. ID No. 4) and two kinds of Primer (5'-CTGCCCCAGCAGACCGGTGACCGTGCTGGCATCAAG-3' (hTMEM173 (H232R)-F) (SEQ. ID No. 5) and 5'-ATAATAGCGGCCGCTCAAGAGAAATCCGTGCGGAGAGG-3' (hTMEM173-st-Not-R) (SEQ. ID No. 6). The PCR was each performed using PrimeStar MAX DNA Polymerase (Takara Bio Inc.) successively (1) at 98° C. for 1 min, (2) 25-times repetitions of at 98° C. for 10 sec and at 72° C. for 10 sec, and (3) at 72° C. for 1 min. Then, the PCR was performed using the obtained segment as a template, and using two kinds of Primer (C-hTMEM(139aa)-F and hTMEM173-st-Not-R). The PCR was performed using PrimeStar GXL DNA Polymerase (Takara Bio Inc.) successively (1) at 98° C. for 1 min, (2) 35-times repetitions of at 98° C. for 10 sec and at 72° C. for 1.5 min, and (3) at 72° C. for 1 min. The obtained segment was cut with Not I (Takara Bio Inc.), inserted into the Stu I/Not I site of vector wherein His-Avi-SUMO Tag was attached to pET21a (Novagen), using Ligation High (Toyobo Co., Ltd), and transfected to ECOS JM109 (Nippon Gene Co., Ltd.), whereby pET21HH/His-Avi-SUMO-hTMEM173(139-379XH232R) was constructed.

Second, the PCR was performed using this plasmid as a template, and using two kinds of Primer (5'-CGACTACAAGGACGACGATGACAAGG-GATCCCTGGCCCCAGCTGAGATCTCTG-3' (C-FLAG-Bam-hTMEM173(139aa)-F) (SEQ. ID No. 7) and hTMEM173-st-Not-R). The PCR was performed using PrimeStar MAX DNA Polymerase successively (1) at 98° C. for 1 min, (2) 25-times repetitions of at 98° C. for 10 sec and at 72° C. for 10 sec, and (3) at 72° C. for 1 min. The obtained segment was cut with Not 1, inserted into the Stu I/Not I site of pET21a to which His-Avi-SUMO Tag was attached, using Ligation High, as mentioned above, and transfected to ECOS JM 109, whereby pET21 HH/His-Avi-SUMO-FLAG-hTMEM 173(139-379)(H232R) was constructed.

Expression plasmid for Reporter Assay was obtained by overlap extension PCR for introduction of mutation using human TMEM 173 cDNA Clone as a template, as mentioned above. First, PCRs were performed using two kinds of Primer (5'-GTACCCATACGATGTTCCAGATTACGCTG-GATCCGCCACCATGCCCCACTCCAGC CTGCATC-3' (HA-Bam-ko-hTMEM173-F) (SEQ. ID No. 8) and hTMEM173(H232R)-R) and two kinds of Primer (hTMEM173(H232R)-F and hTMEM173-st-Not-R). The PCR was each performed using PrimeStar MAX DNA Polymerase successively (1) at 98° C. for 1 min, (2) 25-times repetitions of at 98° C. for 10 sec and at 72° C. for 10 sec, and (3) at 72° C. for 1 min. Then, the PCR was performed using the obtained segment as a template, and using two kinds of Primer (5'-ATAATATCTAGAATTCGCCAC-CATGTACCCATACGATGTTCCAGATTACGC-3' (Xba-Eco-ko-HA-F) (SEQ. ID No. 9) and hTMEM173-st-Not-R). The PCR was performed using PrimeStar GXL DNA Polymerase successively (1) at 98° C. for 1 min, (2) 35-times repetitions of at 98° C. for 10 sec, at 65° C. for 5 sec and at 72° C. for 1.5 min, and (3) at 72° C. for 1 min. The obtained segment was cut with Xba I (Takara Bio Inc.) and Not I, inserted into the Nhe I/Not I site of Zeocin-resistance vector wherein multiple cloning site was inserted into pcDNA3.3 (Invitrogen), using Ligation High, and transfected to ECOS JM109, whereby pcDNA3.3zeo/HA-hTMEM173(H232R) was constructed.

Plasmid expressing human mutated-type TMEM173 (R232H) was constructed by PCR using human TMEM 173 cDNA Clone (GeneCopoeia) as a template, and using two kinds of Primer (5'-TTCCAGATTACGCTGGATCCGC-CACCATGCCCCACTCCAGCCTGCATC-3' (Bam-ko-hTEME173v1-F) (SEQ. ID No. 10) and 5'-CCTCTA-GACTCGAGCGGCCGCTCAAGAGAAATCCGTGC GGAGAGG-3' (hTMEM 173-st-Not-R2) (SEQ. ID No. 11). The PCR was performed using PrimeStar MAX DNA Polymerase (Takara Bio Inc.) successively (1) at 98° C. for 1 min, (2) 30-times repetitions of at 98° C. for 10 sec and at 68° C. for 10 sec, and (3) at 72° C. for 1 min. The obtained segment was inserted into the Bam HI/Not I site of vector wherein HA-Tag was attached to pcDNA3.1(+) (ThermoFischer), using Gibson Assembly (NEB), and transfected to ECOS JM 109 (Nippon Gene Co., Ltd.), whereby pcDNA3.1 HA/HA-hTMEM 173v 1 was constructed.

Plasmid expressing human wild-type TMEM173 (H232R) was constructed by PCR using pcDNA3.3zeo/HA-hTMEM173(H232R) plasmid as a template, and using two kinds of Primer (5'-GGAGACCCAAGCTGGCTAGCGC-CACCATGTACCCATACGATG-3' (Nhe-ko-HA-F) (SEQ. ID No. 12) and 5'-CCTCTAGACTCGAGCGGCCGCT-CAAGAGAAATCCGTGCGGAGAGG-3' (hTMEM 173-st-Not-R2) (SEQ. ID No. 11). The PCR was performed using PrimeStar MAX DNA Polymerase successively (1) at 98° C. for 1 min, (2) 30-times repetitions of at 98° C. for 10 sec and at 72° C. for 35 sec, and (3) at 72° C. for 1 min. The obtained segment was inserted into the Nhe I/Not I site of pcDNA3.1zeo (ThermoFischer) using Gibson Assembly, and transfected to ECOS JM109, whereby pcDNA3.1zeo/HA-hTMEM173(H232R) was constructed.

(ii) Firefly Luciferase Expression Plasmid Construction

Firefly luciferase expression plasmid was constructed by inserting CMV Promoter into Reporter vector. The PCR was performed using pcDNA3.1(+) vector (Invitrogen) as a template, and using two kinds of Primer (5'-ATAATAA-GATCTGTTGACATTGATTATTGACTAGTTAT-TAATAG-3' (CMVPro-BglII-F) (SEQ. ID No. 13) and 5'-ATAATAAAGCTTGAGCTCTGCTTATATA-GACCTCCC-3' (CMVPro-HindIII-R) (SEQ. ID No. 14). The PCR was performed using PrimeStar MAX DNA Polymerase successively (1) at 98° C. for 1 min, (2) 25-times repetitions of at 98° C. for 10 sec and at 68° C. for 3 sec, and (3) at 72° C. for 1 min. The obtained segment was cut with Bgl II and Hind III (Takara Bio Inc.), inserted into the Bgl II/Hind III site of pGL4.17 (Promega Corporation) using Ligation High (Toyobo Co., Ltd), and transfected to ECOS JM109, whereby pGL4.17/CMV Pro was constructed.

Reporter Gene Assay (1)

A stable expressing 293T cell line transfected with pNL [NLucP/ISRE/Hygro]vector (Promega, Fitchburg, WI, US) was constructed. pcDNA3.3zeo/HA-hTMEM 173(H232R) was transfected to the cells using FugeneHD (Promega, Fitchburg, WI, US), and the cells were cultured for one day using Dulbecco's Modified Eagle's Medium (DMEM) (Wako Pure Chemical Industries, Ltd.) containing 10% fetal bovine serum. The cells were collected, and cryopreserved by CELLBANKER 1 (Nippon Zenyaku Kogyo Co., Ltd.).

On the day of the assay, the test compound diluted with assay buffer (DMEM containing 0.1% bovine serum albumin free of fatty acid) was added to a white 384-well plate (Corning, NY, US) by 10 μL/well. The cryopreserved cells were thawed, and the cells suspended in assay buffer were seeded thereto by 10 μL/well (10000 cells/well). The cells were cultured at 37° C. under 5% $CO_2$ condition for 20 hr, and NanoGlo reagent (Promega, Fitchburg, WI, US) solution (20 μL) was added thereto. After incubated for 5 min, the luminescence level was measured using EnVision (PerkinElmer, Waltham, MA, US). The activity level of each test compound was calculated when the count in the cells treated with 2',3'-cGAMP (30 μM) was considered as 100%, and the count in the cells treated with the solvent was considered as 0%. The results are shown in Table 3.

TABLE 3

| STING agonistic activity test | |
|---|---|
| Example No. | activity level of test compound (30 μM) |
| 1 | 77% |
| 2 | 77% |

TABLE 3-continued

| STING agonistic activity test | |
|---|---|
| Example No. | activity level of test compound (30 μM) |
| 3 | 76% |
| 3a | 107% |
| 5 | 100% |
| 14 | 71% |
| 15 | 81% |
| 16 | 123% |
| 17 | 99% |
| 18 | 81% |
| 20 | 125% |

As is clear from the above-mentioned results, the compound of the present disclosure has an agonist activity against wild-type STING.

Reporter Gene Assay (2)

A stable expressing 293T cell line transfected with pNL [NLucP/ISRE/Hygro]vector (Promega, Fitchburg, WI, US) was constructed. A suspension, which was prepared by transfecting pcDNA3.1zeo/HA-hTMEM173(H232R) or pcDNA3.1HA/HA-hTMEM173v1 together with firefly luciferase expression plasmid to the cells using FugeneHD (Promega, Fitchburg, WI, US), was added to a 384-well plate (Corning, NY, US), and the cells were cultured for two days. The culture solution was removed, and the test compound diluted with assay buffer (50 mM HEPES pH 7.0, 100 mM KCl, 3 mM $MgCl_2$, 85 mM Sucrose, 0.1 mM DTT, 0.2% BSA, 1 mM ATP, 0.1 mM GTP, 10 μg/ml Digitonin) was added thereto by 15 μL/well. The cells were cultured at 37° C. under 5% $CO_2$ condition for 30 min, and the assay buffer was removed. Dulbecco's Modified Eagle's Medium (DMEM) (Wako Pure Chemical Industries, Ltd.) containing 10% fetal bovine serum was added thereto by 20 μL/well, and the cells were cultured at 37° C. under 5°%° $CO_2$ condition for 4 hr. Luminescence signals derived from firefly luciferase and NanoLuc Luciferase were each measured using EnVision (PerkinElmer, Waltham, MA, US) according to Nano-Glo Dual-Luciferase Reporter Assay System (Promega, Fitchburg, WI, US) protocol. The ratio of the count of NanoLuc Luciferase divided by the count of firefly luciferase was used for calculation. The activity level of each test compound was calculated when the ratio in the cells treated with 2',3'-cGAMP (30 μM) was considered as 100%, and the ratio in the cells treated with the solvent was considered as 0%. The results are shown in Table 4.

TABLE 4

| STING agonistic activity test | | |
|---|---|---|
| Example No. | activity level against WT STING of test compound (30 μM) | activity level against mutated-type STING (R232H) of test compound (30 μM) |
| 1 | 97% | 70% |
| 1a | 99% | 92% |
| 2 | 112% | 77% |
| 3 | 97% | 73% |
| 5 | 107% | 95% |
| 13 | 99% | 85% |

TABLE 4-continued

STING agonistic activity test

| Example No. | activity level against WT STING of test compound (30 μM) | activity level against mutated-type STING (R232H) of test compound (30 μM) |
| --- | --- | --- |
| 14 | 99% | 92% |
| 15 | 91% | 100% |
| 16 | 114% | 108% |
| 17 | 110% | 85% |
| 18 | 98% | 96% |
| 19 | 101% | 62% |
| 20 | 113% | 85% |

As is clear from the above-mentioned results, the compound of the present disclosure has an agonist activity against wild-type STING and mutated-type STING (R232H).

Example 37

Phosphorylated IRF3 Protein Detection in FaDu Cell

Human larynx cancer cell line FaDu cell (ATCC) was seeded, the medium was replaced with seam free medium one day after the seeding. After the replacement, the cell was cultured for one day, and to the cell were added the natural ligand 2',3'-cGAMP (the final concentration; 30 μM) and test compound (the final concentration; 15 μM or 30 μM). 6 hr after the addition, the cell was washed with PBS, the cell extract was prepared, and the phosphorylated IRF3 protein was detected by ELISA method or Western blotting method. The IRF3 protein phosphorylation activity of the test compound was calculated when the value in the sample with adding the natural ligand 2',3'-cGAMP at the final concentration of 30 μM was considered as 100%. The results are shown in Table 5.

TABLE 5

IRF3 protein phosphorylation test

| Example No. | activity level of test compound |
| --- | --- |
| 1 | 468.8% at 30 μM |
| 2 | 88.7% at 30 μM |
| 3 | 464.6% at 30 μM |
| 5 | 117.4% at 30 μM |

As is clear from the above-mentioned results, the compound of the present disclosure promotes the phosphorylation of IRF3, which is the downstream signal of STING, as in natural ligand 2',3'-cGAMP. That is to say, the compound of the present disclosure activates the downstream signal of STING, as a STING agonist.

Example 38

Formulation Example

A medicament containing the compound of the present disclosure as an active ingredient can be produced, for example, based on the following composition.

1. capsule

| | |
| --- | --- |
| (1) the compound obtained in Example 1 | 10 mg |
| (2) lactose | 90 mg |
| (3) crystalline cellulose | 70 mg |
| (4) magnesium stearate | 10 mg |
| 1 capsule | 180 mg |

(1), (2), (3) and 5 mg of (4) are blended and granulated. Thereto is added the remaining 5 mg of (4), and the total amount is filled in a gelatin capsule.

2 tablet

| | |
| --- | --- |
| (1) the compound obtained in Example 1 | 10 mg |
| (2) lactose | 35 mg |
| (3) cornstarch | 150 mg |
| (4) crystalline cellulose | 30 mg |
| (5) magnesium stearate | 5 mg |
| 1 tablet | 230 mg |

(1), (2), (3), 20 mg of (4) and 2.5 mg of (5) are blended and granulated. Thereto is added the remaining 10 mg of (4) and the remaining 2.5 mg of (5), and the mixture is compression formed to give a tablet.

INDUSTRIAL APPLICABILITY

The compound of the present disclosure may have a STING agonistic activity. Therefore, the compound of the present disclosure may be used as a STING agonist, and may be useful as an agent for the prophylaxis or treatment of STING-related diseases including cancer and the like.

It is to be understood that the foregoing described embodiments and exemplifications are not intended to be limiting in any respect to the scope of the disclosure, and that the claims presented herein are intended to encompass all embodiments and exemplifications whether or not explicitly presented herein All patents, patent applications, and publications cited herein are fully incorporated by reference in their entirety.

What is claimed is:

1. A method of preparing a compound having Formula (IA):

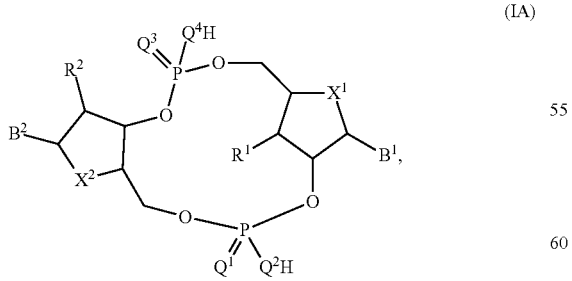

(IA)

or a pharmaceutically acceptable salt thereof, the method comprising deprotecting a compound having Formula (7):

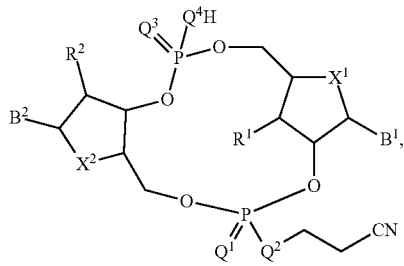

(7)

wherein:

$X^1$ and $X^2$ are each independently an oxygen atom or a sulfur atom;

$R^1$ and $R^2$ are each independently a hydroxy group, a protected hydroxy group, or a halogen atom;

$B^1$ is:

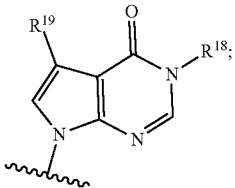

$R^{18}$ is hydrogen or $C_{1-6}$ alkyl;
$R^{19}$ is a halogen atom;
$B^2$ is:

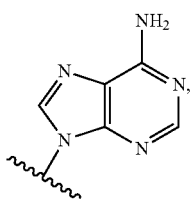 [SMILES: *n1cnc2c(N)ncnc21]

wherein the —NH$_2$ group is optionally protected, or

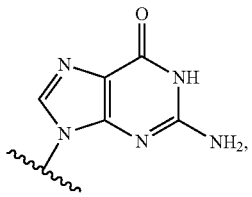 [SMILES: *n1cnc2c(=O)[nH]c(N)nc21]

wherein the —NH$_2$ group is optionally protected; and
$Q^1$, $Q^2$, $Q^3$ and $Q^4$ are each independently an oxygen atom or a sulfur atom, wherein the compound having Formula (IA), or a pharmaceutically acceptable salt thereof, is selected from the group consisting of:

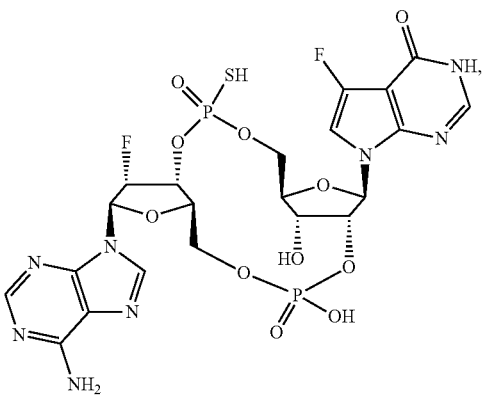

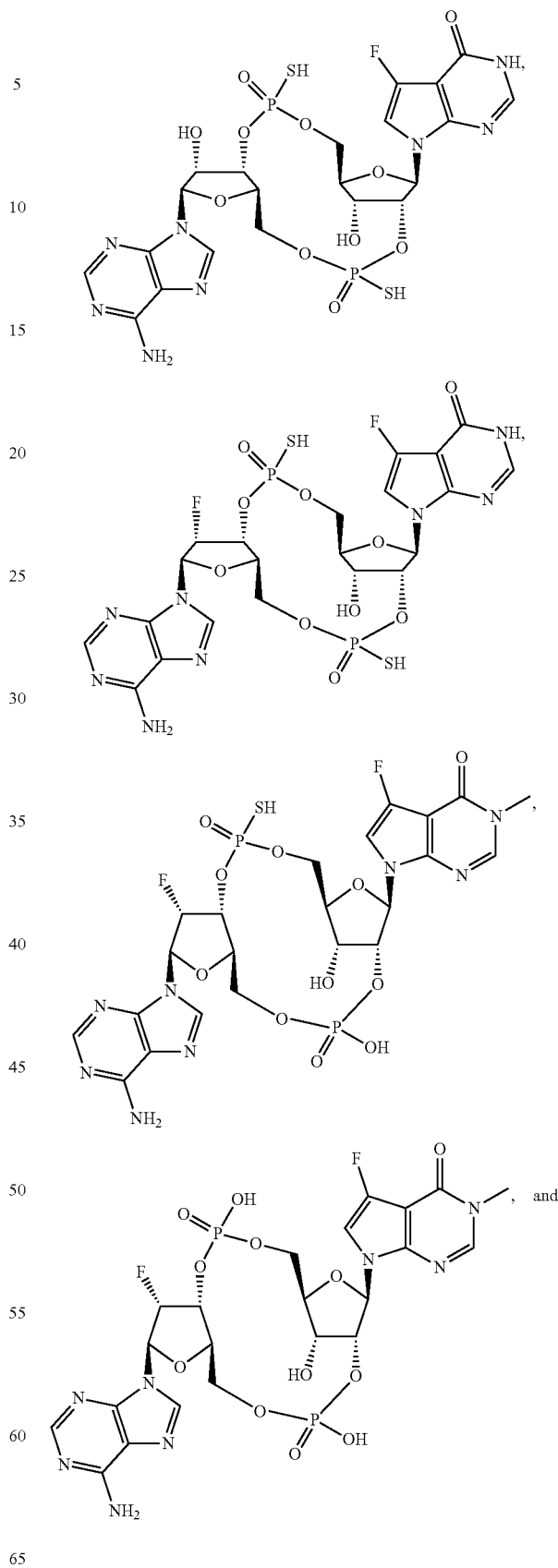

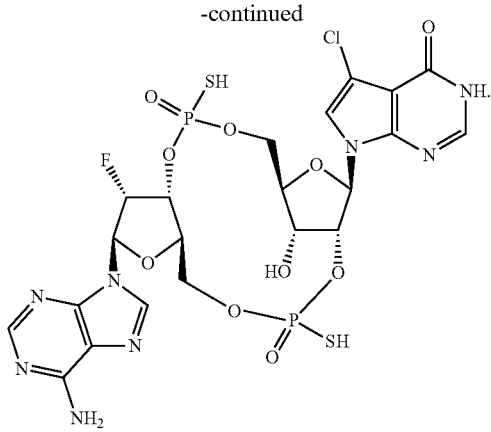

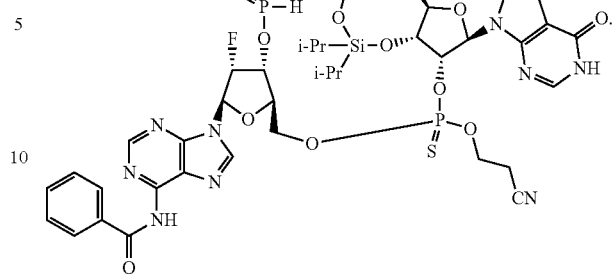

5. The method of claim 3, wherein the compound having Formula (5) is prepared by deprotection of a compound having Formula (4):

(4)

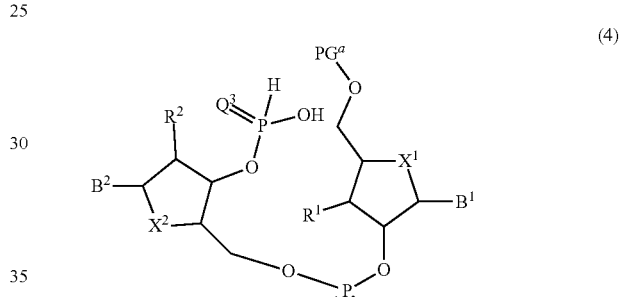

wherein, PG$^a$ is a hydroxyl-protecting group, or when R$^1$ is a hydroxyl group, this hydroxyl group and the hydroxyl group attached to PG$^a$ are protected by a 1,1,3,3-tetraisopropyldisiloxanyl group after removal of PG$^a$.

6. The method of claim 5, wherein the compound having Formula (4) is:

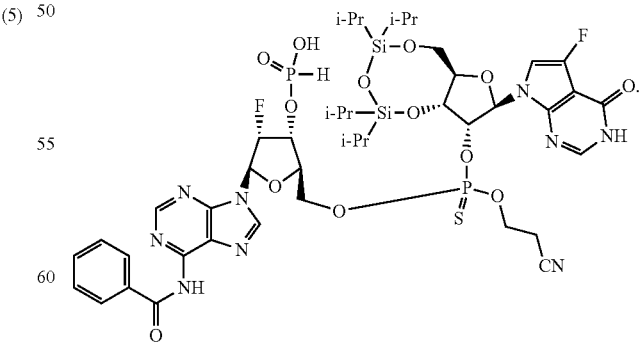

7. The method of claim 5, wherein the compound having Formula (4) is prepared by oxidation or sulfurization of a compound having Formula (3):

2. The method of claim 1, wherein the compound having Formula (7) is prepared by oxidation or sulfurization of a compound having Formula (6):

(6)

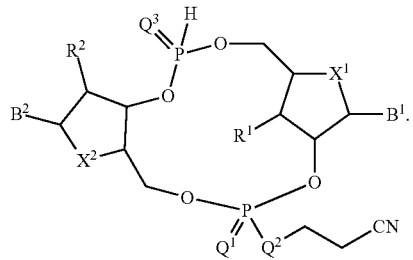

3. The method of claim 2, wherein the compound having Formula (6) is prepared by cyclization of a compound having Formula (5):

(5)

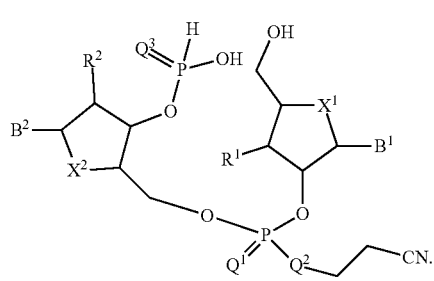

4. The method of claim 3, wherein the compound having Formula (5) is:

(3)

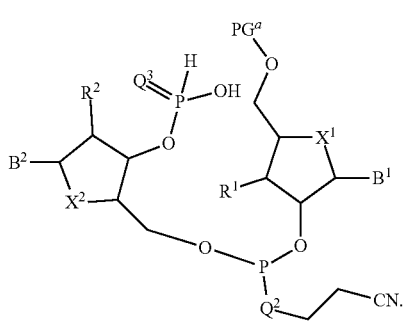

8. The method of claim 7, wherein the compound having Formula (3) is prepared by condensing a compound having Formula (1a):

(1a)

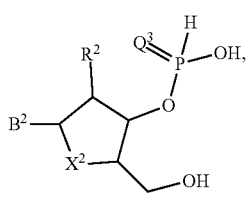

with a compound having Formula (2a):

(2a)

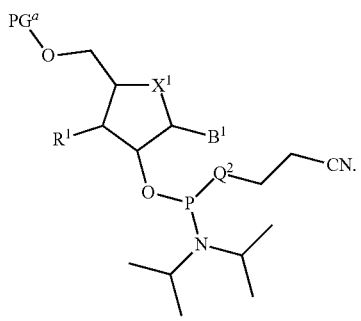

9. The method of claim 8, wherein the compound having Formula (1a) is:

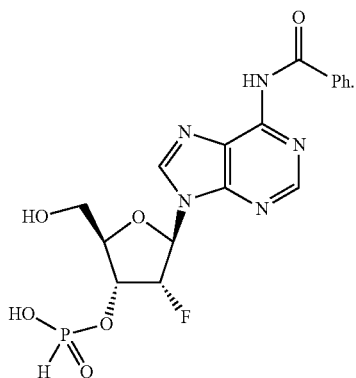 [SMILES: O=C(Nc1ncnc2c1ncn2[C@@H]1O[C@H](CO)[C@@H](O[PH](=O)O)[C@H]1F)c1ccccc1]

10. The method of claim 8, wherein the compound having Formula (2a) is:

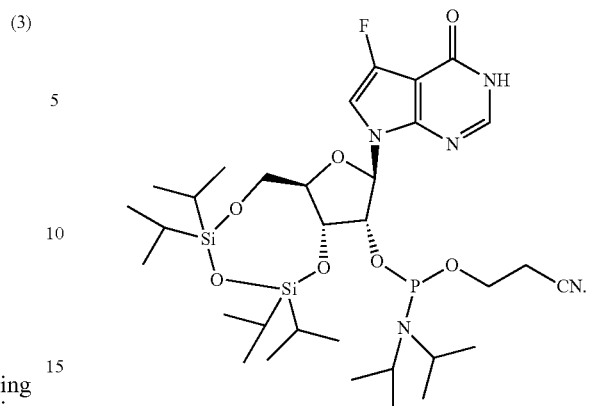

11. The method of claim 8, wherein the compound having Formula (2a) is prepared by condensing a compound having Formula (29):

(29)

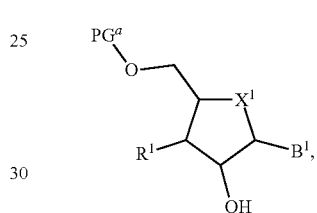

with 2-cyanoethyl N,N,N',N'-tetraisopropylphosphoramidite.

12. The method of claim 11, wherein the compound having Formula (29) is:

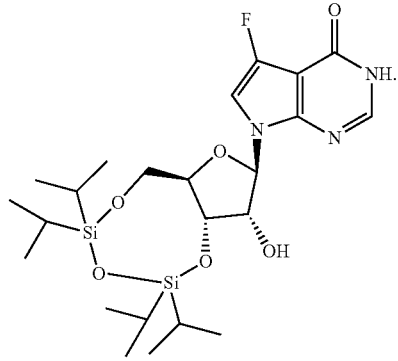

13. The method of claim 1, wherein $B^1$ is:

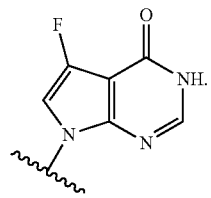 [SMILES: *n1cc(F)c2c(=O)[nH]cnc21]

14. The method of claim 1, wherein B² is:

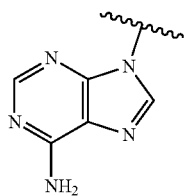

15. The method of claim 1, wherein the pharmaceutically acceptable salt is the di-triethylamine salt.

16. The method of claim 1, wherein the pharmaceutically acceptable salt is the di-sodium salt.

17. The method of claim 1, wherein the compound having Formula (IA) is:

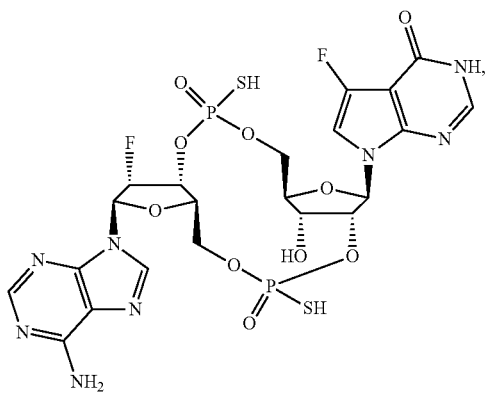 [SMILES: Nc1ncnc2c1ncn2[C@@H]1O[C@@H]2COP(=O)(S)O[C@@H]3[C@H](O)[C@@H](COP(=O)(S)O[C@H]2[C@H]1F)O[C@H]3n1cc(F)c2c(=O)[nH]cnc21]

or a pharmaceutically acceptable salt thereof.

18. The method of claim 17, wherein the pharmaceutically acceptable salt is the di-triethylamine salt.

19. The method of claim 17, wherein the pharmaceutically acceptable salt is the di-sodium salt.

20. A compound that is selected from:

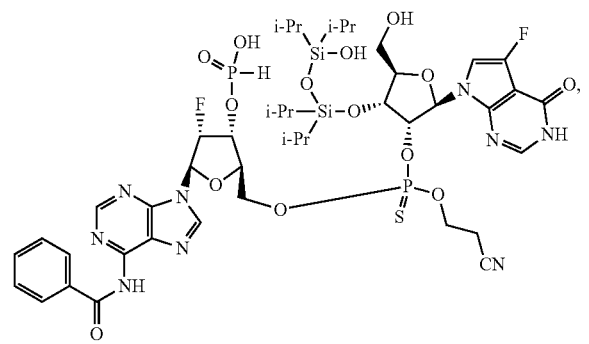

-continued

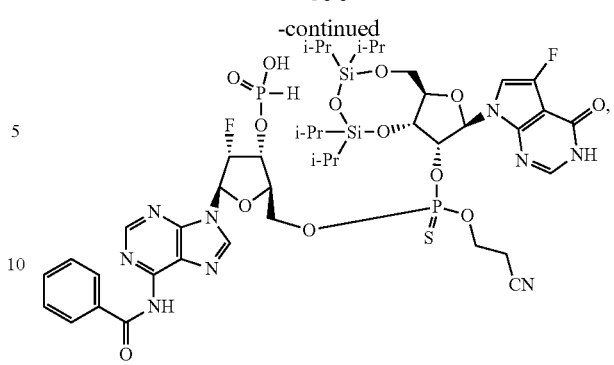

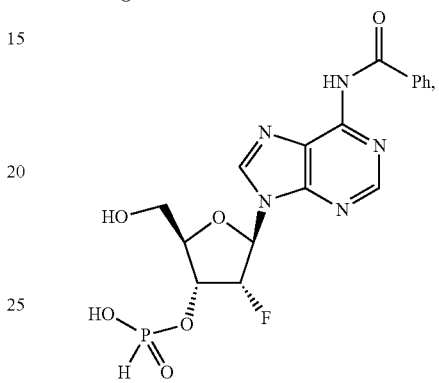

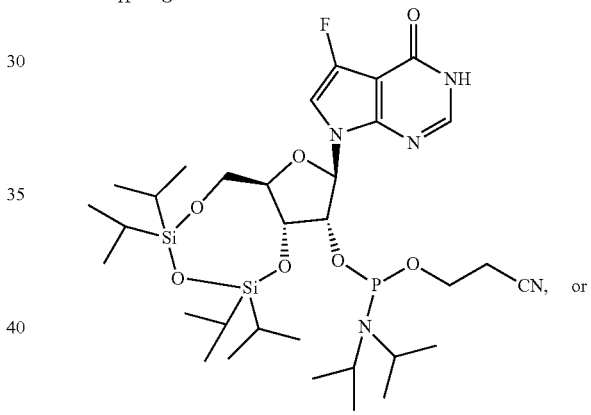

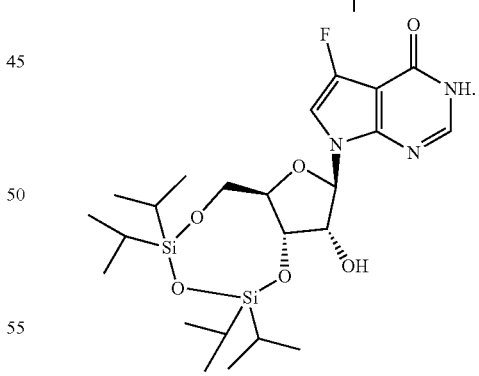

* * * * *

SEQUENCE LISTING

```
Sequence total quantity: 14
SEQ ID NO: 1            moltype = AA  length = 449
FEATURE                 Location/Qualifiers
REGION                  1..449
                        note = Antibody 1 heavy chain
source                  1..449
                        mol_type = protein
                        organism = synthetic construct
SEQUENCE: 1
QVQLQQWGAG LLKPSETLSL TCAVFGGSFS GYYWSWIRQP PGKGLEWIGE INHRGNTNDN   60
PSLKSRVTIS VDTSKNQFAL KLSSVTAADT AVYYCARERG YTYGNFDHWG QGTLVTVSSA  120
STKGPSVFPL APSSKSTSGG TAALGCLVKD YFPEPVTVSW NSGALTSGVH TFPAVLQSSG  180
```

```
LYSLSSVVTV PSSSLGTQTY ICNVNHKPSN TKVDKKVEPK SCDKTHTCPP CPAPELLGGP   240
SVFLFPPKPK DTLMISRTPE VTCVVVDVSH EDPEVKFNWY VDGVEVHNAK TKPREEQYNS   300
TYRVVSVLTV LHQDWLNGKE YKCKVSNKAL PAPIEKTISK AKGQPREPQV YTLPPSRDEL   360
TKNQVSLTCL VKGFYPSDIA VEWESNGQPE NNYKTTPPVL DSDGSFFLYS KLTVDKSRWQ   420
QGNVFSCSVM HEALHNHYTQ KSLSLSPGK                                    449

SEQ ID NO: 2            moltype = AA  length = 214
FEATURE                 Location/Qualifiers
REGION                  1..214
                        note = Antibody 1 light chain
source                  1..214
                        mol_type = protein
                        organism = synthetic construct
SEQUENCE: 2
EIVMTQSPAT LSVSPGERAT LSCRASQSVS RNLAWYQQKP GQAPRLLIYG ASTRATGIPA    60
RFSGSGSGTE FTLTIGSLQS EDFAVYYCQQ YKTWPRTFGQ GTNVEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                              214

SEQ ID NO: 3            moltype = DNA  length = 23
FEATURE                 Location/Qualifiers
source                  1..23
                        mol_type = other DNA
                        organism = synthetic construct
SEQUENCE: 3
cctggcccca gctgagatct ctg                                           23

SEQ ID NO: 4            moltype = DNA  length = 37
FEATURE                 Location/Qualifiers
source                  1..37
                        mol_type = other DNA
                        organism = synthetic construct
SEQUENCE: 4
gtaaacccga tccttgatgc cagcacggtc accggtc                            37

SEQ ID NO: 5            moltype = DNA  length = 36
FEATURE                 Location/Qualifiers
source                  1..36
                        mol_type = other DNA
                        organism = synthetic construct
SEQUENCE: 5
ctgccccagc agaccggtga ccgtgctggc atcaag                             36

SEQ ID NO: 6            moltype = DNA  length = 38
FEATURE                 Location/Qualifiers
source                  1..38
                        mol_type = other DNA
                        organism = synthetic construct
SEQUENCE: 6
ataatagcgg ccgctcaaga gaaatccgtg cggagagg                           38

SEQ ID NO: 7            moltype = DNA  length = 53
FEATURE                 Location/Qualifiers
source                  1..53
                        mol_type = other DNA
                        organism = synthetic construct
SEQUENCE: 7
cgactacaag gacgacgatg acaagggatc cctggcccca gctgagatct ctg          53

SEQ ID NO: 8            moltype = DNA  length = 62
FEATURE                 Location/Qualifiers
source                  1..62
                        mol_type = other DNA
                        organism = synthetic construct
SEQUENCE: 8
gtacccatac gatgttccag attacgctgg atccgccacc atgccccact ccagcctgca   60
tc                                                                  62
```

```
SEQ ID NO: 9           moltype = DNA  length = 51
FEATURE                Location/Qualifiers
source                 1..51
                       mol_type = other DNA
                       organism = synthetic construct
SEQUENCE: 9
ataatatcta gaattcgcca ccatgtaccc atacgatgtt ccagattacg c          51

SEQ ID NO: 10          moltype = DNA  length = 48
FEATURE                Location/Qualifiers
source                 1..48
                       mol_type = other DNA
                       organism = synthetic construct
SEQUENCE: 10
ttccagatta cgctggatcc gccaccatgc cccactccag cctgcatc              48

SEQ ID NO: 11          moltype = DNA  length = 45
FEATURE                Location/Qualifiers
source                 1..45
                       mol_type = other DNA
                       organism = synthetic construct
SEQUENCE: 11
cctctagact cgagcggccg ctcaagagaa atccgtgcgg agagg                 45

SEQ ID NO: 12          moltype = DNA  length = 42
FEATURE                Location/Qualifiers
source                 1..42
                       mol_type = other DNA
                       organism = synthetic construct
SEQUENCE: 12
ggagacccaa gctggctagc gccaccatgt acccatacga tg                   42

SEQ ID NO: 13          moltype = DNA  length = 44
FEATURE                Location/Qualifiers
misc_feature           1..44
                       note = CMVPro-BglII-F
source                 1..44
                       mol_type = other DNA
                       organism = synthetic construct
SEQUENCE: 13
ataataagat ctgttgacat tgattattga ctagttatta atag                 44

SEQ ID NO: 14          moltype = DNA  length = 36
FEATURE                Location/Qualifiers
misc_feature           1..36
                       note = CMVPro-HindIII-R
source                 1..36
                       mol_type = other DNA
                       organism = synthetic construct
SEQUENCE: 14
ataataaagc ttgagctctg cttatataga cctccc                          36
```